US007829665B2

(12) United States Patent
Blatt et al.

(10) Patent No.: US 7,829,665 B2
(45) Date of Patent: Nov. 9, 2010

(54) MACROCYCLIC INHIBITORS OF HEPATITIS C VIRUS REPLICATION

(75) Inventors: Lawrence M. Blatt, Brisbane, CA (US); Scott D. Seiwert, Pacifica, CA (US); Steven W. Andrews, Longmont, CO (US); Pierre Martin, Rheinfelden (CH); Andreas Schumacher, Efringen-Kirchen (DE); Bradley Barnett, Northglenn, CO (US); C. Todd Eary, Longmont, CO (US); Robert Kaus, Longmont, CO (US); Timothy Kercher, Boulder, CO (US); Weidong Liu, Superior, CO (US); Michael Lyon, Superior, CO (US); Paul Nichols, Firestone, CO (US); Bin Wang, Longmont, CO (US); Tarek Sammakia, Boulder, CO (US); April Kennedy, Denver, CO (US); Yutong Jiang, Longmont, CO (US)

(73) Assignee: InterMune, Inc., Brisbane, CA (US)

(*) Notice: Subject to any disclaimer, the term of this patent is extended or adjusted under 35 U.S.C. 154(b) by 117 days.

(21) Appl. No.: 11/491,126

(22) Filed: Jul. 21, 2006

(65) Prior Publication Data
US 2007/0054842 A1 Mar. 8, 2007

Related U.S. Application Data

(60) Provisional application No. 60/702,195, filed on Jul. 25, 2005, provisional application No. 60/725,533, filed on Oct. 11, 2005, provisional application No. 60/789,800, filed on Apr. 6, 2006.

(51) Int. Cl.
C07K 7/50 (2006.01)
(52) U.S. Cl. ............................ 530/317; 514/9; 514/307
(58) Field of Classification Search ................. 530/317; 514/9, 307
See application file for complete search history.

(56) References Cited

U.S. PATENT DOCUMENTS

| 5,034,394 | A | 7/1991 | Daluge |
| 5,232,928 | A | 8/1993 | Skiles |
| 5,624,949 | A | 4/1997 | Heath et al. |
| 5,656,627 | A | 8/1997 | Bemis et al. |
| 5,756,466 | A | 5/1998 | Bemis et al. |
| 5,847,135 | A | 12/1998 | Bemis et al. |
| 5,968,895 | A | 10/1999 | Gefter et al. |
| 6,268,207 | B1 | 7/2001 | Bailey |
| 6,323,180 | B1 | 11/2001 | Llinas-Brunet et al. |
| 6,410,531 | B1 | 6/2002 | Llinas-Brunet et al. |
| 6,420,380 | B2 | 7/2002 | Llinas-Brunet et al. |
| 6,534,523 | B1 | 3/2003 | Llinas-Brunet et al. |
| 6,608,027 | B1 | 8/2003 | Tsantrizo et al. |
| 6,642,204 | B2 | 11/2003 | Llinas-Brunet et al. |
| 6,693,072 | B2 | 2/2004 | Gallion et al. |
| 6,767,991 | B1 | 7/2004 | Llinas-Brunet et al. |
| 6,828,301 | B2 | 12/2004 | Chen et al. |
| 6,846,802 | B2 | 1/2005 | Chen et al. |
| 6,858,600 | B2 | 2/2005 | Hamilton et al. |
| 6,867,185 | B2 | 3/2005 | Campbell et al. |
| 6,867,303 | B2 | 3/2005 | Grela |
| 6,869,964 | B2 | 3/2005 | Campbell et al. |
| 6,872,805 | B2 | 3/2005 | Campbell et al. |
| 6,878,722 | B2 | 4/2005 | Campbell et al. |
| 6,909,000 | B2 | 6/2005 | Farmer et al. |
| 6,914,122 | B2 | 7/2005 | Venkatraman et al. |
| 6,919,423 | B2 | 7/2005 | Llinas-Brunet |
| 6,995,174 | B2 | 2/2006 | Wang et al. |
| 7,012,066 | B2 | 3/2006 | Saksena |
| 7,041,698 | B2 | 5/2006 | Ripka et al. |
| 7,091,184 | B2 | 8/2006 | Llinas-Brunet et al. |
| 7,119,072 | B2 | 10/2006 | Llinas-Brunet et al. |
| 7,125,845 | B2 | 10/2006 | Wu et al. |
| 7,132,504 | B2 | 11/2006 | Scola et al. |
| 7,135,462 | B2 | 11/2006 | Scola et al. |
| 7,148,347 | B2 | 12/2006 | Brandenburg et al. |
| 7,157,424 | B2 | 1/2007 | Chen et al. |
| 7,173,004 | B2 | 2/2007 | McPhee et al. |
| 7,173,057 | B2 | 2/2007 | Chen et al. |
| 7,176,208 | B2 | 2/2007 | Nakajima et al. |
| 7,183,374 | B2 | 2/2007 | Brenner et al. |
| 7,186,747 | B2 | 3/2007 | Arasappan et al. |
| 7,189,844 | B2 | 3/2007 | Gallou et al. |

(Continued)

FOREIGN PATENT DOCUMENTS

CA 2370400 8/2003

(Continued)

OTHER PUBLICATIONS

Abstract of CL 01184-98, issued Mar. 1999.*

(Continued)

Primary Examiner—David Lukton
(74) Attorney, Agent, or Firm—Knobbe Martens Olson & Bear LLP

(57) ABSTRACT

The embodiments provide compounds of the general Formulae I through general Formula VIII, as well as compositions, including pharmaceutical compositions, comprising a subject compound. The embodiments further provide treatment methods, including methods of treating a hepatitis C virus infection and methods of treating liver fibrosis, the methods generally involving administering to an individual in need thereof an effective amount of a subject compound or composition.

29 Claims, No Drawings

U.S. PATENT DOCUMENTS

| | | |
|---|---|---|
| 7,208,600 B2 | 4/2007 | Cottrell et al. |
| 7,273,851 B2 | 9/2007 | Miao et al. |
| 7,273,885 B2 | 9/2007 | Pitlik et al. |
| 7,309,708 B2 | 12/2007 | Tu et al. |
| 7,342,041 B2 | 3/2008 | Njoroge et al. |
| 7,399,749 B2 | 7/2008 | Arasappan et al. |
| 7,449,479 B2 | 11/2008 | Wang et al. |
| 7,470,664 B2 | 12/2008 | Holloway et al. |
| 7,485,625 B2 | 2/2009 | Velazquez et al. |
| 7,491,794 B2 | 2/2009 | Blatt et al. |
| 7,494,660 B2 | 2/2009 | Lin et al. |
| 2002/0016294 A1 | 2/2002 | Venkatraman et al. |
| 2002/0016442 A1 | 2/2002 | Llinas-Brunet et al. |
| 2002/0037998 A1 | 3/2002 | Llinas-Brunet et al. |
| 2002/0107181 A1 | 8/2002 | Chen et al. |
| 2002/0111313 A1 | 8/2002 | Campbell et al. |
| 2003/0181363 A1 | 9/2003 | Llinas-Brunet et al. |
| 2003/0186895 A1 | 10/2003 | Llinas-Brunet et al. |
| 2003/0191067 A1 | 10/2003 | Llinas-Brunet et al. |
| 2003/0195228 A1 | 10/2003 | Chen et al. |
| 2003/0224977 A1 | 12/2003 | Llinas-Brunet et al. |
| 2003/0236242 A1 | 12/2003 | Perni et al. |
| 2004/0002448 A1 | 1/2004 | Tsantrizos et al. |
| 2004/0033959 A1 | 2/2004 | Chen et al. |
| 2004/0038872 A1 | 2/2004 | Campbell et al. |
| 2004/0048802 A1 | 3/2004 | Ripka et al. |
| 2004/0072761 A1 | 4/2004 | Campbell et al. |
| 2004/0077551 A1 | 4/2004 | Campbell et al. |
| 2004/0106559 A1 | 6/2004 | Wang et al. |
| 2004/0138109 A1 | 7/2004 | Chen et al. |
| 2004/0180815 A1 | 9/2004 | Nakaima et al. |
| 2004/0229776 A1 | 11/2004 | Chen et al. |
| 2004/0229777 A1 | 11/2004 | Cerreta et al. |
| 2004/0229848 A1 | 11/2004 | Demuth et al. |
| 2004/0248779 A1 | 12/2004 | Dersch et al. |
| 2004/0259804 A1 | 12/2004 | Karanewsky |
| 2004/0266668 A1 | 12/2004 | Nakajima et al. |
| 2005/0049187 A1 | 3/2005 | Brandenburg et al. |
| 2005/0065073 A1 | 3/2005 | Wu et al. |
| 2005/0075279 A1 | 4/2005 | Llinas-Brunet et al. |
| 2005/0080005 A1 | 4/2005 | Llinas-Brunet et al. |
| 2005/0090432 A1 | 4/2005 | McPhee et al. |
| 2005/0119189 A1 | 6/2005 | Cottrell et al. |
| 2005/0119453 A1 | 6/2005 | Brenner et al. |
| 2005/0136400 A1 | 6/2005 | Lin et al. |
| 2005/0137139 A1 | 6/2005 | Perni et al. |
| 2005/0143416 A1 | 6/2005 | Tu et al. |
| 2005/0153877 A1 | 7/2005 | Miao et al. |
| 2005/0153900 A1 | 7/2005 | Velazquez et al. |
| 2005/0154186 A1 | 7/2005 | Gallou et al. |
| 2005/0192212 A1 | 9/2005 | Llinas-Brunet et al. |
| 2005/0197301 A1 | 9/2005 | Njoroge et al. |
| 2005/0209135 A1 | 9/2005 | Busacca et al. |
| 2005/0215423 A1 | 9/2005 | Brenner et al. |
| 2005/0215486 A1 | 9/2005 | Cottrell et al. |
| 2005/0222047 A1 | 10/2005 | Chen et al. |
| 2005/0245458 A1 | 11/2005 | Arasappan et al. |
| 2005/0261200 A1 | 11/2005 | Miao et al. |
| 2005/0267018 A1 | 12/2005 | Blatt et al. |
| 2005/0267040 A1 | 12/2005 | Scola et al. |
| 2005/0267043 A1 | 12/2005 | Bogen et al. |
| 2005/0267151 A1 | 12/2005 | Busacca et al. |
| 2005/0272663 A1 | 12/2005 | Arasappan et al. |
| 2006/0019905 A1 | 1/2006 | Bailey et al. |
| 2006/0046956 A1 | 3/2006 | Sannigrahi et al. |
| 2006/0046965 A1 | 3/2006 | Bailey et al. |
| 2006/0063915 A1 | 3/2006 | Gallou et al. |
| 2006/0063916 A1 | 3/2006 | Gallou |
| 2006/0069099 A1 | 3/2006 | Fu et al. |
| 2006/0122123 A1 | 6/2006 | Chaudhary et al. |
| 2006/0183694 A1 | 8/2006 | Sin et al. |
| 2006/0198824 A1 | 9/2006 | Malcolm et al. |
| 2006/0205638 A1 | 9/2006 | Busacca et al. |
| 2006/0210969 A1 | 9/2006 | Rice et al. |
| 2006/0252698 A1 | 11/2006 | Malcolm |
| 2006/0252951 A1 | 11/2006 | Leitner et al. |
| 2006/0275366 A1 | 12/2006 | Malcolm et al. |
| 2006/0276404 A1 | 12/2006 | Ghosal et al. |
| 2006/0276405 A1 | 12/2006 | Albrecht |
| 2006/0276407 A1 | 12/2006 | Albrecht et al. |
| 2006/0281688 A1 | 12/2006 | Zhang et al. |
| 2006/0281689 A1 | 12/2006 | Malcolm |
| 2006/0287248 A1 | 12/2006 | Malcolm |
| 2007/0004635 A1 | 1/2007 | Albrecht et al. |
| 2007/0010431 A1 | 1/2007 | Malcolm et al. |
| 2007/0010455 A1 | 1/2007 | Hewawasam et al. |
| 2007/0021351 A1 | 1/2007 | White et al. |
| 2007/0027071 A1 | 2/2007 | Holloway et al. |
| 2007/0032433 A1 | 2/2007 | Saksena et al. |
| 2007/0072809 A1 | 3/2007 | Cho et al. |
| 2007/0078081 A1 | 4/2007 | Casarez et al. |
| 2007/0093414 A1 | 4/2007 | Carini et al. |
| 2007/0099825 A1 | 5/2007 | D'Andrea et al. |
| 2007/0161574 A1 | 7/2007 | Rosenquist et al. |
| 2007/0274951 A1 | 11/2007 | Tong et al. |
| 2007/0281885 A1 | 12/2007 | Sun et al. |
| 2007/0287664 A1 | 12/2007 | Ralston, II et al. |
| 2007/0299078 A1 | 12/2007 | Niu et al. |
| 2008/0019942 A1 | 1/2008 | Seiwert et al. |
| 2008/0125444 A1 | 5/2008 | Sun et al. |
| 2008/0187516 A1 | 8/2008 | Sun et al. |
| 2009/0048297 A1 | 2/2009 | Phadke et al. |
| 2009/0075869 A1 | 3/2009 | Holloway et al. |
| 2009/0093533 A1 | 4/2009 | Beigelman et al. |
| 2009/0105471 A1 | 4/2009 | Blatt et al. |
| 2009/0111969 A1 | 4/2009 | Blatt et al. |
| 2009/0111982 A1 | 4/2009 | Blatt et al. |
| 2009/0124661 A1 | 5/2009 | Holloway et al. |
| 2009/0124808 A1 | 5/2009 | Busacca et al. |
| 2009/0148407 A1 | 6/2009 | Blatt et al. |
| 2009/0155209 A1 | 6/2009 | Blatt et al. |
| 2009/0169510 A1 | 7/2009 | Blatt et al. |
| 2009/0203008 A1 | 8/2009 | Ludmerer et al. |
| 2009/0297476 A1 | 12/2009 | Seiwert et al. |

FOREIGN PATENT DOCUMENTS

| | | |
|---|---|---|
| CL | 2703-97 | 12/1997 |
| CL | 1797-99 | 8/1999 |
| CL | 1804-99 | 8/1999 |
| CL | 795-00 | 4/2000 |
| CL | 766-01 | 10/2001 |
| CL | 144-03 | 1/2003 |
| CL | 167-03 | 1/2003 |
| CL | 168-03 | 1/2003 |
| CL | 1161-04 | 12/2004 |
| CL | 120-05 | 1/2005 |
| EA | 2006 07738 B1 | 12/2006 |
| EP | 0206497 A2 | 12/1986 |
| EP | 0349242 A2 | 1/1990 |
| JP | 2002/542160 | 10/2000 |
| RU | 2247126 C2 | 2/2005 |
| WO | WO 97/18207 | 5/1997 |
| WO | WO 98/17679 | 4/1998 |
| WO | WO 98/46630 | 10/1998 |
| WO | WO 98/51665 | 11/1998 |
| WO | WO 99/07733 | 2/1999 |
| WO | WO 99/07734 | 2/1999 |
| WO | WO 99/47545 | 9/1999 |
| WO | WO 00/09543 A | 2/2000 |
| WO | WO 00/09558 | 2/2000 |
| WO | WO 00/23421 | 4/2000 |
| WO | WO 00/59929 | 10/2000 |
| WO | WO 01/74768 | 10/2001 |

| | | |
|---|---|---|
| WO | WO 01/81325 | 11/2001 |
| WO | WO 02/18369 | 3/2002 |
| WO | WO 02/060926 | 8/2002 |
| WO | WO 03/002518 | 1/2003 |
| WO | WO 03/053349 | 7/2003 |
| WO | WO 03/062228 | 7/2003 |
| WO | WO 03/062265 | 7/2003 |
| WO | WO 03/064416 | 8/2003 |
| WO | WO 03/064455 A | 8/2003 |
| WO | WO 03/064456 A | 8/2003 |
| WO | WO 03/066103 | 8/2003 |
| WO | WO 03/099274 | 12/2003 |
| WO | WO 2004/009121 A1 | 1/2004 |
| WO | WO 2004/026896 | 4/2004 |
| WO | WO 2004/037855 A1 | 5/2004 |
| WO | WO 2004/039833 | 5/2004 |
| WO | WO 2004/072243 A2 | 8/2004 |
| WO | WO 2004/089974 A1 | 10/2004 |
| WO | WO 2004/092203 | 10/2004 |
| WO | WO 2004/093798 | 11/2004 |
| WO | WO 2004/093915 | 11/2004 |
| WO | WO 2004/094452 | 11/2004 |
| WO | WO 2004/096286 | 11/2004 |
| WO | WO 2004/103996 | 12/2004 |
| WO | WO 2004/113365 | 12/2004 |
| WO | WO 2005/002626 | 1/2005 |
| WO | WO 2005/010029 | 2/2005 |
| WO | WO 2005/021584 | 3/2005 |
| WO | WO 2005/028501 | 3/2005 |
| WO | WO 2005/035525 A2 | 4/2005 |
| WO | WO 2005/037214 | 4/2005 |
| WO | WO 2005/046712 | 5/2005 |
| WO | WO 2005/051410 | 6/2005 |
| WO | WO 2005/051980 | 6/2005 |
| WO | WO 2005/056182 A1 | 6/2005 |
| WO | WO 2005/070955 | 8/2005 |
| WO | WO 2005/073195 A2 | 8/2005 |
| WO | WO 2005/073216 A2 | 8/2005 |
| WO | WO 2005/075502 A1 | 8/2005 |
| WO | WO 2005/095403 | 10/2005 |
| WO | WO 2005/097820 A1 | 10/2005 |
| WO | WO 2005/107745 | 11/2005 |
| WO | WO 2005/113581 | 12/2005 |
| WO | WO 2006/000085 | 1/2006 |
| WO | WO 2006/020276 | 2/2006 |
| WO | WO 2006/043145 | 4/2006 |
| WO | WO 2006/045096 A2 | 4/2006 |
| WO | WO 2006/075021 A1 | 7/2006 |
| WO | WO 2006/086381 | 8/2006 |
| WO | WO 2006/113942 | 10/2006 |
| WO | WO 2006/119061 | 11/2006 |
| WO | WO 2007/014919 | 2/2007 |
| WO | WO 2007/016441 | 2/2007 |
| WO | WO 2007/016476 A2 | 2/2007 |
| WO | WO 2007/022459 | 2/2007 |
| WO | WO 2007/030656 | 3/2007 |
| WO | WO 2007/044893 | 4/2007 |
| WO | WO 2007/044933 | 4/2007 |
| WO | WO 2007/056120 | 5/2007 |
| WO | WO 2007/089618 | 8/2007 |
| WO | WO 2007/092616 A2 | 8/2007 |
| WO | WO 2007/106317 | 9/2007 |
| WO | WO 2007/111866 A2 | 10/2007 |
| WO | WO 2007/133865 A2 | 11/2007 |
| WO | WO 2007/143694 | 12/2007 |
| WO | WO 2007/146695 | 12/2007 |
| WO | WO 2008/005565 | 1/2008 |

OTHER PUBLICATIONS

Abstract of CL 01958-96, issued Jul. 1997.*
Tsantrizos, et al., "Macrocyclic Inhibitors of the NS3 Protease as Potential Therapeutic Agents of Hepatitis C Virus Infection," *Angew. Chem. Int. Ed.*, vol. 42, No. 12, pp. 1356-1360, Mar. 28, 2003.
Galgoci, et al., "A convenient synthesis of methyl (Z)-1-carbamoyl-2-ethenylcyclopropanecarboxylate and (Z)-1-carbamoyl-2-ethenylcyclopropanecarboxylic acid," *Synthetic Communications*, 24(17), 2477-2483 (1994).
Beaulieu, et al., "Synthesis of (1R,2S)-1-Amino-2-vinylcyclopropanecarboxylic Acid Vinyl-ACCA) Derivatives: Key Intermediates for the Preparation of Inhibitors of the Hepatitis C Virus NS3 Protease," *J. Org. Chem.* 2005, 70, 5869-5879.
Belokon, et al., "General Method for the Asymmetric Synthesis of *anti*-Diastereoisomers of β-Substituted L-2-Aminobutanoic Acids . . . ", *J. Chem. Soc. Perkin Trans.*, No. 8, pp. 2301-2310, 1990.
Invitation to Pay Additional Fees received in International Application No. PCT/US2006/027738, mailed Feb. 23, 2007.
Thorstensson, et al., "Synthesis of Novel Potent Hepatitis C Virus NS3 Protease Inhibitors. Discovery of 4-Hydroxy-cyclopent-2-ene-1,2-dicarboxylic Acid as a *N*-Acyl-L-Hydroxyproline Bioisostere," accepted by *Bioorganic & Medicinal Chemistry*, accepted Oct. 23, 2006.
Franciscus, "What Did We Learn From AASLD? Part 3", *HCV Advocate* Newsletter (2003) 6(2): pp. 1, 3, 6 & 9. Link: http://www.hcvadvocate.org/news/NewsUpdates_pdf/2.4.
1_HCV_Advocate_2003/advocate0203.pdf, 4 pages.
Gonzalez et al., "Synthetic studies on *L*-Proline and (4*R*)-hydroxy-*L*-proline derivatives" *Synthesis* (2004) 8:1171-82.
Perni et al, "Inhibitors of Hepatitis C Virus NS3-4A protease 1. Non-Charged Tetrapeptide Variants" *Bioorg. Med. Chem. Lett.* (2003) 13(22):4059-63.
Perni et al, "Inhibitors of hepatitis C virus NS3-4A protease 2. Warhead SAR and optimization" *Bioorg. Med. Chem. Lett.* (2004) 14(6):1441-6.
Perni et al, "Inhibitors of hepatitis C virus NS3-4A protease. Part 3. P2 proline variants" *Bioorg. Med. Chem. Lett.* (2004) 14(8):1939-42.
Sun et al, "P4 cap modified tetrapeptidyl α-ketoamides as potent HCV NS3 protease inhibitors" *Bioorg. Med. Chem. Lett.* (2004) 14(16):4333-8.
Sulkowski, "Orally available Hepatitis C Virus (HCV) protease inhibitor (BILN 2061, Boehringer Ingelheim Pharma) demonstrates potent anti-viral activity in persons infected with HCV genotype 1" AASLD Conference Report (2002) 1 page, Link: www.natap.org/2002/AASLD/day14.htm.
Office Action mailed Oct. 18, 2007 in U.S. Appl. No. 11/093,884, filed Mar. 29, 2005.
International Report on Patentability & Written Opinion issued Oct. 4, 2006 in PCT/US05/010494 filed Mar. 29, 2005.
A. Marchetti et al., "Synthesis of Two Novel Cyclic Biphenyl Ether Analogs of an Inhibitor of HCV NS3 Protease", *Synlett*, 1999, S1, 1000-1002.
A. Faucher et al., "Synthesis of BILN 2061, an HCV NS3 Protease Inhibitor with Proven Antiviral Effect in Humans," *Org. Lett.*, 2004, 6(17), 2901-2904.
D. Thibeault et al., "Sensitivity of NS3 serine proteases from hepatitis C virus genotypes 2 and 3 to the inhibitor BILN 2061", *J. Virol.*, 2004, 78(14), 7352-7359.
N. Goudreau et al., "Potent Inhibitors of the Hepatitis C Virus NS3 Protease: Design and Synthesis of Macrocyclic Substrate-Based β-Strand Mimics," *J. Org. Chem.*, 2004, 69(19), 6185-6201.
N. Goudreau & Montse Llinas-Brunet, "The Therapeutic Potential of NS3 Protease Inhibitors in HCV Infection," *Expert Opin. Investig. Drugs*, 2005, pp. 1129-1144.
L. Lu et al., "Mutations Conferring Resistance to a Potent Hepatitis C Virus Serine Protease Inhibitor In Vitro," *Antimicrob. Agents Chemother.* 2004, 48(6), 2260-2266.
H. Hinrichsen et al., "Short-term Antiviral Efficacy of BILN 2061, a Hepatitis C Virus Serine Protease Inhibitor, in Hepatitis C Genotype 1 Patients," *Gastroenterology*, 2004, 127(5), 1347-1355.

N. Zhi-Jie; et al., "Progress and development of small molecule HCV antivirals," *Current Opinion in Drug Discovery & Development*, 2004, 7(4), 446-459. (Abstract only).

Y. Tsantrizos, "The Design of a Potent Inhibitor of the Hepatitis C Virus NS3 Protease: BILN 2061—From the NMR tube to the Clinic," *Biopolymers*, 2004, 76(4), 309-323. (Abstract Only).

S. Laplante, et al., "Dynamics and Structure-Based Design of Drugs Targeting the Critical Serine Protease of the Hepatitis C Virus—from a Peptidic Substrate to BILN 2061," *Current Medicinal Chemistry: Anti-Infective Agents*, 2005, 4(2), 111-132. (Abstract Only).

M. Llinàs-Brunet, et al., "Structure-Activity Study on a Novel Series of Macrocyclic Inhibitors of the Hepatitis C Virus NS3 Protease Leading to the Discovery of BILN 2061," *J. Med. Chem.* 2004, 47, 1605-1608.

G. Foster, "Past, Present, and Future Hepatitis C Treatments," *Seminars in Liver Disease*, 2004, 24(Supplement 2), 97-104.

V. Farina, "Efficient Synthesis of BILN 2061, a Potent HCV Protease inhibitor, by a Convergent Approach Based on Ring-Closing Metathesis," *ACS ProSpectives Conference Series, Process Chemistry in the Pharmaceutical Industry*, Feb. 6-9, 2005.

Notification Concerning Transmittal of International Preliminary Report on Patentability (Chapter 1 of the Patent Cooperation Treaty) for PCT/US2004/033970 (filed on Oct. 13, 2004), mailed on Apr. 27, 2006.

International Search Report for PCT/US/2005/010494 . . . , issued Oct. 19, 2005.

International Search Report for PCT/US04/33970 . . . , issued Apr. 18, 2006.

International Search Report and Written Opinion for PCT/US2006/027738 . . . , Nov. 23, 2007.

F. Thorstensson, et al., "Synthesis of Novel Potent Hepatitis C Virus N53 Protease Inhibitors: Discovery of 4-Hydroxy-cyclopent-2-ene-1,2-dicarboxylic Acid as a N-acyl-L-hydroxyproline Bioisostere," *Bioorg. & Med. Chem.*, 2007, 15,(2), 827-838.

Notification Concerning Transmittal of International Preliminary Report on Patentability (Chapter 1 of the Patent Cooperation Treaty) for PCT/US2006/027738 (filed on Jul. 27, 2006), mailed on Nov. 23, 2007.

CL Reg. 39715, Jun. 30, 1998, Eli Lilly & Co.

LaPlante et al., "Dynamics and structure-based design of drugs targeting the critical serine protease of the hepatitis C virus from a peptidic substrate to BILN 2061", *Current Medicinal Chemistry: Anti-Infective Agents* (2005), 4(2), 111-132 (Abstract Only).

Ni et al., "Progress and development of small molecule HCV antivirals," *Current Opinion in Drug Discovery & Development* (2004), 7(4), 446-459. (Abstract only).

Office Action mailed Apr. 21, 2008 in U.S. Appl. No. 11/093,884, filed Mar. 29, 2005.

Notice of Allowance mailed Aug. 22, 2008 in U.S. Appl. No. 11/093,884, filed Mar. 29, 2005.

International Search Report and Written Opinion mailed Aug. 13, 2008 in PCT/US2006/040049 filed Oct. 10, 2006.

Opposition Notice by ALAFAR filed Jul. 11, 2008 in Ecuador Patent Application No. SP-08-8208.

Chilean Office Action dated Jun. 13, 2008 in Chilean Patent Application No. 1932-2006.

Syrian Patent Committee Meeting #10 on May 25, 2008 in Syrian Patent Application No. 7769.

Bedossa et al.—The French Metavir Cooperative Study Group, "Intraobserver and Interobserver Variations in Liver Biopsy Interpretation in Patients with Chronic Hepatitis C" *Hepatology*, 1994, 20:15-20.

Goodman & Gilman Pharmacological Basis of Therapeutics, 9th Edition, vol. I, *McGraw-Hill*, Hill, Interamericana, Mexico (1996) p. 47, with partial translation, 2 pages.

Khan et al., "Diastereoselective Synthesis of trans-2-(1-Triphenylmethyl-1H-imidazol-4-yl)Cyclopropanecarboxylic Acids: Key Intermediates for the Preparation of Potent and Chiral Histamine $H_3$ Receptor Agents" *Bioorg. Med. Chem. Lett.*, 1997, 7(23):3017-3022.

Lin et al., "Combination of a Hepatitis C Virus NS3-NS4A Protease Inhibitor and Alpha Interferon Synergistically Inhibits Viral RNA Replication and Facilitates Viral RNA Clearance in Replicon Cells," *Antimicrob. Agents Chemother.*, 2004, 48(12): 4784-4792.

Ma et al., "Accelerating Effect Induced by the Structure of α-Amino Acid in the Copper-Catalyzed Coupling Reaction of Aryl Halides with α-Amino Acids. Synthesis of Benzolactam-V8," *J. Am. Chem. Soc.*, 1998, 120, 12459-12467.

Mckenna et al., "The scope and limitations of the Suzuki-Miyaura cross-coupling reactions of 6- and 8-substituted 1,2,3,4-tetrahydroisoquinoline-3-carboxylates," *Tetrahedron Lett.*, 2001, 42, 5795-5800.

Yao et al., "Molecular views of viral polyprotein processing revealed by the crystal structure of the hepatitis C virus bifunctional protease-helicase," *Structure*, 1999, 7(11):1353-1363.

2nd Chilean Office Action dated Jan. 12, 2009 in Chilean Patent Application No. 1932- 2006, filed Jul. 25, 2006.

EFS File History of U.S. Appl. No. 11/093,884, filed Mar. 29, 2005 (US Patent No. 7,491,794, issued Feb. 17, 2009), Uploaded in 4 Parts.

European Examination Report dated Jan. 7, 2009 in EP Application No. 06800088.4, filed Jul. 17, 2006.

Georgian Search Report dated Apr. 27, 2009 in Georgian Patent Application No. AP 2006 10529, filed Jul. 17, 2006.

Australian Search Report dated May 13, 2009 in Singapore Application No. 200800580-3, filed Jul. 17, 2006.

Partial European Examination Report dated Sep. 1, 2009 in European Application No. 09164272.8.

EFS File History of U.S. Appl. No. 11/773,912, filed Jul. 5, 2007 as of Oct. 7, 2009, Uploaded in 2 parts.

The Merck Index, An Encyclopedia of Chemicals, Drugs, and Biologicals, "ABACAVIR", 14th Edition, 2006, p. 1.

The Merck Index, An Encyclopedia of Chemicals, Drugs, and Biologicals, "DIDANOSINE", 14th Edition, 2006, p. 525.

Zucca et al., Regioselective Solid-phase 4-Amino-de-chlorination of 2,3,6-Trichloropyrimidine by Resin-supported N-Potassium Carbamates, Tetra Lttr., 2001, 42: 1033-1035.

* cited by examiner

MACROCYCLIC INHIBITORS OF HEPATITIS C VIRUS REPLICATION

RELATED APPLICATIONS

This application claims the benefit under 35 U.S.C. §119 (e) of U.S. Provisional Application Nos. 60/702,195, filed Jul. 25, 2005; 60/725,533, filed Oct. 11, 2005; and 60/789,800 filed Apr. 6, 2006; all of which are incorporated herein by reference in their entirety.

BACKGROUND OF THE INVENTION

1. Field of the Invention

The present invention relates to compounds, processes for their synthesis, compositions and methods for the treatment of hepatitis C virus (HCV) infection.

2. Description of the Related Art

Hepatitis C virus (HCV) infection is the most common chronic blood borne infection in the United States. Although the numbers of new infections have declined, the burden of chronic infection is substantial, with Centers for Disease Control estimates of 3.9 million (1.8%) infected persons in the United States. Chronic liver disease is the tenth leading cause of death among adults in the United States, and accounts for approximately 25,000 deaths annually, or approximately 1% of all deaths. Studies indicate that 40% of chronic liver disease is HCV-related, resulting in an estimated 8,000-10,000 deaths each year. HCV-associated end-stage liver disease is the most frequent indication for liver transplantation among adults.

Antiviral therapy of chronic hepatitis C has evolved rapidly over the last decade, with significant improvements seen in the efficacy of treatment. Nevertheless, even with combination therapy using pegylated IFN-α plus ribavirin, 40% to 50% of patients fail therapy, i.e., are nonresponders or relapsers. These patients currently have no effective therapeutic alternative. In particular, patients who have advanced fibrosis or cirrhosis on liver biopsy are at significant risk of developing complications of advanced liver disease, including ascites, jaundice, variceal bleeding, encephalopathy, and progressive liver failure, as well as a markedly increased risk of hepatocellular carcinoma.

The high prevalence of chronic HCV infection has important public health implications for the future burden of chronic liver disease in the United States. Data derived from the National Health and Nutrition Examination Survey (NHANES III) indicate that a large increase in the rate of new HCV infections occurred from the late 1960s to the early 1980s, particularly among persons between 20 to 40 years of age. It is estimated that the number of persons with long-standing HCV infection of 20 years or longer could more than quadruple from 1990 to 2015, from 750,000 to over 3 million. The proportional increase in persons infected for 30 or 40 years would be even greater. Since the risk of HCV-related chronic liver disease is related to the duration of infection, with the risk of cirrhosis progressively increasing for persons infected for longer than 20 years, this will result in a substantial increase in cirrhosis-related morbidity and mortality among patients infected between the years of 1965-1985.

HCV is an enveloped positive strand RNA virus in the Flaviviridae family. The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins of the virus. In the case of HCV, the generation of mature non-structural proteins (NS2, NS3, NS4, NS4A, NS4B, NS5A, and NS5B) is effected by two viral proteases. The first viral protease cleaves at the NS2-NS3 junction of the polyprotein. The second viral protease is serine protease contained within the N-terminal region of NS3 (herein referred to as "NS3 protease"). NS3 protease mediates all of the subsequent cleavage events at sites downstream relative to the position of NS3 in the polyprotein (i.e., sites located between the C-terminus of NS3 and the C-terminus of the polyprotein). NS3 protease exhibits activity both in cis, at the NS3-NS4 cleavage site, and in trans, for the remaining NS4A-NS4B, NS4B-NS5A, and NS5A-NS5B sites. The NS4A protein is believed to serve multiple functions, acting as a cofactor for the NS3 protease and possibly assisting in the membrane localization of NS3 and other viral replicase components. Apparently, the formation of the complex between NS3 and NS4A is necessary for NS3-mediated processing events and enhances proteolytic efficiency at all sites recognized by NS3. The NS3 protease also exhibits nucleoside triphosphatase and RNA helicase activities. NS5B is an RNA-dependent RNA polymerase involved in the replication of HCV RNA.

LITERATURE

METAVIR (1994) *Hepatology* 20:15-20; Brunt (2000) *Hepatol.* 31:241-246; Alpini (1997) *J. Hepatol.* 27:371-380; Baroni et al. (1996) *Hepatol.* 23:1189-1199; Czaja et al. (1989) *Hepatol.* 10:795-800; Grossman et al. (1998) *J. Gastroenterol. Hepatol.* 13:1058-1060; Rockey and Chung (1994) *J. Invest. Med.* 42:660-670; Sakaida et al. (1998) *J. Hepatol.* 28:471-479; Shi et al. (1997) *Proc. Natl. Acad. Sci. USA* 94:10663-10668; Baroni et al. (1999) *Liver* 19:212-219; Lortat-Jacob et al. (1997) *J. Hepatol.* 26:894-903; Llorent et al. (1996) *J. Hepatol.* 24:555-563; U.S. Pat. No. 5,082,659; European Patent Application EP 294, 160; U.S. Pat. No. 4,806,347; Balish et al. (1992) *J. Infect. Diseases* 166:1401-1403; Katayama et al. (2001) *J. Viral Hepatitis* 8:180-185; U.S. Pat. No. 5,082,659; U.S. Pat. No. 5,190,751; U.S. Pat. No. 4,806,347; Wandl et al. (1992) *Br. J. Haematol.* 81:516-519; European Patent Application No. 294,160; Canadian Patent No. 1,321,348; European Patent Application No. 276, 120; Wandl et al. (1992) *Sem. Oncol.* 19:88-94; Balish et al. (1992) *J. Infectious Diseases* 166:1401-1403; Van Dijk et al. (1994) *Int. J. Cancer* 56:262-268; Sundmacher et al. (1987) *Current Eye Res.* 6:273-276; U.S. Pat. Nos. 6,172,046; 6,245, 740; 5,824,784; 5,372,808; 5,980,884; published international patent applications WO 96/21468; WO 96/11953; WO 00/59929; WO 00/66623; WO2003/064416; WO2003/064455; WO2003/064456; WO 97/06804; WO 98/17679; WO 98/22496; WO 97/43310; WO 98/46597; WO 98/46630; WO 99/07733; WO 99/07734, WO 00/09543; WO 00/09558; WO 99/38888; WO 99/64442; WO 99/50230; WO 95/33764; Torre et al. (2001) *J. Med. Virol.* 64:455-459; Bekkering et al. (2001) *J. Hepatol.* 34:435-440; Zeuzem et al. (2001) *Gastroenterol.* 120:1438-1447; Zeuzem (1999) *J. Hepatol.* 31:61-64; Keeffe and Hollinger (1997) *Hepatol.* 26:11 S-107S; Wills (1990) *Clin. Pharmacokinet.* 19:390-399; Heathcote et al. (2000) *New Engl. J. Med.* 343:1673-1680; Husa and Husova (2001) *Bratisl. Lek. Listy* 102:248-252; Glue et al. (2000) *Clin. Pharmacol.* 68:556-567; Bailon et al. (2001) *Bioconj. Chem.* 12:195-202; and Neumann et al. (2001) *Science* 282:103; Zalipsky (1995) Adv. Drug Delivery Reviews S. 16, 157-182; Mann et al. (2001) *Lancet* 358:958-965; Zeuzem et al. (2000) *New Engl. J. Med.* 343:1666-1672; U.S. Pat. Nos. 5,633,388; 5,866,684; 6,018,020; 5,869,253; 6,608, 027; 5,985,265; 5,908,121; 6,177,074; 5,985,263; 5,711,944; 5,382,657; and 5,908,121; Osborn et al. (2002) *J. Pharmacol. Exp. Therap.* 303:540-548; Sheppard et al. (2003) *Nat. Immunol.* 4:63-68; Chang et al. (1999) *Nat. Biotechnol.* 17:793-797; Adolf (1995) *Multiple Sclerosis* 1 Suppl. 1:S44-S47; Chu et al., *Tet. Lett.* (1996), 7229-7232; Ninth Conference on Antiviral Research, Urabandai, Fukyshima, Japan (1996)

(*Antiviral Research*, (1996), 30:1, A23 (abstract 19)); Steinkuhler et al., *Biochem.*, 37: 8899-8905; Ingallinella et al., *Biochem.*, 37: 8906-8914.

SUMMARY OF THE INVENTION

The present embodiments provide compounds of the general formula (Ia) or (Ib):

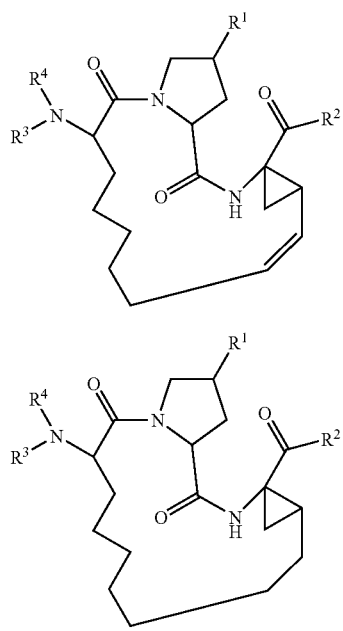

or a pharmaceutically acceptable salt, prodrug, or ester thereof wherein:

$R^1$ is H or OC(=O)—$R^{1a}$ wherein $R^{1a}$ is an optionally-substituted heteroaryl comprising N in the heteroaryl system;

$R^2$ is hydroxyl or $NHR^5$;

$R^3$ is selected from the group consisting of H, $CH_2R^6$, $COR^6CO_2R^7$, $CSNH_2$, optionally substituted 2-thiazole, and

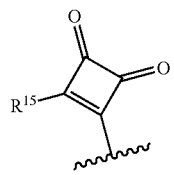

$R^4$ is hydrogen or cyclopropylmethyl;

$R^5$ is selected from the group consisting of phenyl, $CH_2C(CF_3)_2OH$, $C_3$ alkyl, cyclopropylcarbonyl, $SO_2R^8$, CN, and

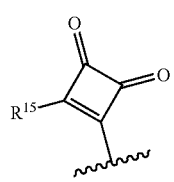

$R^6$ is selected from the group consisting of $R^9$, optionally-substituted phenyl, cyclopropyl, cyclobutyl, optionally-substituted furanyl, fluorinated alkyl; and hydroxylated alkyl;

$R^7$ is cyclopentyl or $C_1$-$C_6$ alkyl;

$R^8$ is selected from the group consisting of $NR^{11}R^{12}$, tert-butyl, chloropyridinyl,

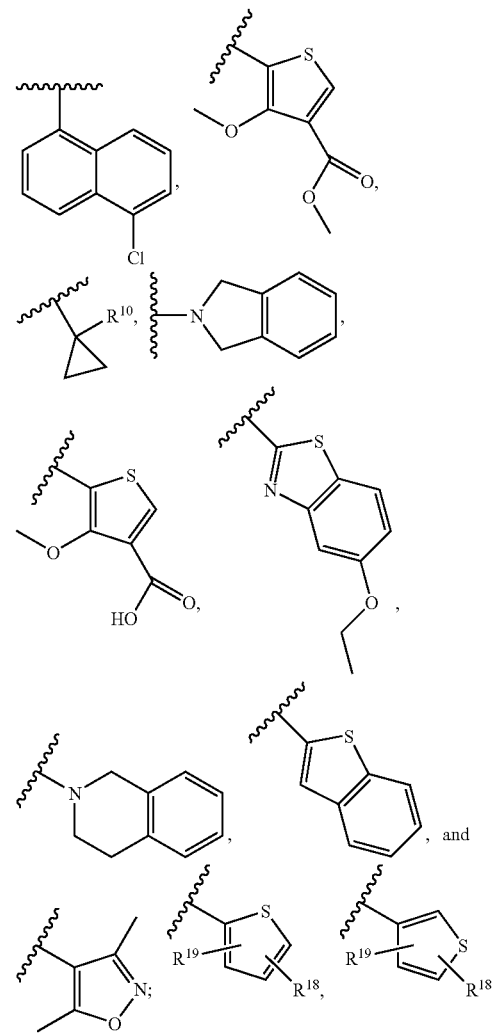

$R^9$ is selected from the group consisting of tert-butyl, trifluoromethyl, trifluoroethyl, and methyl trifluoromethyl;

$R^{10}$ is selected from the group consisting of H, $C_1$ to $C_3$ alkyl, 3-propenyl, methylmethoxyl, and benzyl;

$R^{11}$ is H, methyl, $C_{1-4}$ alkyl or $C_{1-4}$ fluorinated alkyl $R^{12}$ is selected from the group consisting of $C_1$ to $C_3$ alkyl, 3-propenyl, phenyl,

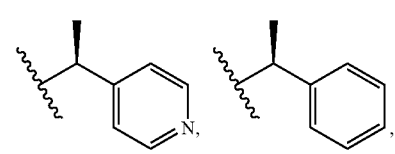

chlorophenyl, dichlorophenyl, benzyl, pyridinyl, CH$_2$R$^{13}$, CH$_2$R$^{16}$R$^{17}$, and fluorinated alkyl or R$_{11}$ and R$_{12}$ taken together can form a 4 or 5 membered ring optionally substituted with 2 fluorines R$^{13}$ is pyridinyl or R$^{14}$;

R$^{14}$ is selected from the group consisting of pyridinyl, chlorophenyl, naphthyl, and anisolyl;

R$^{15}$ is NR$^{11}$R$^{12}$ or alkyl or cycloalkyl;

R$^{16}$ is pyridinyl;

R$^{17}$ is H or methyl.

R$^{18}$ and R$^{19}$ are each independently H, halogen, methyl or CF$_3$

Another embodiment provides compound of the general formula (II)

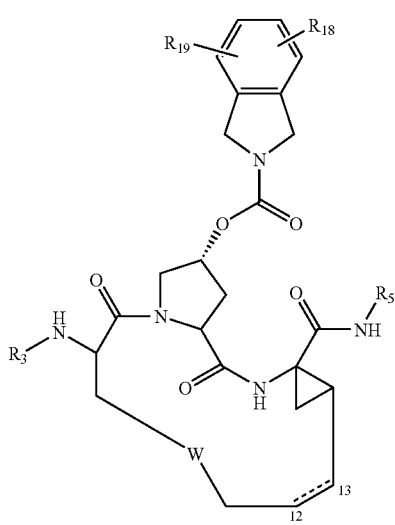

(II)

or a pharmaceutically acceptable salt, prodrug, or ester thereof wherein:

R$^3$ is selected from the group consisting of H, CH$_2$R$^6$, COR$^6$, CO$_2$R$^{7\prime}$, optionally substituted 2-thiazole R$^5$ is selected from the group consisting of cyclopropylmethyl or SO$_2$R$^8$, R$^6$ is selected from the group consisting of R$^9$, optionally-substituted phenyl, cyclopropyl, cyclobutyl, optionally-substituted furanyl, fluorinated alkyl; and hydroxylated alkyl;

R$^7$ is cyclopentyl or C$_1$-C$_6$ alkyl;

R$^8$ is selected from the group consisting of NR$^{11}$R$^{12}$, optionally substituted phenyl, and

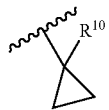

R$^{10}$ is selected from the group consisting of H, C$_1$ to C$_3$ alkyl, 3-propenyl, methylmethoxyl, and benzyl;

R$^{11}$ is H, methyl, C$_{1-4}$ alkyl or C$_{1-4}$ fluorinated alkyl

R$^{12}$ is selected from the group consisting of C$_1$ to C$_3$ alkyl, 3-propenyl, phenyl,

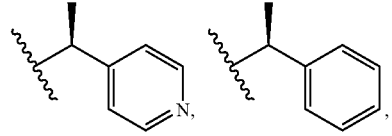

chlorophenyl, dichlorophenyl, benzyl, pyridinyl, CH$_2$R$^{13}$, CH$_2$R$^{16}$R$^{17}$, and fluorinated alkyl or R$_{11}$ and R$_{12}$ taken together can form a 4 or 5 membered ring optionally substituted with 2 fluorines R$^{17}$ is H or methyl.

R$^{18}$ and R$^{19}$ is independently H, halogen, methyl or CF$_3$

W is selected from the groups

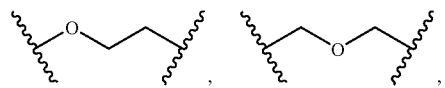

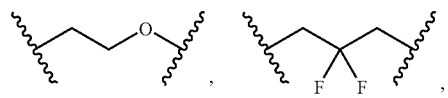

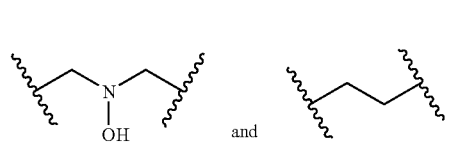

R$^{20}$ is H, CH$_3$, alkyl, fluorinated alkyl, SO$_2$Ar, the 12-13 bond is a single or double bond.

Preferred embodiments provide a compound having the Formula III

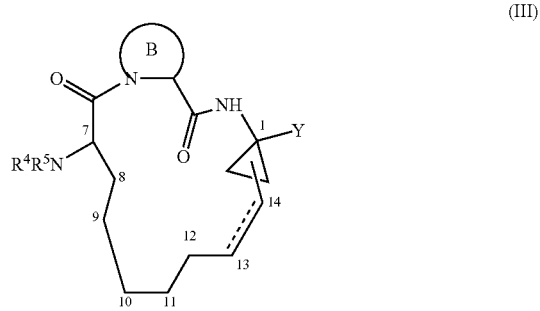

(III)

or a pharmaceutically acceptable salt, prodrug, or ester thereof wherein:

B ring is selected from

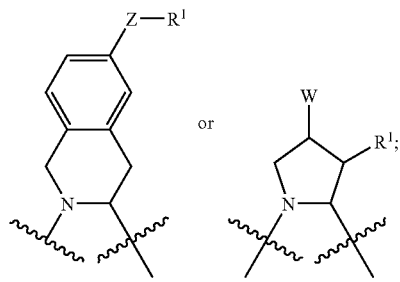

Z is bond, O, or S;

R$^1$ is H, C$_{1-7}$ alkyl, C$_{3-7}$ cycloalkyl, pyridyl, thioazolo, naphthyl, fused heterocycle, phenyl, substituted phenyl, benzyloxy, or substituted benzyloxy;

W is selected from hydrogen, halogen, OCH$_3$, SR$^3$, NHR$^3$, CH(R$^3$)$_2$, or

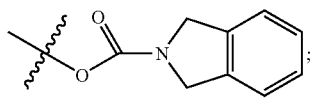

R$^3$ is H, C$_{1-8}$ alkyl, C$_{3-7}$ cycloalkyl, C$_{4-10}$ cycloalkyl-alkyl, C$_{1-6}$ alkyl, C$_{4-10}$ cycloalkyl-alkyl, C$_{7-10}$ arylalkyl, or C$_{6-12}$ heteroarylalkyl;

R$^4$ and R$^5$ are each independently substituted or unsubstituted groups selected from H, C$_{1-6}$ alkyl, C(O)R$^8$, C(O)OR$^8$, C$_{3-7}$ cycloalkyl, alkyl-C$_{4-10}$ cycloalkyl, phenyl, benzyl, C(O)NR$^8$R$^8$, C(S)NR$^8$R$^8$, S(O)$_2$R$^8$, or (CO)CHR$^{21}$NH(CO)R$^{22}$;

wherein R$^8$ is a substituted or unsubstituted group selected from H, C$_{1-6}$ alkyl, C$_{3-7}$ cycloalkyl, alkyl-C$_{3-7}$ cycloalkyl, C$_{6\ or\ 10}$ aryl, alkyl-C$_{6\ or\ 10}$ aryl, C$_{3-7}$ cycloalkyl fused to C$_6$ aryl or C$_6$ aryl heterocyclyl, tetrahydrofuran ring, tetrahydropyran ring, benzyl, or phenyl;

R$^{21}$ is a substituted or unsubstituted group selected from C$_{1-6}$ alkyl, C$_{3-7}$ cycloalkyl, C$_{4-10}$ cycloalkyl-alkyl, phenyl, C$_{6\ or\ 10}$ aryl, pyridyl, pyrimidyl, pyrazinyl, thienyl, furanyl, thiazolyl, oxazolyl, phenoxy, or thiophenoxy;

R$^{22}$ is a substituted or unsubstituted group selected from C$_{1-6}$ alkyl, C$_{3-7}$ cycloalkyl, C$_{4-10}$ cycloalkyl-alkyl, or phenyl;

Y has a formula selected from —C(O)NHS(O)$_2$R$^{1a}$, —C(O)NHS(O)$_2$NR$^{1a}$R$^{1b}$, —C(O)NHR$^{1a}$, —C(O)R$^{1a}$, —C(O)NHC(O)R$^{1a}$, —C(O)NHS(O)$_2$R$^{1a}$, —C(O)NHS(O)R$^{1a}$, or —C(O)OH;

wherein R$^{1a}$ and R$^{1b}$ are each independently substituted or unsubstituted groups selected from H, CN, CF$_3$, C$_{1-6}$ alkyl, C$_{1-6}$ alkenyl, C$_{1-6}$ alkynyl, C$_{3-7}$ cycloalkyl, alkyl-C$_{3-10}$ cycloalkyl, C$_{6\ or\ 10}$ aryl, alkyl-C$_{6\ or\ 10}$ aryl, alkenyl-C$_{6\ or\ 10}$ aryl, heterocycle, heteroaromatic ring, or alkyl-heteroaryl, alkyl-heterocycle, or NR$^{1a}$R$^{1b}$ form a substituted or unsubstituted three- to six-membered alkyl cyclic secondary amine, or NR$^{1a}$R$^{1b}$ is a heteroaryl selected from the group consisting of:

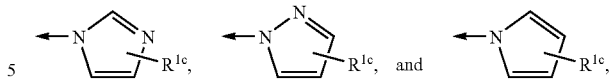

wherein R$^{1c}$ is H, halo, C$_{1-6}$ alkyl, C$_{3-6}$ cycloalkyl, C$_{1-6}$ alkoxy, C$_{3-6}$ cycloalkoxy, NO$_2$, N(R$^{1d}$)$_2$, NH(CO)R$^{1d}$, or NH(CO)NHR$^{1d}$, wherein each R$^{1d}$ is independently H, C$_{1-6}$ alkyl, or C$_{3-6}$ cycloalkyl, or R$^{1c}$ is NH(CO)OR$^{1e}$, wherein R$^{1e}$ is C$_{1-6}$ alkyl or C$_{3-6}$ cycloalkyl; and the dashed line represents an optional double bond.

Preferred embodiments provide a compound having the Formula IV:

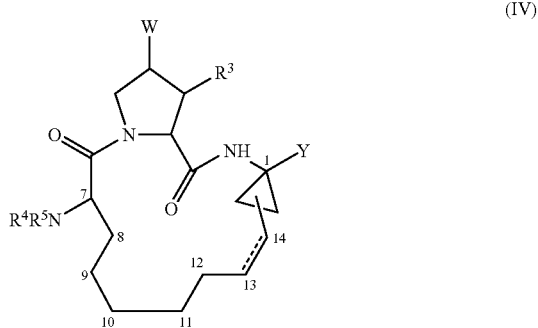

(IV)

or a pharmaceutically acceptable salt, prodrug, or ester thereof wherein:

W is selected from hydrogen, OCH$_3$, SR$^3$, NHR$^3$, CH(R$^3$)$_2$, or

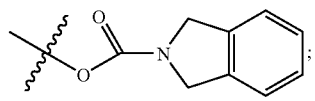

R$^3$ is H or C$_{1-3}$ alkyl;

R$^4$ and R$^5$ are independently substituted or unsubstituted groups selected from H, C$_{1-6}$ alkyl, C(O)R$^8$, C(O)OR$^8$, C$_{3-7}$ cycloalkyl, alkyl-C$_{4-10}$ cycloalkyl, phenyl, or benzyl;

wherein R$^8$ is a substituted or unsubstituted group selected from C$_{1-6}$ alkyl, C$_{3-7}$ cycloalkyl, alkyl-C$_{3-7}$ cycloalkyl, C$_{6\ or\ 10}$ aryl, or alkyl-C$_{6\ or\ 10}$ aryl;

Y has a formula selected from —C(O)NHS(O)$_2$R$^{1a}$, —C(O)NHS(O)$_2$NR$^{1a}$R$^{1b}$, —C(O)NHR$^{1a}$, —C(O)R$^{1a}$, —C(O)NHC(O)R$^{1a}$, —C(O)NHS(O)$_2$R$^{1a}$, —C(O)NHS(O)R$^{1a}$, or —C(O)OH;

wherein R$^{1a}$ and R$^{1b}$ are each independently substituted or unsubstituted groups selected from H, CN, CF$_3$, C$_{1-6}$ alkyl, C$_{1-6}$ alkenyl, C$_{1-6}$ alkynyl, C$_{3-7}$ cycloalkyl, alkyl-C$_{3-10}$ cycloalkyl, C$_{6\ or\ 10}$ aryl, alkyl-C$_{6\ or\ 10}$ aryl, alkenyl-C$_{6\ or\ 10}$ aryl, heterocycle, or alkyl-heterocycle, or NR$^{1a}$R$^{1b}$ form a substituted or unsubstituted three- to seven-membered ring, and the dashed line represents an optional double bond.

Preferred embodiments provide a compound having the Formula V:

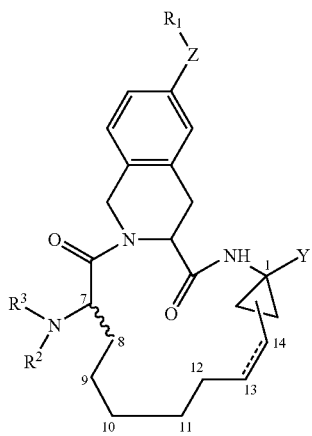

(V)

or a pharmaceutically acceptable salt, prodrug, or ester thereof wherein:

$R^1$ is H, $C_{1-7}$ alkyl, $C_{3-7}$ cycloalkyl, pyridyl, thioazolo, naphthyl, fused heterocycle, phenyl, substituted phenyl, benzyloxy, or substituted benzyloxy;

$R^2$ is H, $C_{1-6}$ alkyl, $C_{3-7}$ cycloalkyl, $C_{4-10}$ cycloalkyl-alkyl, phenyl, substituted phenyl, $C_{1-6}$ alkoxy, or substituted $C_{1-6}$ alkoxy;

$R^3$ is H, $C_{1-6}$ alkyl, $C(O)R^5$, $C(O)OR^5$, $C(O)NR^5R^6$, $C(S)NR^5R^6$, or $S(O)_2R^5$;

$R^5$ and $R^6$ are each independently selected from H, $C_{1-6}$ alkyl, $C_{3-7}$ cycloalkyl, $C_{4-10}$ cycloalkyl-alkyl, $C_{3-7}$ cycloalkyl fused to $C_6$ aryl or $C_6$ aryl heterocyclyl, benzyl, phenyl, or substituted phenyl;

Y is a sulfonimide of the formula —$C(O)NHS(O)_2R^4$ or a carboxylic acid of the formula —$C(O)OH$;

wherein $R^4$ is $C_{1-6}$ alkyl, $C_{3-7}$ cycloalkyl, $C_{4-10}$ cycloalkyl-alkyl, $C_6$ aryl, or substituted $C_6$ aryl;

Z is a bond, O, or S; and the dashed line represents an optional double bond.

In some embodiments, the phenyl on $R^1$ is substituted with halo, $C_{1-3}$ alkyl, substituted $C_{1-3}$ alkyl with up to 3 fluoro, $C_{1-3}$ alkoxy, substituted $C_{1-3}$ alkoxy substituted with up to 3 fluoro, cyano, hydroxy, nitro, $NH_2$, $NHR_2$, or $NR_2R_3$, wherein $R^2$ is H, $C_{1-6}$ alkyl, $C_{3-7}$ cycloalkyl, $C_{4-10}$ cycloalkyl-alkyl, phenyl, substituted phenyl, $C_{1-6}$ alkoxy, or substituted $C_{1-6}$ alkoxy;

$R^3$ is H, $C_{1-6}$ alkyl, $C(O)R^5$, $C(O)OR^5$, $C(O)NR^5R^6$, $C(S)NR^5R^6$, or $S(O)_2R^5$; and $R^5$ and $R^6$ are each independently selected from H, $C_{1-6}$ alkyl, $C_{3-7}$ cycloalkyl, $C_{4-10}$ cycloalkyl-alkyl, $C_{3-7}$ cycloalkyl fused to $C_6$ aryl or $C_6$ aryl heterocyclyl, benzyl, phenyl, or substituted phenyl.

Preferred embodiments provide a compound having the Formula VI:

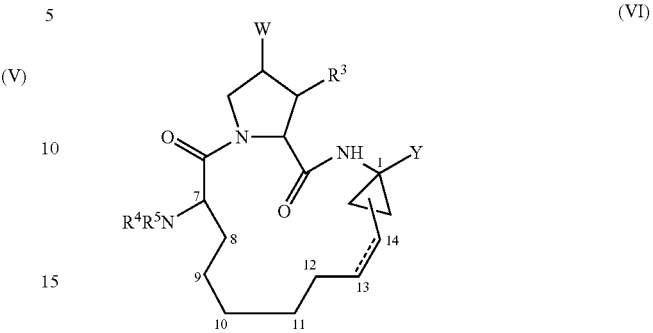

(VI)

or a pharmaceutically acceptable salt, prodrug, or ester thereof wherein:

W is selected from halogen, $OCH_3$, $SR^{15}$, $NHR^{15}$, or $CHR^3R^{15}$, wherein $R^{15}$ is a substituted or unsubstituted group selected from H, $C_{1-8}$ alkyl, $C_{3-7}$ cycloalkyl, $C_{4-10}$ cycloalkyl-alkyl, $C_{1-6}$ alkyl, $C_{4-10}$ cycloalkyl-alkyl, $C_{7-10}$ arylalkyl, or $C_{6-12}$ heteroarylalkyl;

$R^3$ is H or $C_{1-3}$ alkyl;

$R^4$ is H, $C_{1-6}$ alkyl, $C_{3-7}$ cycloalkyl, $C_{4-10}$ cycloalkyl-alkyl, substituted or unsubstituted phenyl, or substituted or unsubstituted benzyl;

$R^5$ is H, $C_{1-6}$ alkyl, $C(O)NR^6R^7$, $C(S)NR^6R^7$, $C(O)R^8$, $C(O)OR^8$, $S(O)_2R^8$, or $(CO)CHR^{21}NH(CO)R^{22}$;

$R^6$ and $R^7$ are each independently H, $C_{1-6}$ alkyl, $C_{3-7}$ cycloalkyl, $C_{4-10}$ cycloalkyl-alkyl, or substituted or unsubstituted phenyl, or $R^6$ and $R^7$ are taken together with the nitrogen to which they are attached to form indolinyl, pyrrolidinyl, piperidinyl, piperazinyl, or morpholinyl;

$R^8$ is a substituted or unsubstituted group selected from $C_{1-6}$ alkyl, $C_{3-7}$ cycloalkyl, $C_{4-10}$ cycloalkyl-alkyl, $C_{6\ or\ 10}$ aryl, tetrahydrofuran ring, or tetrahydropyran ring;

Y is an amide of the formula —$C(O)NHR^9$, wherein $R^9$ is a substituted or unsubstituted group selected from $C_{1-6}$ alkyl, phenyl, cyano, $C_{3-7}$ cycloalkyl, $C_{4-10}$ cycloalkyl-alkyl, $C_{5-10}$ arylalkyl, or heteroarylalkyl, or Y is an acyl sulfonamide of the formula —$C(O)NHS(O)_2R^9$ or an acyl sulfonimide of the formula —$C(O)NHS(O)R^9$, wherein $R^9$ is a substituted or unsubstituted group selected from $C_{1-6}$ alkyl, $C_{3-7}$ cycloalkyl, $C_{4-10}$ cycloalkyl-alkyl, $C_{5-10}$ arylalkyl, $C_{6\ or\ 10}$ aryl, or heteroaromatic ring;

or Y is a acyl sulfamide of the formula —$C(O)NHS(O)_2NR^{1a}R^{1b}$, wherein $R^{1a}$ and $R^{1b}$ are each independently substituted or unsubstituted groups selected from H, $C_{1-6}$ alkyl, $C_{3-7}$ cycloalkyl, $C_{4-10}$ cycloalkyl-alkyl, and $C_{6\ or\ 10}$ aryl, or heterocycle, or $NR^{1a}R^{1b}$ form a substituted or unsubstituted three- to six-membered alkyl cyclic secondary amine, or $NR^{1a}R^{1b}$ is a heteroaryl selected from the group consisting of:

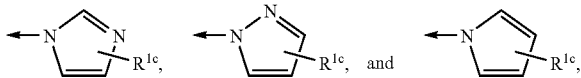

wherein $R^{1c}$ is H, halo, $C_{1-6}$ alkyl, $C_{3-6}$ cycloalkyl, $C_{1-6}$ alkoxy, $C_{3-6}$ cycloalkoxy, $NO_2$, $N(R^{1d})_2$, $NH(CO)R^{1d}$, or $NH(CO)NHR^{1d}$, wherein each $R^{1d}$ is independently H, $C_{1-6}$ alkyl, or $C_{3-6}$ cycloalkyl, or $R^{1c}$ is $NH(CO)OR^{1e}$, wherein $R^{1e}$ is $C_{1-6}$ alkyl or $C_{3-6}$ cycloalkyl;

the dashed line represents an optional double bond;

$R^{21}$ is a substituted or unsubstituted group selected from $C_{1-6}$ alkyl, $C_{3-7}$ cycloalkyl, $C_{4-10}$ cycloalkyl-alkyl, phenyl, $C_{6\ or\ 10}$ aryl, pyridyl, pyrimidyl, pyrazinyl, thienyl, furanyl, thiazolyl, oxazolyl, phenoxy, or thiophenoxy; and $R^{22}$ is a substituted or unsubstituted group selected from $C_{1-6}$ alkyl, $C_{3-7}$ cycloalkyl, $C_{4-10}$ cycloalkyl-alkyl, or phenyl.

Preferred embodiments provide a compound having the Formula VII:

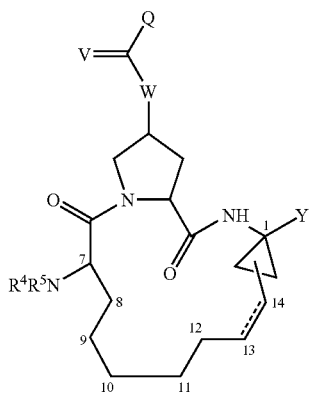

(VII)

or a pharmaceutically acceptable salt, prodrug, or ester thereof wherein:

Q is a unsubstituted or substituted core ring where

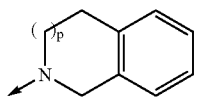

p is 0 or 1, or Q is $R^1$-$R^2$, wherein $R^1$ is a substituted or unsubstituted group selected from $C_{1-6}$ alkyl, $C_{3-7}$ cycloalkyl, $C_{4-10}$ cycloalkyl-alkyl, phenyl, pyridine, pyrazine, pyrimidine, pyridazine, pyrrole, furan, thiophene, thiazole, oxazole, imidazole, isoxazole, pyrazole, isothiazole, naphthyl, quinoline, isoquinoline, quinoxaline, benzothiazole, benzothiophene, benzofuran, indole, or benzimidazole; and $R^2$ is a substituted or unsubstituted group selected from H, phenyl, pyridine, pyrazine, pyrimidine, pyridazine, pyrrole, furan, thiophene, thiazole, oxazole, imidazole, isoxazole, pyrazole, isothiazole, naphthyl, quinoline, isoquinoline, quinoxaline, benzothiazole, benzothiophene, benzofuran, indole, or benzimidazole;

$R^4$ is selected from H, $C_{1-6}$ alkyl, $C_{3-7}$ cycloalkyl, $C_{4-10}$ cycloalkyl-alkyl, substituted or unsubstituted phenyl, or substituted or unsubstituted benzyl;

$R^5$ is H, $C_{1-6}$ alkyl, $C(O)NR^6R^7$, $C(S)NR^6R^7$, $C(O)R^8$, $C(O)OR^8$, $S(O)_2R^8$, or $(CO)CHR^{21}NH(CO)R^{22}$;

$R^6$ and $R^7$ are each independently H, $C_{1-6}$ alkyl, $C_{3-7}$ cycloalkyl, $C_{4-10}$ cycloalkyl-alkyl, or substituted or unsubstituted phenyl; or $R^6$ and $R^7$ are taken together with the nitrogen to which they are attached to form indolinyl, pyrrolidinyl, piperidinyl, piperazinyl, or morpholinyl;

$R^8$ is a substituted or unsubstituted group selected from $C_{1-6}$ alkyl, $C_{3-7}$ cycloalkyl, $C_{4-10}$ cycloalkyl-alkyl, phenyl, $C_{6\ or\ 10}$ aryl, $C_{1-6}$ alkoxy, $C_{1-6}$ alkyl, tetrahydrofuran ring, or tetrahydropyran ring;

V is selected from O, S, or NH;

W is selected from O, NH, or $CH_2$;

Y is an amide of the formula —$C(O)NHR^9$, wherein $R^9$ is a substituted or unsubstituted group selected from $C_{1-6}$ alkyl, phenyl, cyano, $C_{3-7}$ cycloalkyl, or $C_{4-10}$ cycloalkyl-alkyl, $C_{5-10}$ arylalkyl, or heteroarylalkyl;

or Y is an acyl sulfonimide of the formula —$C(O)NHS(O)R^9$, wherein $R^9$ is a substituted or unsubstituted group selected from $C_{1-6}$ alkyl, $C_{3-7}$ cycloalkyl, $C_{4-10}$ cycloalkyl-alkyl, $C_{5-10}$ arylalkyl, $C_{6\ or\ 10}$ aryl, heteroaromatic ring;

the dashed line represents an optional double bond;

$R^{21}$ is a substituted or unsubstituted group selected from $C_{1-6}$ alkyl, $C_{3-7}$ cycloalkyl, $C_{4-10}$ cycloalkyl-alkyl, phenyl, $C_{6\ or\ 10}$ aryl, pyridyl, pyrimidyl, pyrazinyl, thienyl, furanyl, thiazolyl, oxazolyl, phenoxy, or thiophenoxy; and $R^{22}$ is a substituted or unsubstituted group selected from $C_{1-6}$ alkyl, $C_{3-7}$ cycloalkyl, $C_{4-10}$ cycloalkyl-alkyl, or phenyl.

Preferred embodiments provide a compound having the Formula VIII:

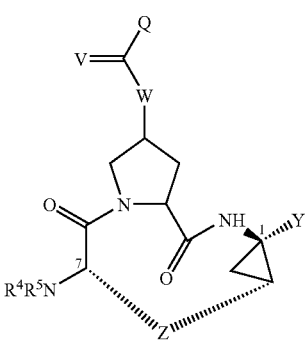

(VIII)

or a pharmaceutically acceptable salt, prodrug, or ester thereof wherein:

Q is an unsubstituted or substituted core ring selected from:

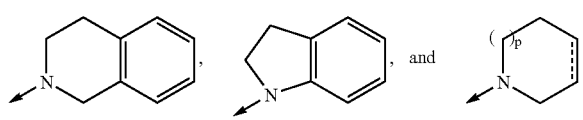

where p is 0 or 1, or Q is $R^1$-$R^2$, wherein $R^1$ is a substituted or unsubstituted group selected from $C_{1-6}$ alkyl, $C_{3-7}$ cycloalkyl, $C_{4-10}$ cycloalkyl-alkyl, phenyl, pyridine, pyrazine, pyrimidine, pyridazine, pyrrole, furan, thiophene, thiazole, oxazole, imidazole, isoxazole, pyrazole, isothiazole, naphthyl, quinoline, isoquinoline, quinoxaline, benzothiazole, benzothiophene, benzofuran, indole, or benzimidazole; and $R^2$ is a substituted or unsubstituted group selected from H, phenyl, pyridine, pyrazine, pyrimidine, pyridazine, pyrrole, furan, thiophene, thiazole, oxazole, imidazole, isoxazole, pyrazole, isothiazole, naphthyl, quinoline, isoquinoline, quinoxaline, benzothiazole, benzothiophene, benzofuran, indole, or benzimidazole;

Z is a $C_{5-7}$ saturated or unsaturated chain containing one or two heteroatoms selected from O, S, or $NR^6$;

$R^4$ is H, $C_{1-6}$ alkyl, $C_{3-7}$ cycloalkyl, $C_{4-10}$ cycloalkyl-alkyl, substituted or unsubstituted phenyl, or substituted or unsubstituted benzyl;

$R^5$ is H, $C_{1-6}$ alkyl, $C(O)NR^6R^7$, $C(S)NR^6R^7$, $C(O)R^8$, $C(O)OR^8$, $S(O)_2R^8$, or $(CO)CHR^{21}NH(CO)R^{22}$;

$R^6$ and $R^7$ are each independently H, $C_{1-6}$ alkyl, $C_{3-7}$ cycloalkyl, $C_{4-10}$ cycloalkyl-alkyl, or substituted or unsubstituted phenyl; or $R^6$ and $R^7$ are taken together with the nitrogen to which they are attached to form indolinyl, pyrrolidinyl, piperidinyl, piperazinyl, or morpholinyl;

$R^8$ is a substituted or unsubstituted group selected from $C_{1-6}$ alkyl, $C_{3-7}$ cycloalkyl, $C_{4-10}$ cycloalkyl-alkyl, phenyl, $C_{6\ or\ 10}$ aryl, $C_{1-6}$ alkyl, tetrahydrofuran ring, tetrahydropyran ring;

Y is a sulfonimide of the formula $—C(O)NHS(O)_2R^9$, wherein $R^9$ is a substituted or unsubstituted group selected from $C_{1-6}$ alkyl, $C_{3-7}$ cycloalkyl, or $C_{4-10}$ cycloalkyl-alkyl, $C_{6\ or\ 10}$ aryl, $C_{1-6}$ alkyl, $NR^6R^7$, $NR^{1a}R^{1b}$, heteroaromatic ring, or Y is a carboxylic acid or pharmaceutically acceptable salt, solvate, or prodrug thereof;

wherein $R^{1a}$ and $R^{1b}$ are each independently H, $C_{1-6}$ alkyl, $C_{3-7}$ cycloalkyl, $C_{4-10}$ cycloalkyl-alkyl, $C_{6\ or\ 10}$ aryl or $R^{1a}$ and $R^{1b}$ are each independently H, heterocycle, which is a five-, six-, or seven-membered, saturated or unsaturated heterocyclic molecule, containing from one to four heteroatoms selected from the group consisting of nitrogen, oxygen, and sulfur, or $NR^{1a}R^{1b}$ is a three- to six-membered alkyl cyclic secondary amine, or $NR^{1a}R^{1b}$ is a heteroaryl selected from the group consisting of:

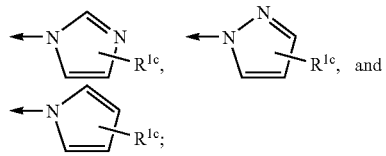

wherein $R^{1c}$ is H, halo, $C_{1-6}$ alkyl, $C_{3-6}$ cycloalkyl, $C_{1-6}$ alkoxy, $C_{3-6}$ cycloalkoxy, $NO_2$, $N(R^{1d})_2$, $NH(CO)R^{1d}$, or $NH(CO)NHR^{1d}$, wherein each $R^{1d}$ is independently H, $C_{1-6}$ alkyl, or $C_{3-6}$ cycloalkyl, or $R^{1c}$ is $NH(CO)OR^{1e}$, wherein $R^{1e}$ is $C_{1-6}$ alkyl or $C_{3-6}$ cycloalkyl;

p=0 or 1;

V is selected from O, S, or NH;

W is selected from O, $NR^{15}$, or $CHR^{15}$, wherein $R^{15}$ is H, $C_{1-6}$ alkyl, $C_{3-7}$ cycloalkyl, $C_{4-10}$ cycloalkyl-alkyl, or substituted or unsubstituted $C_{1-6}$ alkyl;

the dashed lines represent an optional double bond;

$R^{21}$ is a substituted or unsubstituted group selected from $C_{1-6}$ alkyl, $C_{3-7}$ cycloalkyl, $C_{4-10}$ cycloalkyl-alkyl, phenyl, $C_{6\ or\ 10}$ aryl, pyridyl, pyrimidyl, pyrazinyl, thienyl, furanyl, thiazolyl, oxazolyl, phenoxy, or thiophenoxy; and $R^{22}$ is a substituted or unsubstituted group selected from $C_{1-6}$ alkyl, $C_{3-7}$ cycloalkyl, or $C_{4-10}$ cycloalkyl-alkyl, or phenyl.

Preferred embodiments provide a compound having the general Formula VIIIa:

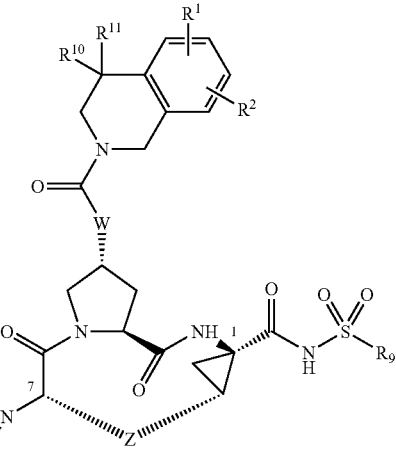

(VIIIa)

or a pharmaceutically acceptable salt, prodrug, or ester thereof wherein:

$R^1$ and $R^2$ are each independently H, halo, cyano, hydroxy, $C_{1-3}$ alkyl, or $C_{1-3}$ alkoxy;

$R^5$ is H, $C(O)OR^8$ or $C(O)NHR^8$;

$R^8$ is $C_{1-6}$ alkyl, $C_{5-6}$ cycloalkyl, or 3-tetrahydrofuryl;

$R^9$ is $C_{1-3}$ alkyl, $C_{3-4}$ cycloalkyl, or phenyl which is optionally substituted by up to two halo, cyano, hydroxy, $C_{1-3}$ alkyl, $C_{1-3}$ alkoxy;

$R^{10}$ and $R^{11}$ are each independently H, $C_{1-3}$ alkyl, or $R^{10}$ and $R^{11}$ are taken together with the carbon to which they are attached to form cyclopropyl, cyclobutyl, cyclopentyl, or cyclohexyl;

W is selected from O or NH;

the dashed line represents an optional double bond.

Z is a $C_{5-7}$ saturated or unsaturated chain containing one or two heteroatoms selected from O, S, or $NR^6$.

Preferred embodiments provide a compound having the general Formula VIIIb:

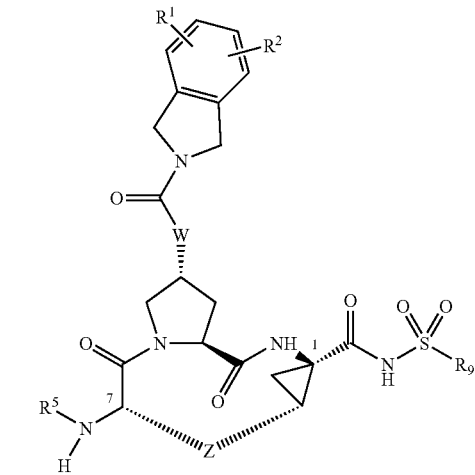

(VIIIb)

or a pharmaceutically acceptable salt, prodrug, or ester thereof wherein:

$R^1$ and $R^2$ are each independently H, halo, cyano, hydroxy, $C_{1-3}$ alkyl, or $C_{1-3}$ alkoxy;

$R^5$ is H, $C(O)OR^8$ or $C(O)NHR^8$;

$R^8$ is $C_{1-6}$ alkyl, $C_{5-6}$ cycloalkyl, or 3-tetrahydrofuryl;

$R^9$ is $C_{1-3}$ alkyl, $C_{3-5}$ cycloalkyl, or phenyl which is optionally substituted by up to two halo, cyano, hydroxy, $C_{1-3}$ alkyl, or $C_{1-3}$ alkoxy;

$R^{10}$ and $R^{11}$ are each independently H, $C_{1-3}$ alkyl, or $C_{4-5}$ cycloalkyl;

W is selected from O or NH;

the dashed line represents an optional double bond; and

Z is a $C_{5-7}$ saturated or unsaturated chain containing one or two heteroatoms selected from O, S, or $NR^6$.

Preferred embodiments provide a compound having the Formula VIIIc:

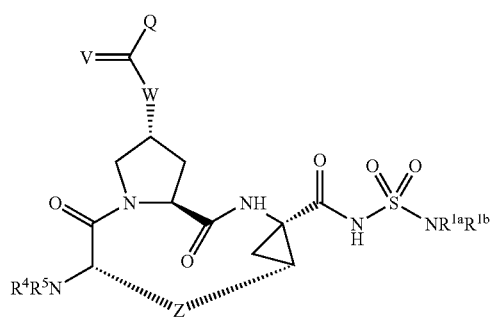

(VIIIc)

or a pharmaceutically acceptable salt, prodrug, or ester thereof wherein:

$R^{1a}$ and $R^{1b}$ are each independently H, $C_{1-6}$ alkyl, $C_{3-7}$ cycloalkyl, or $C_{4-10}$ cycloalkyl-alkyl, which are all optionally substituted from one to three times with halo, cyano, nitro, $C_{1-6}$ alkoxy, amido, or phenyl;

or $R^{1a}$ and $R^{1b}$ are each independently H and $C_{6\,or\,10}$ aryl which is optionally substituted by up to three halo, cyano, nitro, hydroxy, $C_{1-6}$ alkyl, $C_{3-7}$ cycloalkyl, $C_{4-10}$ cycloalkyl-alkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro;

or $R^{1a}$ and $R^{1b}$ are each independently H or heterocycle, which is a five-, six-, or seven-membered, saturated or unsaturated heterocyclic molecule, containing from one to four heteroatoms selected from the group consisting of nitrogen, oxygen and sulfur;

or $NR^{1a}R^{1b}$ is a three- to six-membered alkyl cyclic secondary amine, which optionally has one to three hetero atoms incorporated in the ring, and which is optionally substituted from one to three times with halo, cyano, nitro, $C_{1-6}$ alkoxy, amido, or phenyl;

or $NR^{1a}R^{1b}$ is a heteroaryl selected from the group consisting of:

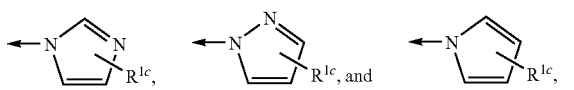

wherein $R^{1c}$ is H, halo, $C_{1-6}$ alkyl, $C_{3-6}$ cycloalkyl, $C_{1-6}$ alkoxy, $C_{3-6}$ cycloalkoxy, $NO_2$, $N(R^{1d})_2$, $NH(CO)R^{1d}$, or $NH(CO)NHR^{1d}$, wherein each $R^{1d}$ is independently H, $C_{1-6}$ alkyl, or $C_{3-6}$ cycloalkyl;

or $R^{1c}$ is $NH(CO)OR^{1e}$ wherein $R^{1e}$ is $C_{1-6}$ alkyl, or $C_{3-6}$ cycloalkyl;

W is O or NH;

V is selected from O, S, or NH;

when V is O or S, W is selected from O, $NR^{15}$, or $CHR^{15}$;

when V is NH, W is selected from $NR^{15}$ or $CHR^{15}$, where $R^{15}$ is H, $C_{1-6}$ alkyl, $C_{3-7}$ cycloalkyl, $C_{4-10}$ cycloalkyl-alkyl, or $C_{1-6}$ alkyl optionally substituted with up to 5 fluoro;

Q is a bicyclic secondary amine with the structure of:

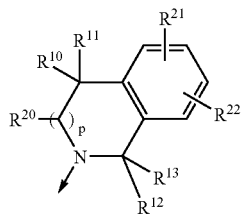

wherein $R^{21}$ and $R^{22}$ are each independently H, halo, cyano, nitro, hydroxy, $C_{1-6}$ alkyl, $C_{3-7}$ cycloalkyl, $C_{4-10}$ cycloalkyl-alkyl, $C_{2-6}$ alkenyl, $C_{1-6}$ alkoxy, hydroxy-$C_{1-6}$ alkyl, $C_{1-6}$ alkyl optionally substituted with up to 5 fluoro, $C_{1-6}$ alkoxy optionally substituted with up to 5 fluoro, $C_{6\,or\,10}$ aryl, pyridyl, pyrimidyl, thienyl, furanyl, thiazolyl, oxazolyl, phenoxy, thiophenoxy, $S(O)_2NR^6R^7$, $NHC(O)NR^6R^7$, $NHC(S)NR^6R^7$, $C(O)NR^6R^7$, $NR^6R^7$, $C(O)R^8$, $C(O)OR^8$, $NHC(O)R^8$, $NHC(O)OR^8$, $SO_mR^8$ (m=0, 1 or 2), or $NHS(O)_2R^8$; said thienyl, pyrimidyl, furanyl, thiazolyl and oxazolyl in the definition of $R^{21}$ and $R^{22}$ are optionally substituted by up to two halo, cyano, nitro, hydroxy, $C_{1-6}$ alkyl, $C_{3-7}$ cycloalkyl, $C_{4-10}$ cycloalkyl-alkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro; said $C_{6\,or\,10}$ aryl, pyridyl, phenoxy and thiophenoxy in the definition of $R^{21}$ and $R^{22}$ are optionally substituted by up to three halo, cyano, nitro, hydroxy, $C_{1-6}$ alkyl, $C_{3-7}$ cycloalkyl, $C_{4-10}$ cycloalkyl-alkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro;

wherein $R^{10}$ and $R^{11}$ are each independently H, $C_{1-6}$ alkyl, $C_{3-7}$ cycloalkyl, $C_{4-10}$ cycloalkyl-alkyl, $C_{6\,or\,10}$ aryl, hydroxy-$C_{1-6}$ alkyl, $C_{1-6}$ alkyl optionally substituted with up to 5 fluoro, $(CH_2)_nNR^6R^7$, or $(CH_2)_nC(O)OR^{14}$ where $R^{14}$ is H, $C_{1-6}$ alkyl, $C_{3-7}$ cycloalkyl, or $C_{4-10}$ cycloalkyl-alkyl, which are all optionally substituted from one to three times with halo, cyano, nitro, hydroxy, $C_{1-6}$ alkoxy, or phenyl; or $R^{14}$ is $C_{6\,or\,10}$ aryl which is optionally substituted by up to three halo, cyano, nitro, hydroxy, $C_{1-6}$ alkyl, $C_{3-7}$ cycloalkyl, $C_{4-10}$ cycloalkyl-alkyl, $C_{2-6}$ alkenyl, $C_{1-6}$ alkoxy, hydroxy-$C_{1-6}$ alkyl, $C_{1-6}$ alkyl optionally substituted with up to 5 fluoro, $C_{1-6}$ alkoxy optionally substituted with up to 5 fluoro; said $C_{6\,or\,10}$ aryl, in the definition of $R^{12}$ and $R^{13}$ is optionally substituted by up to three halo, cyano, nitro, hydroxy, $C_{1-6}$ alkyl, $C_{3-7}$ cycloalkyl, $C_{4-10}$ cycloalkyl-alkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro; or $R^{10}$ and $R^{11}$ are taken together with the carbon to which they are attached to form cyclopropyl, cyclobutyl, cyclopentyl, or cyclohexyl; or $R^{10}$ and $R^{11}$ are combined as O;

wherein p=0 or 1;

wherein $R^{12}$ and $R^{13}$ are each independently H, $C_{1-6}$ alkyl, $C_{3-7}$ cycloalkyl, $C_{4-10}$ cycloalkyl-alkyl, $C_{6 \, or \, 10}$ aryl, hydroxy-$C_{1-6}$ alkyl, $C_{1-6}$ alkyl optionally substituted with up to 5 fluoro, $(CH_2)_n NR^6R^7$, $(CH_2)_n C(O)OR^{14}$ where $R^{14}$ is H, $C_{1-6}$ alkyl, $C_{3-7}$ cycloalkyl, or $C_{4-10}$ cycloalkyl-alkyl, which are all optionally substituted from one to three times with halo, cyano, nitro, hydroxy, $C_{1-6}$ alkoxy, or phenyl; or $R^{14}$ is $C_{6 \, or \, 10}$ aryl which is optionally substituted by up to three halo, cyano, nitro, hydroxy, $C_{1-6}$ alkyl, $C_{3-7}$ cycloalkyl, $C_{4-10}$ cycloalkyl-alkyl, $C_{2-6}$ alkenyl, $C_{1-6}$ alkoxy, hydroxy-$C_{1-6}$ alkyl, $C_{1-6}$ alkyl optionally substituted with up to 5 fluoro, $C_{1-6}$ alkoxy optionally substituted with up to 5 fluoro; said $C_{6 \, or \, 10}$ aryl, in the definition of $R^{12}$ and $R^{13}$ is optionally substituted by up to three halo, cyano, nitro, hydroxy, $C_{1-6}$ alkyl, $C_{3-7}$ cycloalkyl, $C_{4-10}$ cycloalkyl-alkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro; or $R^{12}$ and $R^{13}$ are taken together with the carbon to which they are attached to form cyclopropyl, cyclobutyl, cyclopentyl, or cyclohexyl;

wherein $R^{20}$ is H, $C_{1-6}$ alkyl, $C_{3-7}$ cycloalkyl, $C_{4-10}$ cycloalkyl-alkyl, $C_{6 \, or \, 10}$ aryl, hydroxy-$C_{1-6}$ alkyl, $C_{1-6}$ alkyl optionally substituted with up to 5 fluoro, $(CH_2)_n NR^6R^7$, or $(CH_2)_n C(O)OR^{14}$ where $R^{14}$ is H, $C_{1-6}$ alkyl, $C_{3-7}$ cycloalkyl, or $C_{4-10}$-cycloalkyl-alkyl, which are all optionally substituted from one to three times with halo, cyano, nitro, hydroxy, $C_{1-6}$ alkoxy, or phenyl; or $R^{14}$ is $C_{6 \, or \, 10}$ aryl which is optionally substituted by up to three halo, cyano, nitro, hydroxy, $C_{1-6}$ alkyl, $C_{3-7}$ cycloalkyl, $C_{4-10}$ cycloalkyl-alkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro; said $C_{6 \, or \, 10}$ aryl, in the definition of $R^{12}$ and $R^{13}$ is optionally substituted by up to three halo, cyano, nitro, hydroxy, $C_{1-6}$ alkyl, $C_{3-7}$ cycloalkyl, $C_{4-10}$ cycloalkyl-alkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro;

wherein n=0-4;

wherein $R^6$ and $R^7$ are each independently H, $C_{1-6}$ alkyl, $C_{3-7}$ cycloalkyl, $C_{4-10}$ cycloalkyl-alkyl, or phenyl, said phenyl optionally substituted by up to three halo, cyano, nitro, hydroxy, $C_{1-6}$ alkyl, $C_{3-7}$ cycloalkyl, $C_{4-10}$ cycloalkyl-alkyl, $C_{2-6}$ alkenyl, hydroxy-$C_{1-6}$ alkyl, $C_{1-6}$ alkyl optionally substituted with up to 5 fluoro, or $C_{1-6}$ alkoxy optionally substituted with up to 5 fluoro; or $R^6$ and $R^7$ are taken together with the nitrogen to which they are attached to form indolinyl, pyrrolidinyl, piperidinyl, piperazinyl, or morpholinyl;

or $R^2$ is $R^{2a}R^{2b}$ when W=NH and V=O, wherein $R^{2a}$ is $C_{1-6}$ alkyl, $C_{3-7}$ cycloalkyl, $C_{4-10}$ cycloalkyl-alkyl, phenyl, pyridine, pyrazine, pyrimidine, pyridazine, pyrrole, furan, thiophene, thiazole, oxazole, imidazole, isoxazole, pyrazole, isothiazole, naphthyl, quinoline, isoquinoline, quinoxaline, benzothiazole, benzothiophene, benzofuran, indole, or benzimidazole, each optionally substituted with up to three $NR^{2c}R^{2d}$, halo, cyano, nitro, hydroxy, $C_{1-6}$ alkyl, $C_{3-7}$ cycloalkyl, $C_{4-10}$ cycloalkyl-alkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro;

$R^{2b}$ is H, phenyl, pyridine, pyrazine, pyrimidine, pyridazine, pyrrole, furan, thiophene, thiazole, oxazole, imidazole, isoxazole, pyrazole, isothiazole, naphthyl, quinoline, isoquinoline, quinoxaline, benzothiazole, benzothiophene, benzofuran, indole, or benzimidazole, each optionally substituted with up to three $NR^{2c}R^{2d}$, halo, cyano, nitro, hydroxy, $C_{1-6}$ alkyl, $C_{3-7}$ cycloalkyl, $C_{4-10}$ cycloalkyl-alkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro;

said $R^{2c}$ and $R^{2d}$ are each independently H, $C_{1-6}$ alkyl, $C_{3-7}$ cycloalkyl, $C_{4-10}$ cycloalkyl-alkyl, or phenyl, said phenyl optionally substituted by up to three halo, cyano, nitro, hydroxy, $C_{1-6}$ alkyl, $C_{3-7}$ cycloalkyl, $C_{4-10}$ cycloalkyl-alkyl, $C_{2-6}$ alkenyl, hydroxy-$C_{1-6}$ alkyl, $C_{1-6}$ alkyl optionally substituted with up to 5 fluoro, or $C_{1-6}$ alkoxy optionally substituted with up to 5 fluoro; or $R^{2c}$ and $R^{2d}$ are taken together with the nitrogen to which they are attached to form indolinyl, pyrrolidinyl, piperidinyl, piperazinyl, or morpholinyl;

Z is a $C_{5-7}$ saturated or unsaturated chain containing one or two heteroatoms selected from O, S, or $NR^6$.

$R^4$ is H, $C_{1-6}$ alkyl, $C_{3-7}$ cycloalkyl, $C_{4-10}$ cycloalkyl-alkyl, or phenyl, said phenyl optionally substituted by up to three halo, cyano, nitro, hydroxy, $C_{1-6}$ alkyl, $C_{3-7}$ cycloalkyl, $C_{4-10}$ cycloalkyl-alkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro;

$R^5$ is H, $C_{1-6}$ alkyl, $C(O)NR^6R^7$, $C(S)NR^6R^7$, $C(O)R^8$, $C(O)OR^8$, or $S(O)_2R^8$;

$R^8$ is $C_{1-6}$ alkyl, $C_{3-7}$ cycloalkyl, or $C_{4-10}$ cycloalkyl-alkyl, which are all optionally substituted from one to three times with halo, cyano, nitro, hydroxy, $C_{1-6}$ alkoxy, or phenyl; or $R^8$ is $C_{6 \, or \, 10}$ aryl which is optionally substituted by up to three halo, cyano, nitro, hydroxy, $C_{1-6}$ alkyl, $C_{3-7}$ cycloalkyl, $C_{4-10}$ cycloalkyl-alkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro; and the dashed line represents an optional double bond.

Preferred embodiments provide a compound having the Formula VIIId:

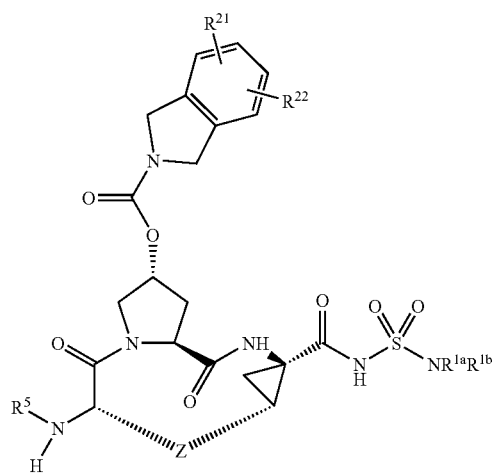

(VIIId)

or a pharmaceutically acceptable salt, prodrug, or ester thereof wherein:

(a) $R^{1a}$ and $R^{1b}$ are each independently H, $C_{1-6}$ alkyl, $C_{3-7}$ cycloalkyl, or $C_{4-10}$ cycloalkyl-alkyl, which are all optionally substituted from one to three times with halo, cyano, nitro, $C_{1-6}$ alkoxy, amido, or phenyl;

or $R^{1a}$ and $R^{1b}$ are each independently H or heteroaryl selected from the group consisting of:

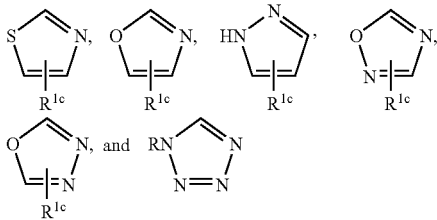

wherein $R^{1c}$ is H, halo, $C_{1-6}$ alkyl, $C_{3-6}$ cycloalkyl, $C_{1-6}$ alkoxy, $C_{3-6}$ cycloalkoxy, $NO_2$, $N(R^{1d})_2$, $NH(CO)R^{1d}$, or $NH(CO)NHR^{1d}$, wherein each $R^{1d}$ is independently H, $C_{1-6}$ alkyl, or $C_{3-6}$ cycloalkyl;

or $NR^{1a}R^{1b}$ is a three- to six-membered alkyl cyclic secondary amine, which optionally has one to three hetero atoms incorporated in the ring, and which is optionally substituted from one to three times with halo, cyano, nitro, $C_{1-6}$ alkoxy, amido, or phenyl;

(b) $R^{21}$ and $R^{22}$ are each independently H, halo, cyano, hydroxy, $C_{1-3}$ alkyl, or $C_{1-3}$ alkoxy;

(c) $R^5$ is H, $C(O)NR^6R^7$, $C(O)R^8$, or $C(O)OR^8$;

(d) $R^6$ and $R^7$ are each independently H, $C_{1-6}$ alkyl, $C_{3-7}$ cycloalkyl, $C_{4-10}$ cycloalkyl-alkyl, or phenyl;

(e) $R^8$ is $C_{1-6}$ alkyl, $C_{3-7}$ cycloalkyl, $C_{4-10}$ cycloalkyl-alkyl, or 3-tetrahydrofuryl; and (f) the dashed line represents an optional double bond.

Preferred embodiments provide a compound having the Formula VIIIe:

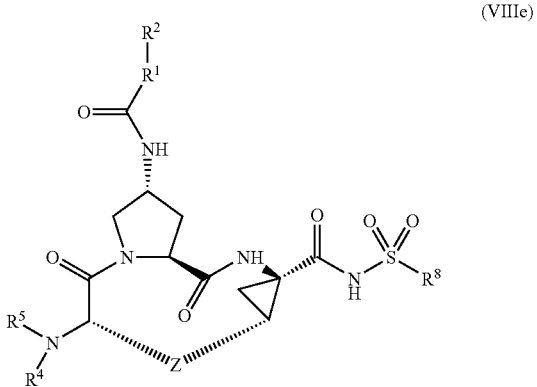

(VIIIe)

or a pharmaceutically acceptable salt, prodrug, or ester thereof wherein:

$R^1$ is $C_{1-6}$ alkyl, $C_{3-7}$ cycloalkyl, $C_{4-10}$ cycloalkyl-alkyl, phenyl, pyridine, pyrazine, pyrimidine, pyridazine, pyrrole, furan, thiophene, thiazole, oxazole, imidazole, isoxazole, pyrazole, isothiazole, naphthyl, quinoline, isoquinoline, quinoxaline, benzothiazole, benzothiophene, benzofuran, indole, or benzimidazole, each optionally substituted with up to three $NR^5R^6$, halo, cyano, nitro, hydroxy, $C_{1-6}$ alkyl, $C_{3-7}$ cycloalkyl, $C_{4-10}$ cycloalkyl-alkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro;

$R^2$ is H, phenyl, pyridine, pyrazine, pyrimidine, pyridazine, pyrrole, furan, thiophene, thiazole, oxazole, imidazole, isoxazole, pyrazole, isothiazole, naphthyl, quinoline, isoquinoline, quinoxaline, benzothiazole, benzothiophene, benzofuran, indole, or benzimidazole, each optionally substituted with up to three $NR^5R^6$, halo, cyano, nitro, hydroxy, $C_{1-6}$ alkyl, $C_{3-7}$ cycloalkyl, $C_{4-10}$ cycloalkyl-alkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro;

$R^3$ is H, $C_{1-6}$ alkyl, $C_{3-7}$ cycloalkyl, $C_{4-10}$ cycloalkyl-alkyl or phenyl, said phenyl optionally substituted by up to three halo, cyano, nitro, hydroxy, $C_{1-6}$ alkyl, $C_{3-7}$ cycloalkyl, $C_{4-10}$ cycloalkyl-alkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro;

Z is a $C_{5-7}$ saturated or unsaturated chain containing one or two heteroatoms selected from O, S, or $NR^6$.

$R^4$ is $C_{1-6}$ alkyl, $C(O)NR^5R^6$, $C(S)NR^5R^6$, $C(O)R^7$, $C(O)OR^7$, or $S(O)_2R^7$;

$R^5$ and $R^6$ are each independently H, $C_{1-6}$ alkyl, $C_{3-7}$ cycloalkyl, $C_{4-10}$ cycloalkyl-alkyl or phenyl, said phenyl optionally substituted by up to three halo, cyano, nitro, hydroxy, $C_{1-6}$ alkyl, $C_{3-7}$ cycloalkyl, $C_{4-10}$ cycloalkyl-alkyl, $C_{2-6}$ alkenyl, hydroxy-$C_{1-6}$ alkyl, or $C_{1-6}$ alkyl optionally substituted with up to 5 fluoro, $C_{1-6}$ alkoxy optionally substituted with up to 5 fluoro; or $R^5$ and $R^6$ are taken together with the nitrogen to which they are attached to form indolinyl, pyrrolidinyl, piperidinyl, piperazinyl, or morpholinyl;

$R^7$ is $C_{1-6}$ alkyl, $C_{3-7}$ cycloalkyl, $C_{4-10}$ cycloalkyl-alkyl, which are all optionally substituted from one to three times with halo, cyano, nitro, hydroxy, $C_{1-6}$ alkoxy, or phenyl; or $R^7$ is $C_{6\,or\,10}$ aryl which is optionally substituted by up to three halo, cyano, nitro, hydroxy, $C_{1-6}$ alkyl, $C_{3-7}$ cycloalkyl, $C_{4-10}$ cycloalkyl-alkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro;

$R^8$ is $C_{1-3}$ alkyl, $C_{3-4}$ cycloalkyl, or phenyl which is optionally substituted by up to two halo, cyano, hydroxy, $C_{1-3}$ alkyl, or $C_{1-3}$ alkoxy; and the dashed line represents an optional double bond;

or a pharmaceutically acceptable salt thereof.

Preferred embodiments provide a compound of the formula (IX):

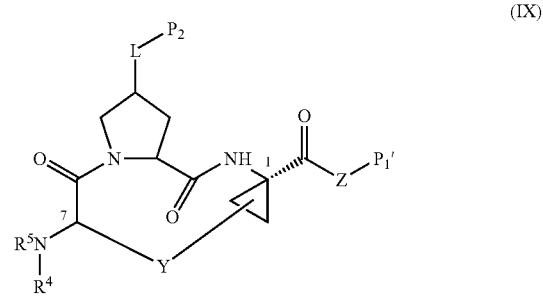

(IX)

or a pharmaceutically acceptable salt, prodrug, or ester thereof wherein:
  (a) Z is a group configured to hydrogen bond to an NS3 protease His57 imidazole moiety and to hydrogen bond to a NS3 protease Gly137 nitrogen atom;
  (b) P$_1$' is a group configured to form a non-polar interaction with at least one NS3 protease S1' pocket moiety selected from the group consisting of Lys136, Gly137, Ser139, His57, Gly58, Gln41, Ser42, and Phe43;
  (c) L is a linker group consisting of from 1 to 5 atoms selected from the group consisting of carbon, oxygen, nitrogen, hydrogen, and sulfur;
  (d) P$_2$ is selected from the group consisting of unsubstituted aryl, substituted aryl, unsubstituted heteroaryl, substituted heteroaryl, unsubstituted heterocyclic and substituted heterocyclic; P$_2$ being positioned by L to form a non-polar interaction with at least one NS3 protease S2 pocket moiety selected from the group consisting of His57, Arg155, Val78, Asp79, Gln80 and Asp81;
  (e) R$^5$ is selected from the group consisting of H, C(O)NR$^6$R$^7$ and C(O)OR$^8$;
  (f) R$^6$ and R$^7$ are each independently H, C$_{1-6}$ alkyl, C$_{3-7}$ cycloalkyl, C$_{4-10}$ alkylcycloalkyl or phenyl, said phenyl optionally substituted by up to three halo, cyano, nitro, hydroxy, C$_{1-6}$ alkyl, C$_{3-7}$ cycloalkyl, C$_{4-10}$ alkylcycloalkyl, C$_{2-6}$ alkenyl, hydroxy-C$_{1-6}$ alkyl, C$_{1-6}$ alkyl optionally substituted with up to 5 fluoro, C$_{1-6}$ alkoxy optionally substituted with up to 5 fluoro; or R$^6$ and R$^7$ are taken together with the nitrogen to which they are attached to form indolinyl, pyrrolidinyl, piperidinyl, piperazinyl, or morpholinyl;
  (g) R$^8$ is C$_{1-6}$ alkyl, C$_{3-7}$ cycloalkyl, C$_{4-10}$ alkylcycloalkyl, which are all optionally substituted from one to three times with halo, cyano, nitro, hydroxy, C$_{1-6}$ alkoxy, or phenyl; or R$^8$ is C$_{6\ or\ 10}$ aryl which is optionally substituted by up to three halo, cyano, nitro, hydroxy, C$_{1-6}$ alkyl, C$_{3-7}$ cycloalkyl, C$_{4-10}$ alkylcycloalkyl, C$_{2-6}$ alkenyl, C$_{1-6}$ alkoxy, hydroxy-C$_{1-6}$ alkyl, C$_{1-6}$ alkyl optionally substituted with up to 5 fluoro, C$_{1-6}$ alkoxy optionally substituted with up to 5 fluoro; or R$^8$ is C$_{1-6}$ alkyl optionally substituted with up to 5 fluoro groups; or R$^8$ is a tetrahydrofuran ring linked through the C$_3$ or C$_4$ position of the tetrahydrofuran ring; or R$^8$ is a tetrahydropyran ring linked through the C$_4$ position of the tetrahydropyran ring;
  (h) Y is a C$_{5-7}$ saturated or unsaturated chain containing one or two heteroatoms selected from O, S, or NR$^9$; and
  (i) R$^9$ and R$^{10}$ are each independently H, C$_{1-6}$ alkyl, C$_{3-7}$ cycloalkyl, C$_{4-10}$ cycloalkyl-alkyl, or substituted or unsubstituted phenyl; or R$^9$ and R$^{10}$ are taken together with the nitrogen to which they are attached to form indolinyl, pyrrolidinyl, piperidinyl, piperazinyl, or morpholinyl.

The present embodiments provide for a method of inhibiting NS3/NS4 protease activity comprising contacting a NS3/NS4 protease with a compound disclosed herein.

The present embodiments provide for a method of treating hepatitis by modulating NS3/NS4 protease comprising contacting a NS3/NS4 protease with a compound disclosed herein.

Preferred embodiments provide a pharmaceutical composition comprising: a) a preferred compound; and b) a pharmaceutically acceptable carrier.

Preferred embodiments provide a method of treating a hepatitis C virus infection in an individual, the method comprising administering to the individual an effective amount of a composition comprising a preferred compound.

Preferred embodiments provide a method of treating liver fibrosis in an individual, the method comprising administering to the individual an effective amount of a composition comprising a preferred compound.

Preferred embodiments provide a method of increasing liver function in an individual having a hepatitis C virus infection, the method comprising administering to the individual an effective amount of a composition comprising a preferred compound.

Preferred embodiments provide a compound having the formula (I):

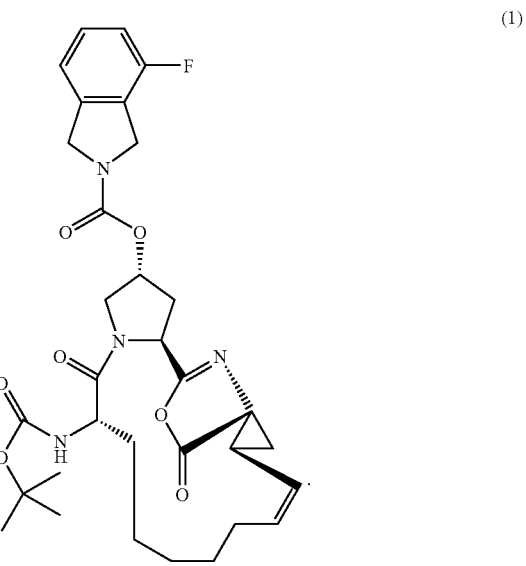

(1)

Preferred embodiments provide a method of making the compound of formula (I), comprising intermixing compound (1a) with TBTU and DIEA.

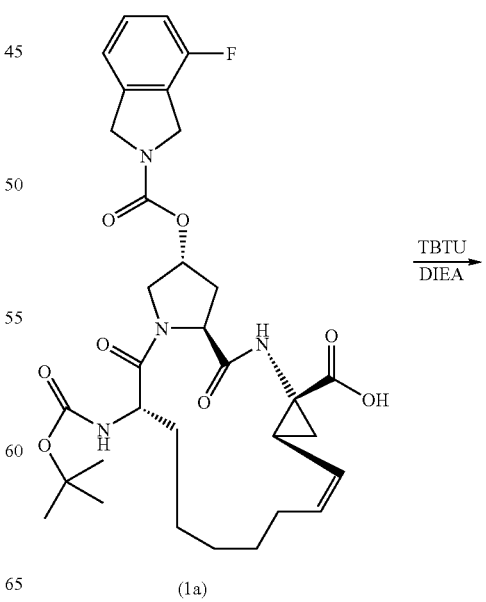

(1a)

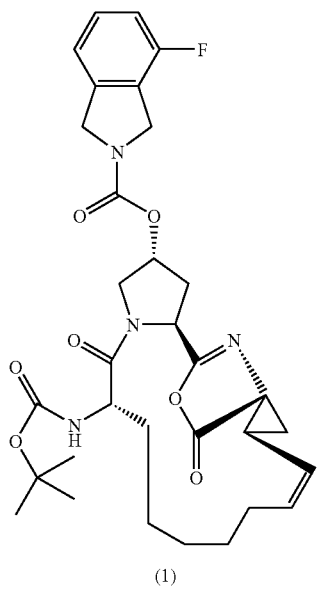

(1)

Preferred embodiments provide a method of making a compound of formula (3), comprising intermixing a compound of (2) with sodium methanolate and water:

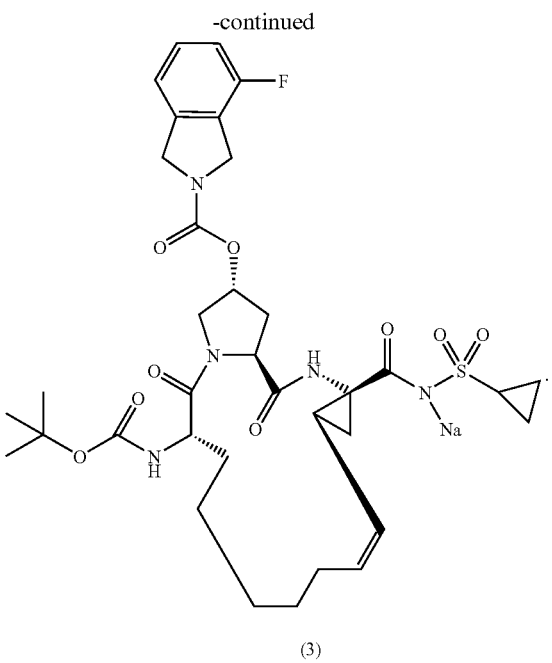

(3)

Preferred embodiments provide a method of making a compound of formula (7), comprising intermixing a compound formula (4) with a compound of formula (5) and a compound of formula (6):

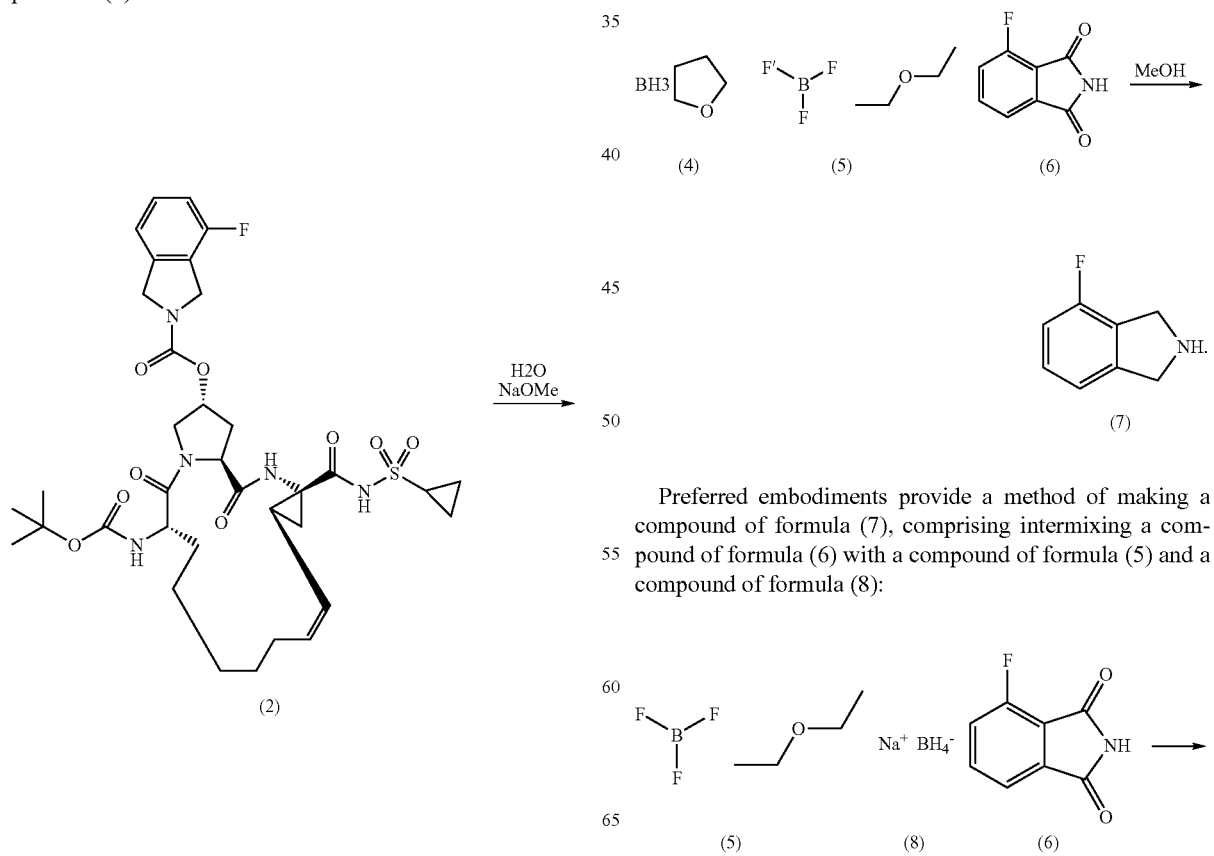

Preferred embodiments provide a method of making a compound of formula (7), comprising intermixing a compound of formula (6) with a compound of formula (5) and a compound of formula (8):

Preferred embodiments provide a method of purifying a compound of formula (7), comprising intermixing a compound of formula (7) with a compound of formula (8) and a compound of formula (9) and treating the product thereof with hydrochloric acid:

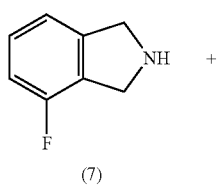

(7)

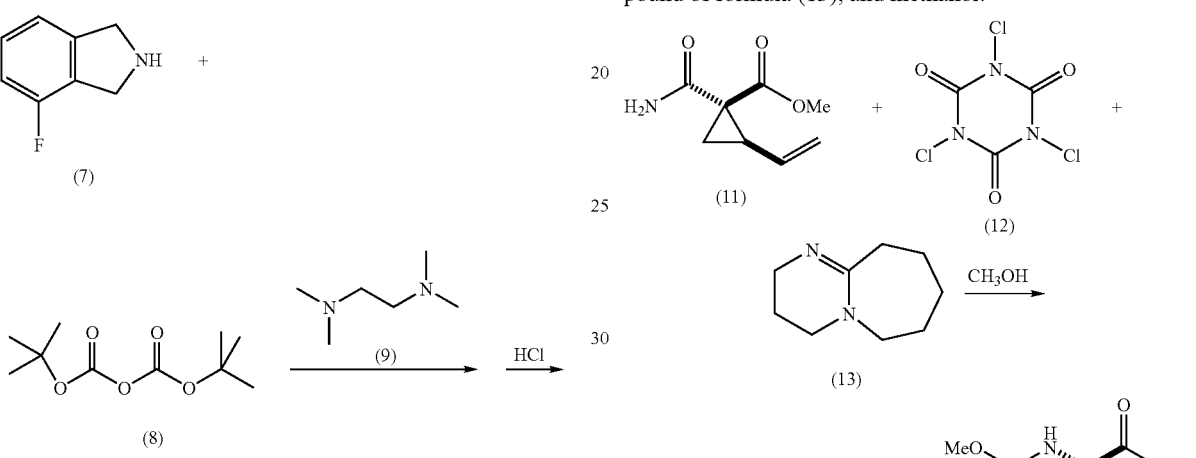

Preferred embodiments provide a method of making a compound of formula (11):

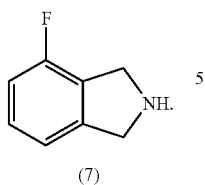

(11)

comprising:
intermixing (E)-1,4-dibromobut-2-ene, methanol, and dimethyl malonate;
hydrolyzing the product thereof with an acid; and
reacting the hydrolyzed product with ammonia.

Preferred embodiments provide a method of making a compound of formula (14), comprising intermixing a compound of formula (11), a compound of formula (12), a compound of formula (13), and methanol:

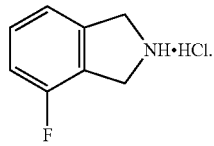

Preferred embodiments provide a method of making a compound of formula (15), comprising intermixing a compound of formula (14), N,N-dimethylpyridin-4-amine, and boc anhydride:

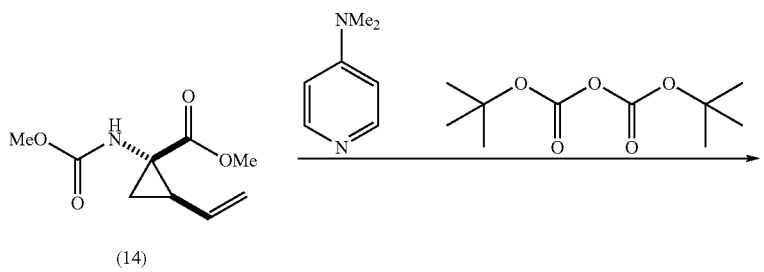

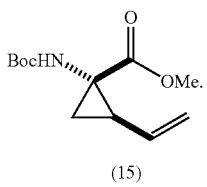

(15)

Preferred embodiments provide a method for making a compound of formula (15), comprising:
converting an amide of formula (11) to a carbamate of formula (14):

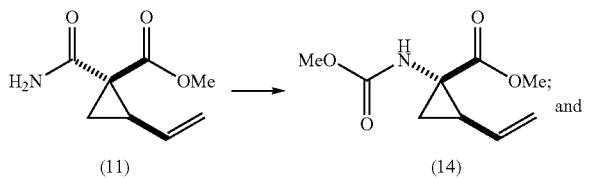

(11)       (14)

adding a boc functionality to the carbamate (14) to obtain a compound of formula (15):

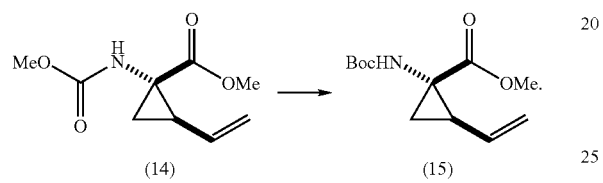

(14)       (15)

Preferred embodiments provide a method of making a compound of formula (19), comprising intermixing a dihalobutene and a compound of formula (18):

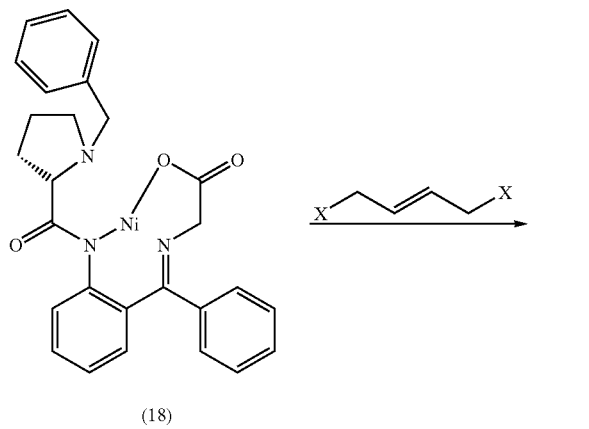

(18)

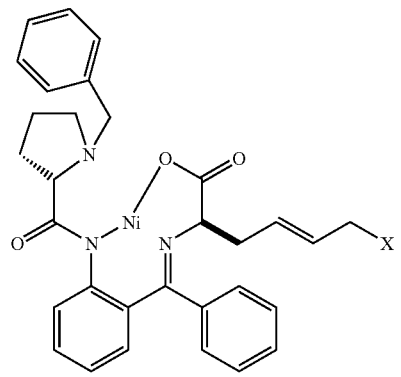

(19)

wherein X is a halogen.

Preferred embodiments provide a method of making a compound of formula (20), comprising intermixing lithium hexamethyldisilazide and compound (19):

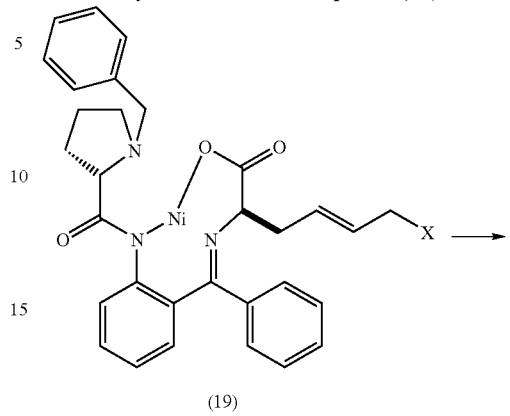

(19)

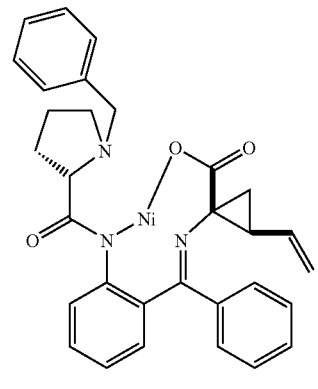

(20)

wherein X is a halogen.

Preferred embodiments provide a method of making a compound of formula (21):

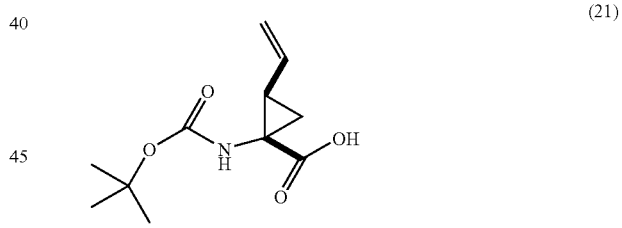

(21)

comprising:
intermixing a compound of formula (20) and an acid:

(20)

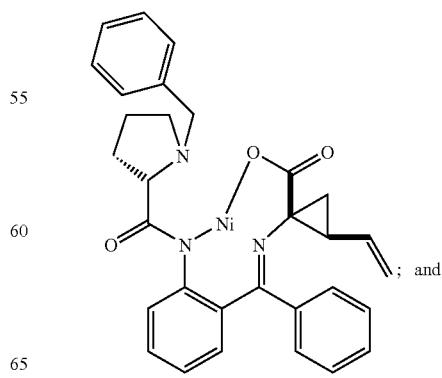

; and treating the resulting product with boc anhydride.

Preferred embodiments provide a method of making a compound of formula (22), comprising intermixing a compound of formula (21) and iodoethane and a base:

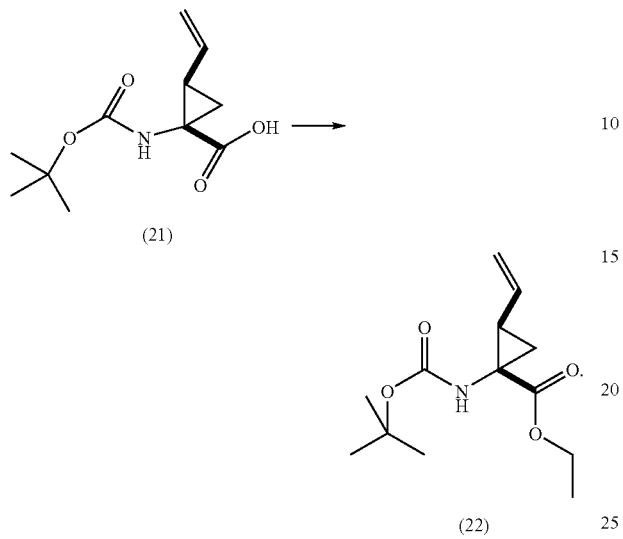

(21)

(22)

Preferred embodiments provide a method of making a compound of formula (22), comprising:

intermixing a dihalobutene and a compound of formula (18) to form a compound of formula (19):

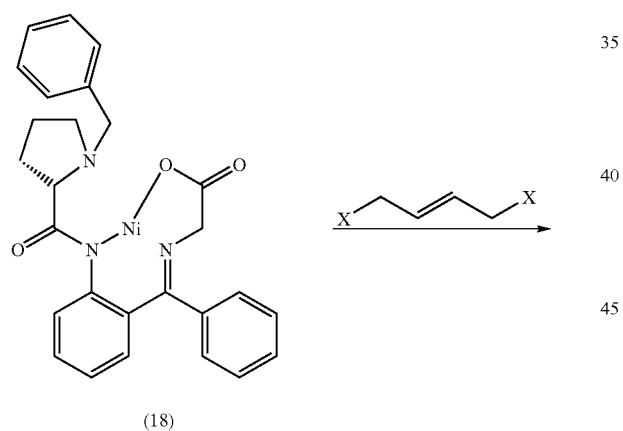

(18)

(19)

intermixing lithium hexamethyldisilazide and the compound of formula (19) to form a compound of formula (20):

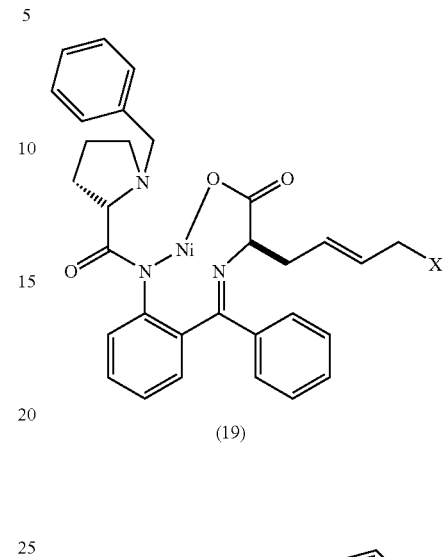

(19)

(20)

intermixing the compound of formula (20) and an acid and treating the resulting product with boc anhydride and to form a compound of formula (21):

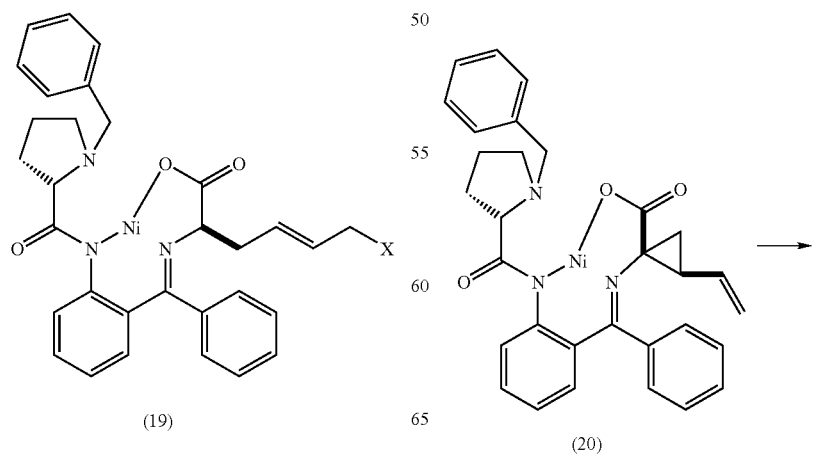

(20)

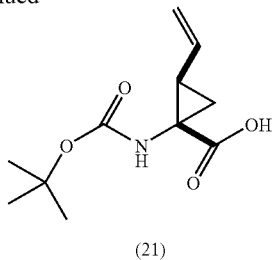

(21)

intermixing the compound of formula (21) and iodoethane and a base to form the compound of formula (22):

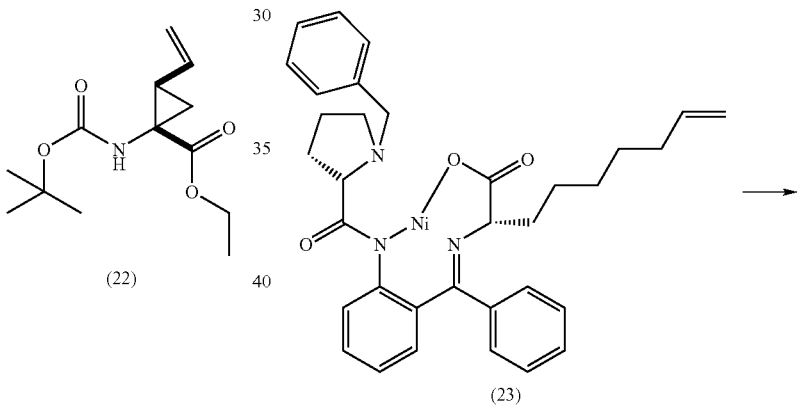

wherein X is a halogen.

Preferred embodiments provide a method of making a compound of formula (23), comprising intermixing a 7-Bromo-1-heptene and a compound of formula (18):

Preferred embodiments provide a method of making a compound of formula (24), comprising intermixing an acid and a compound of formula (23), and treating the resulting product with boc anhydride:

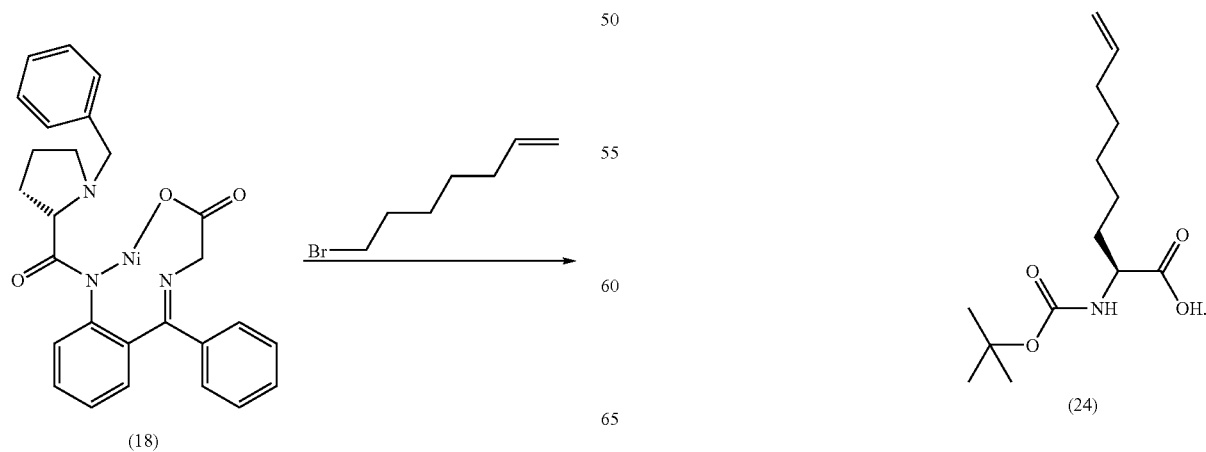

Preferred embodiments provide a method of making a compound of formula (24), comprising:

intermixing a 7-Bromo-1-heptene and a compound of formula (18) to form a compound of formula (23):

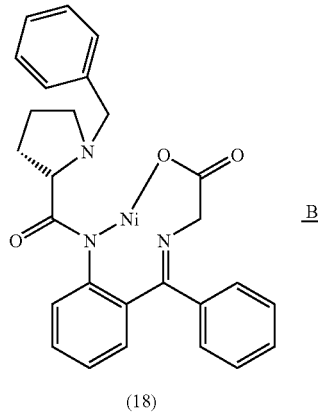

(18)

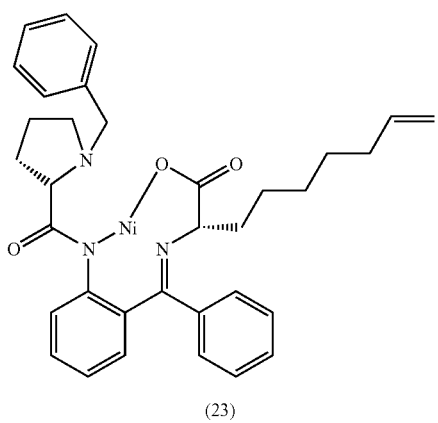

(23)

intermixing an acid and the compound of formula (23), and treating the resulting product with boc anhydride to form the compound of formula (24):

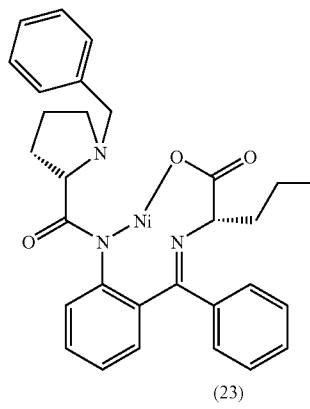

(23)

-continued

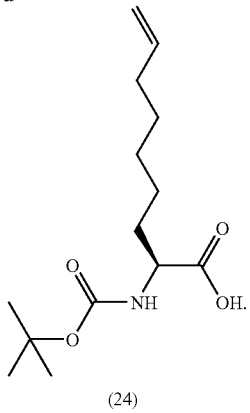

(24)

DETAILED DESCRIPTION OF THE EMBODIMENTS

Definitions

As used herein, the term "hepatic fibrosis," used interchangeably herein with "liver fibrosis," refers to the growth of scar tissue in the liver that can occur in the context of a chronic hepatitis infection.

The terms "individual," "host," "subject," and "patient" are used interchangeably herein, and refer to a mammal, including, but not limited to, primates, including simians and humans.

As used herein, the term "liver function" refers to a normal function of the liver, including, but not limited to, a synthetic function, including, but not limited to, synthesis of proteins such as serum proteins (e.g., albumin, clotting factors, alkaline phosphatase, aminotransferases (e.g., alanine transaminase, aspartate transaminase), 5'-nucleosidase, γ-glutaminyl-transpeptidase, etc.), synthesis of bilirubin, synthesis of cholesterol, and synthesis of bile acids; a liver metabolic function, including, but not limited to, carbohydrate metabolism, amino acid and ammonia metabolism, hormone metabolism, and lipid metabolism; detoxification of exogenous drugs; a hemodynamic function, including splanchnic and portal hemodynamics; and the like.

The term "sustained viral response" (SVR; also referred to as a "sustained response" or a "durable response"), as used herein, refers to the response of an individual to a treatment regimen for HCV infection, in terms of serum HCV titer. Generally, a "sustained viral response" refers to no detectable HCV RNA (e.g., less than about 500, less than about 200, or less than about 100 genome copies per milliliter serum) found in the patient's serum for a period of at least about one month, at least about two months, at least about three months, at least about four months, at least about five months, or at least about six months following cessation of treatment.

"Treatment failure patients" as used herein generally refers to HCV-infected patients who failed to respond to previous therapy for HCV (referred to as "non-responders") or who initially responded to previous therapy, but in whom the therapeutic response was not maintained (referred to as "relapsers"). The previous therapy generally can include treatment with IFN-α monotherapy or IFN-α combination therapy, where the combination therapy may include administration of IFN-α and an antiviral agent such as ribavirin.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The terms "individual," "host," "subject," and "patient" are used interchangeably herein, and refer to a mammal, including, but not limited to, murines, simians, humans, mammalian farm animals, mammalian sport animals, and mammalian pets.

As used herein, the term "a Type I interferon receptor agonist" refers to any naturally occurring or non-naturally occurring ligand of human Type I interferon receptor, which binds to and causes signal transduction via the receptor. Type I interferon receptor agonists include interferons, including naturally-occurring interferons, modified interferons, synthetic interferons, pegylated interferons, fusion proteins comprising an interferon and a heterologous protein, shuffled interferons; antibody specific for an interferon receptor; non-peptide chemical agonists; and the like.

As used herein, the term "Type II interferon receptor agonist" refers to any naturally occurring or non-naturally occurring ligand of human Type II interferon receptor that binds to and causes signal transduction via the receptor. Type II interferon receptor agonists include native human interferon-γ, recombinant IFN-γ species, glycosylated IFN-γ species, pegylated IFN-γ species, modified or variant IFN-γ species, IFN-γ fusion proteins, antibody agonists specific for the receptor, non-peptide agonists, and the like.

As used herein, the term "a Type III interferon receptor agonist" refers to any naturally occurring or non-naturally occurring ligand of humanIL-28 receptor α ("IL-28R"), the amino acid sequence of which is described by Sheppard, et al., infra., that binds to and causes signal transduction via the receptor.

As used herein, the term "interferon receptor agonist" refers to any Type I interferon receptor agonist, Type II interferon receptor agonist, or Type III interferon receptor agonist.

The term "dosing event" as used herein refers to administration of an antiviral agent to a patient in need thereof, which event may encompass one or more releases of an antiviral agent from a drug dispensing device. Thus, the term "dosing event," as used herein, includes, but is not limited to, installation of a continuous delivery device (e.g., a pump or other controlled release injectable system); and a single subcutaneous injection followed by installation of a continuous delivery system.

"Continuous delivery" as used herein (e.g., in the context of "continuous delivery of a substance to a tissue") is meant to refer to movement of drug to a delivery site, e.g., into a tissue in a fashion that provides for delivery of a desired amount of substance into the tissue over a selected period of time, where about the same quantity of drug is received by the patient each minute during the selected period of time.

"Controlled release" as used herein (e.g., in the context of "controlled drug release") is meant to encompass release of substance (e.g., a Type I or Type III interferon receptor agonist, e.g., IFN-α) at a selected or otherwise controllable rate, interval, and/or amount, which is not substantially influenced by the environment of use. "Controlled release" thus encompasses, but is not necessarily limited to, substantially continuous delivery, and patterned delivery (e.g., intermittent delivery over a period of time that is interrupted by regular or irregular time intervals).

"Patterned" or "temporal" as used in the context of drug delivery is meant delivery of drug in a pattern, generally a substantially regular pattern, over a pre-selected period of time (e.g., other than a period associated with, for example a bolus injection). "Patterned" or "temporal" drug delivery is meant to encompass delivery of drug at an increasing, decreasing, substantially constant, or pulsatile, rate or range of rates (e.g., amount of drug per unit time, or volume of drug formulation for a unit time), and further encompasses delivery that is continuous or substantially continuous, or chronic.

The term "controlled drug delivery device" is meant to encompass any device wherein the release (e.g., rate, timing of release) of a drug or other desired substance contained therein is controlled by or determined by the device itself and not substantially influenced by the environment of use, or releasing at a rate that is reproducible within the environment of use.

By "substantially continuous" as used in, for example, the context of "substantially continuous infusion" or "substantially continuous delivery" is meant to refer to delivery of drug in a manner that is substantially uninterrupted for a pre-selected period of drug delivery, where the quantity of drug received by the patient during any 8 hour interval in the pre-selected period never falls to zero. Furthermore, "substantially continuous" drug delivery can also encompass delivery of drug at a substantially constant, pre-selected rate or range of rates (e.g., amount of drug per unit time, or volume of drug formulation for a unit time) that is substantially uninterrupted for a pre-selected period of drug delivery.

By "substantially steady state" as used in the context of a biological parameter that may vary as a function of time, it is meant that the biological parameter exhibits a substantially constant value over a time course, such that the area under the curve defined by the value of the biological parameter as a function of time for any 8 hour period during the time course (AUC8hr) is no more than about 20% above or about 20% below, and preferably no more than about 15% above or about 15% below, and more preferably no more than about 10% above or about 10% below, the average area under the curve of the biological parameter over an 8 hour period during the time course (AUC8hr average). The AUC8hr average is defined as the quotient (q) of the area under the curve of the biological parameter over the entirety of the time course (AUCtotal) divided by the number of 8 hour intervals in the time course (total/3 days), i.e., q=(AUCtotal)/(total/3 days). For example, in the context of a serum concentration of a drug, the serum concentration of the drug is maintained at a substantially steady state during a time course when the area under the curve of serum concentration of the drug over time for any 8 hour period during the time course (AUC8hr) is no more than about 20% above or about 20% below the average area under the curve of serum concentration of the drug over an 8 hour period in the time course (AUC8hr average), i.e., the AUC8hr is no more than 20% above or 20% below the AUC8hr average for the serum concentration of the drug over the time course.

As used herein, "hydrogen bond" refers to an attractive force between an electronegative atom (such as oxygen, nitrogen, sulfur or halogen) and a hydrogen atom which is linked covalently to another electronegative atom (such as oxygen, nitrogen, sulfur or halogen). See, e.g., Stryer et. al. "Biochemistry", Fifth Edition 2002, Freeman & Co. N.Y. Typically, the hydrogen bond is between a hydrogen atom and two unshared electrons of another atom. A hydrogen bond between hydrogen and an electronegative atom not covalently bound to the hydrogen may be present when the hydrogen atom is at a distance of about 2.5 angstroms to about 3.8 angstroms from the not-covalently bound electronegative atom, and the angle formed by the three atoms (electronegative atom covalently bound to hydrogen, hydrogen, and electronegative atom not-covalently bound electronegative atom) deviates from 180 degrees by about 45 degrees or less. The distance between the hydrogen atom and the not-covalently bound electronegative atom may be referred to herein as the "hydrogen bond length," and the angle formed by the three atoms (electronegative atom covalently bound to hydrogen, hydrogen, and electronegative atom not-covalently bound electronegative atom) may be referred to herein as the "hydrogen bond angle." In some instances, stronger hydrogen bonds are formed when the hydrogen bond length is shorter; thus, in some instances, hydrogen bond lengths may range from about 2.7 angstroms to about 3.6 angstroms, or about 2.9 angstroms to about 3.4 angstroms. In some instances, stronger hydrogen bonds are formed when the hydrogen bond angle is closer to being linear; thus, in some instances, hydrogen bond angles may deviate from 180 degrees by about 25 degrees or less, or by about 10 degrees or less.

As used herein, "non-polar interaction" refers to proximity of non-polar molecules or moieties, or proximity of molecules or moieties with low polarity, sufficient for van der Waals interaction between the moieties and/or sufficient to exclude polar solvent molecules such as water molecules. See, e.g., Stryer et. al. "Biochemistry", Fifth Edition 2002, Freeman & Co. N.Y. Typically, the distance between atoms (excluding hydrogen atoms) of non-polar interacting moieties may range from about 2.9 angstroms to about 6 angstroms. In some instances, the space separating non-polar interacting moieties is less than the space that would accommodate a water molecule. As used herein a non-polar moiety or moiety with low polarity refers to moieties with low dipolar moments (typically dipolar moments less than the dipolar moment of O—H bonds of $H_2O$ and N—H bonds of $NH_3$) and/or moieties that are not typically present in hydrogen bonding or electrostatic interactions. Exemplary moieties with low polarity are alkyl, alkenyl, and unsubstituted aryl moieties.

As used herein, an NS3 protease S1' pocket moiety refers to a moiety of the NS3 protease that interacts with the amino acid positioned one residue C-terminal to the cleavage site of the substrate polypeptide cleaved by NS3 protease (e.g., the NS3 protease moieties that interact with amino acid S in the polypeptide substrate DLEVVT-STWVLV). Exemplary moieties include, but are not limited to, atoms of the peptide backbone or side chains of amino acids Lys136, Gly137, Ser139, His57, Gly58, Gln41, Ser42, and Phe43, see Yao. et. al., Structure 1999, 7, 1353.

As used herein, an NS3 protease S2 pocket moiety refers to a moiety of the NS3 protease that interacts with the amino acid positioned two residues N-terminal to the cleavage site of the substrate polypeptide cleaved by NS3 protease (e.g., the NS3 protease moieties that interact with amino acid V in the polypeptide substrate DLEVVT-STWVLV). Exemplary moieties include, but are not limited to, atoms of the peptide backbone or side chains of amino acids His57, Arg155, Val78, Asp79, Gln80 and Asp81, see Yao. et. al., Structure 1999, 7, 1353.

As used herein, a first moiety "positioned by" a second moiety refers to the spatial orientation of a first moiety as determined by the properties of a second moiety to which the first atom or moiety is covalently bound. For example, a phenyl carbon may position an oxygen atom bonded to the phenyl carbon in a spatial position such that the oxygen atom hydrogen bonds with a hydroxyl moiety in an NS3 active site.

The term "alkyl" used herein refers to a monovalent straight or branched chain radical of from one to twenty carbon atoms, including, but not limited to, methyl, ethyl, n-propyl, isopropyl, n-butyl, isobutyl, tert-butyl, n-hexyl, and the like.

The term "halo" used herein refers to fluoro, chloro, bromo, or iodo.

The term "alkoxy" used herein refers to straight or branched chain alkyl radical covalently bonded to the parent molecule through an —O— linkage. Examples of alkoxy groups include, but are not limited to, methoxy, ethoxy, propoxy, isopropoxy, butoxy, n-butoxy, sec-butoxy, t-butoxy and the like.

The term "alkenyl" used herein refers to a monovalent straight or branched chain radical of from two to twenty carbon atoms containing a carbon double bond including, but not limited to, 1-propenyl, 2-propenyl, 2-methyl-1-propenyl, 1-butenyl, 2-butenyl, and the like.

The term "alkynyl" used herein refers to a monovalent straight or branched chain radical of from two to twenty carbon atoms containing a carbon triple bond including, but not limited to, 1-propynyl, 1-butynyl, 2-butynyl, and the like.

The term "aryl" used herein refers to homocyclic aromatic radical whether fused or not fused. Examples of aryl groups include, but are not limited to, phenyl, naphthyl, biphenyl, phenanthrenyl, naphthacenyl, and the like.

The term "cycloalkyl" used herein refers to saturated aliphatic ring system radical having three to twenty carbon atoms including, but not limited to, cyclopropyl, cyclopentyl, cyclohexyl, cycloheptyl, and the like.

The term "cycloalkenyl" used herein refers to aliphatic ring system radical having three to twenty carbon atoms having at least one carbon-carbon double bond in the ring. Examples of cycloalkenyl groups include, but are not limited to, cyclopropenyl, cyclopentenyl, cyclohexenyl, cycloheptenyl, and the like.

The term "polycycloalkyl" used herein refers to saturated aliphatic ring system radical having at least two rings that are fused with or without bridgehead carbons. Examples of polycycloalkyl groups include, but are not limited to, bicyclo[4.4.0]decanyl, bicyclo[2.2.1]heptanyl, adamantyl, norbornyl, and the like.

The term "polycycloalkenyl" used herein refers to aliphatic ring system radical having at least two rings that are fused with or without bridgehead carbons in which at least one of the rings has a carbon-carbon double bond. Examples of polycycloalkenyl groups include, but are not limited to, norbornylenyl, 1,1'-bicyclopentenyl, and the like.

The term "polycyclic hydrocarbon" used herein refers to a ring system radical in which all of the ring members are carbon atoms. Polycyclic hydrocarbons can be aromatic or can contain less than the maximum number of non-cumulative double bonds. Examples of polycyclic hydrocarbon include, but are not limited to, naphthyl, dihydronaphthyl, indenyl, fluorenyl, and the like.

The term "heterocyclic" or "heterocyclyl" used herein refers to cyclic ring system radical having at least one ring system in which one or more ring atoms are not carbon, namely heteroatom. Heterocycles can be nonaromatic or aromatic. Examples of heterocyclic groups include, but are not limited to, morpholinyl, tetrahydrofuranyl, dioxolanyl, pyrrolidinyl, oxazolyl, pyranyl, pyridyl, pyrimidinyl, pyrrolyl, and the like.

The term "heteroaryl" used herein refers to heterocyclic group, whether one or more rings, formally derived from an arene by replacement of one or more methine and/or vinylene groups by trivalent or divalent heteroatoms, respectively, in such a way as to maintain the aromatic system in one or more rings. Examples of heteroaryl groups include, but are not limited to, pyridyl, pyrrolyl, oxazolyl, indolyl, and the like.

The term "arylalkyl" used herein refers to one or more aryl groups appended to an alkyl radical. Examples of arylalkyl groups include, but are not limited to, benzyl, phenethyl, phenpropyl, phenbutyl, and the like.

The term "cycloalkylalkyl" used herein refers to one or more cycloalkyl groups appended to an alkyl radical. Examples of cycloalkylalkyl include, but are not limited to, cyclohexylmethyl, cyclohexylethyl, cyclopentylmethyl, cyclopentylethyl, and the like.

The term "heteroarylalkyl" used herein refers to one or more heteroaryl groups appended to an alkyl radical. Examples of heteroarylalkyl include, but are not limited to, pyridylmethyl, furanylmethyl, thiophenylethyl, and the like.

The term "heterocyclylalkyl" used herein refers to one or more heterocyclyl groups appended to an alkyl radical. Examples of heterocyclylalkyl include, but are not limited to, morpholinylmethyl, morpholinylethyl, morpholinylpropyl, tetrahydrofuranylmethyl, pyrrolidinylpropyl, and the like.

The term "aryloxy" used herein refers to an aryl radical covalently bonded to the parent molecule through an —O— linkage.

The term "alkylthio" used herein refers to straight or branched chain alkyl radical covalently bonded to the parent molecule through an —S— linkage. Examples of alkoxy groups include, but are not limited to, methoxy, ethoxy, propoxy, isopropoxy, butoxy, n-butoxy, sec-butoxy, t-butoxy and the like.

The term "arylthio" used herein refers to an aryl radical covalently bonded to the parent molecule through an —S— linkage.

The term "alkylamino" used herein refers to nitrogen radical with one or more alkyl groups attached thereto. Thus, monoalkylamino refers to nitrogen radical with one alkyl group attached thereto and dialkylamino refers to nitrogen radical with two alkyl groups attached thereto.

The term "cyanoamino" used herein refers to nitrogen radical with nitrile group attached thereto.

The term "carbamyl" used herein refers to RNHCOO—.

The term "keto" and "carbonyl" used herein refers to C=O.

The term "carboxy" used herein refers to —COOH.
The term "sulfamyl" used herein refers to —SO$_2$NH$_2$.
The term "sulfonyl" used herein refers to —SO$_2$—.
The term "sulfinyl" used herein refers to —SO—.
The term "thiocarbonyl" used herein refers to C=S.
The term "thiocarboxy" used herein refers to CSOH.

As used herein, a radical indicates species with a single, unpaired electron such that the species containing the radical can be covalently bonded to another species. Hence, in this context, a radical is not necessarily a free radical. Rather, a radical indicates a specific portion of a larger molecule. The term "radical" can be used interchangeably with the term "group."

As used herein, a substituted group is derived from the unsubstituted parent structure in which there has been an exchange of one or more hydrogen atoms for another atom or group. When substituted, the substituent group(s) is (are) one or more group(s) individually and independently selected from $C_1$-$C_6$ alkyl, $C_1$-$C_6$ alkenyl, $C_1$-$C_6$ alkynyl, $C_3$-$C_6$ cycloalkyl, $C_3$-$C_6$ heterocycloalkyl (e.g., tetrahydrofuryl), aryl, heteroaryl, halo (e.g., chloro, bromo, iodo and fluoro), cyano, hydroxy, $C_1$-$C_6$ alkoxy, aryloxy, sulfhydryl (mercapto), $C_1$-$C_6$ alkylthio, arylthio, mono- and di-($C_1$-$C_6$)alkyl amino, quaternary ammonium salts, amino($C_1$-$C_6$)alkoxy, hydroxy($C_1$-$C_6$)alkylamino, amino($C_1$-$C_6$)alkylthio, cyanoamino, nitro, carbamyl, keto (oxy), carbonyl, carboxy, glycolyl, glycyl, hydrazino, guanyl, sulfamyl, sulfonyl, sulfinyl, thiocarbonyl, thiocarboxy, and combinations thereof. The protecting groups that can form the protective derivatives of the above substituents are known to those of skill in the art and can be found in references such as Greene and Wuts *Protective Groups in Organic Synthesis*; John Wiley and Sons: New York, 1999. Wherever a substituent is described as "optionally substituted" that substituent can be substituted with the above substituents.

Asymmetric carbon atoms may be present in the compounds described. All such isomers, including diastereomers and enantiomers, as well as the mixtures thereof are intended to be included in the scope of the recited compound. In certain cases, compounds can exist in tautomeric forms. All tautomeric forms are intended to be included in the scope. Likewise, when compounds contain an alkenyl or alkenylene group, there exists the possibility of cis- and trans-isomeric forms of the compounds. Both cis- and trans-isomers, as well as the mixtures of cis- and trans-isomers, are contemplated. Thus, reference herein to a compound includes all of the aforementioned isomeric forms unless the context clearly dictates otherwise.

Various forms are included in the embodiments, including polymorphs, solvates, hydrates, conformers, salts, and prodrug derivatives. A polymorph is a composition having the same chemical formula, but a different structure. A solvate is a composition formed by solvation (the combination of solvent molecules with molecules or ions of the solute). A hydrate is a compound formed by an incorporation of water. A conformer is a structure that is a conformational isomer. Conformational isomerism is the phenomenon of molecules with the same structural formula but different conformations (conformers) of atoms about a rotating bond. Salts of compounds can be prepared by methods known to those skilled in the art. For example, salts of compounds can be prepared by reacting the appropriate base or acid with a stoichiometric equivalent of the compound. A prodrug is a compound that undergoes biotransformation (chemical conversion) before exhibiting its pharmacological effects. For example, a prodrug can thus be viewed as a drug containing specialized protective groups used in a transient manner to alter or to eliminate undesirable properties in the parent molecule. Thus, reference herein to a compound includes all of the aforementioned forms unless the context clearly dictates otherwise.

Where a range of values is provided, it is understood that each intervening value, to the tenth of the unit of the lower limit unless the context clearly dictates otherwise, between the upper and lower limit of that range and any other stated or intervening value in that stated range is encompassed within the embodiments. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the embodiments.

Unless defined otherwise, all technical and scientific terms used herein have the same meaning as commonly understood by one of ordinary skill in the art to which the embodiments belong. Although any methods and materials similar or equivalent to those described herein can also be used in the practice or testing of the embodiments, the preferred methods and materials are now described. All publications mentioned herein are incorporated herein by reference to disclose and describe the methods and/or materials in connection with which the publications are cited.

It must be noted that as used herein and in the appended claims, the singular forms "a," "and," and "the" include plural referents unless the context clearly dictates otherwise. Thus, for example, reference to "a method" includes a plurality of such methods and reference to "a dose" includes reference to one or more doses and equivalents thereof known to those skilled in the art, and so forth.

The present embodiments provide compounds of Formulas I-VIII, as well as pharmaceutical compositions and formulations comprising any compound of Formulas I-VIII. A subject compound is useful for treating HCV infection and other disorders, as discussed below.

Compositions

The present embodiments provide compounds of the general formula (Ia) or (Ib)

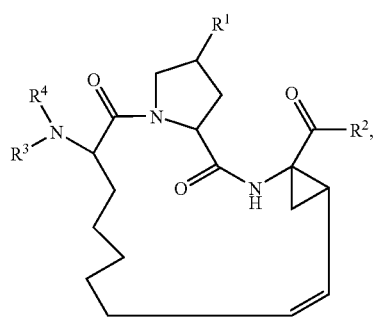
(Ia)

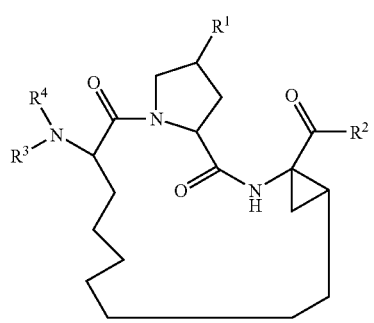
(Ib)

or a pharmaceutically acceptable salt, prodrug, or ester thereof wherein:

$R^1$ is H or OC(=O)—$R^{1a}$ wherein $R^{1a}$ is an optionally-substituted heteroaryl comprising N in the heteroaryl system;

$R^2$ is hydroxyl or $NHR^5$;

$R^3$ is selected from the group consisting of H, $CH_2R^6$, $COR^6CO_2R^7$, $CSNH_2$, optionally substituted 2-thiazole, and

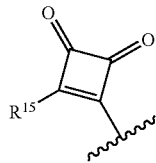

$R^4$ is hydrogen or methylcyclopropyl;

$R^5$ is selected from the group consisting of phenyl, $CH_2C(CF_3)_2OH$, $C_3$ alkyl, carbonylcyclopropyl, $SO_2R^8$, CN, and

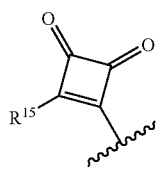

$R^6$ is selected from the group consisting of $R^9$, optionally-substituted phenyl, cyclopropyl, cyclobutyl, optionally-substituted furanyl, fluorinated alkyl; and hydroxylated alkyl;

$R^7$ is cyclopentyl or $C_1$-$C_6$ alkyl;

$R^8$ is selected from the group consisting of $NR^{11}R^{12}$, tert-butyl, chloropyridinyl,

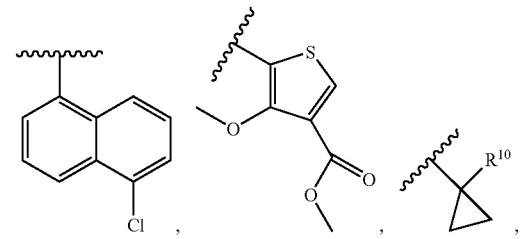

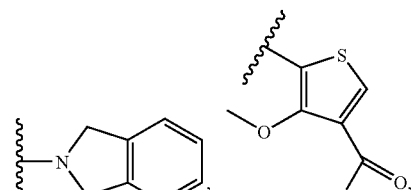

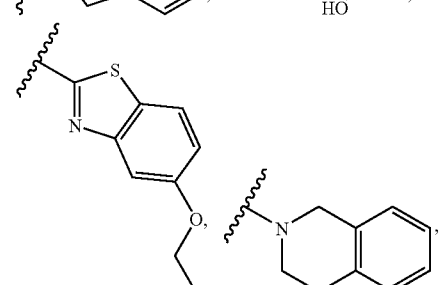

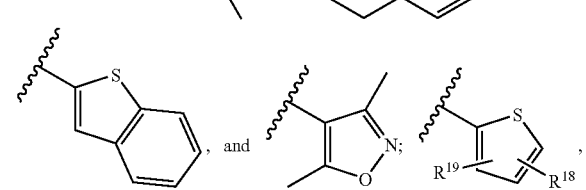

-continued

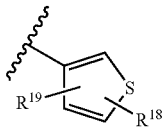

R⁹ is selected from the group consisting of tert-butyl, trifluoromethyl, trifluoroethyl, and methyltrifluoromethyl;
R¹⁰ is selected from the group consisting of H, $C_1$ to $C_3$ alkyl, 3-propenyl, methylmethoxyl, and benzyl;
R¹¹ is H, methyl, $C_{1-4}$ alkyl or $C_{1-4}$ fluorinated alkyl
R¹² is selected from the group consisting of $C_1$ to $C_3$ alkyl, 3-propenyl, phenyl,

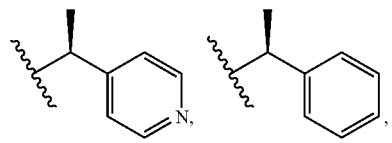

chlorophenyl, dichlorophenyl, benzyl, pyridinyl, $CH_2R^{13}$, $CH_2R^{16}R^{17}$, and fluorinated alkyl
   or $R_{11}$, and $R_{12}$ taken together can form a 4 or 5 membered ring optionally substituted with 2 fluorines
R¹³ is pyridinyl or R¹⁴;
R¹⁴ is selected from the group consisting of pyridinyl, chlorophenyl, naphthyl, and anisolyl;
R¹⁵ is $NR^{11}R^{12}$ or alkyl or cycloalkyl;
R¹⁶ is pyridinyl;
R¹⁷ is H or methyl.
R¹⁸ and R¹⁹ is independently H, halogen, methyl or $CF_3$ Another embodiment provides compound to the general formula (II)

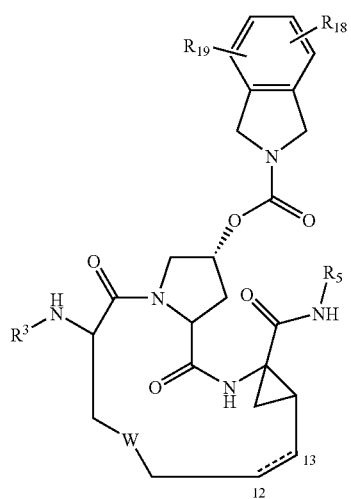
(II)

or a pharmaceutically acceptable salt, prodrug, or ester thereof wherein:
R³ is selected from the group consisting of H, $CH_2R^6$, $COR^6$, $CO_2R^{7'}$, optionally substituted 2-thiazole
R⁵ is selected from the group consisting of methylcyclopropyl or $SO_2R^8$,
R⁶ is selected from the group consisting of R⁹, optionally-substituted phenyl, cyclopropyl, cyclobutyl, optionally-substituted furanyl, fluorinated alkyl; and hydroxylated alkyl;
R⁷ is cyclopentyl or $C_1$-$C_6$ alkyl;
R⁸ is selected from the group consisting of $NR^{11}R^{12}$, optionally substituted phenyl, and

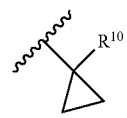

R¹⁰ is selected from the group consisting of H, $C_1$ to $C_3$ alkyl, 3-propenyl, methylmethoxyl, and benzyl;
R¹¹ is H, methyl, $C_{1-4}$ alkyl or $C_{1-4}$ fluorinated alkyl
R¹² is selected from the group consisting of $C_1$ to $C_3$ alkyl, 3-propenyl, phenyl,

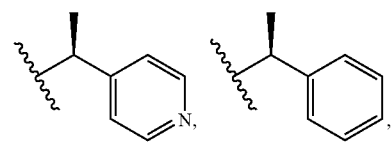

chlorophenyl, dichlorophenyl, benzyl, pyridinyl, $CH_2R^{13}$, $CH_2R^{16}R^{17}$, and fluorinated alkyl
   or $R_{11}$, and $R_{12}$ taken together can form a 4 or 5 membered ring optionally substituted with 2 fluorines
R¹⁷ is H or methyl.
R¹⁸ and R¹⁹ is independently H, halogen, methyl or $CF_3$
W is selected from the groups

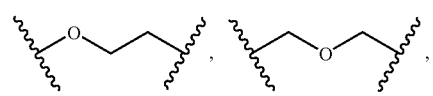

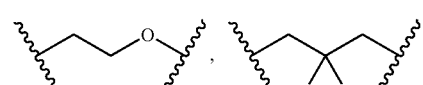

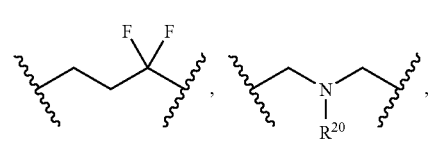

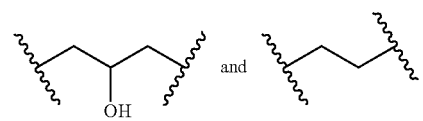

R²⁰ is H, $CH_3$, alkyl, fluorinated alkyl, $SO_2Ar$,
the 12-13 bond is a single or double bond.

The present embodiments provide compounds having the general Formula III:

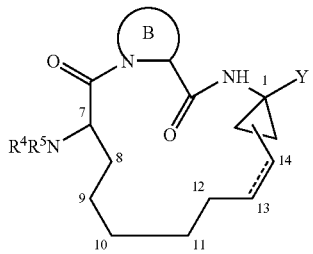

(III)

or a pharmaceutically acceptable salt, prodrug, or ester thereof wherein:

B ring is selected from

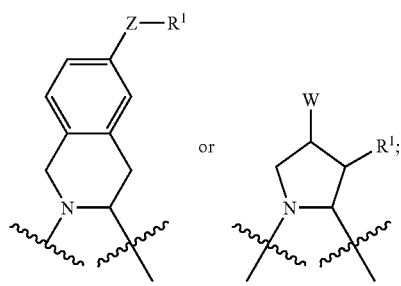

Z is bond, O, or S;
$R^1$ is H, $C_{1-7}$ alkyl, $C_{3-7}$ cycloalkyl, pyridyl, thioazolo, naphthyl, fused heterocycle, phenyl, substituted phenyl, benzyloxy, or substituted benzyloxy;
W is selected from hydrogen, halogen, $OCH_3$, $SR^3$, $NHR^3$, $CH(R^3)_2$, or

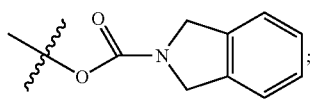

$R^3$ is H, $C_{1-8}$ alkyl, $C_{3-7}$ cycloalkyl, $C_{4-10}$ cycloalkyl-alkyl, $C_{1-6}$ alkyl, $C_{4-10}$ cycloalkyl-alkyl, $C_{7-10}$ arylalkyl, or $C_{6-12}$ heteroarylalkyl;
$R^4$ and $R^5$ are each independently substituted or unsubstituted groups selected from H, $C_{1-6}$ alkyl, $C(O)R^8$, $C(O)OR^8$, $C_{3-7}$ cycloalkyl, alkyl-$C_{4-10}$ cycloalkyl, phenyl, benzyl, $C(O)NR^8R^8$, $C(S)NR^8R^8$, $S(O)_2R^8$, or (CO)$CHR^{21}NH(CO)R^{22}$;
wherein $R^8$ is a substituted or unsubstituted group selected from H, $C_{1-6}$ alkyl, $C_{3-7}$ cycloalkyl, alkyl-$C_{3-7}$ cycloalkyl, $C_{6\ or\ 10}$ aryl, alkyl-$C_{6\ or\ 10}$ aryl, $C_{3-7}$ cycloalkyl fused to $C_6$ aryl or $C_6$ aryl heterocyclyl, tetrahydrofuran ring, tetrahydropyran ring, benzyl, or phenyl;
$R^{21}$ is a substituted or unsubstituted group selected from $C_{1-6}$ alkyl, $C_{3-7}$ cycloalkyl, $C_{4-10}$ cycloalkyl-alkyl, phenyl, $C_{6\ or\ 10}$ aryl, pyridyl, pyrimidyl, pyrazinyl, thienyl, furanyl, thiazolyl, oxazolyl, phenoxy, or thiophenoxy;
$R^{22}$ is a substituted or unsubstituted group selected from $C_{1-6}$ alkyl, $C_{3-7}$ cycloalkyl, $C_{4-10}$ cycloalkyl-alkyl, or phenyl;

Y has a formula selected from $—C(O)NHS(O)_2R^{1a}$, $—C(O)NHS(O)_2NR^{1a}R^{1b}$, $—C(O)NHR^{1a}$, $—C(O)R^{1a}$, $—C(O)NHC(O)R^{1a}$, $—C(O)NHS(O)_2R^{1a}$, $—C(O)NHS(O)R^{1a}$, or $—C(O)OH$;
wherein $R^{1a}$ and $R^{1b}$ are each independently substituted or unsubstituted groups selected from H, CN, $CF_3$, $C_{1-6}$ alkyl, $C_{1-6}$ alkenyl, $C_{1-6}$ alkynyl, $C_{3-7}$ cycloalkyl, alkyl-$C_{3-10}$ cycloalkyl, $C_{6\ or\ 10}$ aryl, alkyl-$C_{6\ or\ 10}$ aryl, alkenyl-$C_{6\ or\ 10}$ aryl, heterocycle, heteroaromatic ring, or alkyl-heteroaryl, alkyl-heterocycle,
or $NR^{1a}R^{1b}$ form a substituted or unsubstituted three- to six-membered alkyl cyclic secondary amine, or $NR^{1a}R^{1b}$ is a heteroaryl selected from the group consisting of:

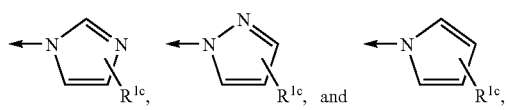

wherein $R^{1c}$ is H, halo, $C_{1-6}$ alkyl, $C_{3-6}$ cycloalkyl, $C_{1-6}$ alkoxy, $C_{3-6}$ cycloalkoxy, $NO_2$, $N(R^{1d})_2$, $NH(CO)R^{1d}$, or $NH(CO)NHR^{1d}$, wherein each $R^{1d}$ is independently H, $C_{1-6}$ alkyl, or $C_{3-6}$ cycloalkyl,
or $R^{1c}$ is $NH(CO)OR^{1e}$, wherein $R^{1e}$ is $C_{1-6}$ alkyl or $C_{3-6}$ cycloalkyl; and
the dashed line represents an optional double bond.

The present embodiments provide compounds having the general Formula IV:

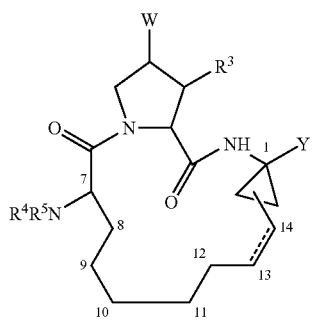

(IV)

or a pharmaceutically acceptable salt, prodrug, or ester thereof wherein:
W is selected from hydrogen, $OCH_3$, $SR^3$, $NHR^3$, $CH(R^3)_2$, or

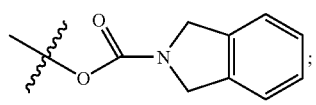

$R^3$ is H or $C_{1-3}$ alkyl;
and $R^5$ are independently substituted or unsubstituted groups selected from H, $C_{1-6}$ alkyl, $C(O)R^8$, $C(O)OR^8$, $C_{3-7}$ cycloalkyl, alkyl-$C_{4-10}$ cycloalkyl, phenyl, or benzyl;
wherein $R^8$ is a substituted or unsubstituted group selected from $C_{1-6}$ alkyl, $C_{3-7}$ cycloalkyl, alkyl-$C_{3-7}$ cycloalkyl, $C_{6\ or\ 10}$ aryl, or alkyl-$C_{6\ or\ 10}$ aryl;

Y has a formula selected from —C(O)NHS(O)$_2$R$^{1a}$, —C(O)NHS(O)$_2$NR$^{1a}$R$^{1b}$, —C(O)NHR$^{1a}$, —C(O)R$^{1a}$, —C(O)NHC(O)R$^{1a}$, —C(O)NHS(O)$_2$R$^{1a}$, —C(O)NHS(O)R$^{1a}$, or —C(O)OH;

wherein R$^{1a}$ and R$^{1b}$ are each independently substituted or unsubstituted groups selected from H, CN, CF$_3$, C$_{1-6}$ alkyl, C$_{1-6}$ alkenyl, C$_{1-6}$ alkynyl, C$_{3-7}$ cycloalkyl, alkyl-C$_{3-10}$ cycloalkyl, C$_{6\text{ or }10}$ aryl, alkyl-C$_{6\text{ or }10}$ aryl, alkenyl-C$_{6\text{ or }10}$ aryl, heterocycle, or alkyl-heterocycle, or NR$^{1a}$R$^{1b}$ form a substituted or unsubstituted three- to seven-membered ring, and the dashed line represents an optional double bond.

The present embodiments provide compounds having the general Formula V:

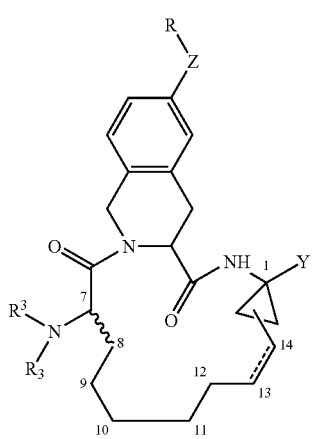

(V)

or a pharmaceutically acceptable salt, prodrug, or ester thereof wherein:

R$^1$ is H, C$_{1-7}$ alkyl, C$_{3-7}$ cycloalkyl, pyridyl, thioazolo, naphthyl, fused heterocycle, phenyl, substituted phenyl, benzyloxy, or substituted benzyloxy;

R$^2$ is H, C$_{1-6}$ alkyl, C$_{3-7}$ cycloalkyl, C$_{4-10}$ cycloalkyl-alkyl, phenyl, substituted phenyl, C$_{1-6}$ alkoxy, or substituted C$_{1-6}$ alkoxy;

R$^3$ is H, C$_{1-6}$ alkyl, C(O)R$^5$, C(O)OR$^5$, C(O)NR$^5$R$^6$, C(S)NR$^5$R$^6$, or S(O)$_2$R$^5$;

R$^5$ and R$^6$ are each independently selected from H, C$_{1-6}$ alkyl, C$_{3-7}$ cycloalkyl, C$_{4-10}$ cycloalkyl-alkyl, C$_{3-7}$ cycloalkyl fused to C$_6$ aryl or C$_6$ aryl heterocyclyl, benzyl, phenyl, or substituted phenyl;

Y is a sulfonimide of the formula —C(O)NHS(O)$_2$R$^4$ or a carboxylic acid of the formula —C(O)OH;

wherein R$^4$ is C$_{1-6}$ alkyl, C$_{3-7}$ cycloalkyl, C$_{4-10}$ cycloalkyl-alkyl, C$_6$ aryl, or substituted C$_6$ aryl;

Z is a bond, O, or S; and the dashed line represents an optional double bond.

In some embodiments, the phenyl on R$^1$ is substituted with halo, C$_{1-3}$ alkyl, substituted C$_{1-3}$ alkyl with up to 3 fluoro, C$_{1-3}$ alkoxy, substituted C$_{1-3}$ alkoxy substituted with up to 3 fluoro, cyano, hydroxy, nitro, NH$_2$, NHR$_2$, or NR$_2$R$_3$, wherein R$^2$ is H, C$_{1-6}$ alkyl, C$_{3-7}$ cycloalkyl, C$_{4-10}$ cycloalkyl-alkyl, phenyl, substituted phenyl, C$_{1-6}$ alkoxy, or substituted C$_{1-6}$ alkoxy;

R$^3$ is H, C$_{1-6}$ alkyl, C(O)R$^5$, C(O)OR$^5$, C(O)NR$^5$R$^6$, C(S)NR$^5$R$^6$, or S(O)$_2$R$^5$; and R$^5$ and R$^6$ are each independently selected from H, C$_{1-6}$ alkyl, C$_{3-7}$ cycloalkyl, C$_{4-10}$ cycloalkyl-alkyl, C$_{3-7}$ cycloalkyl fused to C$_6$ aryl or C$_6$ aryl heterocyclyl, benzyl, phenyl, or substituted phenyl.

In an embodiment, the benzyloxy on R$^1$ is substituted with halo, C$_{1-3}$ alkyl, substituted C$_{1-3}$ alkyl with up to 3 fluoro, C$_{1-3}$ alkoxy, substituted C$_{1-3}$ alkoxy substituted with up to 3 fluoro, cyano, hydroxy, nitro, NH$_2$, NHR$_2$, or NR$_2$R$_3$, wherein R$^2$ is H, C$_{1-6}$ alkyl, C$_{3-7}$ cycloalkyl, C$_{4-10}$ cycloalkyl-alkyl, phenyl, substituted phenyl, C$_{1-6}$ alkoxy, or substituted C$_{1-6}$ alkoxy;

R$^3$ is H, C$_{1-6}$ alkyl, C(O)R$^5$, C(O)OR$^5$, C(O)NR$^5$R$^6$, C(S)NR$^5$R$^6$, or S(O)$_2$R$^5$; and R$^5$ and R$^6$ are each independently selected from H, C$_{1-6}$ alkyl, C$_{3-7}$ cycloalkyl, C$_{4-10}$ cycloalkyl-alkyl, C$_{3-7}$ cycloalkyl fused to C$_6$ aryl or C$_6$ aryl heterocyclyl, benzyl, phenyl, or substituted phenyl.

In another embodiment, the phenyl on R$^2$ is substituted with halo, cyano, nitro, hydroxy, C$_{1-6}$ alkyl, C$_{3-7}$ cycloalkyl, C$_{4-10}$ cycloalkyl-alkyl, C$_{2-6}$ alkenyl, C$_{1-6}$ alkoxy, hydroxy-C$_{1-6}$ alkyl, C$_{1-6}$ alkyl, substituted C$_{1-6}$ alkyl with up to 5 fluoro, C$_{1-6}$ alkoxy, substituted C$_{1-6}$ alkoxy with up to 5 fluoro.

In another embodiment, the phenyl on R$^5$ and R$^6$ is substituted with halo, cyano, nitro, hydroxy, C$_{1-6}$ alkyl, C$_{3-7}$ cycloalkyl, C$_{4-10}$ cycloalkyl-alkyl, C$_{2-6}$ alkenyl, C$_{1-6}$ alkoxy, hydroxy-C$_{1-6}$ alkyl, C$_{1-6}$ alkyl, substituted C$_{1-6}$ alkyl with up to 5 fluoro, C$_{1-6}$ alkoxy, substituted C$_{1-6}$ alkoxy with up to 5 fluoro.

In another embodiment, the C$_6$ aryl on R$^4$ is substituted with up to three halo.

The present embodiments provide compounds having the general Formula VI:

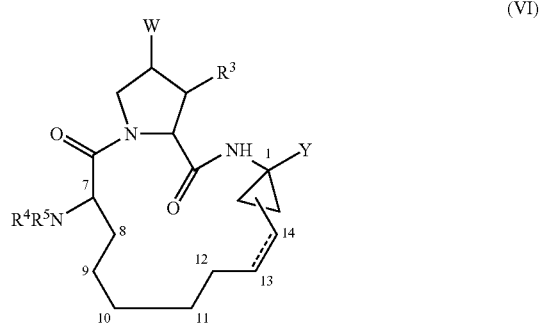

(VI)

or a pharmaceutically acceptable salt, prodrug, or ester thereof wherein:

W is selected from halogen, OCH$_3$, SR$^{15}$, NHR$^{15}$, or CHR$^3$R$^{15}$, wherein R$^{15}$ is a substituted or unsubstituted group selected from H, C$_{1-8}$ alkyl, C$_{3-7}$ cycloalkyl, C$_{4-10}$ cycloalkyl-alkyl, C$_{1-6}$ alkyl, C$_{4-10}$ cycloalkyl-alkyl, C$_{7-10}$ arylalkyl, or C$_{6-12}$ heteroarylalkyl;

R$^3$ is H or C$_{1-3}$ alkyl;

R$^4$ is H, C$_{1-6}$ alkyl, C$_{3-7}$ cycloalkyl, C$_{4-10}$ cycloalkyl-alkyl, substituted or unsubstituted phenyl, or substituted or unsubstituted benzyl;

R$^5$ is H, C$_{1-6}$ alkyl, C(O)NR$^6$R$^7$, C(S)NR$^6$R$^7$, C(O)R$^8$, C(O)OR$^8$, S(O)$_2$R$^8$, or (CO)CHR$^{21}$NH(CO)R$^{22}$;

R$^6$ and R$^7$ are each independently H, C$_{1-6}$ alkyl, C$_{3-7}$ cycloalkyl, C$_{4-10}$ cycloalkyl-alkyl, or substituted or unsubstituted phenyl, or R$^6$ and R$^7$ are taken together with the nitrogen to which they are attached to form indolinyl, pyrrolidinyl, piperidinyl, piperazinyl, or morpholinyl;

$R^8$ is a substituted or unsubstituted group selected from $C_{1-6}$ alkyl, $C_{3-7}$ cycloalkyl, $C_{4-10}$ cycloalkyl-alkyl, $C_{6\,or\,10}$ aryl, tetrahydrofuran ring, or tetrahydropyran ring;

Y is an amide of the formula —C(O)NHR$^9$, wherein R$^9$ is a substituted or unsubstituted group selected from $C_{1-6}$ alkyl, phenyl, cyano, $C_{3-7}$ cycloalkyl, $C_{4-10}$ cycloalkyl-alkyl, $C_{5-10}$ arylalkyl, or heteroarylalkyl, or Y is an acyl sulfonamide of the formula —C(O)NHS(O)$_2$R$^9$ or an acyl sulfonimide of the formula —C(O)NHS(O)R$^9$, wherein R$^9$ is a substituted or unsubstituted group selected from $C_{1-6}$ alkyl, $C_{3-7}$ cycloalkyl, $C_{4-10}$ cycloalkyl-alkyl, $C_{5-10}$ arylalkyl, $C_{6\,or\,10}$ aryl, or heteroaromatic ring;

or Y is a acyl sulfamide of the formula —C(O)NHS(O)$_2$NR$^{1a}$R$^{1b}$, wherein R$^{1a}$ and R$^{1b}$ are each independently substituted or unsubstituted groups selected from H, $C_{1-6}$ alkyl, $C_{3-7}$ cycloalkyl, $C_{4-10}$ cycloalkyl-alkyl, and $C_{6\,or\,10}$ aryl, or heterocycle, or NR$^{1a}$R$^{1b}$ form a substituted or unsubstituted three- to six-membered alkyl cyclic secondary amine, or NR$^{1a}$R$^{1b}$ is a heteroaryl selected from the group consisting of:

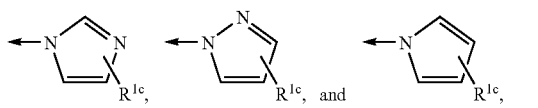

wherein R$^{1c}$ is H, halo, $C_{1-6}$ alkyl, $C_{3-6}$ cycloalkyl, $C_{1-6}$ alkoxy, $C_{3-6}$ cycloalkoxy, NO$_2$, N(R$^{1d}$)$_2$, NH(CO)R$^{1d}$, or NH(CO)NHR$^{1d}$, wherein each R$^{1d}$ is independently H, $C_{1-6}$ alkyl, or $C_{3-6}$ cycloalkyl, or R$^{1c}$ is NH(CO)OR$^{1e}$, wherein R$^{1e}$ is $C_{1-6}$ alkyl or $C_{3-6}$ cycloalkyl;

the dashed line represents an optional double bond;

R$^{21}$ is a substituted or unsubstituted group selected from $C_{1-6}$ alkyl, $C_{3-7}$ cycloalkyl, $C_{4-10}$ cycloalkyl-alkyl, phenyl, $C_{6\,or\,10}$ aryl, pyridyl, pyrimidyl, pyrazinyl, thienyl, furanyl, thiazolyl, oxazolyl, phenoxy, or thiophenoxy; and R$^{22}$ is a substituted or unsubstituted group selected from $C_{1-6}$ alkyl, $C_{3-7}$ cycloalkyl, $C_{4-10}$ cycloalkyl-alkyl, or phenyl.

The present embodiments provide compounds having the general Formula VII:

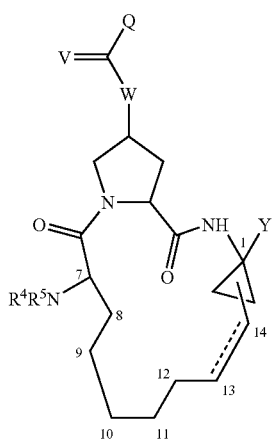

(VII)

or a pharmaceutically acceptable salt, prodrug, or ester thereof wherein:

Q is a unsubstituted or substituted core ring

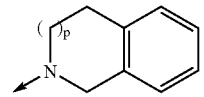

where p is 0 or 1, or Q is R$^1$-R$^2$, wherein R$^1$ is a substituted or unsubstituted group selected from $C_{1-6}$ alkyl, $C_{3-7}$ cycloalkyl, $C_{4-10}$ cycloalkyl-alkyl, phenyl, pyridine, pyrazine, pyrimidine, pyridazine, pyrrole, furan, thiophene, thiazole, oxazole, imidazole, isoxazole, pyrazole, isothiazole, naphthyl, quinoline, isoquinoline, quinoxaline, benzothiazole, benzothiophene, benzofuran, indole, or benzimidazole; and R$^2$ is a substituted or unsubstituted group selected from H, phenyl, pyridine, pyrazine, pyrimidine, pyridazine, pyrrole, furan, thiophene, thiazole, oxazole, imidazole, isoxazole, pyrazole, isothiazole, naphthyl, quinoline, isoquinoline, quinoxaline, benzothiazole, benzothiophene, benzofuran, indole, or benzimidazole;

R$^4$ is selected from H, $C_{1-6}$ alkyl, $C_{3-7}$ cycloalkyl, $C_{4-10}$ cycloalkyl-alkyl, substituted or unsubstituted phenyl, or substituted or unsubstituted benzyl;

R$^5$ is H, $C_{1-6}$ alkyl, C(O)NR$^6$R$^7$, C(S)NR$^6$R$^7$, C(O)R$^8$, C(O)OR$^8$, S(O)$_2$R$^8$, or (CO)CHR$^{21}$NH(CO)R$^{22}$;

R$^6$ and R$^7$ are each independently H, $C_{1-6}$ alkyl, $C_{3-7}$ cycloalkyl, $C_{4-10}$ cycloalkyl-alkyl, or substituted or unsubstituted phenyl; or R$^6$ and R$^7$ are taken together with the nitrogen to which they are attached to form indolinyl, pyrrolidinyl, piperidinyl, piperazinyl, or morpholinyl;

R$^8$ is a substituted or unsubstituted group selected from $C_{1-6}$ alkyl, $C_{3-7}$ cycloalkyl, $C_{4-10}$ cycloalkyl-alkyl, phenyl, $C_{6\,or\,10}$ aryl, $C_{1-6}$ alkoxy, $C_{1-6}$ alkyl, tetrahydrofuran ring, or tetrahydropyran ring;

V is selected from O, S, or NH;

W is selected from O, NH, or CH$_2$;

Y is an amide of the formula —C(O)NHR$^9$, wherein R$^9$ is a substituted or unsubstituted group selected from $C_{1-6}$ alkyl, phenyl, cyano, $C_{3-7}$ cycloalkyl, or $C_{4-10}$ cycloalkyl-alkyl, $C_{5-10}$ arylalkyl, or heteroarylalkyl;

or Y is an acyl sulfonimide of the formula —C(O)NHS(O)R$^9$, wherein R$^9$ is a substituted or unsubstituted group selected from $C_{1-6}$ alkyl, $C_{3-7}$ cycloalkyl, $C_{4-10}$ cycloalkyl-alkyl, $C_{5-10}$ arylalkyl, $C_{6\,or\,10}$ aryl, heteroaromatic ring;

the dashed line represents an optional double bond;

R$^{21}$ is a substituted or unsubstituted group selected from $C_{1-6}$ alkyl, $C_{3-7}$ cycloalkyl, $C_{4-10}$ cycloalkyl-alkyl, phenyl, $C_{6\,or\,10}$ aryl, pyridyl, pyrimidyl, pyrazinyl, thienyl, furanyl, thiazolyl, oxazolyl, phenoxy, or thiophenoxy; and R$^{22}$ is a substituted or unsubstituted group selected from $C_{1-6}$ alkyl, $C_{3-7}$ cycloalkyl, $C_{4-10}$ cycloalkyl-alkyl, or phenyl.

The present embodiments provide compounds having the general Formula VI:

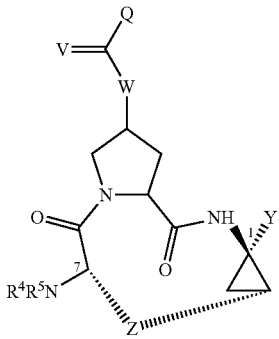

(VIII)

or a pharmaceutically acceptable salt, prodrug, or ester thereof wherein:

Q is an unsubstituted or substituted core ring selected from:

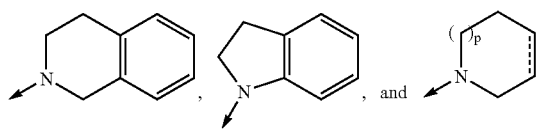

where p is 0 or 1, or Q is $R_1$-$R^2$, wherein $R^1$ is a substituted or unsubstituted group selected from $C_{1-6}$ alkyl, $C_{3-7}$ cycloalkyl, $C_{4-10}$ cycloalkyl-alkyl, phenyl, pyridine, pyrazine, pyrimidine, pyridazine, pyrrole, furan, thiophene, thiazole, oxazole, imidazole, isoxazole, pyrazole, isothiazole, naphthyl, quinoline, isoquinoline, quinoxaline, benzothiazole, benzothiophene, benzofuran, indole, or benzimidazole; and $R^2$ is a substituted or unsubstituted group selected from H, phenyl, pyridine, pyrazine, pyrimidine, pyridazine, pyrrole, furan, thiophene, thiazole, oxazole, imidazole, isoxazole, pyrazole, isothiazole, naphthyl, quinoline, isoquinoline, quinoxaline, benzothiazole, benzothiophene, benzofuran, indole, or benzimidazole;

Z is a $C_{5-7}$ saturated or unsaturated chain containing one or two heteroatoms selected from O, S, or $NR^6$;

$R^4$ is H, $C_{1-6}$ alkyl, $C_{3-7}$ cycloalkyl, $C_{4-10}$ cycloalkyl-alkyl, substituted or unsubstituted phenyl, or substituted or unsubstituted benzyl;

$R^5$ is H, $C_{1-6}$ alkyl, $C(O)NR^6R^7$, $C(S)NR^6R^7$, $C(O)R^8$, $C(O)OR^8$, $S(O)_2R^8$, or $(CO)CHR^{21}NH(CO)R^{22}$;

$R^6$ and $R^7$ are each independently H, $C_{1-6}$ alkyl, $C_{3-7}$ cycloalkyl, $C_{4-10}$ cycloalkyl-alkyl, or substituted or unsubstituted phenyl; or $R^6$ and $R^7$ are taken together with the nitrogen to which they are attached to form indolinyl, pyrrolidinyl, piperidinyl, piperazinyl, or morpholinyl;

$R^8$ is a substituted or unsubstituted group selected from $C_{1-6}$ alkyl, $C_{3-7}$ cycloalkyl, $C_{4-10}$ cycloalkyl-alkyl, phenyl, $C_{6\ or\ 10}$ aryl, $C_{1-6}$ alkyl, tetrahydrofuran ring, tetrahydropyran ring;

Y is a sulfonimide of the formula —$C(O)NHS(O)_2R^9$, wherein $R^9$ is a substituted or unsubstituted group selected from $C_{1-6}$ alkyl, $C_{3-7}$ cycloalkyl, or $C_{4-10}$ cycloalkyl-alkyl, $C_{6\ or\ 10}$ aryl, $C_{1-6}$ alkyl, $NR^6R^7$, $NR^{1a}R^{1b}$, heteroaromatic ring, or Y is a carboxylic acid or pharmaceutically acceptable salt, solvate, or prodrug thereof;

wherein $R^{1a}$ and $R^{1b}$ are each independently H, $C_{1-6}$ alkyl, $C_{3-7}$ cycloalkyl, $C_{4-10}$ cycloalkyl-alkyl, $C_{6\ or\ 10}$ aryl or $R^{1a}$ and $R^{1b}$ are each independently H, heterocycle, which is a five-, six-, or seven-membered, saturated or unsaturated heterocyclic molecule, containing from one to four heteroatoms selected from the group consisting of nitrogen, oxygen, and sulfur, or $NR^{1a}R^{1b}$ is a three- to six-membered alkyl cyclic secondary amine, or $NR^{1a}R^{1b}$ is a heteroaryl selected from the group consisting of:

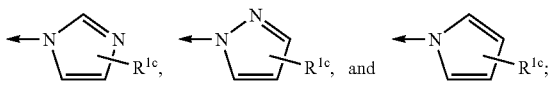

wherein $R^{1c}$ is H, halo, $C_{1-6}$ alkyl, $C_{3-6}$ cycloalkyl, $C_{1-6}$ alkoxy, $C_{3-6}$ cycloalkoxy, $NO_2$, $N(R^{1d})_2$, $NH(CO)R^{1d}$, or $NH(CO)NHR^{1d}$, wherein each $R^{1d}$ is independently H, $C_{1-6}$ alkyl, or $C_{3-6}$ cycloalkyl, or $R^{1c}$ is $NH(CO)OR^{1e}$, wherein $R^{1e}$ is $C_{1-6}$ alkyl or $C_{3-6}$ cycloalkyl;

p=0 or 1;

V is selected from O, S, or NH;

W is selected from O, $NR^{15}$, or $CHR^{15}$, wherein $R^{15}$ is H, $C_{1-6}$ alkyl, $C_{3-7}$ cycloalkyl, $C_{4-10}$ cycloalkyl-alkyl, or substituted or unsubstituted $C_{1-6}$ alkyl;

the dashed lines represent an optional double bond;

$R^{21}$ is a substituted or unsubstituted group selected from $C_{1-6}$ alkyl, $C_{3-7}$ cycloalkyl, $C_{4-10}$ cycloalkyl-alkyl, phenyl, $C_{6\ or\ 10}$ aryl, pyridyl, pyrimidyl, pyrazinyl, thienyl, furanyl, thiazolyl, oxazolyl, phenoxy, or thiophenoxy; and $R^{22}$ is a substituted or unsubstituted group selected from $C_{1-6}$ alkyl, $C_{3-7}$ cycloalkyl, or $C_{4-10}$ cycloalkyl-alkyl, or phenyl.

The present embodiments provide compounds having the general Formula VIIIa:

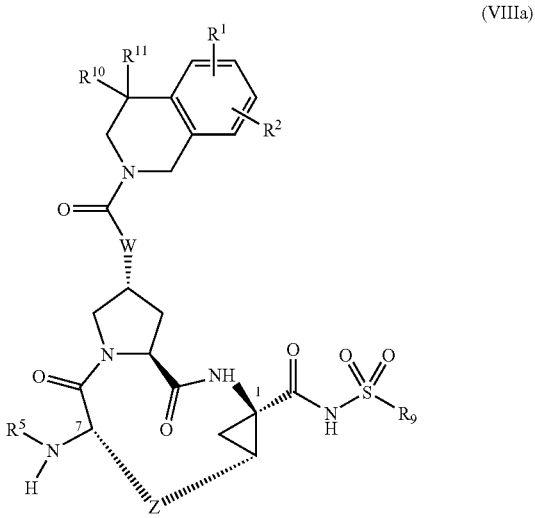

(VIIIa)

or a pharmaceutically acceptable salt, prodrug, or ester thereof wherein:

$R^1$ and $R^2$ are each independently H, halo, cyano, hydroxy, $C_{1-3}$ alkyl, or $C_{1-3}$ alkoxy;

$R^5$ is H, $C(O)OR^8$ or $C(O)NHR^8$;

$R^8$ is $C_{1-6}$ alkyl, $C_{5-6}$ cycloalkyl, or 3-tetrahydrofuryl;

$R^9$ is $C_{1-3}$ alkyl, $C_{3-4}$ cycloalkyl, or phenyl which is optionally substituted by up to two halo, cyano, hydroxy, $C_{1-3}$ alkyl, $C_{1-3}$ alkoxy;

$R^{10}$ and $R^{11}$ are each independently H, $C_{1-3}$ alkyl, or $R^{10}$ and $R^{11}$ are taken together with the carbon to which they are attached to form cyclopropyl, cyclobutyl, cyclopentyl, or cyclohexyl;

W is selected from O or NH;

the dashed line represents an optional double bond.

Z is a $C_{5-7}$ saturated or unsaturated chain containing one or two heteroatoms selected from O, S, or $NR^6$ The present embodiments provide compounds having the general Formula VIIIb:

(VIIIb)

or a pharmaceutically acceptable salt, prodrug, or ester thereof wherein:

$R^1$ and $R^2$ are each independently H, halo, cyano, hydroxy, $C_{1-3}$ alkyl, or $C_{1-3}$ alkoxy;

$R^5$ is H, $C(O)OR^8$ or $C(O)NHR^8$;

$R^8$ is $C_{1-6}$ alkyl, $C_{5-6}$ cycloalkyl, or 3-tetrahydrofuryl;

$R^9$ is $C_{1-3}$ alkyl, $C_{3-5}$ cycloalkyl, or phenyl which is optionally substituted by up to two halo, cyano, hydroxy, $C_{1-3}$ alkyl, or $C_{1-3}$ alkoxy;

$R^{10}$ and $R^{11}$ are each independently H, $C_{1-3}$ alkyl, or $C_{4-5}$ cycloalkyl;

W is selected from O or NH;

the dashed line represents an optional double bond; and

Z is a $C_{5-7}$ saturated or unsaturated chain containing one or two heteroatoms selected from O, S, or $NR^6$.

The present embodiments provide compounds having the general Formula VIIIc:

(VIIIc)

or a pharmaceutically acceptable salt, prodrug, or ester thereof wherein:

$R^{1a}$ and $R^{1b}$ are each independently H, $C_{1-6}$ alkyl, $C_{3-7}$ cycloalkyl, or $C_{4-10}$ cycloalkyl-alkyl, which are all optionally substituted from one to three times with halo, cyano, nitro, $C_{1-6}$ alkoxy, amido, or phenyl;

or $R^{1a}$ and $R^{1b}$ are each independently H and $C_{6\,or\,10}$ aryl which is optionally substituted by up to three halo, cyano, nitro, hydroxy, $C_{1-6}$ alkyl, $C_{3-7}$ cycloalkyl, $C_{4-10}$ cycloalkyl-alkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro;

or $R^{1a}$ and $R^{1b}$ are each independently H or heterocycle, which is a five-, six-, or seven-membered, saturated or unsaturated heterocyclic molecule, containing from one to four heteroatoms selected from the group consisting of nitrogen, oxygen and sulfur;

or $NR^{1a}R^{1b}$ is a three- to six-membered alkyl cyclic secondary amine, which optionally has one to three hetero atoms incorporated in the ring, and which is optionally substituted from one to three times with halo, cyano, nitro, $C_{1-6}$ alkoxy, amido, or phenyl;

or $NR^{1a}R^{1b}$ is a heteroaryl selected from the group consisting of:

wherein $R^{1c}$ is H, halo, $C_{1-6}$ alkyl, $C_{3-6}$ cycloalkyl, $C_{1-6}$ alkoxy, $C_{3-6}$ cycloalkoxy, $NO_2$, $N(R^{1d})_2$, $NH(CO)R^{1d}$, or $NH(CO)NHR^{1d}$, wherein each $R^{1d}$ is independently H, $C_{1-6}$ alkyl, or $C_{3-6}$ cycloalkyl;

or $R^{1c}$ is $NH(CO)OR^{1e}$ wherein $R^{1e}$ is $C_{1-6}$ alkyl, or $C_{3-6}$ cycloalkyl;

W is O or NH;

V is selected from O, S, or NH;

when V is O or S, W is selected from O, $NR^{15}$, or $CHR^{15}$;
when V is NH, W is selected from $NR^{15}$ or $CHR^{15}$,
where $R^{15}$ is H, $C_{1-6}$ alkyl, $C_{3-7}$ cycloalkyl, $C_{4-10}$ cycloalkyl-alkyl, or $C_{1-6}$ alkyl optionally substituted with up to 5 fluoro;

Q is a bicyclic secondary amine with the structure of:

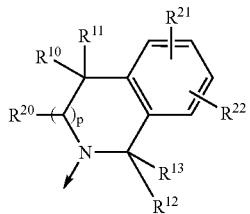

wherein $R^{21}$ and $R^{22}$ are each independently H, halo, cyano, nitro, hydroxy, $C_{1-6}$ alkyl, $C_{3-7}$ cycloalkyl, $C_{4-10}$ cycloalkyl-alkyl, $C_{2-6}$ alkenyl, $C_{1-6}$ alkoxy, hydroxy-$C_{1-6}$ alkyl, $C_{1-6}$ alkyl optionally substituted with up to 5 fluoro, $C_{1-6}$ alkoxy optionally substituted with up to 5 fluoro, $C_{6\ or\ 10}$ aryl, pyridyl, pyrimidyl, thienyl, furanyl, thiazolyl, oxazolyl, phenoxy, thiophenoxy, $S(O)_2NR^6R^7$, $NHC(O)NR^6R^7$, $NHC(S)NR^6R^7$, $C(O)NR^6R^7$, $NR^6R^7$, $C(O)R^8$, $C(O)OR^8$, $NHC(O)R^8$, $NHC(O)OR^8$, $SO_mR^8$ (m=0, 1 or 2), or $NHS(O)_2R^8$; said thienyl, pyrimidyl, furanyl, thiazolyl and oxazolyl in the definition of $R^{21}$ and $R^{22}$ are optionally substituted by up to two halo, cyano, nitro, hydroxy, $C_{1-6}$ alkyl, $C_{3-7}$ cycloalkyl, $C_{4-10}$ cycloalkyl-alkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro; said $C_{6\ or\ 10}$ aryl, pyridyl, phenoxy and thiophenoxy in the definition of $R^{21}$ and $R^{22}$ are optionally substituted by up to three halo, cyano, nitro, hydroxy, $C_{1-6}$ alkyl, $C_{3-7}$ cycloalkyl, $C_{4-10}$ cycloalkyl-alkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro;

wherein $R^{10}$ and $R^{11}$ are each independently H, $C_{1-6}$ alkyl, $C_{3-7}$ cycloalkyl, $C_{4-10}$ cycloalkyl-alkyl, $C_{6\ or\ 10}$ aryl, hydroxy-$C_{1-6}$ alkyl, $C_{1-6}$ alkyl optionally substituted with up to 5 fluoro, $(CH_2)_nNR^6R^7$, or $(CH_2)_nC(O)OR^{14}$ where $R^{14}$ is H, $C_{1-6}$ alkyl, $C_{3-7}$ cycloalkyl, or $C_{4-10}$ cycloalkyl-alkyl, which are all optionally substituted from one to three times with halo, cyano, nitro, hydroxy, $C_{1-6}$ alkoxy, or phenyl; or $R^{14}$ is $C_{6\ or\ 10}$ aryl which is optionally substituted by up to three halo, cyano, nitro, hydroxy, $C_{1-6}$ alkyl, $C_{3-7}$ cycloalkyl, $C_{4-10}$ cycloalkyl-alkyl, $C_{2-6}$ alkenyl, $C_{1-6}$ alkoxy, hydroxy-$C_{1-6}$ alkyl, $C_{1-6}$ alkyl optionally substituted with up to 5 fluoro, $C_{1-6}$ alkoxy optionally substituted with up to 5 fluoro; said $C_{6\ or\ 10}$ aryl, in the definition of $R^{12}$ and $R^{13}$ is optionally substituted by up to three halo, cyano, nitro, hydroxy, $C_{1-6}$ alkyl, $C_{3-7}$ cycloalkyl, $C_{4-10}$ cycloalkyl-alkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro; or $R^{10}$ and $R^{11}$ are taken together with the carbon to which they are attached to form cyclopropyl, cyclobutyl, cyclopentyl, or cyclohexyl; or $R^{10}$ and $R^{11}$ are combined as O;

wherein p=0 or 1;

wherein $R^{12}$ and $R^{13}$ are each independently H, $C_{1-6}$ alkyl, $C_{3-7}$ cycloalkyl, $C_{4-10}$ cycloalkyl-alkyl, $C_{6\ or\ 10}$ aryl, hydroxy-$C_{1-6}$ alkyl, $C_{1-6}$ alkyl optionally substituted with up to 5 fluoro, $(CH_2)_nNR^6R^7$, $(CH_2)_nC(O)OR^{14}$ where $R^{14}$ is H, $C_{1-6}$ alkyl, $C_{3-7}$ cycloalkyl, or $C_{4-10}$ cycloalkyl-alkyl, which are all optionally substituted from one to three times with halo, cyano, nitro, hydroxy, $C_{1-6}$ alkoxy, or phenyl; or $R^{14}$ is $C_{6\ or\ 10}$ aryl which is optionally substituted by up to three halo, cyano, nitro, hydroxy, $C_{1-6}$ alkyl, $C_{3-7}$ cycloalkyl, $C_{4-10}$ cycloalkyl-alkyl, $C_{2-6}$ alkenyl, $C_{1-6}$ alkoxy, hydroxy-$C_{1-6}$ alkyl, $C_{1-6}$ alkyl optionally substituted with up to 5 fluoro, $C_{1-6}$ alkoxy optionally substituted with up to 5 fluoro; said $C_{6\ or\ 10}$ aryl, in the definition of $R^{12}$ and $R^{13}$ is optionally substituted by up to three halo, cyano, nitro, hydroxy, $C_{1-6}$ alkyl, $C_{3-7}$ cycloalkyl, $C_{4-10}$ cycloalkyl-alkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro; or $R^{12}$ and $R^{13}$ are taken together with the carbon to which they are attached to form cyclopropyl, cyclobutyl, cyclopentyl, or cyclohexyl;

wherein $R^{20}$ is H, $C_{1-6}$ alkyl, $C_{3-7}$ cycloalkyl, $C_{4-10}$ cycloalkyl-alkyl, $C_{6\ or\ 10}$ aryl, hydroxy-$C_{1-6}$ alkyl, $C_{1-6}$ alkyl optionally substituted with up to 5 fluoro, $(CH_2)_nNR^6R^7$, or $(CH_2)_nC(O)OR^4$ where $R^{14}$ is H, $C_{1-6}$ alkyl, $C_{3-7}$ cycloalkyl, or $C_{4-10}$ cycloalkyl-alkyl, which are all optionally substituted from one to three times with halo, cyano, nitro, hydroxy, $C_{1-6}$ alkoxy, or phenyl; or $R^{14}$ is $C_{6\ or\ 10}$ aryl which is optionally substituted by up to three halo, cyano, nitro, hydroxy, $C_{1-6}$ alkyl, $C_{3-7}$ cycloalkyl, $C_{4-10}$ cycloalkyl-alkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro; said $C_{6\ or\ 10}$ aryl, in the definition of $R^{12}$ and $R^{13}$ is optionally substituted by up to three halo, cyano, nitro, hydroxy, $C_{1-6}$ alkyl, $C_{3-7}$ cycloalkyl, $C_{4-10}$ cycloalkyl-alkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro;

wherein n=0-4;

wherein $R^6$ and $R^7$ are each independently H, $C_{1-6}$ alkyl, $C_{3-7}$ cycloalkyl, $C_{4-10}$ cycloalkyl-alkyl, or phenyl, said phenyl optionally substituted by up to three halo, cyano, nitro, hydroxy, $C_{1-6}$ alkyl, $C_{3-7}$ cycloalkyl, $C_{4-10}$ cycloalkyl-alkyl, $C_{2-6}$ alkenyl, hydroxy-$C_{1-6}$ alkyl, $C_{1-6}$ alkyl optionally substituted with up to 5 fluoro, or $C_{1-6}$ alkoxy optionally substituted with up to 5 fluoro; or $R^6$ and $R^7$ are taken together with the nitrogen to which they are attached to form indolinyl, pyrrolidinyl, piperidinyl, piperazinyl, or morpholinyl;

or $R^2$ is $R^{2a}R^{2b}$ when W=NH and V=O, wherein $R^{2a}$ is $C_{1-6}$ alkyl, $C_{3-7}$ cycloalkyl, $C_{4-10}$ cycloalkyl-alkyl, phenyl, pyridine, pyrazine, pyrimidine, pyridazine, pyrrole, furan, thiophene, thiazole, oxazole, imidazole, isoxazole, pyrazole, isothiazole, naphthyl, quinoline, isoquinoline, quinoxaline, benzothiazole, benzothiophene, benzofuran, indole, or benzimidazole, each optionally substituted with up to three $NR^{2c}R^{2d}$, halo, cyano, nitro, hydroxy, $C_{1-6}$ alkyl, $C_{3-7}$ cycloalkyl, $C_{4-10}$ cycloalkyl-alkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro;

$R^{2b}$ is H, phenyl, pyridine, pyrazine, pyrimidine, pyridazine, pyrrole, furan, thiophene, thiazole, oxazole, imidazole, isoxazole, pyrazole, isothiazole, naphthyl, quinoline, isoquinoline, quinoxaline, benzothiazole, benzothiophene, benzofuran, indole, or benzimidazole, each optionally substituted with up to three $NR^{2c}R^{2d}$, halo, cyano, nitro, hydroxy, $C_{1-6}$ alkyl, $C_{3-7}$ cycloalkyl, $C_{4-10}$ cycloalkyl-alkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro;

said $R^{2c}$ and $R^{2d}$ are each independently H, $C_{1-6}$ alkyl, $C_{3-7}$ cycloalkyl, $C_{4-10}$ cycloalkyl-alkyl, or phenyl, said phenyl optionally substituted by up to three halo, cyano, nitro, hydroxy, $C_{1-6}$ alkyl, $C_{3-7}$ cycloalkyl, $C_{4-10}$ cycloalkyl-alkyl, $C_{2-6}$ alkenyl, hydroxy-$C_{1-6}$ alkyl, $C_{1-6}$ alkyl optionally substituted with up to 5 fluoro, or $C_{1-6}$ alkoxy optionally substituted with up to 5 fluoro; or $R^{2c}$ and $R^{2d}$ are taken together with the nitrogen to which they are attached to form indolinyl, pyrrolidinyl, piperidinyl, piperazinyl, or morpholinyl;

Z is a $C_{5-7}$ saturated or unsaturated chain containing one or two heteroatoms selected from O, S, or $NR^6$;

$R^4$ is H, $C_{1-6}$ alkyl, $C_{3-7}$ cycloalkyl, $C_{4-10}$ cycloalkyl-alkyl, or phenyl, said phenyl optionally substituted by up to three halo, cyano, nitro, hydroxy, $C_{1-6}$ alkyl, $C_{3-7}$ cycloalkyl, $C_{4-10}$ cycloalkyl-alkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro;

$R^5$ is H, $C_{1-6}$ alkyl, $C(O)NR^6R^7$, $C(S)NR^6R^7$, $C(O)R^8$, $C(O)OR^8$, or $S(O)_2R^8$;

$R^8$ is $C_{1-6}$ alkyl, $C_{3-7}$ cycloalkyl, or $C_{4-10}$ cycloalkyl-alkyl, which are all optionally substituted from one to three times with halo, cyano, nitro, hydroxy, $C_{1-6}$ alkoxy, or phenyl; or $R^8$ is $C_{6\ or\ 10}$ aryl which is optionally substituted by up to three halo, cyano, nitro, hydroxy, $C_{1-6}$ alkyl, $C_{3-7}$ cycloalkyl, $C_{4-10}$ cycloalkyl-alkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro; and the dashed line represents an optional double bond.

The present embodiments provide compounds having the Formula VIIId:

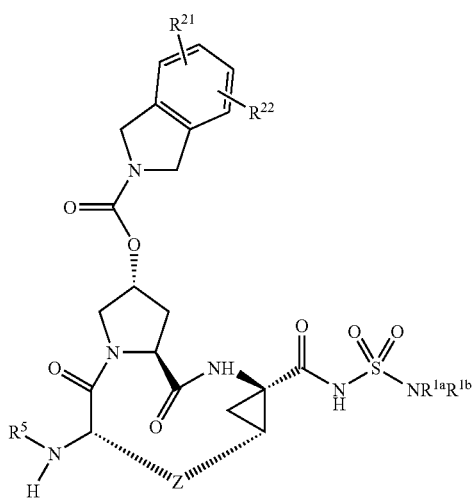

(VIIId)

or a pharmaceutically acceptable salt, prodrug, or ester thereof wherein:

(a) $R^{1a}$ and $R^{1b}$ are each independently H, $C_{1-6}$ alkyl, $C_{3-7}$ cycloalkyl, or $C_{4-10}$ cycloalkyl-alkyl, which are all optionally substituted from one to three times with halo, cyano, nitro, $C_{1-6}$ alkoxy, amido, or phenyl;

or $R^{1a}$ and $R^{1b}$ are each independently H or heteroaryl selected from the group consisting of:

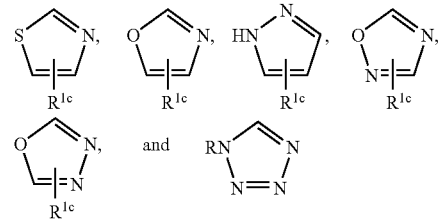

wherein $R^{1c}$ is H, halo, $C_{1-6}$ alkyl, $C_{3-6}$ cycloalkyl, $C_{1-6}$ alkoxy, $C_{3-6}$ cycloalkoxy, $NO_2$, $N(R^{1d})_2$, $NH(CO)R^{1d}$, or $NH(CO)NHR^{1d}$, wherein each $R^{1d}$ is independently H, $C_{1-6}$ alkyl, or $C_{3-6}$ cycloalkyl;

or $NR^{1a}R^{1b}$ is a three- to six-membered alkyl cyclic secondary amine, which optionally has one to three hetero atoms incorporated in the ring, and which is optionally substituted from one to three times with halo, cyano, nitro, $C_{1-6}$ alkoxy, amido, or phenyl;

(b) $R^{21}$ and $R^{22}$ are each independently H, halo, cyano, hydroxy, $C_{1-3}$ alkyl, or $C_{1-3}$ alkoxy;

(c) $R^5$ is H, $C(O)NR^6R^7$, $C(O)R^8$, or $C(O)OR^8$;

(d) $R^6$ and $R^7$ are each independently H, $C_{1-6}$ alkyl, $C_{3-7}$ cycloalkyl, $C_{4-10}$ cycloalkyl-alkyl, or phenyl;

(e) $R^8$ is $C_{1-6}$ alkyl, $C_{3-7}$ cycloalkyl, $C_{4-10}$ cycloalkyl-alkyl, or 3-tetrahydrofuryl; and (f) the dashed line represents an optional double bond.

The present embodiments provide compounds having the general Formula VIIIe:

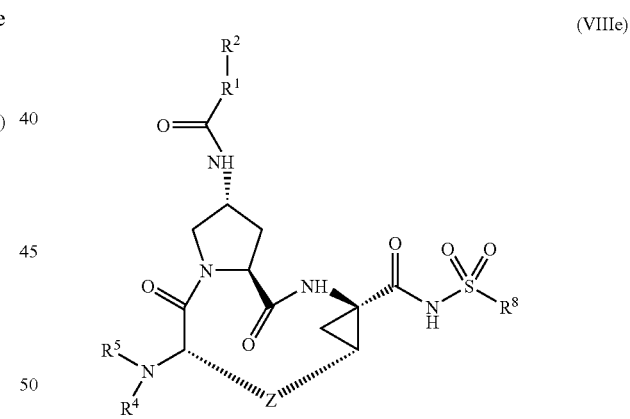

(VIIIe)

or a pharmaceutically acceptable salt, prodrug, or ester thereof wherein:

$R^1$ is $C_{1-6}$ alkyl, $C_{3-7}$ cycloalkyl, $C_{4-10}$ cycloalkyl-alkyl, phenyl, pyridine, pyrazine, pyrimidine, pyridazine, pyrrole, furan, thiophene, thiazole, oxazole, imidazole, isoxazole, pyrazole, isothiazole, naphthyl, quinoline, isoquinoline, quinoxaline, benzothiazole, benzothiophene, benzofuran, indole, or benzimidazole, each optionally substituted with up to three $NR^5R^6$, halo, cyano, nitro, hydroxy, $C_{1-6}$ alkyl, $C_{3-7}$ cycloalkyl, $C_{4-10}$ cycloalkyl-alkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro;

$R^2$ is H, phenyl, pyridine, pyrazine, pyrimidine, pyridazine, pyrrole, furan, thiophene, thiazole, oxazole, imidazole, isoxazole, pyrazole, isothiazole, naphthyl, quinoline, isoquinoline, quinoxaline, benzothiazole, benzothiophene, benzofuran, indole, or benzimidazole, each optionally substituted with up to three $NR^5R^6$, halo, cyano, nitro, hydroxy, $C_{1-6}$ alkyl, $C_{3-7}$ cycloalkyl, $C_{4-10}$ cycloalkyl-alkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro;

$R^3$ is H, $C_{1-6}$ alkyl, $C_{3-7}$ cycloalkyl, $C_{4-10}$ cycloalkyl-alkyl or phenyl, said phenyl optionally substituted by up to three halo, cyano, nitro, hydroxy, $C_{1-6}$ alkyl, $C_{3-7}$ cycloalkyl, $C_{4-10}$ cycloalkyl-alkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro;

Z is a $C_{5-7}$ saturated or unsaturated chain containing one or two heteroatoms selected from O, S, or $NR^6$;

$R^4$ is $C_{1-6}$ alkyl, $C(O)NR^5R^6$, $C(S)NR^5R^6$, $C(O)R^7$, $C(O)OR^7$, or $S(O)_2R^7$;

$R^5$ and $R^6$ are each independently H, $C_{1-6}$ alkyl, $C_{3-7}$ cycloalkyl, $C_{4-10}$ cycloalkyl-alkyl or phenyl, said phenyl optionally substituted by up to three halo, cyano, nitro, hydroxy, $C_{1-6}$ alkyl, $C_{3-7}$ cycloalkyl, $C_{4-10}$ cycloalkyl-alkyl, $C_{2-6}$ alkenyl, hydroxy-$C_{1-6}$ alkyl, or $C_{1-6}$ alkyl optionally substituted with up to 5 fluoro, $C_{1-6}$ alkoxy optionally substituted with up to 5 fluoro; or $R^5$ and $R^6$ are taken together with the nitrogen to which they are attached to form indolinyl, pyrrolidinyl, piperidinyl, piperazinyl, or morpholinyl;

$R^7$ is $C_{1-6}$ alkyl, $C_{3-7}$ cycloalkyl, $C_{4-10}$ cycloalkyl-alkyl, which are all optionally substituted from one to three times with halo, cyano, nitro, hydroxy, $C_{1-6}$ alkoxy, or phenyl; or $R^7$ is $C_{6\ or\ 10}$ aryl which is optionally substituted by up to three halo, cyano, nitro, hydroxy, $C_{1-6}$ alkyl, $C_{3-7}$ cycloalkyl, $C_{4-10}$ cycloalkyl-alkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro;

$R^8$ is $C_{1-3}$ alkyl, $C_{3-4}$ cycloalkyl, or phenyl which is optionally substituted by up to two halo, cyano, hydroxy, $C_{1-3}$ alkyl, or $C_{1-3}$ alkoxy; and the dashed line represents an optional double bond.

The present embodiments provide compounds having the formula IX:

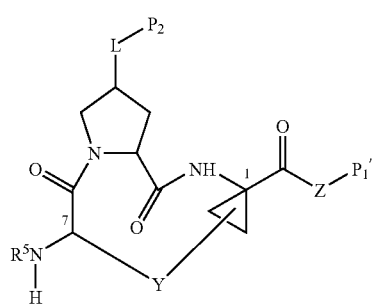

(IX)

or a pharmaceutically acceptable salt, prodrug, or ester thereof wherein:

(a) Z is a group configured to hydrogen bond to an NS3 protease His57 imidazole moiety and to hydrogen bond to a NS3 protease Gly137 nitrogen atom;

(b) $P_1'$ is a group configured to form a non-polar interaction with at least one NS3 protease S1' pocket moiety selected from the group consisting of Lys136, Gly137, Ser139, His57, Gly58, Gln41, Ser42, and Phe43;

(c) L is a linker group consisting of from 1 to 5 atoms selected from the group consisting of carbon, oxygen, nitrogen, hydrogen, and sulfur;

(d) $P_2$ is selected from the group consisting of unsubstituted aryl, substituted aryl, unsubstituted heteroaryl, substituted heteroaryl, unsubstituted heterocyclic and substituted heterocyclic; $P_2$ being positioned by L to form a non-polar interaction with at least one NS3 protease S2 pocket moiety selected from the group consisting of His57, Arg155, Val78, Asp79, Gln80 and Asp81;

(e) $R^5$ is selected from the group consisting of H, $C(O)NR^6R^7$ and $C(O)OR^8$;

(f) $R^6$ and $R^7$ are each independently H, $C_{1-6}$ alkyl, $C_{3-7}$ cycloalkyl, $C_{4-10}$ alkylcycloalkyl or phenyl, said phenyl optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, hydroxy-$C_{1-6}$ alkyl, $C_{1-6}$ alkyl optionally substituted with up to 5 fluoro, $C_{1-6}$ alkoxy optionally substituted with up to 5 fluoro; or $R^6$ and $R^7$ are taken together with the nitrogen to which they are attached to form indolinyl, pyrrolidinyl, piperidinyl, piperazinyl, or morpholinyl;

(g) $R^8$ is $C_{1-6}$ alkyl, $C_{3-7}$ cycloalkyl, $C_{4-10}$ alkylcycloalkyl, which are all optionally substituted from one to three times with halo, cyano, nitro, hydroxy, $C_{1-6}$ alkoxy, or phenyl; or $R^8$ is $C_{6\ or\ 10}$ aryl which is optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, $C_{1-6}$ alkoxy optionally substituted with up to 5 fluoro; or $R^8$ is $C_{1-6}$ alkyl optionally substituted with up to 5 fluoro groups; or $R^8$ is a tetrahydrofuran ring linked through the $C_3$ or $C_4$ position of the tetrahydrofuran ring; or $R^8$ is a tetrahydropyran ring linked through the $C_4$ position of the tetrahydropyran ring;

(h) Y is a $C_{5-7}$ saturated or unsaturated chain containing one or two heteroatoms selected from O, S, or $NR^9$; and (i) $R^9$ and $R^{10}$ are each independently H, $C_{1-6}$ alkyl, $C_{3-7}$ cycloalkyl, $C_{4-10}$ cycloalkyl-alkyl, or substituted or unsubstituted phenyl; or $R^9$ and $R^{10}$ are taken together with the nitrogen to which they are attached to form indolinyl, pyrrolidinyl, piperidinyl, piperazinyl, or morpholinyl.

Also provided herein are compounds containing moieties configured to interact with particular regions, particular amino acid residues, or particular atoms of NS3 protease. Some compounds provided herein contain one or more moieties configured to form a hydrogen bond with NS3 protease at a particular region, amino acid residue, or atom. Some compounds provided herein contain one or more moieties configured to form a non-polar interaction with NS3 protease at a particular region, amino acid residue, or atom. For example, the compound having the general Formula IX may contain one or more moieties that form a hydrogen bond with a peptide backbone atom or side chain moiety located in the substrate binding pocket of NS3 protease. In another example, the compound having the general Formula IX may contain one or more moieties that form non-polar interactions with peptide backbone or side chain atom or atoms located in the substrate binding pocket of NS3 protease. In the compound of formula IX, the dashed line between carbons 13 and 14 may be a single bond or a double bond.

As provided in the compound having the general formula IX, Z may be configured to form a hydrogen bond with a peptide backbone atom or side chain moiety located in the substrate binding pocket of NS3 protease, including, but not limited to, NS3 protease His57 imidazole moiety and NS3 protease Gly137 nitrogen atom. In some instances, Z may be configured to form a hydrogen bond with both the NS3 protease His57 imidazole moiety and the NS3 protease Gly137 nitrogen atom.

The P1' group of the compound having the general formula IX may be configured to form a non-polar interaction with peptide backbone or side chain atom or atoms located in the substrate binding pocket of NS3 protease, including, but not limited to amino acid residues that form the NS3 protease S1' pocket. For example the P1' group may form a non-polar interaction with at least one amino acid selected from Lys136, Gly137, Ser139, His57, Gly58, Gln41, Ser42, and Phe43.

The $P_2$ group of the compound having the general formula IX may be configured to form a non-polar interaction with peptide backbone or side chain atom or atoms located in the substrate binding pocket of NS3 protease, including, but not limited to amino acid residues that form the NS3 protease S2 pocket. For example the $P_2$ group may form a non-polar interaction with at least one amino acid selected from His57, Arg155, Val78, Asp79, Gln80 and Asp81. The $P_2$ group also may be configured to form a hydrogen bond with peptide backbone or side chain atom or atoms located in the substrate binding pocket of NS3 protease, including, but not limited to amino acid residues that form the NS3 protease S2 pocket. For example the $P_2$ group may form a hydrogen bond with at least one amino acid selected from His57, Arg155, Val78, Asp79, Gln80 and Asp81. In some instances, $P_2$ may form both a non-polar interaction and a hydrogen bond with peptide backbone or side chain moieties or atoms located in the substrate binding pocket of NS3 protease, such amino acids selected from His57, Arg155, Val78, Asp79, Gln80 and Asp81. Such hydrogen bond and non-polar interactions may occur with the same amino acid residue or with different amino acid residues in the NS3 protease S2 pocket. In some embodiments, $P_2$ may be selected from the group consisting of unsubstituted aryl, substituted aryl, unsubstituted heteroaryl, substituted heteroaryl, unsubstituted heterocyclic and substituted heterocyclic.

In some embodiments, the position of the $P_2$ group is determined by the linker L. For example, $P_2$ may be positioned by linker L to form a non-polar interaction with peptide backbone or side chain atom or atoms located in the substrate binding pocket of NS3 protease, including, but not limited to amino acid residues that form the NS3 protease S2 pocket. For example the $P_2$ group may be positioned by L to form a non-polar interaction with at least one amino acid selected from His57, Arg155, Val78, Asp79, Gln80 and Asp81. In another example, $P_2$ may be positioned by linker L to form a hydrogen bond with peptide backbone or side chain atom or atoms located in the substrate binding pocket of NS3 protease, including, but not limited to amino acid residues that form the NS3 protease S2 pocket. For example the $P_2$ group may be positioned by L to form a hydrogen bond with at least one amino acid selected from His57, Arg155, Val78, Asp79, Gln80 and Asp81. In some instances, $P_2$ may be positioned to form both a non-polar interaction and a hydrogen bond peptide backbone or side chain atom or atoms located in the substrate binding pocket of NS3 protease, such as an amino acid selected from His57, Arg155, Val78, Asp79, Gln80 and Asp81. Such hydrogen bond and non-polar interactions may occur with the same amino acid residue or with different amino acid residues in the NS3 protease S2 pocket.

As provided in the compound having the general formula IX, L may be a linker group that links $P_2$ to the heterocyclic backbone of the compound of formula IX. Linker L may contain any of a variety of atoms and moieties suitable for positioning $P_2$ in the NS3 protease substrate binding pocket. In one embodiment, L may contain 1 to 5 atoms selected from the group consisting of carbon, oxygen, nitrogen, hydrogen, and sulfur. In another embodiment, L may contain 2 to 5 atoms selected from the group consisting of carbon, oxygen, nitrogen, hydrogen, and sulfur. For example, L may contain a group having the formula —W—C(=V)—, where V and W are each individually selected from O, S or NH. Specific exemplary groups for L include, but are not limited to, ester, amide, carbamate, thioester, and thioamide.

The compound of formula IX also may contain an $R^5$ group, where the $R^5$ group may contain a carboxyl moiety. Exemplary carboxyl moieties of $R^5$ include $C(O)NR^6R^7$ and $C(O)OR^8$ where $R^6$ and $R^7$ are each independently H, $C_{1-6}$ alkyl, $C_{3-7}$ cycloalkyl, $C_{4-10}$ alkylcycloalkyl or phenyl, said phenyl optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, hydroxy-$C_{1-6}$ alkyl, $C_{1-6}$ alkyl optionally substituted with up to 5 fluoro, $C_{1-6}$ alkoxy optionally substituted with up to 5 fluoro; or $R^6$ and $R^7$ are taken together with the nitrogen to which they are attached to form indolinyl, pyrrolidinyl, piperidinyl, piperazinyl, or morpholinyl; and where $R^8$ is $C_{1-6}$ alkyl, $C_{3-7}$ cycloalkyl, $C_{4-10}$ alkylcycloalkyl, which are all optionally substituted from one to three times with halo, cyano, nitro, hydroxy, $C_{1-6}$ alkoxy, or phenyl; or $R^8$ is $C_{6 \text{ or } 10}$ aryl which is optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, $C_{1-6}$ alkoxy optionally substituted with up to 5 fluoro; or $R^8$ is $C_{1-6}$ alkyl optionally substituted with up to 5 fluoro groups; or $R^8$ is a tetrahydrofuran ring linked through the $C_3$ or $C_4$ position of the tetrahydrofuran ring; or $R^8$ is a tetrahydropyran ring linked through the $C_4$ position of the tetrahydropyran ring In some embodiments, several bonds of the compound of formula IX may have a particular chirality. For example, in some embodiments, the compound of formula IX has the structure:

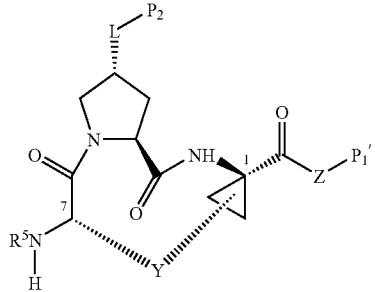

In preferred embodiments, L consists of from 2 to 5 atoms.

In preferred embodiments, L comprises a —W—C(=V)— group, where V and W are each individually selected from O, S or NH.

In preferred embodiments, L is selected from the group consisting of ester, amide, carbamate, thioester, and thioamide.

In preferred embodiments, $P_2$ is further positioned by L to form a hydrogen bonding interaction with at least one NS3 protease S2 pocket moiety selected from the group consisting of His57, Arg155, Val78, Asp79, Gln80 and Asp81.

In preferred embodiments, $P_2$ is

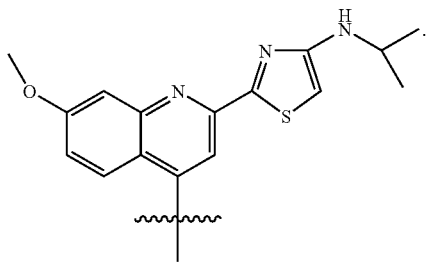

In preferred embodiments, compounds of formula IX have the structure:

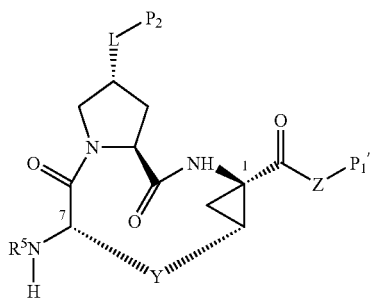

Compounds of the Formula IX may be prepared in the same general manner as the compounds of the Formulas Ia-XIIIe.

The present embodiments provide for a method of inhibiting NS3/NS4 protease activity comprising contacting a NS3/NS4 protease with a compound disclosed herein.

The present embodiments provide for a method of treating hepatitis by modulating NS3/NS4 protease comprising contacting a NS3/NS4 protease with a compound disclosed herein.

Exemplary compounds of Formula Ia, Ib, II, III, IV, V, VI, VII, VIII, VIIIa, VIIIb, VIIIc, VIIId, VIIIe, and IX are set forth in Tables 1 through 8 and compounds 100, 701-706, 801, 922, 927, 2001-2011, 2101-2154, 2201-2252, 2301-2322, 2401-2404, 2501-2502, and 2601-2604 below.

Preferred compounds include Compounds 100-1032 and 2001-2322.

Preferred embodiments provide a method of treating a hepatitis C virus infection in an individual, the method comprising administering to the individual an effective amount of a composition comprising a preferred compound.

Preferred embodiments provide a method of treating liver fibrosis in an individual, the method comprising administering to the individual an effective amount of a composition comprising a preferred compound.

Preferred embodiments provide a method of increasing liver function in an individual having a hepatitis C virus infection, the method comprising administering to the individual an effective amount of a composition comprising a preferred compound.

The present embodiments further provide compositions, including pharmaceutical compositions, comprising compounds of the general Formula Ia, Ib, II, III, IV, V, VI, VII, VIII, VIIIa, VIIIb, VIIIc, VIIId, VIIIe, or IX, including salts, esters, or other derivatives thereof. The present embodiments further provide compositions, including pharmaceutical compositions, comprising compounds of the general Formula Ia, including salts, esters, or other derivatives thereof. A subject pharmaceutical composition comprises a subject compound; and a pharmaceutically acceptable excipient. A wide variety of pharmaceutically acceptable excipients is known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In many embodiments, a subject compound inhibits the enzymatic activity of a hepatitis virus C (HCV) NS3 protease. Whether a subject compound inhibits HCV NS3 protease can be readily determined using any known method. Typical methods involve a determination of whether an HCV polyprotein or other polypeptide comprising an NS3 recognition site is cleaved by NS3 in the presence of the agent. In many embodiments, a subject compound inhibits NS3 enzymatic activity by at least about 10%, at least about 15%, at least about 20%, at least about 25%, at least about 30%, at least about 40%, at least about 50%, at least about 60%, at least about 70%, at least about 80%, or at least about 90%, or more, compared to the enzymatic activity of NS3 in the absence of the compound.

In many embodiments, a subject compound inhibits enzymatic activity of an HCV NS3 protease with an $IC_{50}$ of less than about 50 µM, e.g., a subject compound inhibits an HCV NS3 protease with an $IC_{50}$ of less than about 40 µM, less than about 25 µM, less than about 10 µM, less than about 1 µM, less than about 100 nM, less than about 80 nM, less than about 60 nM, less than about 50 nM, less than about 25 nM, less than about 10 nM, or less than about 1 nM, or less.

In many embodiments, a subject compound inhibits the enzymatic activity of a hepatitis virus C (HCV) NS3 helicase. Whether a subject compound inhibits HCV NS3 helicase can be readily determined using any known method. In many embodiments, a subject compound inhibits NS3 enzymatic activity by at least about 10%, at least about 15%, at least about 20%, at least about 25%, at least about 30%, at least about 40%, at least about 50%, at least about 60%, at least about 70%, at least about 80%, or at least about 90%, or more, compared to the enzymatic activity of NS3 in the absence of the compound.

In many embodiments, a subject compound inhibits HCV viral replication. For example, a subject compound inhibits HCV viral replication by at least about 10%, at least about 15%, at least about 20%, at least about 25%, at least about 30%, at least about 40%, at least about 50%, at least about 60%, at least about 70%, at least about 80%, or at least about 90%, or more, compared to HCV viral replication in the absence of the compound. Whether a subject compound inhibits HCV viral replication can be determined using methods known in the art, including an in vitro viral replication assay.

Treating a Hepatitis Virus Infection

The methods and compositions described herein are generally useful in treatment of an of HCV infection.

Whether a subject method is effective in treating an HCV infection can be determined by a reduction in viral load, a reduction in time to seroconversion (virus undetectable in patient serum), an increase in the rate of sustained viral response to therapy, a reduction of morbidity or mortality in clinical outcomes, or other indicator of disease response.

In general, an effective amount of a compound of Formula I, and optionally one or more additional antiviral agents, is an amount that is effective to reduce viral load or achieve a sustained viral response to therapy.

Whether a subject method is effective in treating an HCV infection can be determined by measuring viral load, or by measuring a parameter associated with HCV infection, including, but not limited to, liver fibrosis, elevations in serum transaminase levels, and necroinflammatory activity in the liver. Indicators of liver fibrosis are discussed in detail below.

The method involves administering an effective amount of a compound of Formula I, optionally in combination with an effective amount of one or more additional antiviral agents. In some embodiments, an effective amount of a compound of Formula I, and optionally one or more additional antiviral agents, is an amount that is effective to reduce viral titers to undetectable levels, e.g., to about 1000 to about 5000, to about 500 to about 1000, or to about 100 to about 500 genome copies/mL serum. In some embodiments, an effective amount of a compound of Formula I, and optionally one or more additional antiviral agents, is an amount that is effective to reduce viral load to lower than 100 genome copies/mL serum.

In some embodiments, an effective amount of a compound of Formula Ia, Ib, II, III, IV, V, VI, VII, VIII, VIIIa, VIIIb, VIIIc, VIIId, VIIIe, or IX, and optionally one or more additional antiviral agents, is an amount that is effective to achieve a 1.5-log, a 2-log, a 2.5-log, a 3-log, a 3.5-log, a 4-log, a 4.5-log, or a 5-log reduction in viral titer in the serum of the individual.

In many embodiments, an effective amount of a compound of Formula I, and optionally one or more additional antiviral agents, is an amount that is effective to achieve a sustained viral response, e.g., non-detectable or substantially non-detectable HCV RNA (e.g., less than about 500, less than about 400, less than about 200, or less than about 100 genome copies per milliliter serum) is found in the patient's serum for a period of at least about one month, at least about two months, at least about three months, at least about four months, at least about five months, or at least about six months following cessation of therapy.

As noted above, whether a subject method is effective in treating an HCV infection can be determined by measuring a parameter associated with HCV infection, such as liver fibrosis. Methods of determining the extent of liver fibrosis are discussed in detail below. In some embodiments, the level of a serum marker of liver fibrosis indicates the degree of liver fibrosis.

As one non-limiting example, levels of serum alanine aminotransferase (ALT) are measured, using standard assays. In general, an ALT level of less than about 45 international units is considered normal. In some embodiments, an effective amount of a compound of formula I, and optionally one or more additional antiviral agents, is an amount effective to reduce ALT levels to less than about 45 IU/ml serum.

A therapeutically effective amount of a compound of Formula Ia, Ib, II, III, IV, V, VI, VII, VIII, VIIIa, VIIIb, VIIIc, VIIId, VIIIe, or IX, and optionally one or more additional antiviral agents, is an amount that is effective to reduce a serum level of a marker of liver fibrosis by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%, or more, compared to the level of the marker in an untreated individual, or to a placebo-treated individual. Methods of measuring serum markers include immunological-based methods, e.g., enzyme-linked immunosorbent assays (ELISA), radioimmunoassays, and the like, using antibody specific for a given serum marker.

In many embodiments, an effective amount of a compound of Formula Ia, Ib, II, III, IV, V, VI, VII, VIII, VIIIa, VIIIb, VIIIc, VIIId, VIIIe, or IX and an additional antiviral agent is a synergistic amount. As used herein, a "synergistic combination" or a "synergistic amount" of a compound of Formula Ia, Ib, II, III, IV, V, VI, VII, VIII, VIIIa, VIIIb, VIIIc, VIIId, VIIIe, or IX and an additional antiviral agent is a combined dosage that is more effective in the therapeutic or prophylactic treatment of an HCV infection than the incremental improvement in treatment outcome that could be predicted or expected from a merely additive combination of (i) the therapeutic or prophylactic benefit of the compound of Formula Ia, Ib, II, III, IV, V, VI, VII, VIII, VIIIa, VIIIb, VIIIc, VIIId, VIIIe, or IX when administered at that same dosage as a monotherapy and (ii) the therapeutic or prophylactic benefit of the additional antiviral agent when administered at the same dosage as a monotherapy.

In some embodiments, a selected amount of a compound of Formula Ia, Ib, II, III, IV, V, VI, VII, VIII, VIIIa, VIIIb, VIIIc, VIIId, VIIIe, or IX and a selected amount of an additional antiviral agent are effective when used in combination therapy for a disease, but the selected amount of the compound of Formula Ia, Ib, II, III, IV, V, VI, VII, VIII, VIIIa, VIIIb, VIIIc, VIIId, VIIIe, or IX and/or the selected amount of the additional antiviral agent is ineffective when used in monotherapy for the disease. Thus, the embodiments encompass (1) regimens in which a selected amount of the additional antiviral agent enhances the therapeutic benefit of a selected amount of the compound of Formula Ia, Ib, II, III, IV, V, VI, VII, VIII, VIIIa, VIIIb, VIIIc, VIIId, VIIIe, or IX when used in combination therapy for a disease, where the selected amount of the additional antiviral agent provides no therapeutic benefit when used in monotherapy for the disease (2) regimens in which a selected amount of the compound of Formula Ia, Ib, II, III, IV, V, VI, VII, VIII, VIIIa, VIIIb, VIIIc, VIIId, VIIIe, or IX enhances the therapeutic benefit of a selected amount of the additional antiviral agent when used in combination therapy for a disease, where the selected amount of the compound of Formula Ia, Ib, II, III, IV, V, VI, VII, VIII, VIIIa, VIIIb, VIIIc, VIIId, VIIIe, or IX provides no therapeutic benefit when used in monotherapy for the disease and (3) regimens in which a selected amount of the compound of Formula Ia, Ib, II, III, IV, V, VI, VII, VIII, VIIIa, VIIIb, VIIIc, VIIId, VIIIe, or IX and a selected amount of the additional antiviral agent provide a therapeutic benefit when used in combination therapy for a disease, where each of the selected amounts of the compound of Formula Ia, Ib, II, III, IV, V, VI, VII, VIII, VIIIa, VIIIb, VIIIc, VIIId, VIIIe, or IX and the additional antiviral agent, respectively, provides no therapeutic benefit when used in monotherapy for the disease. As used herein, a "synergistically effective amount" of a compound of Formula Ia, Ib, II, III, IV, V, VI, VII, VIII, VIIIa, VIIIb, VIIIc, VIIId, VIIIe, or IX and an additional antiviral agent, and its grammatical equivalents, shall be understood to include any regimen encompassed by any of (1)-(3) above.

Fibrosis

The embodiments provides methods for treating liver fibrosis (including forms of liver fibrosis resulting from, or associated with, HCV infection), generally involving administering a therapeutic amount of a compound of Formula I, and optionally one or more additional antiviral agents. Effective amounts of compounds of Formula I, with and without one or more additional antiviral agents, as well as dosing regimens, are as discussed below.

Whether treatment with a compound of Formula I, and optionally one or more additional antiviral agents, is effective in reducing liver fibrosis is determined by any of a number of well-established techniques for measuring liver fibrosis and liver function. Liver fibrosis reduction is determined by analyzing a liver biopsy sample. An analysis of a liver biopsy comprises assessments of two major components: necroinflammation assessed by "grade" as a measure of the severity and ongoing disease activity, and the lesions of fibrosis and parenchymal or vascular remodeling as assessed by "stage" as being reflective of long-term disease progression. See, e.g., Brunt (2000) Hepatol. 31:241-246; and METAVIR (1994) Hepatology 20:15-20. Based on analysis of the liver biopsy, a score is assigned. A number of standardized scoring systems exist which provide a quantitative assessment of the degree and severity of fibrosis. These include the METAVIR, Knodell, Scheuer, Ludwig, and Ishak scoring systems.

The METAVIR scoring system is based on an analysis of various features of a liver biopsy, including fibrosis (portal fibrosis, centrilobular fibrosis, and cirrhosis); necrosis (piecemeal and lobular necrosis, acidophilic retraction, and ballooning degeneration); inflammation (portal tract inflammation, portal lymphoid aggregates, and distribution of portal inflammation); bile duct changes; and the Knodell index (scores of periportal necrosis, lobular necrosis, portal inflammation, fibrosis, and overall disease activity). The definitions of each stage in the METAVIR system are as follows: score: 0, no fibrosis; score: 1, stellate enlargement of portal tract but without septa formation; score: 2, enlargement of portal tract with rare septa formation; score: 3, numerous septa without cirrhosis; and score: 4, cirrhosis.

Knodell's scoring system, also called the Hepatitis Activity Index, classifies specimens based on scores in four categories of histologic features: I. Periportal and/or bridging necrosis; II. Intralobular degeneration and focal necrosis; III. Portal inflammation; and IV. Fibrosis. In the Knodell staging system, scores are as follows: score: 0, no fibrosis; score: 1, mild fibrosis (fibrous portal expansion); score: 2, moderate fibrosis; score: 3, severe fibrosis (bridging fibrosis); and score: 4, cirrhosis. The higher the score, the more severe the liver tissue damage. Knodell (1981) Hepatol. 1:431.

In the Scheuer scoring system scores are as follows: score: 0, no fibrosis; score: 1, enlarged, fibrotic portal tracts; score: 2, periportal or portal-portal septa, but intact architecture; score: 3, fibrosis with architectural distortion, but no obvious cirrhosis; score: 4, probable or definite cirrhosis. Scheuer (1991) J. Hepatol. 13:372.

The Ishak scoring system is described in Ishak (1995) J. Hepatol. 22:696-699. Stage 0, No fibrosis; Stage 1, Fibrous expansion of some portal areas, with or without short fibrous septa; stage 2, Fibrous expansion of most portal areas, with or without short fibrous septa; stage 3, Fibrous expansion of most portal areas with occasional portal to portal (P-P) bridging; stage 4, Fibrous expansion of portal areas with marked bridging (P-P) as well as portal-central (P-C); stage 5, Marked bridging (P-P and/or P-C) with occasional nodules (incomplete cirrhosis); stage 6, Cirrhosis, probable or definite.

The benefit of anti-fibrotic therapy can also be measured and assessed by using the Child-Pugh scoring system which comprises a multicomponent point system based upon abnormalities in serum bilirubin level, serum albumin level, prothrombin time, the presence and severity of ascites, and the presence and severity of encephalopathy. Based upon the presence and severity of abnormality of these parameters, patients may be placed in one of three categories of increasing severity of clinical disease: A, B, or C.

In some embodiments, a therapeutically effective amount of a compound of formula I, and optionally one or more additional antiviral agents, is an amount that effects a change of one unit or more in the fibrosis stage based on pre- and post-therapy liver biopsies. In particular embodiments, a therapeutically effective amount of a compound of formula I, and optionally one or more additional antiviral agents, reduces liver fibrosis by at least one unit in the METAVIR, the Knodell, the Scheuer, the Ludwig, or the Ishak scoring system.

Secondary, or indirect, indices of liver function can also be used to evaluate the efficacy of treatment with a compound of Formula I. Morphometric computerized semi-automated assessment of the quantitative degree of liver fibrosis based upon specific staining of collagen and/or serum markers of liver fibrosis can also be measured as an indication of the efficacy of a subject treatment method. Secondary indices of liver function include, but are not limited to, serum transaminase levels, prothrombin time, bilirubin, platelet count, portal pressure, albumin level, and assessment of the Child-Pugh score.

An effective amount of a compound of Formula I, and optionally one or more additional antiviral agents, is an amount that is effective to increase an index of liver function by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%, or more, compared to the index of liver function in an untreated individual, or to a placebo-treated individual. Those skilled in the art can readily measure such indices of liver function, using standard assay methods, many of which are commercially available, and are used routinely in clinical settings.

Serum markers of liver fibrosis can also be measured as an indication of the efficacy of a subject treatment method. Serum markers of liver fibrosis include, but are not limited to, hyaluronate, N-terminal procollagen III peptide, 7S domain of type IV collagen, C-terminal procollagen I peptide, and laminin. Additional biochemical markers of liver fibrosis include α-2-macroglobulin, haptoglobin, gamma globulin, apolipoprotein A, and gamma glutamyl transpeptidase.

A therapeutically effective amount of a compound of Formula I, and optionally one or more additional antiviral agents, is an amount that is effective to reduce a serum level of a marker of liver fibrosis by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%, or more, compared to the level of the marker in an untreated individual, or to a placebo-treated individual. Those skilled in the art can readily measure such serum markers of liver fibrosis, using standard assay methods, many of which are commercially available, and are used routinely in clinical settings. Methods of measuring serum markers include immunological-based methods, e.g., enzyme-linked immunosorbent assays (ELISA), radioimmunoassays, and the like, using antibody specific for a given serum marker.

Quantitative tests of functional liver reserve can also be used to assess the efficacy of treatment with an interferon receptor agonist and pirfenidone (or a pirfenidone analog). These include: indocyanine green clearance (ICG), galactose elimination capacity (GEC), aminopyrine breath test (ABT), antipyrine clearance, monoethylglycine-xylidide (MEG-X) clearance, and caffeine clearance.

As used herein, a "complication associated with cirrhosis of the liver" refers to a disorder that is a sequellae of decompensated liver disease, i.e., or occurs subsequently to and as a result of development of liver fibrosis, and includes, but it not limited to, development of ascites, variceal bleeding, portal hypertension, jaundice, progressive liver insufficiency, encephalopathy, hepatocellular carcinoma, liver failure requiring liver transplantation, and liver-related mortality.

A therapeutically effective amount of a compound of Formula I, and optionally one or more additional antiviral agents, is an amount that is effective in reducing the incidence (e.g., the likelihood that an individual will develop) of a disorder associated with cirrhosis of the liver by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%, or more, compared to an untreated individual, or to a placebo-treated individual.

Whether treatment with a compound of Formula I, and optionally one or more additional antiviral agents, is effective in reducing the incidence of a disorder associated with cirrhosis of the liver can readily be determined by those skilled in the art.

Reduction in liver fibrosis increases liver function. Thus, the embodiments provide methods for increasing liver function, generally involving administering a therapeutically effective amount of a compound of Formula I, and optionally one or more additional antiviral agents. Liver functions include, but are not limited to, synthesis of proteins such as serum proteins (e.g., albumin, clotting factors, alkaline phosphatase, aminotransferases (e.g., alanine transaminase, aspartate transaminase), 5'-nucleosidase, γ-glutaminyl-transpeptidase, etc.), synthesis of bilirubin, synthesis of cholesterol, and synthesis of bile acids; a liver metabolic function, including, but not limited to, carbohydrate metabolism, amino acid and ammonia metabolism, hormone metabolism, and lipid metabolism; detoxification of exogenous drugs; a hemodynamic function, including splanchnic and portal hemodynamics; and the like.

Whether a liver function is increased is readily ascertainable by those skilled in the art, using well-established tests of liver function. Thus, synthesis of markers of liver function such as albumin, alkaline phosphatase, alanine transaminase, aspartate transaminase, bilirubin, and the like, can be assessed by measuring the level of these markers in the serum, using standard immunological and enzymatic assays. Splanchnic circulation and portal hemodynamics can be measured by portal wedge pressure and/or resistance using standard methods. Metabolic functions can be measured by measuring the level of ammonia in the serum.

Whether serum proteins normally secreted by the liver are in the normal range can be determined by measuring the levels of such proteins, using standard immunological and enzymatic assays. Those skilled in the art know the normal ranges for such serum proteins. The following are non-limiting examples. The normal level of alanine transaminase is about 45 IU per milliliter of serum. The normal range of aspartate transaminase is from about 5 to about 40 units per liter of serum. Bilirubin is measured using standard assays. Normal bilirubin levels are usually less than about 1.2 mg/dL. Serum albumin levels are measured using standard assays. Normal levels of serum albumin are in the range of from about 35 to about 55 g/L. Prolongation of prothrombin time is measured using standard assays. Normal prothrombin time is less than about 4 seconds longer than control.

A therapeutically effective amount of a compound of Formula I, and optionally one or more additional antiviral agents, is one that is effective to increase liver function by at least about 10%, at least about 20%, at least about 30%, at least about 40%, at least about 50%, at least about 60%, at least about 70%, at least about 80%, or more. For example, a therapeutically effective amount of a compound of Formula I, and optionally one or more additional antiviral agents, is an amount effective to reduce an elevated level of a serum marker of liver function by at least about 10%, at least about 20%, at least about 30%, at least about 40%, at least about 50%, at least about 60%, at least about 70%, at least about 80%, or more, or to reduce the level of the serum marker of liver function to within a normal range. A therapeutically effective amount of a compound of Formula I, and optionally one or more additional antiviral agents, is also an amount effective to increase a reduced level of a serum marker of liver function by at least about 10%, at least about 20%, at least about 30%, at least about 40%, at least about 50%, at least about 60%, at least about 70%, at least about 80%, or more, or to increase the level of the serum marker of liver function to within a normal range.

Dosages, Formulations, and Routes of Administration

In the subject methods, the active agent(s) (e.g., compound of Formula I, and optionally one or more additional antiviral agents) may be administered to the host using any convenient means capable of resulting in the desired therapeutic effect. Thus, the agent can be incorporated into a variety of formulations for therapeutic administration. More particularly, the agents of the embodiments can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

Formulations

The above-discussed active agent(s) can be formulated using well-known reagents and methods. Compositions are provided in formulation with a pharmaceutically acceptable excipient(s). A wide variety of pharmaceutically acceptable excipients is known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In some embodiments, an agent is formulated in an aqueous buffer. Suitable aqueous buffers include, but are not limited to, acetate, succinate, citrate, and phosphate buffers varying in strengths from about 5 mM to about 100 mM. In some embodiments, the aqueous buffer includes reagents that provide for an isotonic solution. Such reagents include, but are not limited to, sodium chloride; and sugars e.g., mannitol, dextrose, sucrose, and the like. In some embodiments, the aqueous buffer further includes a non-ionic surfactant such as polysorbate 20 or 80. Optionally the formulations may further include a preservative. Suitable preservatives include, but are not limited to, a benzyl alcohol, phenol, chlorobutanol, benzalkonium chloride, and the like. In many cases, the formulation is stored at about 4° C. Formulations may also be lyophilized, in which case they generally include cryoprotectants such as sucrose, trehalose, lactose, maltose, mannitol, and the like. Lyophilized formulations can be stored over extended periods of time, even at ambient temperatures.

As such, administration of the agents can be achieved in various ways, including oral, buccal, rectal, parenteral, intraperitoneal, intradermal, subcutaneous, intramuscular, transdermal, intratracheal, etc., administration. In many embodiments, administration is by bolus injection, e.g., subcutaneous bolus injection, intramuscular bolus injection, and the like.

The pharmaceutical compositions of the embodiments can be administered orally, parenterally or via an implanted reservoir. Oral administration or administration by injection is preferred.

Subcutaneous administration of a pharmaceutical composition of the embodiments is accomplished using standard methods and devices, e.g., needle and syringe, a subcutaneous injection port delivery system, and the like. See, e.g., U.S. Pat. Nos. 3,547,119; 4,755,173; 4,531,937; 4,311,137; and 6,017,328. A combination of a subcutaneous injection port and a device for administration of a pharmaceutical composition of the embodiments to a patient through the port is referred to herein as "a subcutaneous injection port delivery system." In many embodiments, subcutaneous administration is achieved by bolus delivery by needle and syringe.

In pharmaceutical dosage forms, the agents may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Furthermore, the agents can be made into suppositories by mixing with a variety of bases such as emulsifying bases or water-soluble bases. The compounds of the embodiments can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the embodiments calculated in an amount sufficient to produce the desired effect in association with a pharmaceutically acceptable diluent, carrier or vehicle. The specifications for the novel unit dosage forms of the embodiments depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Other Antiviral or Antifibrotic Agents

As discussed above, a subject method will in some embodiments be carried out by administering an NS3 inhibitor that is a compound of Formula Ia, Ib, II, III, IV, V, VI, VII, VIII, VIIIa, VIIIb, VIIIc, VIIId, VIIIe, or IX, and optionally one or more additional antiviral agent(s).

In some embodiments, the method further includes administration of one or more interferon receptor agonist(s). Interferon receptor agonists are described above.

In other embodiments, the method further includes administration of pirfenidone or a pirfenidone analog. Pirfenidone and pirfenidone analogs are described above.

Additional antiviral agents that are suitable for use in combination therapy include, but are not limited to, nucleotide and nucleoside analogs. Non-limiting examples include azidothymidine (AZT) (zidovudine), and analogs and derivatives thereof; 2',3'-dideoxyinosine (DDI) (didanosine), and analogs and derivatives thereof; 2',3'-dideoxycytidine (DDC) (dideoxycytidine), and analogs and derivatives thereof; 2'3,'-didehydro-2',3'-dideoxythymidine (D4T) (stavudine), and analogs and derivatives thereof; combivir; abacavir; adefovir dipoxil; cidofovir; ribavirin; ribavirin analogs; and the like.

In some embodiments, the method further includes administration of ribavirin. Ribavirin, 1-β-D-ribofuranosyl-1H-1,2,4-triazole-3-carboxamide, available from ICN Pharmaceuticals, Inc., Costa Mesa, Calif., is described in the Merck Index, compound No. 8199, Eleventh Edition. Its manufacture and formulation is described in U.S. Pat. No. 4,211,771. Some embodiments also involve use of derivatives of ribavirin (see, e.g., U.S. Pat. No. 6,277,830). The ribavirin may be administered orally in capsule or tablet form, or in the same or different administration form and in the same or different route as the interferon receptor agonist. Of course, other types of administration of both medicaments, as they become available are contemplated, such as by nasal spray, transdermally, intravenously, by suppository, by sustained release dosage form, etc. Any form of administration will work so long as the proper dosages are delivered without destroying the active ingredient.

In some embodiments, the method further includes administration of ritonavir. Ritonavir, 10-hydroxy-2-methyl-5-(1-methylethyl)-1-[2-(1-methylethyl)-4-thiazolyl]-3,6-dioxo-8,11-bis(phenylmethyl)-2,4,7,12-tetraazamidecan-13-oic acid, 5-thiazolylmethyl ester[5S-(5R*,8R*,10R*,11R*)], available from Abbott Laboratories, is an inhibitor of the protease of the human immunodeficiency virus and also of the cytochrome P450 3A and P450 2D6 liver enzymes frequently involved in hepatic metabolism of therapeutic molecules in man. Because of its strong inhibitory effect on cytochrome P450 3A and the inhibitory effect on cytochrome P450 2D6, ritonavir at doses below the normal therapeutic dosage may be combined with other protease inhibitors to achieve therapeutic levels of the second protease inhibitor while reducing the number of dosage units required, the dosing frequency, or both.

Coadministration of low-dose ritonavir may also be used to compensate for drug interactions that tend to decrease levels of a protease inhibitor metabolized by CYP3A. Its structure, synthesis, manufacture and formulation are described in U.S. Pat. No. 5,541,206 U.S. Pat. No. 5,635,523 U.S. Pat. No. 5,648,497 U.S. Pat. No. 5,846,987 and U.S. Pat. No. 6,232,333. The ritonavir may be administered orally in capsule or tablet or oral solution form, or in the same or different administration form and in the same or different route as the NS-3 inhibitor compound. Of course, other types of administration of both medicaments, as they become available are contemplated, such as by nasal spray, transdermally, intravenously, by suppository, by sustained release dosage form, etc. Any form of administration will work so long as the proper dosages are delivered without destroying the active ingredient.

In some embodiments, an additional antiviral agent is administered during the entire course of NS3 inhibitor compound treatment. In other embodiments, an additional antiviral agent is administered for a period of time that is overlapping with that of the NS3 inhibitor compound treatment, e.g., the additional antiviral agent treatment can begin before the NS3 inhibitor compound treatment begins and end before the NS3 inhibitor compound treatment ends; the additional antiviral agent treatment can begin after the NS3 inhibitor compound treatment begins and end after the NS3 inhibitor compound treatment ends; the additional antiviral agent treatment can begin after the NS3 inhibitor compound treatment begins and end before the NS3 inhibitor compound treatment ends; or the additional antiviral agent treatment can begin before the NS3 inhibitor compound treatment begins and end after the NS3 inhibitor compound treatment ends.

Methods of Treatment

Monotherapies

The NS3 inhibitor compounds described herein may be used in acute or chronic therapy for HCV disease. In many embodiments, the NS3 inhibitor compound is administered for a period of about 1 day to about 7 days, or about 1 week to about 2 weeks, or about 2 weeks to about 3 weeks, or about 3 weeks to about 4 weeks, or about 1 month to about 2 months, or about 3 months to about 4 months, or about 4 months to about 6 months, or about 6 months to about 8 months, or about 8 months to about 12 months, or at least one year, and may be administered over longer periods of time. The NS3 inhibitor compound can be administered 5 times per day, 4 times per day, tid, bid, qd, qod, biw, tiw, qw, qow, three times per month, or once monthly. In other embodiments, the NS3 inhibitor compound is administered as a continuous infusion.

In many embodiments, an NS3 inhibitor compound of the embodiments is administered orally.

In connection with the above-described methods for the treatment of HCV disease in a patient, an NS3 inhibitor compound as described herein may be administered to the patient at a dosage from about 0.01 mg to about 100 mg/kg patient bodyweight per day, in 1 to 5 divided doses per day. In some embodiments, the NS3 inhibitor compound is administered at a dosage of about 0.5 mg to about 75 mg/kg patient bodyweight per day, in 1 to 5 divided doses per day.

The amount of active ingredient that may be combined with carrier materials to produce a dosage form can vary depending on the host to be treated and the particular mode of administration. A typical pharmaceutical preparation can contain from about 5% to about 95% active ingredient (w/w). In other embodiments, the pharmaceutical preparation can contain from about 20% to about 80% active ingredient.

Those of skill will readily appreciate that dose levels can vary as a function of the specific NS3 inhibitor compound, the severity of the symptoms and the susceptibility of the subject to side effects. Preferred dosages for a given NS3 inhibitor compound are readily determinable by those of skill in the art by a variety of means. A preferred means is to measure the physiological potency of a given interferon receptor agonist.

In many embodiments, multiple doses of NS3 inhibitor compound are administered. For example, an NS3 inhibitor compound is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid), over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

Combination Therapies with Ribavirin

In some embodiments, the methods provide for combination therapy comprising administering an NS3 inhibitor compound as described above, and an effective amount of ribavirin. Ribavirin can be administered in dosages of about 400 mg, about 800 mg, about 1000 mg, or about 1200 mg per day.

One embodiment provides any of the above-described methods modified to include co-administering to the patient a therapeutically effective amount of ribavirin for the duration of the desired course of NS3 inhibitor compound treatment.

Another embodiment provides any of the above-described methods modified to include co-administering to the patient about 800 mg to about 1200 mg ribavirin orally per day for the duration of the desired course of NS3 inhibitor compound treatment. In another embodiment, any of the above-described methods may be modified to include co-administering to the patient (a) 1000 mg ribavirin orally per day if the patient has a body weight less than 75 kg or (b) 1200 mg ribavirin orally per day if the patient has a body weight greater than or equal to 75 kg, where the daily dosage of ribavirin is optionally divided into to 2 doses for the duration of the desired course of NS3 inhibitor compound treatment.

Combination Therapies with Levovirin

In some embodiments, the methods provide for combination therapy comprising administering an NS3 inhibitor compound as described above, and an effective amount of levovirin. Levovirin is generally administered in an amount ranging from about 30 mg to about 60 mg, from about 60 mg to about 125 mg, from about 125 mg to about 200 mg, from about 200 mg to about 300 gm, from about 300 mg to about 400 mg, from about 400 mg to about 1200 mg, from about 600 mg to about 1000 mg, or from about 700 to about 900 mg per day, or about 10 mg/kg body weight per day. In some embodiments, levovirin is administered orally in dosages of about 400, about 800, about 1000, or about 1200 mg per day for the desired course of NS3 inhibitor compound treatment.

Combination Therapies with Viramidine

In some embodiments, the methods provide for combination therapy comprising administering an NS3 inhibitor compound as described above, and an effective amount of viramidine. Viramidine is generally administered in an amount ranging from about 30 mg to about 60 mg, from about 60 mg to about 125 mg, from about 125 mg to about 200 mg, from about 200 mg to about 300 gm, from about 300 mg to about 400 mg, from about 400 mg to about 1200 mg, from about 600 mg to about 1000 mg, or from about 700 to about 900 mg per day, or about 10 mg/kg body weight per day. In some embodiments, viramidine is administered orally in dosages of about 800, or about 1600 mg per day for the desired course of NS3 inhibitor compound treatment.

Combination Therapies with Ritonavir

In some embodiments, the methods provide for combination therapy comprising administering an NS3 inhibitor compound as described above, and an effective amount of ritonavir. Ritonavir is generally administered in an amount ranging from about 50 mg to about 100 mg, from about 100 mg to about 200 mg, from about 200 mg to about 300 mg, from about 300 mg to about 400 mg, from about 400 mg to about 500 mg, or from about 500 mg to about 600 mg, twice per day. In some embodiments, ritonavir is administered orally in dosages of about 300 mg, or about 400 mg, or about 600 mg twice per day for the desired course of NS3 inhibitor compound treatment.

Combination Therapies with Alpha-Glucosidase Inhibitors

Suitable α-glucosidase inhibitors include any of the above-described imino-sugars, including long-alkyl chain derivatives of imino sugars as disclosed in U.S. Patent Publication No. 2004/0110795; inhibitors of endoplasmic reticulum-associated α-glucosidases; inhibitors of membrane bound α-glucosidase; miglitol (Glyset®), and active derivatives, and analogs thereof; and acarbose (Precose®), and active derivatives, and analogs thereof.

In many embodiments, the methods provide for combination therapy comprising administering an NS3 inhibitor compound as described above, and an effective amount of an α-glucosidase inhibitor administered for a period of about 1 day to about 7 days, or about 1 week to about 2 weeks, or about 2 weeks to about 3 weeks, or about 3 weeks to about 4 weeks, or about 1 month to about 2 months, or about 3 months to about 4 months, or about 4 months to about 6 months, or about 6 months to about 8 months, or about 8 months to about 12 months, or at least one year, and may be administered over longer periods of time.

An α-glucosidase inhibitor can be administered 5 times per day, 4 times per day, tid (three times daily), bid, qd, qod, biw, tiw, qw, qow, three times per month, or once monthly. In other embodiments, an α-glucosidase inhibitor is administered as a continuous infusion.

In many embodiments, an α-glucosidase inhibitor is administered orally.

In connection with the above-described methods for the treatment of a flavivirus infection, treatment of HCV infection, and treatment of liver fibrosis that occurs as a result of an HCV infection, the methods provide for combination therapy comprising administering an NS3 inhibitor compound as described above, and an effective amount of α-glucosidase inhibitor administered to the patient at a dosage of from about 10 mg per day to about 600 mg per day in divided doses, e.g., from about 10 mg per day to about 30 mg per day, from about 30 mg per day to about 60 mg per day, from about 60 mg per day to about 75 mg per day, from about 75 mg per day to about 90 mg per day, from about 90 mg per day to about 120 mg per day, from about 120 mg per day to about 150 mg per day, from about 150 mg per day to about 180 mg per day, from about 180 mg per day to about 210 mg per day, from about 210 mg per day to about 240 mg per day, from about 240 mg per day to about 270 mg per day, from about 270 mg per day to about 300 mg per day, from about 300 mg per day to about 360 mg per day, from about 360 mg per day to about 420 mg per day, from about 420 mg per day to about 480 mg per day, or from about 480 mg to about 600 mg per day.

In some embodiments, the methods provide for combination therapy comprising administering an NS3 inhibitor compound as described above, and an effective amount of α-glucosidase inhibitor administered in a dosage of about 10 mg three times daily. In some embodiments, an α-glucosidase inhibitor is administered in a dosage of about 15 mg three times daily. In some embodiments, an α-glucosidase inhibitor is administered in a dosage of about 20 mg three times daily. In some embodiments, an α-glucosidase inhibitor is administered in a dosage of about 25 mg three times daily. In some embodiments, an α-glucosidase inhibitor is administered in a dosage of about 30 mg three times daily. In some embodiments, an α-glucosidase inhibitor is administered in a dosage of about 40 mg three times daily. In some embodiments, an α-glucosidase inhibitor is administered in a dosage of about 50 mg three times daily. In some embodiments, an α-glucosidase inhibitor is administered in a dosage of about 100 mg three times daily. In some embodiments, an α-glucosidase inhibitor is administered in a dosage of about 75 mg per day to about 150 mg per day in two or three divided doses, where the individual weighs 60 kg or less. In some embodiments, an α-glucosidase inhibitor is administered in a dosage of about 75 mg per day to about 300 mg per day in two or three divided doses, where the individual weighs 60 kg or more.

The amount of active ingredient (e.g., α-glucosidase inhibitor) that may be combined with carrier materials to produce a dosage form can vary depending on the host to be treated and the particular mode of administration. A typical pharmaceutical preparation can contain from about 5% to about 95% active ingredient (w/w). In other embodiments, the pharmaceutical preparation can contain from about 20% to about 80% active ingredient.

Those of skill will readily appreciate that dose levels can vary as a function of the specific α-glucosidase inhibitor, the severity of the symptoms and the susceptibility of the subject to side effects. Preferred dosages for a given α-glucosidase inhibitor are readily determinable by those of skill in the art by a variety of means. A typical means is to measure the physiological potency of a given active agent.

In many embodiments, multiple doses of an α-glucosidase inhibitor are administered. For example, the methods provide for combination therapy comprising administering an NS3 inhibitor compound as described above, and an effective amount of α-glucosidase inhibitor administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid), over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

Combination Therapies with Thymosin-α

In some embodiments, the methods provide for combination therapy comprising administering an NS3 inhibitor compound as described above, and an effective amount of thymosin-α. Thymosin-α (Zadaxin™) is generally administered by subcutaneous injection. Thymosin-α can be administered tid, bid, qd, qod, biw, tiw, qw, qow, three times per month, once monthly, substantially continuously, or continuously for the desired course of NS3 inhibitor compound treatment. In many embodiments, thymosin-α is administered twice per week for the desired course of NS3 inhibitor compound treatment. Effective dosages of thymosin-α range from about 0.5 mg to about 5 mg, e.g., from about 0.5 mg to about 1.0 mg, from about 1.0 mg to about 1.5 mg, from about 1.5 mg to about 2.0 mg, from about 2.0 mg to about 2.5 mg, from about 2.5 mg to about 3.0 mg, from about 3.0 mg to about 3.5 mg, from about 3.5 mg to about 4.0 mg, from about 4.0 mg to about 4.5 mg, or from about 4.5 mg to about 5.0 mg. In particular embodiments, thymosin-α is administered in dosages containing an amount of 1.0 mg or 1.6 mg.

Thymosin-α can be administered over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more. In one embodiment, thymosin-α is administered for the desired course of NS3 inhibitor compound treatment.

Combination Therapies with Interferon(s)

In many embodiments, the methods provide for combination therapy comprising administering an NS3 inhibitor compound as described above, and an effective amount of an interferon receptor agonist. In some embodiments, a compound of Formula Ia, Ib, II, III, IV, V, VI, VII, VIII, VIIIa, VIIIb, VIIIc, VIIId, VIIIe, or IX and a Type I or III interferon receptor agonist are co-administered in the treatment methods described herein. Type I interferon receptor agonists suitable for use herein include any interferon-α (IFN-α). In certain embodiments, the interferon-α is a PEGylated interferon-α. In certain other embodiments, the interferon-α is a consensus interferon, such as INFERGEN® interferon alfacon-1. In still other embodiments, the interferon-α is a monoPEG (30 kD, linear)-ylated consensus interferon.

Effective dosages of an IFN-α range from about 3 μg to about 27 μg, from about 3 MU to about 10 MU, from about 90 μg to about 180 μg, or from about 18 μg to about 90 μg. Effective dosages of Infergen® consensus IFN-α include about 3 μg, about 6 μg, about 9 μg, about 12 μg, about 15 μg, about 18 μg, about 21 μg, about 24 μg, about 27 μg, or about 30 μg, of drug per dose. Effective dosages of IFN-α2a and IFN-α2b range from 3 million Units (MU) to 10 MU per dose. Effective dosages of PEGASYS® PEGylated IFN-α2a contain an amount of about 90 μg to 270 μg, or about 180 μg, of drug per dose. Effective dosages of PEG-INTRON® PEGylated IFN-α2b contain an amount of about 0.5 μg to 3.0 μg of drug per kg of body weight per dose. Effective dosages of PEGylated consensus interferon (PEG-CIFN) contain an amount of about 18 μg to about 90 μg, or from about 27 μg to about 60 μg, or about 45 μg, of CIFN amino acid weight per dose of PEG-CIFN. Effective dosages of monoPEG (30 kD, linear)-ylated CIFN contain an amount of about 45 μg to about 270 μg, or about 60 μg to about 180 μg, or about 90 μg to about 120 μg, of drug per dose. IFN-α can be administered daily, every other day, once a week, three times a week, every other week, three times per month, once monthly, substantially continuously or continuously.

In many embodiments, the Type I or Type III interferon receptor agonist and/or the Type II interferon receptor agonist is administered for a period of about 1 day to about 7 days, or about 1 week to about 2 weeks, or about 2 weeks to about 3 weeks, or about 3 weeks to about 4 weeks, or about 1 month to about 2 months, or about 3 months to about 4 months, or about 4 months to about 6 months, or about 6 months to about 8 months, or about 8 months to about 12 months, or at least one year, and may be administered over longer periods of time. Dosage regimens can include tid, bid, qd, qod, biw, tiw, qw, qow, three times per month, or monthly administrations. Some embodiments provide any of the above-described methods in which the desired dosage of IFN-α is administered subcutaneously to the patient by bolus delivery qd, qod, tiw, biw, qw, qow, three times per month, or monthly, or is administered subcutaneously to the patient per day by substantially continuous or continuous delivery, for the desired treatment duration. In other embodiments, any of the above-described methods may be practiced in which the desired dosage of PEGylated IFN-α (PEG-IFN-α) is administered subcutaneously to the patient by bolus delivery qw, qow, three times per month, or monthly for the desired treatment duration.

In other embodiments, an NS3 inhibitor compound and a Type II interferon receptor agonist are co-administered in the treatment methods of the embodiments. Type II interferon receptor agonists suitable for use herein include any interferon-γ (IFN-γ).

Effective dosages of IFN-γ can range from about 0.5 μg/m$^2$ to about 500 μg/m$^2$, usually from about 1.5 μg/m$^2$ to 200 μg/m$^2$, depending on the size of the patient. This activity is based on 10$^6$ international units (U) per 50 μg of protein. IFN-γ can be administered daily, every other day, three times a week, or substantially continuously or continuously.

In specific embodiments of interest, IFN-γ is administered to an individual in a unit dosage form of from about 25 μg to about 500 μg, from about 50 μg to about 400 μg, or from about 100 μg to about 300 μg. In particular embodiments of interest, the dose is about 200 μg IFN-γ. In many embodiments of interest, IFN-γ1b is administered.

Where the dosage is 200 μg IFN-γ per dose, the amount of IFN-γ per body weight (assuming a range of body weights of from about 45 kg to about 135 kg) is in the range of from about 4.4 μg IFN-γ per kg body weight to about 1.48 μg IFN-γ per kg body weight.

The body surface area of subject individuals generally ranges from about 1.33 m$^2$ to about 2.50 m$^2$. Thus, in many embodiments, an IFN-γ dosage ranges from about 150 μg/m$^2$ to about 20 μg/m$^2$. For example, an IFN-γ dosage ranges from about 20 μg/m$^2$ to about 30 μg/m$^2$, from about 30 μg/m$^2$ to about 40 μg/m$^2$, from about 40 μg/m$^2$ to about 50 μg/m$^2$, from about 50 μg/m$^2$ to about 60 μg/m$^2$, from about 60 μg/m$^2$ to about 70 μg/m$^2$, from about 70 μg/m$^2$ to about 80 μg/m$^2$, from about 80 µg/m² to about 90 µg/m², from about 90 µg/m² to about 100 µg/m², from about 100 µg/m² to about 110 µg/m², from about 110 µg/m² to about 120 µg/m², from about 120 µg/m² to about 130 µg/m², from about 130 µg/m² to about 140 µg/m², or from about 140 µg/m² to about 150 µg/m². In some embodiments, the dosage groups range from about 25 µg/m² to about 100 µg/m². In other embodiments, the dosage groups range from about 25 µg/m² to about 50 µg/m².

In some embodiments, a Type I or a Type III interferon receptor agonist is administered in a first dosing regimen, followed by a second dosing regimen. The first dosing regimen of Type I or a Type III interferon receptor agonist (also referred to as "the induction regimen") generally involves administration of a higher dosage of the Type I or Type III interferon receptor agonist. For example, in the case of Infergen® consensus IFN-α (CIFN), the first dosing regimen comprises administering CIFN at about 9 µg, about 15 µg, about 18 µg, or about 27 µg. The first dosing regimen can encompass a single dosing event, or at least two or more dosing events. The first dosing regimen of the Type I or Type III interferon receptor agonist can be administered daily, every other day, three times a week, every other week, three times per month, once monthly, substantially continuously or continuously.

The first dosing regimen of the Type I or Type III interferon receptor agonist is administered for a first period of time, which time period can be at least about 4 weeks, at least about 8 weeks, or at least about 12 weeks.

The second dosing regimen of the Type I or Type III interferon receptor agonist (also referred to as "the maintenance dose") generally involves administration of a lower amount of the Type I or Type III interferon receptor agonist. For example, in the case of CIFN, the second dosing regimen comprises administering CIFN at a dose of at least about 3 µg, at least about 9 µg, at least about 15 µg, or at least about 18 µg. The second dosing regimen can encompass a single dosing event, or at least two or more dosing events.

The second dosing regimen of the Type I or Type III interferon receptor agonist can be administered daily, every other day, three times a week, every other week, three times per month, once monthly, substantially continuously or continuously.

In some embodiments, where an "induction"/"maintenance" dosing regimen of a Type I or a Type III interferon receptor agonist is administered, a "priming" dose of a Type II interferon receptor agonist (e.g., IFN-γ) is included. In these embodiments, IFN-γ is administered for a period of time from about 1 day to about 14 days, from about 2 days to about 10 days, or from about 3 days to about 7 days, before the beginning of treatment with the Type I or Type III interferon receptor agonist. This period of time is referred to as the "priming" phase.

In some of these embodiments, the Type II interferon receptor agonist treatment is continued throughout the entire period of treatment with the Type I or Type III interferon receptor agonist. In other embodiments, the Type II interferon receptor agonist treatment is discontinued before the end of treatment with the Type I or Type III interferon receptor agonist. In these embodiments, the total time of treatment with Type II interferon receptor agonist (including the "priming" phase) is from about 2 days to about 30 days, from about 4 days to about 25 days, from about 8 days to about 20 days, from about 10 days to about 18 days, or from about 12 days to about 16 days. In still other embodiments, Type II interferon receptor agonist treatment is discontinued once Type I or a Type III interferon receptor agonist treatment begins.

In other embodiments, the Type I or Type III interferon receptor agonist is administered in single dosing regimen. For example, in the case of CIFN, the dose of CIFN is generally in a range of from about 3 µg to about 15 µg, or from about 9 µg to about 15 µg. The dose of Type I or a Type III interferon receptor agonist is generally administered daily, every other day, three times a week, every other week, three times per month, once monthly, or substantially continuously. The dose of the Type I or Type III interferon receptor agonist is administered for a period of time, which period can be, for example, from at least about 24 weeks to at least about 48 weeks, or longer.

In some embodiments, where a single dosing regimen of a Type I or a Type III interferon receptor agonist is administered, a "priming" dose of a Type II interferon receptor agonist (e.g., IFN-γ) is included. In these embodiments, IFN-γ is administered for a period of time from about 1 day to about 14 days, from about 2 days to about 10 days, or from about 3 days to about 7 days, before the beginning of treatment with the Type I or Type III interferon receptor agonist. This period of time is referred to as the "priming" phase. In some of these embodiments, the Type II interferon receptor agonist treatment is continued throughout the entire period of treatment with the Type I or Type III interferon receptor agonist. In other embodiments, the Type II interferon receptor agonist treatment is discontinued before the end of treatment with the Type I or Type III interferon receptor agonist. In these embodiments, the total time of treatment with the Type II interferon receptor agonist (including the "priming" phase) is from about 2 days to about 30 days, from about 4 days to about 25 days, from about 8 days to about 20 days, from about 10 days to about 18 days, or from about 12 days to about 16 days. In still other embodiments, Type II interferon receptor agonist treatment is discontinued once Type I or a Type III interferon receptor agonist treatment begins.

In additional embodiments, an NS3 inhibitor compound, a Type I or III interferon receptor agonist, and a Type II interferon receptor agonist are co-administered for the desired duration of treatment in the methods described herein. In some embodiments, an NS3 inhibitor compound, an interferon-α, and an interferon-γ are co-administered for the desired duration of treatment in the methods described herein.

In some embodiments, the invention provides methods using an amount of a Type I or Type III interferon receptor agonist, a Type II interferon receptor agonist, and an NS3 inhibitor compound, effective for the treatment of HCV infection in a patient. Some embodiments provide methods using an effective amount of an IFN-α, IFN-γ, and an NS3 inhibitor compound in the treatment of HCV infection in a patient. One embodiment provides a method using an effective amount of a consensus IFN-α, IFN-γ and an NS3 inhibitor compound in the treatment of HCV infection in a patient.

In general, an effective amount of a consensus interferon (CIFN) and IFN-γ suitable for use in the methods of the embodiments is provided by a dosage ratio of 1 µg CIFN:10 µg IFN-γ, where both CIFN and IFN-γ are unPEGylated and unglycosylated species.

In one embodiment, the invention provides any of the above-described methods modified to use an effective amount of INFERGEN® consensus IFN-α and IFN-γ in the treatment of HCV infection in a patient comprising administering to the patient a dosage of INFERGEN® containing an amount of about 1 µg to about 30 µg, of drug per dose of INFERGEN®, subcutaneously qd, qod, tiw, biw, qw, qow, three times per month, once monthly, or per day substantially continuously or continuously, in combination with a dosage of IFN-γ containing an amount of about 10 µg to about 300 µg of drug per dose of IFN-γ, subcutaneously qd, qod, tiw, biw, qw, qow, three times per month, once monthly, or per day substantially continuously or continuously, for the desired duration of treatment with an NS3 inhibitor compound.

Another embodiment provides any of the above-described methods modified to use an effective amount of INFERGEN® consensus IFN-α and IFN-γ in the treatment of virus infection in a patient comprising administering to the patient a dosage of INFERGEN® containing an amount of about 1 μg to about 9 μg, of drug per dose of INFERGEN®, subcutaneously qd, qod, tiw, biw, qw, qow, three times per month, once monthly, or per day substantially continuously or continuously, in combination with a dosage of IFN-γ containing an amount of about 10 μg to about 100 μg of drug per dose of IFN-γ, subcutaneously qd, qod, tiw, biw, qw, qow, three times per month, once monthly, or per day substantially continuously or continuously, for the desired duration of treatment with an NS3 inhibitor compound.

Another embodiment provides any of the above-described methods modified to use an effective amount of INFERGEN® consensus IFN-α and IFN-γ in the treatment of virus infection in a patient comprising administering to the patient a dosage of INFERGEN® containing an amount of about 1 μg of drug per dose of INFERGEN®, subcutaneously qd, qod, tiw, biw, qw, qow, three times per month, once monthly, or per day substantially continuously or continuously, in combination with a dosage of IFN-γ containing an amount of about 10 μg to about 50 μg of drug per dose of IFN-γ, subcutaneously qd, qod, tiw, biw, qw, qow, three times per month, once monthly, or per day substantially continuously or continuously, for the desired duration of treatment with an NS3 inhibitor compound.

Another embodiment provides any of the above-described methods modified to use an effective amount of INFERGEN® consensus IFN-α and IFN-γ in the treatment of a virus infection in a patient comprising administering to the patient a dosage of INFERGEN® containing an amount of about 9 μg of drug per dose of INFERGEN®, subcutaneously qd, qod, tiw, biw, qw, qow, three times per month, once monthly, or per day substantially continuously or continuously, in combination with a dosage of IFN-γ containing an amount of about 90 μg to about 100 μg of drug per dose of IFN-γ, subcutaneously qd, qod, tiw, biw, qw, qow, three times per month, once monthly, or per day substantially continuously or continuously, for the desired duration of treatment with an NS3 inhibitor compound.

Another embodiment provides any of the above-described methods modified to use an effective amount of INFERGEN® consensus IFN-α and IFN-γ in the treatment of a virus infection in a patient comprising administering to the patient a dosage of INFERGEN® containing an amount of about 30 μg of drug per dose of INFERGEN®, subcutaneously qd, qod, tiw, biw, qw, qow, three times per month, once monthly, or per day substantially continuously or continuously, in combination with a dosage of IFN-γ containing an amount of about 200 μg to about 300 μg of drug per dose of IFN-γ, subcutaneously qd, qod, tiw, biw, qw, qow, three times per month, once monthly, or per day substantially continuously or continuously, for the desired duration of treatment with an NS3 inhibitor compound.

Another embodiment provides any of the above-described methods modified to use an effective amount of PEGylated consensus IFN-α and IFN-γ in the treatment of a virus infection in a patient comprising administering to the patient a dosage of PEGylated consensus IFN-α (PEG-CIFN) containing an amount of about 4 μg to about 60 μg of CIFN amino acid weight per dose of PEG-CIFN, subcutaneously qw, qow, three times per month, or monthly, in combination with a total weekly dosage of IFN-γ containing an amount of about 30 μg to about 1,000 μg of drug per week in divided doses administered subcutaneously qd, qod, tiw, biw, or administered substantially continuously or continuously, for the desired duration of treatment with an NS3 inhibitor compound.

Another embodiment provides any of the above-described methods modified to use an effective amount of PEGylated consensus IFN-α and IFN-γ in the treatment of a virus infection in a patient comprising administering to the patient a dosage of PEGylated consensus IFN-α (PEG-CIFN) containing an amount of about 18 μg to about 24 μg of CIFN amino acid weight per dose of PEG-CIFN, subcutaneously qw, qow, three times per month, or monthly, in combination with a total weekly dosage of IFN-γ containing an amount of about 100 μg to about 300 μg of drug per week in divided doses administered subcutaneously qd, qod, tiw, biw, or substantially continuously or continuously, for the desired duration of treatment with an NS3 inhibitor compound.

In general, an effective amount of IFN-α2a or 2b or 2c and IFN-γ suitable for use in the methods of the embodiments is provided by a dosage ratio of 1 million Units (MU) IFN-α 2a or 2b or 2c: 30 μg IFN-γ, where both IFN-α 2a or 2b or 2c and IFN-γ are unPEGylated and unglycosylated species.

Another embodiment provides any of the above-described methods modified to use an effective amount of IFN-α2a or 2b or 2c and IFN-γ in the treatment of a virus infection in a patient comprising administering to the patient a dosage of IFN-α2a, 2b or 2c containing an amount of about 1 MU to about 20 MU of drug per dose of IFN-α2a, 2b or 2c subcutaneously qd, qod, tiw, biw, or per day substantially continuously or continuously, in combination with a dosage of IFN-γ containing an amount of about 30 μg to about 600 μg of drug per dose of IFN-γ, subcutaneously qd, qod, tiw, biw, or per day substantially continuously or continuously, for the desired duration of treatment with an NS3 inhibitor compound.

Another embodiment provides any of the above-described methods modified to use an effective amount of IFN-α 2a or 2b or 2c and IFN-γ in the treatment of a virus infection in a patient comprising administering to the patient a dosage of IFN-α 2a, 2b or 2c containing an amount of about 3 MU of drug per dose of IFN-α 2a, 2b or 2c subcutaneously qd, qod, tiw, biw, or per day substantially continuously or continuously, in combination with a dosage of IFN-γ containing an amount of about 100 μg of drug per dose of IFN-γ, subcutaneously qd, qod, tiw, biw, or per day substantially continuously or continuously, for the desired duration of treatment with an NS3 inhibitor compound.

Another embodiment provides any of the above-described methods modified to use an effective amount of IFN-α 2a or 2b or 2c and IFN-γ in the treatment of a virus infection in a patient comprising administering to the patient a dosage of IFN-α 2a, 2b or 2c containing an amount of about 10 MU of drug per dose of IFN-α 2a, 2b or 2c subcutaneously qd, qod, tiw, biw, or per day substantially continuously or continuously, in combination with a dosage of IFN-γ containing an amount of about 300 μg of drug per dose of IFN-γ, subcutaneously qd, qod, tiw, biw, or per day substantially continuously or continuously, for the desired duration of treatment with an NS3 inhibitor compound.

Another embodiment provides any of the above-described methods modified to use an effective amount of PEGASYS® PEGylated IFN-α2a and IFN-γ in the treatment of a virus infection in a patient comprising administering to the patient a dosage of PEGASYS® containing an amount of about 90 μg to about 360 μg, of drug per dose of PEGASYS®, subcutaneously qw, qow, three times per month, or monthly, in combination with a total weekly dosage of IFN-γ containing an amount of about 30 μg to about 1,000 μg, of drug per week administered in divided doses subcutaneously qd, qod, tiw, or biw, or administered substantially continuously or continuously, for the desired duration of treatment with an NS3 inhibitor compound.

Another embodiment provides any of the above-described methods modified to use an effective amount of PEGASYS® PEGylated IFN-α2a and IFN-γ in the treatment of a virus infection in a patient comprising administering to the patient a dosage of PEGASYS® containing an amount of about 180 μg of drug per dose of PEGASYS®, subcutaneously qw, qow, three times per month, or monthly, in combination with a total weekly dosage of IFN-γ containing an amount of about 100 μg to about 300 μg, of drug per week administered in divided doses subcutaneously qd, qod, tiw, or biw, or administered substantially continuously or continuously, for the desired duration of treatment with an NS3 inhibitor compound.

Another embodiment provides any of the above-described methods modified to use an effective amount of PEG-INTRON® PEGylated IFN-α2b and IFN-γ in the treatment of a virus infection in a patient comprising administering to the patient a dosage of PEG-INTRON® containing an amount of about 0.75 μg to about 3.0 μg of drug per kilogram of body weight per dose of PEG-INTRON®, subcutaneously qw, qow, three times per month, or monthly, in combination with a total weekly dosage of IFN-γ containing an amount of about 30 μg to about 1,000 μg of drug per week administered in divided doses subcutaneously qd, qod, tiw, or biw, or administered substantially continuously or continuously, for the desired duration of treatment with an NS3 inhibitor compound.

Another embodiment provides any of the above-described methods modified to use an effective amount of PEG-INTRON® PEGylated IFN-α2b and IFN-γ in the treatment of a virus infection in a patient comprising administering to the patient a dosage of PEG-INTRON® containing an amount of about 1.5 μg of drug per kilogram of body weight per dose of PEG-INTRON®, subcutaneously qw, qow, three times per month, or monthly, in combination with a total weekly dosage of IFN-γ containing an amount of about 100 μg to about 300 μg of drug per week administered in divided doses subcutaneously qd, qod, tiw, or biw, or administered substantially continuously or continuously, for the desired duration of treatment with an NS3 inhibitor compound.

One embodiment provides any of the above-described methods modified to comprise administering to an individual having an HCV infection an effective amount of an NS3 inhibitor; and a regimen of 9 μg INFERGEN® consensus IFN-α administered subcutaneously qd or tiw, and ribavirin administered orally qd, where the duration of therapy is 48 weeks. In this embodiment, ribavirin is administered in an amount of 1000 mg for individuals weighing less than 75 kg, and 1200 mg for individuals weighing 75 kg or more.

One embodiment provides any of the above-described methods modified to comprise administering to an individual having an HCV infection an effective amount of an NS3 inhibitor; and a regimen of 9 μg INFERGEN® consensus IFN-α administered subcutaneously qd or tiw; 50 μg Actimmune® human IFN-γ1b administered subcutaneously tiw; and ribavirin administered orally qd, where the duration of therapy is 48 weeks. In this embodiment, ribavirin is administered in an amount of 1000 mg for individuals weighing less than 75 kg, and 1200 mg for individuals weighing 75 kg or more.

One embodiment provides any of the above-described methods modified to comprise administering to an individual having an HCV infection an effective amount of an NS3 inhibitor; and a regimen of 9 μg INFERGEN® consensus IFN-α administered subcutaneously qd or tiw; 100 μg Actimmune® human IFN-γ1b administered subcutaneously tiw; and ribavirin administered orally qd, where the duration of therapy is 48 weeks. In this embodiment, ribavirin is administered in an amount of 1000 mg for individuals weighing less than 75 kg, and 1200 mg for individuals weighing 75 kg or more.

One embodiment provides any of the above-described methods modified to comprise administering to an individual having an HCV infection an effective amount of an NS3 inhibitor; and a regimen of 9 μg INFERGEN® consensus IFN-α administered subcutaneously qd or tiw; and 50 μg Actimmune® human IFN-γ1b administered subcutaneously tiw, where the duration of therapy is 48 weeks.

One embodiment provides any of the above-described methods modified to comprise administering to an individual having an HCV infection an effective amount of an NS3 inhibitor; and a regimen of 9 μg INFERGEN® consensus IFN-α administered subcutaneously qd or tiw; and 100 μg Actimmune® human IFN-γ1b administered subcutaneously tiw, where the duration of therapy is 48 weeks.

One embodiment provides any of the above-described methods modified to comprise administering to an individual having an HCV infection an effective amount of an NS3 inhibitor; and a regimen of 9 μg INFERGEN® consensus IFN-α administered subcutaneously qd or tiw; 25 μg Actimmune® human IFN-γ1b administered subcutaneously tiw; and ribavirin administered orally qd, where the duration of therapy is 48 weeks. In this embodiment, ribavirin is administered in an amount of 1000 mg for individuals weighing less than 75 kg, and 1200 mg for individuals weighing 75 kg or more.

One embodiment provides any of the above-described methods modified to comprise administering to an individual having an HCV infection an effective amount of an NS3 inhibitor; and a regimen of 9 μg INFERGEN® consensus IFN-α administered subcutaneously qd or tiw; 200 μg Actimmune® human IFN-γ1b administered subcutaneously tiw; and ribavirin administered orally qd, where the duration of therapy is 48 weeks. In this embodiment, ribavirin is administered in an amount of 1000 mg for individuals weighing less than 75 kg, and 1200 mg for individuals weighing 75 kg or more.

One embodiment provides any of the above-described methods modified to comprise administering to an individual having an HCV infection an effective amount of an NS3 inhibitor; and a regimen of 9 μg INFERGEN® consensus IFN-α administered subcutaneously qd or tiw; and 25 μg Actimmune® human IFN-γ1b administered subcutaneously tiw, where the duration of therapy is 48 weeks.

One embodiment provides any of the above-described methods modified to comprise administering to an individual having an HCV infection an effective amount of an NS3 inhibitor; and a regimen of 9 μg INFERGEN® consensus IFN-α administered subcutaneously qd or tiw; and 200 μg Actimmune® human IFN-γ1b administered subcutaneously tiw, where the duration of therapy is 48 weeks.

One embodiment provides any of the above-described methods modified to comprise administering to an individual having an HCV infection an effective amount of an NS3 inhibitor; and a regimen of 100 μg monoPEG (30 kD, linear)-ylated consensus IFN-α administered subcutaneously every 10 days or qw, and ribavirin administered orally qd, where the duration of therapy is 48 weeks. In this embodiment, ribavirin is administered in an amount of 1000 mg for individuals weighing less than 75 kg, and 1200 mg for individuals weighing 75 kg or more.

One embodiment provides any of the above-described methods modified to comprise administering to an individual having an HCV infection an effective amount of an NS3 inhibitor; and a regimen of 100 µg monoPEG (30 kD, linear)-ylated consensus IFN-α administered subcutaneously every 10 days or qw; 50 µg Actimmune® human IFN-γ1b administered subcutaneously tiw; and ribavirin administered orally qd, where the duration of therapy is 48 weeks. In this embodiment, ribavirin is administered in an amount of 1000 mg for individuals weighing less than 75 kg, and 1200 mg for individuals weighing 75 kg or more.

One embodiment provides any of the above-described methods modified to comprise administering to an individual having an HCV infection an effective amount of an NS3 inhibitor; and a regimen of 100 µg monoPEG (30 kD, linear)-ylated consensus IFN-α administered subcutaneously every 10 days or qw; 100 µg Actimmune® human IFN-γ1b administered subcutaneously tiw; and ribavirin administered orally qd, where the duration of therapy is 48 weeks. In this embodiment, ribavirin is administered in an amount of 1000 mg for individuals weighing less than 75 kg, and 1200 mg for individuals weighing 75 kg or more.

One embodiment provides any of the above-described methods modified to comprise administering to an individual having an HCV infection an effective amount of an NS3 inhibitor; and a regimen of 100 µg monoPEG (30 kD, linear)-ylated consensus IFN-α administered subcutaneously every 10 days or qw; and 50 µg Actimmune® human IFN-γ1b administered subcutaneously tiw, where the duration of therapy is 48 weeks.

One embodiment provides any of the above-described methods modified to comprise administering to an individual having an HCV infection an effective amount of an NS3 inhibitor; and a regimen of 100 µg monoPEG (30 kD, linear)-ylated consensus IFN-α administered subcutaneously every 10 days or qw; and 100 µg Actimmune® human IFN-γ1b administered subcutaneously tiw, where the duration of therapy is 48 weeks.

One embodiment provides any of the above-described methods modified to comprise administering to an individual having an HCV infection an effective amount of an NS3 inhibitor; and a regimen of 150 µg monoPEG (30 kD, linear)-ylated consensus IFN-α administered subcutaneously every 10 days or qw, and ribavirin administered orally qd, where the duration of therapy is 48 weeks. In this embodiment, ribavirin is administered in an amount of 1000 mg for individuals weighing less than 75 kg, and 1200 mg for individuals weighing 75 kg or more.

One embodiment provides any of the above-described methods modified to comprise administering to an individual having an HCV infection an effective amount of an NS3 inhibitor; and a regimen of 150 µg monoPEG (30 kD, linear)-ylated consensus IFN-α administered subcutaneously every 10 days or qw; 50 µg Actimmune® human IFN-γ1b administered subcutaneously tiw; and ribavirin administered orally qd, where the duration of therapy is 48 weeks. In this embodiment, ribavirin is administered in an amount of 1000 mg for individuals weighing less than 75 kg, and 1200 mg for individuals weighing 75 kg or more.

One embodiment provides any of the above-described methods modified to comprise administering to an individual having an HCV infection an effective amount of an NS3 inhibitor; and a regimen of 150 µg monoPEG (30 kD, linear)-ylated consensus IFN-α administered subcutaneously every 10 days or qw; 100 µg Actimmune® human IFN-γ1b administered subcutaneously tiw; and ribavirin administered orally qd, where the duration of therapy is 48 weeks. In this embodiment, ribavirin is administered in an amount of 1000 mg for individuals weighing less than 75 kg, and 1200 mg for individuals weighing 75 kg or more.

One embodiment provides any of the above-described methods modified to comprise administering to an individual having an HCV infection an effective amount of an NS3 inhibitor; and a regimen of 150 µg monoPEG (30 kD, linear)-ylated consensus IFN-α administered subcutaneously every 10 days or qw; and 50 µg Actimmune® human IFN-γ1b administered subcutaneously tiw, where the duration of therapy is 48 weeks.

One embodiment provides any of the above-described methods modified to comprise administering to an individual having an HCV infection an effective amount of an NS3 inhibitor; and a regimen of 150 µg monoPEG (30 kD, linear)-ylated consensus IFN-α administered subcutaneously every 10 days or qw; and 100 µg Actimmune® human IFN-γ1b administered subcutaneously tiw, where the duration of therapy is 48 weeks.

One embodiment provides any of the above-described methods modified to comprise administering to an individual having an HCV infection an effective amount of an NS3 inhibitor; and a regimen of 200 µg monoPEG (30 kD, linear)-ylated consensus IFN-α administered subcutaneously every 10 days or qw, and ribavirin administered orally qd, where the duration of therapy is 48 weeks. In this embodiment, ribavirin is administered in an amount of 1000 mg for individuals weighing less than 75 kg, and 1200 mg for individuals weighing 75 kg or more.

One embodiment provides any of the above-described methods modified to comprise administering to an individual having an HCV infection an effective amount of an NS3 inhibitor; and a regimen of 200 µg monoPEG (30 kD, linear)-ylated consensus IFN-α administered subcutaneously every 10 days or qw; 50 µg Actimmune® human IFN-γ1b administered subcutaneously tiw; and ribavirin administered orally qd, where the duration of therapy is 48 weeks. In this embodiment, ribavirin is administered in an amount of 1000 mg for individuals weighing less than 75 kg, and 1200 mg for individuals weighing 75 kg or more.

One embodiment provides any of the above-described methods modified to comprise administering to an individual having an HCV infection an effective amount of an NS3 inhibitor; and a regimen of 200 µg monoPEG (30 kD, linear)-ylated consensus IFN-α administered subcutaneously every 10 days or qw; 100 µg Actimmune® human IFN-γ1b administered subcutaneously tiw; and ribavirin administered orally qd, where the duration of therapy is 48 weeks. In this embodiment, ribavirin is administered in an amount of 1000 mg for individuals weighing less than 75 kg, and 1200 mg for individuals weighing 75 kg or more.

One embodiment provides any of the above-described methods modified to comprise administering to an individual having an HCV infection an effective amount of an NS3 inhibitor; and a regimen of 200 µg monoPEG (30 kD, linear)-ylated consensus IFN-α administered subcutaneously every 10 days or qw; and 50 µg Actimmune® human IFN-γ1b administered subcutaneously tiw, where the duration of therapy is 48 weeks.

One embodiment provides any of the above-described methods modified to comprise administering to an individual having an HCV infection an effective amount of an NS3 inhibitor; and a regimen of 200 µg monoPEG (30 kD, linear)-ylated consensus IFN-α administered subcutaneously every 10 days or qw; and 100 µg Actimmune® human IFN-γ1b administered subcutaneously tiw, where the duration of therapy is 48 weeks.

Any of the above-described methods involving administering an NS3 inhibitor, a Type I interferon receptor agonist (e.g., an IFN-α), and a Type II interferon receptor agonist (e.g., an IFN-γ), can be augmented by administration of an effective amount of a TNF-α antagonist (e.g., a TNF-α antagonist other than pirfenidone or a pirfenidone analog). Exemplary, non-limiting TNF-α antagonists that are suitable for use in such combination therapies include ENBREL®, REMICADE®, and HUMIRA™.

One embodiment provides a method using an effective amount of ENBREL®; an effective amount of IFN-α; an effective amount of IFN-γ; and an effective amount of an NS3 inhibitor in the treatment of an HCV infection in a patient, comprising administering to the patient a dosage ENBREL® containing an amount of from about 0.1 µg to about 23 mg per dose, from about 0.1 µg to about 1 µg, from about 1 µg to about 10 µg, from about 10 µg to about 100 µg, from about 100 µg to about 1 µg, from about 1 µg to about 5 mg, from about 5 mg to about 10 mg, from about 10 mg to about 15 mg, from about 15 mg to about 20 mg, or from about 20 mg to about 23 mg of ENBREL®, subcutaneously qd, qod, tiw, biw, qw, qow, three times per month, once monthly, or once every other month, or per day substantially continuously or continuously, for the desired duration of treatment.

One embodiment provides a method using an effective amount of REMICADE®, an effective amount of IFN-α; an effective amount of IFN-γ; and an effective amount of an NS3 inhibitor in the treatment of an HCV infection in a patient, comprising administering to the patient a dosage of REMICADE® containing an amount of from about 0.1 mg/kg to about 4.5 mg/kg, from about 0.1 mg/kg to about 0.5 mg/kg, from about 0.5 mg/kg to about 1.0 mg/kg, from about 1.0 mg/kg to about 1.5 mg/kg, from about 1.5 mg/kg to about 2.0 mg/kg, from about 2.0 mg/kg to about 2.5 mg/kg, from about 2.5 mg/kg to about 3.0 mg/kg, from about 3.0 mg/kg to about 3.5 mg/kg, from about 3.5 mg/kg to about 4.0 mg/kg, or from about 4.0 mg/kg to about 4.5 mg/kg per dose of REMICADE®, intravenously qd, qod, tiw, biw, qw, qow, three times per month, once monthly, or once every other month, or per day substantially continuously or continuously, for the desired duration of treatment.

One embodiment provides a method using an effective amount of HUMIRA™, an effective amount of IFN-α; an effective amount of IFN-γ; and an effective amount of an NS3 inhibitor in the treatment of an HCV infection in a patient, comprising administering to the patient a dosage of HUMIRA™ containing an amount of from about 0.1 µg to about 35 mg, from about 0.1 µg to about 1 µg, from about 1 µg to about 10 µg, from about 10 µg to about 100 µg, from about 100 µg to about 1 mg, from about 1 mg to about 5 mg, from about 5 mg to about 10 mg, from about 10 mg to about 15 mg, from about 15 mg to about 20 mg, from about 20 mg to about 25 mg, from about 25 mg to about 30 mg, or from about 30 mg to about 35 mg per dose of a HUMIRA™, subcutaneously qd, qod, tiw, biw, qw, qow, three times per month, once monthly, or once every other month, or per day substantially continuously or continuously, for the desired duration of treatment.

Combination Therapies with Pirfenidone

In many embodiments, the methods provide for combination therapy comprising administering an NS3 inhibitor compound as described above, and an effective amount of pirfenidone or a pirfenidone analog. In some embodiments, an NS3 inhibitor compound, one or more interferon receptor agonist(s), and pirfenidone or pirfenidone analog are co-administered in the treatment methods of the embodiments. In certain embodiments, an NS3 inhibitor compound, a Type I interferon receptor agonist, and pirfenidone (or a pirfenidone analog) are co-administered. In other embodiments, an NS3 inhibitor compound, a Type I interferon receptor agonist, a Type II interferon receptor agonist, and pirfenidone (or a pirfenidone analog) are co-administered. Type I interferon receptor agonists suitable for use herein include any IFN-α, such as interferon alfa-2a, interferon alfa-2b, interferon alfacon-1, and PEGylated IFN-α's, such as peginterferon alfa-2a, peginterferon alfa-2b, and PEGylated consensus interferons, such as monoPEG (30 kD, linear)-ylated consensus interferon. Type II interferon receptor agonists suitable for use herein include any interferon-γ.

Pirfenidone or a pirfenidone analog can be administered once per month, twice per month, three times per month, once per week, twice per week, three times per week, four times per week, five times per week, six times per week, daily, or in divided daily doses ranging from once daily to 5 times daily over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

Effective dosages of pirfenidone or a specific pirfenidone analog include a weight-based dosage in the range from about 5 mg/kg/day to about 125 mg/kg/day, or a fixed dosage of about 400 mg to about 3600 mg per day, or about 800 mg to about 2400 mg per day, or about 1000 mg to about 1800 mg per day, or about 1200 mg to about 1600 mg per day, administered orally in one to five divided doses per day. Other doses and formulations of pirfenidone and specific pirfenidone analogs suitable for use in the treatment of fibrotic diseases are described in U.S. Pat. Nos. 5,310,562; 5,518,729; 5,716,632; and 6,090,822.

One embodiment provides any of the above-described methods modified to include co-administering to the patient a therapeutically effective amount of pirfenidone or a pirfenidone analog for the duration of the desired course of NS3 inhibitor compound treatment.

Combination Therapies with TNF-α Antagonists

In many embodiments, the methods provide for combination therapy comprising administering an effective amount of an NS3 inhibitor compound as described above, and an effective amount of TNF-α antagonist, in combination therapy for treatment of an HCV infection.

Effective dosages of a TNF-α antagonist range from 0.1 µg to 40 mg per dose, e.g., from about 0.1 µg to about 0.5 µg per dose, from about 0.5 µg to about 1.0 µg per dose, from about 1.0 µg per dose to about 5.0 µg per dose, from about 5.0 µg to about 10 µg per dose, from about 10 µg to about 20 µg per dose, from about 20 µg per dose to about 30 µg per dose, from about 30 µg per dose to about 40 µg per dose, from about 40 µg per dose to about 50 µg per dose, from about 50 µg per dose to about 60 µg per dose, from about 60 µg per dose to about 70 µg per dose, from about 70 µg to about 80 µg per dose, from about 80 µg per dose to about 100 µg per dose, from about 100 µg to about 150 µg per dose, from about 150 µg to about 200 µg per dose, from about 200 µg per dose to about 250 µg per dose, from about 250 µg to about 300 µg per dose, from about 300 µg to about 400 µg per dose, from about 400 µg to about 500 µg per dose, from about 500 µg to about 600 µg per dose, from about 600 µg to about 700 µg per dose, from about 700

µg to about 800 µg per dose, from about 800 µg to about 900 µg per dose, from about 900 µg to about 1000 µg per dose, from about 1 mg to about 10 mg per dose, from about 10 mg to about 15 mg per dose, from about 15 mg to about 20 mg per dose, from about 20 mg to about 25 mg per dose, from about 25 mg to about 30 mg per dose, from about 30 mg to about 35 mg per dose, or from about 35 mg to about 40 mg per dose.

In some embodiments, effective dosages of a TNF-α antagonist are expressed as mg/kg body weight. In these embodiments, effective dosages of a TNF-α antagonist are from about 0.1 mg/kg body weight to about 10 mg/kg body weight, e.g., from about 0.1 mg/kg body weight to about 0.5 mg/kg body weight, from about 0.5 mg/kg body weight to about 1.0 mg/kg body weight, from about 1.0 mg/kg body weight to about 2.5 mg/kg body weight, from about 2.5 mg/kg body weight to about 5.0 mg/kg body weight, from about 5.0 mg/kg body weight to about 7.5 mg/kg body weight, or from about 7.5 mg/kg body weight to about 10 mg/kg body weight.

In many embodiments, a TNF-α antagonist is administered for a period of about 1 day to about 7 days, or about 1 week to about 2 weeks, or about 2 weeks to about 3 weeks, or about 3 weeks to about 4 weeks, or about 1 month to about 2 months, or about 3 months to about 4 months, or about 4 months to about 6 months, or about 6 months to about 8 months, or about 8 months to about 12 months, or at least one year, and may be administered over longer periods of time. The TNF-α antagonist can be administered tid, bid, qd, qod, biw, tiw, qw, qow, three times per month, once monthly, substantially continuously, or continuously.

In many embodiments, multiple doses of a TNF-α antagonist are administered. For example, a TNF-α antagonist is administered once per month, twice per month, three times per month, every other week (qow), once per week (qw), twice per week (biw), three times per week (tiw), four times per week, five times per week, six times per week, every other day (qod), daily (qd), twice a day (bid), or three times a day (tid), substantially continuously, or continuously, over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

A TNF-α antagonist and an NS3 inhibitor are generally administered in separate formulations. A TNF-α antagonist and an NS3 inhibitor may be administered substantially simultaneously, or within about 30 minutes, about 1 hour, about 2 hours, about 4 hours, about 8 hours, about 16 hours, about 24 hours, about 36 hours, about 72 hours, about 4 days, about 7 days, or about 2 weeks of one another.

One embodiment provides a method using an effective amount of a TNF-α antagonist and an effective amount of an NS3 inhibitor in the treatment of an HCV infection in a patient, comprising administering to the patient a dosage of a TNF-α antagonist containing an amount of from about 0.1 µg to about 40 mg per dose of a TNF-α antagonist, subcutaneously qd, qod, tiw, or biw, or per day substantially continuously or continuously, for the desired duration of treatment with an NS3 inhibitor compound.

One embodiment provides a method using an effective amount of ENBREL® and an effective amount of an NS3 inhibitor in the treatment of an HCV infection in a patient, comprising administering to the patient a dosage ENBREL® containing an amount of from about 0.1 µg to about 23 mg per dose, from about 0.1 µg to about 1 µg, from about 1 µg to about 10 µg, from about 10 µg to about 100 µg, from about 100 µg to about 1 mg, from about 1 mg to about 5 mg, from about 5 mg to about 10 mg, from about 10 mg to about 15 mg, from about 15 mg to about 20 mg, or from about 20 mg to about 23 mg of ENBREL®, subcutaneously qd, qod, tiw, biw, qw, qow, three times per month, once monthly, or once every other month, or per day substantially continuously or continuously, for the desired duration of treatment with an NS3 inhibitor compound.

One embodiment provides a method using an effective amount of REMICADE® and an effective amount of an NS3 inhibitor in the treatment of an HCV infection in a patient, comprising administering to the patient a dosage of REMICADE® containing an amount of from about 0.1 mg/kg to about 4.5 mg/kg, from about 0.1 mg/kg to about 0.5 mg/kg, from about 0.5 mg/kg to about 1.0 mg/kg, from about 1.0 mg/kg to about 1.5 mg/kg, from about 1.5 mg/kg to about 2.0 mg/kg, from about 2.0 mg/kg to about 2.5 mg/kg, from about 2.5 mg/kg to about 3.0 mg/kg, from about 3.0 mg/kg to about 3.5 mg/kg, from about 3.5 mg/kg to about 4.0 mg/kg, or from about 4.0 mg/kg to about 4.5 mg/kg per dose of REMICADE®, intravenously qd, qod, tiw, biw, qw, qow, three times per month, once monthly, or once every other month, or per day substantially continuously or continuously, for the desired duration of treatment with an NS3 inhibitor compound.

One embodiment provides a method using an effective amount of HUMIRA™ and an effective amount of an NS3 inhibitor in the treatment of an HCV infection in a patient, comprising administering to the patient a dosage of HUMIRA™ containing an amount of from about 0.1 µg to about 35 mg, from about 0.1 µg to about 1 µg, from about 1 µg to about 10 µg, from about 10 µg to about 100 µg, from about 100 µg to about 1 mg, from about 1 mg to about 5 mg, from about 5 mg to about 10 mg, from about 10 mg to about 15 mg, from about 15 mg to about 20 mg, from about 20 mg to about 25 mg, from about 25 mg to about 30 mg, or from about 30 mg to about 35 mg per dose of a HUMIRA™, subcutaneously qd, qod, tiw, biw, qw, qow, three times per month, once monthly, or once every other month, or per day substantially continuously or continuously, for the desired duration of treatment with an NS3 inhibitor compound.

Combination Therapies with Thymosin-α

In many embodiments, the methods provide for combination therapy comprising administering an effective amount of an NS3 inhibitor compound as described above, and an effective amount of thymosin-α, in combination therapy for treatment of an HCV infection.

Effective dosages of thymosin-α range from about 0.5 mg to about 5 mg, e.g., from about 0.5 mg to about 1.0 mg, from about 1.0 mg to about 1.5 mg, from about 1.5 mg to about 2.0 mg, from about 2.0 mg to about 2.5 mg, from about 2.5 mg to about 3.0 mg, from about 3.0 mg to about 3.5 mg, from about 3.5 mg to about 4.0 mg, from about 4.0 mg to about 4.5 mg, or from about 4.5 mg to about 5.0 mg. In particular embodiments, thymosin-α is administered in dosages containing an amount of 1.0 mg or 1.6 mg.

One embodiment provides a method using an effective amount of ZADAXIN™ thymosin-α and an effective amount of an NS3 inhibitor in the treatment of an HCV infection in a patient, comprising administering to the patient a dosage of ZADAXIN™ containing an amount of from about 1.0 mg to about 1.6 mg per dose, subcutaneously twice per week for the desired duration of treatment with the NS3 inhibitor compound.

Combination Therapies with a TNF-α Antagonist and an Interferon

Some embodiments provide a method of treating an HCV infection in an individual having an HCV infection, the method comprising administering an effective amount of an NS3 inhibitor, and effective amount of a TNF-α antagonist, and an effective amount of one or more interferons.

One embodiment provides any of the above-described methods modified to use an effective amount of IFN-γ and an effective amount of a TNF-α antagonist in the treatment of HCV infection in a patient comprising administering to the patient a dosage of IFN-γ containing an amount of about 10 µg to about 300 µg of drug per dose of IFN-γ, subcutaneously qd, qod, tiw, biw, qw, qow, three times per month, once monthly, or per day substantially continuously or continuously, in combination with a dosage of a TNF-α antagonist containing an amount of from about 0.1 µg to about 40 mg per dose of a TNF-α antagonist, subcutaneously qd, qod, tiw, or biw, or per day substantially continuously or continuously, for the desired duration of treatment with an NS3 inhibitor compound.

One embodiment provides any of the above-described methods modified to use an effective amount of IFN-γ and an effective amount of a TNF-α antagonist in the treatment of HCV infection in a patient comprising administering to the patient a dosage of IFN-γ containing an amount of about 10 µg to about 100 µg of drug per dose of IFN-γ, subcutaneously qd, qod, tiw, biw, qw, qow, three times per month, once monthly, or per day substantially continuously or continuously, in combination with a dosage of a TNF-α antagonist containing an amount of from about 0.1 µg to about 40 mg per dose of a TNF-α antagonist, subcutaneously qd, qod, tiw, or biw, or per day substantially continuously or continuously, for the desired duration of treatment with an NS3 inhibitor compound.

Another embodiment provides any of the above-described methods modified to use an effective amount of IFN-γ and an effective amount of a TNF-α antagonist in the treatment of a virus infection in a patient comprising administering to the patient a total weekly dosage of IFN-γ containing an amount of about 30 µg to about 1,000 µg of drug per week in divided doses administered subcutaneously qd, qod, tiw, biw, or administered substantially continuously or continuously, in combination with a dosage of a TNF-α antagonist containing an amount of from about 0.1 µg to about 40 mg per dose of a TNF-α antagonist, subcutaneously qd, qod, tiw, or biw, or per day substantially continuously or continuously, for the desired duration of treatment with an NS3 inhibitor compound.

Another embodiment provides any of the above-described methods modified to use an effective amount of IFN-γ and an effective amount of a TNF-α antagonist in the treatment of a virus infection in a patient comprising administering to the patient a total weekly dosage of IFN-γ containing an amount of about 100 µg to about 300 µg of drug per week in divided doses administered subcutaneously qd, qod, tiw, biw, or administered substantially continuously or continuously, in combination with a dosage of a TNF-α antagonist containing an amount of from about 0.1 µg to about 40 mg per dose of a TNF-α antagonist, subcutaneously qd, qod, tiw, or biw, or per day substantially continuously or continuously, for the desired duration of treatment with an NS3 inhibitor compound.

One embodiment provides any of the above-described methods modified to use an effective amount of INFERGEN® consensus IFN-α and a TNF-α antagonist in the treatment of HCV infection in a patient comprising administering to the patient a dosage of INFERGEN® containing an amount of about 1 µg to about 30 µg, of drug per dose of INFERGEN®, subcutaneously qd, qod, tiw, biw, qw, qow, three times per month, once monthly, or per day substantially continuously or continuously, in combination with a dosage of a TNF-α antagonist containing an amount of from about 0.1 µg to about 40 mg per dose of a TNF-α antagonist, subcutaneously qd, qod, tiw, or biw, or per day substantially continuously or continuously, for the desired duration of treatment with an NS3 inhibitor compound.

One embodiment provides any of the above-described methods modified to use an effective amount of INFERGEN® consensus IFN-α and a TNF-α antagonist in the treatment of HCV infection in a patient comprising administering to the patient a dosage of INFERGEN® containing an amount of about 1 µg to about 9 µg, of drug per dose of INFERGEN®, subcutaneously qd, qod, tiw, biw, qw, qow, three times per month, once monthly, or per day substantially continuously or continuously, in combination with a dosage of a TNF-α antagonist containing an amount of from about 0.1 µg to about 40 mg per dose of a TNF-α antagonist, subcutaneously qd, qod, tiw, or biw, or per day substantially continuously or continuously, for the desired duration of treatment with an NS3 inhibitor compound.

Another embodiment provides any of the above-described methods modified to use an effective amount of PEGylated consensus IFN-α and an effective amount of a TNF-α antagonist in the treatment of a virus infection in a patient comprising administering to the patient a dosage of PEGylated consensus IFN-α (PEG-CIFN) containing an amount of about 4 µg to about 60 µg of CIFN amino acid weight per dose of PEG-CIFN, subcutaneously qw, qow, three times per month, or monthly, in combination with a dosage of a TNF-α antagonist containing an amount of from about 0.1 µg to about 40 mg per dose of a TNF-α antagonist, subcutaneously qd, qod, tiw, or biw, or per day substantially continuously or continuously, for the desired duration of treatment with an NS3 inhibitor compound.

Another embodiment provides any of the above-described methods modified to use an effective amount of PEGylated consensus IFN-α and an effective amount of a TNF-α antagonist in the treatment of a virus infection in a patient comprising administering to the patient a dosage of PEGylated consensus IFN-α (PEG-CIFN) containing an amount of about 18 µg to about 24 µg of CIFN amino acid weight per dose of PEG-CIFN, subcutaneously qw, qow, three times per month, or monthly, in combination with a dosage of a TNF-α antagonist containing an amount of from about 0.1 µg to about 40 mg per dose of a TNF-α antagonist, subcutaneously qd, qod, tiw, or biw, or per day substantially continuously or continuously, for the desired duration of treatment with an NS3 inhibitor compound.

Another embodiment provides any of the above-described methods modified to use an effective amount of IFN-α 2a or 2b or 2c and an effective amount of a TNF-α antagonist in the treatment of a virus infection in a patient comprising administering to the patient a dosage of IFN-α 2a, 2b or 2c containing an amount of about 1 MU to about 20 MU of drug per dose of IFN-α2a, 2b or 2c subcutaneously qd, qod, tiw, biw, or per day substantially continuously or continuously, in combination with a dosage of a TNF-α antagonist containing an amount of from about 0.1 µg to about 40 mg per dose of a TNF-α antagonist, subcutaneously qd, qod, tiw, or biw, or per day substantially continuously or continuously, for the desired duration of treatment with an NS3 inhibitor compound.

Another embodiment provides any of the above-described methods modified to use an effective amount of IFN-α 2a or 2b or 2c and an effective amount of a TNF-α antagonist in the treatment of a virus infection in a patient comprising administering to the patient a dosage of IFN-α 2a, 2b or 2c containing an amount of about 3 MU of drug per dose of IFN-α 2a, 2b or 2c subcutaneously qd, qod, tiw, biw, or per day substantially continuously or continuously, in combination with a dosage of a TNF-α antagonist containing an amount of from about 0.1 µg to about 40 mg per dose of a TNF-α antagonist, subcutaneously qd, qod, tiw, or biw, or per day substantially continuously or continuously, for the desired duration of treatment with an NS3 inhibitor compound.

Another embodiment provides any of the above-described methods modified to use an effective amount of IFN-α 2a or 2b or 2c and an effective amount of a TNF-α antagonist in the treatment of a virus infection in a patient comprising administering to the patient a dosage of IFN-α 2a, 2b or 2c containing an amount of about 10 MU of drug per dose of IFN-α 2a, 2b or 2c subcutaneously qd, qod, tiw, biw, or per day substantially continuously or continuously, in combination with a dosage of a TNF-α antagonist containing an amount of from about 0.1 µg to about 40 mg per dose of a TNF-α antagonist, subcutaneously qd, qod, tiw, or biw, or per day substantially continuously or continuously, for the desired duration of treatment with an NS3 inhibitor compound.

Another embodiment provides any of the above-described methods modified to use an effective amount of PEGASYS® PEGylated IFN-α2a and an effective amount of a TNF-α antagonist in the treatment of a virus infection in a patient comprising administering to the patient a dosage of PEGASYS® containing an amount of about 90 µg to about 360 µg, of drug per dose of PEGASYS®, subcutaneously qw, qow, three times per month, or monthly, in combination with a dosage of a TNF-α antagonist containing an amount of from about 0.1 µg to about 40 mg per dose of a TNF-α antagonist, subcutaneously qd, qod, tiw, or biw, or per day substantially continuously or continuously, for the desired duration of treatment with an NS3 inhibitor compound.

Another embodiment provides any of the above-described methods modified to use an effective amount of PEGASYS® PEGylated IFN-α2a and an effective amount of a TNF-α antagonist in the treatment of a virus infection in a patient comprising administering to the patient a dosage of PEGASYS® containing an amount of about 180 µg, of drug per dose of PEGASYS®, subcutaneously qw, qow, three times per month, or monthly, in combination with a dosage of a TNF-α antagonist containing an amount of from about 0.1 µg to about 40 mg per dose of a TNF-α antagonist, subcutaneously qd, qod, tiw, or biw, or per day substantially continuously or continuously, for the desired duration of treatment with an NS3 inhibitor compound.

Another embodiment provides any of the above-described methods modified to use an effective amount of PEG-INTRON® PEGylated IFN-α2b and an effective amount of a TNF-α antagonist in the treatment of a virus infection in a patient comprising administering to the patient a dosage of PEG-INTRON® containing an amount of about 0.75 µg to about 3.0 µg of drug per kilogram of body weight per dose of PEG-INTRON®, subcutaneously qw, qow, three times per month, or monthly, in combination with a dosage of a TNF-α antagonist containing an amount of from about 0.1 µg to about 40 mg per dose of a TNF-α antagonist, subcutaneously qd, qod, tiw, or biw, or per day substantially continuously or continuously, for the desired duration of treatment with an NS3 inhibitor compound.

Another embodiment provides any of the above-described methods modified to use an effective amount of PEG-INTRON® PEGylated IFN-α2b and an effective amount of a TNF-α antagonist in the treatment of a virus infection in a patient comprising administering to the patient a dosage of PEG-INTRON® containing an amount of about 1.5 µg of drug per kilogram of body weight per dose of PEG-INTRON®, subcutaneously qw, qow, three times per month, or monthly, in combination with a dosage of a TNF-α antagonist containing an amount of from about 0.1 µg to about 40 mg per dose of a TNF-α antagonist, subcutaneously qd, qod, tiw, or biw, or per day substantially continuously or continuously, for the desired duration of treatment with an NS3 inhibitor compound.

Combination Therapies with Other Antiviral Agents

Other agents such as inhibitors of HCV NS3 helicase are also attractive drugs for combinational therapy, and are contemplated for use in combination therapies described herein. Ribozymes such as Heptazyme™ and phosphorothioate oligonucleotides which are complementary to HCV protein sequences and which inhibit the expression of viral core proteins are also suitable for use in combination therapies described herein.

In some embodiments, the additional antiviral agent(s) is administered during the entire course of treatment with the NS3 inhibitor compound described herein, and the beginning and end of the treatment periods coincide. In other embodiments, the additional antiviral agent(s) is administered for a period of time that is overlapping with that of the NS3 inhibitor compound treatment, e.g., treatment with the additional antiviral agent(s) begins before the NS3 inhibitor compound treatment begins and ends before the NS3 inhibitor compound treatment ends; treatment with the additional antiviral agent(s) begins after the NS3 inhibitor compound treatment begins and ends after the NS3 inhibitor compound treatment ends; treatment with the additional antiviral agent(s) begins after the NS3 inhibitor compound treatment begins and ends before the NS3 inhibitor compound treatment ends; or treatment with the additional antiviral agent(s) begins before the NS3 inhibitor compound treatment begins and ends after the NS3 inhibitor compound treatment ends.

The NS3 inhibitor compound can be administered together with (i.e., simultaneously in separate formulations; simultaneously in the same formulation; administered in separate formulations and within about 48 hours, within about 36 hours, within about 24 hours, within about 16 hours, within about 12 hours, within about 8 hours, within about 4 hours, within about 2 hours, within about 1 hour, within about 30 minutes, or within about 15 minutes or less) one or more additional antiviral agents.

As non-limiting examples, any of the above-described methods featuring an IFN-α regimen can be modified to replace the subject IFN-α regimen with a regimen of monoPEG (30 kD, linear)-ylated consensus IFN-α comprising administering a dosage of monoPEG (30 kD, linear)-ylated consensus IFN-α containing an amount of 100 µg of drug per dose, subcutaneously once weekly, once every 8 days, or once every 10 days for the desired treatment duration with an NS3 inhibitor compound.

As non-limiting examples, any of the above-described methods featuring an IFN-α regimen can be modified to replace the subject IFN-α regimen with a regimen of monoPEG (30 kD, linear)-ylated consensus IFN-α comprising administering a dosage of monoPEG (30 kD, linear)-ylated consensus IFN-α containing an amount of 150 µg of drug per dose, subcutaneously once weekly, once every 8 days, or once every 10 days for the desired treatment duration with an NS3 inhibitor compound.

As non-limiting examples, any of the above-described methods featuring an IFN-α regimen can be modified to replace the subject IFN-α regimen with a regimen of monoPEG (30 kD, linear)-ylated consensus IFN-α comprising administering a dosage of monoPEG (30 kD, linear)-ylated consensus IFN-α containing an amount of 200 μg of drug per dose, subcutaneously once weekly, once every 8 days, or once every 10 days for the desired treatment duration with an NS3 inhibitor compound.

As non-limiting examples, any of the above-described methods featuring an IFN-α regimen can be modified to replace the subject IFN-α regimen with a regimen of INFERGEN® interferon alfacon-1 comprising administering a dosage of INFERGEN® interferon alfacon-1 containing an amount of 9 μg of drug per dose, subcutaneously once daily or three times per week for the desired treatment duration with an NS3 inhibitor compound.

As non-limiting examples, any of the above-described methods featuring an IFN-α regimen can be modified to replace the subject IFN-α regimen with a regimen of INFERGEN® interferon alfacon-1 comprising administering a dosage of INFERGEN® interferon alfacon-1 containing an amount of 15 μg of drug per dose, subcutaneously once daily or three times per week for the desired treatment duration with an NS3 inhibitor compound.

As non-limiting examples, any of the above-described methods featuring an IFN-γ regimen can be modified to replace the subject IFN-γ regimen with a regimen of IFN-γ comprising administering a dosage of IFN-γ containing an amount of 25 μg of drug per dose, subcutaneously three times per week for the desired treatment duration with an NS3 inhibitor compound.

As non-limiting examples, any of the above-described methods featuring an IFN-γ regimen can be modified to replace the subject IFN-γ regimen with a regimen of IFN-γ comprising administering a dosage of IFN-γ containing an amount of 50 μg of drug per dose, subcutaneously three times per week for the desired treatment duration with an NS3 inhibitor compound.

As non-limiting examples, any of the above-described methods featuring an IFN-γ regimen can be modified to replace the subject IFN-γ regimen with a regimen of IFN-γ comprising administering a dosage of IFN-γ containing an amount of 100 μg of drug per dose, subcutaneously three times per week for the desired treatment duration with an NS3 inhibitor compound.

As non-limiting examples, any of the above-described methods featuring an IFN-α and IFN-γ combination regimen can be modified to replace the subject IFN-α and IFN-γ combination regimen with an IFN-α and IFN-γ combination regimen comprising: (a) administering a dosage of monoPEG (30 kD, linear)-ylated consensus IFN-α containing an amount of 100 μg of drug per dose, subcutaneously once weekly, once every 8 days, or once every 10 days; and (b) administering a dosage of IFN-γ containing an amount of 50 μg of drug per dose, subcutaneously three times per week; for the desired treatment duration with an NS3 inhibitor compound.

As non-limiting examples, any of the above-described methods featuring a TNF antagonist regimen can be modified to replace the subject TNF antagonist regimen with a TNF antagonist regimen comprising administering a dosage of a TNF antagonist selected from the group of: (a) etanercept in an amount of 25 mg of drug per dose subcutaneously twice per week, (b) infliximab in an amount of 3 mg of drug per kilogram of body weight per dose intravenously at weeks 0, 2 and 6, and every 8 weeks thereafter, or (c) adalimumab in an amount of 40 mg of drug per dose subcutaneously once weekly or once every 2 weeks; for the desired treatment duration with an NS3 inhibitor compound.

As non-limiting examples, any of the above-described methods featuring an IFN-α and IFN-γ combination regimen can be modified to replace the subject IFN-α and IFN-γ combination regimen with an IFN-α and IFN-γ combination regimen comprising: (a) administering a dosage of monoPEG (30 kD, linear)-ylated consensus IFN-α containing an amount of 100 μg of drug per dose, subcutaneously once weekly, once every 8 days, or once every 10 days; and (b) administering a dosage of IFN-γ containing an amount of 100 μg of drug per dose, subcutaneously three times per week; for the desired treatment duration with an NS3 inhibitor compound.

As non-limiting examples, any of the above-described methods featuring an IFN-α and IFN-γ combination regimen can be modified to replace the subject IFN-α and IFN-γ combination regimen with an IFN-α and IFN-γ combination regimen comprising: (a) administering a dosage of monoPEG (30 kD, linear)-ylated consensus IFN-α containing an amount of 150 μg of drug per dose, subcutaneously once weekly, once every 8 days, or once every 10 days; and (b) administering a dosage of IFN-γ containing an amount of 50 μg of drug per dose, subcutaneously three times per week; for the desired treatment duration with an NS3 inhibitor compound.

As non-limiting examples, any of the above-described methods featuring an IFN-α and IFN-γ combination regimen can be modified to replace the subject IFN-α and IFN-γ combination regimen with an IFN-α and IFN-γ combination regimen comprising: (a) administering a dosage of monoPEG (30 kD, linear)-ylated consensus IFN-α containing an amount of 150 μg of drug per dose, subcutaneously once weekly, once every 8 days, or once every 10 days; and (b) administering a dosage of IFN-γ containing an amount of 100 μg of drug per dose, subcutaneously three times per week; for the desired treatment duration with an NS3 inhibitor compound.

As non-limiting examples, any of the above-described methods featuring an IFN-α and IFN-γ combination regimen can be modified to replace the subject IFN-α and IFN-γ combination regimen with an IFN-α and IFN-γ combination regimen comprising: (a) administering a dosage of monoPEG (30 kD, linear)-ylated consensus IFN-α containing an amount of 200 μg of drug per dose, subcutaneously once weekly, once every 8 days, or once every 10 days; and (b) administering a dosage of IFN-γ containing an amount of 50 μg of drug per dose, subcutaneously three times per week; for the desired treatment duration with an NS3 inhibitor compound.

As non-limiting examples, any of the above-described methods featuring an IFN-α and IFN-γ combination regimen can be modified to replace the subject IFN-α and IFN-γ combination regimen with an IFN-α and IFN-γ combination regimen comprising: (a) administering a dosage of monoPEG (30 kD, linear)-ylated consensus IFN-α containing an amount of 200 μg of drug per dose, subcutaneously once weekly, once every 8 days, or once every 10 days; and (b) administering a dosage of IFN-γ containing an amount of 100 μg of drug per dose, subcutaneously three times per week; for the desired treatment duration with an NS3 inhibitor compound.

As non-limiting examples, any of the above-described methods featuring an IFN-α and IFN-γ combination regimen can be modified to replace the subject IFN-α and IFN-γ combination regimen with an IFN-α and IFN-γ combination regimen comprising: (a) administering a dosage of INFERGEN® interferon alfacon-1 containing an amount of 9 μg of drug per dose, subcutaneously three times per week; and (b) administering a dosage of IFN-γ containing an amount of 25 μg of drug per dose, subcutaneously three times per week; for the desired treatment duration with an NS3 inhibitor compound.

As non-limiting examples, any of the above-described methods featuring an IFN-α and IFN-γ combination regimen can be modified to replace the subject IFN-α and IFN-γ combination regimen with an IFN-α and IFN-γ combination regimen comprising: (a) administering a dosage of INFERGEN® interferon alfacon-1 containing an amount of 9 μg of drug per dose, subcutaneously three times per week; and (b) administering a dosage of IFN-γ containing an amount of 50 μg of drug per dose, subcutaneously three times per week; for the desired treatment duration with an NS3 inhibitor compound.

As non-limiting examples, any of the above-described methods featuring an IFN-α and IFN-γ combination regimen can be modified to replace the subject IFN-α and IFN-γ combination regimen with an IFN-α and IFN-γ combination regimen comprising: (a) administering a dosage of INFERGEN® interferon alfacon-1 containing an amount of 9 μg of drug per dose, subcutaneously three times per week; and (b) administering a dosage of IFN-γ containing an amount of 100 μg of drug per dose, subcutaneously three times per week; for the desired treatment duration with an NS3 inhibitor compound.

As non-limiting examples, any of the above-described methods featuring an IFN-α and IFN-γ combination regimen can be modified to replace the subject IFN-α and IFN-γ combination regimen with an IFN-α and IFN-γ combination regimen comprising: (a) administering a dosage of INFERGEN® interferon alfacon-1 containing an amount of 9 μg of drug per dose, subcutaneously once daily; and (b) administering a dosage of IFN-γ containing an amount of 25 μg of drug per dose, subcutaneously three times per week; for the desired treatment duration with an NS3 inhibitor compound.

As non-limiting examples, any of the above-described methods featuring an IFN-α and IFN-γ combination regimen can be modified to replace the subject IFN-α and IFN-γ combination regimen with an IFN-α and IFN-γ combination regimen comprising: (a) administering a dosage of INFERGEN® interferon alfacon-1 containing an amount of 9 μg of drug per dose, subcutaneously once daily; and (b) administering a dosage of IFN-γ containing an amount of 50 μg of drug per dose, subcutaneously three times per week; for the desired treatment duration with an NS3 inhibitor compound.

As non-limiting examples, any of the above-described methods featuring an IFN-α and IFN-γ combination regimen can be modified to replace the subject IFN-α and IFN-γ combination regimen with an IFN-α and IFN-γ combination regimen comprising: (a) administering a dosage of INFERGEN® interferon alfacon-1 containing an amount of 9 μg of drug per dose, subcutaneously once daily; and (b) administering a dosage of IFN-γ containing an amount of 100 μg of drug per dose, subcutaneously three times per week; for the desired treatment duration with an NS3 inhibitor compound.

As non-limiting examples, any of the above-described methods featuring an IFN-α and IFN-γ combination regimen can be modified to replace the subject IFN-α and IFN-γ combination regimen with an IFN-α and IFN-γ combination regimen comprising: (a) administering a dosage of INFERGEN® interferon alfacon-1 containing an amount of 15 μg of drug per dose, subcutaneously three times per week; and (b) administering a dosage of IFN-γ containing an amount of 25 μg of drug per dose, subcutaneously three times per week; for the desired treatment duration with an NS3 inhibitor compound.

As non-limiting examples, any of the above-described methods featuring an IFN-α and IFN-γ combination regimen can be modified to replace the subject IFN-α and IFN-γ combination regimen with an IFN-α and IFN-γ combination regimen comprising: (a) administering a dosage of INFERGEN® interferon alfacon-1 containing an amount of 15 μg of drug per dose, subcutaneously three times per week; and (b) administering a dosage of IFN-γ containing an amount of 50 μg of drug per dose, subcutaneously three times per week; for the desired treatment duration with an NS3 inhibitor compound.

As non-limiting examples, any of the above-described methods featuring an IFN-α and IFN-γ combination regimen can be modified to replace the subject IFN-α and IFN-γ combination regimen with an IFN-α and IFN-γ combination regimen comprising: (a) administering a dosage of INFERGEN® interferon alfacon-1 containing an amount of 15 μg of drug per dose, subcutaneously three times per week; and (b) administering a dosage of IFN-γ containing an amount of 100 μg of drug per dose, subcutaneously three times per week; for the desired treatment duration with an NS3 inhibitor compound.

As non-limiting examples, any of the above-described methods featuring an IFN-α and IFN-γ combination regimen can be modified to replace the subject IFN-α and IFN-γ combination regimen with an IFN-α and IFN-γ combination regimen comprising: (a) administering a dosage of INFERGEN® interferon alfacon-1 containing an amount of 15 μg of drug per dose, subcutaneously once daily; and (b) administering a dosage of IFN-γ containing an amount of 25 μg of drug per dose, subcutaneously three times per week; for the desired treatment duration with an NS3 inhibitor compound.

As non-limiting examples, any of the above-described methods featuring an IFN-α and IFN-γ combination regimen can be modified to replace the subject IFN-α and IFN-γ combination regimen with an IFN-α and IFN-γ combination regimen comprising: (a) administering a dosage of INFERGEN® interferon alfacon-1 containing an amount of 15 μg of drug per dose, subcutaneously once daily; and (b) administering a dosage of IFN-γ containing an amount of 50 μg of drug per dose, subcutaneously three times per week; for the desired treatment duration with an NS3 inhibitor compound.

As non-limiting examples, any of the above-described methods featuring an IFN-α and IFN-γ combination regimen can be modified to replace the subject IFN-α and IFN-γ combination regimen with an IFN-α and IFN-γ combination regimen comprising: (a) administering a dosage of INFERGEN® interferon alfacon-1 containing an amount of 15 μg of drug per dose, subcutaneously once daily; and (b) administering a dosage of IFN-γ containing an amount of 100 μg of drug per dose, subcutaneously three times per week; for the desired treatment duration with an NS3 inhibitor compound.

As non-limiting examples, any of the above-described methods featuring an IFN-α, IFN-γ and TNF antagonist combination regimen can be modified to replace the subject IFN-α, IFN-γ and TNF antagonist combination regimen with an IFN-α, IFN-γ and TNF antagonist combination regimen comprising: (a) administering a dosage of monoPEG (30 kD, linear)-ylated consensus IFN-α containing an amount of 100 μg of drug per dose, subcutaneously once weekly, once every 8 days, or once every 10 days; (b) administering a dosage of IFN-γ containing an amount of 100 μg of drug per dose, subcutaneously three times per week; and (c) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α, IFN-γ and TNF antagonist combination regimen can be modified to replace the subject IFN-α, IFN-γ and TNF antagonist combination regimen with an IFN-α, IFN-γ and TNF antagonist combination regimen comprising: (a) administering a dosage of monoPEG (30 kD, linear)-ylated consensus IFN-α containing an amount of 100 μg of drug per dose, subcutaneously once weekly, once every 8 days, or once every 10 days; (b) administering a dosage of IFN-γ containing an amount of 50 μg of drug per dose, subcutaneously three times per week; and (c) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α, IFN-γ and TNF antagonist combination regimen can be modified to replace the subject IFN-α, IFN-γ and TNF antagonist combination regimen with an IFN-α, IFN-γ and TNF antagonist combination regimen comprising: (a) administering a dosage of monoPEG (30 kD, linear)-ylated consensus IFN-α containing an amount of 150 μg of drug per dose, subcutaneously once weekly, once every 8 days, or once every 10 days; (b) administering a dosage of IFN-γ containing an amount of 50 μg of drug per dose, subcutaneously three times per week; and (c) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α, IFN-γ and TNF antagonist combination regimen can be modified to replace the subject IFN-α, IFN-γ and TNF antagonist combination regimen with an IFN-α, IFN-γ and TNF antagonist combination regimen comprising: (a) administering a dosage of monoPEG (30 kD, linear)-ylated consensus IFN-α containing an amount of 150 μg of drug per dose, subcutaneously once weekly, once every 8 days, or once every 10 days; (b) administering a dosage of IFN-γ containing an amount of 100 μg of drug per dose, subcutaneously three times per week; and (c) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α, IFN-γ and TNF antagonist combination regimen can be modified to replace the subject IFN-α, IFN-γ and TNF antagonist combination regimen with an IFN-α, IFN-γ and TNF antagonist combination regimen comprising: (a) administering a dosage of monoPEG (30 kD, linear)-ylated consensus IFN-α containing an amount of 200 μg of drug per dose, subcutaneously once weekly, once every 8 days, or once every 10 days; (b) administering a dosage of IFN-γ containing an amount of 50 μg of drug per dose, subcutaneously three times per week; and (c) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α, IFN-γ and TNF antagonist combination regimen can be modified to replace the subject IFN-α, IFN-γ and TNF antagonist combination regimen with an IFN-α, IFN-γ and TNF antagonist combination regimen comprising: (a) administering a dosage of monoPEG (30 kD, linear)-ylated consensus IFN-α containing an amount of 200 μg of drug per dose, subcutaneously once weekly, once every 8 days, or once every 10 days; (b) administering a dosage of IFN-γ containing an amount of 100 μg of drug per dose, subcutaneously three times per week; and (c) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α, IFN-γ and TNF antagonist combination regimen can be modified to replace the subject IFN-α, IFN-γ and TNF antagonist combination regimen with an IFN-α, IFN-γ and TNF antagonist combination regimen comprising: (a) administering a dosage of INFERGEN® interferon alfacon-1 containing an amount of 9 μg of drug per dose, subcutaneously three times per week; (b) administering a dosage of IFN-γ containing an amount of 25 μg of drug per dose, subcutaneously three times per week; and (c) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α, IFN-γ and TNF antagonist combination regimen can be modified to replace the subject IFN-α, IFN-γ and TNF antagonist combination regimen with an IFN-α, IFN-γ and TNF antagonist combination regimen comprising: (a) administering a dosage of INFERGEN® interferon alfacon-1 containing an amount of 9 μg of drug per dose, subcutaneously three times per week; (b) administering a dosage of IFN-γ containing an amount of 50 μg of drug per dose, subcutaneously three times per week; and (c) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α, IFN-γ and TNF antagonist combination regimen can be modified to replace the subject IFN-α, IFN-γ and TNF antagonist combination regimen with an IFN-α, IFN-γ and TNF antagonist combination regimen comprising: (a) administering a dosage of INFERGEN® interferon alfacon-1 containing an amount of 9 μg of drug per dose, subcutaneously three times per week; (b) administering a dosage of IFN-γ containing an amount of 100 μg of drug per dose, subcutaneously three times per week; and (c) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α, IFN-γ and TNF antagonist combination regimen can be modified to replace the subject IFN-α, IFN-γ and TNF antagonist combination regimen with an IFN-α, IFN-γ and TNF antagonist combination regimen comprising: (a) administering a dosage of INFERGEN® interferon alfacon-1 containing an amount of 9 μg of drug per dose, subcutaneously once daily; (b) administering a dosage of IFN-γ containing an amount of 25 μg of drug per dose, subcutaneously three times per week; and (c) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α, IFN-γ and TNF antagonist combination regimen can be modified to replace the subject IFN-α, IFN-γ and TNF antagonist combination regimen with an IFN-α, IFN-γ and TNF antagonist combination regimen comprising: (a) administering a dosage of INFERGEN® interferon alfacon-1 containing an amount of 9 μg of drug per dose, subcutaneously once daily; (b) administering a dosage of IFN-γ containing an amount of 50 μg of drug per dose, subcutaneously three times per week; and (c) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α, IFN-γ and TNF antagonist combination regimen can be modified to replace the subject IFN-α, IFN-γ and TNF antagonist combination regimen with an IFN-α, IFN-γ and TNF antagonist combination regimen comprising: (a) administering a dosage of INFERGEN® interferon alfacon-1 containing an amount of 9 μg of drug per dose, subcutaneously once daily; (b) administering a dosage of IFN-γ containing an amount of 100 μg of drug per dose, subcutaneously three times per week; and (c) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α, IFN-γ and TNF antagonist combination regimen can be modified to replace the subject IFN-α, IFN-γ and TNF antagonist combination regimen with an IFN-α, IFN-γ and TNF antagonist combination regimen comprising: (a) administering a dosage of INFERGEN® interferon alfacon-1 containing an amount of 15 μg of drug per dose, subcutaneously three times per week; (b) administering a dosage of IFN-γ containing an amount of 25 μg of drug per dose, subcutaneously three times per week; and (c) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α, IFN-γ and TNF antagonist combination regimen can be modified to replace the subject IFN-α, IFN-γ and TNF antagonist combination regimen with an IFN-α, IFN-γ and TNF antagonist combination regimen comprising: (a) administering a dosage of INFERGEN® interferon alfacon-1 containing an amount of 15 μg of drug per dose, subcutaneously three times per week; (b) administering a dosage of IFN-γ containing an amount of 50 μg of drug per dose, subcutaneously three times per week; and (c) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α, IFN-γ and TNF antagonist combination regimen can be modified to replace the subject IFN-α, IFN-γ and TNF antagonist combination regimen with an IFN-α, IFN-γ and TNF antagonist combination regimen comprising: (a) administering a dosage of INFERGEN® interferon alfacon-1 containing an amount of 15 μg of drug per dose, subcutaneously three times per week; (b) administering a dosage of IFN-γ containing an amount of 100 μg of drug per dose, subcutaneously three times per week; and (c) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α, IFN-γ and TNF antagonist combination regimen can be modified to replace the subject IFN-α, IFN-γ and TNF antagonist combination regimen with an IFN-α, IFN-γ and TNF antagonist combination regimen comprising: (a) administering a dosage of INFERGEN® interferon alfacon-1 containing an amount of 15 μg of drug per dose, subcutaneously once daily; (b) administering a dosage of IFN-γ containing an amount of 25 μg of drug per dose, subcutaneously three times per week; and (c) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α, IFN-γ and TNF antagonist combination regimen can be modified to replace the subject IFN-α, IFN-γ and TNF antagonist combination regimen with an IFN-α, IFN-γ and TNF antagonist combination regimen comprising: (a) administering a dosage of INFERGEN® interferon alfacon-1 containing an amount of 15 μg of drug per dose, subcutaneously once daily; (b) administering a dosage of IFN-γ containing an amount of 50 μg of drug per dose, subcutaneously three times per week; and (c) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α, IFN-γ and TNF antagonist combination regimen can be modified to replace the subject IFN-α, IFN-γ and TNF antagonist combination regimen with an IFN-α, IFN-γ and TNF antagonist combination regimen comprising: (a) administering a dosage of INFERGEN® interferon alfacon-1 containing an amount of 15 μg of drug per dose, subcutaneously once daily; (b) administering a dosage of IFN-γ containing an amount of 100 μg of drug per dose, subcutaneously three times per week; and (c) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α and TNF antagonist combination regimen can be modified to replace the subject IFN-α and TNF antagonist combination regimen with an IFN-α and TNF antagonist combination regimen comprising: (a) administering a dosage of monoPEG (30 kD, linear)-ylated consensus IFN-α containing an amount of 100 μg of drug per dose, subcutaneously once weekly, once every 8 days, or once every 10 days; and (b) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α and TNF antagonist combination regimen can be modified to replace the subject IFN-α and TNF antagonist combination regimen with an IFN-α and TNF antagonist combination regimen comprising: (a) administering a dosage of monoPEG (30 kD, linear)-ylated consensus IFN-α containing an amount of 150 μg of drug per dose, subcutaneously once weekly, once every 8 days, or once every 10 days; and (b) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α and TNF antagonist combination regimen can be modified to replace the subject IFN-α and TNF antagonist combination regimen with an IFN-α and TNF antagonist combination regimen comprising: (a) administering a dosage of monoPEG (30 kD, linear)-ylated consensus IFN-α containing an amount of 200 μg of drug per dose, subcutaneously once weekly, once every 8 days, or once every 10 days; and (b) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α and TNF antagonist combination regimen can be modified to replace the subject IFN-α and TNF antagonist combination regimen with an IFN-α and TNF antagonist combination regimen comprising: (a) administering a dosage of INFERGEN® interferon alfacon-1 containing an amount of 9 μg of drug per dose, subcutaneously once daily or three times per week; and (b) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α and TNF antagonist combination regimen can be modified to replace the subject IFN-α and TNF antagonist combination regimen with an IFN-α and TNF antagonist combination regimen comprising: (a) administering a dosage of INFERGEN® interferon alfacon-1 containing an amount of 15 μg of drug per dose, subcutaneously once daily or three times per week; and (b) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-γ and TNF antagonist combination regimen can be modified to replace the subject IFN-γ and TNF antagonist combination regimen with an IFN-γ and TNF antagonist combination regimen comprising: (a) administering a dosage of IFN-γ containing an amount of 25 μg of drug per dose, subcutaneously three times per week; and (b) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-γ and TNF antagonist combination regimen can be modified to replace the subject IFN-γ and TNF antagonist combination regimen with an IFN-γ and TNF antagonist combination regimen comprising: (a) administering a dosage of IFN-γ containing an amount of 50 μg of drug per dose, subcutaneously three times per week; and (b) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-γ and TNF antagonist combination regimen can be modified to replace the subject IFN-γ and TNF antagonist combination regimen with an IFN-γ and TNF antagonist combination regimen comprising: (a) administering a dosage of IFN-γ containing an amount of 100 μg of drug per dose, subcutaneously three times per week; and (b) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods that includes a regimen of monoPEG (30 kD, linear)-ylated consensus IFN-α can be modified to replace the regimen of monoPEG (30 kD, linear)-ylated consensus IFN-α with a regimen of peginterferon alfa-2a comprising administering a dosage of peginterferon alfa-2a containing an amount of 180 μg of drug per dose, subcutaneously once weekly for the desired treatment duration with an NS3 inhibitor compound.

As non-limiting examples, any of the above-described methods that includes a regimen of monoPEG (30 kD, linear)-ylated consensus IFN-α can be modified to replace the regimen of monoPEG (30 kD, linear)-ylated consensus IFN-α with a regimen of peginterferon alfa-2b comprising administering a dosage of peginterferon alfa-2b containing an amount of 1.0 μg to 1.5 μg of drug per kilogram of body weight per dose, subcutaneously once or twice weekly for the desired treatment duration with an NS3 inhibitor compound.

As non-limiting examples, any of the above-described methods can be modified to include administering a dosage of ribavirin containing an amount of 400 mg, 800 mg, 1000 mg or 1200 mg of drug orally per day, optionally in two or more divided doses per day, for the desired treatment duration with an NS3 inhibitor compound.

As non-limiting examples, any of the above-described methods can be modified to include administering a dosage of ribavirin containing (i) an amount of 1000 mg of drug orally per day for patients having a body weight of less than 75 kg or (ii) an amount of 1200 mg of drug orally per day for patients having a body weight of greater than or equal to 75 kg, optionally in two or more divided doses per day, for the desired treatment duration with an NS3 inhibitor compound.

As non-limiting examples, any of the above-described methods can be modified to replace the subject NS3 inhibitor regimen with an NS3 inhibitor regimen comprising administering a dosage of 0.01 mg to 0.1 mg of drug per kilogram of body weight orally daily, optionally in two or more divided doses per day, for the desired treatment duration with the NS3 inhibitor compound.

As non-limiting examples, any of the above-described methods can be modified to replace the subject NS3 inhibitor regimen with an NS3 inhibitor regimen comprising administering a dosage of 0.1 mg to 1 mg of drug per kilogram of body weight orally daily, optionally in two or more divided doses per day, for the desired treatment duration with the NS3 inhibitor compound.

As non-limiting examples, any of the above-described methods can be modified to replace the subject NS3 inhibitor regimen with an NS3 inhibitor regimen comprising administering a dosage of 1 mg to 10 mg of drug per kilogram of body weight orally daily, optionally in two or more divided doses per day, for the desired treatment duration with the NS3 inhibitor compound.

As non-limiting examples, any of the above-described methods can be modified to replace the subject NS3 inhibitor regimen with an NS3 inhibitor regimen comprising administering a dosage of 10 mg to 100 mg of drug per kilogram of body weight orally daily, optionally in two or more divided doses per day, for the desired treatment duration with the NS3 inhibitor compound.

As non-limiting examples, any of the above-described methods featuring an NS5B inhibitor regimen can be modified to replace the subject NS5B inhibitor regimen with an NS5B inhibitor regimen comprising administering a dosage of 0.01 mg to 0.1 mg of drug per kilogram of body weight orally daily, optionally in two or more divided doses per day, for the desired treatment duration with an NS3 inhibitor compound.

As non-limiting examples, any of the above-described methods featuring an NS5B inhibitor regimen can be modified to replace the subject NS5B inhibitor regimen with an NS5B inhibitor regimen comprising administering a dosage of 0.1 mg to 1 mg of drug per kilogram of body weight orally daily, optionally in two or more divided doses per day, for the desired treatment duration with an NS3 inhibitor compound.

As non-limiting examples, any of the above-described methods featuring an NS5B inhibitor regimen can be modified to replace the subject NS5B inhibitor regimen with an NS5B inhibitor regimen comprising administering a dosage of 1 mg to 10 mg of drug per kilogram of body weight orally daily, optionally in two or more divided doses per day, for the desired treatment duration with an NS3 inhibitor compound.

As non-limiting examples, any of the above-described methods featuring an NS5B inhibitor regimen can be modified to replace the subject NS5B inhibitor regimen with an NS5B inhibitor regimen comprising administering a dosage of 10 mg to 100 mg of drug per kilogram of body weight orally daily, optionally in two or more divided doses per day, for the desired treatment duration with an NS3 inhibitor compound.

Patient Identification

In certain embodiments, the specific regimen of drug therapy used in treatment of the HCV patient is selected according to certain disease parameters exhibited by the patient, such as the initial viral load, genotype of the HCV infection in the patient, liver histology and/or stage of liver fibrosis in the patient.

Thus, some embodiments provide any of the above-described methods for the treatment of HCV infection in which the subject method is modified to treat a treatment failure patient for a duration of 48 weeks.

Other embodiments provide any of the above-described methods for HCV in which the subject method is modified to treat a non-responder patient, where the patient receives a 48 week course of therapy.

Other embodiments provide any of the above-described methods for the treatment of HCV infection in which the subject method is modified to treat a relapser patient, where the patient receives a 48 week course of therapy.

Other embodiments provide any of the above-described methods for the treatment of HCV infection in which the subject method is modified to treat a naïve patient infected with HCV genotype 1, where the patient receives a 48 week course of therapy.

Other embodiments provide any of the above-described methods for the treatment of HCV infection in which the subject method is modified to treat a naïve patient infected with HCV genotype 4, where the patient receives a 48 week course of therapy.

Other embodiments provide any of the above-described methods for the treatment of HCV infection in which the subject method is modified to treat a naïve patient infected with HCV genotype 1, where the patient has a high viral load (HVL), where "HVL" refers to an HCV viral load of greater than $2 \times 10^6$ HCV genome copies per mL serum, and where the patient receives a 48 week course of therapy.

One embodiment provides any of the above-described methods for the treatment of an HCV infection, where the subject method is modified to include the steps of (1) identifying a patient having advanced or severe stage liver fibrosis as measured by a Knodell score of 3 or 4 and then (2) administering to the patient the drug therapy of the subject method for a time period of about 24 weeks to about 60 weeks, or about 30 weeks to about one year, or about 36 weeks to about 50 weeks, or about 40 weeks to about 48 weeks, or at least about 24 weeks, or at least about 30 weeks, or at least about 36 weeks, or at least about 40 weeks, or at least about 48 weeks, or at least about 60 weeks.

Another embodiment provides any of the above-described methods for the treatment of an HCV infection, where the subject method is modified to include the steps of (1) identifying a patient having advanced or severe stage liver fibrosis as measured by a Knodell score of 3 or 4 and then (2) administering to the patient the drug therapy of the subject method for a time period of about 40 weeks to about 50 weeks, or about 48 weeks.

Another embodiment provides any of the above-described methods for the treatment of an HCV infection, where the subject method is modified to include the steps of (1) identifying a patient having an HCV genotype 1 infection and an initial viral load of greater than 2 million viral genome copies per ml of patient serum and then (2) administering to the patient the drug therapy of the subject method for a time period of about 24 weeks to about 60 weeks, or about 30 weeks to about one year, or about 36 weeks to about 50 weeks, or about 40 weeks to about 48 weeks, or at least about 24 weeks, or at least about 30 weeks, or at least about 36 weeks, or at least about 40 weeks, or at least about 48 weeks, or at least about 60 weeks.

Another embodiment provides any of the above-described methods for the treatment of an HCV infection, where the subject method is modified to include the steps of (1) identifying a patient having an HCV genotype 1 infection and an initial viral load of greater than 2 million viral genome copies per ml of patient serum and then (2) administering to the patient the drug therapy of the subject method for a time period of about 40 weeks to about 50 weeks, or about 48 weeks.

Another embodiment provides any of the above-described methods for the treatment of an HCV infection, where the subject method is modified to include the steps of (1) identifying a patient having an HCV genotype 1 infection and an initial viral load of greater than 2 million viral genome copies per ml of patient serum and no or early stage liver fibrosis as measured by a Knodell score of 0, 1, or 2 and then (2) administering to the patient the drug therapy of the subject method for a time period of about 24 weeks to about 60 weeks, or about 30 weeks to about one year, or about 36 weeks to about 50 weeks, or about 40 weeks to about 48 weeks, or at least about 24 weeks, or at least about 30 weeks, or at least about 36 weeks, or at least about 40 weeks, or at least about 48 weeks, or at least about 60 weeks.

Another embodiment provides any of the above-described methods for the treatment of an HCV infection, where the subject method is modified to include the steps of (1) identifying a patient having an HCV genotype 1 infection and an initial viral load of greater than 2 million viral genome copies per ml of patient serum and no or early stage liver fibrosis as measured by a Knodell score of 0, 1, or 2 and then (2) administering to the patient the drug therapy of the subject method for a time period of about 40 weeks to about 50 weeks, or about 48 weeks.

Another embodiment provides any of the above-described methods for the treatment of an HCV infection, where the subject method is modified to include the steps of (1) identifying a patient having an HCV genotype 1 infection and an initial viral load of less than or equal to 2 million viral genome copies per ml of patient serum and then (2) administering to the patient the drug therapy of the subject method for a time period of about 20 weeks to about 50 weeks, or about 24 weeks to about 48 weeks, or about 30 weeks to about 40 weeks, or up to about 20 weeks, or up to about 24 weeks, or up to about 30 weeks, or up to about 36 weeks, or up to about 48 weeks.

Another embodiment provides any of the above-described methods for the treatment of an HCV infection, where the subject method is modified to include the steps of (1) identifying a patient having an HCV genotype 1 infection and an initial viral load of less than or equal to 2 million viral genome copies per ml of patient serum and then (2) administering to the patient the drug therapy of the subject method for a time period of about 20 weeks to about 24 weeks.

Another embodiment provides any of the above-described methods for the treatment of an HCV infection, where the subject method is modified to include the steps of (1) identifying a patient having an HCV genotype 1 infection and an initial viral load of less than or equal to 2 million viral genome copies per ml of patient serum and then (2) administering to the patient the drug therapy of the subject method for a time period of about 24 weeks to about 48 weeks.

Another embodiment provides any of the above-described methods for the treatment of an HCV infection, where the subject method is modified to include the steps of (1) identifying a patient having an HCV genotype 2 or 3 infection and then (2) administering to the patient the drug therapy of the subject method for a time period of about 24 weeks to about 60 weeks, or about 30 weeks to about one year, or about 36 weeks to about 50 weeks, or about 40 weeks to about 48 weeks, or at least about 24 weeks, or at least about 30 weeks, or at least about 36 weeks, or at least about 40 weeks, or at least about 48 weeks, or at least about 60 weeks.

Another embodiment provides any of the above-described methods for the treatment of an HCV infection, where the subject method is modified to include the steps of (1) identifying a patient having an HCV genotype 2 or 3 infection and then (2) administering to the patient the drug therapy of the subject method for a time period of about 20 weeks to about 50 weeks, or about 24 weeks to about 48 weeks, or about 30 weeks to about 40 weeks, or up to about 20 weeks, or up to about 24 weeks, or up to about 30 weeks, or up to about 36 weeks, or up to about 48 weeks.

Another embodiment provides any of the above-described methods for the treatment of an HCV infection, where the subject method is modified to include the steps of (1) identifying a patient having an HCV genotype 2 or 3 infection and then (2) administering to the patient the drug therapy of the subject method for a time period of about 20 weeks to about 24 weeks.

Another embodiment provides any of the above-described methods for the treatment of an HCV infection, where the subject method is modified to include the steps of (1) identifying a patient having an HCV genotype 2 or 3 infection and then (2) administering to the patient the drug therapy of the subject method for a time period of at least about 24 weeks.

Another embodiment provides any of the above-described methods for the treatment of an HCV infection, where the subject method is modified to include the steps of (1) identifying a patient having an HCV genotype 1 or 4 infection and then (2) administering to the patient the drug therapy of the subject method for a time period of about 24 weeks to about 60 weeks, or about 30 weeks to about one year, or about 36 weeks to about 50 weeks, or about 40 weeks to about 48 weeks, or at least about 24 weeks, or at least about 30 weeks, or at least about 36 weeks, or at least about 40 weeks, or at least about 48 weeks, or at least about 60 weeks.

Another embodiment provides any of the above-described methods for the treatment of an HCV infection, where the subject method is modified to include the steps of (1) identifying a patient having an HCV infection characterized by any of HCV genotypes 5, 6, 7, 8 and 9 and then (2) administering to the patient the drug therapy of the subject method for a time period of about 20 weeks to about 50 weeks.

Another embodiment provides any of the above-described methods for the treatment of an HCV infection, where the subject method is modified to include the steps of (1) identifying a patient having an HCV infection characterized by any of HCV genotypes 5, 6, 7, 8 and 9 and then (2) administering to the patient the drug therapy of the subject method for a time period of at least about 24 weeks and up to about 48 weeks.

Subjects Suitable for Treatment

Any of the above treatment regimens can be administered to individuals who have been diagnosed with an HCV infection. Any of the above treatment regimens can be administered to individuals who have failed previous treatment for HCV infection ("treatment failure patients," including non-responders and relapsers).

Individuals who have been clinically diagnosed as infected with HCV are of particular interest in many embodiments. Individuals who are infected with HCV are identified as having HCV RNA in their blood, and/or having anti-HCV antibody in their serum. Such individuals include anti-HCV ELISA-positive individuals, and individuals with a positive recombinant immunoblot assay (RIBA). Such individuals may also, but need not, have elevated serum ALT levels.

Individuals who are clinically diagnosed as infected with HCV include naïve individuals (e.g., individuals not previously treated for HCV, particularly those who have not previously received IFN-α-based and/or ribavirin-based therapy) and individuals who have failed prior treatment for HCV ("treatment failure" patients). Treatment failure patients include non-responders (i.e., individuals in whom the HCV titer was not significantly or sufficiently reduced by a previous treatment for HCV, e.g., a previous IFN-α monotherapy, a previous IFN-α and ribavirin combination therapy, or a previous pegylated IFN-α and ribavirin combination therapy); and relapsers (i.e., individuals who were previously treated for HCV, e.g., who received a previous IFN-α monotherapy, a previous IFN-α and ribavirin combination therapy, or a previous pegylated IFN-α and ribavirin combination therapy, whose HCV titer decreased, and subsequently increased).

In particular embodiments of interest, individuals have an HCV titer of at least about $10^5$, at least about $5 \times 10^5$, or at least about $10^6$, or at least about $2 \times 10^6$, genome copies of HCV per milliliter of serum. The patient may be infected with any HCV genotype (genotype 1, including 1a and 1b, 2, 3, 4, 6, etc. and subtypes (e.g., 2a, 2b, 3a, etc.)), particularly a difficult to treat genotype such as HCV genotype 1 and particular HCV subtypes and quasispecies.

Also of interest are HCV-positive individuals (as described above) who exhibit severe fibrosis or early cirrhosis (non-decompensated, Child's-Pugh class A or less), or more advanced cirrhosis (decompensated, Child's-Pugh class B or C) due to chronic HCV infection and who are viremic despite prior anti-viral treatment with IFN-α-based therapies or who cannot tolerate IFN-α-based therapies, or who have a contraindication to such therapies. In particular embodiments of interest, HCV-positive individuals with stage 3 or 4 liver fibrosis according to the METAVIR scoring system are suitable for treatment with the methods described herein. In other embodiments, individuals suitable for treatment with the methods of the embodiments are patients with decompensated cirrhosis with clinical manifestations, including patients with far-advanced liver cirrhosis, including those awaiting liver transplantation. In still other embodiments, individuals suitable for treatment with the methods described herein include patients with milder degrees of fibrosis including those with early fibrosis (stages 1 and 2 in the METAVIR, Ludwig, and Scheuer scoring systems; or stages 1, 2, or 3 in the Ishak scoring system.).

Preparation of NS3 Inhibitors

The NS3 inhibitors in the following sections can be prepared according to the procedures and schemes shown in each section. The numberings in each Preparation of NS3 Inhibitor Section are meant for that specific section only, and should not be construed as or confused with same numberings in other sections.

Methodology

The HCV protease inhibitors in the following sections can be prepared according to the procedures and schemes shown in each section. Certain compounds and intermediates used in the syntheses have been described elsewhere. For instance, in Scheme 1 of Section I below, the syntheses of intermediates 1(R)-tert-butoxycarbonylamino-2(S)-vinyl-cyclopropan-ecarboxylic acid ethyl ester (1a) and 2(S)-tert-butoxycarbonylamino-non-8-enoic acid (1c), and the ring-closing-metathesis of tripeptide 4 were carried out in a manner similar to that described in International Application PCT/US2004/033970 (International Publication No. WO 2005/037214) and PCT/CA00/00353 (Publication No. WO 00/59929). The numberings in each of the following Preparation of NS3

Inhibitor sections are meant for that specific section only, and should not be construed or confused with the same numberings in other sections.

Preparation of NS3 Inhibitors

Section I

A general synthetic scheme for the preparation of NS3 inhibitors described in this section is illustrated in Scheme 1 below and exemplified by the following description of the synthesis of compound 100:

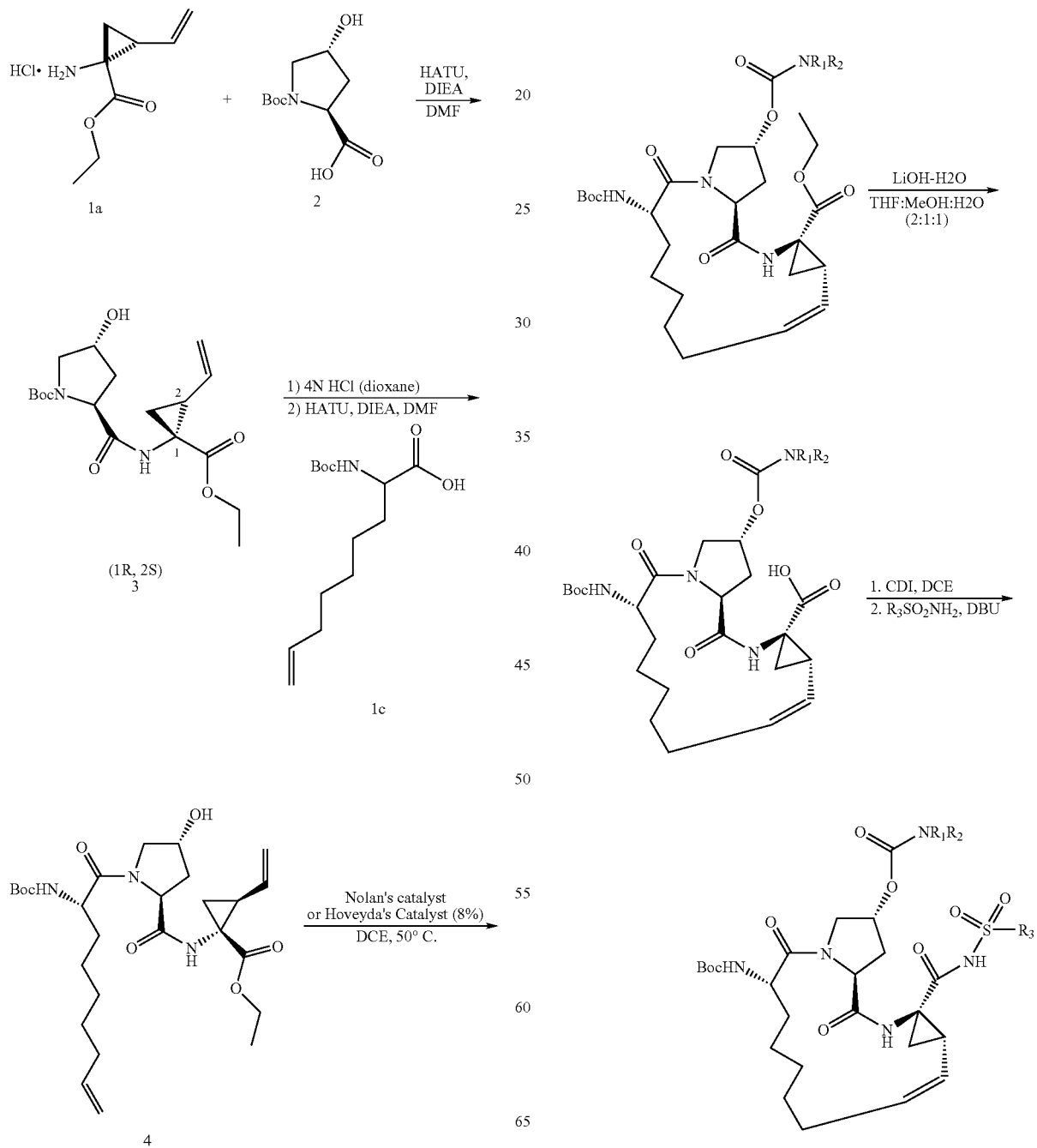

Synthesis of Compound 100:

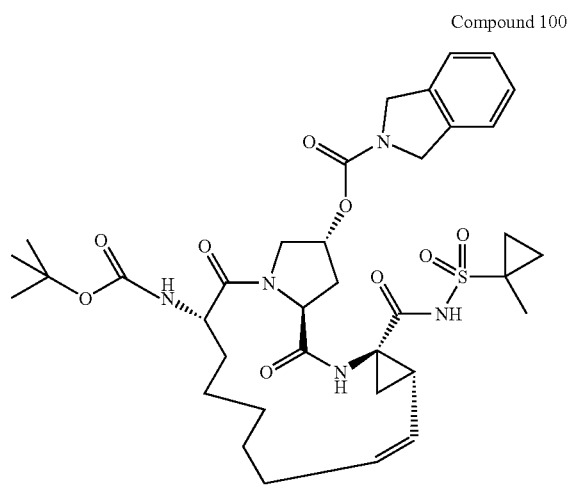

Compound 100

A. Step 1: Synthesis of 2S-(1-Ethoxycarbonyl-2-vinyl-cyclopropylcarbamoyl)-4R-hydroxy-pyrrolidine-1-carboxylic acid tert-butyl ester (3)

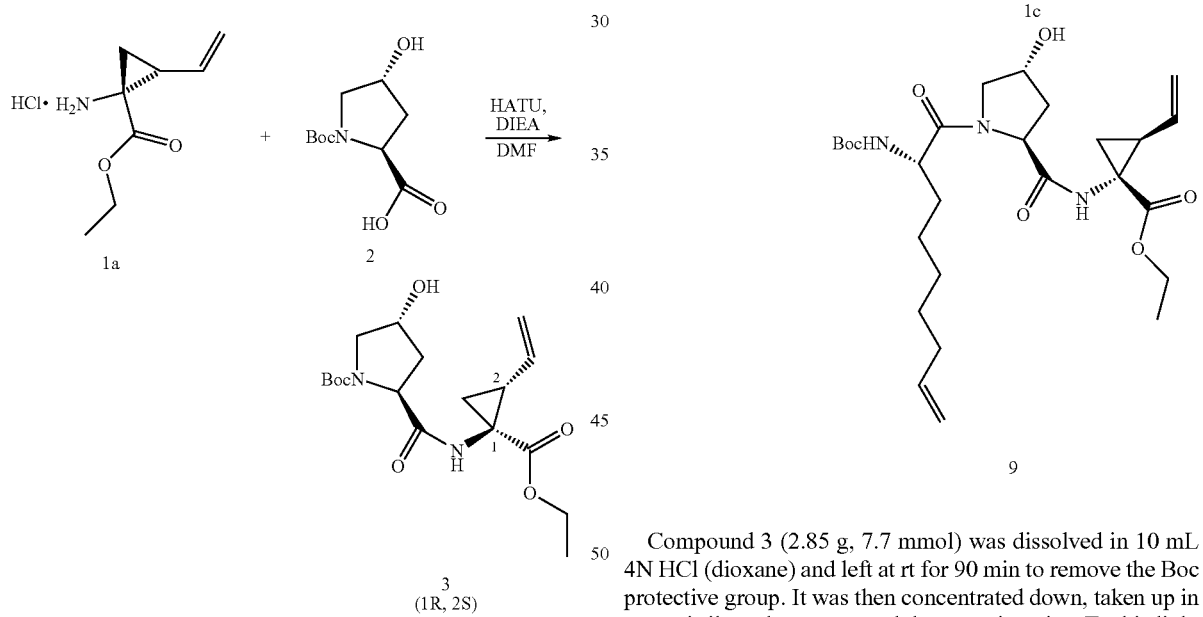

To a flask charged with ethyl-(1R,2S)/(1S,2R)-1-amino-2-vinylcyclopropyl carboxylate (1a, 1.0 g, 5.2 mmol), trans-N-(tert-Butoxycarbonyl)-4-hydroxy-L-proline (2, 1.3 g, 1.1 equiv), and HATU (2.7 g, 1.1 equiv) were added 30 mL DMF to make a solution. It was cooled to 0° C. in an ice-water bath, followed by slow addition of a solution of DIEA (4.4 mL, 4 equiv) in DMF (15 mL) while stirring. The reaction was allowed to warm up to rt and stirred overnight.

After 16 h, the reaction was complete as monitored by HPLC. It was diluted with EtOAc (100 mL), washed with water (3×40 mL), sat. NaHCO$_3$ (2×40 mL), and brine (2×40 mL), then dried over Na$_2$SO$_4$ and concentrated down to give a dark copper colored oil. The crude was purified on silica gel (eluent: acetone/hexanes 3:7), giving pure 3 as tan foamy powder (770 mg, 32%).

Step 2: Synthesis of 1R-{[1-(2S-tert-Butoxycarbonylamino-non-8-enoyl)-4R-hydroxy-pyrrolidine-2S-carbonyl]-amino}-2S-vinyl-cyclopropanecarboxylic acid ethyl ester (9)

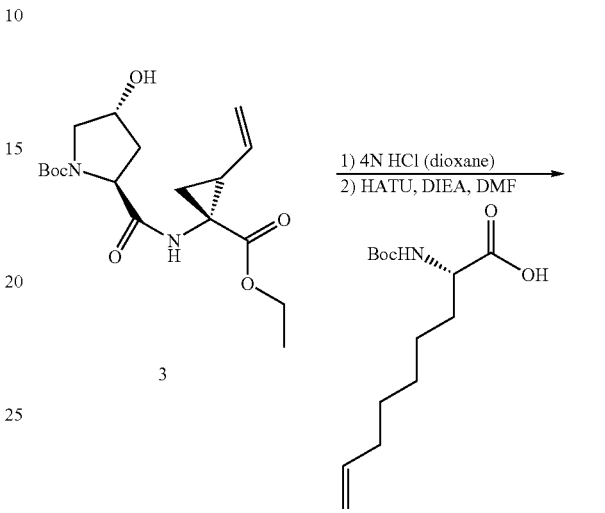

Compound 3 (2.85 g, 7.7 mmol) was dissolved in 10 mL 4N HCl (dioxane) and left at rt for 90 min to remove the Boc protective group. It was then concentrated down, taken up in acetonitrile and concentrated down again twice. To this light brownish residue was added 1c (2.2 g, 8.1 mmol) and HATU (3.2 g, 8.5 mmol), followed by 80 mL DMF under nitrogen. The reaction was cooled on ice-water bath for 15 min, after which a 5 mL DMF solution of DIEA (5.4 mL, 30.9 mmol) was added to the reaction drop-wise while stirring. The ice bath was left to slowly rise to rt and the reaction stirred overnight.

After 18 h, TLC showed reaction complete. The reaction was diluted with EtOAc (300 mL) and washed with water (3×150 mL), sat. NaHCO$_3$ (2×150 mL), brine (150 mL), dried (Na$_2$SO$_4$), and solvent removed. The crude was purified by silica gel flash chromatography on Biotage 40M (eluent=3% to 5% MeOH in DCM) to give 9 as a brownish foamy solid (3.5 g, 87%).

115

Step 3: Synthesis of (1S,4R,6S,14S,18R)-14-tert-Butoxycarbonylamino-18-hydroxy-2,15-dioxo-3,16-diaza-tricyclo[14.3.0.0$^{4,6}$]nonadec-7-ene-4-carboxylic acid ethyl ester (10)

116

Step 4: Synthesis of (1S,4R,6S,14S,18R)-14-tert-Butoxycarbonylamino-18-(1,3-dihydro-isoindole-2-carbonyloxy)-2,15-dioxo-3,16-diaza-tricyclo[14.3.0.0$^{4,6}$]nonadec-7-ene-4-carboxylic acid ethyl ester (11)

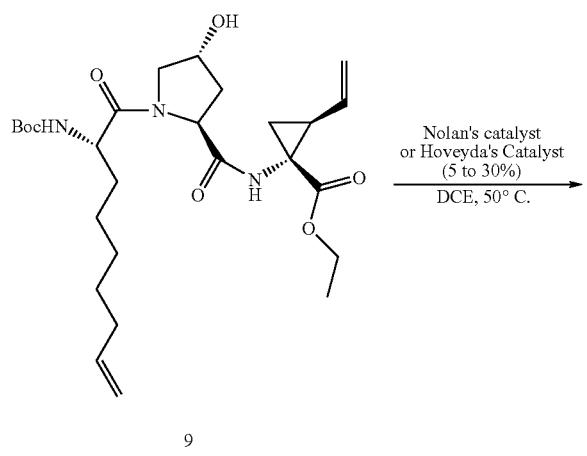

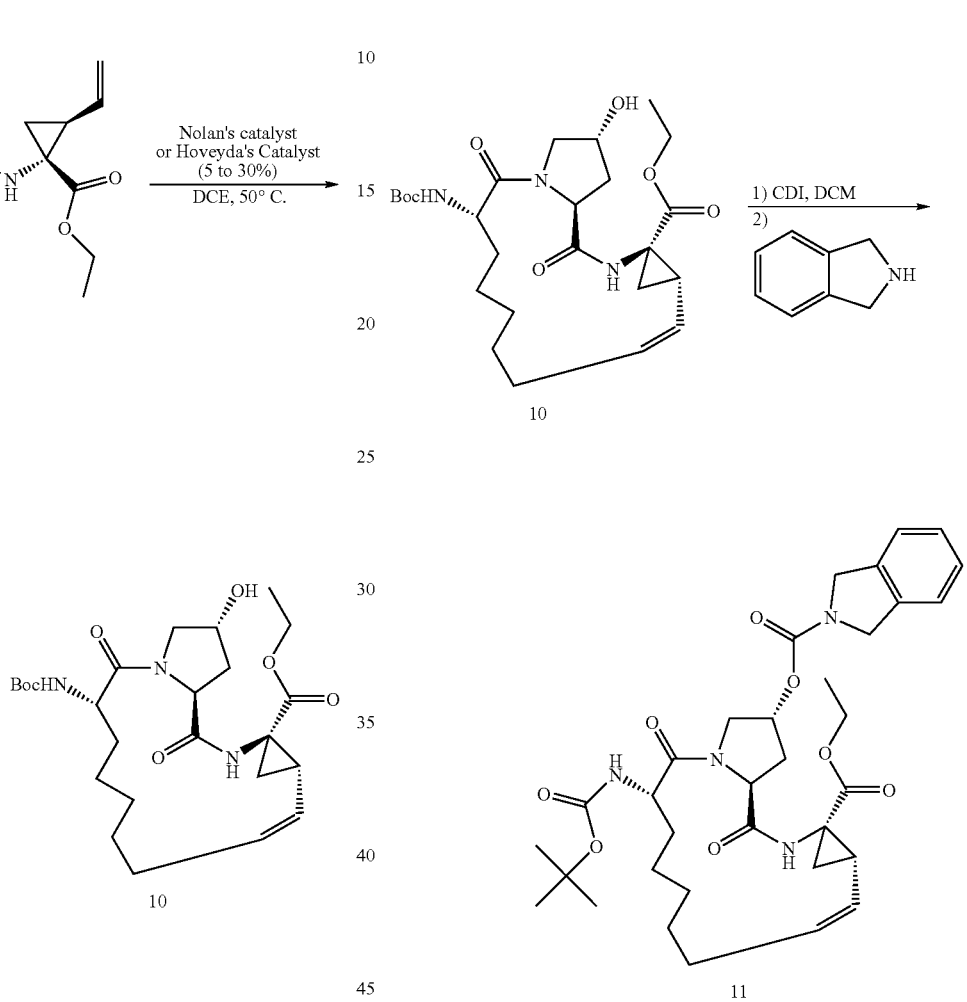

Compound 9 (2.6 g, 5.0 mmol) was dissolved in 500 mL DriSolve® DCE in a 1 L round-bottomed flask to make a solution. It was degassed by bubbling nitrogen through for 1 h. Then the Hoveyda catalyst (0.25 equiv) was added at rt under nitrogen. The reaction was put on a pre-heated oil bath (50 C) and stirred for overnight. After 16 h, the reaction had turned dark brownish. TLC (DCM/EtOAc 1:1) showed clean conversion to a new spot with slightly lower $R_f$. The reaction was concentrated down and purified on silica gel (Biotage 40 M, eluent=DCM/EtOAc gradient from 1:1 to 1:2), giving product 10 as a tan foamy powder (0.64 g, 52%). $^1$H NMR (CDCl$_3$, 400 MHz) δ 1.21 (t, J=7.0 Hz, 3H), 1.43 (s, 9H), 1.20-1.50 (m, 6H), 1.53-1.68 (m, 2H), 1.83-1.96 (m, 2H), 1.98-2.28 (m, 4H), 2.60 (m, 1H), 3.13 (brs, 1H), 3.68 (m, 1H), 3.94 (m, 1H), 4.01-4.19 (m, 2H), 4.48 (m, 1H), 4.56 (brs, 1H), 4.79 (m, 1H), 5.26 (t, J=9.4 Hz, 1H), 5.36 (d, J=7.8 Hz, 1H), 5.53 (m, 1H), 7.19 (brs, 1H). MS m/e 494.0 (M$^+$+1).

The macrocyclic intermediate 10 (110 mg, 0.22 mmol) was dissolved in DCM (2.2 mL), followed by addition of CDI (45 mg, 0.27 mmol) in one portion. The reaction was stirred at rt overnight. After 15 h, the reaction was complete as monitored by TLC (DCM/MeOH 9:1). 2,3-Dihydro-1H-isoindole (0.14 mL, 1.1 mmol) was added to the reaction drop-wise, and the reaction was stirred at rt overnight. After 22 h, TLC showed reaction complete. The reaction was diluted with DCM (6 mL) and washed with 1N aq. HCl (2×2 mL), sat. sodium bicarbonate (2 mL), brine (2 mL), dried (Na$_2$SO$_4$), and concentrated down. The crude was purified on silica gel (Biotage 40S, eluent: 2 to 4% MeOH in DCM), giving 11 as a pale yellowish foamy powder (131 mg, 90%).

B. Step 5: Synthesis of (1S,4R,6S,14S,18R)-14-tert-Butoxycarbonylamino-18-(1,3-dihydro-isoindole-2-carbonyloxy)-2,15-dioxo-3,16-diaza-tricyclo[14.3.0.0⁴,⁶]nonadec-7-ene-4-carboxylic acid

C. Step 6: Synthesis of (1S,4R,6S,14S,18R)-1,3-Dihydro-isoindole-2-carboxylic acid 14-tert-butoxycarbonylamino-4-(1-methylcyclopropane-1-sulfonyl)aminocarbonyl-2,15-dioxo-3,16-diaza-tricyclo[14.3.0.0⁴,⁶]nonadec-7-en-18-yl ester (Compound 100)

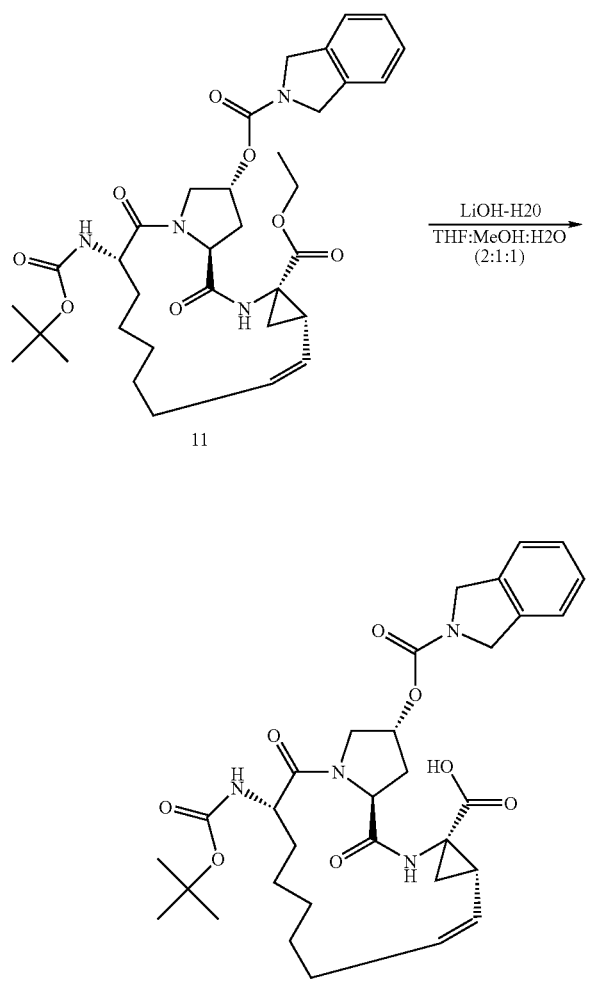

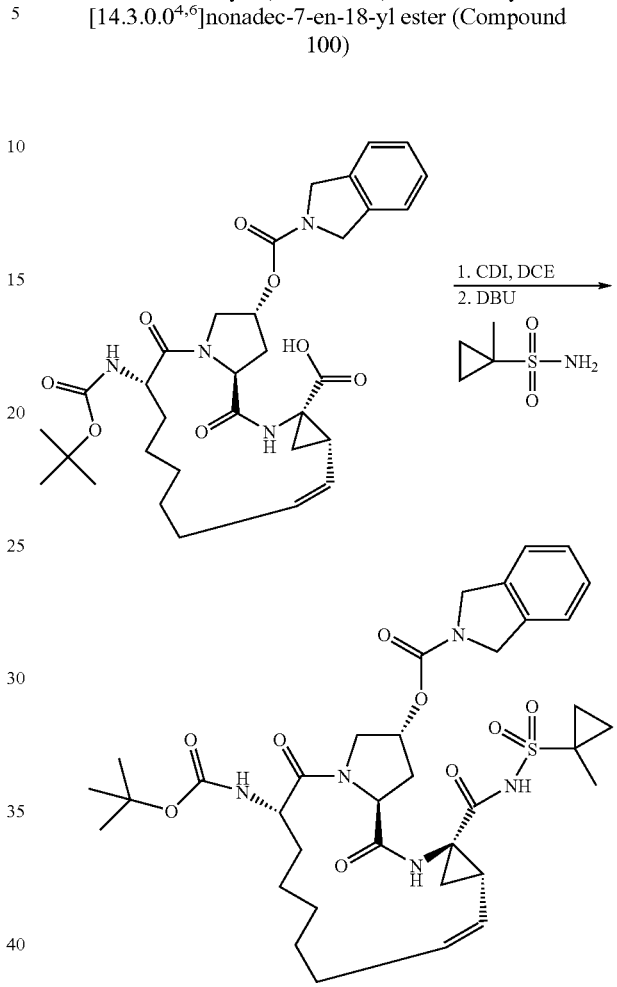

The macrocyclic ester 11 (60 mg, 0.092 mmol) was dissolved in 0.9 mL of a mixed solvent (THF/MeOH/H2O 2:1:1), followed by addition of LiOH—H₂O (23 mg, 6 equiv). The mixture was stirred at rt for overnight. After 18 h, TLC (DCM/MeOH 9:1) showed a clean new spot with a lower Rf. The reaction was concentrated down to almost dryness and partitioned between 1N aq. HCl (15 mL) and DCM (20 mL). The aqueous layer was extracted with DCM (2×10 mL). The organic layers were combined, dried over Na₂SO₄ and concentrated down, giving the desired compound as a light brownish foamy powder (50 mg, 87%). ¹H NMR (CDCl₃, 500 MHz) δ1.21-1.44 (m, 8H), 1.32 (s, 9H), 1.54-1.62 (m, 2H), 1.78-1.88 (m, 2H), 2.04-2.13 (m, 1H), 2.16-2.23 (m, 1H), 2.24-2.36 (m, 2H), 2.66-2.74 (m, 1H), 3.87-3.90 (m, 1H), 4.15 (d, J=11.0 Hz, 1H), 4.37-4.43 (m, 1H), 4.61-4.77 (m, 5H), 5.18 (t, J=10.3 Hz, 1H), 5.24-5.31 (m, 1H), 5.40-5.45 (m, 1H), 5.58-5.66 (m, 1H), 7.11-7.30 (m, 4H). MS m/e 611.0 (M⁺+1).

The macrocyclic acid (50 mg, 0.082 mmol) was dissolved in 0.8 mL DriSolve® DCE, followed by addition of CDI (15.1 mg, 1.1 equiv). The mixture was stirred in a 50° C. sand bath for 15 min, and TLC showed reaction complete. Then 1-methylcyclopropane-1-sulfonamide (11.1 mg, 1.0 equiv) was added to the reaction, followed by DBU (13.7 mg, 1.1 equiv) at rt. The reaction was stirred at 50° C. for 1 h, and LCMS showed reaction complete. The crude was directly loaded onto a Biotage 12S silica column, and purified by flash chromatography (eluent=40% EtOAc in hexanes with 1% formic acid), giving the desired final product as a white solid (35 mg, 58%). ¹H NMR (400 MHz, d⁶-Acetone) δ 10.54 (bs, 1H), 8.40 (br s, 1H), 7.23-7.35 (m, 4H), 6.16 (d, 1H), 5.69 (q, 1H) 5.45 (br s, 1H) 5.00 (t, 1H), 4.61-4.72 (m, 5H), 4.46-4.51 (m, 1H), 4.15-4.18 (m, 1H), 3.85-3.89 (m, 1H), 2.60-2.65 (m, 1H), 2.35-2.52 (m, 3H), 1.87-1.91 (m, 2H), 1.72-1.75 (m, 1H), 1.61-1.65 (m, 1H), 1.19-1.58 (m, 21H), 0.82-0.90 (m, 2H). MS m/z 727.3 (M+, APCI−).

The 1-methylcyclopropane-1-sulfonamide used in the above synthesis was prepared in a manner similar to that described US Patent Application No. 2004/0048802 A1. Other 1-substituted cyclopropane-1-sulfonamides described herein were also prepared in a similar fashion.

The substituted isolindolines used were either purchased from commercial sources or prepared in a similar fashion as described in a patent application (WO 2005/037214 A2), with the exception that the products were isolated as the hydrochloride salts. A general scheme for the synthesis of isoindolines in this section is shown in Scheme 2 below.

Scheme 2

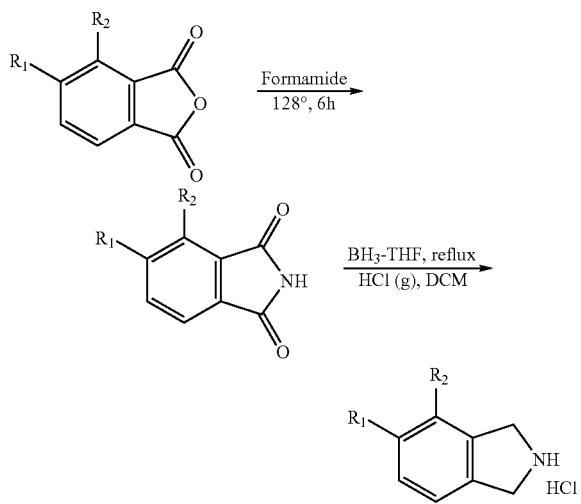

Synthesis of 4-Chloro-2,3-dihydro-1H-isoindoline hydrochloride

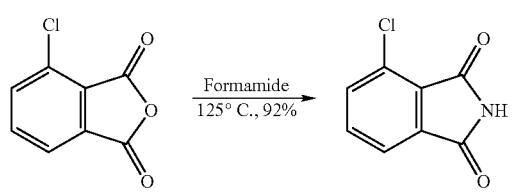

3-Chlorophthalic anhydride (5.00 g, 27.39 mmol) was stirred in formamide (55 mL) and heated at 128° C. for 6 h. Upon completion of the reaction, the heat was removed and the mixture was cooled to room temperature and treated with water (180 mL) and this mixture stirred overnight. The precipitate, which formed, was filtered, washed with water and dried under vacuum overnight to yield the product, a cream solid (4.59 g, 92%).

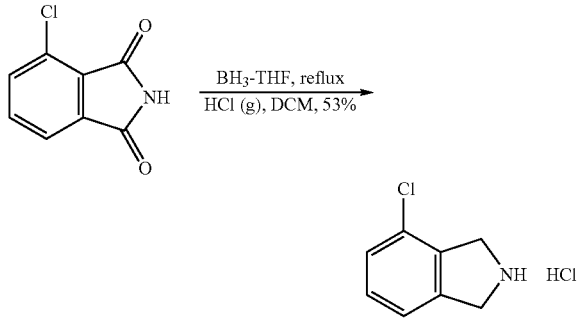

4-Chloroisoindoline-1,3-dione (4.59 g, 25.28 mmol) was treated with BH3-THF complex (101 mL, 101 mmol) and the mixture heated at reflux for 18 h. The solution was cooled to room temperature then to 0° C. in an ice bath. MeOH (70 mL) was added drop wise. The ice bath was removed and the mixture warmed to room temperature. 6N HCl (110 mL) was added and the mixture then heated at reflux for 1 h. The mixture was then cooled and concentrated to about half the volume and washed with DCM (2×). The aqueous was then cooled in an ice bath and brought to pH=11 with NaOH pellets. The amine product was then extracted into EtOAc (3×) and the combined extracts dried (MgSO4), filtered and concentrated to an oil. The oil was re-suspended in DCM-hexanes (2:1) mixture and HCl gas was bubbled into the cooled solution for 15 minutes. Et$_2$O was then added to enhance the salt precipitation. The precipitated salt collected by filtration and washed with Et$_2$O and dried to a light purple crystalline solid (2.54 g, 53%). $^1$H NMR (400 MHz, DMSO d$^6$) δ 10.02 (bs, 2H), 7.46-7.37 (m, 3H), 4.59 (s, 2H), 4.53 (s, 2H).

5-Trifluoromethyl-2,3-dihydro-1H-isoindoline hydrochloride

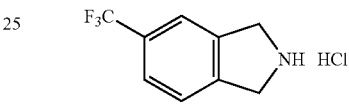

$^1$H NMR (400 MHz, DMSO d 6) δ 10.22 (bs, 2H), 7.82 (s, 1H), 7.74 (d, J=8 Hz, 1H), 7.64 (d, J=8 Hz, 1H), 4.57 (s, 4H).

5-Fluoro-2,3-dihydro-1H-isoindoline hydrochloride

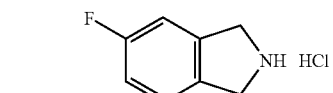

$^1$H NMR (400 MHz, DMSO d$^6$) δ 10.12 (bs, 2H), 7.44 (dd, J=4.8, 9 Hz, 1H), 7.28 (dd, J=2, 9 Hz, 1H) 7.17-7.23 (m, 1H), 5.76 (s, 4H).

4,7-Dichloro-2,3-dihydro-1H-isoindoline

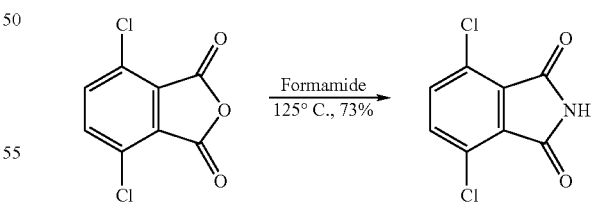

4,7-Dichlorophthalic anhydride (Synth. Commun. 1990, 20, 2139) (1.51 g, 6.95 mmol) in formamide (12 mL) was heated at 128° C. for 6 h. Upon completion of the reaction, the heat was removed and the mixture was cooled to room temperature and treated with water (20 mL) and the resulting mixture stirred overnight. The precipitate which formed was collected by filtration, washed with cold water and dried under vacuum overnight to give the product, a cream solid (1.10 g, 73%).

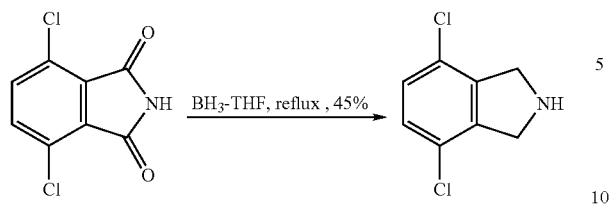

4,7-Dichloroisoindoline-1,3-dione (1.10 g, 5.09 mmol) was treated with BH$_3$-THF complex (20 mL) and the mixture heated at reflux 18 h. The solution was cooled to room temperature then to 0° C. and MeOH (16 mL) was added dropwise. After complete addition of MeOH the ice bath was removed and the mixture warmed to room temperature. 6N HCl (25 mL) was added and the mixture then heated at reflux for 1 h. The mixture was concentrated to about half the volume and washed with dichloromethane. The aqueous layer was then cooled on an ice bath and treated with NaOH pellets until pH 11 was attained. The amine product was then extracted into EtOAc, dried (MgSO$_4$), filtered and concentrated. The product was isolated as a pink solid (432 mg, 45%). $^1$H NMR (400 MHz, CDCl$_3$) δ 7.12 (s, 2H), 4.32 (s, 4H), 2.01 (bs, 1H).

2,3-Dihydro-1H-pyrrolo[3,4-c]pyridine

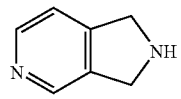

Prepared in a similar fashion as outlined in the patent (U.S. Pat. No. 5,371,090). $^1$H NMR (400 MHz, CDCl$_3$) δ 8.53 (s, 1H), 8.44 (d, J=5.6 Hz, 1H), 7.21 (d, J=5 Hz, 1H) 4.28 (s, 2H), 4.24 (s, 2H), 2.11 (bs, 1H).

For certain NS3 inhibitors shown in this section, additional chemical transformations are utilized to obtain the final products. The preparations of two such examples are described for compounds 153 and 154 below:

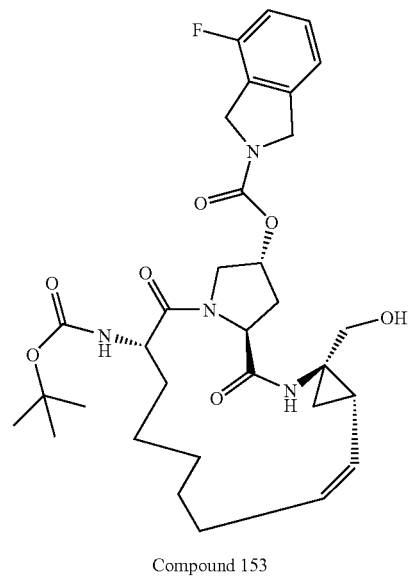

Compound 153

(2R,6S,13aS,14aR,16aS,Z)-6-(tert-botoxycarbonylamino)-2-(4-fluoroisoindoline-2-carbonyloxy)-5,16-dioxo-1,2,3,5,6,7,8,9,10,11,13a,14,14a,15,16,16a-hexadecahydrocyclopropa[e]pyrrolo[1,2-α][1,4]dizacyclopentadecine-14a-carboxylic acid (0.10 g, 0.16 mmol) and TEA (0.024 mL, 0.18 mmol) in THF (5 mL) was added ethyl carbonochlridate (0.016 mL, 0.17 mmol) at 0° C. The reaction was stirred at 0° C. for 2 hrs. Sodium boronhydride (0.012 g, 0.32 mmol) was added and the reaction was stirred at rt for 3 days. Water (5 mL) and ethyl acetate (10 mL) were added. The organic layer was separated, washed with brine and dried over sodium sulfate. After removal of solvent, the residue was purified by column chromatography (ethyl acetate) to give the product (0.060 g, 61.4%) as white solid. $^1$H NMR (400 MHz, d$^6$-DMSO) δ 8.47 (b, 1H), 7.35 (m, 1H), 7.10-7.20 (m, 2H), 7.03 (m, 1H), 5.47 (m, 1H), 5.28 (b, 1H), 4.98 (m, 1H), 4.67 (b, 4H), 4.56 (m, 1H), 4.46 (m, 1H), 4.26 (m, 1H), 3.92 (m, 1H), 3.66 (m, 2H), 3.16 (m, 1H), 2.67 (m, 1H), 2.21 (m, 2H), 1.80 (m, 1H), 1.68 (m, 1H), 1.30 (m, 8H), 1.11-1.20 (m, 9H), 0.85 (m, 1H), 0.77 (m, 1H).

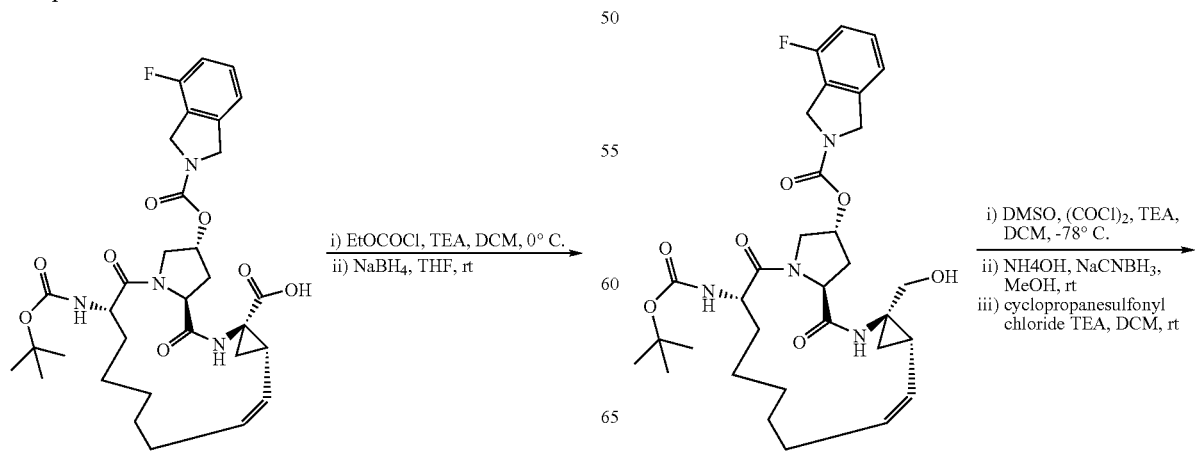

-continued

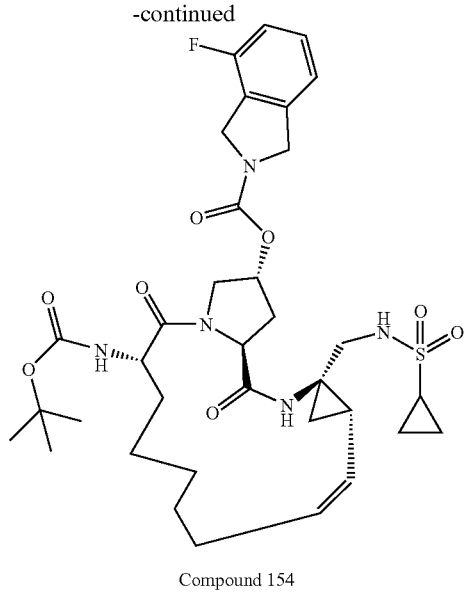

Compound 154

A solution of oxalyl chloride 90.045 mL, 0.089 mmol) in DCM (5 mL) at −78° C. was added a solution of DMSO (0.015 g, 0.020 mmol) in DCM (2 mL) dropwise over 2 ninytes. The reaction was stirred at −78° C. for 10 minutes and the a solution of (2R,6S,13aS,14aR,16aS,Z)-6-(tert-botoxy-carbonylamino)-14a-(hydroxymethyl)-5,16-dioxo-1,2,3,5,6,7,8,9,10,11,13a,14,14a,15,16,16a-hexadecahydrocyclopropa[e]pyrrolo[1,2-α][1,4]dizacyclopentadecin-2-yl-4-fluoroisoindoline-2-carboxylate (0.050 g, 0.081 mmol) in DCM (2 mL) was added. After stirred at −78° C. for 40 min, TEA (0.051 mL, 0.37 mmol) was added. The reaction was warmed to rt, water (5 mL) was added. The organic layer was separated, washed with brine and dried over sodium sulfate. After removal of solvent, the residue was dissolved in MeOH (5 mL) and ammonium hydroxide (0.085 g, 2.45 mmol) and acetic acid (0.014 mL, 0.25 mmol) were added. The reaction stirred at rt for 3 minutes. NaCNBH3 90.015 g, 0.245 mmol) was added and stirred at rt for 30 minutes. The MeOH was removed. DCM (20 mL) and saturated sodium bicarbonate (5 mL) was added. The organic layer was separated, washed with brine and dried over sodium sulfate. After removal of solvent, the residue was dissolved in DCM (5 mL). TEA (0.017 mL, 0.122 mmol) was added and followed by the cyclopropanesulfonyl chloride (0.015 g, 0.098 mmol). The reaction was stirred at rt for 5 hrs. The solvent was removed. The residue was purified by column chromatography (ethyl acetate) to give the product (0.017 g, 28.2%) as white solid. $^1$HNMR (400 MHz, d$^6$-DMSO) δ 8.52 (m, 1H), 7.35 (m, 1H), 7.02-7.20 (m, 4H), 5.56 (m, 1H), 4.99 (m, 1H), 4.97 (m, 1H), 4.67 (m, 2H), 4.66 (s, 2H), 4.46 (m, 1H), 4.24 (m, 1H), 3.92 (m, 1H), 3.67 (m, 1H), 3.46 (m, 1H), 2.74 (m, 1 h), 2.67 (m, 1H), 2.22 (m, 2H), 1.84 (m, 1H), 1.68 (m, 1H), 1.08-1.36 (m, 20H), 0.89 (m, 2H), 0.81 (m, 2H).

Most of the NS3 inhibitors shown in Table 1 below were prepared in a manner similar to that described for Compound 100 and its acid precursor, substituting the isoindoline and cyclopropane sulfonamide with corresponding secondary amines and sulfonamide intermediate, respectively, during the carbamate coupling and the acylsulfonamide coupling steps. The P4 de-protected amino compounds (e.g. compounds 106 and 107; syntheses described in WO2005037214) were prepared by removal of the Boc protective group in 4 M HCl solution in dioxane. The synthesis for compounds with other P4 carbamate and amide groups (e.g. compound 116) may be carried out in a manner similar to that described in published procedures (International Application Number: PCT/US2004/033970).

For Squarate derivatives the general procedure shown below for the synthesis of compound 241 serves as an example.

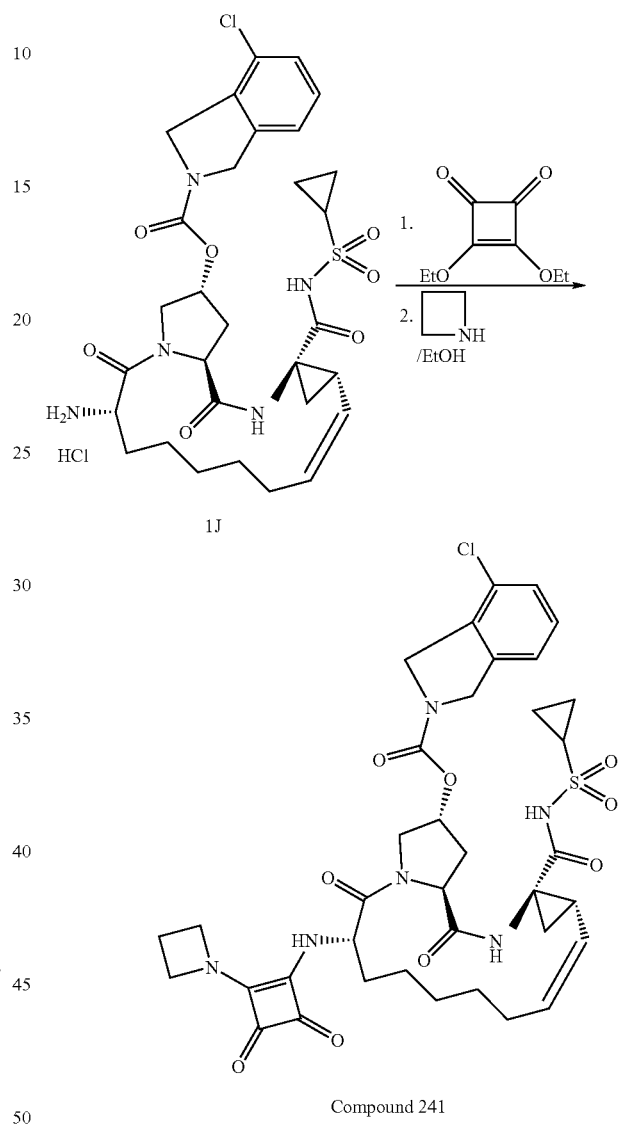

Compound 241

(2R,6S,13aS,14aR,16aS,Z)-6-(2-(azetidin-1-yl)-3,4-dioxocyclobut-1-enylamino)-14a-(cyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-2-yl 4-chloroisoindoline-2-carboxylate (compound 241)

A mixture of 1J (50 mg, 0.07303 mmol) and TEA (d. 0.726) (0.03054 ml, 0.2191 mmol) and 3,4-diethoxycyclobut-3-ene-1,2-dione (0.01283 ml, 0.08764 mmol) was stirred 30 min at room temperature. Azetidine (0.0414 ml, 0.580 mmol) was then added and stirred 5 minutes. The solution was concentrated and purified by reverse phase chromatography (Biotage Horizon, Flash 12+ column using linear 15-85% acetonitrile/H2O gradient) to obtain compound 2 (20 mg, 0.0255 mmol, 35% yield) as a white solid.

TABLE 1

| Compound | Structure | ¹H-NMR/LCMS |
|---|---|---|
| 101 | 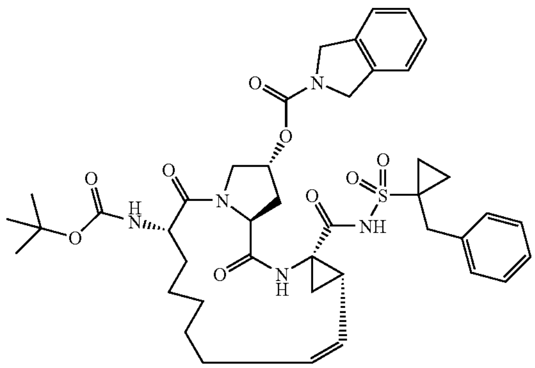 | ¹H NMR (400 MHz, d⁶-Acetone) δ 10.56 (bs, 1 H), 8.33 (br s, 1 H), 7.20-7.35 (m, 9 H), 6.11 (d, 1 H), 5.78 (q, 1 H), 5.44 (br s, 1 H), 5.16 (t, 1 H), 4.60-4.72 (m, 5 H), 4.47-4.50 (m, 1 H), 4.13-4.16 (m, 1 H), 3.84-3.88 (m, 1 H), 3.26-3.39 (m, 2 H), 2.66-2.70 (m, 1 H), 2.37-2.58 (m, 3 H), 1.85-1.91 (m, 2 H), 1.76-1.79 (m, 1 H), 1.21-1.64 (m, 19 H), 0.61-0.65 (m, 2 H). MS m/z 802.4 (M − 1 APCI−). |
| 102 | 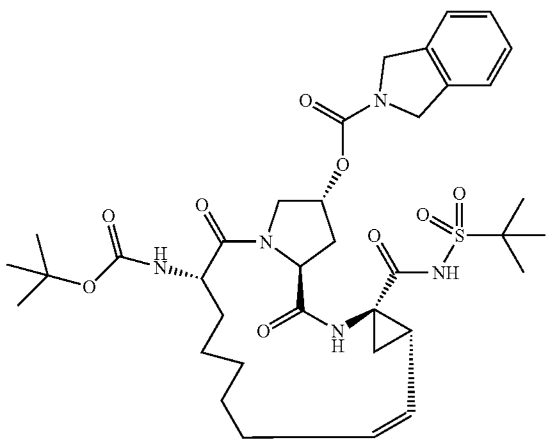 | ¹H NMR (400 MHz, d⁶-Acetone) δ 8.33 (br s, 1 H), 7.23-7.35 (m, 4 H), 6.09 (d, 1 H), 5.70 (q, 1 H), 5.44 (br s, 1 H), 5.01 (t, 1 H), 4.59-4.72 (m, 5 H), 4.47-4.50 (m, 1 H), 4.13-4.17 (m, 1 H), 3.85-3.88 (m, 1 H), 2.60-2.69 (m, 1 H), 2.46-2.50 (m, 2 H), 2.36-2.40 (m, 1 H), 1.86-1.89 (m, 2 H), 1.70-1.73 (m, 1 H), 1.21-1.58 (m, 26 H). MS m/z 728.4 (M − 1 APCI−). |
| 103 | 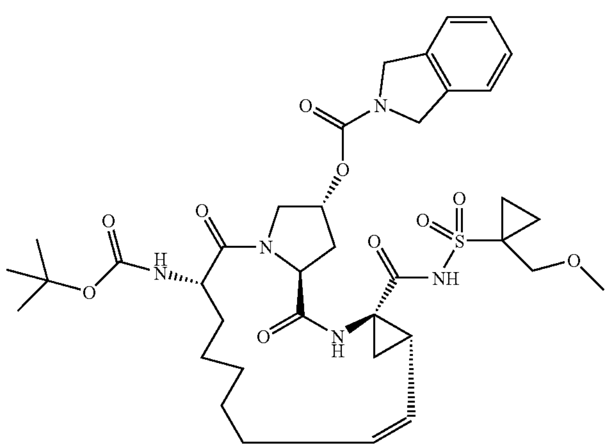 | ¹H NMR (400 MHz, d⁶-Acetone) δ 8.17 (br s, 1 H), 7.24-7.36 (m, 4 H), 6.07 (d, 1 H), 5.60-5.66 (m, 1 H), 5.39-5.45 (m, 1 H), 5.07 (t, 1 H), 4.60-4.72 (m, 5 H), 4.42 (m, 1 H), 4.20-4.26 (m, 1 H), 3.89-3.93 (m, 1 H), 3.76-3.80 (m, 1 H), 3.62-3.67 (m, 1 H), 3.33 (s, 3 H), 2.39-2.52 (m, 4 H), 1.85-1.96 (m, 2 H), 1.69-1.72 (m, 1 H), 0.86-1.63 (m, 21 H). MS m/z 756.3 (M − 1, APCI−) |

TABLE 1-continued

| Compound | Structure | ¹H-NMR/LCMS |
|---|---|---|
| 104 | 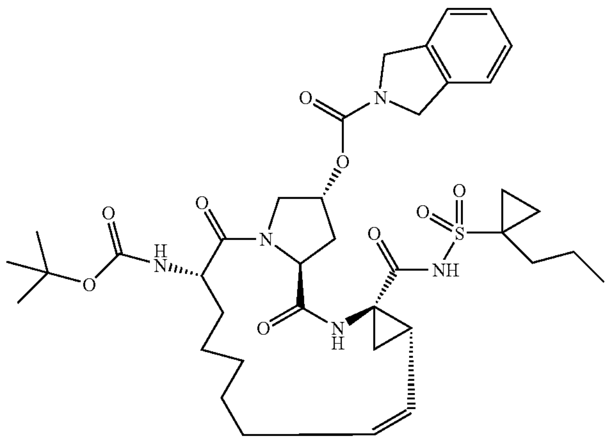 | ¹H NMR (400 MHz, d⁶-Acetone) δ 10.56 (br s, 1 H), 8.36 (br s, 1 H), 7.23-7.36 (m, 4 H), 6.12 (d, 1 H), 5.68 (q, 1 H), 5.46 (br s, 1 H), 4.98 (t, 1 H), 4.60-4.72 (m, 5 H), 4.49 (d, 1 H), 4.15-4.19 (m, 1 H), 3.86-3.89 (m, 1 H), 2.58-2.63 (m, 1 H), 2.45-2.53 (m, 2 H), 2.3 5-2.42 (m, 1 H), 1.86-1.97 (m, 3 H), 1.18-1.74 (m, 23 H), 0.86-0.96 (m, 5 H). MS m/z 754.6 (M − 1, APCI−) |
| 105 | 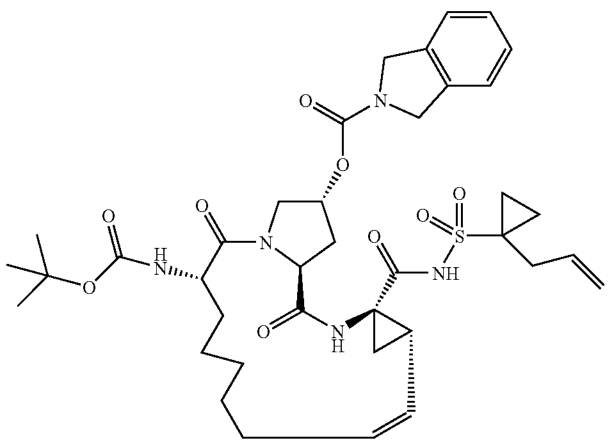 | ¹H NMR (400 MHz, d⁶-Acetone) δ 10.53 (br s, 1 H), 8.36 (br s, 1 H), 7.23-7.36 (m, 4 H), 6.12 (d, 1 H), 5.67-5.82 (m, 2 H), 5.45 (br s, 1 H), 5.08-5.14 (m, 2 H), 5.01 (t, 1 H), 4.60-4.72 (m, 5 H), 4.49 (d, 1 H), 4.14-4.18 (m, 1 H), 3.85-3.88 (m, 1 H), 2.72-2.77 (m, 1 H), 2.40-2.69 (m, 5 H), 1.86-1.91 (m, 2 H), 1.72-1.75 (m, 1 H), 1.18-1.62 (m, 19 H), 0.86-0.95 (m, 2 H). MS m/z 752.3 (M − 1, APCI−) |
| 106 | 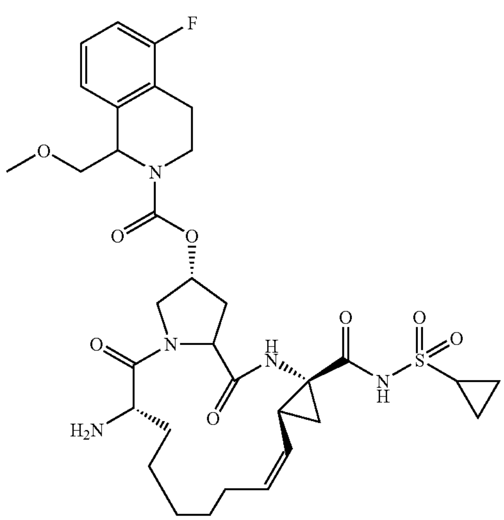 | 690.1 (M+, APCI+) |

US 7,829,665 B2
TABLE 1-continued
| Compound | Structure | ¹H-NMR/LCMS |
|---|---|---|
| 107 | 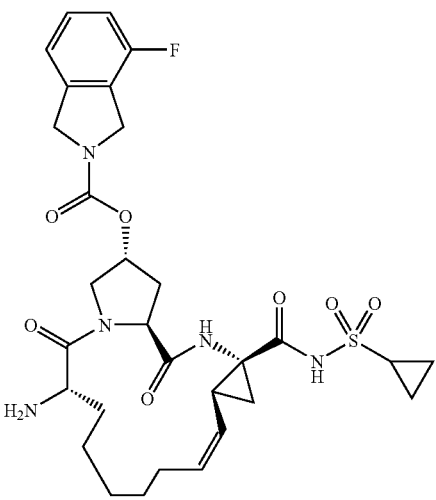 | 632.1 (M+, APCI+) |
| 108 | 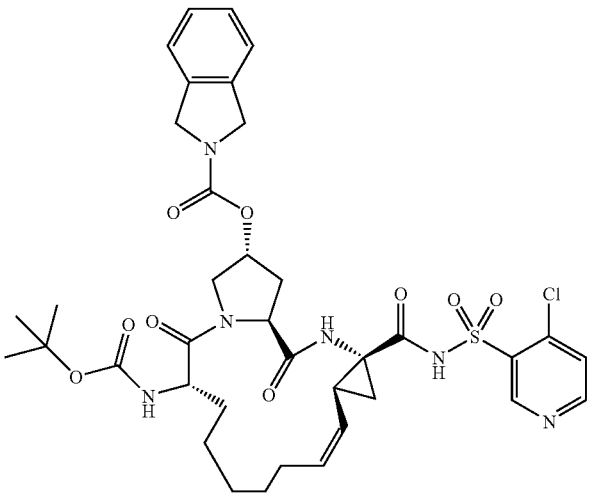 | 784.3 (M − 1, APCI−) |
| 109 | 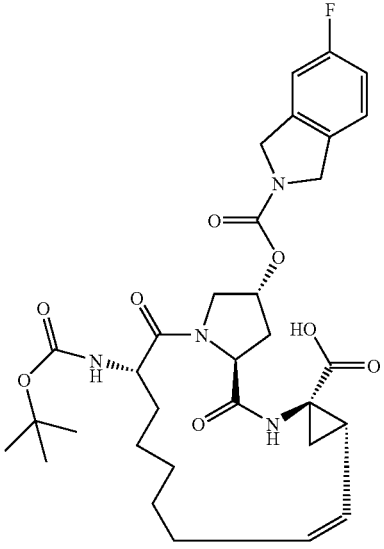 | 629 (M + 1, APCI) |

US 7,829,665 B2
131                                                                                    132
TABLE 1-continued
| Compound | Structure | ¹H-NMR/LCMS |
|---|---|---|
| 110 | 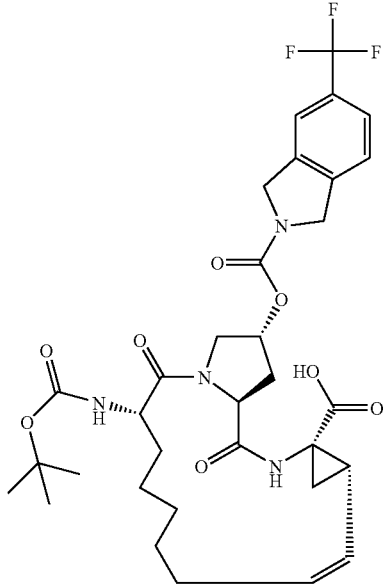 | 579 (M-Boc + 1, APCI) |
| 111 | 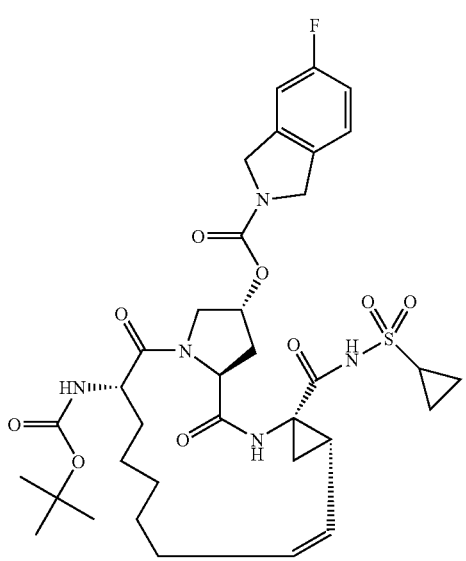 | 632 (M-Boc + 1, APCI) |

TABLE 1-continued

| Compound | Structure | ¹H-NMR/LCMS |
|---|---|---|
| 112 | 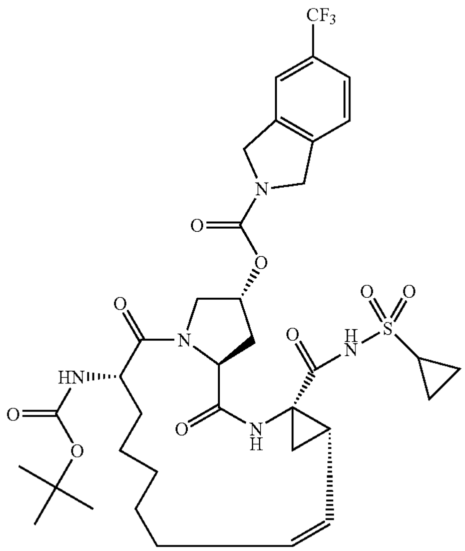 | 682 (M-Boc + 1, APCI) |
| 113 | 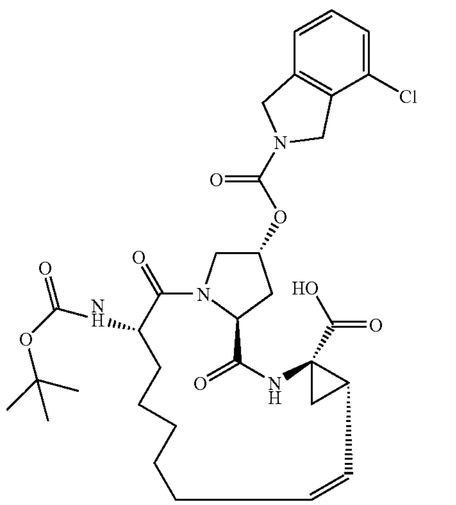 | 545 (M − Boc, APCI) |
| 114 | 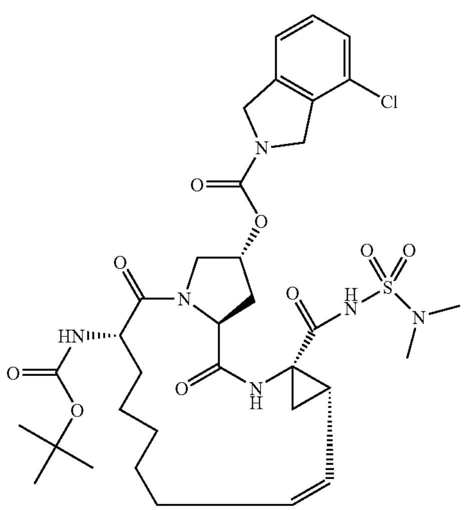 | 651 (M − Boc, APCI) |

TABLE 1-continued

| Compound | Structure | ¹H-NMR/LCMS |
|---|---|---|
| 115 | 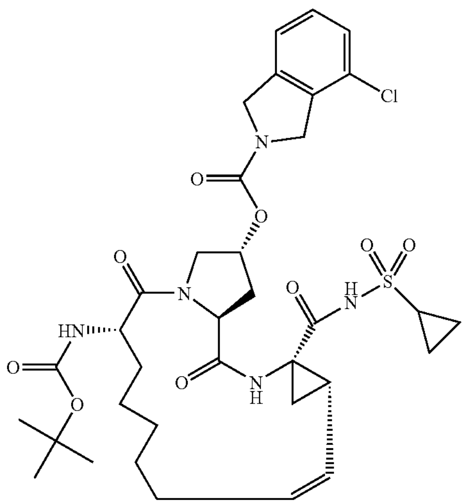 | 648 (M − Boc, APCI) |
| 116 | 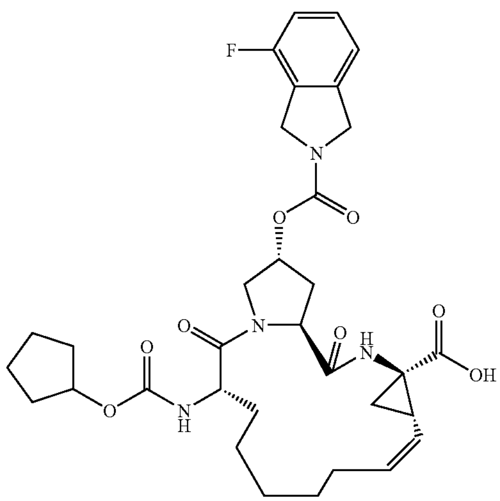 | ¹H NMR (400 MHz, d⁶-DMSO) δ 12.21 (br s, 1 H), 8.64 (br s, 1 H), 7.40-7.03 (m, 4 H), 5.57-5.54 (m, 1 H), 5.32-5.20 (m, 1 H), 4.72-4.57 (m, 2 H), 4.48-4.36 (m, 1 H), 4.37-4.21 (m, 1 H), 4.14-4.06 (m, 1 H), 3.69-3.60 (m, 1 H), 3.21-3.03 (m, 3 H), 2.29-2.04 (m, 2 H), 1.81-1.40 (m, 9H), 1.39-1.19 (m, 4H), 1.17-0.99 (m, 2 H). MS m/z 639.3 (M − 1, APCI−) |
| 117 | 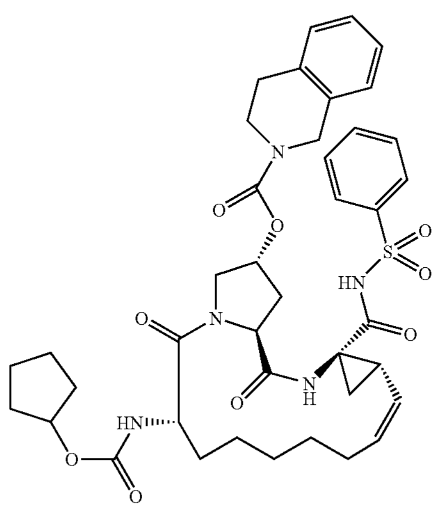 | HNMR (d⁶-Acetone) 8.3 (s, 1H), 7.95 (d, 2H), 7.68 (t, 1H), 7.58 (t, 2H), 7.16 (bs, 4H), 6.28 (d, 1H), 5.62 (s, 1H), 5.45 (bs, 1H), 5.25 (q, 1H), 4.83 (d, 1H), 4.57 (m, 4H), 4.41 (d, 1H), 4.21 (d, 1H), 3.90 (m, 1H), 2.84 (bs, 3H), 2.44 (m, 2H), 2.34 (m, 1H), 1.82 (m, 2H), 1.53 (m, 12H), 1.29 (m, 3H), 0.88 (m, 2H). LCMS(APCI+): 776 (M + H)+ |

TABLE 1-continued

| Compound | Structure | ¹H-NMR/LCMS |
|---|---|---|
| 118 | 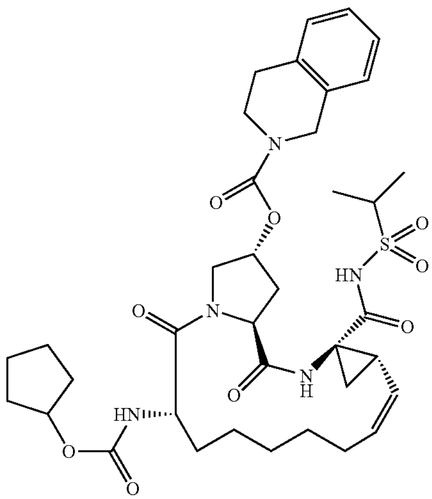 | HNMR (d⁶-Acetone): 8.28 (s, 1H), 7.16 (bs, 4H), 6.31 (d, 1H), 5.66 (m, 1H), 5.43 (bs, 1H), 5.03 (t, 1H), 4.82 (d, 1H), 4.59 (m, 4H), 4.42 (d, 1H), 4.20 (d, 1H), 3.87 (d, 1H), 3.62 (m, 1H), 2.84 (bs, 3H), 2.61 (m, 1H), 2.41 (m, 2H), 1.87 (m, 2H), 1.56 (m, 12H), 1.33 (m, 9H), 0.77 (m, 2H). LCMS(APCI+): 742 (M + H)+ |
| 119 | 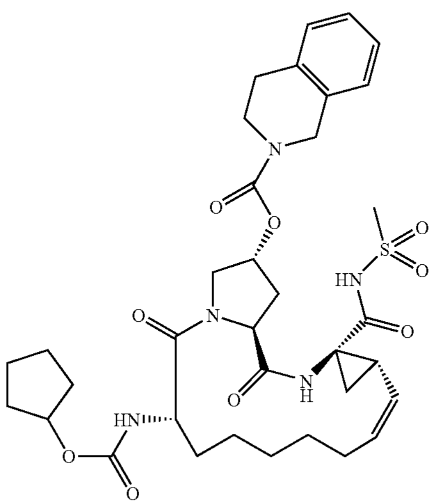 | HNMR (d⁶-Acetone) 8.16 (s, 1H), 7.16 (bs, 4H), 6.26 (d, 1H), 5.62 (m, 1H), 5.42 (bs, 1H), 5.11 (t, 1H), 4.84 (d, 1H), 4.60 (m, 4H), 4.35 (d, 1H), 4.26 (m, 1H), 3.92 (d, 1H), 3.08 (s, 3H), 2.81 (bs, 3H), 2.56 (bs, 1H), 2.40 (m, 2H), 1.88 (m, 2H), 1.53 (m, 12H), 1.30 (m, 3H), 0.77 (m, 2H). LCMS(APCI+): 714 (M + H)+ |
| 120 | 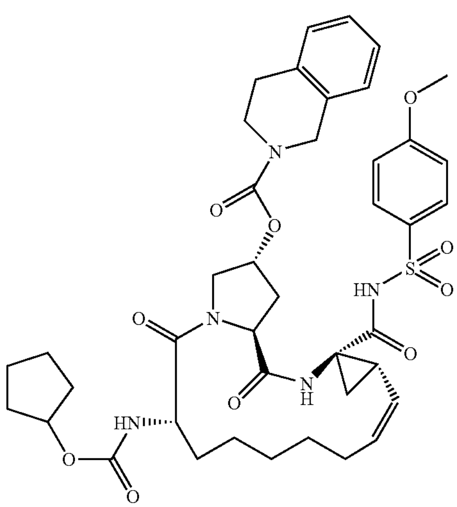 | HNMR (d⁶-Acetone) 10.87 (s, 1H), 8.20 (s, 1H), 7.70 (d, 2H), 7.16 (bs, 4H), 7.08 (d, 2H), 6.25 (d, 1H), 5.62 (s, 1H), 5.49 (bs, 1H), 5.29 (q, 1H), 4.81 (d, 1H), 4.56 (m, 4H), 4.41 (d, 1H), 4.20 (m, 1H), 3.91 (s, 3H), 3.88 (m, 1H), 2.84 (bs, 3H), 2.40 (m, 3H), 1.85 (m, 2H), 1.55 (m, 12H), 1.29 (m, 3H), 0.88 (m, 2H). LCMS(APCI+): 806 (M + H)+ |

TABLE 1-continued

| Compound | Structure | ¹H-NMR/LCMS |
|---|---|---|
| 121 | 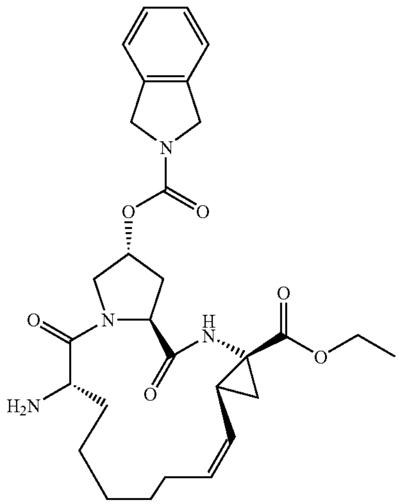 | 539.9 (M+, APCI+) |
| 122 | 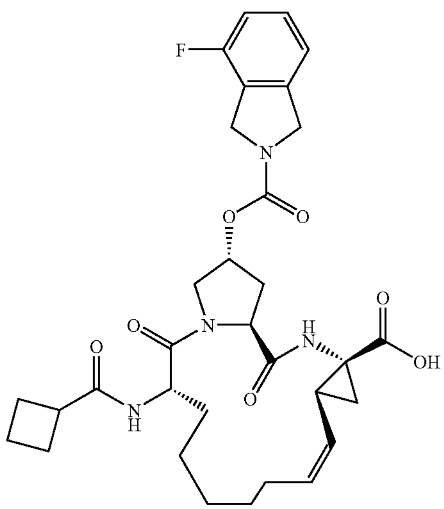 | 609.4 (M − 1, APCI−) |
| 123 | 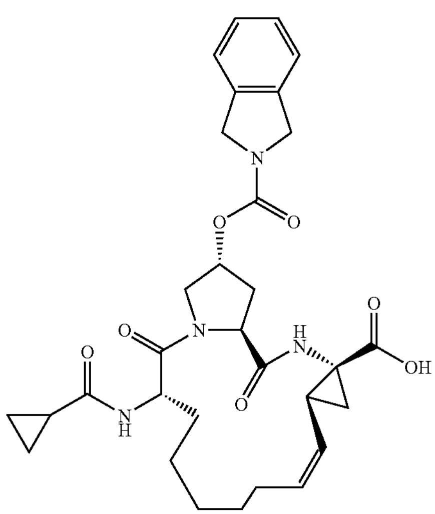 | 577.4 (M − 1, APCI−) |

TABLE 1-continued
| Compound | Structure | ¹H-NMR/LCMS |
|---|---|---|
| 124 | 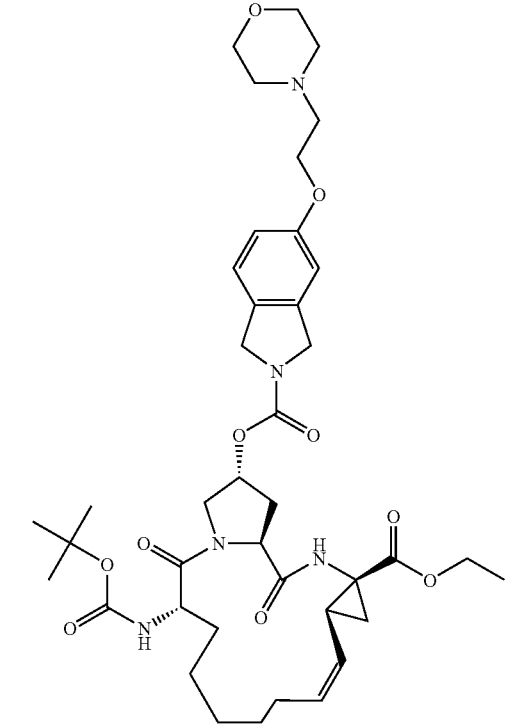 | 768.2 (M + 1, APCI+) |
| 125 | 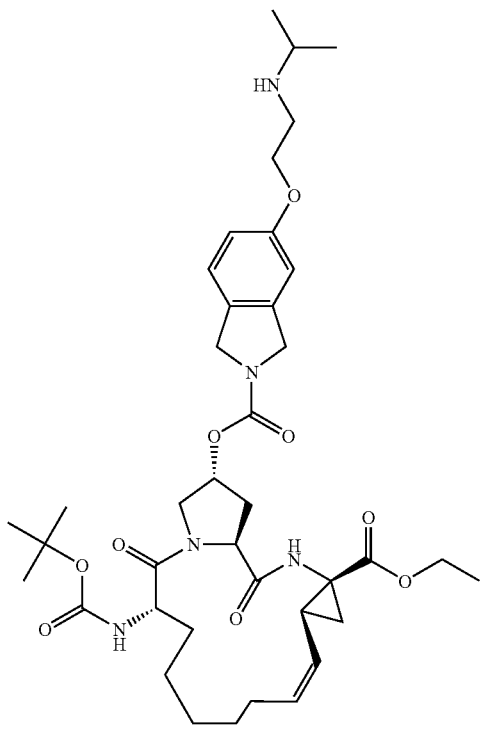 | 740.2 (M + 1, APCI+) |

TABLE 1-continued
| Compound | Structure | ¹H-NMR/LCMS |
|---|---|---|
| 126 | 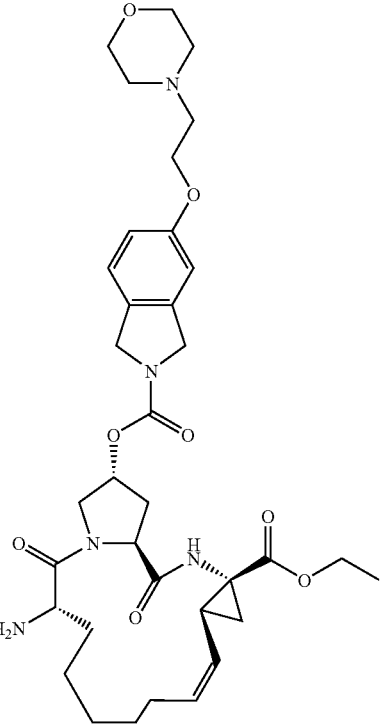 | 668.2 (M + 1, APCI+) |
| 127 | 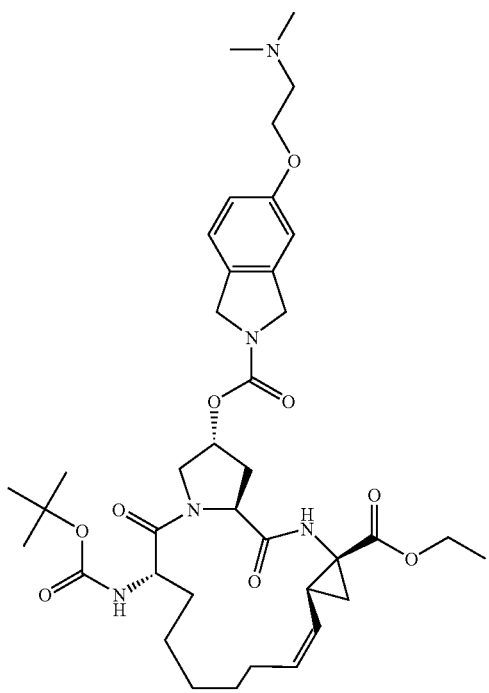 | 726.2 (M + 1, APCI+) |

TABLE 1-continued
| Compound | Structure | $^1$H-NMR/LCMS |
|---|---|---|
| 128 | 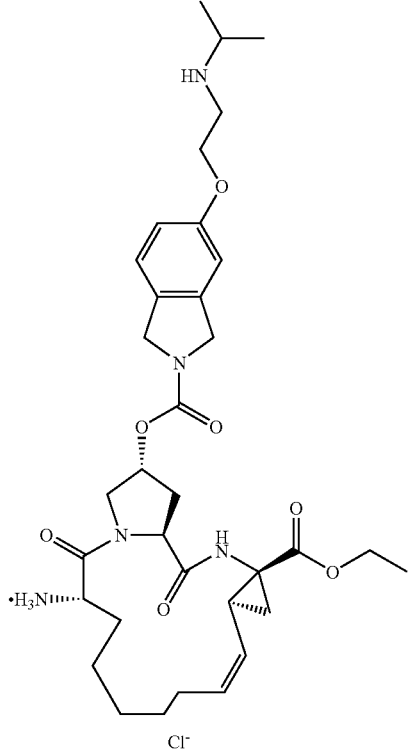 | 640.2 (M + 1, APCI+) |
| 129 | 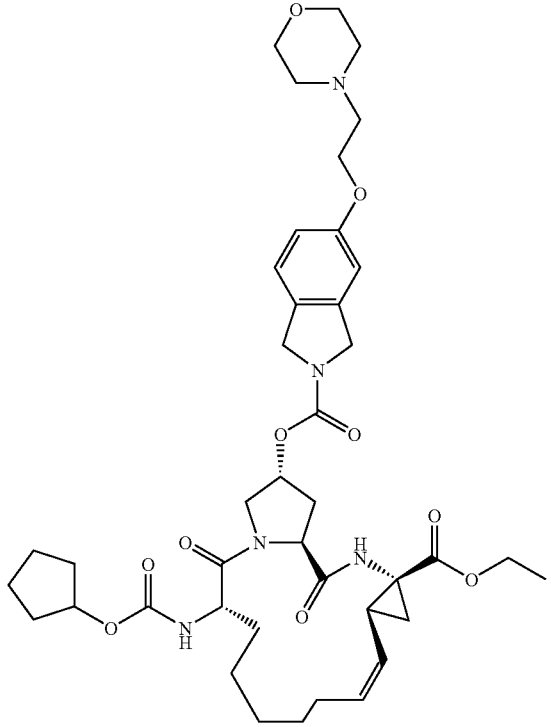 | 780.3 (M + 1, APCI+) |

TABLE 1-continued
| Compound | Structure | ¹H-NMR/LCMS |
|---|---|---|
| 130 | 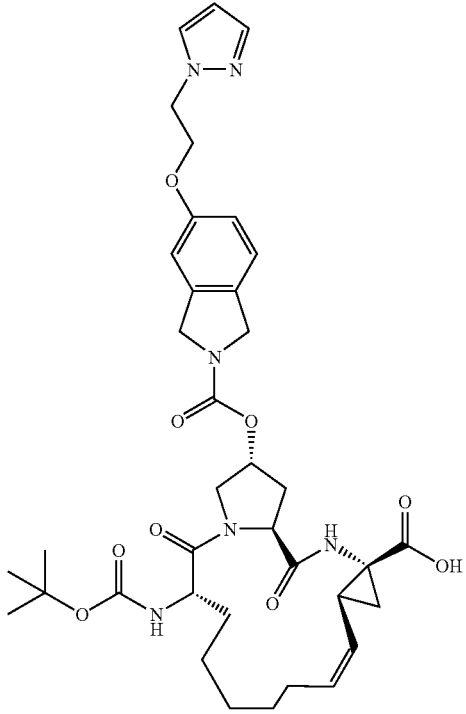 | 719.2 (M − 1, APCI−) |
| 131 | 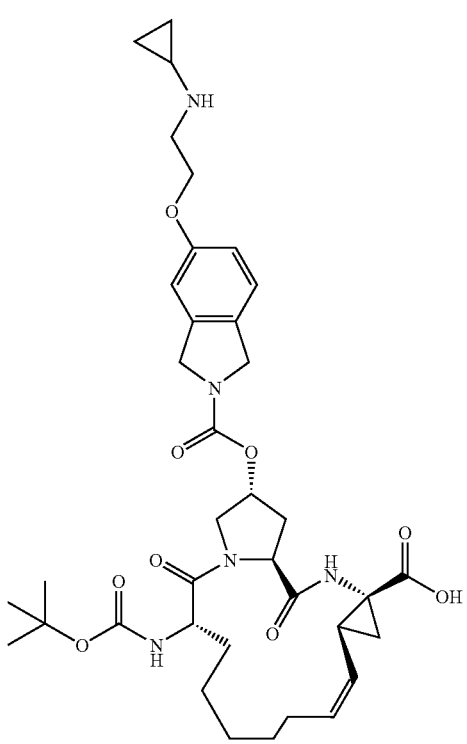 | 708.2 (M − 1, APCI−) |

TABLE 1-continued

| Compound | Structure | ¹H-NMR/LCMS |
|---|---|---|
| 132 | 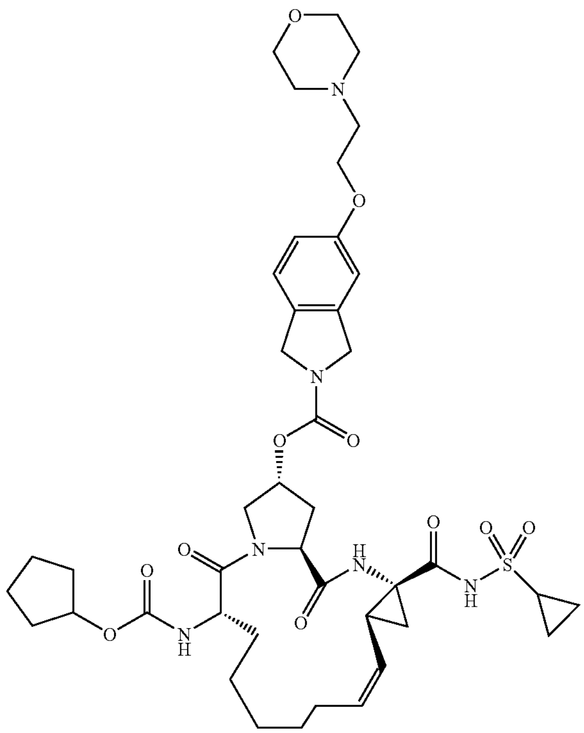 | 853.4 (M − 1, APCI−) |
| 133 | 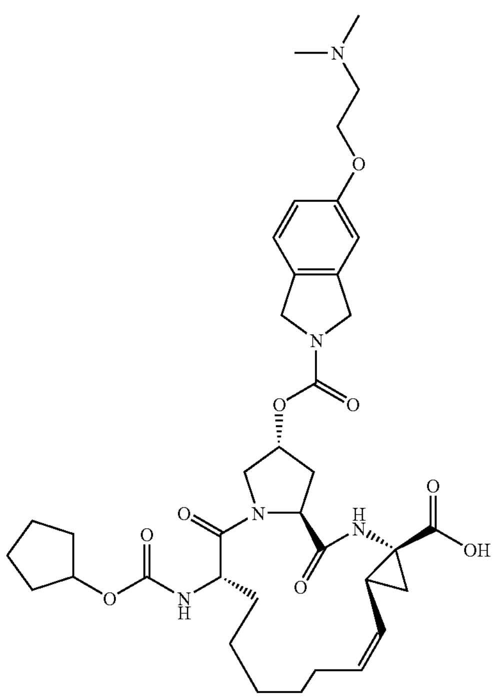 | 708.2 (M − 1, APCI−) |

US 7,829,665 B2
151   152
TABLE 1-continued
| Compound | Structure | ¹H-NMR/LCMS |
|---|---|---|
| 134 | 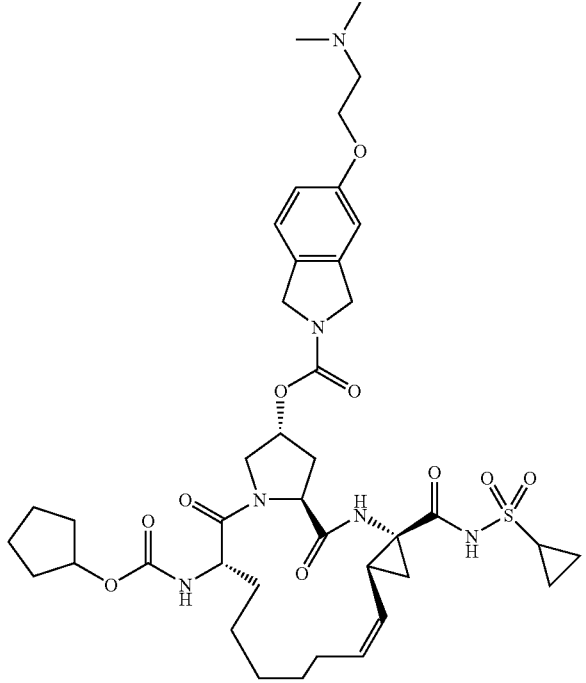 | 811.3 (M − 1, APCI−) |
| 135 | 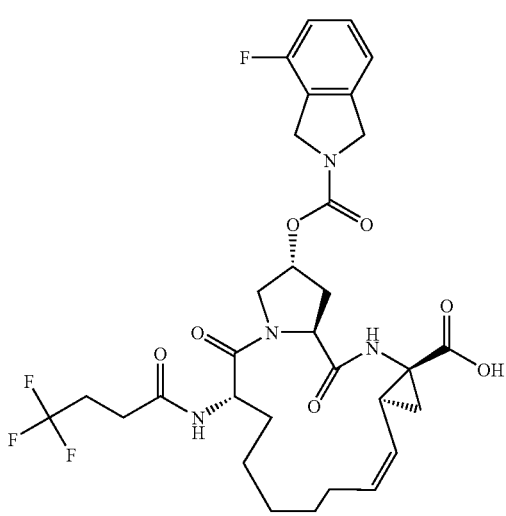 | 651.2 (M − 1, APCI−) |

TABLE 1-continued

| Compound | Structure | ¹H-NMR/LCMS |
|---|---|---|
| 136 | 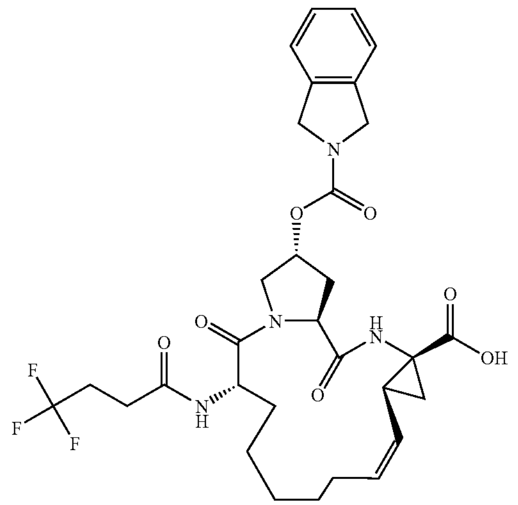 | 633.2 (M − 1, APCI−) |
| 137 | 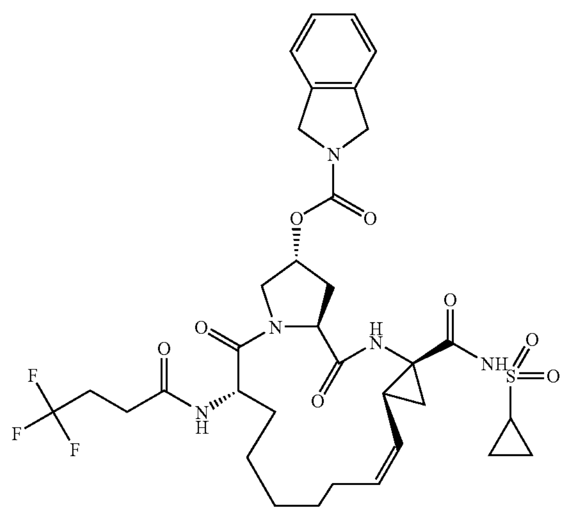 | 737.1 (M − 1, APCI−) |
| 138 | 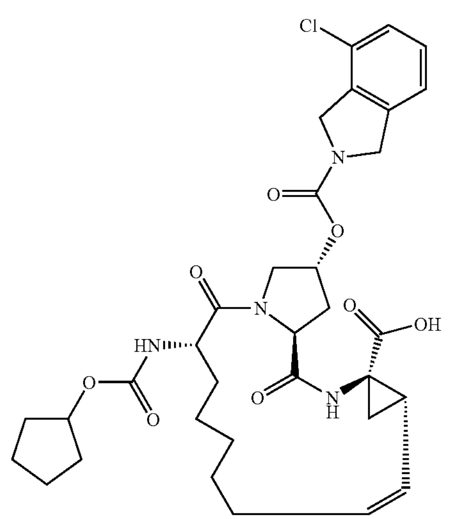 | LCMS (APCI+): 657 (M) |

TABLE 1-continued

| Compound | Structure | ¹H-NMR/LCMS |
|---|---|---|
| 139 | 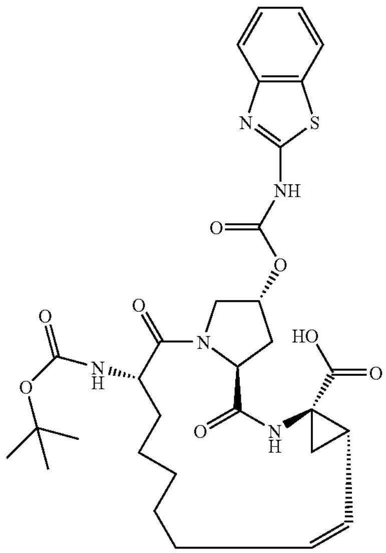 | LCMS (APCI+): 642 (M + 1) |
| 140 | 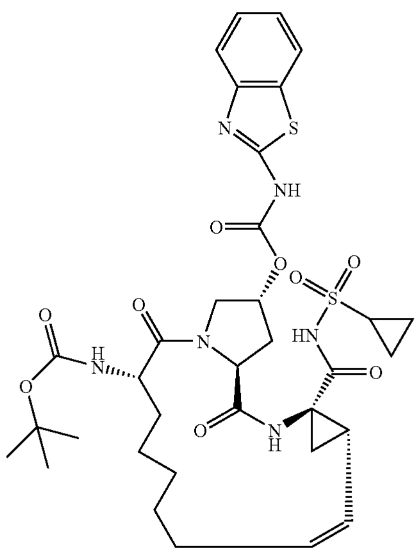 | LCMS (APCI+): 745 (M + 1) |
| 141 | 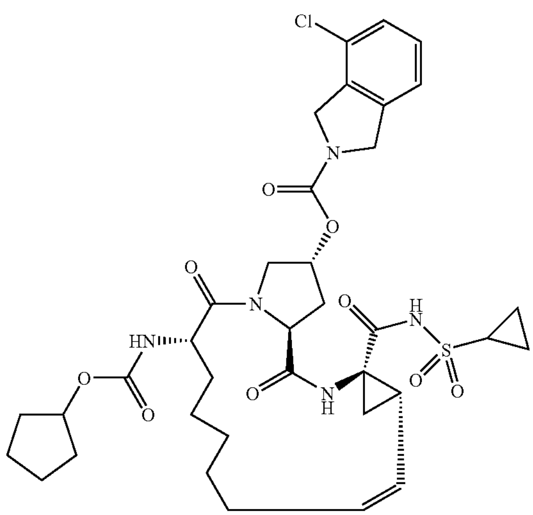 | LCMS (APCI+): 760 (M) |

US 7,829,665 B2
157                                                                                              158
TABLE 1-continued
| Compound | Structure | $^1$H-NMR/LCMS |
|---|---|---|
| 142 | 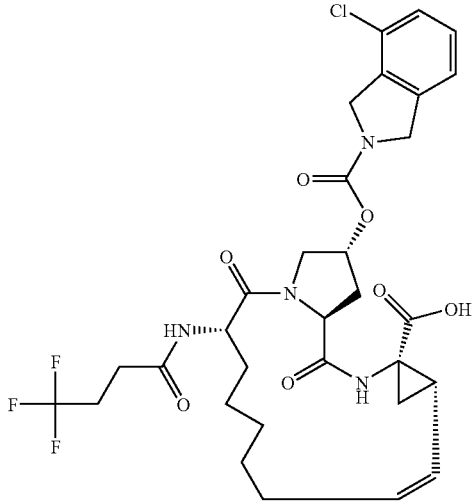 | LCMS (APCI+): 669 (M) |
| 143 | 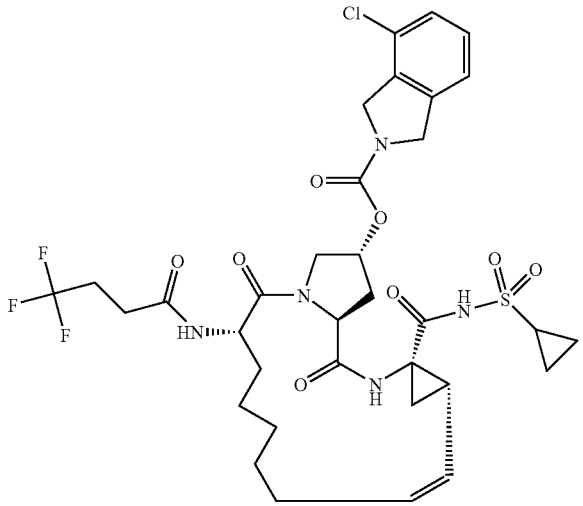 | LCMS (APCI+): 772 (M) |
| 144 | 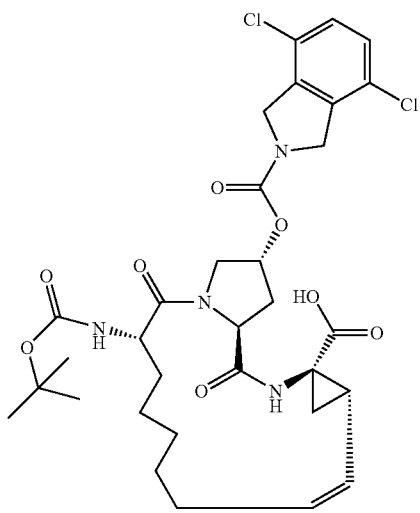 | LCMS (APCI+): 679 (M) |

TABLE 1-continued

| Compound | Structure | ¹H-NMR/LCMS |
|---|---|---|
| 145 | 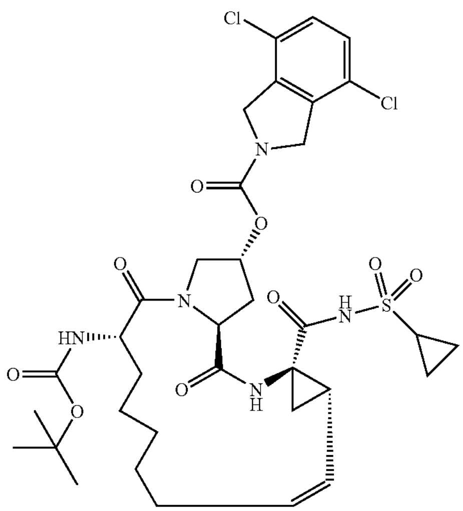 | LCMS (APCI+): 682 (M) |
| 146 | 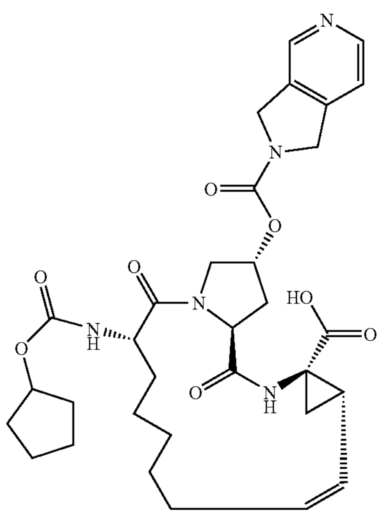 | LCMS (APCI+): 624 (M + 1) |
| 147 | 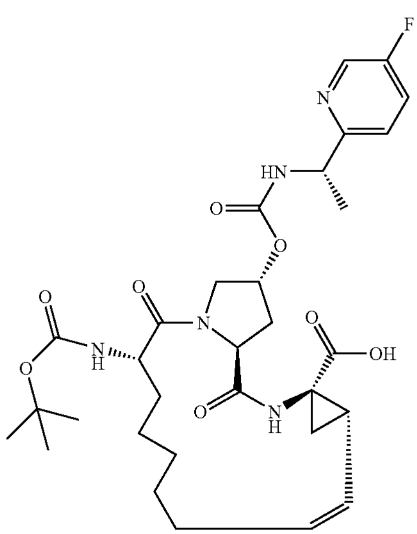 | ¹H NMR (400 MHz, d⁶-DMSO) 12.45 (b, 1H), 8.61 (s, 1H), 8.48 (d, J=2.8 Hz, 1H), 7.84 (d, J=7.6 Hz, 1H), 7.64 (m, 1H), 7.43 (m, 1H), 6.84 (d, J=6.8 Hz, 1H), 5.49 (m, 1H), 5.29 (m, 2H), 4.72 (m, 1 H), 4.35 (m, 1H), 4.13 (m, 2H), 3.81 (m, 1H), 2.38 (m, 1H), 2.12 (m, 3 H), 1.99 (m, 1H), 1.65 (m, 1H), 1.13-1.46(m, 21H). LCMS (APCI+): 632.1 (H+) |

TABLE 1-continued
| Compound | Structure | ¹H-NMR/LCMS |
|---|---|---|
| 148 | 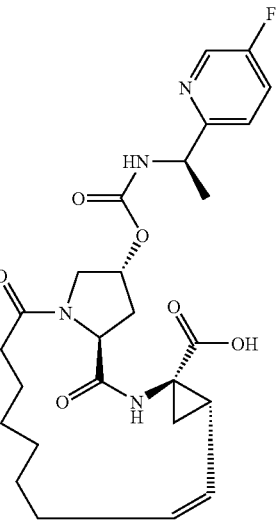 | ¹H NMR (400 MHz, d⁶-DMSO) 12.24 (b, 1H), 8.59 (s, 1H), 8.48 (d, J=2.4 Hz, 1H), 7.79 (d, J=7.2 Hz, 1H), 7.69 (m, 1H), 7.42 (m, 1H), 6.90 (d, J=7.2 Hz, 1H), 5.49 (m, 1H), 5.29 (m, 1H), 5.19 (b, 1H), 4.71 (m, 1 H), 4.33 (m, 1H), 4.12 (m, 1H), 4.01 (m, 1H), 3.78 (m, 1H), 2.41 (m, 1H), 2.13 (m, 3H), 1.83 (m, 1H), 1.67 (m, 1H), 1.16-1.48 (m, 21 H). LCMS (APCI+):632.1 (H+) |
| 149 | 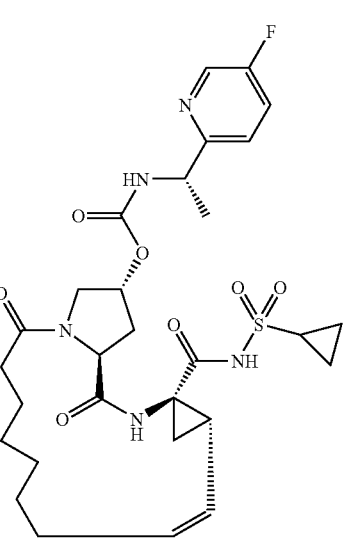 | ¹H NMR (400 MHz, d⁶-DMSO) 11.05 (s, 1H), 8.88 (s, 1H), 8.48 (s, 1H), 7.80 (d, J=7.2 Hz, 1H), 7.64 (m, 1H), 7.44 (m, 1H), 7.04 (d, J=6.8 Hz, 1H), 5.60 (m, 1H), 5.27 (m, 1H), 5.07 (m, 1 H), 4.73 (m, 1H), 4.33 (m, 1H), 4.08 (m, 1H), 3.93 (m, 1H), 3.81 (m, 1H), 2.90 (m, 1H), 2.27 (m, 3H), 1.73 (m, 2H), 1.59 (m, 1H), 1.53 (m, 1H), 0.83-1.36 (m, 24 H). LCMS (APCI+):735.1 (H+) |
| 150 | 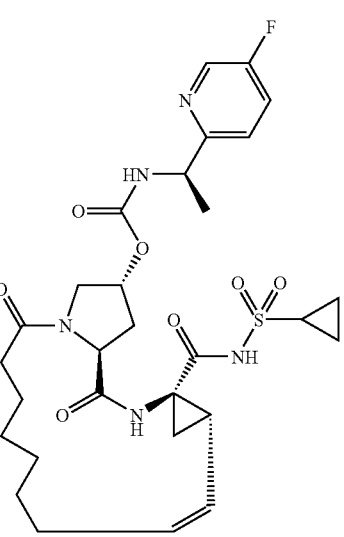 | ¹H NMR (400 MHz, d⁶-DMSO) 11.05 (s, 1H), 8.88 (s, 1H), 8.47 (s, 1H), 7.75 (d, J=7.2 Hz, 1H), 7.69 (m, 1H), 7.42 (m, 1H), 7.08 (d, J=7.2 Hz, 1H), 5.60 (m, 1H), 5.20 (m, 1H), 5.06 (m, 1 H), 4.72 (m, 1H), 4.33 (m, 1H), 4.11 (m, 2H), 3.79 (m, 1H), 2.89 (m, 1H), 2.29 (m, 3H), 1.74 (m, 2H), 1.60 (m, 1H), 1.53 (m, 1H), 0.84-1.37 (m, 24 H). LCMS (APCI+): 735.1 (H+) |

TABLE 1-continued

| Compound | Structure | ¹H-NMR/LCMS |
|---|---|---|
| 151 | 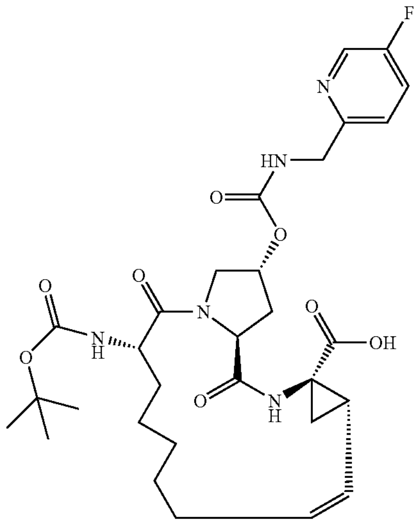 | LCMS (APCI−): 618.1 (M+) |
| 152 | 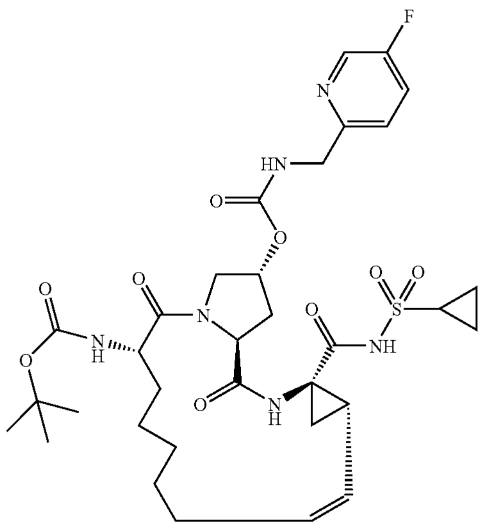 | ¹H NMR (400 MHz, d⁶-DMSO) 11.05 (s, 1H), 8.89 (s, 1H), 8.48 (s, 1H), 7.83 (m, 1H), 7.67 (m, 1H), 7.35 (m, 1H), 7.08 (m, 1H), 5.59 (m, 1H), 5.27 (m, 1H), 5.06 (m, 1 H), 4.34 (m, 1H), 4.26 (m, 2H), 4.10 (m, 2H), 3.83 (m, 1H), 2.90 (m, 1H), 2.33 (s, 2H), 2.28 (m, 1H), 1.76 (m, 2H), 1.59 (m, 1H), 1.53 (m, 1H), 0.85-1.34 (m, 21 H). LCMS (APCI+): 737.9 (H+) |
| 153 | 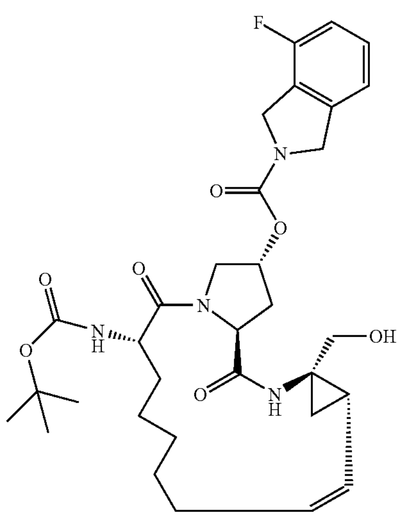 | ¹H NMR (400 MHz, d⁶-DMSO) 8.47 (b, 1H), 7.35 (m, 1H), 7.10-7.20 (m, 2H), 7.03 (m, 1H), 5.47 (m, 1H), 5.28 (b, 1H), 4.98 (m, 1H), 4.67 (b, 4H), 4.56 (m, 1H), 4.46 (m, 1H), 4.26 (m, 1H), 3.92 (m, 1H), 3.66 (m, 2H), 3.16 (m, 1H), 2.67 (m, 1H), 2.21 (m, 2H), 1.80 (m, 1H), 1.68 (m, 1H), 1.30 (m, 8H), 1.11-1.20 (m, 9H), 0.85 (m, 1H), 0.77 (m, 1H). LCMS (APCI+): 615.1 (H+) |

TABLE 1-continued
| Compound | Structure | ¹H-NMR/LCMS |
|---|---|---|
| 154 | 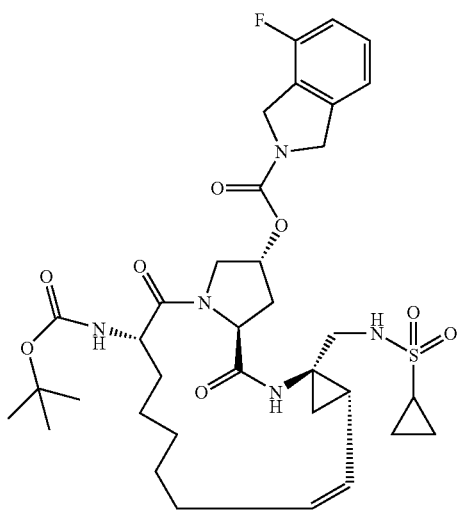 | ¹H NMR (400 MHz, d⁶-DMSO) 8.52 (m 1H), 7.35 (m, 1H), 7.02-7.20 (m, 4H), 5.56 (m, 1H), 4.99 (m, 1H), 4.97 (m, 1H), 4.67 (m, 2H), 4.66 (s, 2H), 4.46 (m, 1H), 4.24 (m, 1H), 3.92 (m, 1H), 3.67 (m, 1H), 3.46 (m, 1H), 2.74 (m, 1h), 2.67 (m, 1H), 2.22 (m, 2H), 1.84 (m, 1 H), 1.68 (m, 1H), 1.08-1.36 (m, 20 H), 0.89 (m, 2H), 0.81 (m, 2H). LCMS (APCI+): 718.1 (H+) |
| 155 | 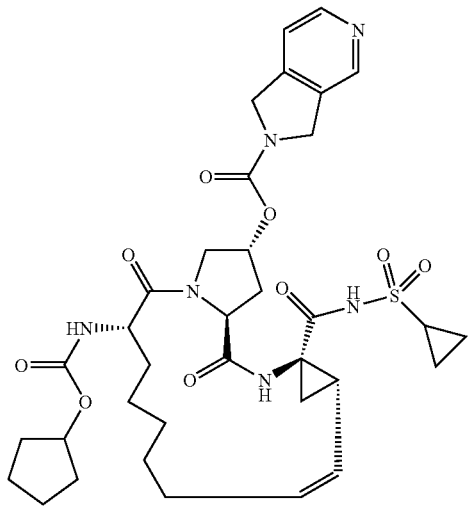 | LCMS (APCI+): 727 (M + 1) |
| 156 | 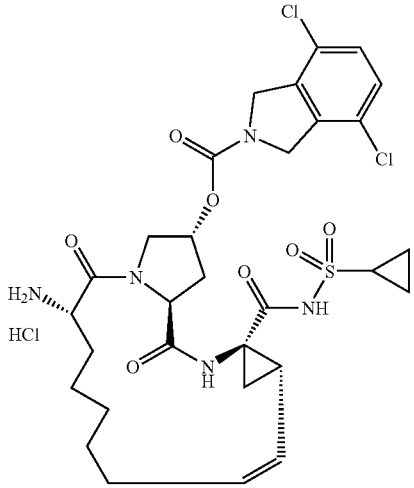 | MS m/z 682 (APCI+, M+) |

TABLE 1-continued

| Compound | Structure | ¹H-NMR/LCMS |
|---|---|---|
| 157 | 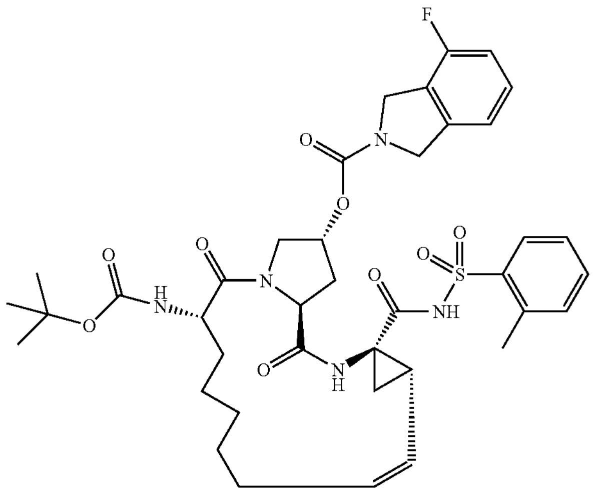 | MS m/z 682 (APCI+, M-Boc + 1). |
| 158 | 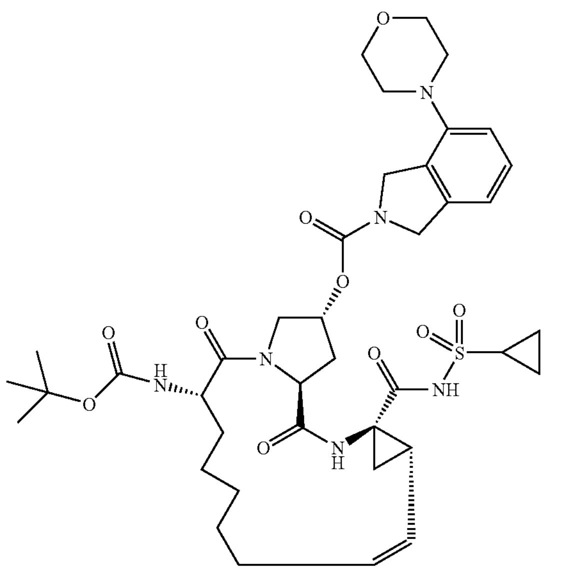 | MS m/z 799 (APCI+, M + 1) |
| 159 | 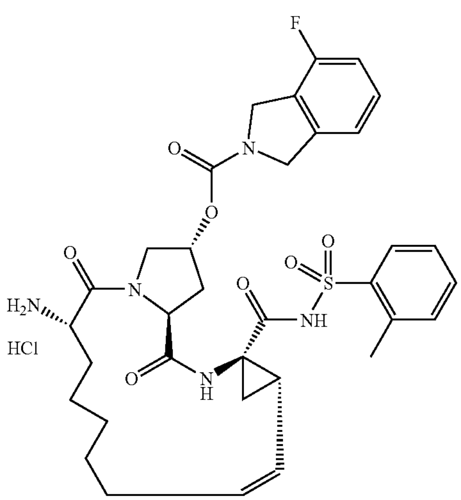 | MS m/z 682 (APCI+, M+) |

TABLE 1-continued

| Compound | Structure | ¹H-NMR/LCMS |
|---|---|---|
| 160 | 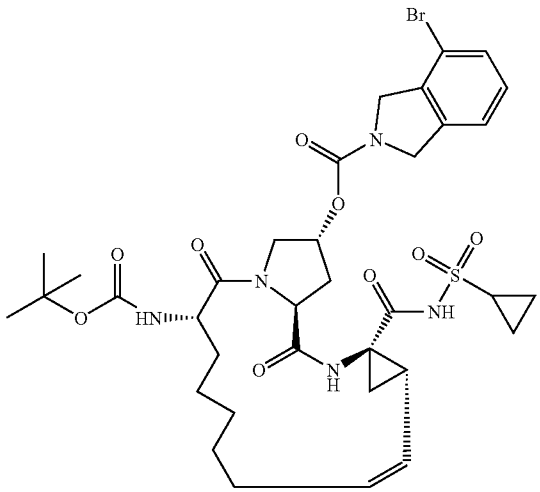 | MS m/z 692 (APCI+, M-Boc) |
| 161 | 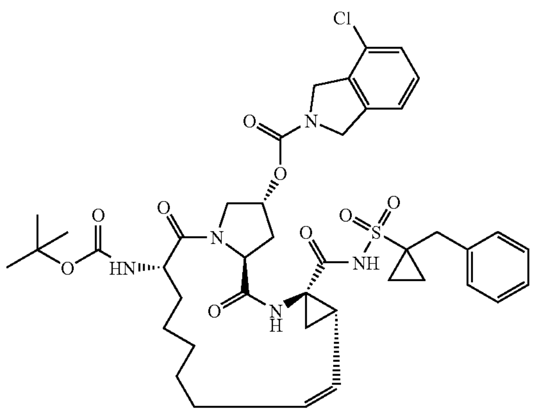 | MS m/z 738 (APCI+, M-Boc) |
| 162 | 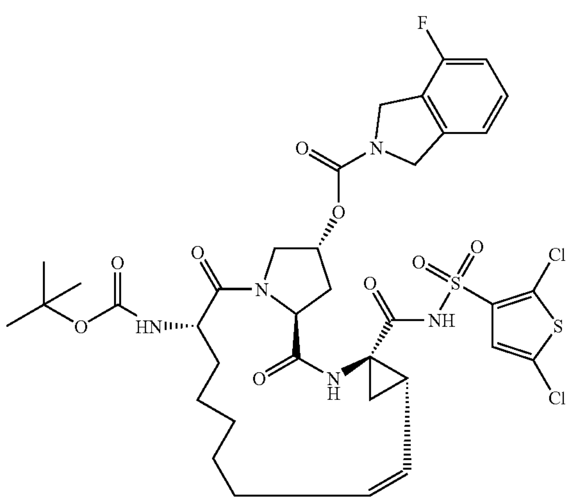 | MS m/z 742 (APCI+, M-Boc). |

TABLE 1-continued

| Compound | Structure | ¹H-NMR/LCMS |
|---|---|---|
| 163 | 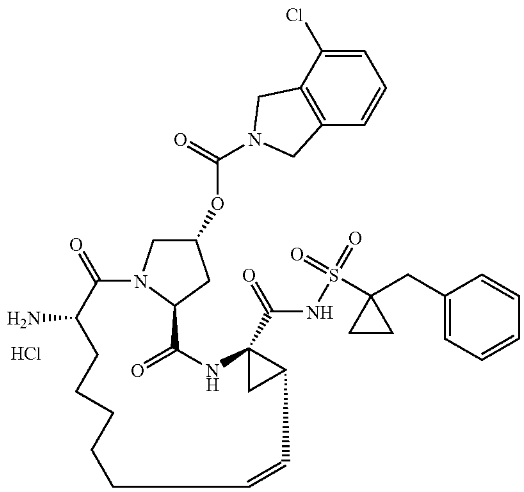 | MS m/z 738 (APCI+, M+) |
| 164 | 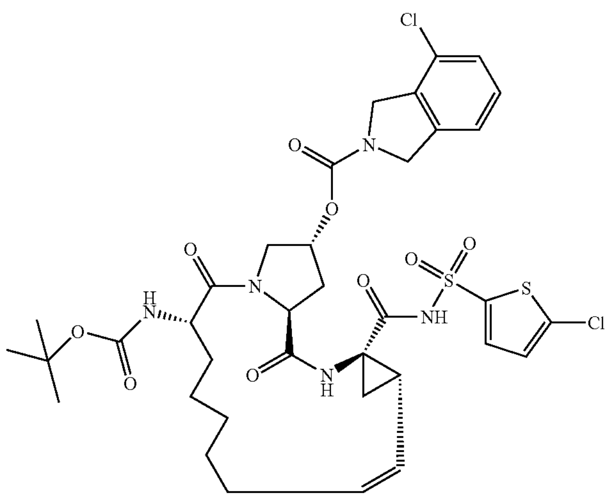 | MS m/z 724 (APCI+, M-Boc) |
| 165 | 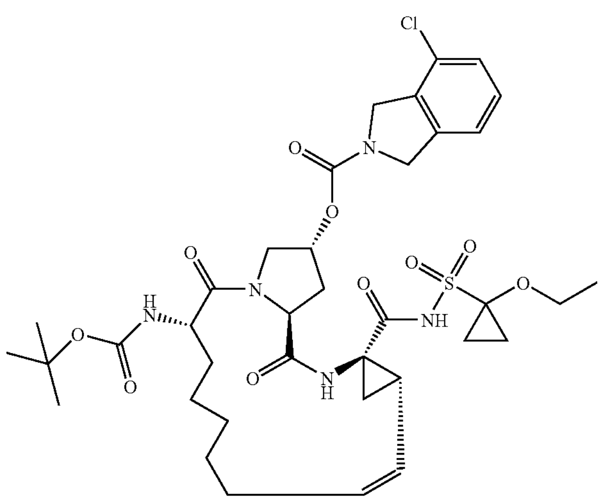 | MS m/z 792 (APCI+, M+) |

TABLE 1-continued

| Compound | Structure | ¹H-NMR/LCMS |
|---|---|---|
| 166 | 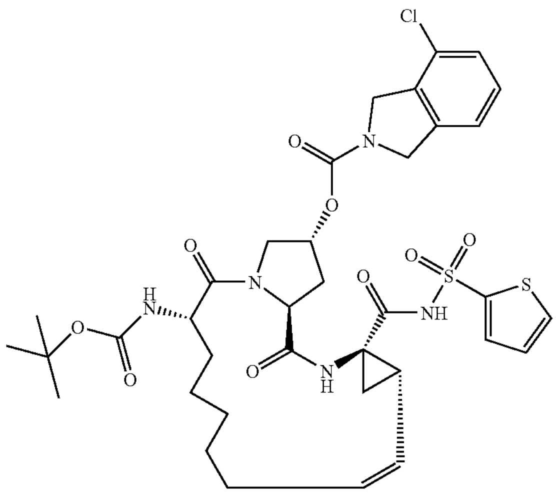 | MS m/z 690 (APCI+, M-Boc) |
| 167 | 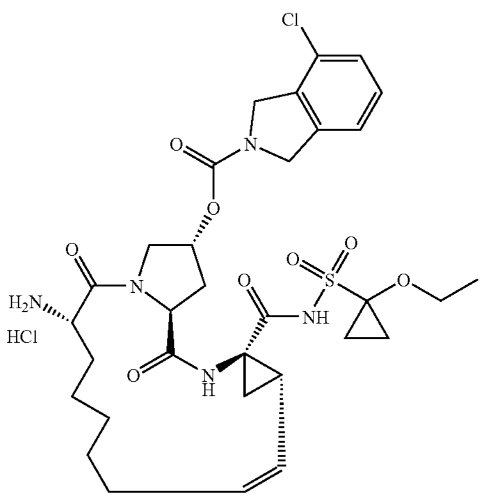 | MS m/z 692 (APCI+, M+) |
| 168 | 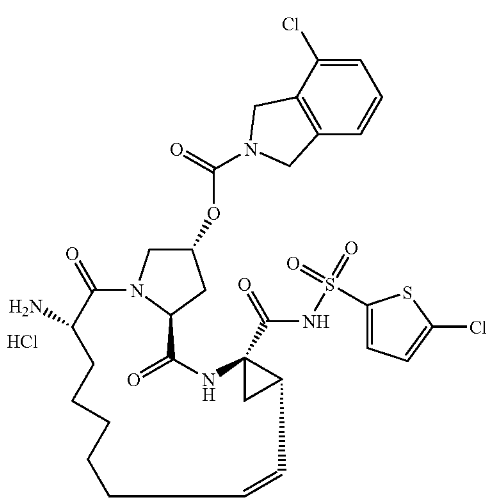 | MS m/z 724 (APCI+, M+) |

TABLE 1-continued

| Compound | Structure | ¹H-NMR/LCMS |
|---|---|---|
| 169 | 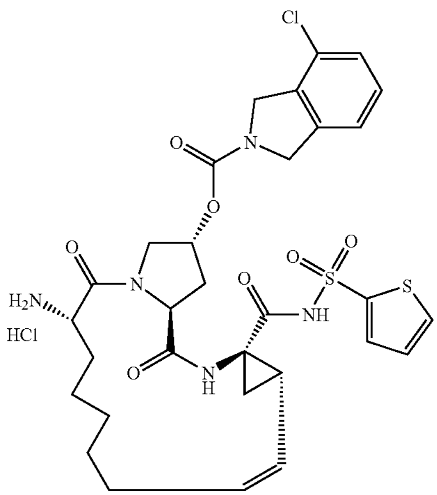 | MS m/z 690 (APCI+, M+) |
| 170 | 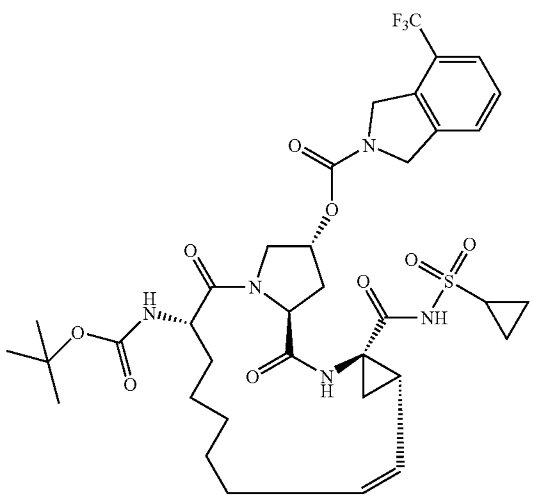 | MS m/z 682 (APCI+, M-Boc + 1) |
| 171 | 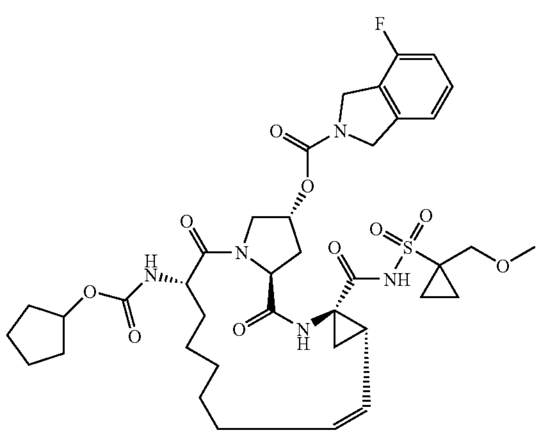 | MS m/z 788 (APCI+, M + 1) |

TABLE 1-continued

| Compound | Structure | ¹H-NMR/LCMS |
|---|---|---|
| 172 | 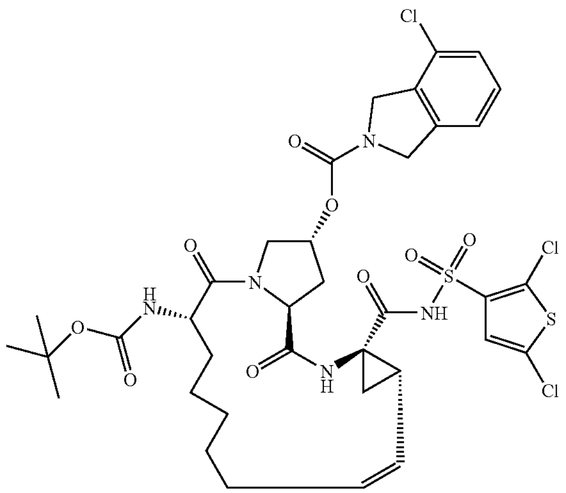 | MS m/z 760 (APCI+, M-Boc + 1) |
| 173 | 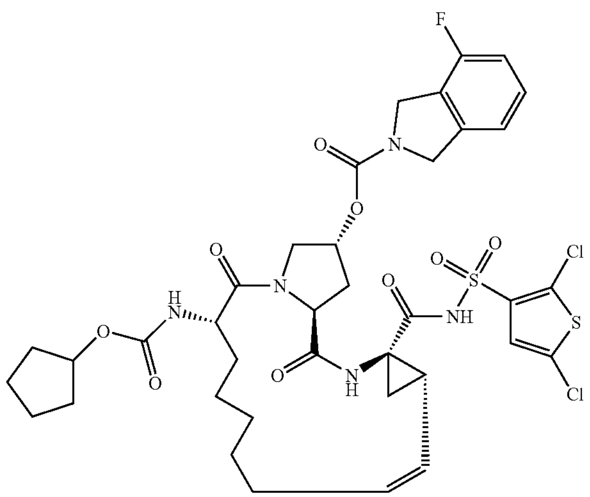 | MS m/z 854 (APCI+, M+) |
| 174 | 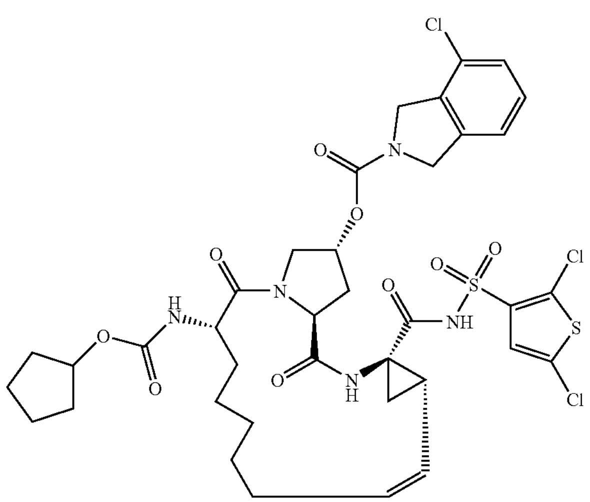 | MS m/z 870 (APCI−, M − 1) |

TABLE 1-continued

| Compound | Structure | ¹H-NMR/LCMS |
|---|---|---|
| 175 | 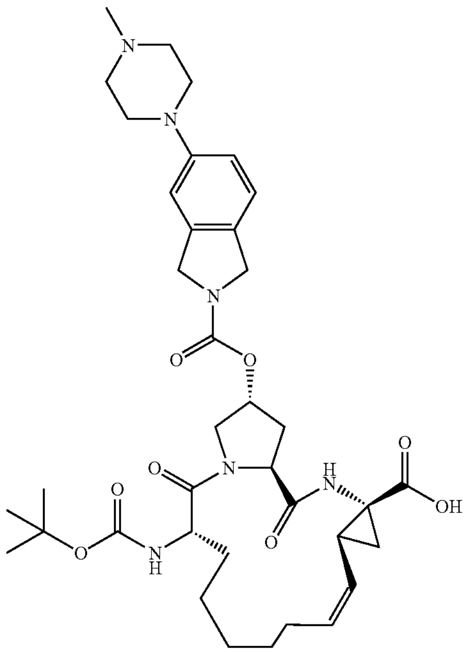 | MS m/z 707.5 (APCI–, M – 1) |
| 176 | 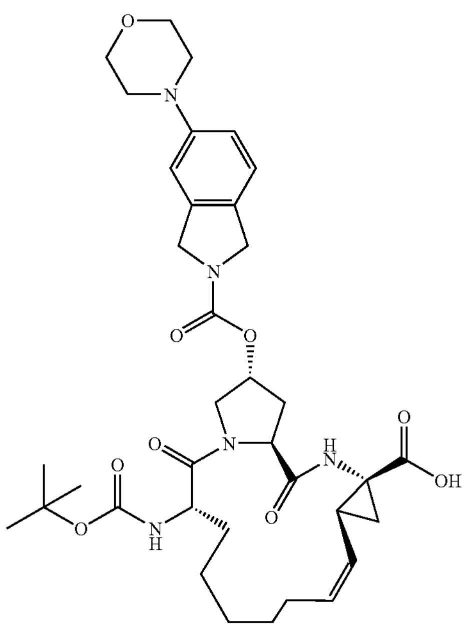 | MS m/z 694.3 (APCI–, M – 1) |

TABLE 1-continued

| Compound | Structure | ¹H-NMR/LCMS |
|---|---|---|
| 177 | [structure] | MS m/z 642.3 (APCI–, M – 1) |
| 178 | [structure] | ¹H NMR (400 MHz, DMSO) δ 0.92-1.82 (m, 24 H), 2.18-2.40 (m, 3 H), 2.86-2.94 (m, 1 H), 3.64-3.75 (m, 1 H), 3.78-3.88 (m, 1 H), 3.97-4.10 (m, 1 H), 4.32-4.50 (m, 2 H), 4.56-4.76 (m, 4 H), 5.06 (t, 1 H), 5.31 (br s, 1 H), 5.61 (q, 1 H), 5.70-5.75 (m, 1 H), 5.91 (d, 1 H), 7.07-7.22 (m, 2H), 7.31-7.38 (m, 1 H), 8.92 (d, 1 H), 11.12 (s, 1 H). MS m/z 741.3 (APCI–, M – 1) |
| 179 | [structure] | MS m/z 645.3 (APCI–, M – 1) |

TABLE 1-continued

| Compound | Structure | ¹H-NMR/LCMS |
|---|---|---|
| 180 | 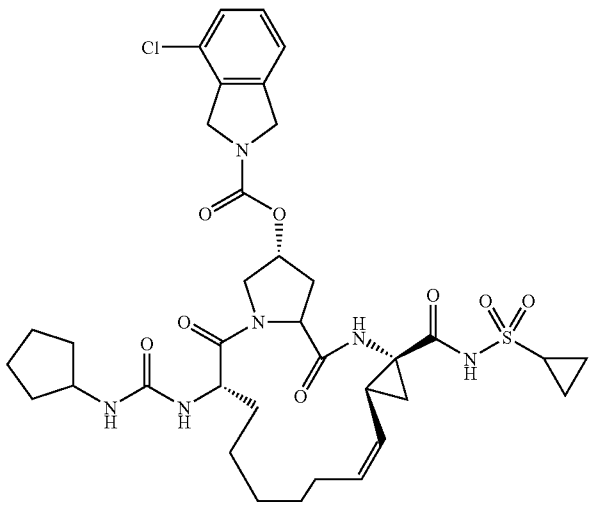 | MS m/z 757.4 (APCI–, M – 1) |
| 181 | 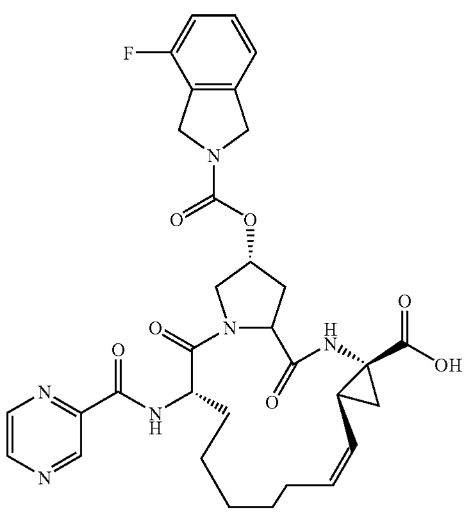 | MS m/z 633.3 (APCI–, M – 1) |
| 182 | 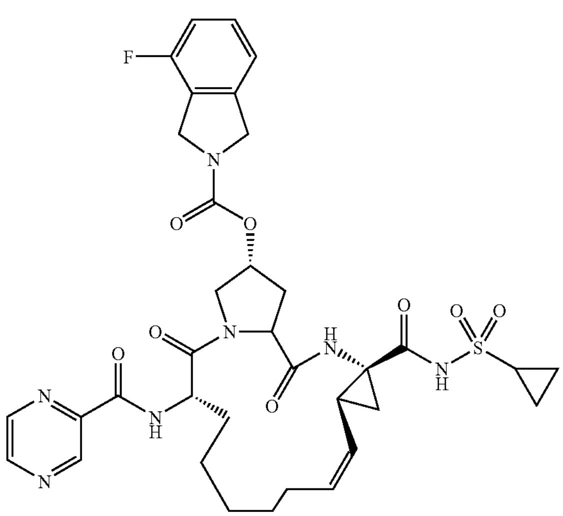 | MS m/z 636.4 (APCI–, M – 1) |

TABLE 1-continued
| Compound | Structure | ¹H-NMR/LCMS |
|---|---|---|
| 183 | 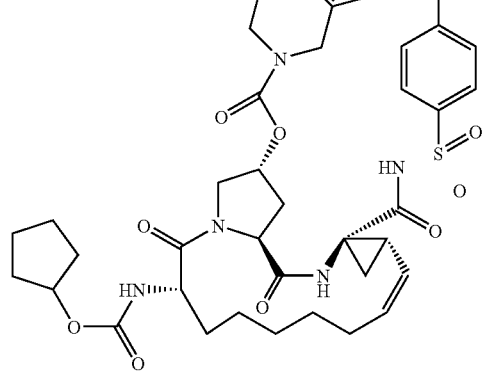 | MS m/z 819.1 (APCI+, M + 1) |
| 184 | 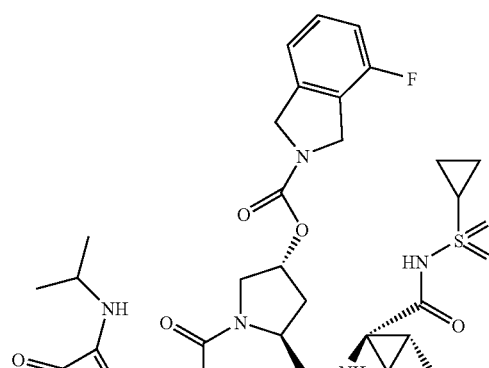 | MS m/z 767.5 (APCI−, M − 1) |
| 185 | 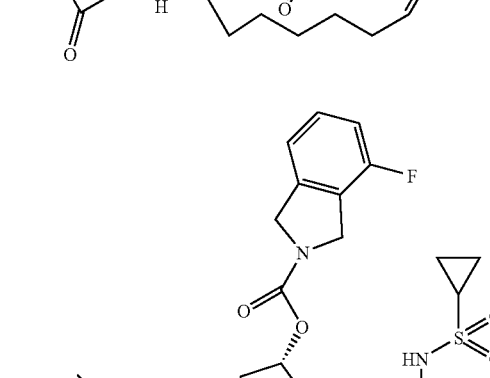 | MS m/z 753.2 (APCI−, M − 1) |

| Compound | Structure | ¹H-NMR/LCMS |
|---|---|---|
| 186 | 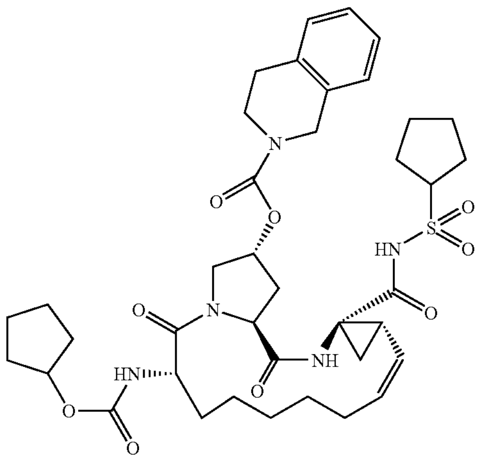 | MS m/z 766.4 (APCI−, M − 1) |
| 187 | 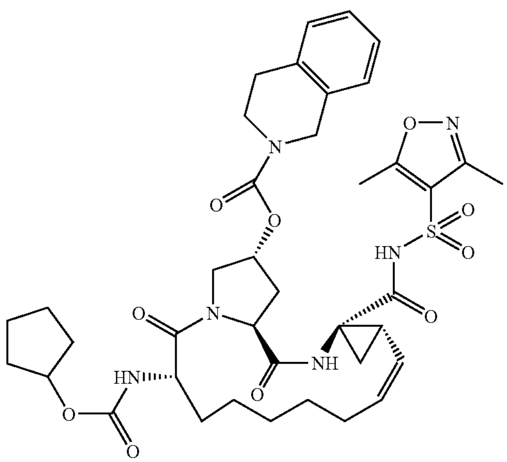 | MS m/z 793.4 (APCI−, M − 1) |
| 188 | 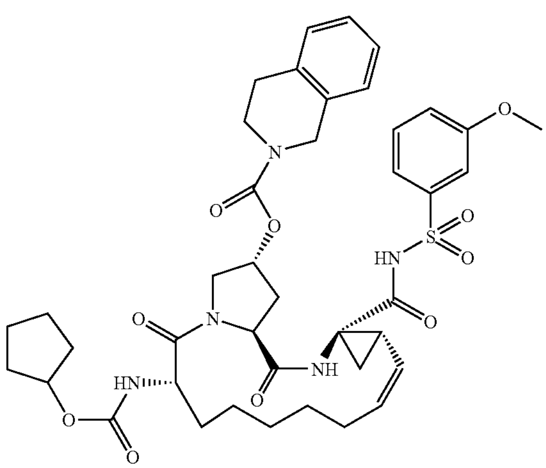 | MS m/z 804.3 (APCI−, M − 1) |

TABLE 1-continued

| Compound | Structure | ¹H-NMR/LCMS |
|---|---|---|
| 189 | 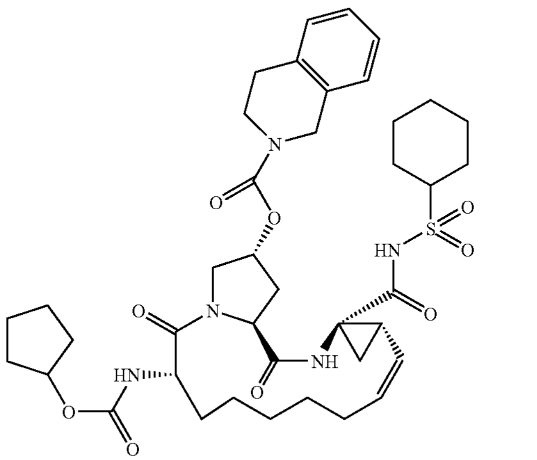 | MS m/z 781.3 (APCI−, M − 1) |
| 190 | 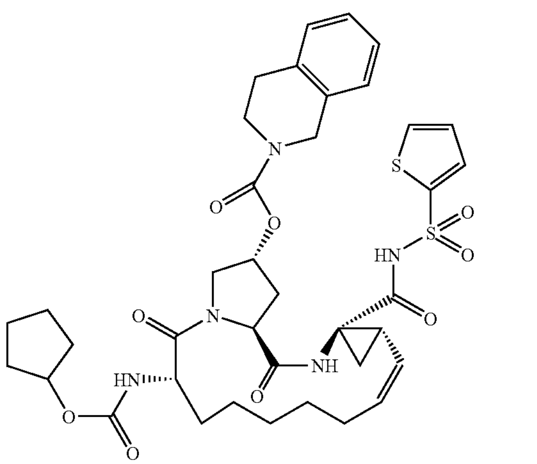 | MS m/z 780.3 (APCI−, M − 1) |
| 191 | 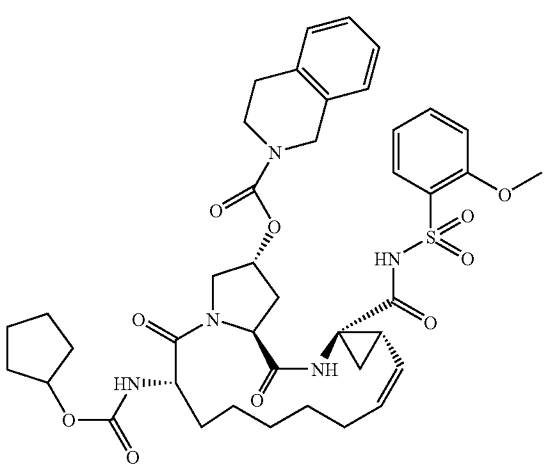 | MS m/z 804.3 (APCI+, M + 1) |

TABLE 1-continued

| Compound | Structure | ¹H-NMR/LCMS |
|---|---|---|
| 192 | 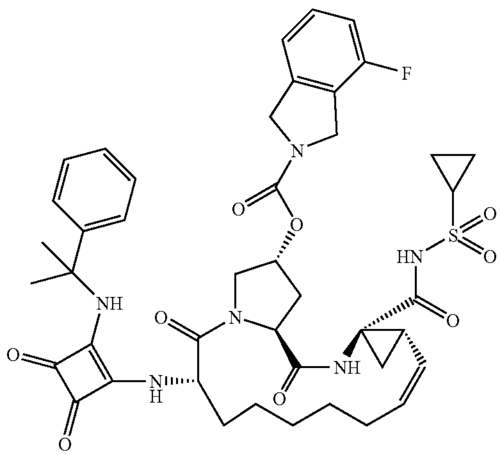 | MS m/z 843.3 (APCI+, M + 1) |
| 193 | 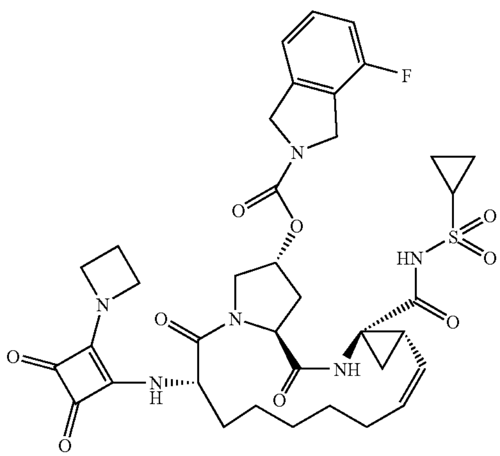 | 1H NMR (400 MHz, d⁶-acetone); 0.87-0.88 (m, 4 H), 1.10-1.59 (m 10 H), 1.75 (m, 2 H), 2.03-2.1 (m, 2 H), 2.40-2.53 (m, 3 H), 2.58-2.72 (m, 1 H), 2.87 (bs, 1 H), 3.48 (bs, 1 H), 4.42-4.49 (m, 4 H), 4.64-4.85 (m, 4 H), 4.78-4.92 (m, 2 H), 5.11-5.20 (m, 2 H), 5.47 (d, 2 H), 7.00-7.06 (m, 1 H), 7.16-7.22 (m, 1 H), 7.32-7.38 (m, 1 H). MS m/z 765.3 (APCI−, M − 1) |
| 194 | 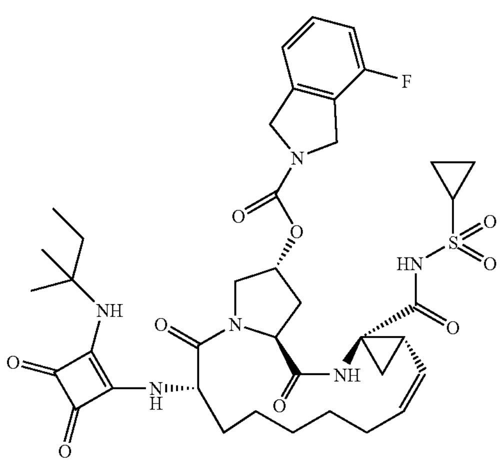 | MS m/z 795.3 (APCI−, M − 1) |

TABLE 1-continued

| Compound | Structure | ¹H-NMR/LCMS |
|---|---|---|
| 195 | 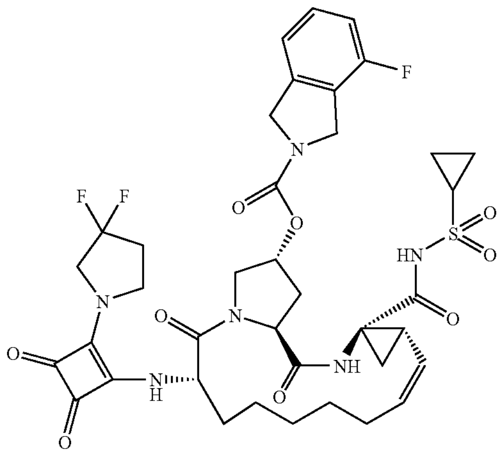 | MS m/z 795.3 (APCI−, M − 1) |
| 196 | 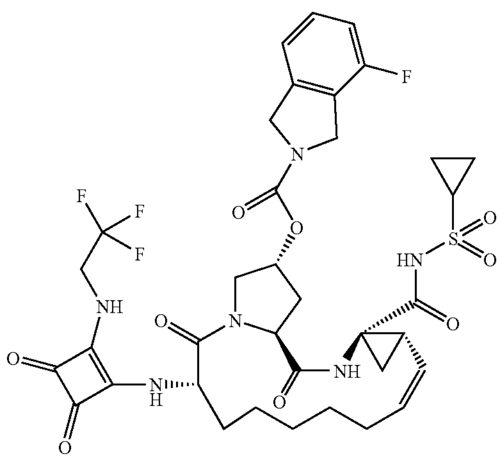 | MS m/z 807.3 (APCI−, M − 1) |
| 197 | 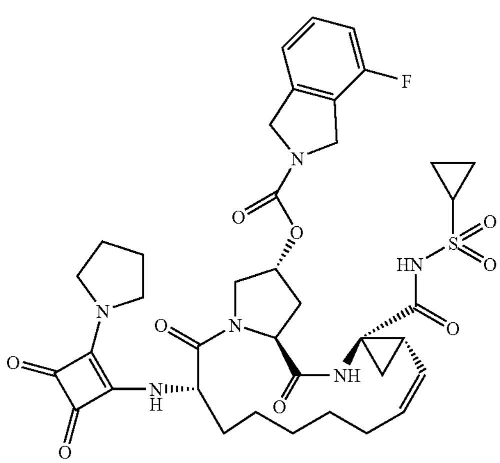 | MS m/z 779.2 (APCI−, M − 1) |

TABLE 1-continued

| Compound | Structure | ¹H-NMR/LCMS |
|---|---|---|
| 198 | 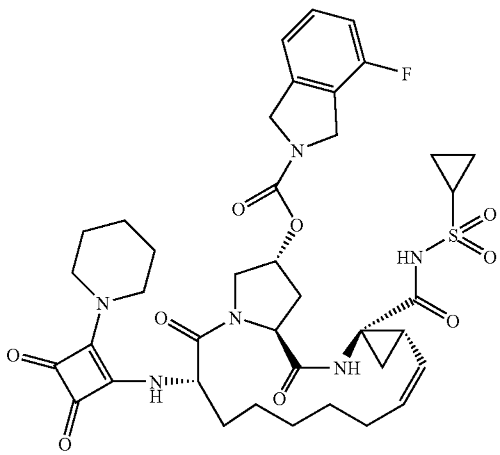 | MS m/z 793.2 (APCI−, M − 1) |
| 199 | 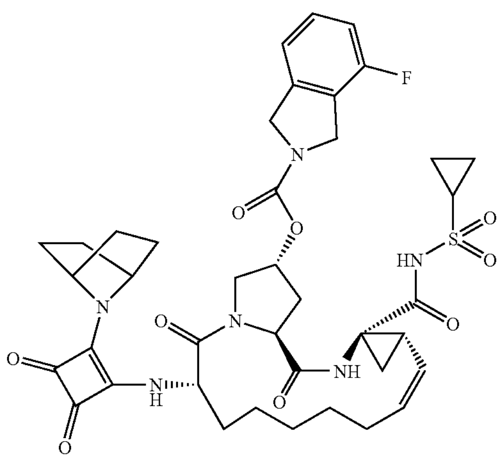 | MS m/z 805.4 (APCI−, M − 1) |
| 237 | 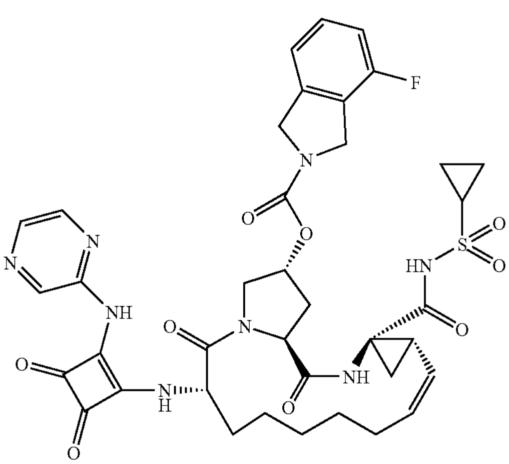 | MS m/z 827.3 (APCI−, M − 1) |

TABLE 1-continued

| Compound | Structure | ¹H-NMR/LCMS |
|---|---|---|
| 238 | 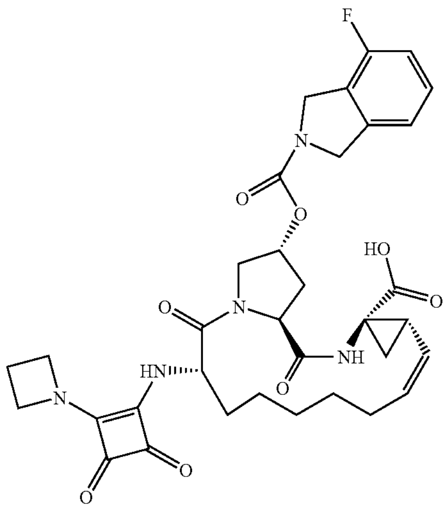 | MS m/z 662.3 (APCI−, M − 1) |
| 239 | 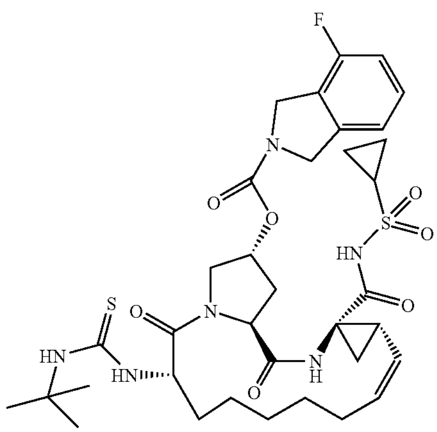 | MS m/z 745.3 (APCI−, M − 1) |
| 240 | 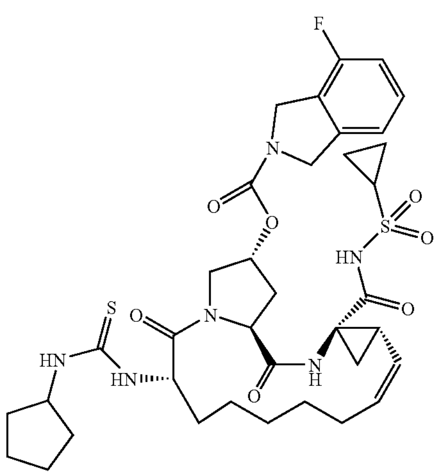 | MS m/z 757.3 (APCI−, M − 1) |

TABLE 1-continued
| Compound | Structure | ¹H-NMR/LCMS |
|---|---|---|
| 241 | 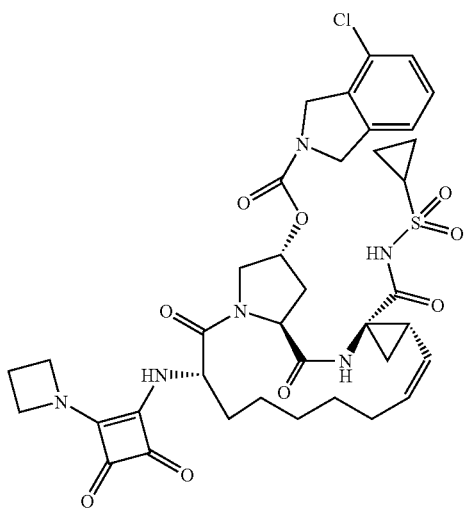 | 1H NMR (400 MHz, d6-acetone); 0.87-0.88 (m, 4 H), 1.18-1.52 (m 10 H), 1.73-1.75 (m, 2 H), 2.04-2.09 (m, 2 H), 2.44-2.54 (m, 3 H), 2.62-2.69 (m, 1 H), 2.86-2.93 (m, 1 H), 4.02 (bs, 1 H), 4.40-4.49 (m, 4 H), 4.57-4.67 (m, 4 H), 4.71-4.92 (m, 2 H), 5.10 (m, 2 H), 5.46-5.50 (d, 2 H), 7.31-7.36 (m, 3 H). MS m/z 782.2 (APCI-, M - 1) |
| 242 | 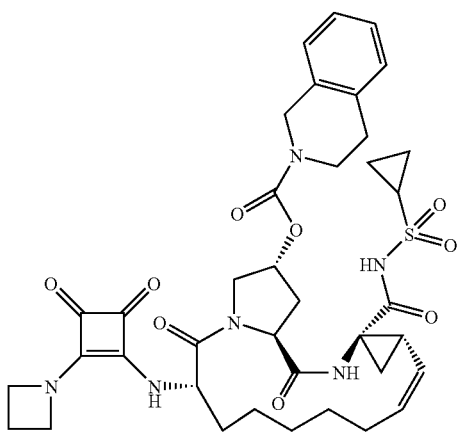 | MS m/z 761.3 (APCI-, M - 1) |
| 243 | 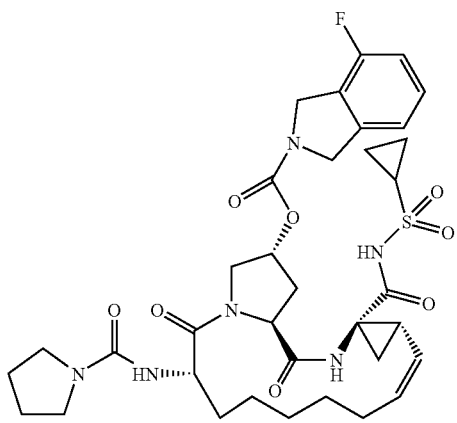 | 1H NMR (400 MHz, d⁶-acetone); 0.80-0.96 (m, 3 H), 1.10-1.18 (m 3 H), 1.29-1.51 (m 6 H), 1.72 (m, 5 H), 1.80-1.89 (m, 4 H), 2.21-2.41 (m, 2 H), 3.06-3.12 (m, 4 H), 4.03 (bs, 1 H), 3.48 (bs, 1 H), 4.15 (m, 1 H), 4.40-4.48 (m, 2 H), 4.57-4.81 (m, 6 H), 5.22-5.48 (m, 2 H), 7.01-7.05 (t, 1 H), 7.12-7.19 (m, 1 H), 7.32-7.37 (m, 1 H). MS m/z 727.4 (APCI-, M - 1) |

TABLE 1-continued

| Compound | Structure | ¹H-NMR/LCMS |
|---|---|---|
| 244 | 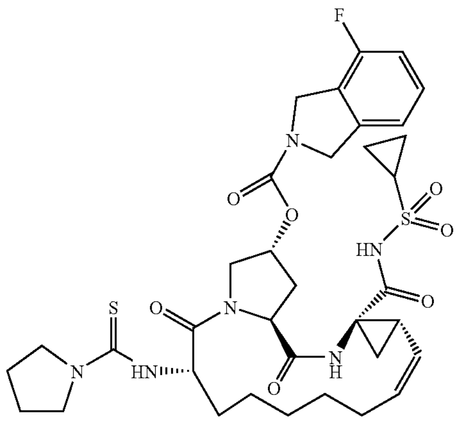 | MS m/z 743.3 (APCI−, M − 1) |
| 245 | 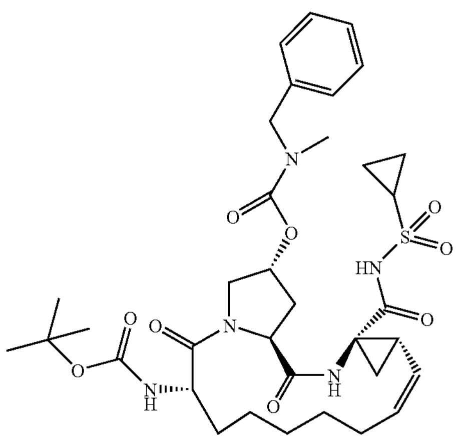 | MS m/z 714.4 (APCI−, M − 1) |
| 246 | 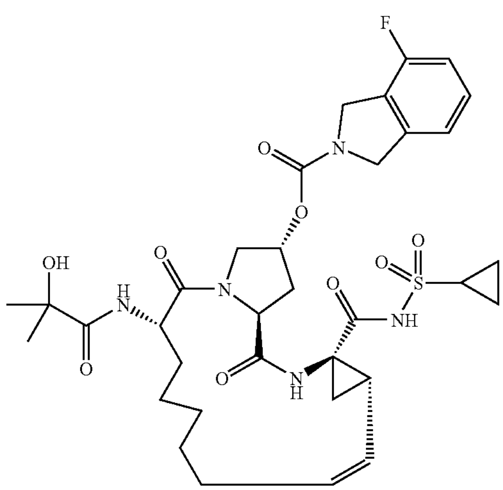 | ¹H NMR (400 MHz, d⁶-acetone) ☐ 0.97-1.62 (m, 19 H), 1.73-1.77 (m, 1 H), 1.87-1.98 (m, 2 H), 2.34-2.50 (m, 3 H), 2.56-2.68 (m, 1 H), 2.90-2.96 (m, 1 H), 3.85-3.91 (m, 1 H), 4.30-4.3 8 (m, 1 H), 4.46-4.54 (m, 2 H), 4.6 1-4.79 (m, 5 H), 5.01 (t, 1 H), 5.45 (br s, 1 H), 5.69 (q, 1 H) 7.01-7.09 (m, 1 H), 7.28-7.38 (m, 2 H), 8.36-8.38 (m, 1 H), 10.69 (br s, 1 H). MS m/z 718.1 (APCI+, M + 1) |

TABLE 1-continued
| Compound | Structure | ¹H-NMR/LCMS |
|---|---|---|
| 247 | 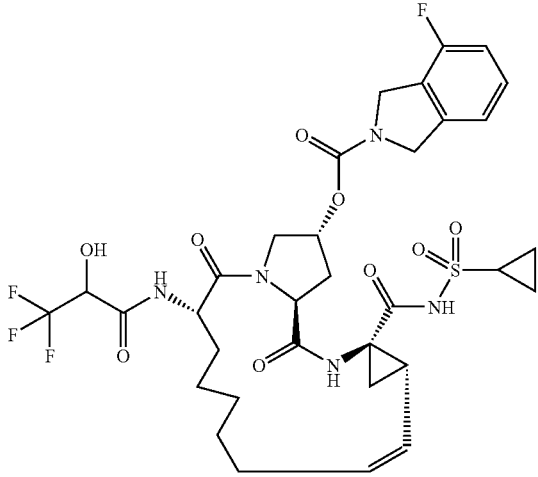 | ¹H NMR (400 MHz, d⁶-acetone) □ 0.88-1.63 (m, 13 H), 1.73-1.76 (m, 1 H), 1.91-1.99 (m, 2 H), 2.36-2.64 (m, 4 H), 2.90-2.96 (m, 1 H), 3.92-3.96 (m, 1 H), 4.37-4.40 (m, 1 H), 4.55-4.77 (m, 6 H), 5.00 (t, 1 H), 5.50 (br s, 1 H), 5.70 (q, 1 H), 7.01-7.09 (m, 1 H), 7.33-7.38 (m, 2 H), 7.48-7.52 (m, 3 H), 7.68-7.74 (m, 1 H), 8.38-8.42 (m, 1 H). MS m/z 637.1 (parent), 758.1 (APCI+, (M + 1) |
| 248 | 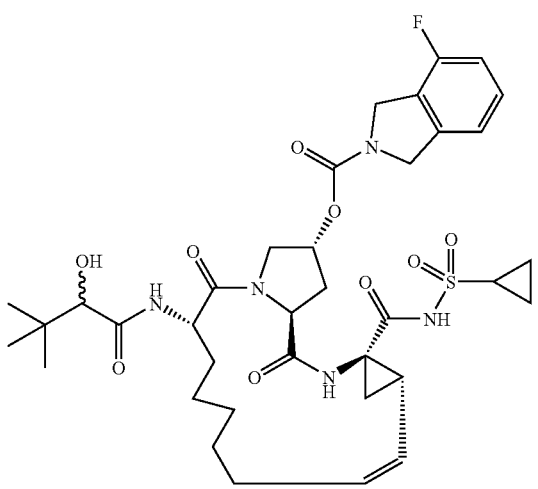 | ¹H NMR (400 MHz, d⁶-acetone) □ 0.80-1.60 (m, 21 H), 1.73-1.77 (m, 1 H), 1.86-1.96 (m, 2 H), 2.35-2.52 (m, 3 H), 2.58-2.66 (m, 1H), 2.88-2.95 (m, 1 H), 3.40 (d, 1H), 3.87-3.91 (m, 1 H), 4.41-4.78 (m, 8 H), 5.00 (t, 1 H), 5.46 (br s, 1 H), 5.70 (q, 1 H), 7.02-7.38 (m, 3 H), 8.38-8.41 (m,1H). MS m/z 746.1 (APCI+, M + 1). [Note:] Two diastereomerically pure products were isolated, but the absolute chiral sense was not assigned. |
| 249 | 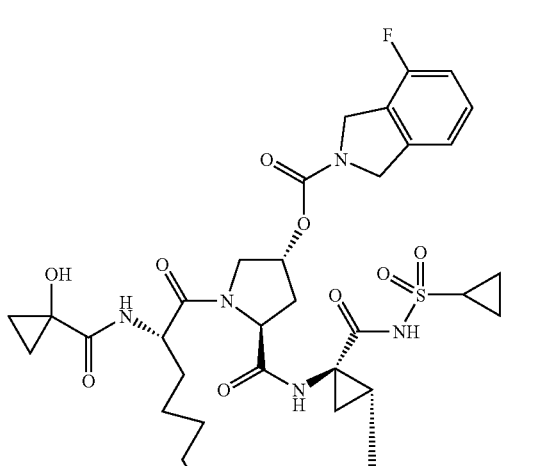 | MS m/z 716.1 (APCI+, M + 1) |

TABLE 1-continued

| Compound | Structure | ¹H-NMR/LCMS |
|---|---|---|
| 250 | 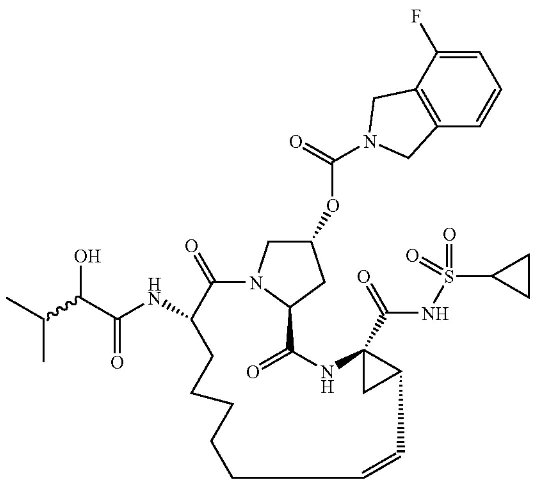 | MS m/z 732.1 (APCI+, M + 1). |
| 251 | 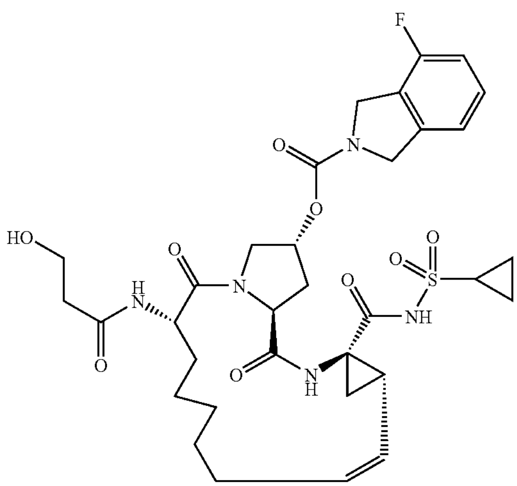 | MS m/z 704.2 (APCI+, M + 1) |
| 252 | 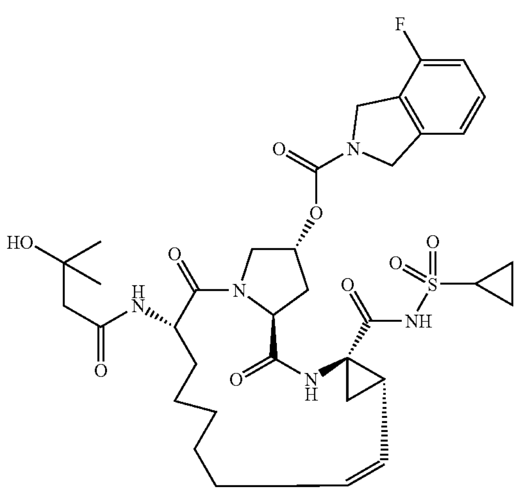 | MS m/z 732.1 (APCI+, M + 1) |

TABLE 1-continued

| Compound | Structure | ¹H-NMR/LCMS |
|---|---|---|
| 253 | 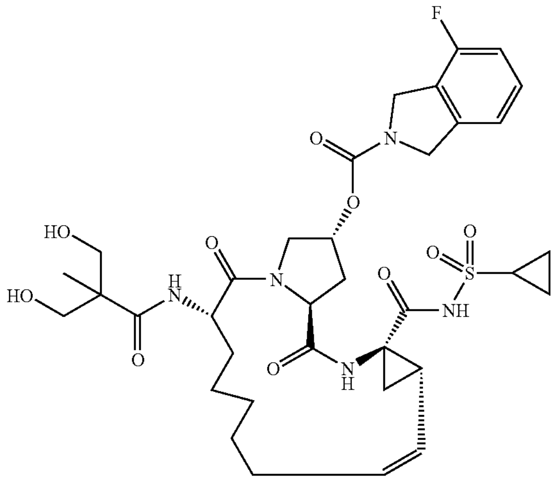 | MS m/z 748.1 (APCI+, M + 1) |
| 254 | 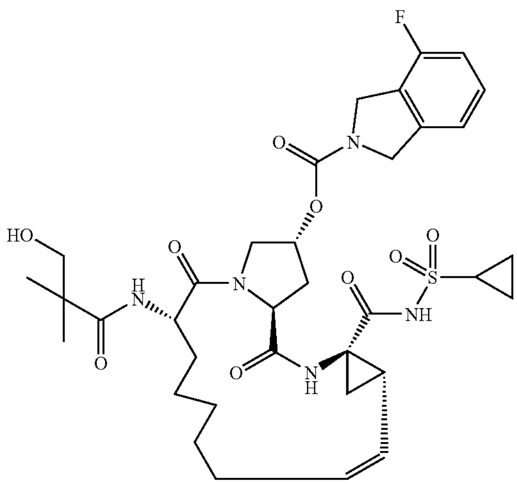 | MS m/z 732.2 (APCI+, M + 1) |
| 255 | 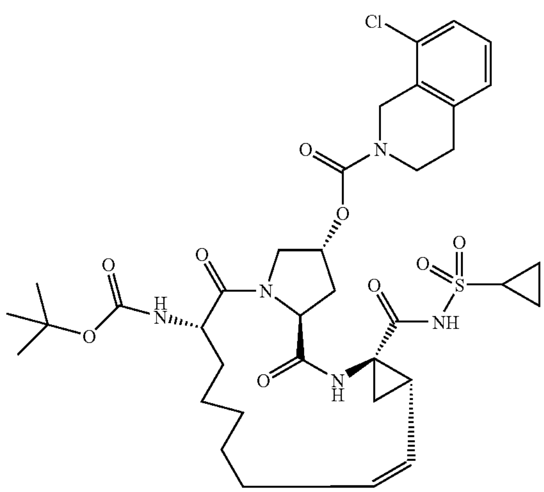 | ¹H NMR (400 MHz, d⁶-acetone) □ 0.96-1.04 (m, 2 H), 1.07-1.14 (m, 1 H), 1.18-1.59 (m, 18 H), 1.72-1.75 (m, 1 H), 1.82-1.98 (m, 2 H), 2.34-2.50 (m, 3 H), 2.58-2.66 (m, 1 H), 2.82-2.94 (m, 3 H), 3.64-3.74 (m, 2 H), 3.88-3.96 (m, 1 H), 4.18-4.22 (m, 1 H), 4.34-4.44 (m, 1 H), 4.54-4.66 (m, 3 H), 5.00 (t, 1 H), 5.45 (br s, 1 H), 5.68 (q, 1 H), 6.02-6.18 (m, 1 H), 7.16-7.29 (m, 3 H), 8.33 (br s, 1 H), 10.59 (br s, 1 H). MS m/z 760.4 (APCI−, M − 1) |

TABLE 1-continued
| Compound | Structure | ¹H-NMR/LCMS |
|---|---|---|
| 256 | 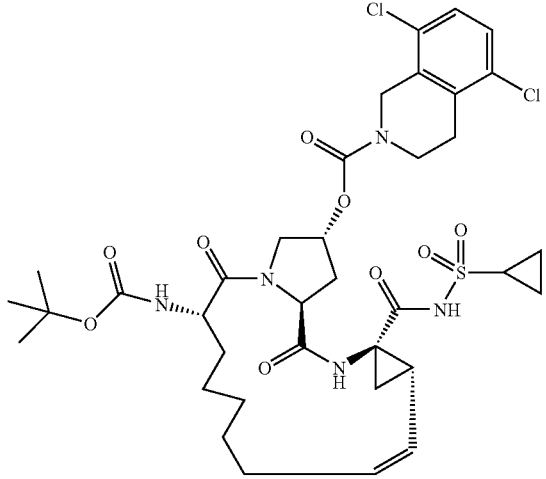 | ¹H NMR (400 MHz, d⁶-acetone) □ 0.95-1.04 (m, 2 H), 1.07-1.12 (m, 1 H), 1.14-1.60 (m, 18 H), 1.72-1.75 (m, 1 H), 1.82-1.98 (m, 2 H), 2.34-2.52 (m, 3 H), 2.58-2.65 (m, 1 H), 2.82-2.95 (m, 3 H), 3.70-3.82 (m, 2 H), 3.88-3.96 (m, f H), 4.16-4.24 (m, 1 H), 4.32-4.48 (m, 1 H), 4.57-4.64 (m, 3 H), 5.02 (t, 1 H), 5.45 (br s, 1 H), 5.68 (q, 1 H), 6.02-6.18 (m, 1 H), 7.35 (d, 2 H), 8.32 (br s, 1 H). MS m/z 794.3 (APCI-, M - 1) |
| 257 | 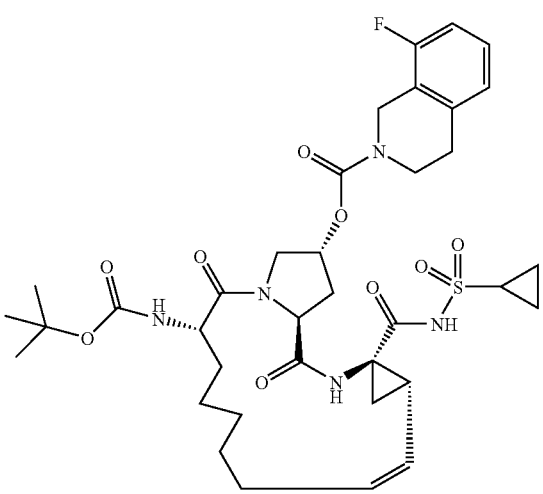 | MS m/z 744.4 (APCI-, M - 1) |
| 258 | 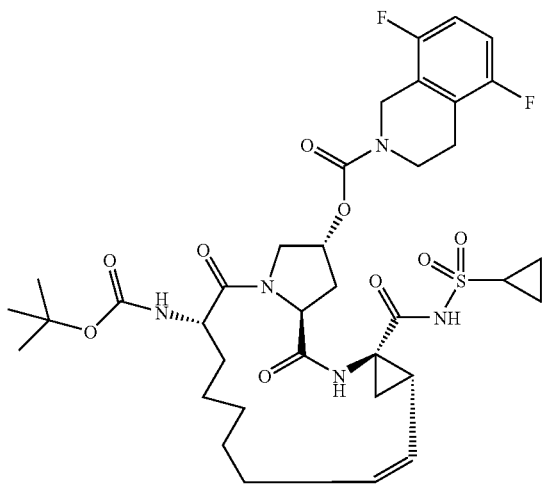 | MS m/z 762.4 (APCI-, M - 1) |

TABLE 1-continued

| Compound | Structure | ¹H-NMR/LCMS |
|---|---|---|
| 259 | 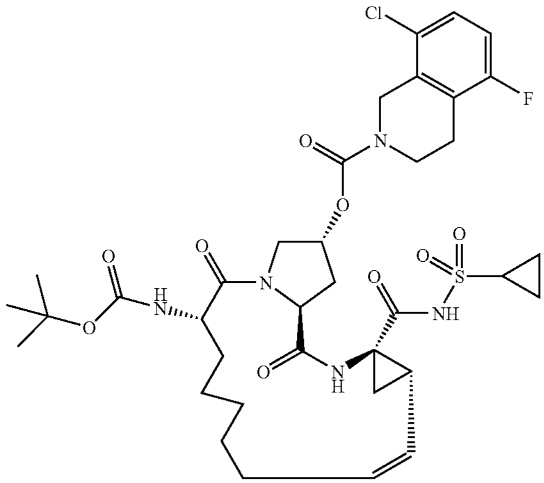 | MS m/z 778.4 (APCI−, M − 1) |
| 260 | 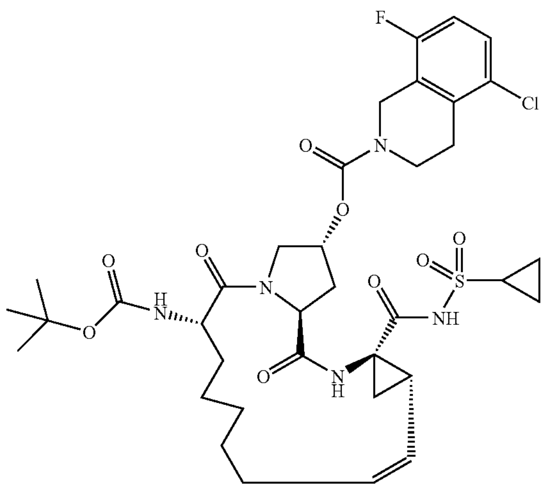 | MS m/z 778.4 (APCI−, M − 1) |
| 261 | 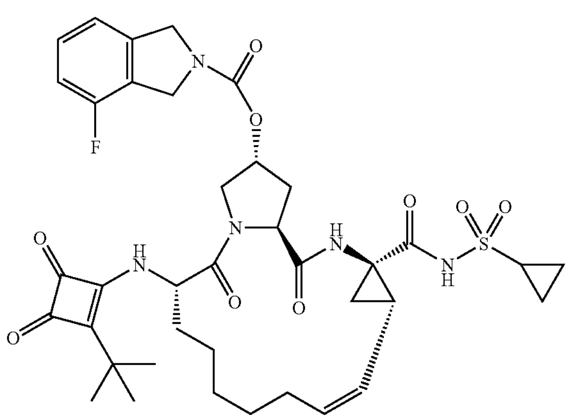 | ¹H NMR (400 MHz, CDCl₃) δ 0.92 (d, 2 H), 1.10 (d, 2 H), 1.26-1.55 (m, 7 H), 1.34 (s, 9 H), 1.76-2.09 (m, 4 H), 2.17-2.28 (m, 1 H), 2.31-2.45 (m, 1 H), 2.45-2.57 (m, 2 H), 2.85-2.95 (m, 1 H), 3.94 (dd, 1 H), 4.11 (dd, 1 H), 4.58-4.67 (m, 3 H), 4.76 (s, 2 H), 4.96 (t, 1 H), 5.09 (t, 1 H), 5.52 (s, 1 H), 5.71 (q, 1 H), 6.21 (dd, 1 H), 6.91-7.17 (m, 3 H), 7.27 (s, 1 H), 10.9 (d, 1 H); MS m/z 766.4 (ESI−, M − 1) |

TABLE 1-continued

| Compound | Structure | ¹H-NMR/LCMS |
|---|---|---|
| 262 | 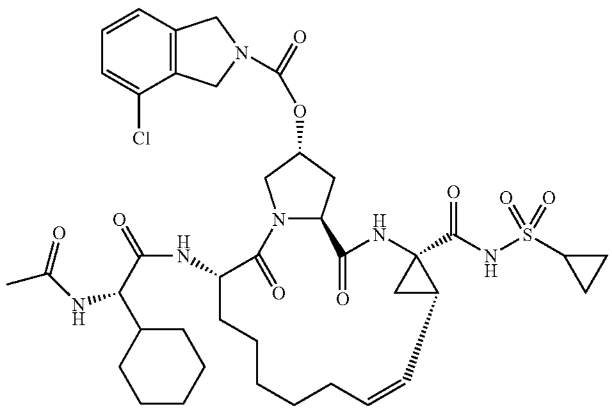 | MS m/z 827.3 (APCI−, M − 1) |
| 263 | 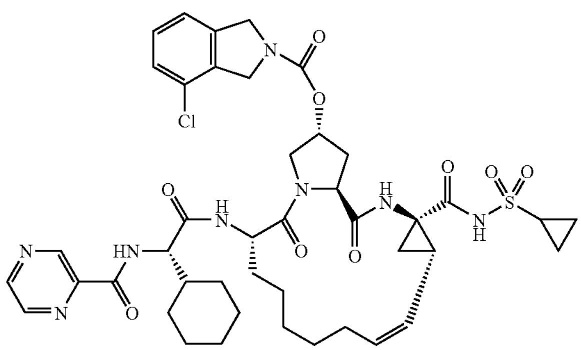 | MS m/z 892.2 (APCI−, M − 1) |
| 264 | 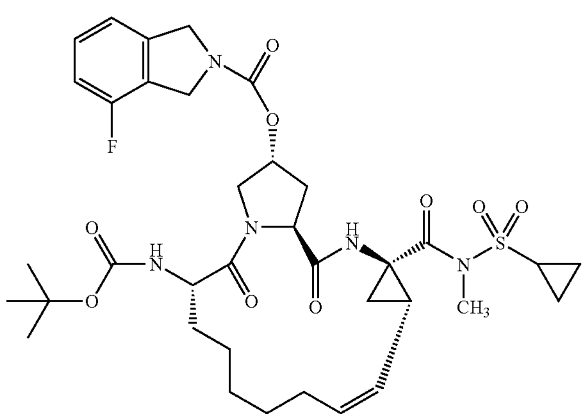 | ¹H NMR (400 MHz, CDCl₃) 1.01-1.57 (m, 10 H), 1.33 (s, 9 H), 1.68 (s, 1 H), 1.86 (dd, 1 H), 1.88-2.03 (m, 2 H), 2.04-2.19 (m, 1 H), 2.19-2.36 (m, 2 H), 2.47 (dd, 2 H), 2.59-2.71 (m, 1 H), 3.20 (s, 3 H), 3.95 (dd, 1 H), 4.05 (d, 1 H), 4.53 (br s, 1 H), 4.61-4.74 (m, 3 H), 4.77 (d, 2H), 5.12 (t, 1 H), 5.34 (d, 1 H), 5.40 (s, 1 H), 5.56 (q, 1 H), 6.90-7.32 (m, 3 H), 7.38 (s, 1 H); MS m/z 745.9 (APCI+, M + 1) |

TABLE 1-continued

| Compound | Structure | ¹H-NMR/LCMS |
|---|---|---|
| 265 | 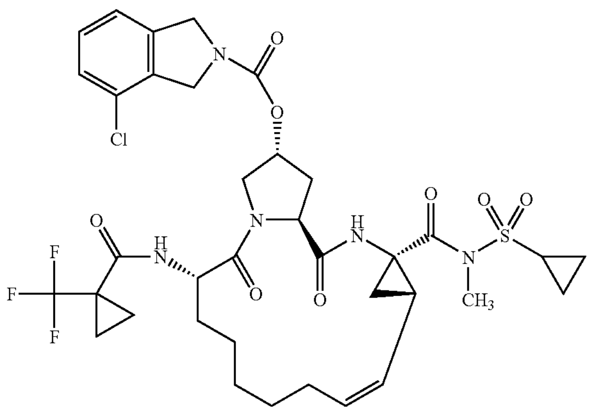 | MS m/z 782.4 (ESI−, M − 1) |
| 266 | 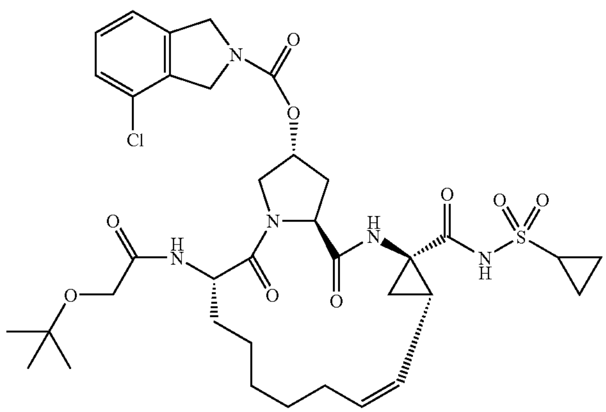 | MS m/z 760.5 (ESI−, M − 1) |
| 267 | 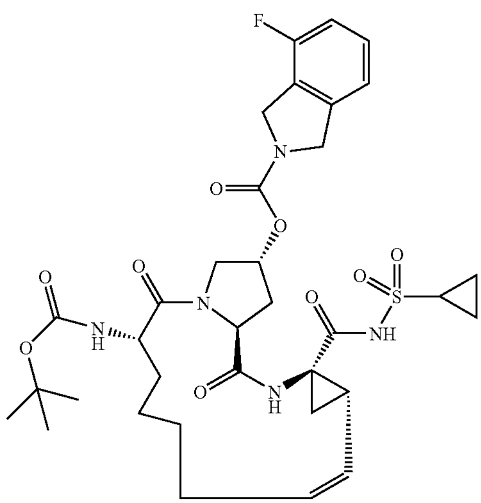 | ¹H NMR (400 MHz, d⁶-DMSO) d 12.23 (s, 1H), 9.02 (d, J=10.4 Hz, 1H), 7.32 (m, 1H), 7.06-7.17 (m, 3H), 5.51 (m, 1H), 5.27 (m, 2H), 4.46 (s, 4H), 4.43 (m, 1H), 4.21 (m, 1H), 3.97 (m, 1H), 3.72 (m, 1H), 2.93 (m 1H), 2.21 (m, 4H), 1.94 (m, 1H), 1.75 (m, 1H), 1.58 (m, 1H), 1.49 (m, 1H), 0.99-1.31 (m, 18 H). MS m/z 718.0 (APCI+, M + 1) |

TABLE 1-continued

| Compound | Structure | ¹H-NMR/LCMS |
|---|---|---|
| 268 | 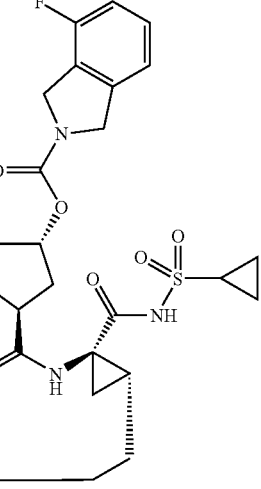 | ¹H NMR (400 MHz, d⁶-Acetone) d 10.82 (s, 1H), 8.38 (s, 1H), 7.39 (m, 1H), 6.99-7.06 (m, 2H), 6.00 (d, 1H), 5.42 (m, 1H), 4.66 (s, 4H), 4.64 (m, 1H), 4.38 (m, 1H), 4.24 (m, 1H), 3.85 (m, 1H), 2.98 (m, 1H), 2.50 (m, 1H), 2.28 (m, 1H), 1.84 (m, 2H), 1.02-1.62 (m, 27 H). MS m/z 734.1 (APCI+, M + 1) |
| 269 | 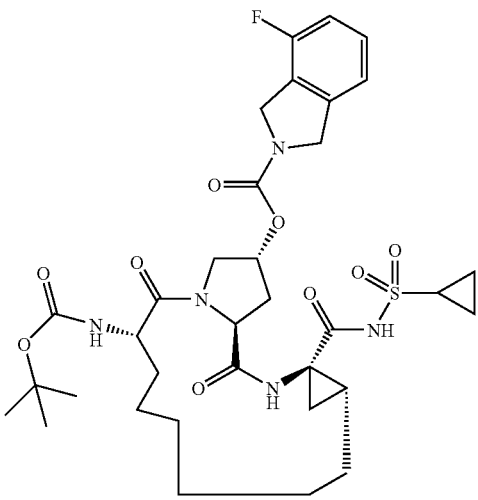 | ¹H NMR (400 MHz, CD₂Cl₂) d 10.85 (s, 1H), 7.21 (m, 1H), 6.86-6.99 (m, 2H), 6.64 (m, 1H), 5.36 (b, 1H), 4.96 (m, 1H), 4.64 (s, 2H), 4.59 (s, 2H), 4.47 (m, 1H), 4.36 (m, 1H), 4.11 (m, 1H), 3.78 (m, 1H), 2.85 (m, 1H), 2.36 (m, 2H), 0.90-1.79 (m, 27 H) MS m/z 720.1 (APCI+, M + 1) |

Preparation of NS3 Inhibitors

Section II

A general synthetic scheme of the NS3 inhibitors in this section is shown in Scheme 3 below:

Scheme 3

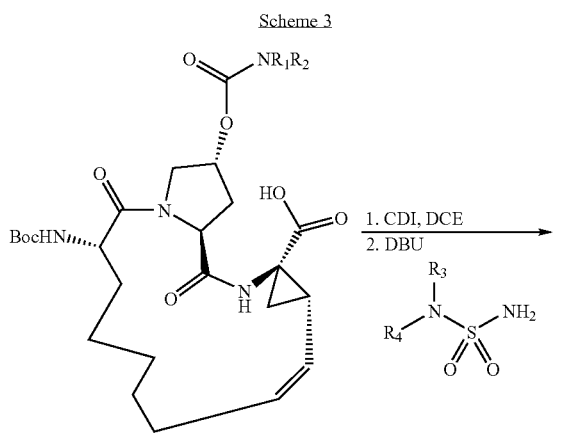

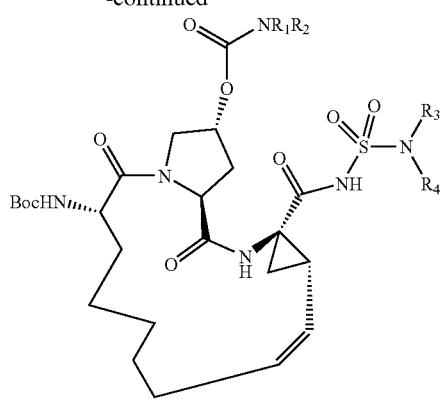

The final acylsulfamide coupling procedures are very similar to those described in the acylsulfonamide coupling step (e.g. Step 6, Compound 100 synthesis) in Section I. The following NS3 inhibitors were prepared by this fashion. The P4 de-protected amino compounds (e.g. Compounds 202 and 203) were prepared by removal of the Boc protective group in 4 M HCl solution in 1,4-dioxane.

TABLE 2

| Compound | Structure | ¹H-NMR/LCMS |
|---|---|---|
| 200 | 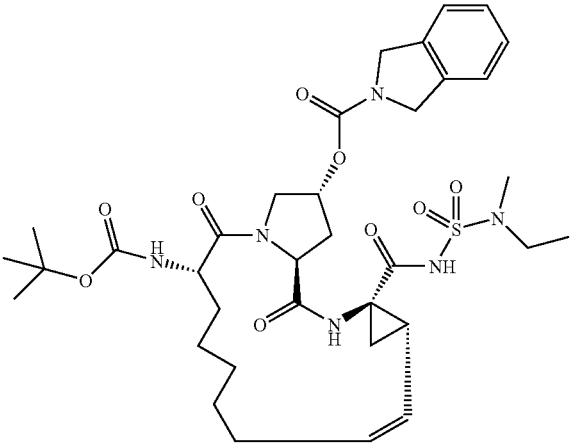 | ¹H NMR (400 MHz, d⁶-acetone) δ 1.12-1.58 (m, 20 H), 1.69-1.72 (m, 1 H), 1.80-1.91 (m, 2 H), 2.36-2.49 (m, 3 H), 2.61-2.71 (m, 1 H), 2.89 (s, 3 H), 3.10-3.19 (m, 1 H), 3.28-3.38 (m, 1 H), 3.84-3.88 (m, 1 H), 4.14-4.18 (m, 1 H), 4.46 (br d, 1 H), 4.58-4.72 (m, 5 H), 5.02 (t, 1 H), 5.44 (s, 1 H), 5.68 (q, 1 H), 6.09 (d, 1 H), 7.23-7.36 (m, 4 H), 8.23 (s, 1 H). MS m/z 729.3 (APCI-, M − 1) |
| 201 | 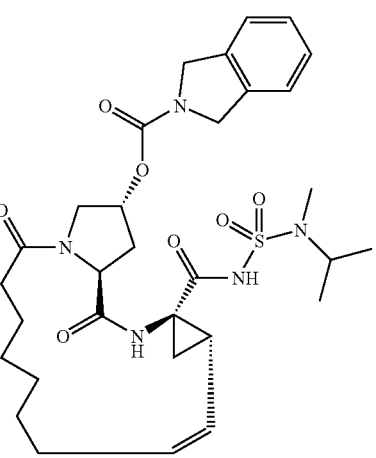 | ¹H NMR (400 MHz, d⁶-acetone) δ 1.12-1.57 (m, 23 H), 1.67-1.71 (m, 1 H), 1.81-1.89 (m, 2 H), 2.40-2.49 (m, 3 H), 2.63-2.69 (m, 1 H), 2.77 (s, 3 H), 3.84-3.87 (m, 1 H), 4.10-4.17 (m, 2 H), 4.47 (br d, 1 H), 4.57-4.72 (m, 5 H), 5.05 (t, 1 H), 5.44 (s, 1 H), 5.63 (q, 1 H), 6.09 (d, 1 H), 7.23-7.36 (m, 4 H), 8.20 (br s, 1 H). MS m/z 743.4 (APCI-, M − 1). |
| 202 | 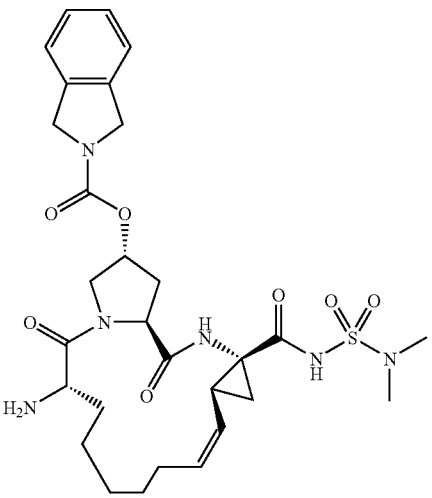 | 617.1 (M+, APCI+) |

TABLE 2-continued
| Compound | Structure | ¹H-NMR/LCMS |
|---|---|---|
| 203 | 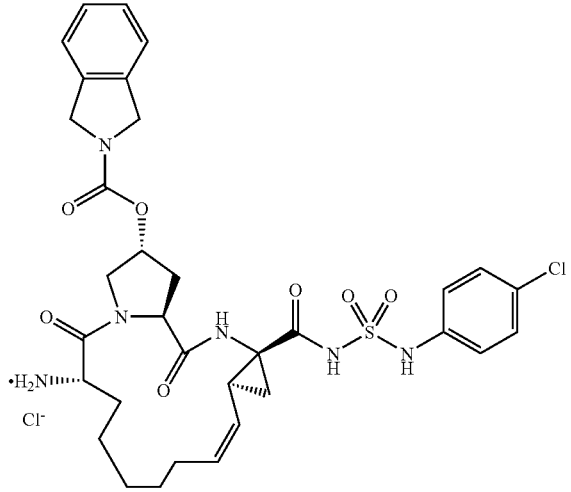 | 698.2 (M − 1, APCI−) |
| 204 | 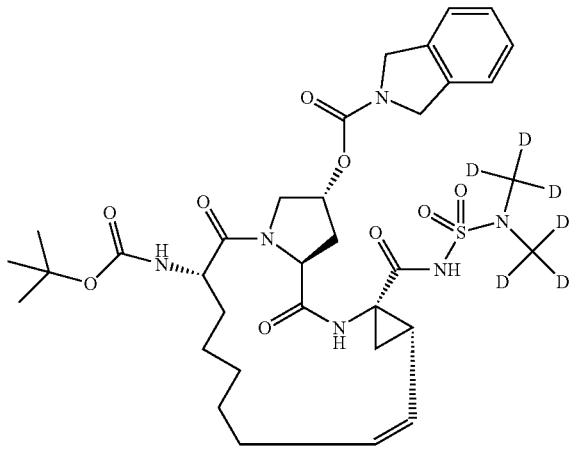 | HNMR (d⁶-acetone): 10.43 (s, 1 H), 8.27 (s, 1 H), 7.23-7.36 (m, 4 H), 6.11 (br d, 1 H), 5.69-5.75 (m, 1 H), 5.44 (br s, 1 H), 5.02 (t, 1 H) 4.58-4.72 (m, 5 H), 4.48 (br d, 1 H), 4.13-4.16 (m, 1 H), 3.83-3.87 (m, 1 H), 2.62-2.72 (m, 1 H), 2.35≧2.49 (m, 3 H), 1.83-1.90 (m, 2 H), 1.70-1.74 (m, 1 H), 1.20-1.58 (m, 17 H). LCMS (APCI+, 623.2, MH-Boc) |
| 205 | 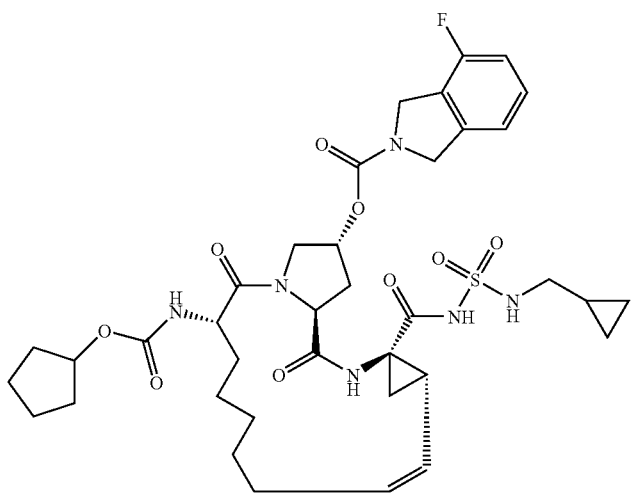 | MS m/z 772 (APCI−, M) |

TABLE 2-continued

| Compound | Structure | ¹H-NMR/LCMS |
|---|---|---|
| 206 | 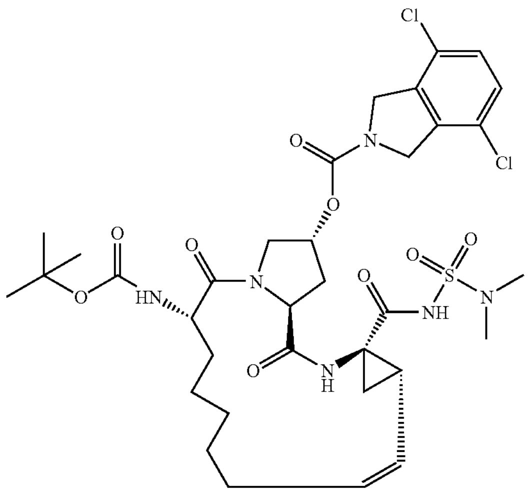 | MS m/z 783 (APCI−, M − 1) |
| 207 | 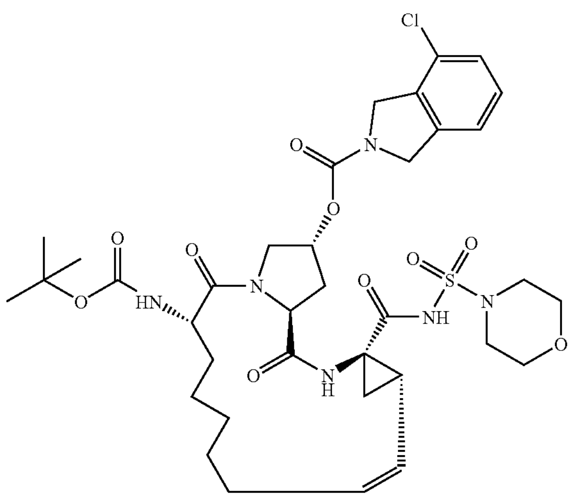 | MS m/z 693 (APCI+, M-Boc) |
| 208 | 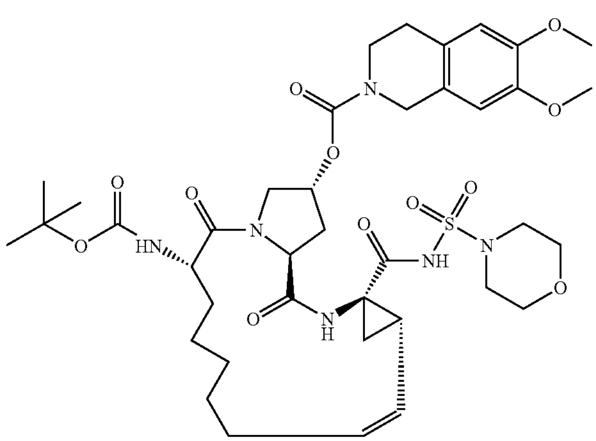 | MS m/z 733 (APCI+, M-Boc + 1) |

TABLE 2-continued

| Compound | Structure | ¹H-NMR/LCMS |
|---|---|---|
| 209 | 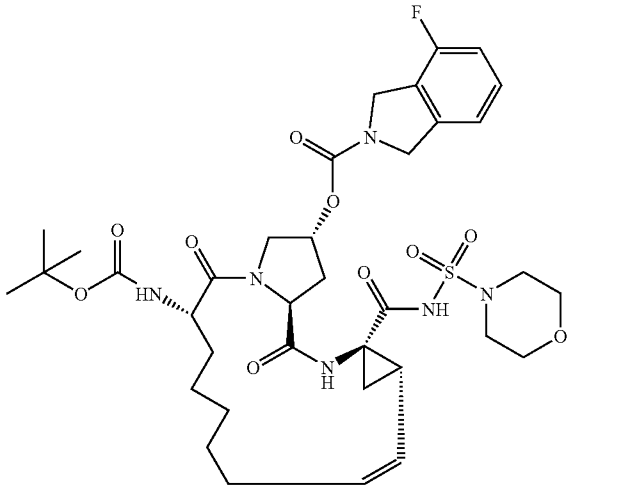 | MS m/z 677 (APCI+, M-Boc + 1) |
| 210 | 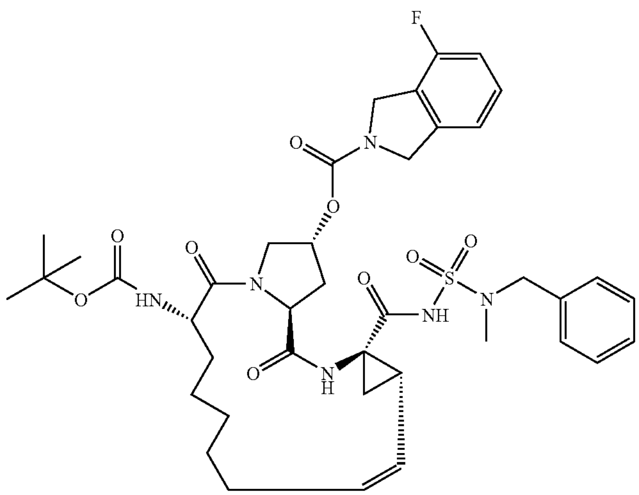 | MS m/z 711 (APCI+, M-Boc + 1) |
| 211 | 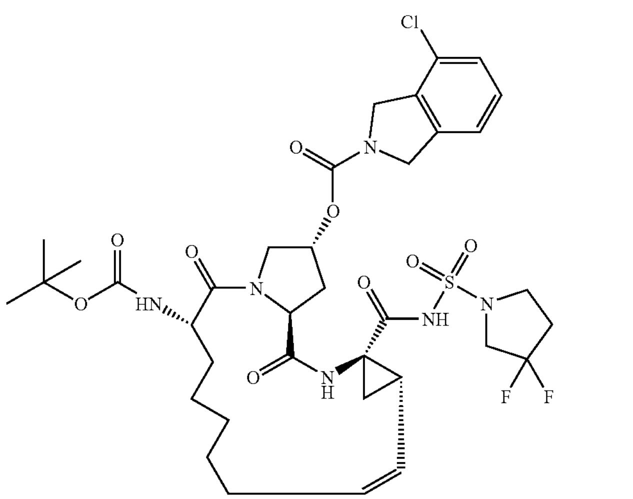 | MS m/z 713 (APCI+, M-Boc) |

TABLE 2-continued
| Compound | Structure | ¹H-NMR/LCMS |
|---|---|---|
| 212 | 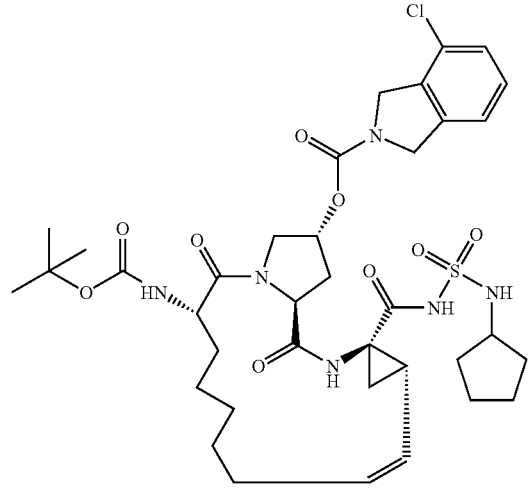 | MS m/z 691 (APCI+, M-Boc) |
| 213 | 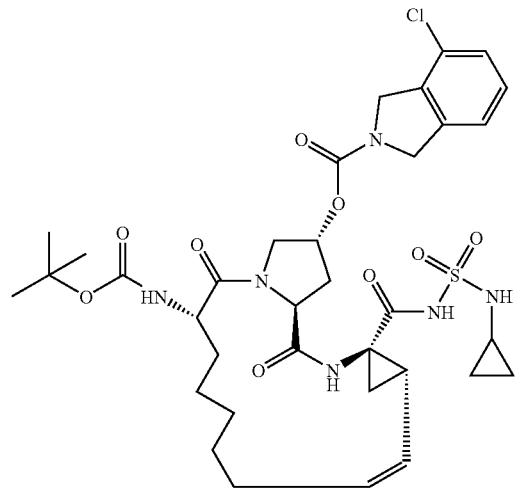 | MS m/z 663 (APCI+, M-Boc) |
| 214 | 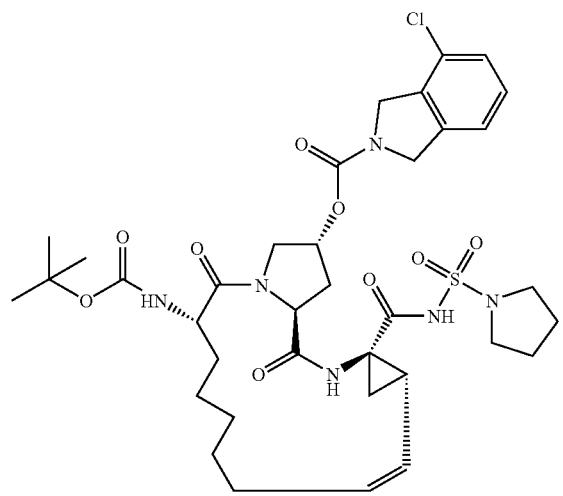 | MS m/z 677 (APCI+, M-Boc) |

TABLE 2-continued

| Compound | Structure | ¹H-NMR/LCMS |
|---|---|---|
| 215 | 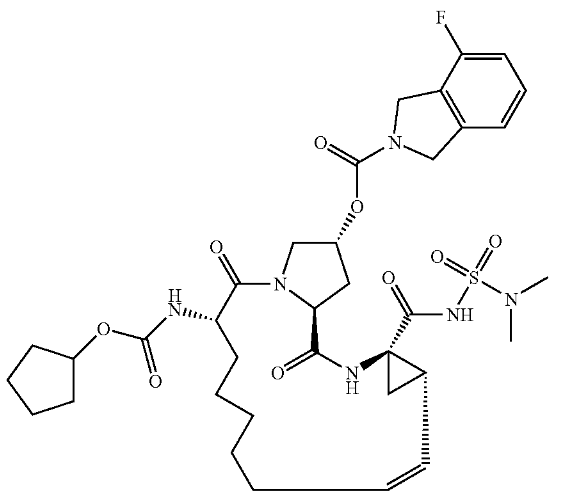 | MS m/z 747 (APCI+, M + 1) |
| 216 | 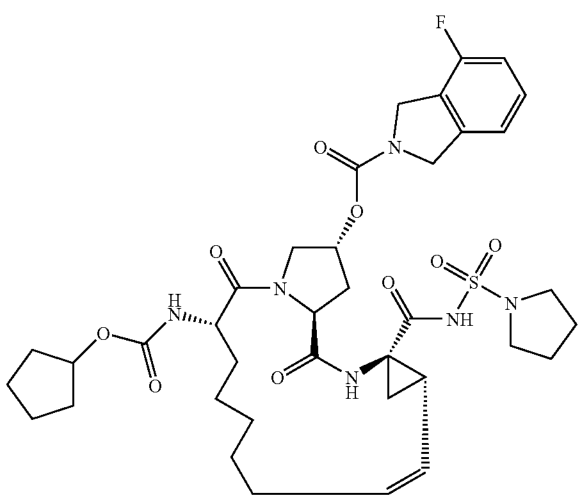 | MS m/z 773 (APCI+, M + 1) |
| 217 | 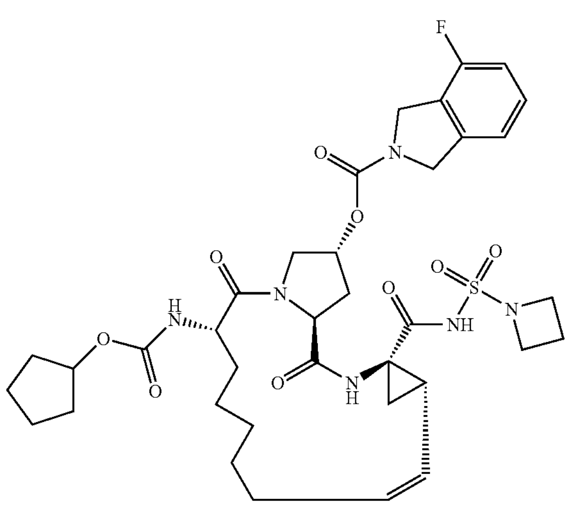 | MS m/z 759 (APCI+, M + 1) |

TABLE 2-continued

| Compound | Structure | ¹H-NMR/LCMS |
|---|---|---|
| 218 | 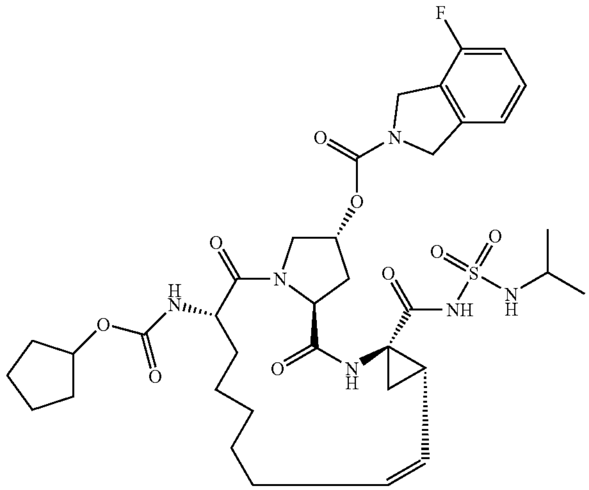 | MS m/z 760 (APCI−, M) |
| 219 | 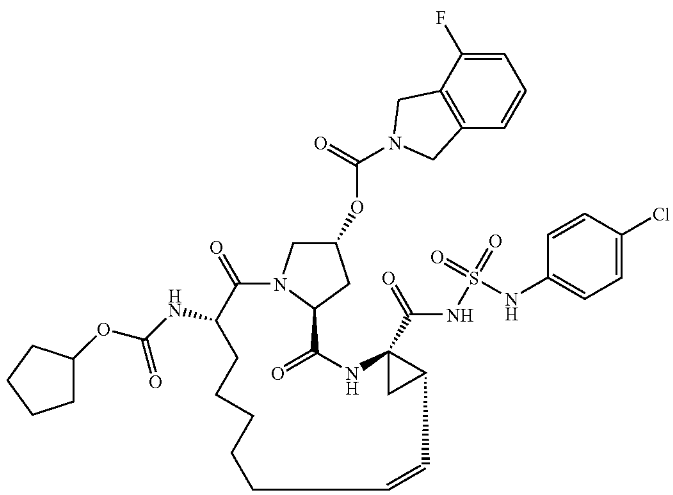 | MS m/z 828 (APCI−, M − 1) |
| 220 | 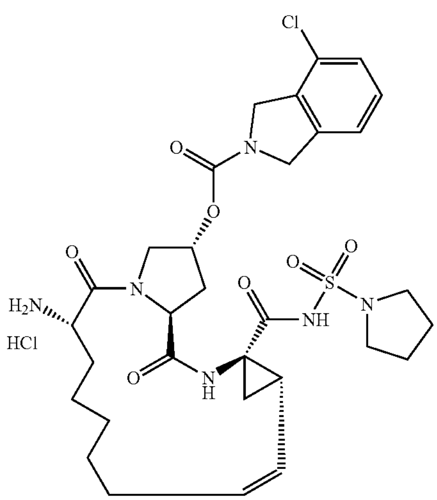 | MS m/z 677 (APCI+, M+) |

TABLE 2-continued

| Compound | Structure | ¹H-NMR/LCMS |
|---|---|---|
| 221 | 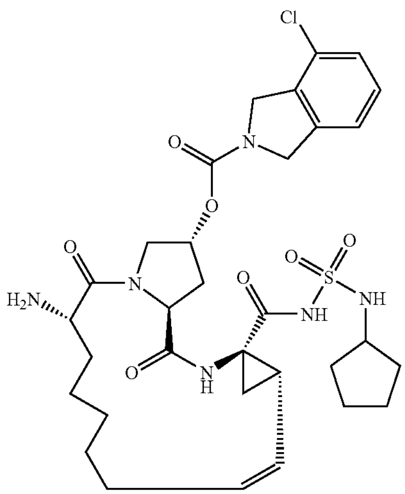 | MS m/z 691 (APCI+, M+) |
| 222 | 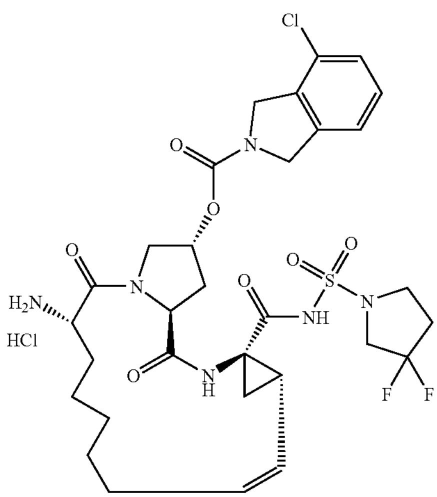 | MS m/z 713 (APCI+, M+) |
| 223 | 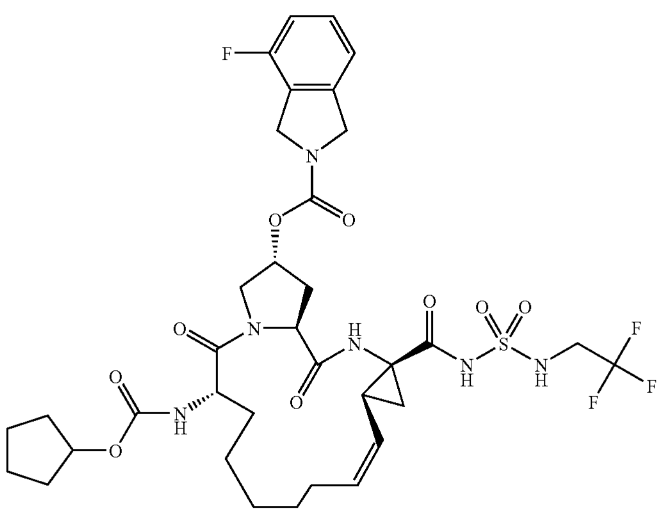 | ¹H NMR (400 MHz, DMSO) □ 1.04-1.76 (m, 19 H), 2.14-2.43 (m, 3 H), 2.57-2.70 (m, 1 H), 3.57-3.72 (m, 3 H), 3.90-3.98 (m, 1 H), 4.15-4.49 (m, 3 H), 4.59-4.78 (m, 4 H), 5.04-5.18 (m, 1 H), 5.29 (s, 1 H), 5.51-5.65 (m, 1 H), 7.05-7.25 (m, 2 H), 7.34 (br s, 2 H), 8.75-8.92 (m, 2 H), 11.10 (s, 1 H). MS m/z 800.2 (APCI−, M − 1) |

TABLE 2-continued

| Compound | Structure | ¹H-NMR/LCMS |
|---|---|---|
| 224 | 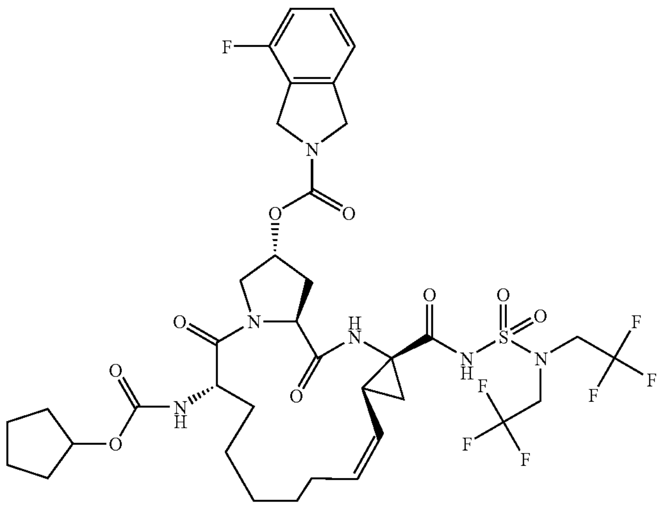 | MS m/z 881.3 (APCI−, M − 1) |
| 225 | 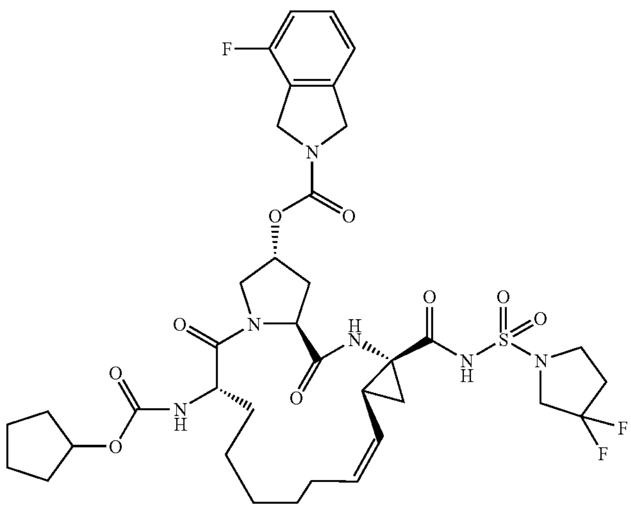 | ¹H NMR (400 MHz, DMSO) d 0.97-1.81 (m, 19 H), 2.13-2.66 (m, 6 H), 3.49-3.89 (m, 4 H), 3.90-4.05 (br s, 1 H), 4.16-4.56 (m, 4 H), 4.58-4.78 (m, 4 H), 4.99-5.21 (m, 1 H), 5.28 (br s, 1 H), 5.46-5.65 (m, 1 H), 7.05-7.44 (m, 4 H), 8.98 (br s, 1 H), 11.14 (br s, 1 H). MS m/z 808.2 (APCI−, M − 1) |
| 226 | 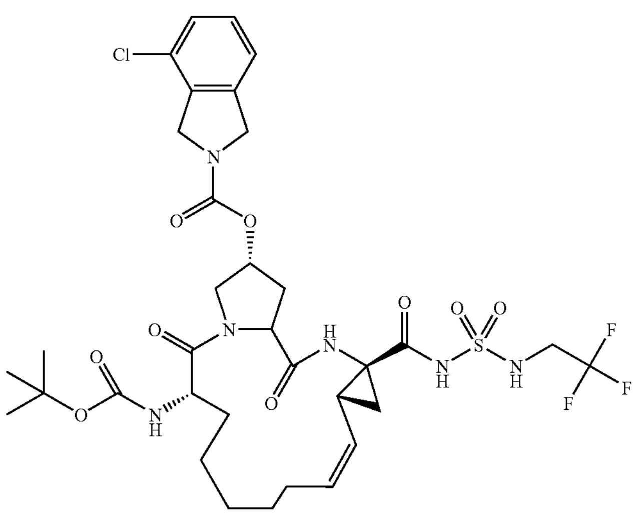 | MS m/z 803.3 (APCI−, M − 1) |

TABLE 2-continued

| Compound | Structure | 1H-NMR/LCMS |
|---|---|---|
| 227 | 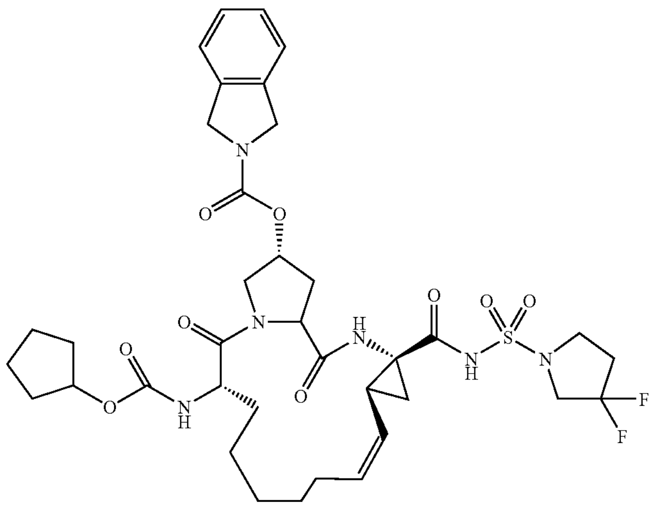 | MS m/z 789.3 (APCI–, M – 1) |
| 228 | 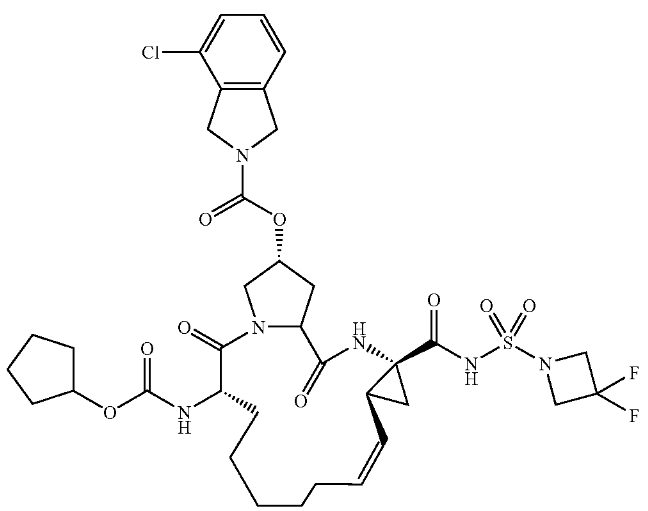 | 1H NMR (400 MHz, DMSO) □ 1.06-1.49 (m, 15 H), 1.56-1.78 (m, 4 H), 2.19-2.45 (m, 3 H), 2.55-2.70 (m, 1 H), 3.62-3.73 (m, 1 H), 3.90-4.01 (m, 1 H), 4.09-4.20 (m, 1 H), 4.24-4.42 (m, 3 H), 4.43-4.79 (m, 7 H), 5.04-5.14 (m, 1 H), 5.29 (d, 1 H), 5.49-5.66 (m, 1 H), 7.24-7.48 (m, 4 H), 9.03 (d, 1 H), 11.34 (s, 1 H). MS m/z 809.3 (APCI–, M – 1) |
| 229 | 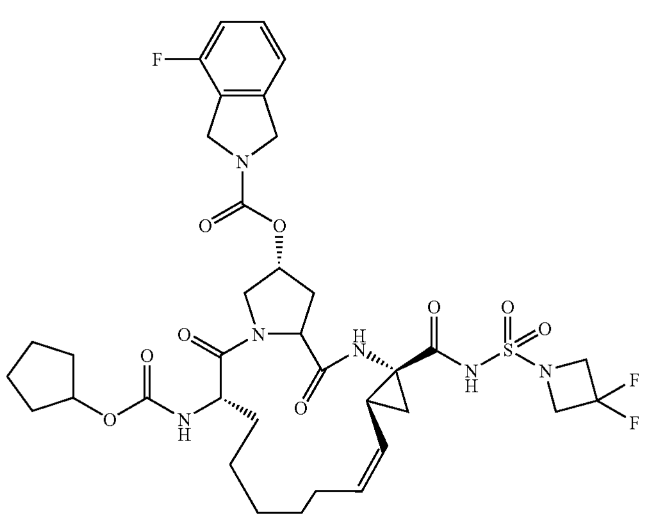 | MS m/z 793.3 (APCI–, M – 1) |

TABLE 2-continued

| Compound | Structure | ¹H-NMR/LCMS |
|---|---|---|
| 230 | 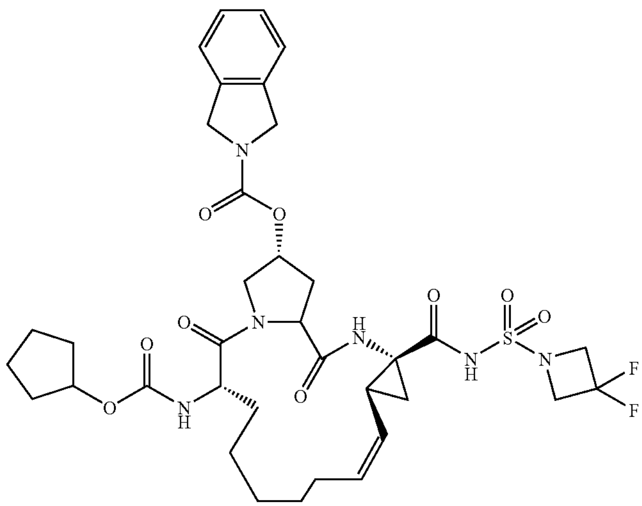 | ¹H NMR (400 MHz, DMSO) 0.79-0.88 (m, 1 H), 1.06-2.03 (m, 18 H), 2.15-2.41 (m, 3 H), 3.17 (d, 2 H), 3.67-3.77 (m, 1 H), 3.94-4.47 (m, 8 H), 4.62 (p, 5 H), 5.26 (br s, 1 H), 7.24-7.38 (m, 5 H), 8.14 (br s, 1 H), 11.35 (br s, 1 H). MS m/z 776.3 (APCI−, M − 1) |
| 231 | 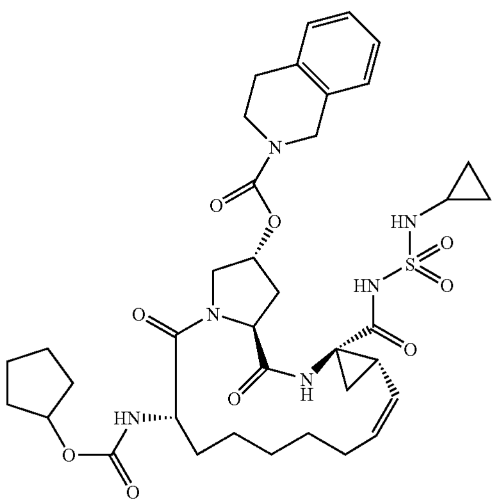 | MS m/z 753.3 (APCI−, M − 1) |
| 232 | 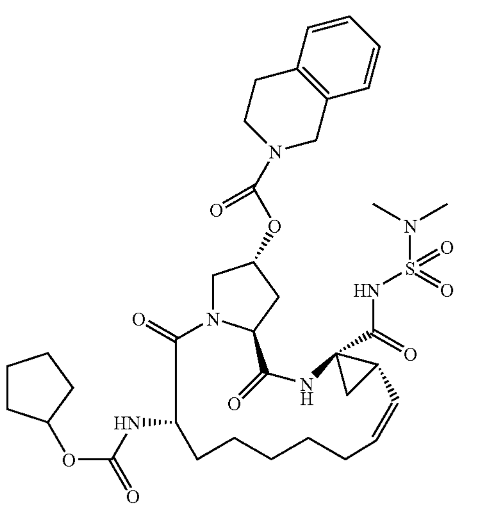 | MS m/z 767.5 (APCI−, M − 1) |

TABLE 2-continued

| Compound | Structure | ¹H-NMR/LCMS |
|---|---|---|
| 233 | 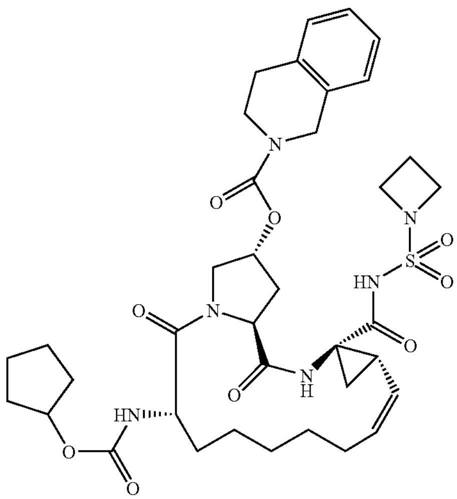 | MS m/z 753.3 (APCI−, M − 1) |
| 234 | 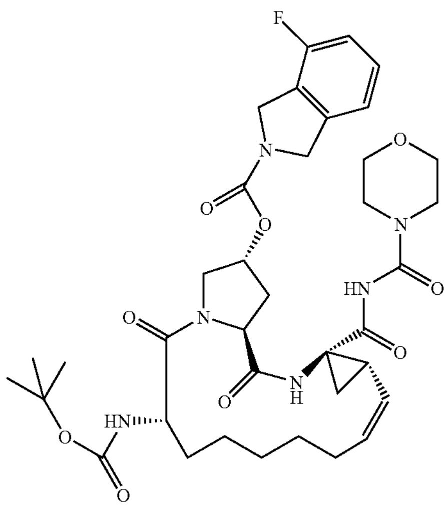 | MS m/z 739.2 (APCI−, M − 1) |
| 235 | 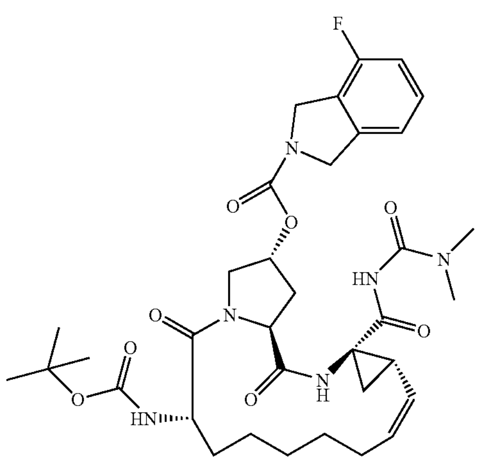 | MS m/z 697.2 (APCI−, M − 1) |

TABLE 2-continued
| Compound | Structure | $^1$H-NMR/LCMS |
|---|---|---|
| 236 | 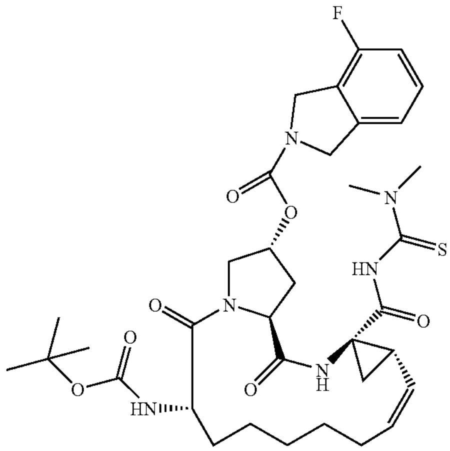 | MS m/z 713.3 (APCI−, M − 1) |
Preparation of NS3 Inhibitors
Section III
The NS3 inhibitors described in this section were prepared in a manner similar to that described for Compound 300 below (Scheme 4), substituting cyclopropanesulfonamide with other appropriate sulfonamides in Step E instead.
Synthesis of Compound 300:
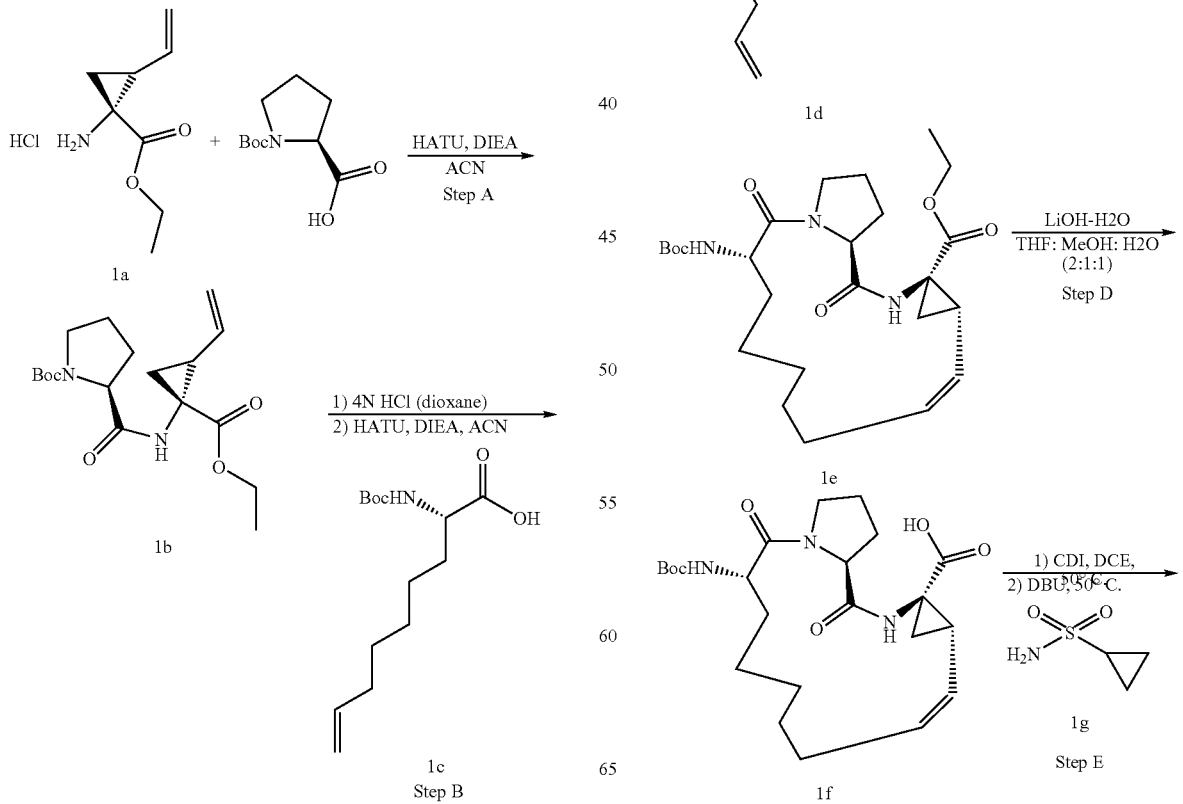
Scheme 4

-continued

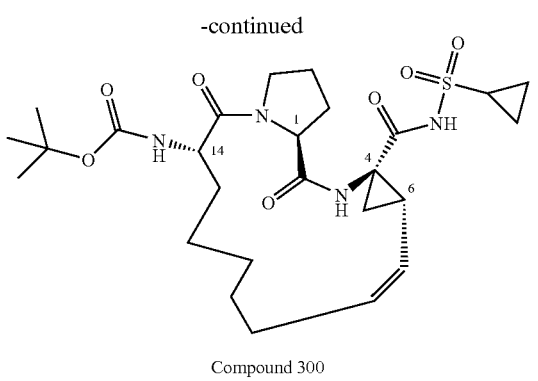

Compound 300

D. Step A: Synthesis of (S)-tert-butyl 2-(((1R,2S)-1-(ethoxycarbonyl)-2-vinylcyclopropyl)carbamoyl)pyrrolidine-1-carboxylate (1b)

(S)-1-(tert-butoxycarbonyl)pyrrolidine-2-carboxylic acid (0.87 g, 4.0 mmol), (1R,2S)-ethyl 1-amino-2-vinylcyclopropanecarboxylate hydrochloride salt (0.67 g, 3.5 mmol), and HATU (1.53 g, 4.0 mmol) were dissolved in acetonitrile (50 mL) and cooled to 0° C. DIEA (5.74 mL, 17.5 mmol) in acetonitrile (50 mL) was added drop-wise. The resulted mixture was allowed to warm to room temperature. The resulted mixture was stirred at room temperature for 10 h, concentrated, mixed with EtOAc, washed with aqueous saturated NaHCO$_3$, and concentrated. The residue was purified by silica gel chromatography (10% EtOAc in hexanes, 30% EtOAc in hexanes, and then 50% EtOAc in hexanes) to give product as pale yellow oil (1.19 g, 96%). MS (ESI+): 375 [M+23] (5) and 253 [M+1−100] (100).

Step B: Synthesis of (1R,2S)-ethyl 1-((S)-1-((S)-2-(tert-butoxycarbonyl)non-8-enoyl)pyrrolidine-5-carboxamido)-2-vinylcyclopropanecarboxylate (1d)

The dipeptide 1b from Step A (1.19 g, 3.38 mmol) was dissolved in HCl in dioxane (4.0 M, 13 mL, 51 mmol) and stirred at rt for 90 min to remove the Boc protective group. It was then concentrated down, taken up in acetonitrile and concentrated down again twice. This light brownish residue, 2(S)-tert-butoxycarbonylamino-non-8-enoic acid (0.95 g, 3.3 mmol) and HATU (1.4 g, 3.6 mmol) were dissolved in acetonitrile and cooled to 0° C. DIEA in acetonitrile was added drop-wise. The resulted mixture was allowed to warm to room temperature and stirred at room temperature for 10 h. The resulted mixture was concentrated, mixed with EtOAc, washed with aqueous saturated sodium bicarbonate, dried with Na$_2$SO$_4$, and concentrated. The residue was purified by silica gel chromatography (10% EtOAc and then 30% EtOAc) to give product 1d as pale yellowish oil (1.5 g, 90%). MS (ESI+): 528 [M+23] (5) and 406 [M+1−100] (100).

Step C: Synthesis of (1S,4R,6S,14S)14-tert-Butoxy-carbonylamino-2,15-dioxo-3,16-diaza-tricyclo[14.3.0.0$^{4,6}$]nonadec-7-ene-4-carboxylic acid ethyl ester (1e)

The product from Step B (1d, 0.61 g, 1.2 mmol) was dissolved in 1,2-dichloroethane (120 mL), then degassed and filled with nitrogen gas (1 atm). Hoveyda 1$^{st}$ generation catalyst (0.036 g, 0.060 mmol) was added. The resulted mixture was further degassed and filled with nitrogen gas (1 atm), heated at 50° C. for 16 h, and concentrated. The residue was purified by silica gel chromatography (30% EtOAc in hexanes, 50% EtOAc in hexanes, and then 60% EtOAc in hexanes) to give product 1e as pale yellowish solid (0.44 g, 76%). MS (ESI+): 478 [M+1] (5) and 378 [M+1−100] (100).

Step D: Synthesis of (1S,4R,6S,14S)14-tert-Butoxy-carbonylamino-2,15-dioxo-3,16-diaza-tricyclo[14.3.0.0$^{4,6}$]nonadec-7-ene-4-carboxylic acid (1f)

The macrocyclic ester 1e from Step C (1.0 g, 2.1 mmol) was first dissolved in THF (3.0 mL), then methanol (3.0 mL) and water (1.5 mL) were added, followed by addition of LiOH—H$_2$O (3 equiv). The resulted mixture was stirred for 4 h and concentrated to dryness. The residue was first re-dissolved in water (10 mL), then acidified with aqueous HCl (3.0 N, 2.2 mL, 6.6 mmol). The aqueous was extracted with EtOAc (3×15 mL). The combined organic layers was dried with sodium sulfate and concentrated to give the acid product 1f (0.93 g, 99%). MS (ESI+): 450 [M+1] (5) and 350 [M+1−100] (100).

Step E: Synthesis of (1S,4R,6S,14S) tert-butyl 4-Cyclopropanesulfonylaminocarbonyl-2,15-dioxo-3,16-diaza-tricyclo[14.3.0.0$^{4,6}$]nonadec-7-ene-14-yl carbamate (Compound 300)

The macrocyclic acid product 1f from Step D (0.983 g, 2.19 mmol) was dissolved in DriSolve® 1,2-dichloroethane (15 mL). Carbonyldiimidazole (0.479 g, 2.95 mmol) was then added. The resulted mixture was stirred at 50° C. for 2 h. The reaction was cooled down to rt, and cyclopropanesulfonamide (0.358 g, 2.95 mmol) was added, followed by addition of DBU (0.406 mL, 2.95 mmol). The reaction mixture was again heated at 50° C. and stirred for 1 h. LCMS showed reaction complete. It was cooled to room temperature, and dichloromethane (15 mL) was added. The resulted mixture was washed with aqueous hydrochloric acid (0.5 N, 5 mL) and water. The organic layer was separated, dried with sodium sulfate, and concentrated. The residue was purified by silica gel chromatography (40% EtOAc in hexanes, 60% EtOAc in hexanes, 80% EtOAc in hexanes, and then 100% EtOAc) to give the desired product as a white solid (Compound 300, 1.05 g, 87%). $^1$H NMR (d$^6$-Acetone, 400 MHz) δ 0.96-1.02 (m, 2H), 1.08-1.13 (m, 1H), 1.18-1.54 (m, 18H), 1.69-1.73 (m, 1H), 1.83-2.05 (m, 3H), 2.19-2.23 (m, 2H), 2.39-2.47 (m, 2H), 2.81-2.92 (m, 2H), 3.64-3.70 (m, 1H), 4.01-4.06 (m, 1H), 4.33-4.42 (m, 2H), 4.97 (t, 1H), 5.64-5.71 (m, 1H), 5.98 (br d, 1H), 8.36 (br s, 1H), 10.70 (br s, 1H). MS (APCI+): 453.1 (MH$^+$-Boc).

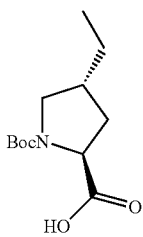

(2S,4R)-1-(tert-butoxycarbonyl)-4-ethylpyrrolidine-2-carboxylic acid was synthesized according to the following scheme:

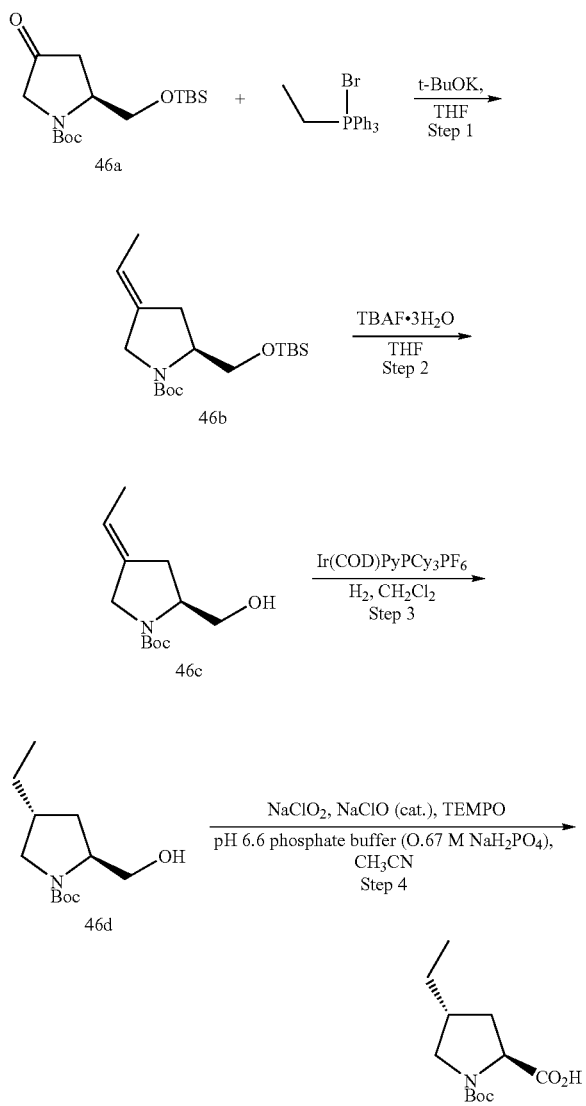

Step 1: Ethylltriphenyl phosphonium bromide (8.17 g, 22 mmol) in THF (25 ml) was added 1 M solution of potassium t-butoxide in THF (22 ml) at room temperature. After 1 h stirring, it was added a solution of the ketone 46a (2.9 g, 8.8 mmol), which was prepared according to a literature procedure from (2S,4R)-1-(tert-butoxycarbonyl)-4-hydroxypyrrolidine-2-carboxylic acid (*J. Org. Chem.* 2003, 68, 3923-3931), in THF (5 ml) and stirred for 3 h. TLC (15% EtOAc-Hexane) showed complete conversion. The reaction mixture quenched with ice-cold water (75 ml) and extracted with diethylether (2×50 ml). The combined organic layers were dried ($Na_2SO_4$), concentrated and purified by column chromatography (10%, 20% EtOAc/Hexane) to give 46b as a light yellowish liquid, 2.85 g (95%). MS (APCI+): m/z 130.1 (M-Boc+1).

Step 2: To a solution of the silyl ether 46b (3 g, 8.78 mmol) in THF (60 ml) was added solid $TBAF \cdot 3H_2O$ (5.54 g, 17.57 mmol) and stirred for 16 h. Reaction mixture concentrated and purified by column chromatography (25, 40% EtOAc-Hexane) to give 46c, 1.98 g (98%). MS (APCI+): m/z 128.1 (M-Boc+1).

Step 3: The alcohol 46c (1.98 g, 8.71 mmol) in $CH_2Cl_2$ (174 ml, 0.2 M) was treated with $Ir(COD)PyPCy_3PF_6$ (Crabtree catalyst) (0.21 g, 0.26 mmol) for 24 h under $H_2$. Reaction mixture concentrated to remove solvent and purified by column chromatography (40% EtOAc-Hexane) to give 46d as an orange oil, 1.94 g (97%). $^1H$ NMR (400 MHz, $CDCl_3$): 4.40 (br s, 1H), 4.05 (m, 1H), 3.65-3.56 (m, 2H), 3.55-3.48 (dd, 1H), 3.02-2.90 (t, 1H), 2.30-2.04 (m, 1H), 1.72-1.60 (m, 2H), 1.46 (s, 9H), 1.80-1.60 (m, 2H), 0.96 (t, 3H). MS (APCI+): m/z 130.1 (M-Boc+1).

Step 4: Two oxidant solutions were prepared prior to carrying out the reaction. The first one consisted of $NaClO_2$ (0.99 g, 8.72 mmol) in 4 ml of water (~2M). The second one comprised of 0.26 ml of bleach (NaOCl) diluted with 4 ml of water. The alcohol 46d (1 g, 4.36 mmol) was dissolved in 3:2 (30 ml: 20 ml) mixture of $CH_3CN:NaH_2PO_4$ buffer (pH 6.6, 0.67 M) and warmed to 45° C. The reaction mixture was treated with TEMPO (0.07 g, 0.44 mmol) followed by the drop wise, simultaneous addition (over 1 h) of the 2-oxidant solutions. After stirring for 15 h at 45° C., the reaction mixture was cooled to room temperature and a sat. $Na_2SO_3$ solution was added drop wise until the reaction mixture became color less. Reaction mixture was concentrated to remove $CH_3CN$ in vacuo and the resulting mixture basified to pH>10 with 1 M NaOH and washed twice with diethyl ether. The solution was carefully acidified with 1 M HCl at 0° C. to pH<3 and extracted with EtOAc (2×20 ml). The combined organic layers were dried ($Na_2SO_4$) and concentrated to give the final desired product, 1 g (99%). MS (APCI-): m/z 242.1 (M-1).

The NS3 inhibitors in Table 3 were prepared in a manner similar to that described for Compound 300 above, substituting cyclopropanesulfonamide with other appropriate sulfonamides in Step E (Scheme 4), or substituting (S)-1-(tert-butoxycarbonyl)pyrrolidine-2-carboxylic acid with (2S,4R)-1-(tert-butoxycarbonyl)-4-ethylpyrrolidine-2-carboxylic acid in Step A (Scheme 4) instead. The sulfonamides used were either purchased from commercial sources or prepared by bubbling anhydrous ammonia gas through a THF solution of the corresponding sulfonyl chlorides at −10° C., followed by filtration to remove the inorganic salt and concentration to yield the clean product, which was generally used directly in the following step without further purification.

TABLE 3

| Compound | Structure | ¹H NMR/LCMS (m/z) |
|---|---|---|
| 300 | 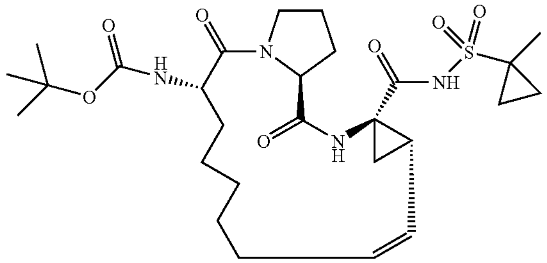 | ¹H NMR (d⁶-Acetone, 400 MHz) δ 0.84-0.89 (m, 3 H), 1.18-1.64 (m, 22 H), 1.68-1.72 (m, 1 H), 1.81-1.86 (m, 1 H), 1.94-2.00 (m, 2 H), 2.21-2.26 (m, 2 H), 2.40-2.47 (m, 2 H), 3.65-3.71 (m, 1 H), 4.00-4.06 (m, 1 H), 4.33-4.42 (m, 2 H), 4.96 (t, 1 H), 5.62-5.70 (m, 1 H), 5.97 (br d, 1 H), 8.39 (br s, 1 H). 565.5 (APCI−, M − 1) |
| 301 | 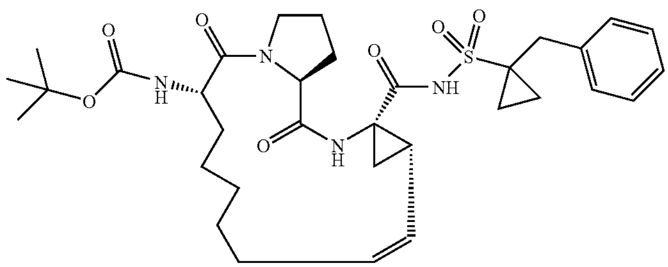 | ¹H NMR (d⁶-Acetone, 400 MHz) δ 0.59-0.67 (m, 2 H), 0.85-0.89 (m, 1 H), 1.14-1.59 (m, 19 H), 1.73-1.76 (m, 1 H), 1.81-1.89 (m, 1 H), 1.94-2.09 (m, 2 H), 2.20-2.26 (m, 2 H), 2.43-2.52 (m, 2 H), 3.24-3.39 (m, 2 H), 3.65-3.71 (m, 1 H), 4.02-4.06 (m, 1 H), 4.33-4.44 (m, 2 H), 5.12 (t, 1 H), 5.76 (q, 1 H), 5.98 (br d, 1 H), 7.20-7.35 (m, 5 H), 8.41 (br s, 1 H), 10.58 (brs, 1 H). 641.7 (APCI−, M − 1) |
| 302 | 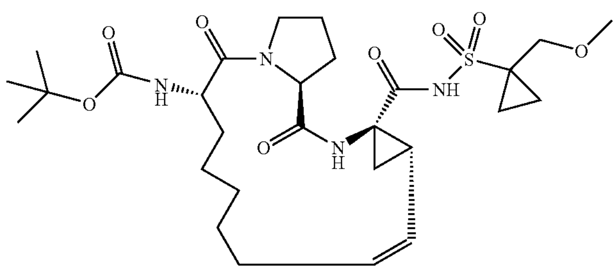 | ¹H NMR (d⁶-Acetone, 400 MHz) δ 0.86-2.08 (m, 26 H), 2.19-2.26 (m, 2 H), 2.36-2.46 (m, 2 H), 3.32 (s, 3 H), 3.64-3.80 (m, 3 H), 3.98 (m, 1 H), 4.35-4.48 (m, 2 H), 4.96-5.01 (m, 1 H), 5.61-5.67 (m, 1 H), 5.93 (br d, 1 H), 8.31 (br s, 1 H), 10.54 (br s, 1 H). 595.3 (APCI−, M − 1) |
| 303 | 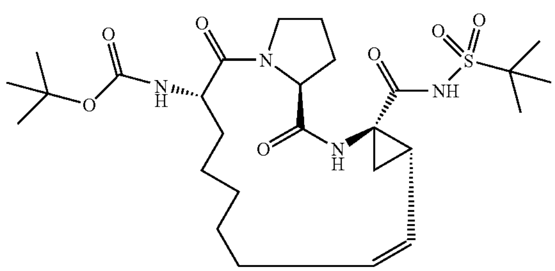 | ¹H NMR (d⁶-Acetone, 400 MHz) δ 0.86-1.56 (m, 27 H), 1.66-1.70 (m, 1 H), 1.84-2.09 (m, 3 H), 2.20-2.26 (m, 2 H), 2.36-2.57 (m, 2 H), 3.65-3.71 (m, 1 H), 4.00-4.06 (m, 1 H), 4.33-4.42 (m, 2 H), 4.96-5.01 (m, 1 H), 5.64-5.70 (m, 1 H), 5.98 (br d, 1 H), 8.40 (br s, 1 H). 567.3 (APCI−, M − 1) |
| 304 | 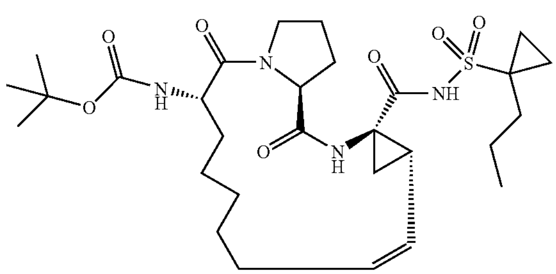 | ¹H NMR (d⁶-Acetone, 400 MHz) δ 0.86-0.96 (m, 5 H), 1.20-1.74 (m, 24 H), 1.84-2.05 (m, 4 H), 2.20-2.27 (m, 2 H), 2.40-2.47 (m, 2 H), 3.65-3.71 (m, 1 H), 4.02-4.06 (m, 1 H), 4.34-4.44 (m, 2 H), 4.94 (t, 1 H), 5.66 (q, 1 H), 6.02 (br d, 1 H), 8.46 (br s, 1 H), 10.58 (br s, 1 H). 593.3 (APCI−, M − 1) |

TABLE 3-continued

| Compound | Structure | ¹H NMR/LCMS (m/z) |
|---|---|---|
| 305 | 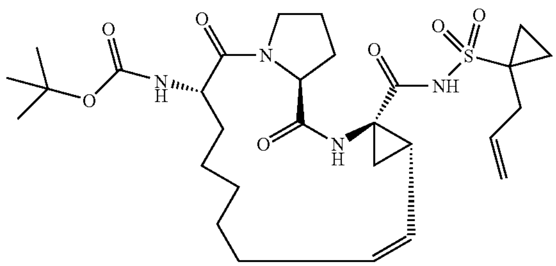 | ¹H NMR (d⁶-Acetone, 400 MHz) δ 0.86-0.95 (m, 2 H), 1.18-1.62 (m, 19 H), 1.68-1.72 (m, 1 H), 1.84-2.05 (m, 4 H), 2.20-2.26 (m, 2 H), 2.40-2.49 (m, 2 H), 2.56-2.61 (m, 1 H), 2.70-2.76 (m, 1 H), 3.65-3.71 (m, 1 H), 4.02-4.06 (m, 1 H), 4.3 3-4.44 (m, 2 H), 4.98 (t, 1 H), 5.07-5.13 (m, 2 H), 5.66-5.82 (m, 2 H), 6.03 (br d, 1 H), 8.45 (br s, 1 H), 10.55 (br s, 1 H). 591.3 (APCI-, M - 1) |
| 306 | 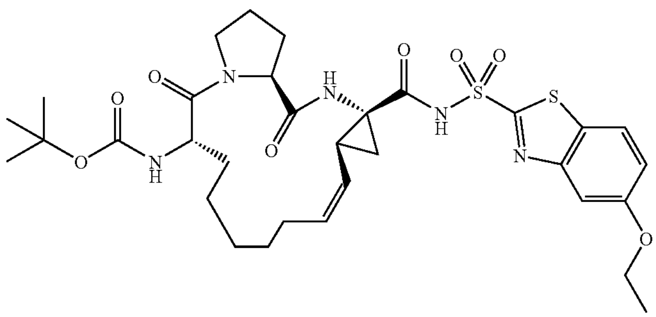 | 688.3 (M - 1, APCI-) |
| 307 | 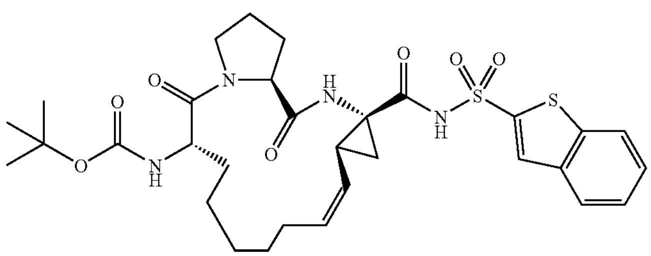 | 643.3 (M - 1, APCI-) |
| 308 | 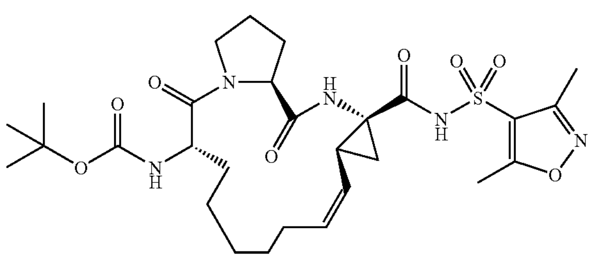 | 606.3 (M - 1, APCI-) |
| 309 | 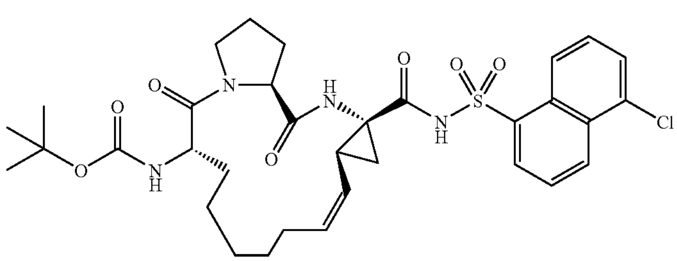 | 671.3 (M - 1, APCI-) |

TABLE 3-continued

| Compound | Structure | ¹H NMR/LCMS (m/z) |
|---|---|---|
| 310 | 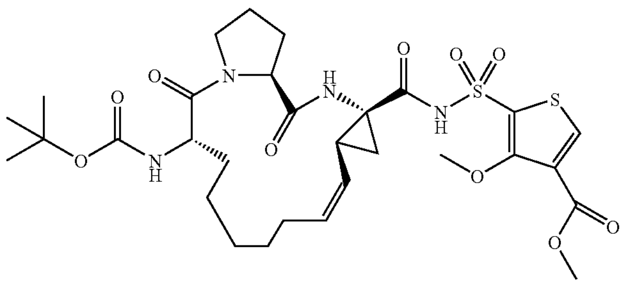 | 681.2 (M − 1, APCI−) |
| 311 | 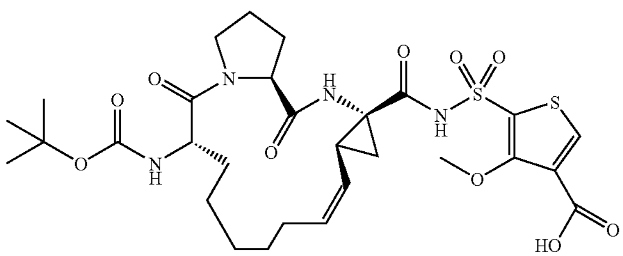 | 667.1 (M − 1, APCI−) |
| 312 | 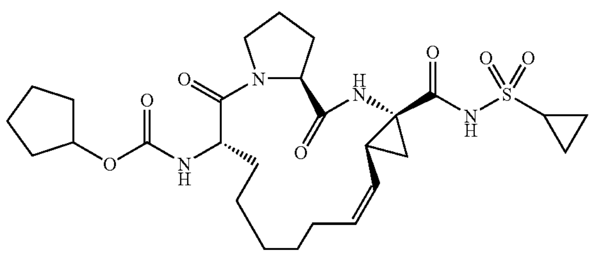 | 1H NMR (400 MHz, d⁶-DMSO) δ 11.09 (s, 1H), 8.79 (s, 1H), 7.25 (d, 1H), 5.61 (q, 1H), 5.00 (t, 1H), 4.94-4.87 (m, 1H), 4.28-4.11 (m, 2H), 3.96-3.85 (m, 1H), 3.55 (q, 1H), 2.94-2.83 (m, 1H), 2.27-2.04 (m, 2H), 1.98-1.68 (m, 7H), 1.67-1.45 (m, 9H), 1.44-1.28 (m, 5H), 1.28-1.03 (m, 4H), 1.02-0.91 (m, 2H). 563.3 (M − 1, APCI−) |
| 313 | 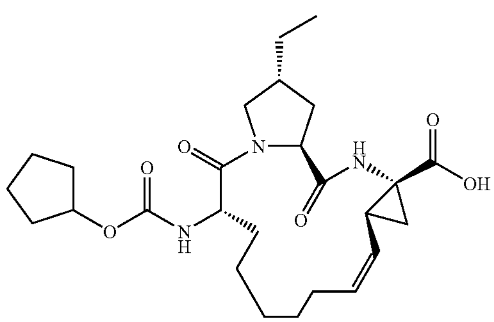 | 488.4 (M − 1, APCI−) |
| 314 | 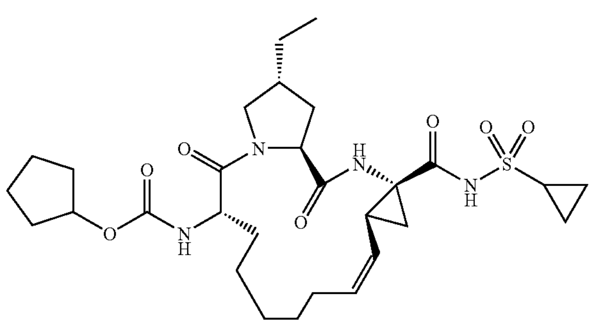 | 591.4 (M − 1, APCI−) |

TABLE 3-continued

| Compound | Structure | $^1$H NMR/LCMS (m/z) |
|---|---|---|
| 315 | 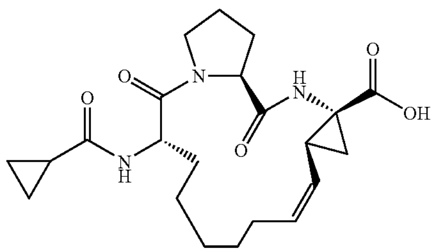 | 416.2 (M − 1, APCI−) |
| 316 | 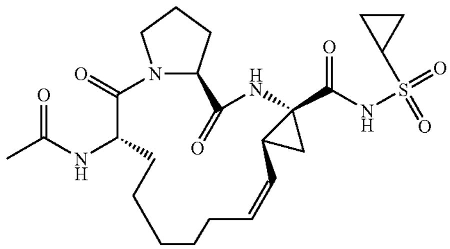 | 493.2 (M − 1, APCI−) |
| 317 | 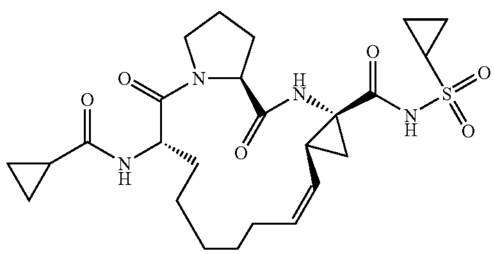 | 519.2 (M − 1, APCI−) |
| 318 | 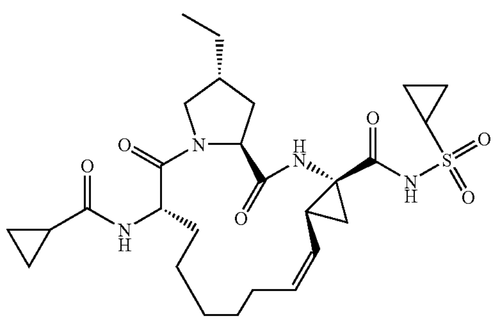 | 547.2 (M − 1, APCI−) |

Preparation of NS3 Inhibitors

Section IV

The NS-3 inhibitor compounds described in this section and summarized in Table 4 below may be synthesized in a manner similar to that described in Scheme 4 of previous section, substituting the sulfonamide in the last coupling step with a sulfamide.

The sulfamides used were either purchased from commercial sources or prepared through Routes A or B described in the following scheme. Similar methods to that of Route A have been described in literature (e.g. *Heteroatom Chemistry*, 2001, 12 (1), 1-5). The sulfamoylating reagent a in Route B was prepared according to a literature procedure (Winum, J-Y et al, *Organic Letters*, 2001, 3, 2241-2243).

Scheme 5

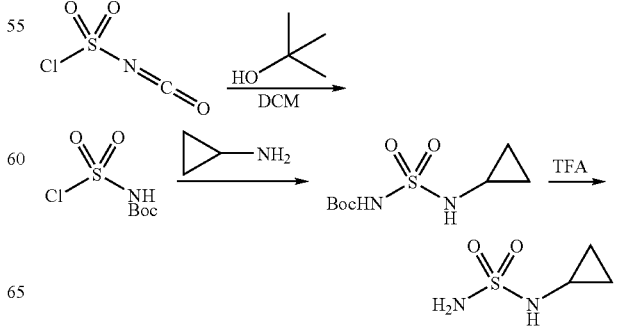

Rout A:

-continued

Route B:

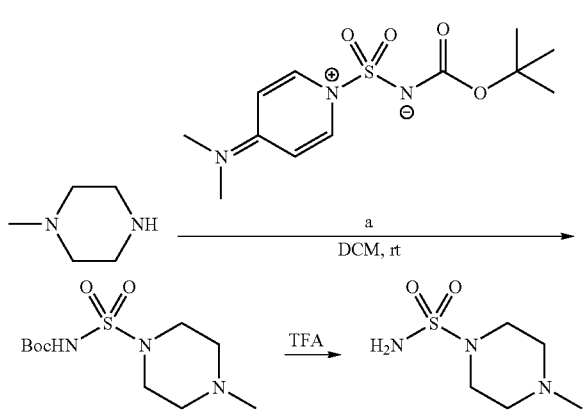

Synthesis of N-Cyclopropylsulfamide

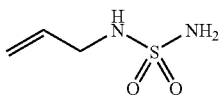

To a stirred solution of chlorosulfonyl isocyanate (1 mL, 11.5 mmol) in 20 mL DriSolve® DCM was added anhydrous t-butanol (1.1 mL, 1 equiv) at 0° C. After stirring for 90 min, the resulting carbamatesulfamoyl chloride solution and 5 mL TEA in 20 mL DCM were added dropwise to a solution of cyclopropyl amine (0.66 g, 1 equiv) in 25 mL DCM and 3 mL TEA. The reaction temperature was kept under 5° C. during addition. The ice bath was removed after addition and the resulting mixture was stirred at rt for 3 h.

TLC (Hex/EA 1:1) showed one major spot with higher $R_f$. LCMS showed that product had formed. The reaction mixture was then diluted with 100 mL DCM and washed with 0.1 N HCl (2×200 mL) and brine (150 mL). The organic layer was dried over $Na_2SO_4$ and concentrated, giving the Boc-protected sulfamide as a light yellowish solid, 1.2 g. $^1$H-NMR showed it to be the desired product plus small amount of impurities. The crude product was recrystallized from EA/Hex (rt to 0° C.), giving 0.64 g offwhite crystalline pure product. $^1$H NMR (CDCl$_3$, 400 MHz) δ0.71-0.77 (m, 4H), 1.51 (s, 9H), 2.44 (m, 1H), 5.58 (br s, 1H), 7.42 (br s, 1H). MS m/z 234.7 (APCI−, M−1).

To remove the Boc protective group, the product from above was dissolved in 10 mL 1:1 (v/v) mix of DCM:TFA and let stay at rt for 1 h. It was then concentrated down on rotovap and then on high vacuum. The thick oil solidified on high vac, giving the titled product as an offwhite solid. $^1$H NMR (CDCl$_3$, 400 MHz) δ0.66-0.74 (m, 4H), 2.57-2.58 (m, 1H), 5.29 (br s, 2H), 5.42 (br s, 1H).

In addition, the following sulfamide intermediates were prepared in a manner similar to that described above for the synthesis of N-cyclopropylsulfamide, substituting cyclopropylamine with the corresponding other amines:

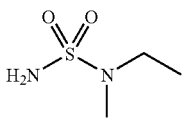

The title compound, (ethyl)methylsulfamide, was prepared in the same fashion as described in Example 17a, substituting azetidine with (ethyl)methylamine (scheme shown below). $^1$H NMR (d$^6$-acetone, 400 MHz) δ1.15 (t, 3H), 2.72 (s, 3H), 3.10 (q, 2H), 5.88 (br s, 2H).

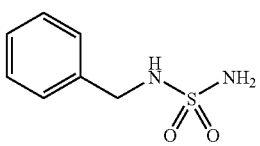

$^1$H NMR (500 MHz, d$^6$-DMSO) δ 6.68 (t, 1H), 6.52 (br s, 2H), 5.90-5.78 (m, 1H), 5.21 (d, 1H), 5.07 (d, 1H), 3.51 t, 2H). MS (APCI−) m/z 134.9 (M−1).

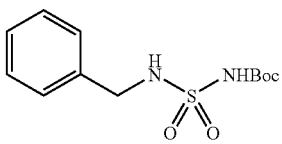

MS (APCI−) m/z 184.9 (M−1).

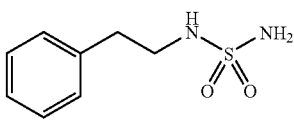

$^1$H NMR (500 MHz, d$^6$-DMSO) δ 10.84 (s, 1H), 8.15 (t, 1H), 7.36-7.22 (m, 5H), 4.12 (d, 2H), 1.39 (s, 9H). MS (APCI−) m/z 284.9 (M−1).

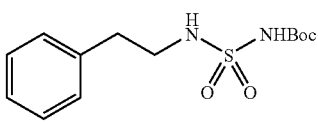

MS (APCI−) m/z 198.9 (M−1).

$^1$H NMR (500 MHz, d$^6$-DMSO) δ 10.85 (s, 1H), 7.64 (br s, 1H), 7.26 (dt, 5H), 3.09 (q, 2H), 2.76 (t, 2H), 1.42 (s, 9H); MS (APCI−) m/z 298.9 (M−1).

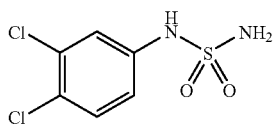

MS (APCI−) m/z 238.9 (M−1).

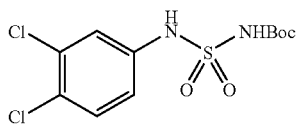

¹H NMR (500 MHz, d⁶-DMSO) δ 11.52 (s, 1H), 10.73 (br s, 1H), 7.60 (d, 1H), 7.36 (s, 1H), 7.13 (dd, 1H), 1.34 (s, 9H); MS (APCI−) m/z 338.9 (M−1).

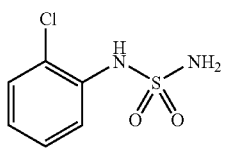

MS (APCI−) m/z 204.9 (M−1).

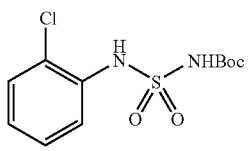

¹H NMR (500 MHz, d⁶-DMSO) δ 11.16 (s, 1H), 9.74 (br s, 1H), 7.51 (d, 1H), 7.42-7.33 (m, 2H), 7.27 (t, 1H), 1.40 (s, 9H); MS (APCI−) m/z 304.9 (M−1).

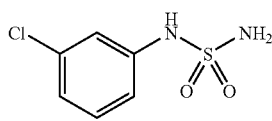

MS (APCI−) m/z 204.9 (M−1).

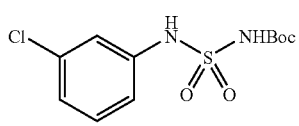

¹H NMR (500 MHz, d⁶-DMSO) δ 11.43 (s, 1H), 10.57 (br s, 1H), 7.35 (t, 1H), 7.20 (s, 1H), 7.18-7.09 (m, 2H), 1.34 (s, 9H); MS (APCI−) m/z 304.9 (M−1).

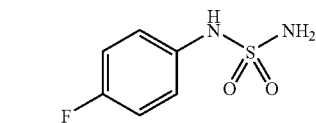

MS (APCI−) m/z 188.9 (M−1).

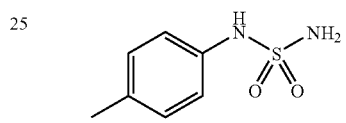

¹H NMR (500 MHz, d⁶-DMSO) δ 11.20 (s, 1H), 10.23 (br s, 1H), 7.24-7.13 (m, 1H), 7.20 (s, 1H), 7.18-7.09 (m, 4H), 1.35 (s, 9H); MS (APCI−) m/z 288.9 (M−1).

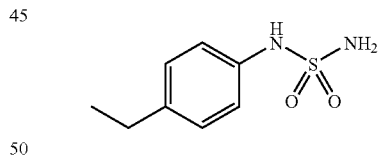

MS (APCI−) m/z 184.9 (M−1).

¹H NMR (500 MHz, d⁶-DMSO) δ 11.08 (s, 1H), 10.05 (br s, 1H), 7.12 (d, 2H), 7.05 (d, 2H), 2.25 (s, 3H), 1.35 (s, 9H); MS (APCI−) m/z 284.9 (M−1).

MS (APCI−) m/z 198.9 (M−1).

¹H NMR (500 MHz, d⁶-DMSO) δ 11.09 (s, 1H), 10.06 (br s, 1H), 7.15 (d, 2H), 7.08 (d, 2H), 2.55 (s, 2H), 1.35 (s, 9H), 1.14 (t, 3H); MS (APCI−) m/z 298.9 (M−1).

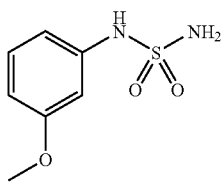

MS (APCI−) m/z 200.9 (M−1).

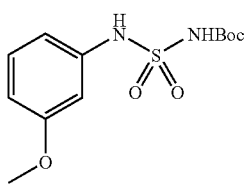

¹H NMR (500 MHz, d⁶-DMSO) δ 11.23 (s, 1H), 10.24 (s, 1H), 7.21 (t, 1H), 6.77-6.72 (m, 2H), 6.67 (d, 1H), 3.72 (s, 3H), 1.34 (s, 9H); MS (APCI−) m/z 300.9 (M−1).

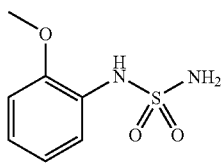

¹H NMR (500 MHz, d⁶-DMSO) δ 7.91 (s, 1H), 7.38 (d, 1H), 7.07-6.98 (m, 4H), 6.90 (t, 1H), 3.80 (s, 3H); MS (APCI−) m/z 200.9 (M−1).

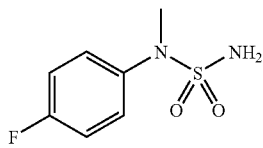

¹H NMR (500 MHz, d⁶-DMSO) δ 7.40-7.34 (m, 2H), 7.21 (t, 2H), 7.02 (s, 2H), 3.35 (s, 3H); MS (APCI−) m/z 203.2 (M−1).

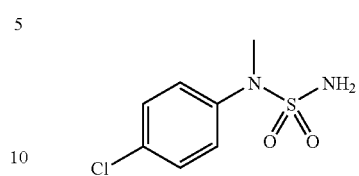

¹H NMR (500 MHz, d⁶-DMSO) δ 7.43 (d, 2H), 7.35 (d, 2H), 7.08 (s, 2H), 3.09 (s, 3H); MS (APCI−) m/z 219.2 (M−1).

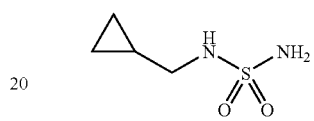

¹H NMR (500 MHz, d⁶-DMSO) δ 6.48 (br s, 2H), 3.43 (br s, 1H), 2.74 (d, 2H), 1.00-0.90 (m, 1H), 0.44-0.36 (m, 2H), 0.18-0.12 (m, 2H); MS (APCI−) m/z 149.0 (M−1).

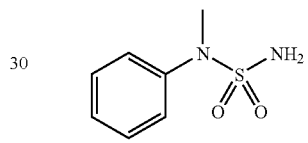

¹H NMR (500 MHz, CDCl₃) δ 7.42-7.31 (m, 4H), 7.28-7.20 (m, 1H), 7.00 (br s, 2H), 3.10 (s, 3H); MS (APCI−) m/z 185.2 (M−1).

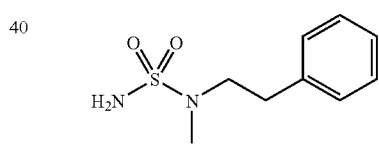

¹H NMR (500 MHz, CDCl₃) δ 7.37-7.20 (m, 5H), 3.44 (m, 2H), 2.91 (t, 2H), 2.85 (s, 3H); MS (APCI−) m/z 213.1 (M−1).

TABLE 4

| Compound | Structure | LCMS (m/z) |
|---|---|---|
| 400 | 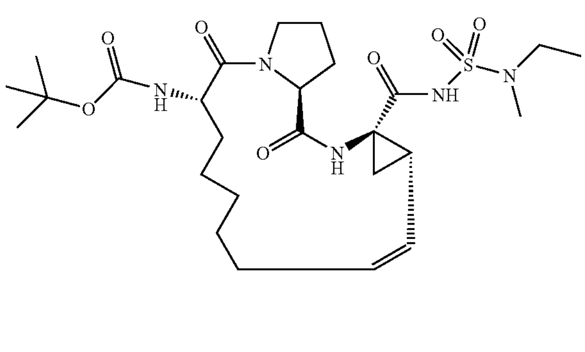 | 568.3 (APCI−, M − 1) |

TABLE 4-continued

| Compound | Structure | LCMS (m/z) |
|---|---|---|
| 401 | 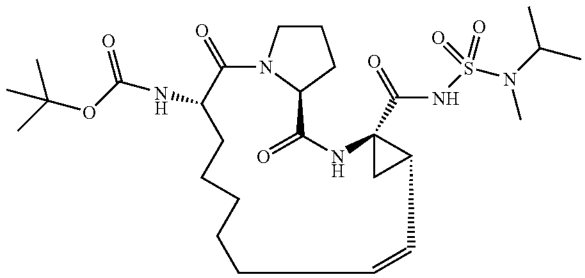 | 582.2 (APCI−, M − 1) |
| 402 | 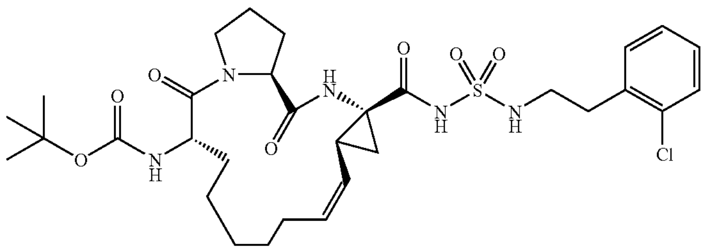 | 664.4 (M − 1, APCI−) |
| 403 | 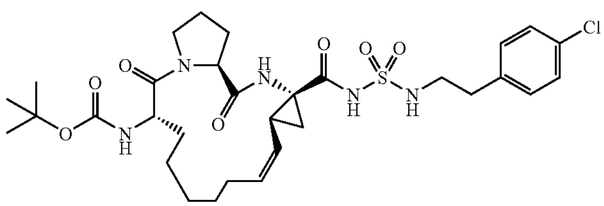 | 664.3 (M − 1, APCI−) |
| 404 | 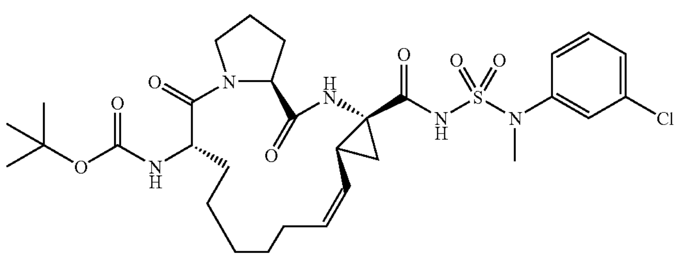 | 650.6 (M − 1, APCI−) |
| 405 | 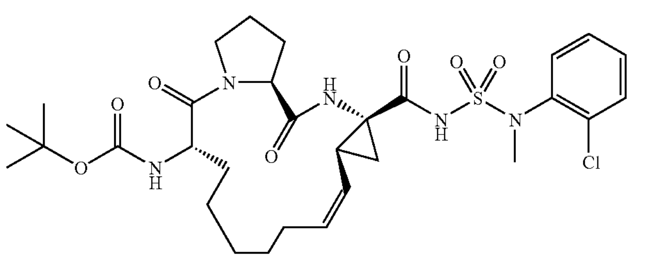 | 650.6 (M − 1, APCI−) |
| 406 | 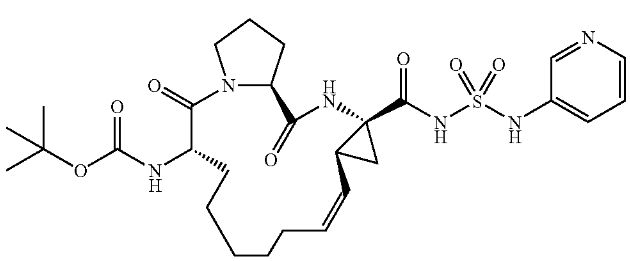 | 603.6 (M − 1, APCI−) |

TABLE 4-continued

| Compound | Structure | LCMS (m/z) |
|---|---|---|
| 407 | 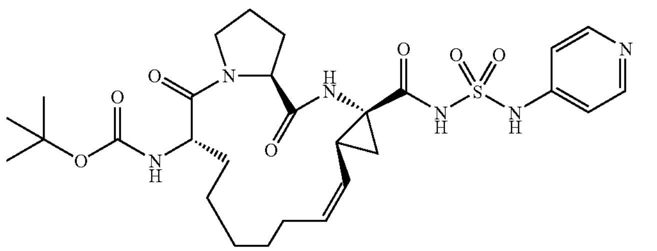 | 603.6 (M − 1, APCI−) |
| 408 | 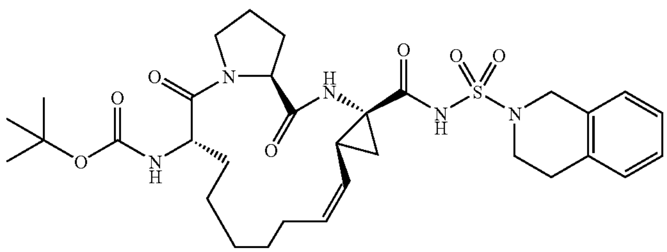 | 642.4 (M − 1, APCI−) |
| 409 | 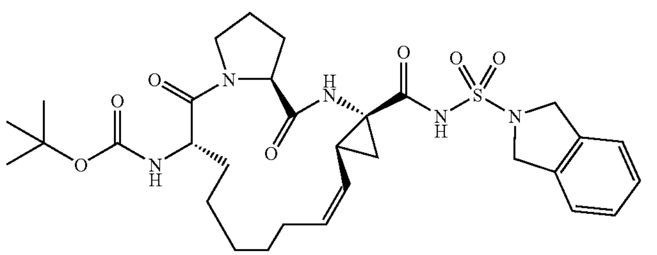 | 628.6 (M − 1, APCI−) |
| 410 | 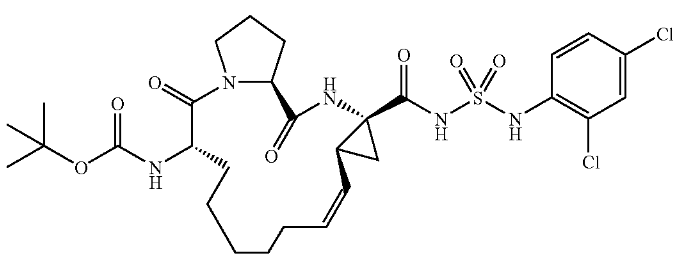 | 670.7 (M − 1, APCI−) |
| 411 | 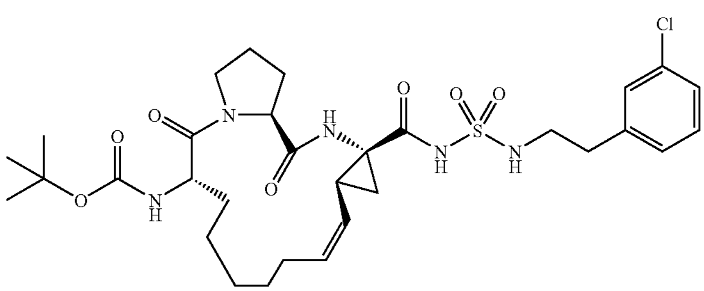 | 664.3 (M − 1, APCI−) |
| 412 | 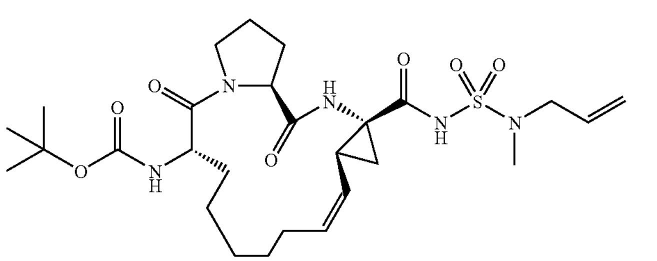 | 580.3 (M − 1, APCI−) |

TABLE 4-continued

| Compound | Structure | LCMS (m/z) |
|---|---|---|
| 413 | 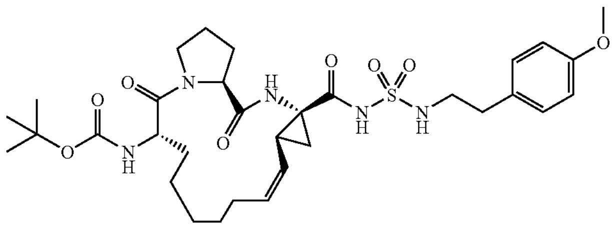 | 660.3 (M − 1, APCI−) |
| 414 | 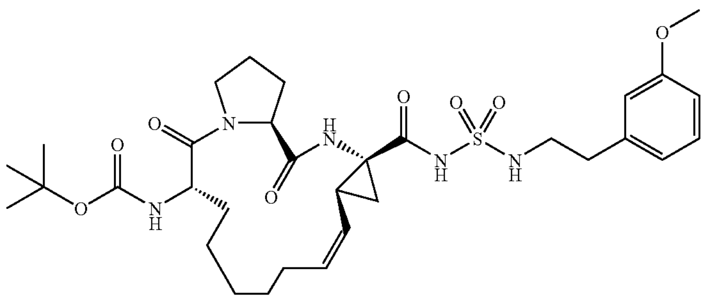 | 660.3 (M − 1, APCI−) |
| 415 | 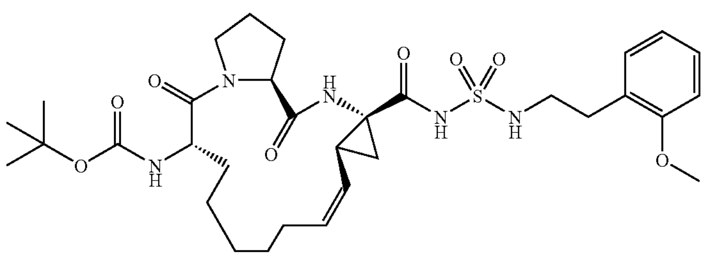 | 660.3 (M − 1, APCI−) |
| 416 | 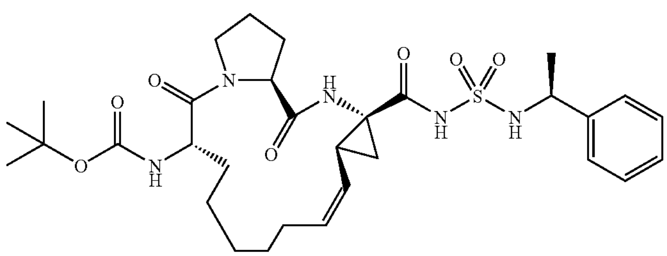 | 630.2 (M − 1, APCI−) |
| 417 | 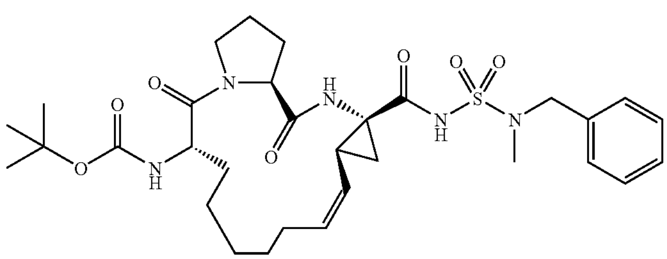 | 630.3 (M − 1, APCI−) |
| 418 | 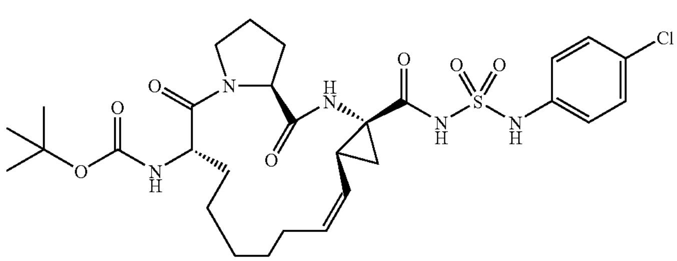 | 623.2 (M − 1, APCI−) |

TABLE 4-continued

| Compound | Structure | LCMS (m/z) |
|---|---|---|
| 419 | 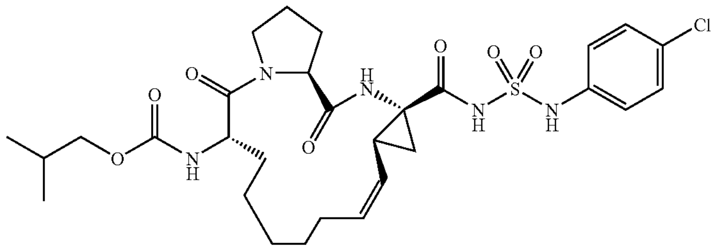 | 637.3 (M − 1, APCI−) |
| 420 | 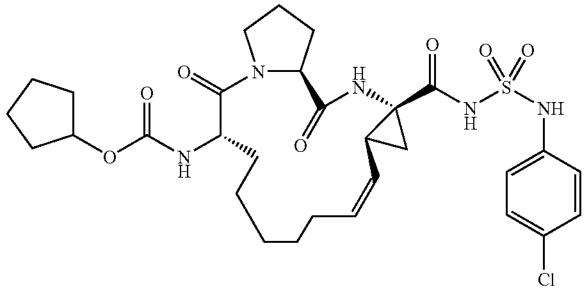 | 649.6 (M − 1, APCI−) |
| 421 | 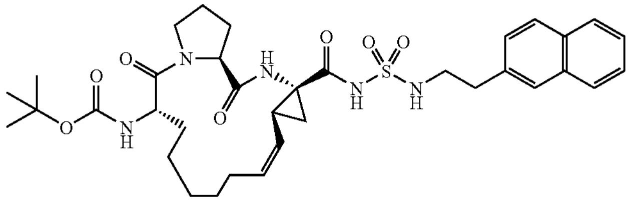 | 680.8 (M − 1, APCI−) |
| 422 | 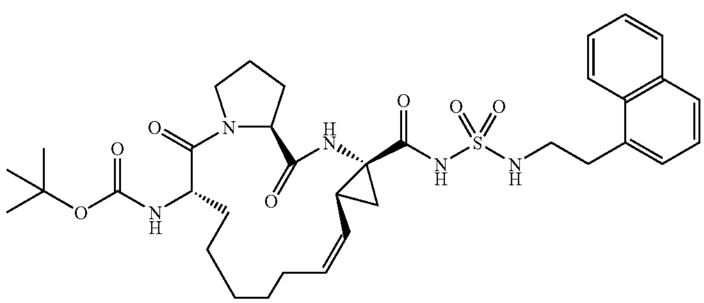 | 680.8 (M − 1, APCI−) |
| 423 | 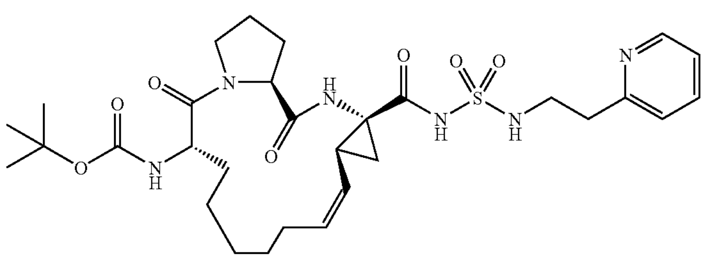 | 631.3 (M − 1, APCI−) |
| 424 | 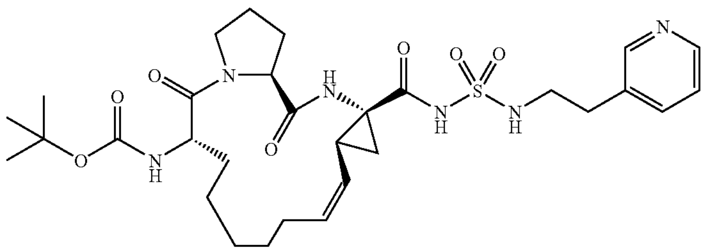 | 631.6 (M − 1, APCI−) |

TABLE 4-continued

| Compound | Structure | LCMS (m/z) |
|---|---|---|
| 425 | 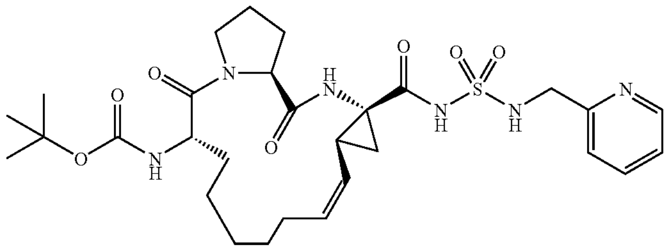 | 617.5 (M − 1, APCI−) |
| 426 | 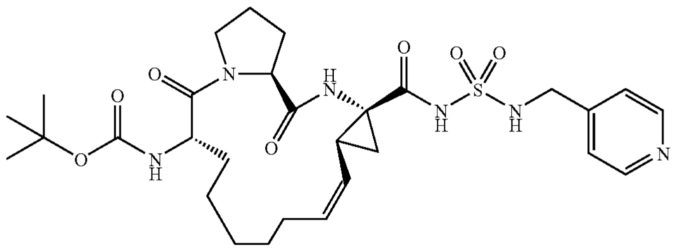 | 617.5 (M − 1, APCI−) |
| 427 | 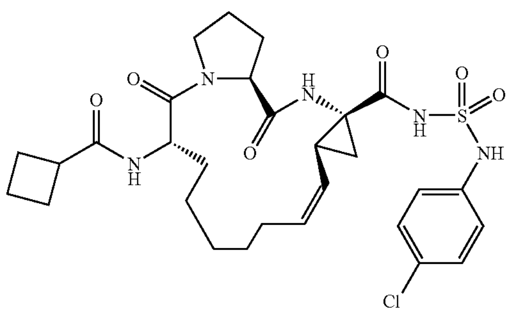 | 619.2 (M − 1, APCI−) |
| 428 | 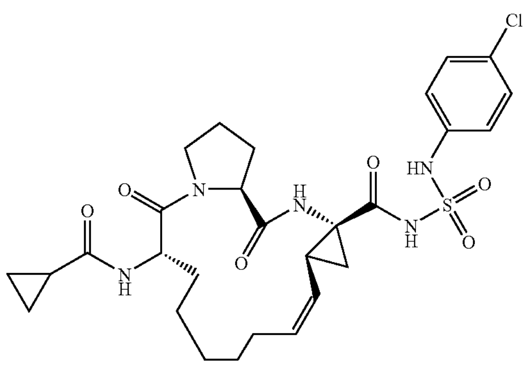 | 605.2 (M − 1, APCI−) |
| 429 | 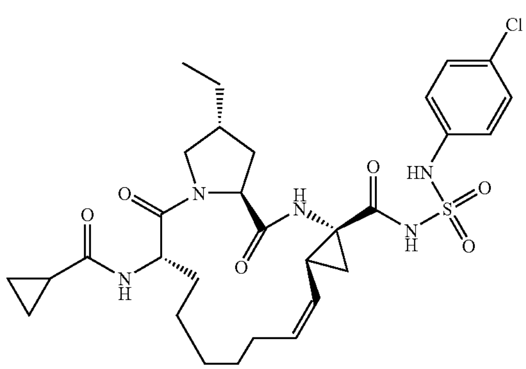 | 633.2 (M − 1, APCI−) |

Preparation of NS3 Inhibitors

Section V

The NS3 inhibitors described in this section and summarized in Table 5 below may be synthesized in a manner similar to that described in Scheme 4, Section III of the inhibitor synthesis, substituting the sulfonamide in the last coupling step with an amine instead.

Synthesis of Compound A:

Compound A

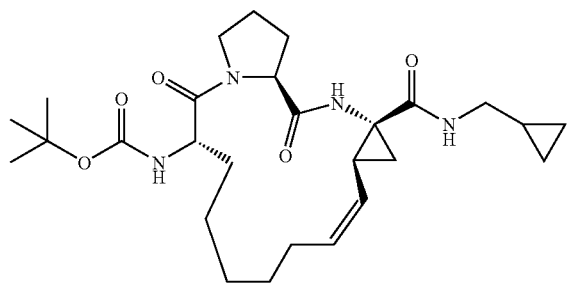

(1S,4R,6S,14S)tert-Butyl 4-(cyclopropyl(methyl))aminocarbonyl-2,15-dioxo-3,16-diaza-tricyclo[14.3.0.0$^{4,6}$]nonadec-7-ene-14-yl carbamate (Compound A) was synthesized according to the procedures as described below:

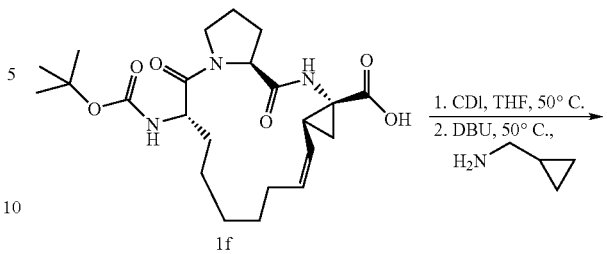

1f

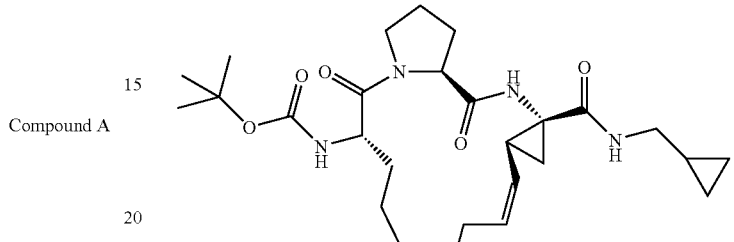

Compound 1f (Scheme 4, Section III, 30 mg, 0.07 mmol) is taken up in THF (DriSolve®, 0.5 mL) and carbonyldiimidazole (CDI, 1.05 equiv.) is then added. The reaction is heated to 50° C. and stirred for an hour at this temperature. Next, the amine (2 equiv.) is added followed by DBU (2 equiv.). The reaction is then stirred at 50° C. overnight. The reaction is then concentrated and taken back up in EtOAc (2 mL) and washed with 1 N NaOH, 1 N HCl, and brine before drying the organic over $Na_2SO_4$. The EtOAc solution is then concentrated to give the desired amide in good purity. MS (APCI-) m/z 501.2 (M-1).

The compounds described in Table 5 were prepared in a manner similar to that described for Compound A, substituting cyclopropyl methyl amine with corresponding amines instead.

TABLE 5

| Compound | Structure | LCMS (m/z) |
| --- | --- | --- |
| 500 | 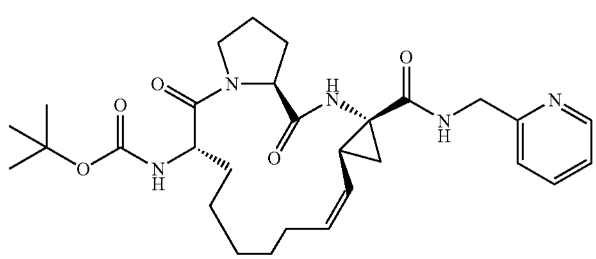 | 538.4 (M − 1, APCI−) |
| 501 | 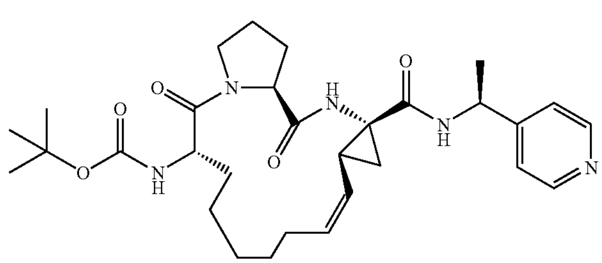 | 552.5 (M − 1, APCI−) |

TABLE 5-continued

| Compound | Structure | LCMS (m/z) |
|---|---|---|
| 502 | 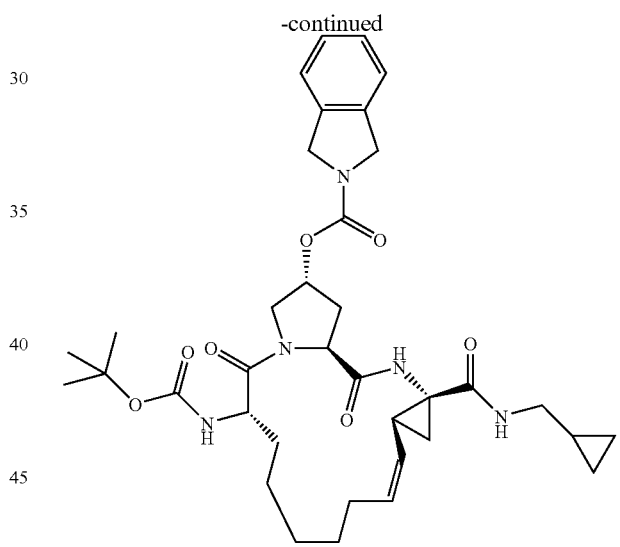 | 538.4 (M − 1, APCI−) |
| 503 | 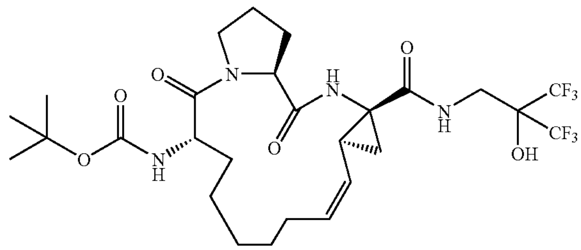 | 627.2 (M − 1, APCI−) |

Preparation of NS3 Inhibitors

Section VI

The NS3 inhibitors described in this section and summarized in Table 6 may be synthesized in a manner similar to that described for the synthesis of Compound A in Section V above, substituting the (1S,4R,6S,14S)14-tert-Butoxycarbonylamino-2,15-dioxo-3,16-diaza-tricyclo[14.3.0.0$^{4,6}$]nonadec-7-ene-4-carboxylic acid (1f) in the coupling step with (1S,4R,6S,14S,18R)-14-tert-Butoxycarbonylamino-18-(1,3-dihydro-isoindole-2-carbonyloxyl)-2,15-dioxo-3,16-diaza-tricyclo[14.3.0.0$^{4,6}$]nonadec-7-ene-4-carboxylic acid (5a) instead. For example:

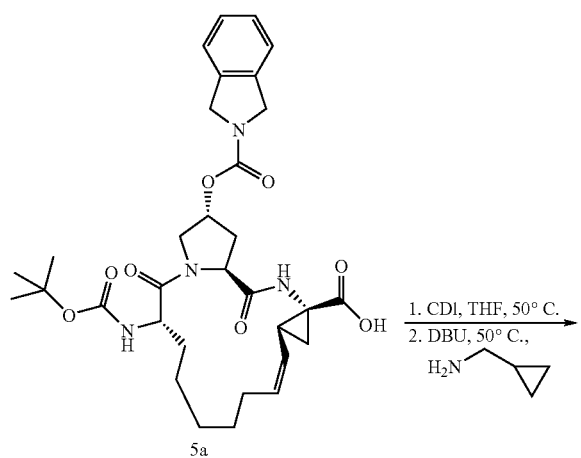

Compound 5a (30 mg, 0.05 mmol) is taken up in THF (DriSolve®, 0.3 mL) and carbonyldiimidazole (CDI, 1.05 equiv.) is then added. The reaction is heated to 50° C. and stirred for an hour at this temperature. Next, the amine (2 equiv.) is added followed by DBU (2 equiv.). The reaction is then stirred at 50° C. overnight. The reaction is then concentrated and taken back up in EtOAc (2 mL) and washed with 1 N NaOH, 1 N HCl, and brine before drying the organic over Na$_2$SO$_4$. The EtOAc solution is then concentrated to give the desired amide in good purity. MS (APCI−) m/z 662.1 (M−1).

The synthesis of compound 5a has been described in detail elsewhere (International Application No. PCT/US2004/033970, International Publication No. WO2005/037214; Compound AR00291871, Example 1-5); see also the description of the synthesis of Compound 100 in Section I above.

TABLE 6

| Compound | Structure | LCMS (m/z) |
|---|---|---|
| 600 | 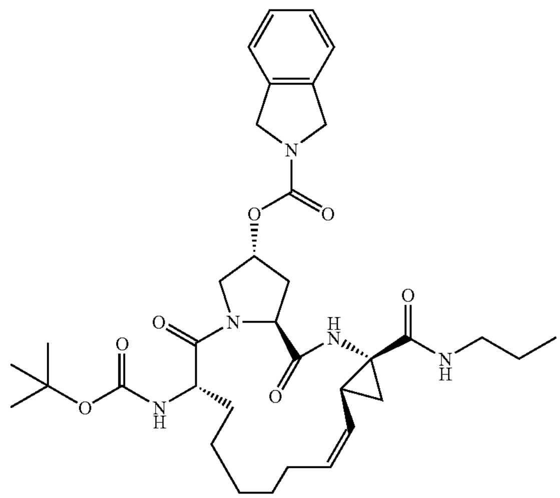 | 650.3 (M − 1, APCI−) |
| 601 | 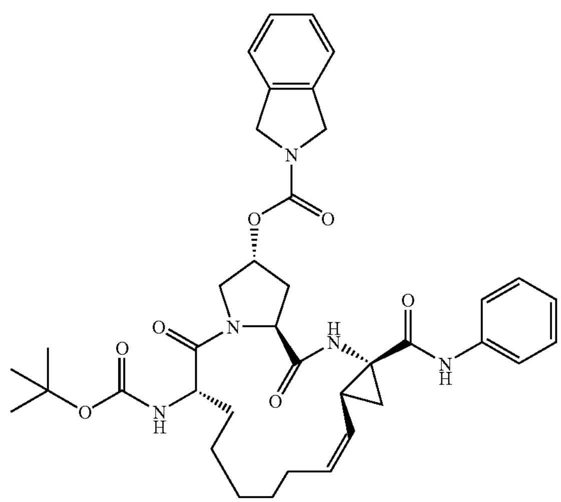 | 684.2 (M − 1, APCI−) |
| 602 | 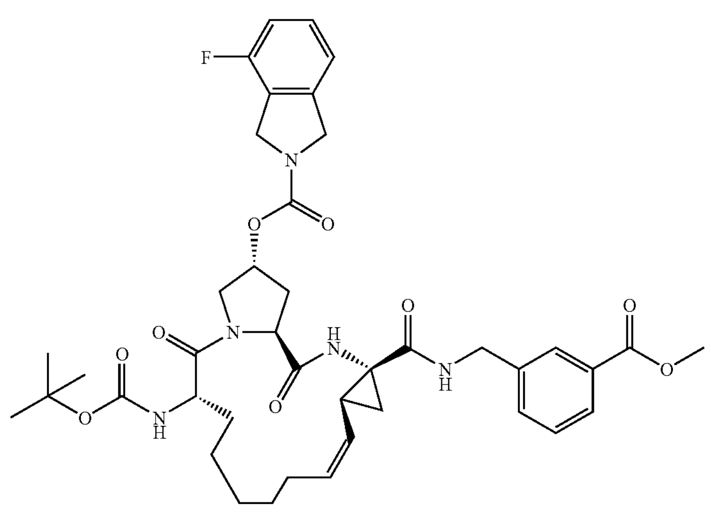 | 774.1 (M − 1, APCI−) |

TABLE 6-continued
| Compound | Structure | LCMS (m/z) |
|---|---|---|
| 603 | 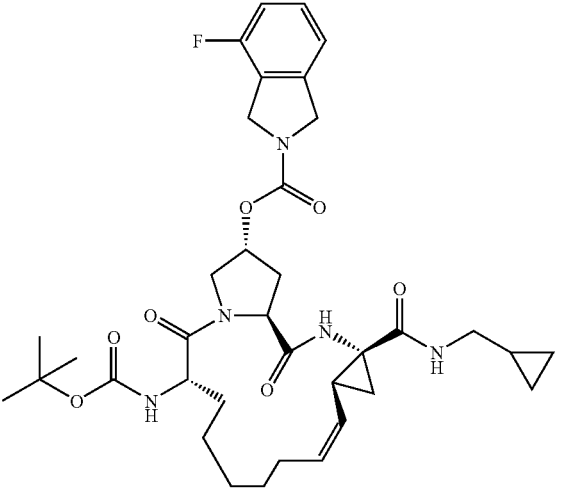 | 680.3 (M − 1, APCI−) |
| 604 | 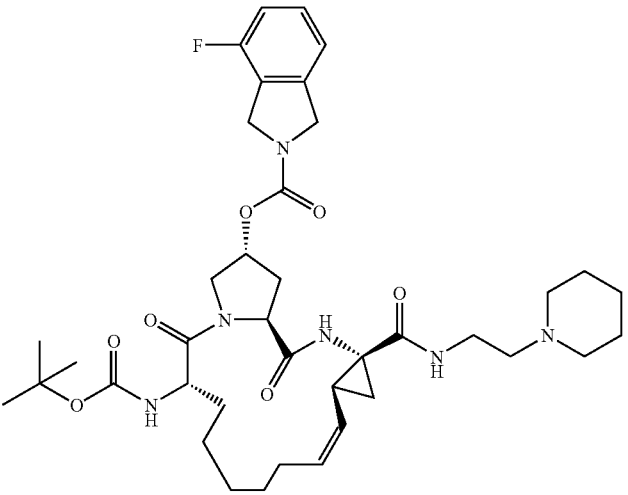 | 738.1 (M −, APCI−) |
| 605 | 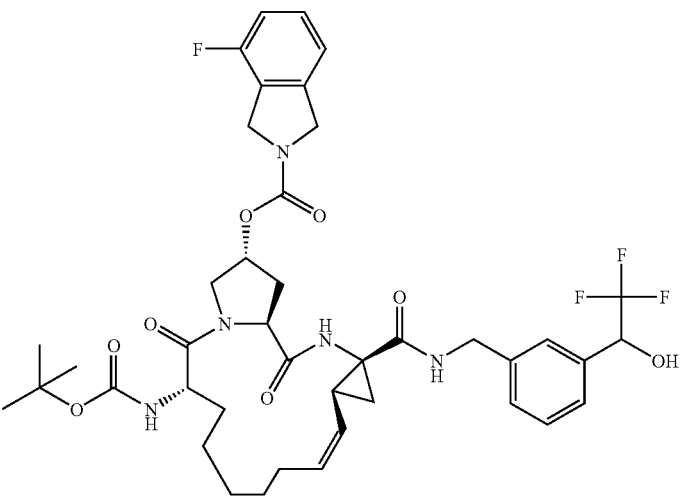 | 814.3 (M − 1, APCI−) |

TABLE 6-continued

| Compound | Structure | LCMS (m/z) |
| --- | --- | --- |
| 606 | 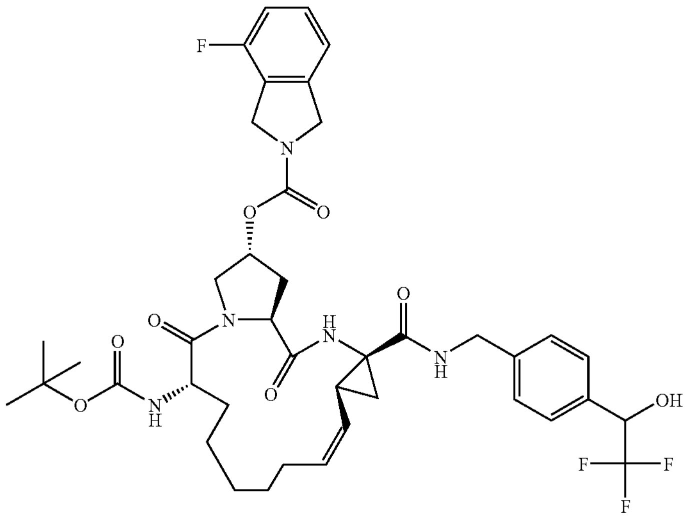 | 814.3 (M − 1, APCI−) |
| 607 | 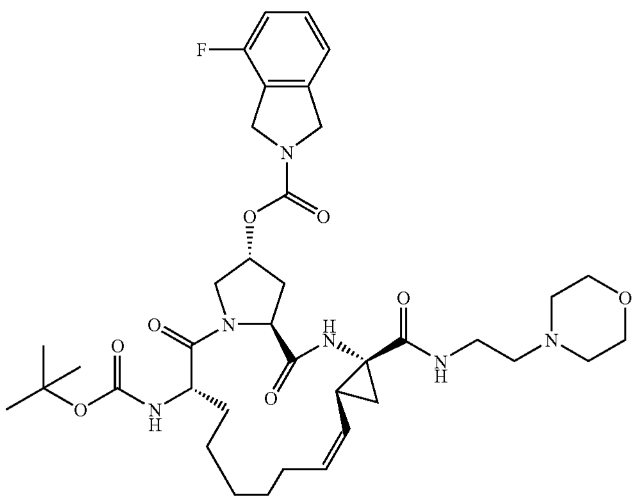 | 741.3 (M + 1, APCI+) |
| 608 | 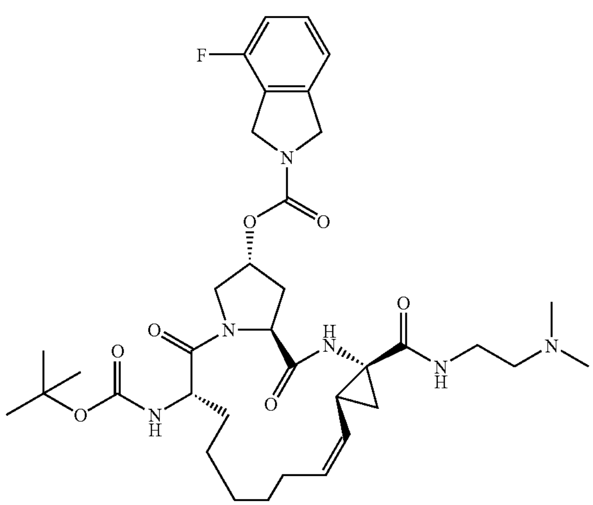 | 699.3 (M + 1, APCI+) |

TABLE 6-continued

| Compound | Structure | LCMS (m/z) |
|---|---|---|
| 609 | 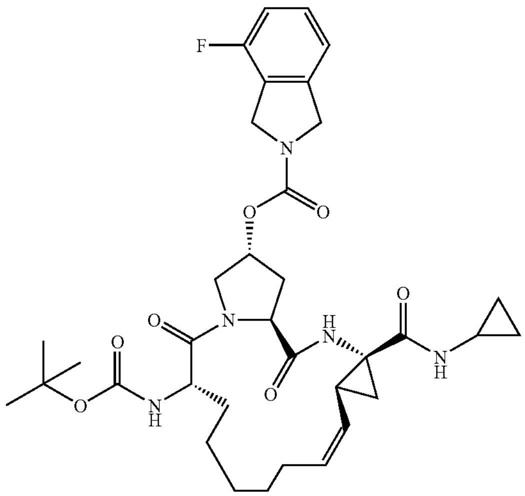 | 668.3 (M + 1, APCI+) |
| 610 | 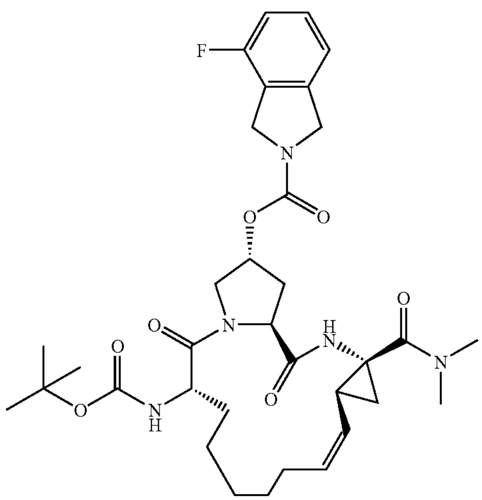 | 656.0 (M + 1, SPCI+) |
| 611 | 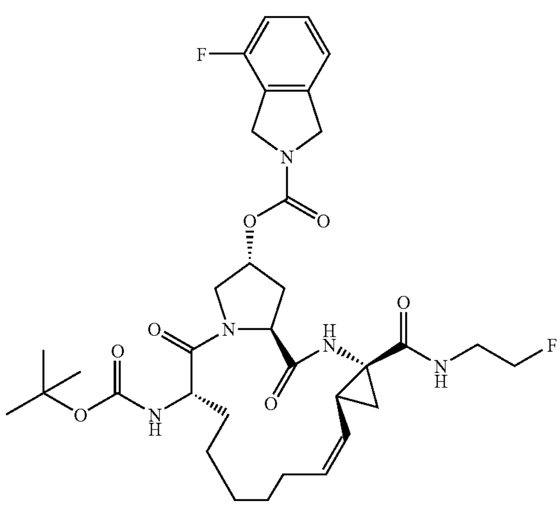 | 574.2 (M + 1-Boc, APCI+) |

TABLE 6-continued
| Compound | Structure | LCMS (m/z) |
|---|---|---|
| 612 | 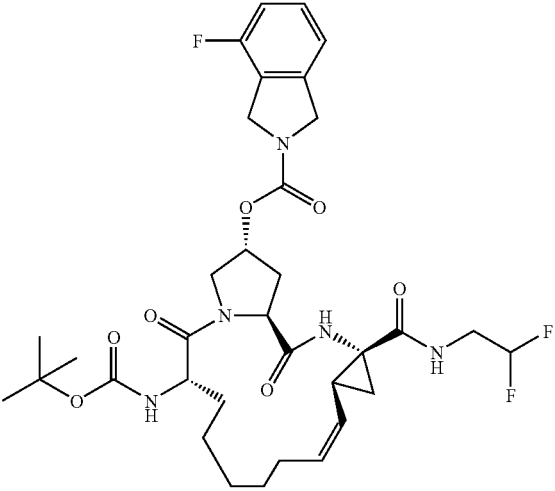 | 592.1 (M + 1-Boc, APCI+) |
| 613 | 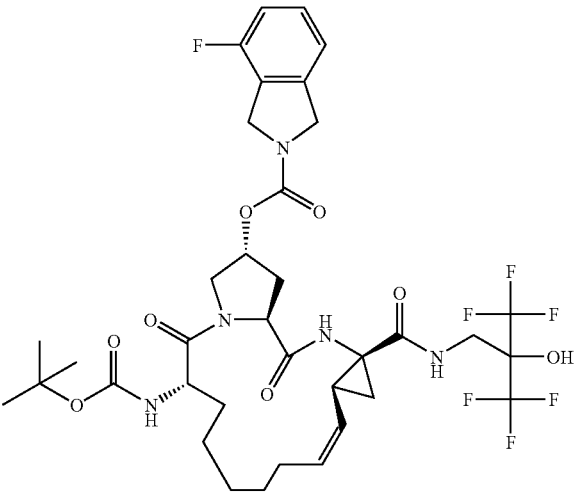 | 708.2 (M + 1-Boc, APCI+) |
| 614 | 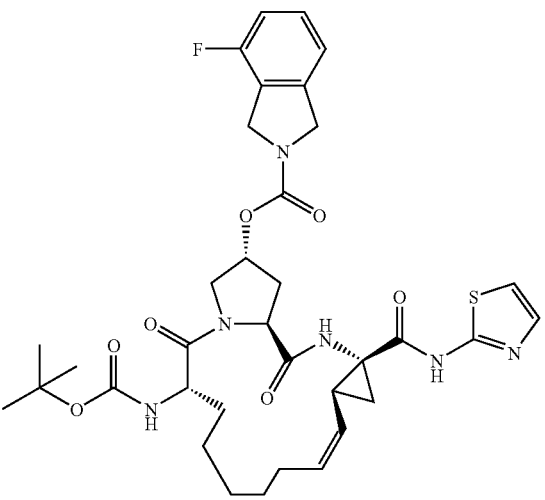 | 709.2 (M − 1, APCI−) |

TABLE 6-continued

| Compound | Structure | LCMS (m/z) |
| --- | --- | --- |
| 615 | 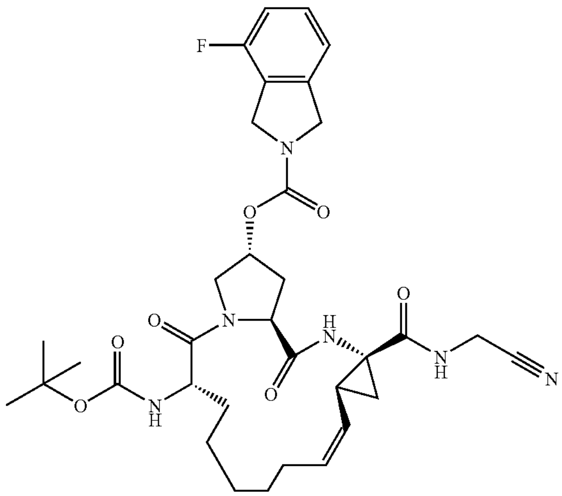 | 667.3 (M + 1, APCI+) |
| 616 | 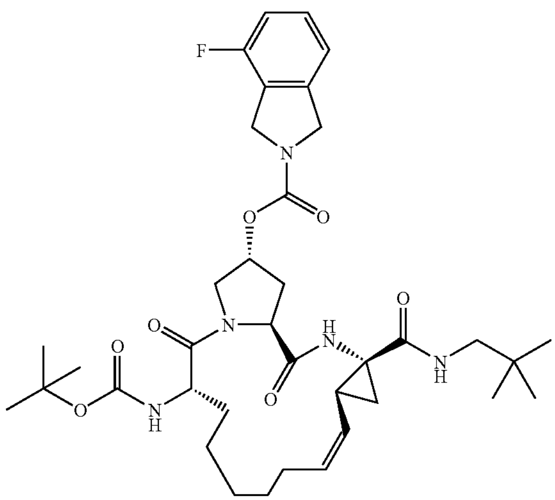 | 598.2 (M + 1-Boc, APCI+) |
| 617 | 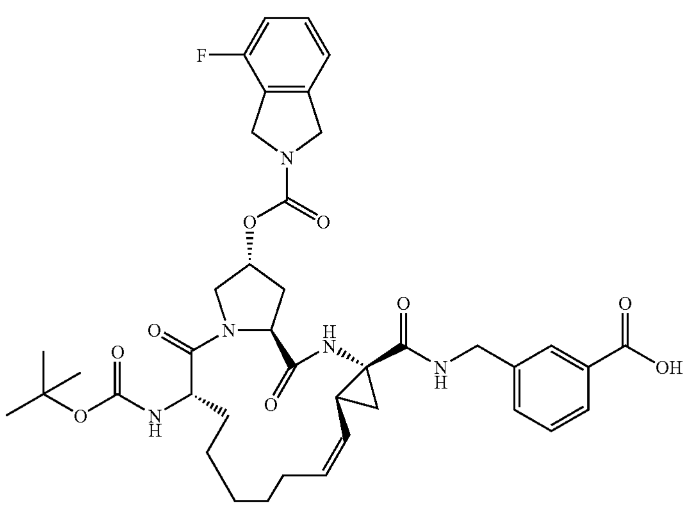 | 760.2 (M − 1, APCI−) |

TABLE 6-continued

| Compound | Structure | LCMS (m/z) |
|---|---|---|
| 618 | 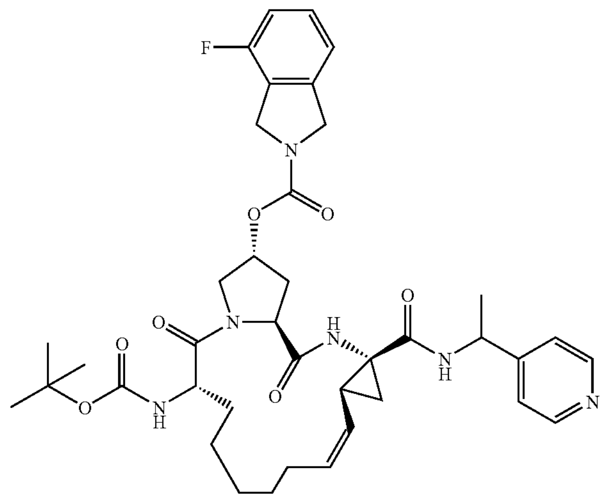 | 733.2 (M + 1, APCI+) |
| 619 | 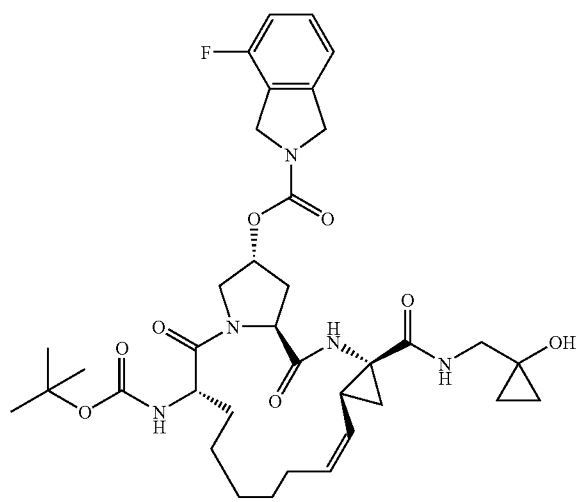 | 698.1 (M + 1, APCI+) |
| 620 | 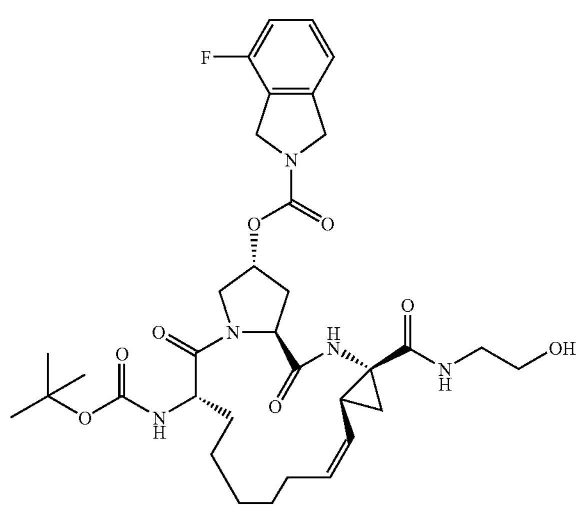 | 572.1 (M + 1-Boc, APCI+) |

TABLE 6-continued

| Compound | Structure | LCMS (m/z) |
|---|---|---|
| 621 | 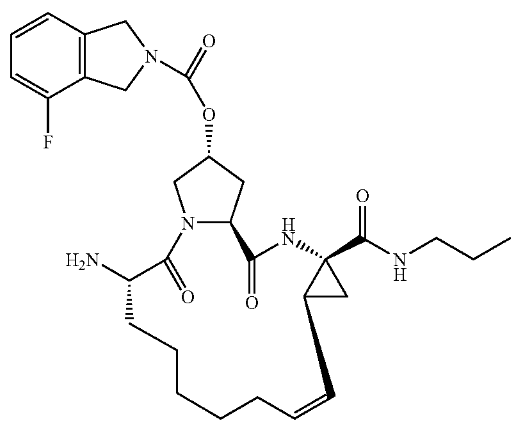 | LCMS: 570.2 |
| 622 | 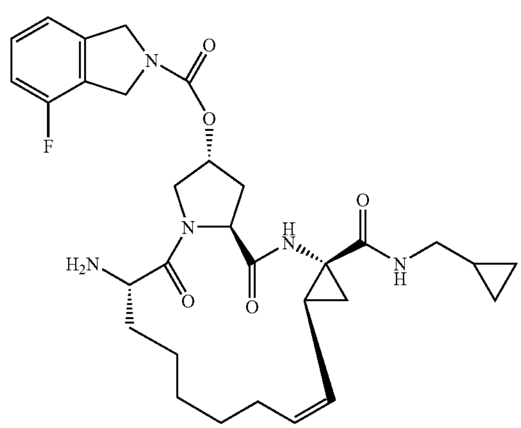 | 1H NMR (DMSOd6, 400 MHz) d 0.09-0.18 (m, 2 H), 0.30-0.39 (m, 2 H), 0.82-0.93 (m, 1 H), 1.10-1.59 (m, 8 H), 1.61-1.90 (m, 3 H), 2.02 (p, 1 H), 2.34-2.44 (m, 3 H), 2.90-3.08 (m, 2 H), 3.62-3.76 (m, 1 H), 3.82-3.92 (m, 1 H), 3.98 (d, 1 H), 4.13 (dd, 1 H), 4.51 (q, 1 H), 4.70 (q, 4 H), 5.21 (t, 1 H), 5.38 (s, 1 H), 5.44 (q, 1 H), 7.10-7.24 (m, 2 H), 7.38 (q, 1 H), 7.49 (t, 1 H), 8.33 (s, 2 H), 8.93 (s, 1 H); LCMS:582.2 |
| 623 | 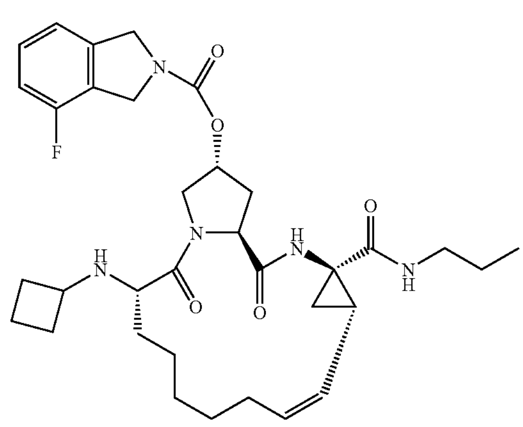 | LCMS:624.4 |

TABLE 6-continued

| Compound | Structure | LCMS (m/z) |
|---|---|---|
| 624 | 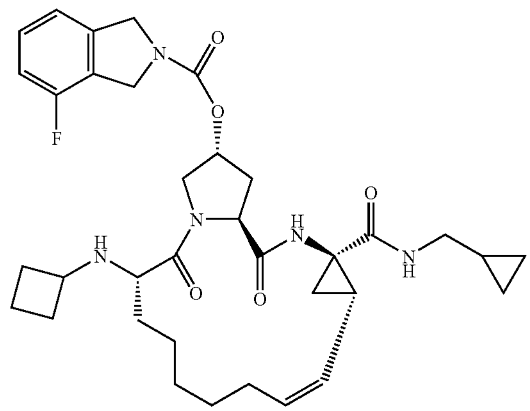 | LCMS:636.4 |
| 625 | 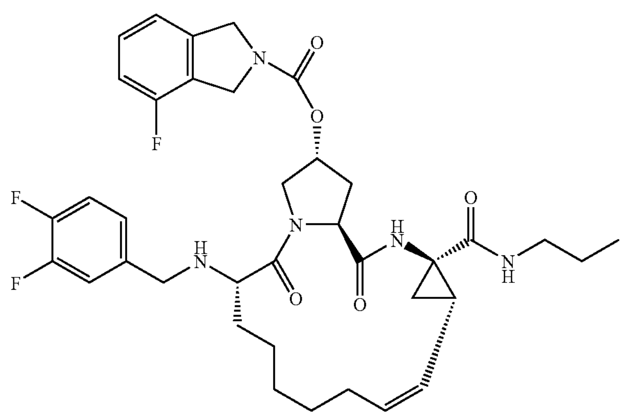 | LCMS:696.3 |
| 626 | 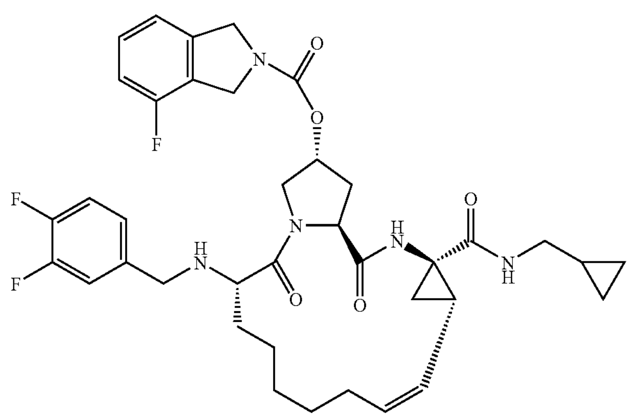 | LCMS:708.3 |

TABLE 6-continued

| Compound | Structure | LCMS (m/z) |
|---|---|---|
| 627 | 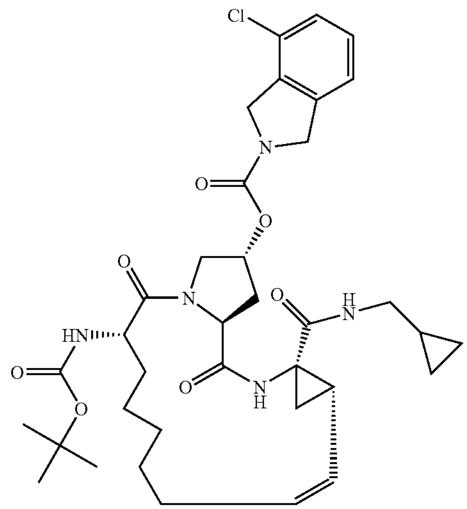 | LCMS (APCI+): 698 (M) |
| 628 | 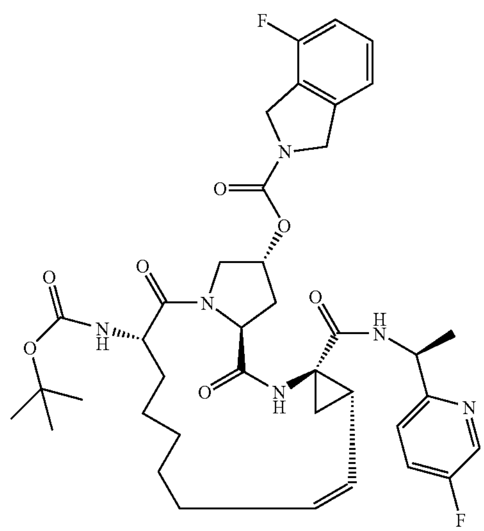 | ¹H NMR (400 MHz, d⁶-DMSO) 8.95 (d, J=8.8 Hz, 1H), 8.48 (s, 1H), 7.93 (d, J=7.2 Hz, 1H), 7.66 (m, 1H), 7.43 (m, 1H), 7.36 (m, 1H), 7.10-7.35 (m, 3H), 5.40 (m, 1H), 5.32 (b, 1H), 5.10 (m, 1H), 4.92 (m, 1H), 4.68 (s, 4H), 4.50 (m, 1H), 4.30 (m, 1H), 3.94 (m, 1H), 3.70 (m, 1H), 2.59 (m, 1H), 2.41 (m, 1H), 2.30 (m, 1H), 2.13 (m, 1H), 1.68 (m, 2H), 1.49 (m, 1H), 1.42 (m, 1H), 1.07-1.33 (m, 18 H), 0.82 (m 1H). LCMS (APCI+): 751.2 (MH+) |
| 629 | 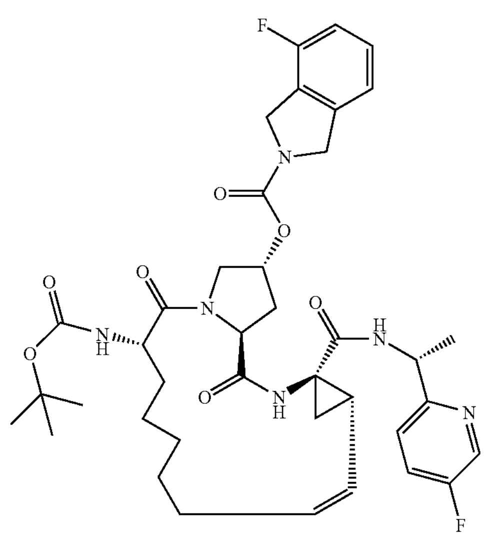 | ¹H NMR (400 MHz, d⁶-DMSO) 7.86 (d, J=6.8 Hz, 1H), 8.51 (s, 1H), 8.02 (d, J=8.0 Hz, 1H), 7.69 (m, 1H), 7.38 (m, 2H), 7.08-7.21 (m, 3H), 5.51 (m, 1H), 5.34 (s, 1H), 5.11 (m, 1H), 4.93 (m, 1H), 4.68 (s, 4H), 4.47 (m, 1H), 4.30 (m, 1H), 3.94 (m, 1H), 3.73 (m, 1H), 2.67 (m, 1H), 2.33 (m, 2H), 2.14 (m, 1H), 1.70 (m, 2 H), 1.47 (m, 1H), 1.07-1.33 (m, 19 H), 0.85 (m, 1H). LCMS (APCI+): 751.2 (MH+) |

TABLE 6-continued

| Compound | Structure | LCMS (m/z) |
|---|---|---|
| 630 | 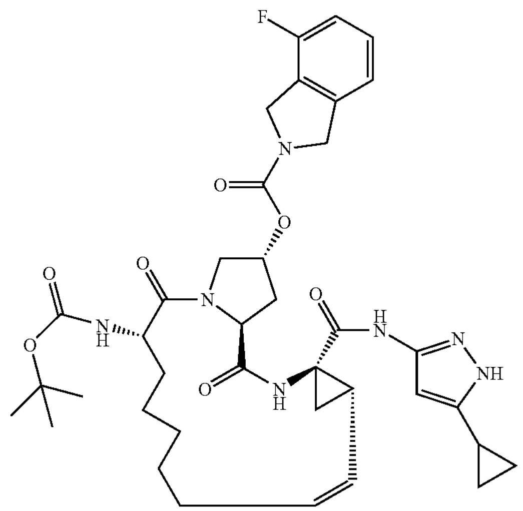 | ¹H NMR (400 MHz, d⁶-DMSO) 12.03 (s, 1H), 9.61 (s, 1H), 8.91 (d, J=11.2 Hz, 1H), 7.34 (m, 1H), 7.08-7.20 (m, 3H), 6.08 (s, 1H), 5.50 (m, 1H), 5.31 (s, 1H), 5.07 (m, 1H), 4.67 (s, 4H), 4.48 (m, 1H), 4.32 (m, 1H), 3.94 (m, 1H), 3.72 (m, 1H), 2.60 (m, 1H), 2.35 (m, 3H), 2.17 (m, 1H), 1.83 (m, 1H), 1.68 (m, 2H), 1.56 (m, 1H), 1.42 (m, 1H), 1.07-1.34 (m, 14 H), 0.89 (m, 3 H), 0.64 (m, 2H). LCMS (APCI+): 734.2 (MH+) |
| 631 | 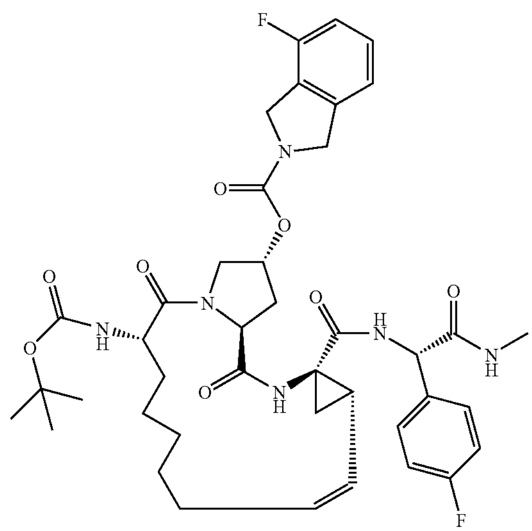 | ¹H NMR (400 MHz, d⁶-DMSO) 8.97 (d, J=6.8 Hz, 1H), 8.29 (m, 1H), 7.96 (d, J=6.4 Hz, 1H), 7.32 (m, 3H), 7.08-7.21 (m, 5H), 5.47 (m, 1H), 5.35 (s, 1H), 5.26 (d, J=6.8 Hz, 1H), 5.13 (m, 1H), 4.68 (s, 4H), 4.50 (m, 1H), 4.30 (m, 1H), 3.95 (m, 1 H), 3.75 (m, 1H), 2.67 (m, 1H), 2.56 (d, J=4.4 Hz, 3H), 2.33 (m, 3 H), 2.14 (m, 1H), 1.68 (m, 2H), 1.09-1.38 (m, 17 H). LCMS (APCI+): 793.1 (MH+) |
| 632 | 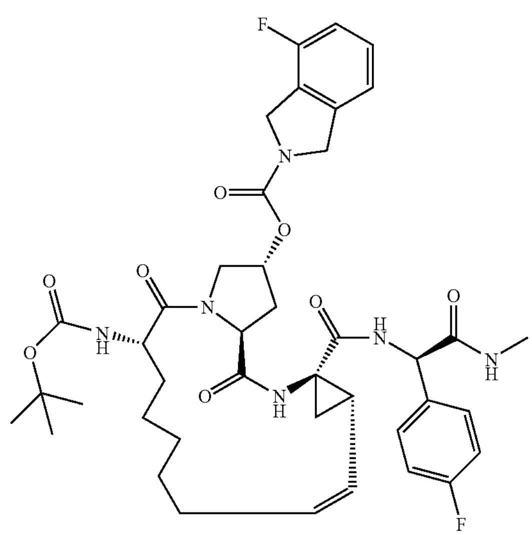 | ¹H NMR (400 MHz, d⁶-DMSO) 9.00 (d, J=6.4 Hz, 1H), 8.36 (d, J=4.4 Hz, 1H), 8.01 (d, J=8.0 Hz, 1H), 7.36 (m, 3H), 7.05-7.21 (m, 5H), 5.29-5.40 (m, 3H), 5.35 (s, 1H), 4.86 (m, 1H), 4.68 (s, 4H), 4.52 (m, 1H), 4.33 (m, 1H), 3.95 (m, 1 H), 3.76 (m, 1H), 2.67 (m, 1H), 2.57 (d, J=4.4 Hz, 3H), 2.32(m, 3H), 2.16 (m, 1H), 1.70 (m, 2H), 1.52 (m, 1H), 1.07-1.38 (m, 16 H). LCMS (APCI+): 793.1 (M + 1) |

TABLE 6-continued
| Compound | Structure | LCMS (m/z) |
|---|---|---|
| 633 | 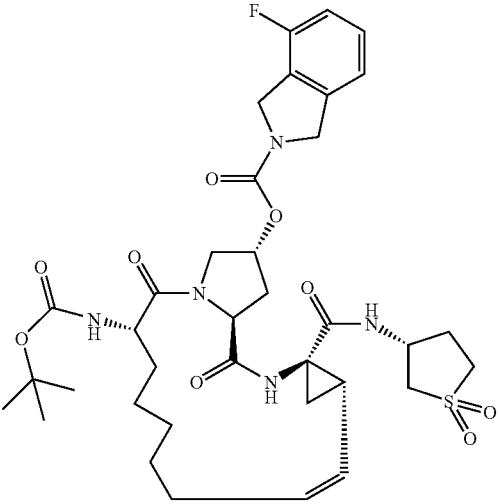 | $^1$H NMR (400 MHz, d$^6$-DMSO) 8.82 (d, J=9.2 Hz, 1H), 7.76 (m, 1H), 7.37 (m, 1H), 7.08-7.21 (m, 3H), 5.45 (m, 1H), 5.29 (s, 1H), 5.22 (m, 1H), 4.67 (s, 4H), 4.47 (m, 2H), 4.29 (m, 1H), 3.91 (m, 1H), 3.68 (m, 1H), 3.36 (m, 1H), 3.23 (m, 1H), 3.10 (m, 1H), 2.92 (m, 1H), 2.61 (m, 1H), 2.31 (m, 2H), 2.23 (m, 2H), 2.11 (m, 1H), 2.02 (m, 1H), 1.67 (m, 2H), 1.44 (m, 2H), 1.07-1.24 (m, 15H). LCMS (APCI+): 746.0 (M + 1) |
| 634 | 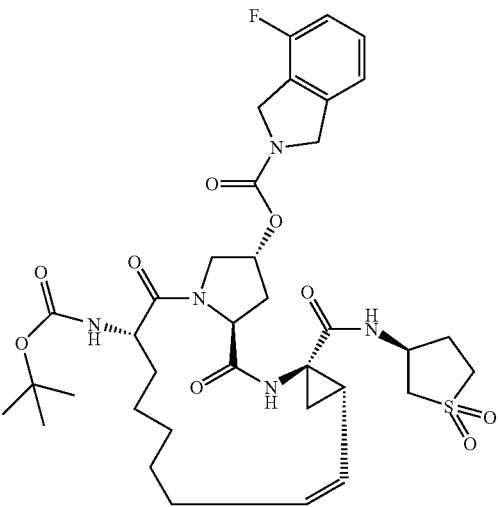 | $^1$H NMR (400 MHz, d$^6$-DMSO) 8.79 (d, J=9.6 Hz, 1H), 7.85 (m, 1H), 7.36 (m, 1H), 7.08-7.15 (m, 3H), 5.46 (m, 1H), 5.29 (s, 1H), 5.19 (m, 1H), 4.67 (s, 2H), 4.66 (s, 2H), 4.46 (m, 2H), 4.31 (m, 1H), 3.91 (m, 1H), 3.69 (m, 1H), 3.29 (m, 1H), 3.25 (m, 1H), 3.13 (m, 1H), 2.90 (m, 1H), 2.61 (m, 1H), 2.31 (m, 4H), 2.11 (m, 1H), 2.01 (m, 1H), 1.67 (m, 2H), 1.43 (m, 2H), 1.07-1.32 (m, 15H). LCMS (APCI+): 746.0 (M + 1) |
| 635 | 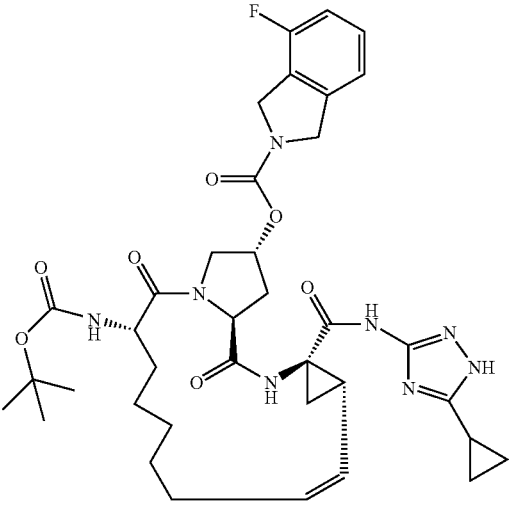 | $^1$H NMR (400 MHz, d$^6$-DMSO) 12.89 (s 1H), 10.89 (s, 1H), 8.81 (m, 1H), 7.35 (m, 1H), 7.11-7.21 (m, 3H), 5.53 (m, 1H), 5.30 (s, 1H), 5.23 (m, 1H), 4.67 (s, 4H), 4.44 (m, 1H), 4.31 (m, 1H), 3.94 (m, 1H), 3.70 (m, 1H), 2.67 (m, 1H), 2.41 (m, 1H), 2.18-2.28 (m, 3H), 1.86 (m, 1H), 1.59 (m, 3H), 0.99-1.24 (m, 16 H), 0.84 (m, 2H), 0.73 (m, 2H). LCMS (APCI+): 735.2 (M + 1) |

TABLE 6-continued
| Compound | Structure | LCMS (m/z) |
|---|---|---|
| 636 | 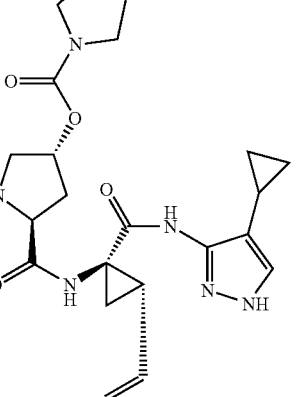 | LCMS (APCI+): 734.2 (M + 1) |
| 637 | 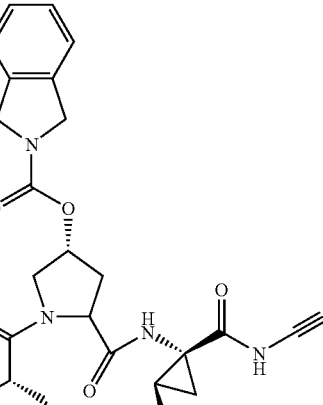 | MS m/z 663.3 (APCI−, M − 1) |
| 638 | 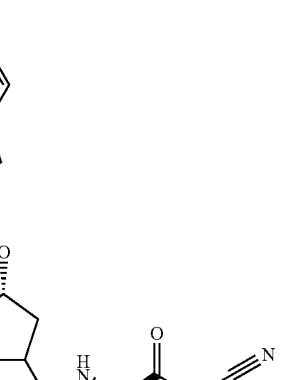 | MS m/z 619.3 (APCI−, M − 1) |

TABLE 6-continued

| Compound | Structure | LCMS (m/z) |
|---|---|---|
| 639 | 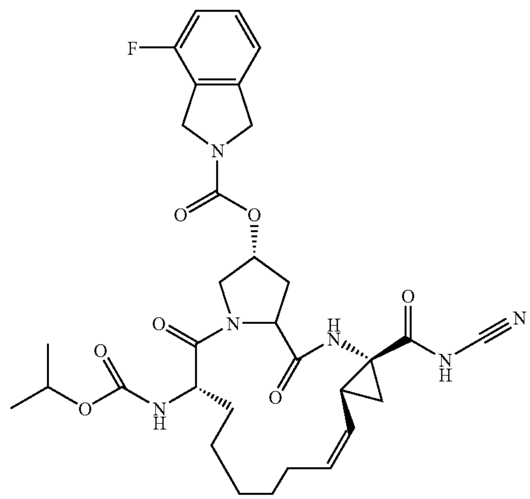 | MS m/z 637.4 (APCI−, M − 1) |
| 640 | 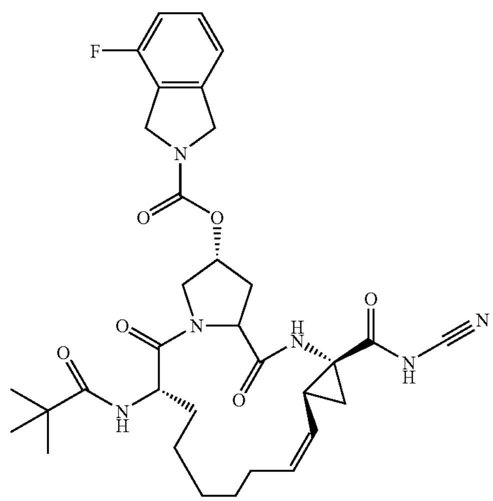 | MS m/z 635.4 (APCI−, M − 1) |
| 641 | 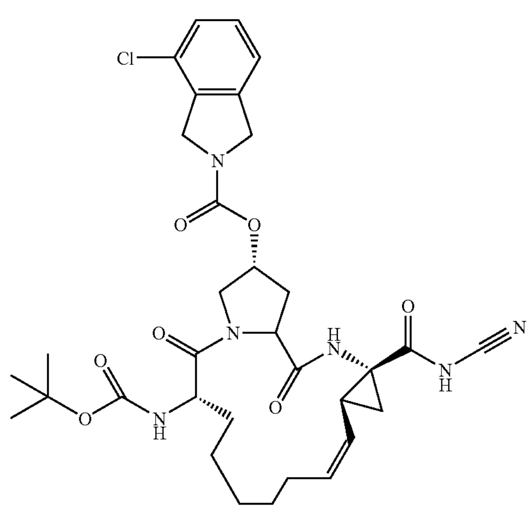 | MS m/z 667.3 (APCI−, M − 1) |

TABLE 6-continued
| Compound | Structure | LCMS (m/z) |
|---|---|---|
| 642 | 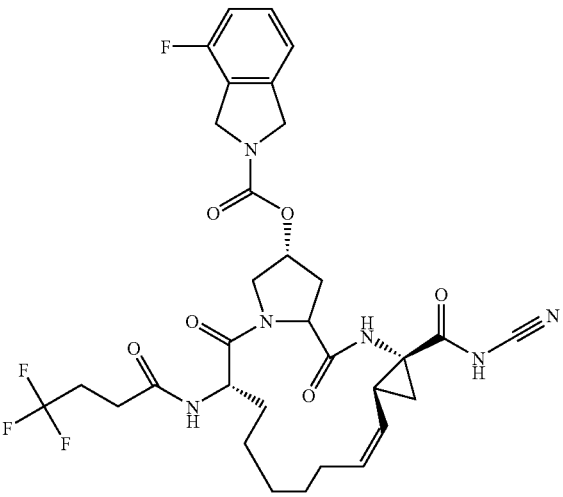 | MS m/z 675.3 (APCI−, M − 1) |
| 643 | 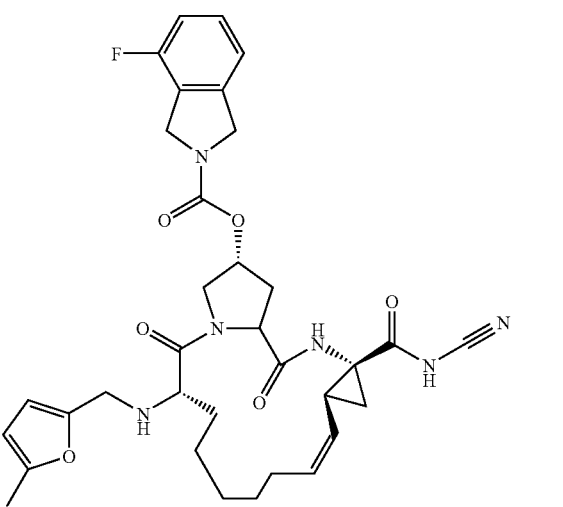 | MS m/z 645.4 (APCI−, M − 1) |
| 644 | 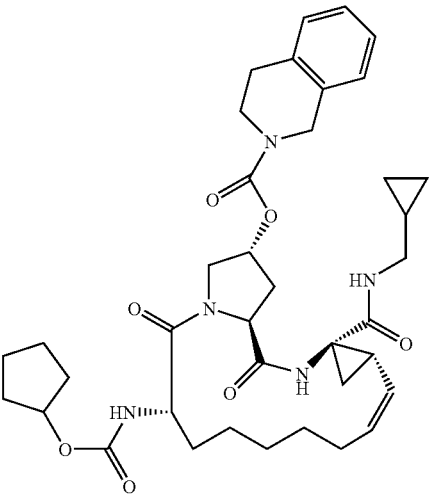 | MS m/z 690.2 (APCI+, M + 1) |

TABLE 6-continued

| Compound | Structure | LCMS (m/z) |
| --- | --- | --- |
| 645 | 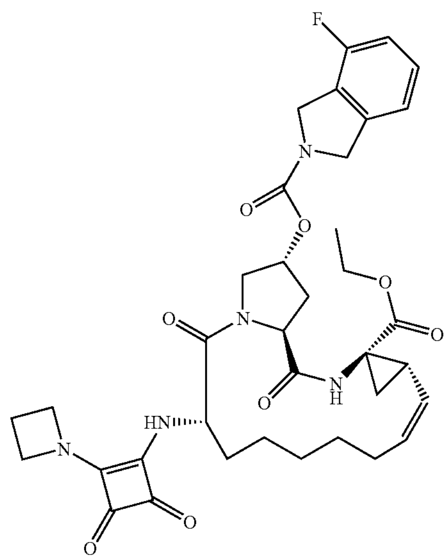 | MS m/z 690.3 (APCI−, M − 1) |
| 646 | 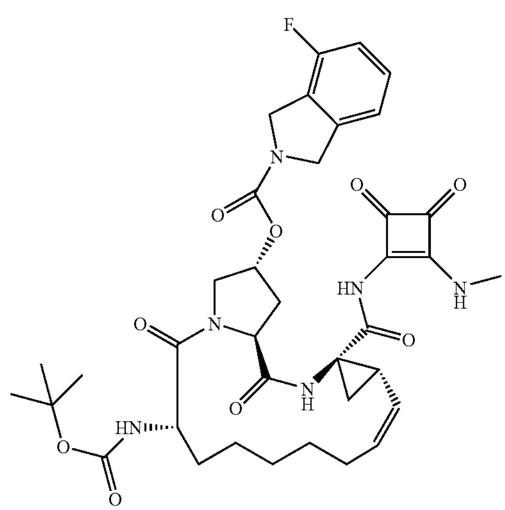 | MS m/z 735.4 (APCI−, M − 1) |
| 647 | 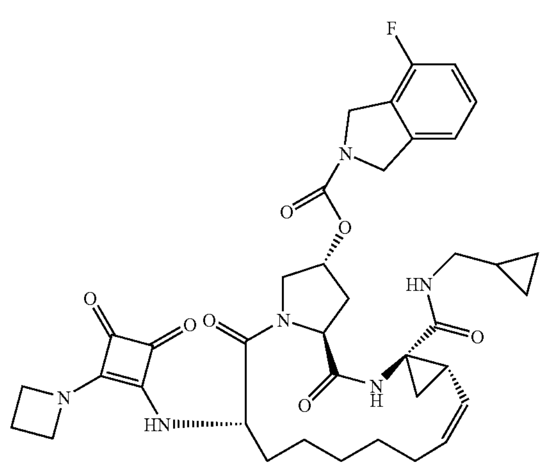 | MS m/z 715.3 (APCI−, M − 1) |

TABLE 6-continued

| Compound | Structure | LCMS (m/z) |
|---|---|---|
| 648 | 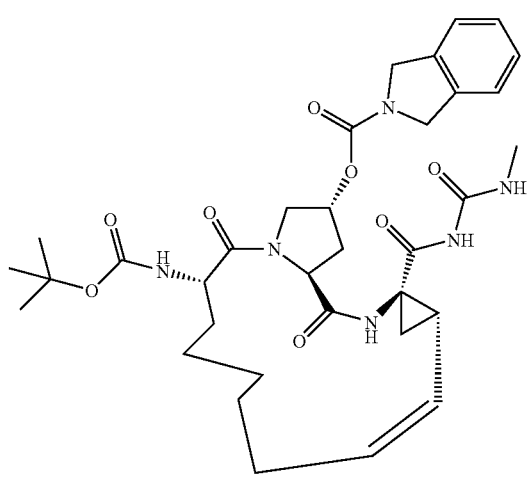 | MS m/z 626.4 (ESI–, M – 1). |

Preparation of NS3 Inhibitors

Section VII

The NS3 inhibitors described in this section may be synthesized in a manner similar to that described in Scheme 4, Section III above, substituting the sulfonamide in the last coupling step with an amide or a urea instead. In addition, in lieu of DBU, the product yield was improved when amide was de-protonated with a stronger base (e.g. NaH) first prior to addition to the activated acid intermediate. In the latter case, THF may be used in lieu of DCE, and the reaction was carried out at room temperature.

Compound 701

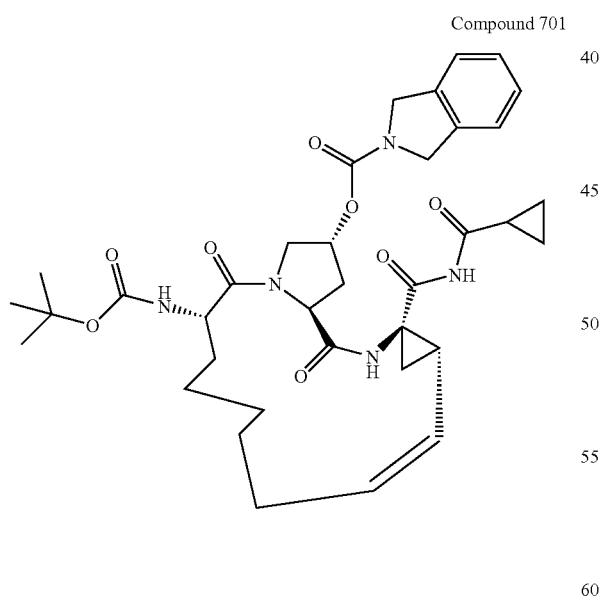

$^1$H NMR (d$^6$-Acetone, 400 MHz) δ0.62-1.76 (m, 24H), 2.40-2.48 (m, 3H), 2.65-2.68 (m, 2H), 3.84-3.87 (m, 1H), 4.15-4.19 (m, 1H), 4.45-4.48 (m, 1H), 4.59-4.72 (m, 5H), 5.08 (t, 1H), 5.43 (br s, 1H), 5.64 (q, 1H), 6.11-6.14 (m, 1H), 7.24-7.36 (m, 4H), 8.27 (br s, 1H), 9.94 (br s, 1H). MS (APCI–) m/z 676.2 (M–1).

Compound 702

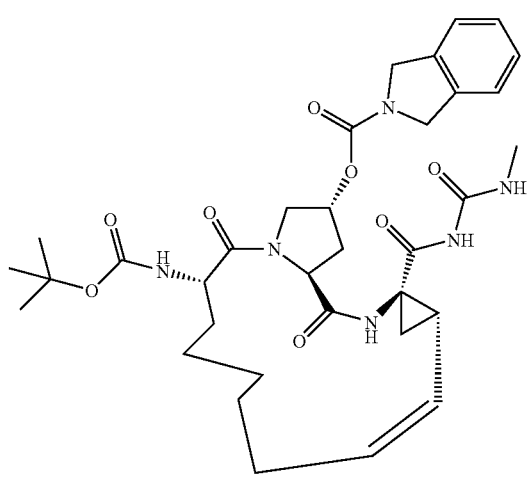

LCMS (APCI–) m/z 665.2 (M–1).

Compound 703

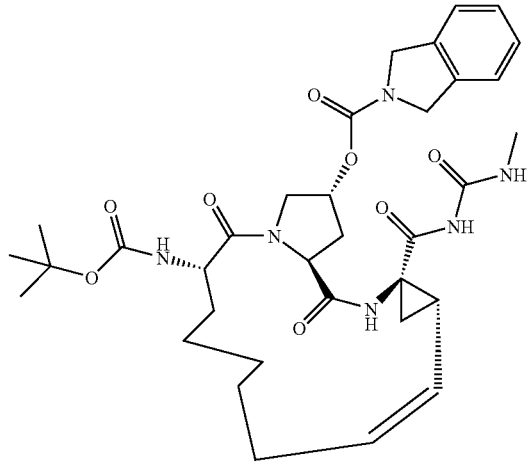

LCMS (APCI–, 665.2, M–1)

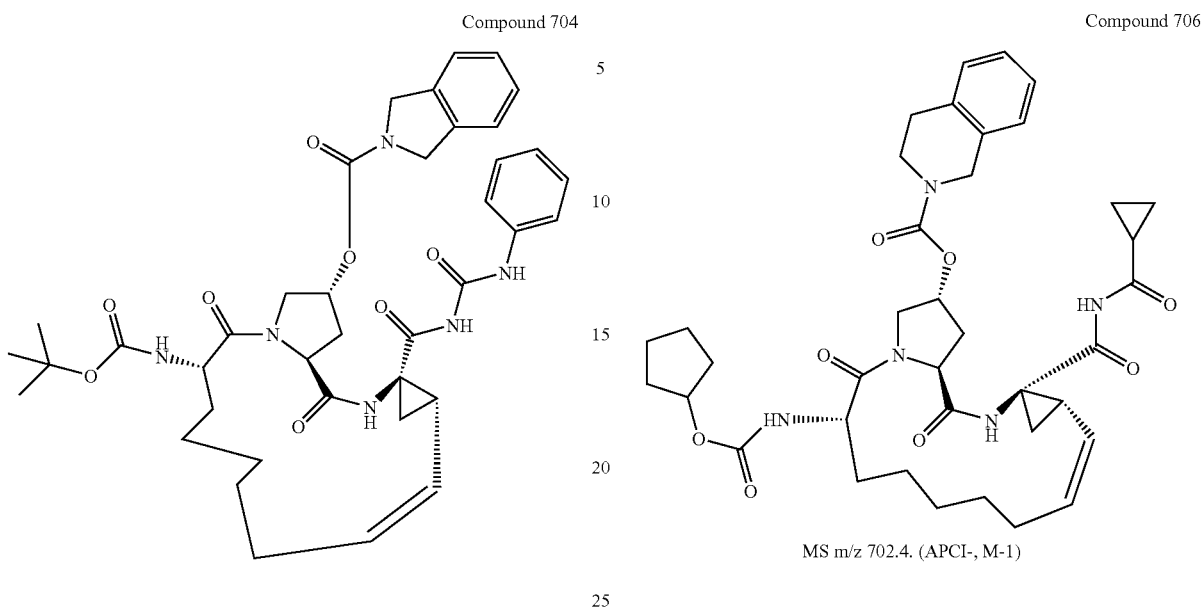

Compound 704

Compound 706

MS m/z 702.4. (APCI-, M-1)

HNMR (d6-acetone): 10.48 (s, 1H), 9.60 (s, 1H), 8.19 (s, 1H), 7.55-7.57 (m, 2H), 7.25-7.36 (m, 6H), 7.06-7.10 (m, 1H), 6.12 (br d, 1H), 5.63-5.70 (m, 1H), 5.45 (br s, 1H), 5.15 (t, 1H), 4.60-4.73 (m, 5H), 4.48 (br d, 1H), 4.15-4.19 (m, 1H), 3.84-3.88 (m, 1H), 2.66-2.76 (m, 1H), 2.46-2.56 (m, 3H), 1.78-1.89 (m, 3H), 1.67-1.70 (m, 1H), 1.21-1.55 (m, 16H). LCMS (APCI+, 629.1, MH-Boc)

Preparation of NS3 Inhibitors

Section VIII

Synthesis of Compound 801:

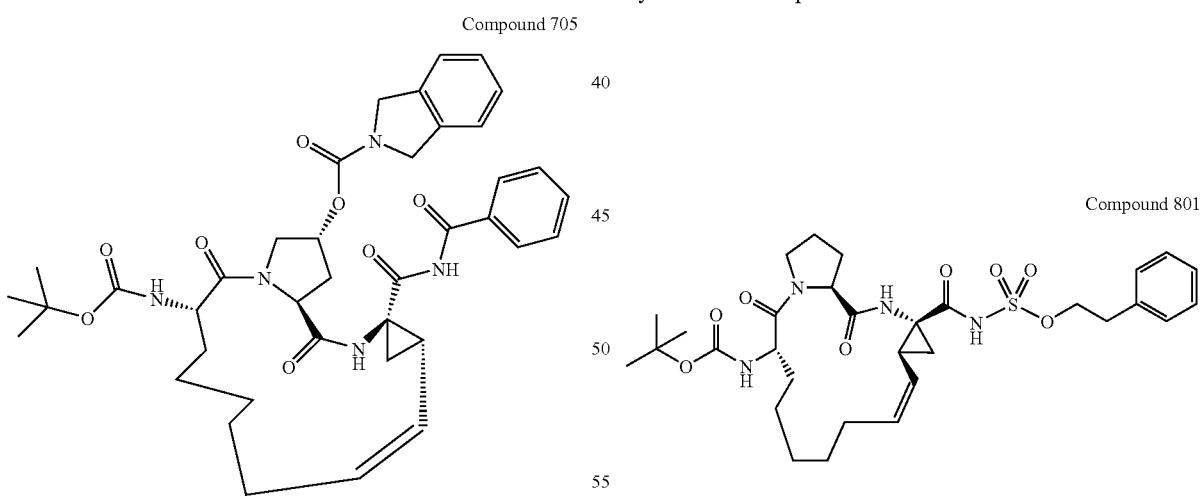

Compound 705

Compound 801

HNMR (d6-acetone): 11.07 (s, 1H), 8.47 (s, 1H), 7.88-7.90 (m, 2H), 7.62-7.66 (m, 1H), 7.54-7.58 (m, 2H), 7.27-7.35 (m, 4H), 6.16 (br d, 1H), 5.61-5.68 (m, 1H), 5.46 (br s, 1H), 5.00 (t, 1H), 4.60-4.72 (m, 5H), 4.49 (br d, 1H), 4.18-4.22 (m, 1H), 3.88-3.92 (m, 1H), 2.66-2.78 (m, 1H), 2.44-2.52 (m, 3H), 1.77-1.94 (m, 3H), 1.23-1.58 (m, 17H). LCMS (APCI+, 614.2, MH-Boc).

Compound 801 was prepared according to the same procedures as described for the inhibitors in Section IV. The phenethyl sulfamate moiety was also prepared in the same fashion as most of the sulfamide intermediates as described in Section IV. A synthetic scheme for preparing Compound 801 is shown below (Scheme 6). LCMS 631.3 (M−1, APCI−)

Scheme 6

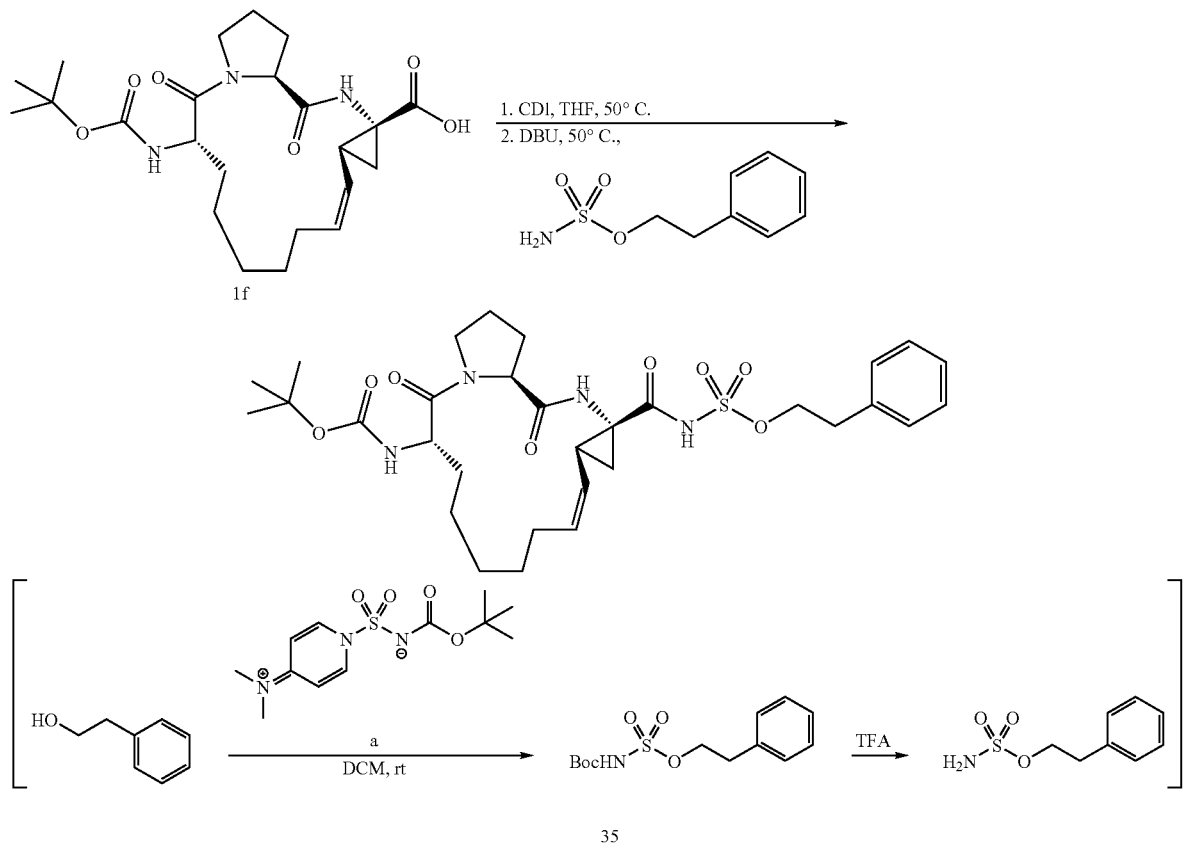

Preparation of NS3 Inhibitors

Section IX

The compounds described in this section and summarized in Table 7 may be synthesized as outlined in Scheme 7 below for which the following description of the synthesis of compound 901 is exemplary. The aldehydes and ketones employed for the synthesis of the compounds of Table 7 were purchased from commercial sources.

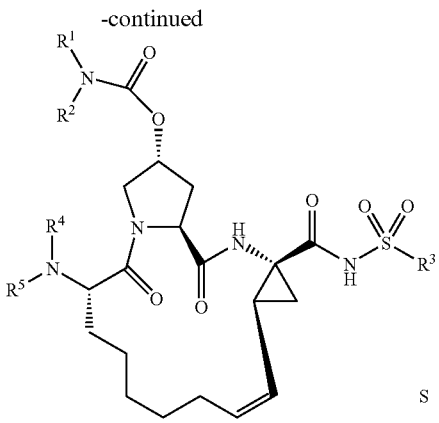

Scheme 7

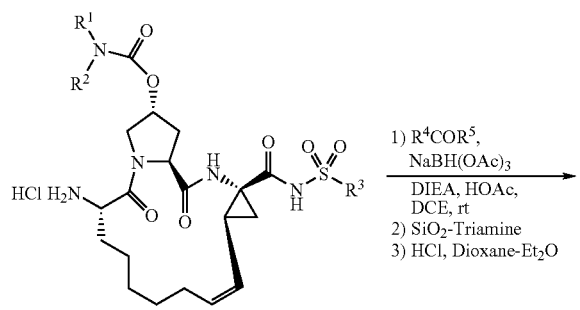

Synthesis of (1S,4R,6S,14S,18R)-14-(3-(trifluoromethyl)benzylamino)-4-(cyclopropanesulfonyl)aminocarbonyl-18-(4-fluoro-1,3-dihydro-isoindole-2-carbonyloxyl)-2,15-dioxo-3,16-diaza-tricyclo[14.3.0.0$^{4,6}$]nonadec-7-ene (901).

To a suspension of Compound 107 from Section I of the inhibitor synthesis (30.0 mg, 0.045 mmol) in dry DCE (0.5 mL) were sequentially added DIEA (1.10 equiv.) and 3-(trifluoro methyl)benzaldehyde (1.10 equiv.) and the resulting homogeneous mixture was stirred at rt for 30 minutes. HOAc (4.00 equiv.) and NaBH(OAc)$_3$ (2.00 equiv.) were sequentially added and the reaction was stirred at rt for 18 h. The mixture was diluted with dry DCE (0.5 mL) and treated with excess SiO$_2$-Triamine (7 equiv., 1.76 mmol/g) and DIEA (2 equiv.). The mixture was stirred for 2 h and was loaded onto a pipette SiO$_2$ column. The column was eluted first with CH$_2$Cl$_2$ then EtOAc. The EtOAc fraction was concentrated and the resultant solid was washed thoroughly with dry hexanes and dried in vacuum to give the title compound (22 mg, 62%) in free base form as a white solid.

The corresponding mono-hydrogen chloride salt was prepared as follows. The above free base amine was treated with dry E$_2$O (2 mL) and EtOAc was added dropwise until homogeneous. To the solution was added 4 M HCl in dioxane (0.25 mL) and the mixture was stirred at rt for 30 minutes and concentrated. The residual solid was washed with dry Et$_2$O and dried in vacuum to give the amine HCl salt as a white powder: $^1$H NMR (DMSOd$^6$, 400 MHz) δ0.97-1.13 (m, 4H), 1.13-1.32 (m, 2H), 1.42 (br, s, 4H), 1.52-1.59 (m, 1H), 1.60-1.67 (m, 1H), 1.85 (br, s, 3H), 2.11-2.21 (m, 1H), 2.38-2.46 (m, 2H), 2.88-2.97 (m, 1H), 3.82-3.92 (m, 1H), 3.97-4.09 (br, m, 2H), 4.31 (br, s, 2H), 4.54 (q, 1H), 4.68 (s, 4H), 5.15 (t, 1H), 5.42 (s, 1H), 5.62 (q, 1H), 6.97-7.19 (m, 2H), 7.25-7.37 (m, 1H), 7.61 (br, t, 1H), 7.74 (t, 2H), 7.86 (br, s, 1H), 9.12 (s, 1H), 9.64 (br, s, 2H), 11.09 (s, 1H); MS calcd for C$_{38}$H$_{44}$F$_4$N$_5$O$_7$S (m/z 790.29, MH+), observed m/z 790.3.

Additional compounds described in this section synthesized as outlined below and for which the following description of the synthesis of compound 927 is exemplary. The bromo-ketones employed for the synthesis of theses compounds were purchased from commercial sources.

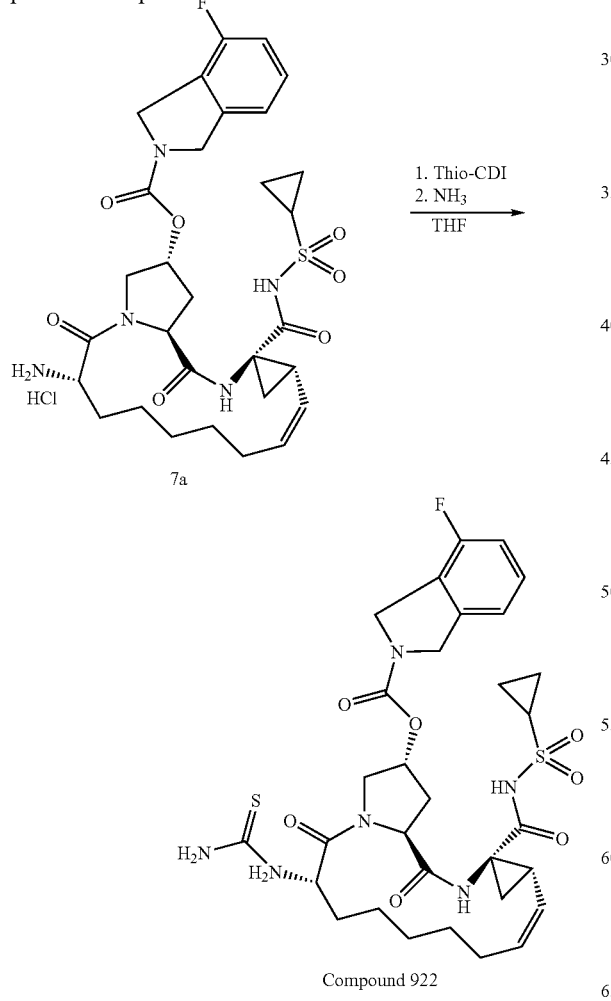

(2R,6S,13aS,14aR,16aS,Z)-14a-(cyclopropylsulfonylcarbamoyl)-5,16-dioxo-6-thioureido-1,2,3,5,6,7,8,9,10,11,13a,14,14a,15,16,16a-hexadecahydrocyclopropa[e]pyrrolo[1,2-a][1,4]diazacyclopentadecin-2-yl-4-fluoroisoindoline-2-carboxylate (compound 922)

To a mixture of compound 7a (250 mg, 0.3742 mmol) in 5 mL THF was added triethylamine (0.1043 ml, 0.7483 mmol) and the resulting mixture was stirred vigorously for 5 minutes to prevent clumping. To the reaction was then added di(1H-imidazol-1-yl)methanethione (100.0 mg, 0.5612 mmol) and mixture was continued to stir vigorously for one hour at rt. Ammonia gas was bubbled into the solution for 30 minutes at the rate of approximately 10 cm$^3$ per minute. The vial was sealed and stirred for 18 hr. LC/MS indicated reaction completion. The solution was concentrated and purified by reverse phase chromatography (Biotage Horizon, Flash 25+ column using linear 15-85% acetonitrile/H2O gradient) to obtain compound 2 (200 mg, 0.290 mmol, 77% yield) as a yellow solid.

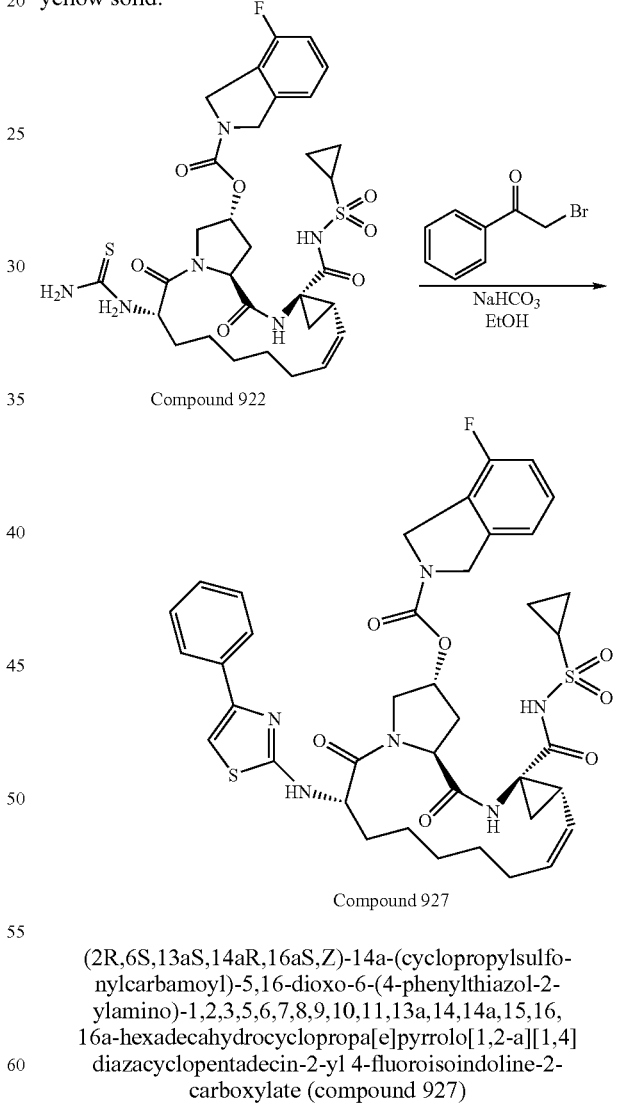

(2R,6S,13aS,14aR,16aS,Z)-14a-(cyclopropylsulfonylcarbamoyl)-5,16-dioxo-6-(4-phenylthiazol-2-ylamino)-1,2,3,5,6,7,8,9,10,11,13a,14,14a,15,16,16a-hexadecahydrocyclopropa[e]pyrrolo[1,2-a][1,4]diazacyclopentadecin-2-yl 4-fluoroisoindoline-2-carboxylate (compound 927)

A mixture of compound 922 (50 mg, 0.0724 mmol), NaHCO3 (12.2 mg, 0.145 mmol), and 2-bromo-1-phenylethanone (15.1 mg, 0.0760 mmol) in 1 mL EtOH was heated in a sealed tube at 100° with stirring for 30 minutes. LCMS indicated reaction completion. Concentrated in vacuo and purified by reverse phase chromatography (Biotage Horizon, Flash 12+ column using linear 15-85% acetonitrile/H2O gradient) to obtain compound 3 (25 mg, 0.032 mmol, 44% yield) as a white solid.

TABLE 7

| Compound | Structure | LCMS (m/z) |
|---|---|---|
| 900 | 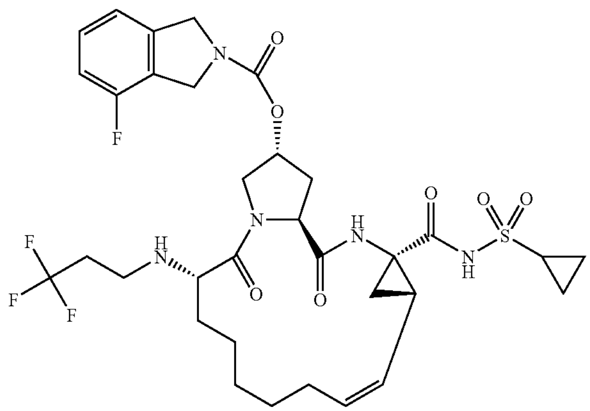 | 728.8 (ESI MS+) |
| 901 | 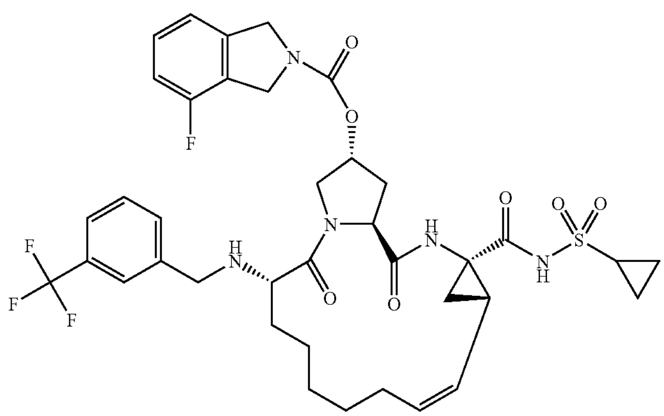 | 790.3 (ESI MS+) |
| 902 | 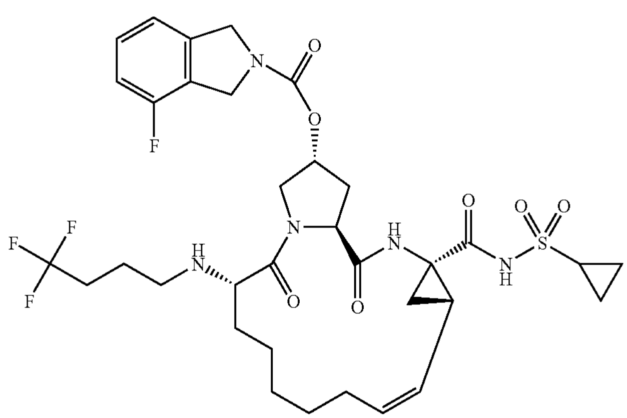 | 742.3 (ESI MS+) |

TABLE 7-continued
| Compound | Structure | LCMS (m/z) |
|---|---|---|
| 903 | 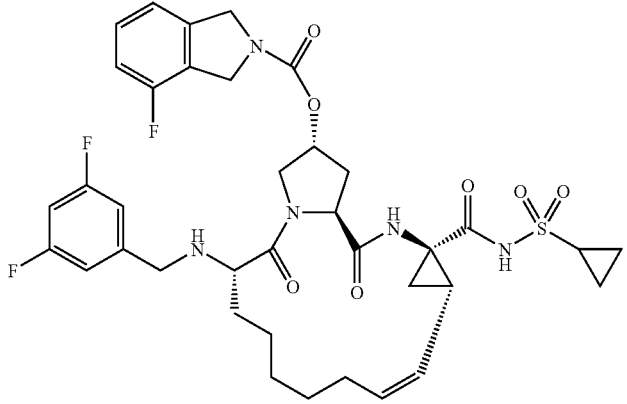 | 758.2 (ESI MS+) |
| 904 | 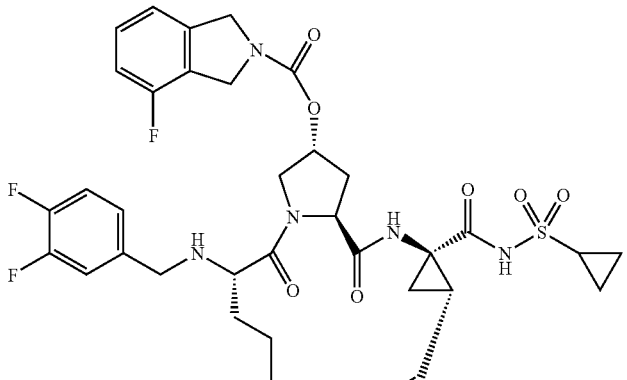 | 758.2 (ESI MS+) |
| 905 | 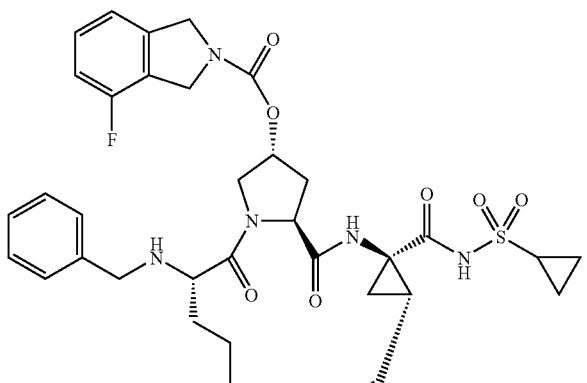 | 722.2 (ESI MS+) |

TABLE 7-continued

| Compound | Structure | LCMS (m/z) |
|---|---|---|
| 906 | 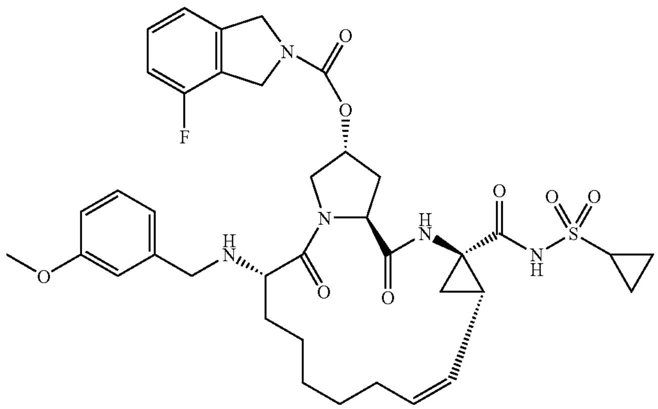 | 752.3 (ESI MS+) |
| 907 | 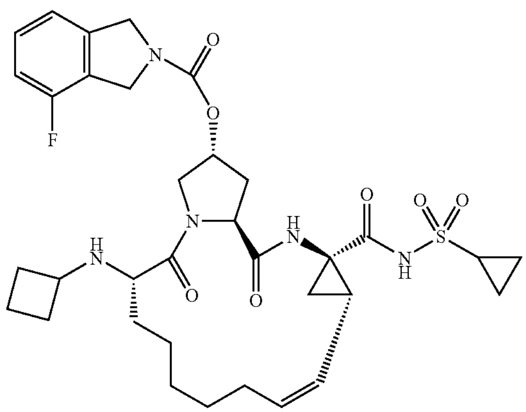 | 686.2 (ESI MS+) |
| 908 | 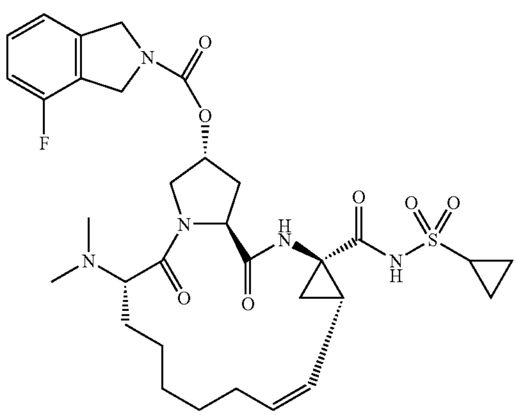 | 660.2 (ESI MS+) |

TABLE 7-continued

| Compound | Structure | LCMS (m/z) |
|---|---|---|
| 909 | 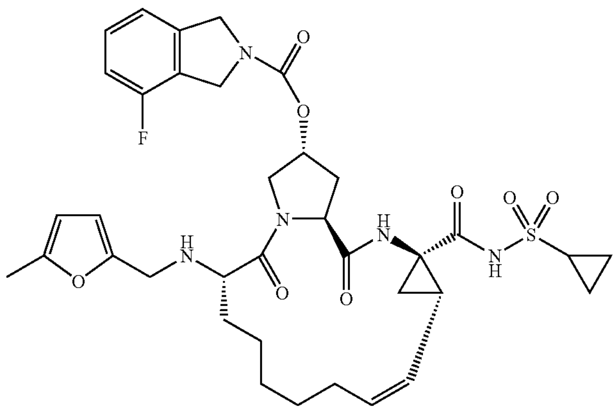 | 726.3 (ESI MS+) |
| 910 | 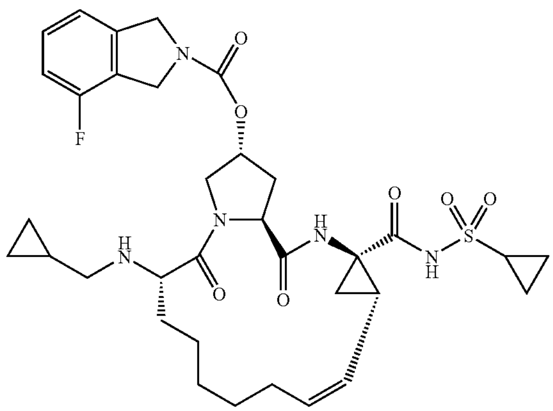 | 686.2 (ESI MS+) |
| 911 | 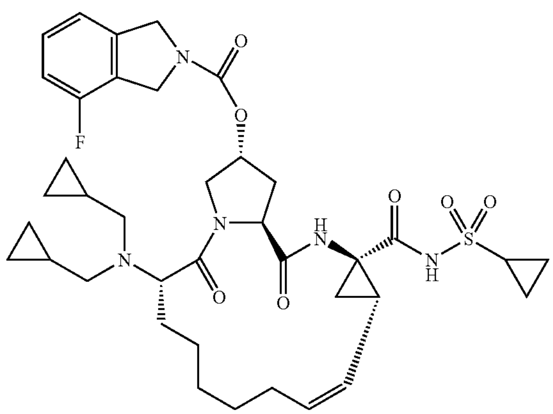 | 740.3 (ESI MS+) |

TABLE 7-continued
| Compound | Structure | LCMS (m/z) |
|---|---|---|
| 912 | 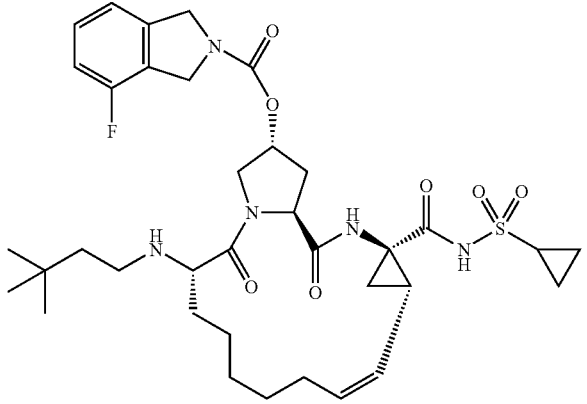 | 716.3 (ESI MS+) |
| 913 | 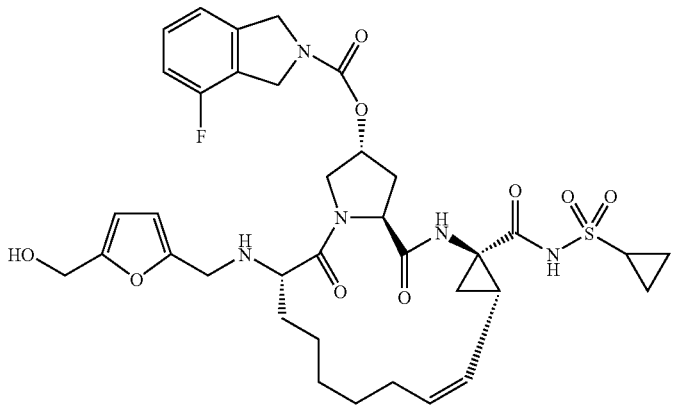 | LCMS:724.4 |
| 914 | 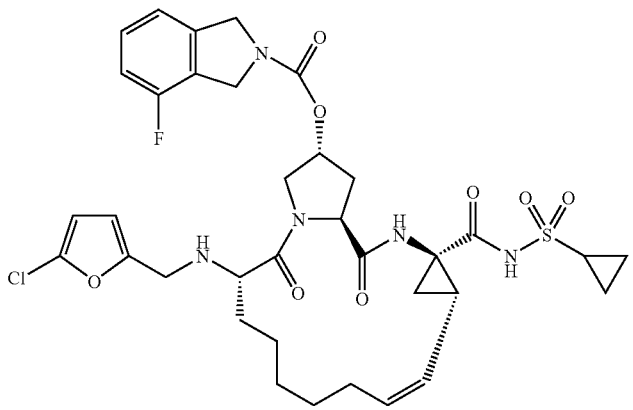 | LCMS:746.2 |

TABLE 7-continued

| Compound | Structure | LCMS (m/z) |
|---|---|---|
| 915 | 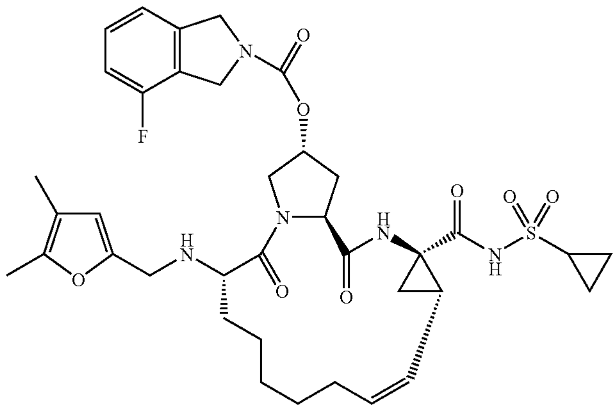 | LCMS:740.3 |
| 916 | 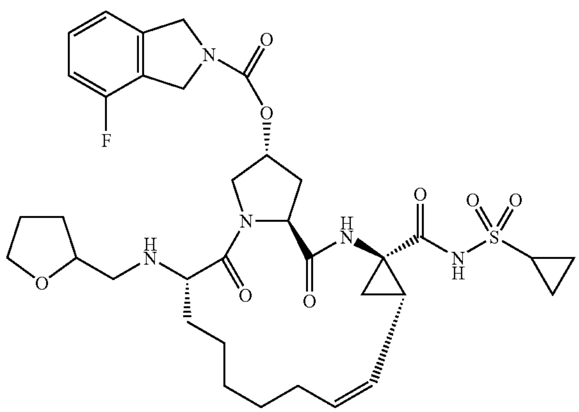 | LCMS:716.3 |
| 917 | 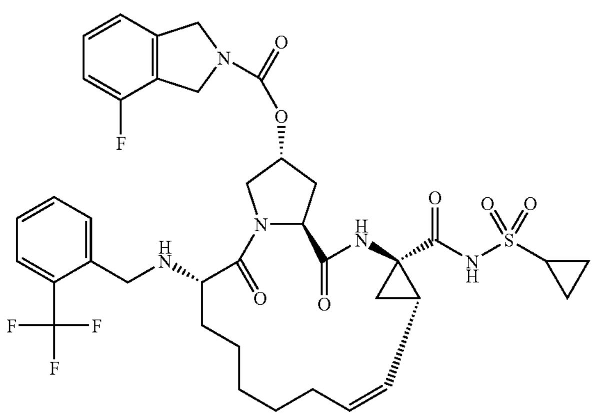 | LCMS:790.3 |

TABLE 7-continued

| Compound | Structure | LCMS (m/z) |
|---|---|---|
| 918 | 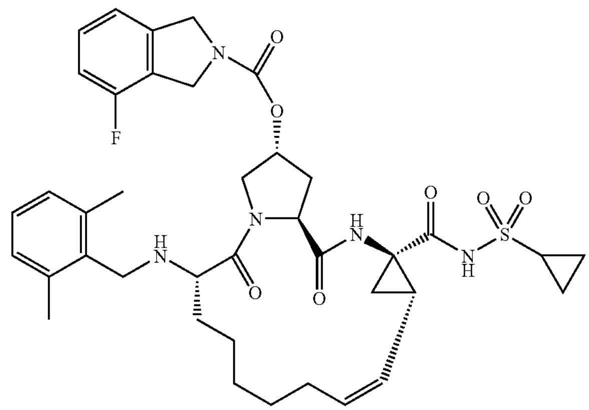 | LCMS:750.4 |
| 919 | 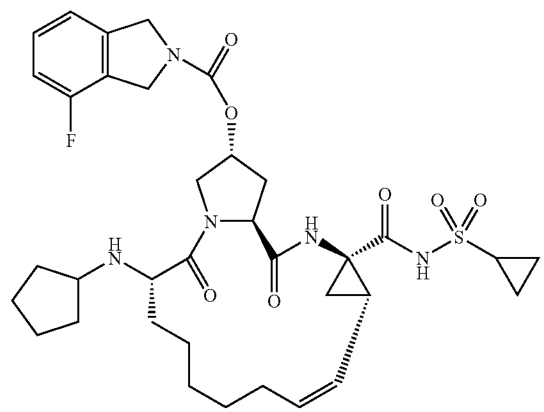 | LCMS:700.3 |
| 920 | 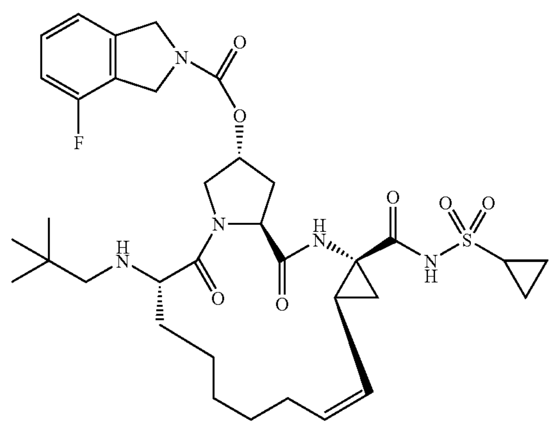 | 1H NMR (CDCl3, 400 MHz) d 0.80 (s, 9 H), 0.80-1.54 (m, 14 H), 1.67 (br, s, 2 H), 1.94 (t, 1 H), 2.19 (d, 2 H), 2.45-2.48 (m, 1 H), 2.53-2.60 (m, 2 H), 2.89-2.93 (m, 1 H), 3.41 (br, s, 1 H), 3.85 (dd, 2 H), 4.54-4.83 (m, 5 H), 5.01 (t, 1 H), 5.46 (s, 1 H), 5.72 (q, 1 H), 6.93-7.06 (m, 3 H), 10.15 (s, 1 H); LCMS (APCI+): 702.5 |

TABLE 7-continued

| Compound | Structure | LCMS (m/z) |
|---|---|---|
| 921 | 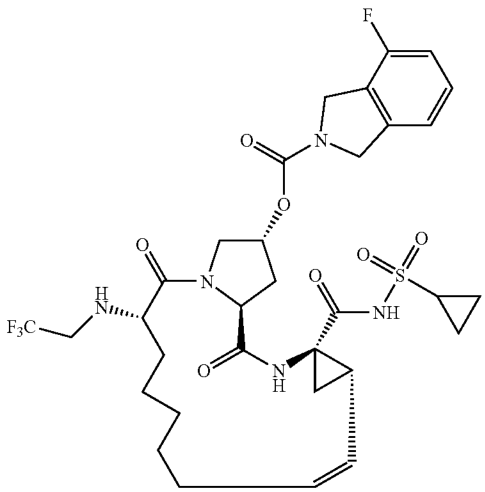 | MS m/z 714 (APCI+, M + 1) |
| 922 | 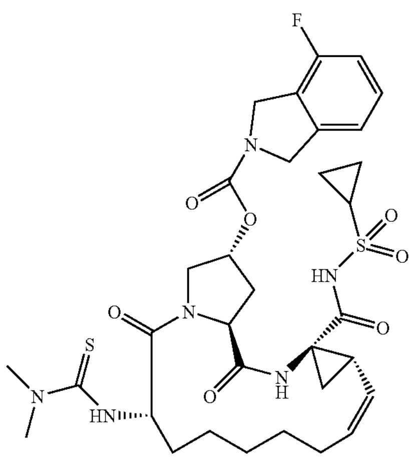 | MS m/z 717.2 (APCI–, M – 1) |
| 923 | 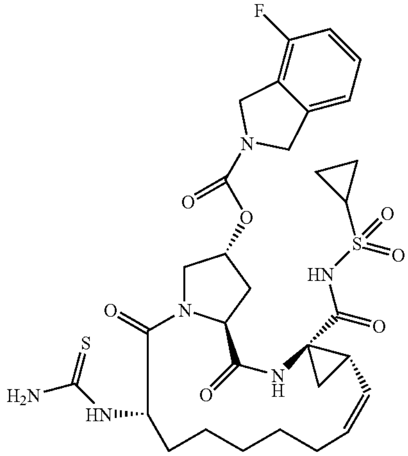 | MS m/z 689.2 (APCI–, M – 1) |

TABLE 7-continued

| Compound | Structure | LCMS (m/z) |
|---|---|---|
| 924 | 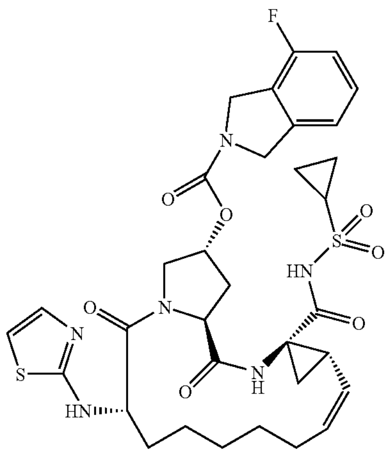 | MS m/z 713.3 (APCI−, M − 1) |
| 925 | 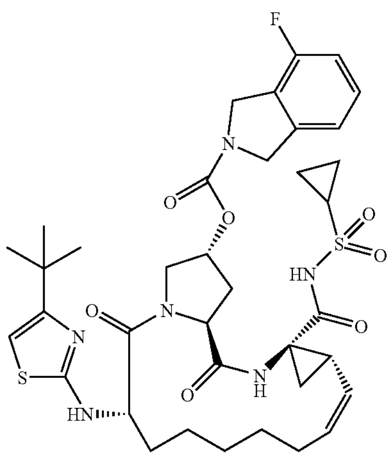 | 1H NMR (400 MHz, d6-acetone); 1.00-1.04 (m, 3 H), 1.13 (m 12 H), 1.25-1.95 (m 12 H), 2.45 (m, 2 H), 2.92 (m, 1 H), 4.1 (m, 1 H), 4.42 (m, 1 H), 4.54-4.66 (m, 4 H), 4.72 (s, 1 H), 4.99-5.04 (m, 1 H), 5.58 (m, 1 H), 5.70 (m, 1 H), 5.92 (d, 1 H), 7.05-7.13 (m, 2 H), 7.22 (d, 1 H), 7.38 (d, 1 H). MS m/z 769.3 (APCI−, M − 1) |
| 926 | 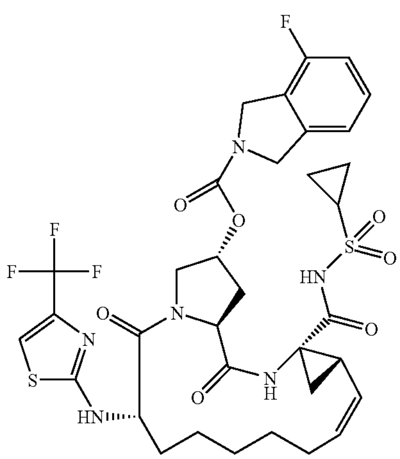 | MS m/z 781.2 (APCI−, M − 1) |

TABLE 7-continued

| Compound | Structure | LCMS (m/z) |
|---|---|---|
| 927 | 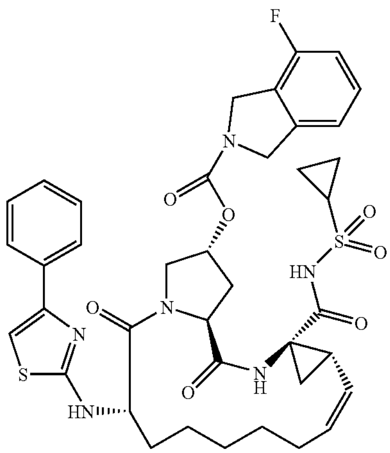 | 1H NMR (400 MHz, d6-acetone); 0.99-1.04 (m, 3 H), 1.10-1.15 (m 3 H), 1.26-1.94 (m 12 H), 2.36-2.42 (m, 1 H), 2.90-2.94 (m, 1 H), 3.89 (m, 1 H), 4.09-4.12 (m, 1 H), 4.18-4.30 (m, 2 H), 4.40-4.44 (m, 1 H), 4.57 (m, 1 H), 4.80-4.88 (m, 1 H), 4.99-5.04 (m, 1 H), 5.71-5.74 (m, 2 H), 6.79 (s, 1 H), 6.88 (d, 1 H), 6.97-7.04 (m, 1 H), 7.06-7.14 (m, 2 H), 7.31 (m, 2 H), 7.63-7.66 (m, 2 H). MS m/z 789.3 (APCI−, M − 1) |
| 928 | 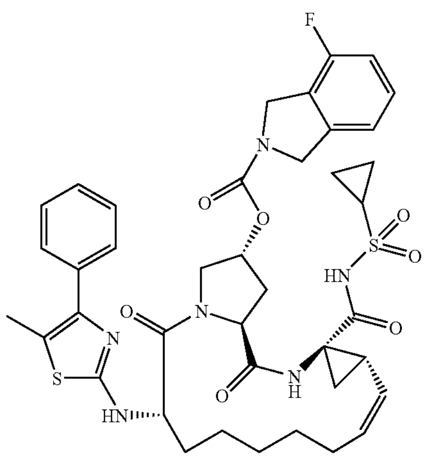 | 1H NMR (400 MHz, d6-acetone); 0.72 (m, 3 H), 0.87-0.94 (m 3 H), 1.19-1.91 (m 12 H), 2.21-2.27 (m, 1 H), 2.31 (s, 3H), 2.58-2.66 (m, 1 H), 4.20 (m, 1 H), 4.36 (m, 2 H), 4.56-4.66 (m, 3 H), 4.94 (bs, 1 H), 5.39 (m, 2 H), 5.52 (m, 1 H), 7.01-7.20 (m, 3 H), 7.29-7.37 (m, 3 H), 7.59 (d, 2 H). MS m/z 803.4 (APCI−, M − 1) |
| 929 | 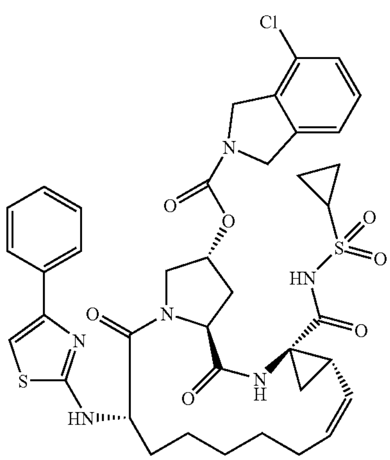 | 1H NMR (400 MHz, d6-acetone); 0.87 (m, 3 H), 1.01 (m 3 H), 1.11-2.01 (m 12 H), 2.36-2.45 (m, 1 H), 2.88-2.95 (m, 1 H), 3.91 (m, 1 H), 4.09-4.60 (m, 5 H), 4.79-4.87 (m, 1 H), 5.00-5.05 (m, 1 H), 5.67-5.76 (m, 2 H), 6.78 (d, 1 H), 6.88 (d, 1 H), 6.99-7.33 (m, 6H), 7.61-7.69 (m, 2 H). MS m/z 805.3 (APCI−, M − 1) |

Preparation of NS3 Inhibitors
Section X
The compounds described in this section and summarized in Table 8 may be synthesized as outlined in Schemes 8-10 below.
The following description in Scheme 8 and following experimental of the synthesis of compounds 1020 and 1022 is exemplary of compounds with the 8-oxa substitution.
Scheme 8
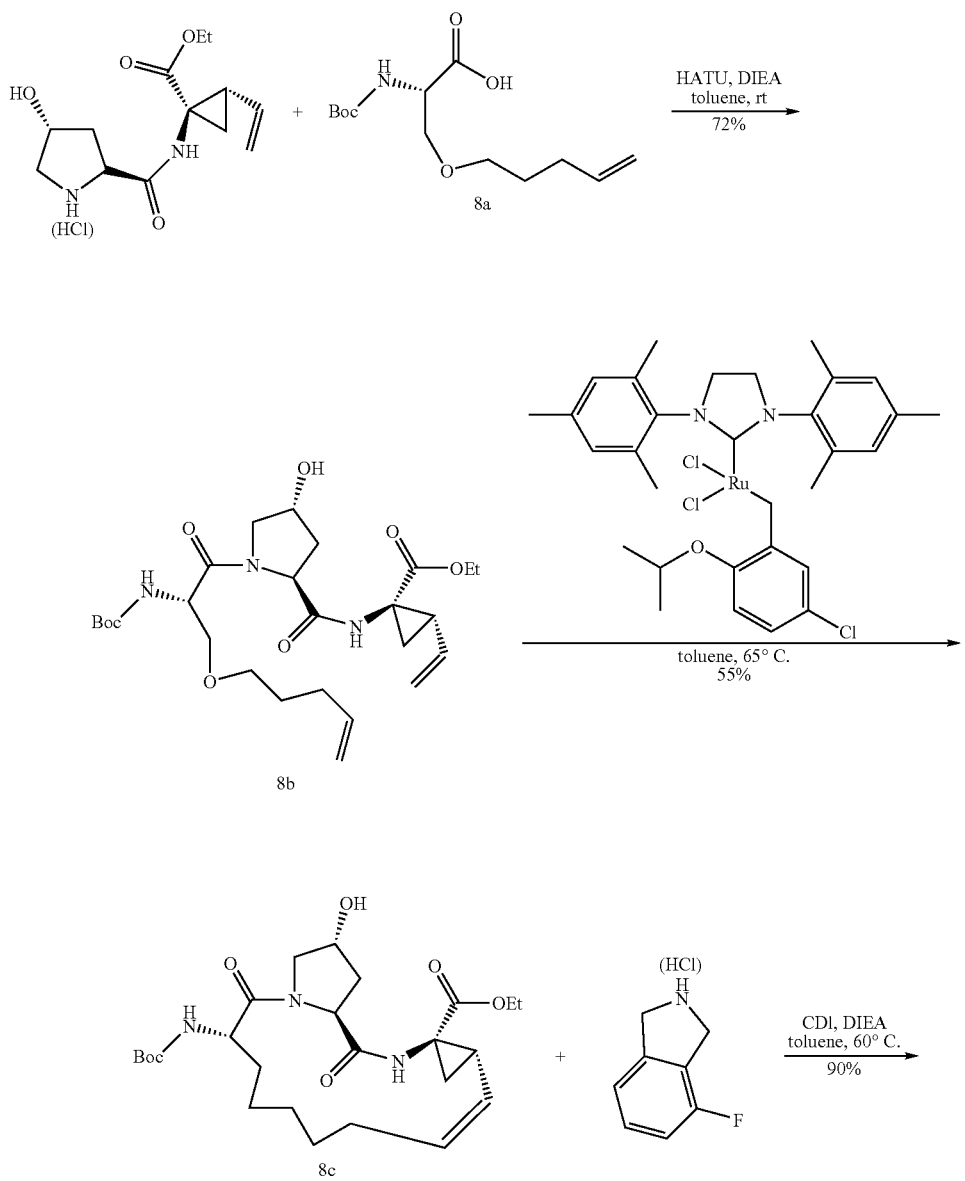

-continued
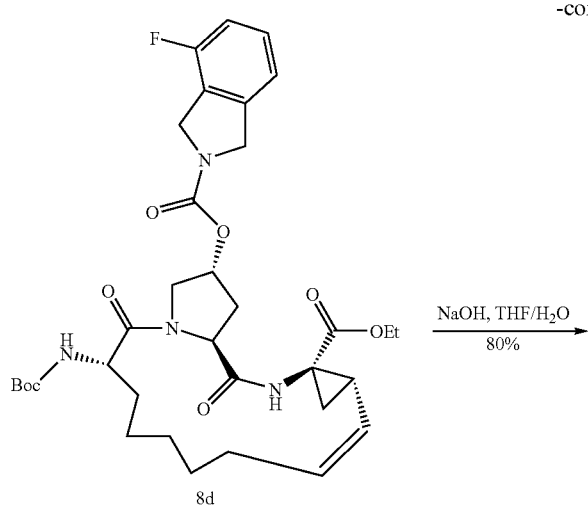
8d
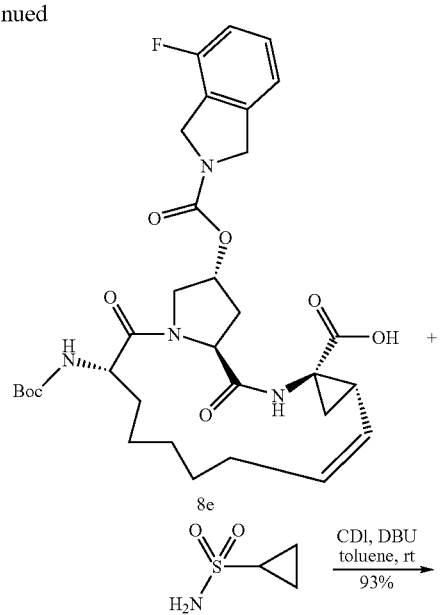
8e
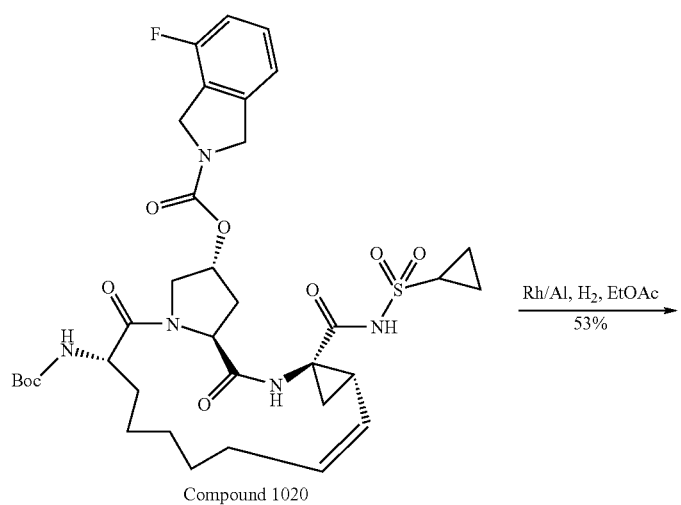
Compound 1020 → Compound 1022
Step 1: Synthesis of (1R,2S)-ethyl 1-((2S,4R)-1-((S)-2-(tert-butoxycarbonylamino)-3-(pent-4-enyloxy) propanoyl)-4-hydroxypyrrolidine-2-carboxamido)-2-vinylcyclopropanecarboxylate (8b)
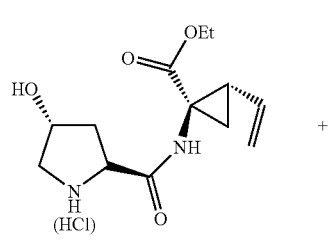
-continued
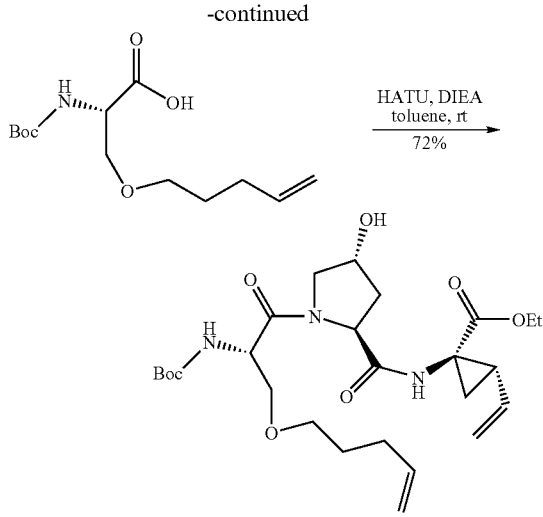

(1R,2S)-ethyl-1-((2S,4R)-4-hydroxypyrrolidine-2-carboxamido)-2-vinylcyclopropanecarboxylate hydrochloride salt (WO2005095403) (0.770 g, 2.45 mmol), (S)-2-(tert-butoxycarbonylamino)-3-(pent-4-enyloxy)propanoic acid (WO2004094452) (0.68 g, 2.50 mmol) and HATU (1.025 g, 2.696 mmol) in toluene (18 mL) and ACN (2 mL) was added DIEA (d 0.742) (1.281 mL, 7.352 mmol) at 0° C. The reaction warmed to rt and stirred at rt for 1 hr. Ethyl acetate (30 mL) and water (20 mL) was added. The organic layer was separated and washed with brine, dried over sodium sulfate. After removal of solvent, the residue was purified by chromatography (Ethyl acetate) to give (1R,2S)-ethyl 1-((2S,4R)-1-((S)-2-(tert-butoxycarbonylamino)-3-(pent-4-enyloxy)propanoyl)-4-hydroxypyrrolidine-2-carboxamido)-2-vinylcyclopropanecarboxylate as white wax solid (0.92 g, 71.7%). MS: Calcd.: 523; Found: [M+H]+ 524.

Step 2: Synthesis of (2R,6S,13aS,14aR,16aS,Z)-ethyl 6-(tert-butoxycarbonylamino)-2-hydroxy-5,16-dioxo-2,3,5,6,7,9,10,11,13a,14,14a,15,16,16a-tetradecahydro-1H-cyclopropa(i)pyrrolo[1,2-e][1,5,8]oxadiazacyclopentadecine-14a-carboxylate (8c)

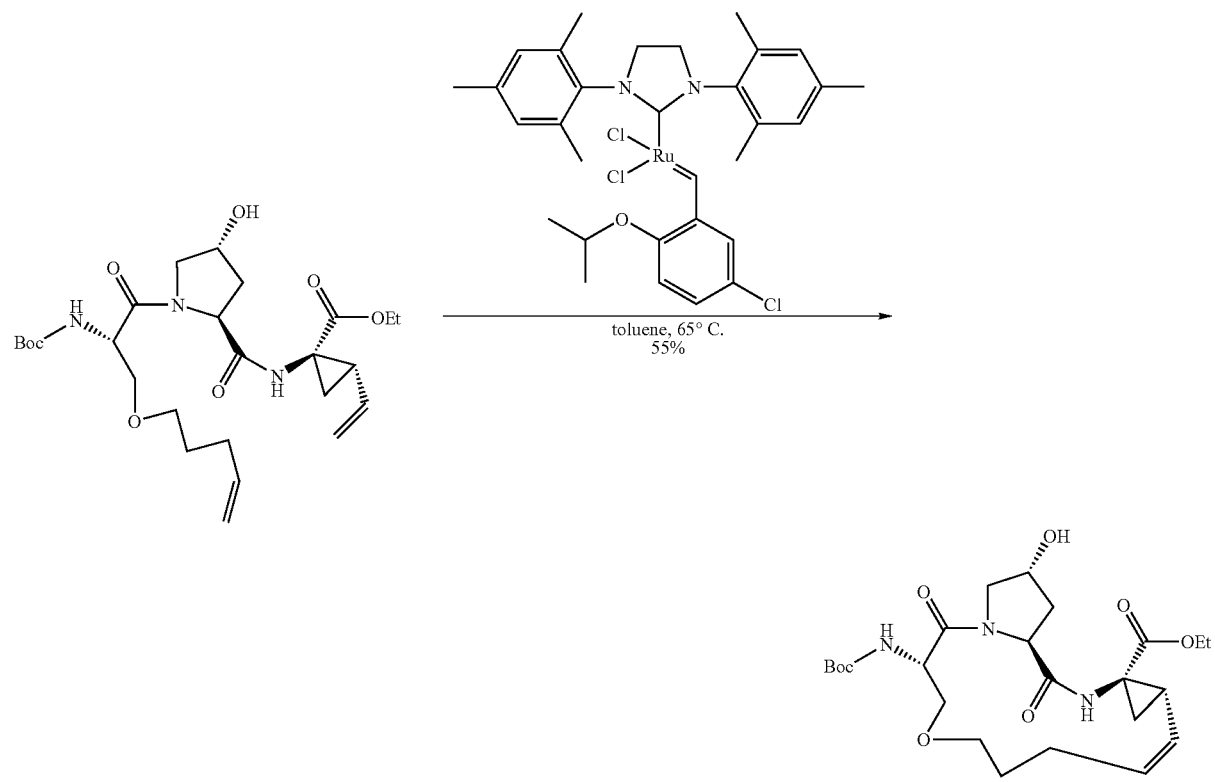

(1R,2S)-ethyl 1-((2S,4R)-1-((S)-2-(tert-butoxycarbonylamino)-3-(pent-4-enyloxy)propanoyl)-4-hydroxypyrrolidine-2-carboxamido)-2-vinylcyclopropanecarboxylate (0.922 g, 1.76 mmol) in toluene (176 mL) was degassed by bubbling a stream of nitrogen through the reaction for 1 hr at rt. (5-chloro-2-isopropoxybenzylidene)(1,3-dimesitylimidazolidin-2-yl)ruthenium(V)chloride (0.0233 g, 0.0352 mmol) was added to the mixture and the mixture was heated to 68° C. (oil bath) and stirred at this temperature for 3 hrs. After removal of solvent, the residue was purified by chromatography (Ethyl acetate) to give (2R,6S,13aS,14aR,16aS,Z)-ethyl 6-(tert-butoxycarbonylamino)-2-hydroxy-5,16-dioxo-2,3,5,6,7,9,10,11,13a,14,14a,15,16,16a-tetradecahydro-1H-cyclopropa(i)pyrrolo[1,2-e][1,5,8]oxadiazacyclopentadecine-14a-carboxylate as off white solid (0.48 g, 55%). MS: Calcd.: 495; Found: [M+H]+ 496. $^1$H NMR (400 MHz, d$^6$-DMSO) δ7.95 (s, 1H), 6.73 (d, J=8 Hz, 1H), 5.51 (m, 1H), 5.27 (m, 1H), 5.16 (d, J=4.0 Hz, 1H), 4.34 (m, 1H), 3.31 (m, 2H), 3.98 (m, 2H), 3.68 (m, 1H), 3.57 (m, 2H), 3.51 (m, 1H), 3.39 (m, 2H), 2.25-1.90 (m, 5H), 1.60 (m, 2H), 1.48 (m, 1H), 1.31 (s, 9H), 1.22 (m, 1H), 1.08 (t, J=7.2 Hz, 3H).

Step 3: Synthesis of (2R,6S,13aS,14aR,16aS,Z)-ethyl 6-(tert-butoxycarbonylamino)-2-(4-fluoroisoindoline-2-carbonyloxy)-5,16-dioxo-2,3,5,6,7,9,10,11,13a,14,14a,15,16,16a-tetradecahydro-1H-cyclopropa(i)pyrrolo[1,2-e][1,5,8]oxadiazacyclopentadecine-14a-carboxylate (8d)

Step 4: Synthesis of (2R,6S,13aS,14aR,16aS,Z)-6-(tert-butoxycarbonylamino)-2-(4-fluoroisoindoline-2-carbonyloxy)-5,16-dioxo-2,3,5,6,7,9,10,11,13a,14,14a,15,16,16a-tetradecahydro-1H-cyclopropa(i)pyrrolo[1,2-e][1,5,8]oxadiazacyclopentadecine-14a-carboxylic acid (8e)

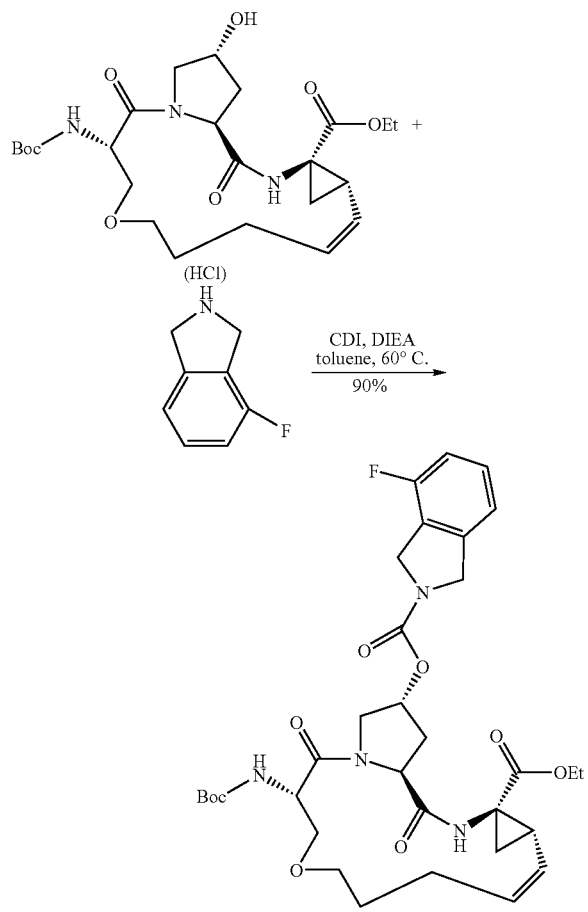

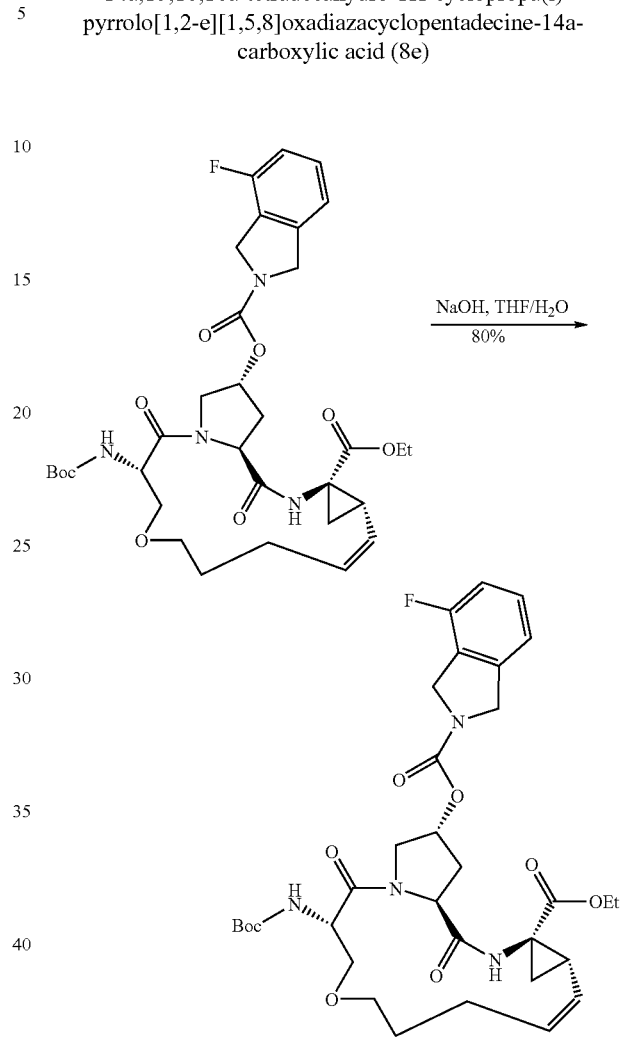

(2R,6S,13aS,14aR,16aS,Z)-ethyl 6-(tert-butoxycarbonylamino)-2-hydroxy-5,16-dioxo-2,3,5,6,7,9,10,11,13a,14,14a,15,16,16a-tetradecahydro-1H-cyclopropa(i)pyrrolo[1,2-e][1,5,8]oxadiazacyclopentadecine-14a-carboxylate (0.14 g, 0.28 mmol) in toluene (5 mL) was added di(1H-imidazol-1-yl)methanone (0.060 g, 0.37 mmol) in one portion. The reaction was stirred at rt for 3 hrs. To the reaction was then added the N-ethyl-N-isopropylpropan-2-amine (0.25 ml, 1.41 mmol), followed by 4-Fluoroisoindoline hydrochloride salts (0.16 g, 0.5650 mmol). The reaction was stirred at 60° C. for 6 hrs. The solvent was removed. The residue was partitioned between ethyl acetate (20 mL) and saturated sodium bicarbonate solution. The organic layer was separated and dried over sodium sulfate. After removal of solvent, the residue was purified by chromatography (Hexane:Ethyl acetate=1:3) to give (2R,6S,13aS,14aR,16aS,Z)-ethyl 6-(tert-butoxycarbonylamino)-2-(4-fluoroisoindoline-2-carbonyloxy)-5,16-dioxo-2,3,5,6, 7, 9, 10,11,13a,14,14a,15,16,16a-tetradecahydro-1H-cyclopropa(i)pyrrolo[1,2-e][1,5,8]oxadiazacyclopentadecine-14a-carboxylate as white solid (0.17 g, 90%). MS: Calcd.: 658; Found: [M+H]+ 659.

(2R,6S,13aS,14aR,16aS,Z)-ethyl 6-(tert-butoxycarbonylamino)-2-(4-fluoroisoindoline-2-carbonyloxy)-5,16-dioxo-2,3,5,6,7,9,10,11,13a,14,14a,15,16,16a-tetradecahydro-1H-cyclopropa(i)pyrrolo[1,2-e][1,5,8]oxadiazacyclopentadecine-14a-carboxylate (0.16 g, 0.25 mmol) in THF (2 mL) was added 0.1 N NaOH solution (6.22 ml, 0.62 mmol) in $H_2O$. The reaction was stirred at rt for 26 hr. Water (5 mL) and ether (15 mL) was added. The aqueous layer was separated and acidified by saturated potassium hydrogen sulfate solution to pH=2~3. The aqueous layer was extracted with EA (2×15 mL), washed with brine and dried over sodium sulfate. After removal of solvent, it gave (2R,6S,13aS,14aR,16aS,Z)-6-(tert-butoxycarbonylamino)-2-(4-fluoroisoindoline-2-carbonyloxy)-5,16-dioxo-2,3,5,6,7,9,10,11,13a,14,14a,15,16,16a-tetradecahydro-1H-cyclopropa(i)pyrrolo[1,2-e][1,5,8]oxadiazacyclopentadecine-14a-carboxylic acid as white solid (0.13 g, 80%). MS: Calcd.: 630; Found: [M+H]+ 631. $^1$H NMR (400 MHz, $d^6$-DMSO) δ12.33 (s, 1H), 8.05 (d, J=19.6 Hz, 1H), 7.32 (m, 1H), 7.05-7.17 (m, 2H), 6.91 (m, 1H), 5.49 (m, 1H), 5.30 (m, 1H), 5.25 (s, 1H), 4.63 (s, 4H), 4.42 (m, 1H), 4.34 (m, 1H), 4.07 (m, 1H), 3.77

(m, 1H), 3.60 (m, 1H), 3.44 (m, 2H), 2.13-2.30 (m, 4H), 1.46-1.55 (m, 3H), 1.38 (m, 1H), 1.26 (m, 1H), 1.13-1.14 (m, 10H).

Step 5: Synthesis of (2R,6S,13aS,14aR,16aS,Z)-6-(tert-butoxycarbonylamino)-14a-(cyclopropylsulfonylcarbamoyl)-5,16-dioxo-2,3,5,6,7,9,10,11,13a,14,14a,15,16,16a-tetradecahydro-1H-cyclopropa(i)pyrrolo[1,2-e][1,5,8]oxadiazacyclopentadecin-2-yl 4-fluoroisoindoline-2-carboxylate (compound 1020)

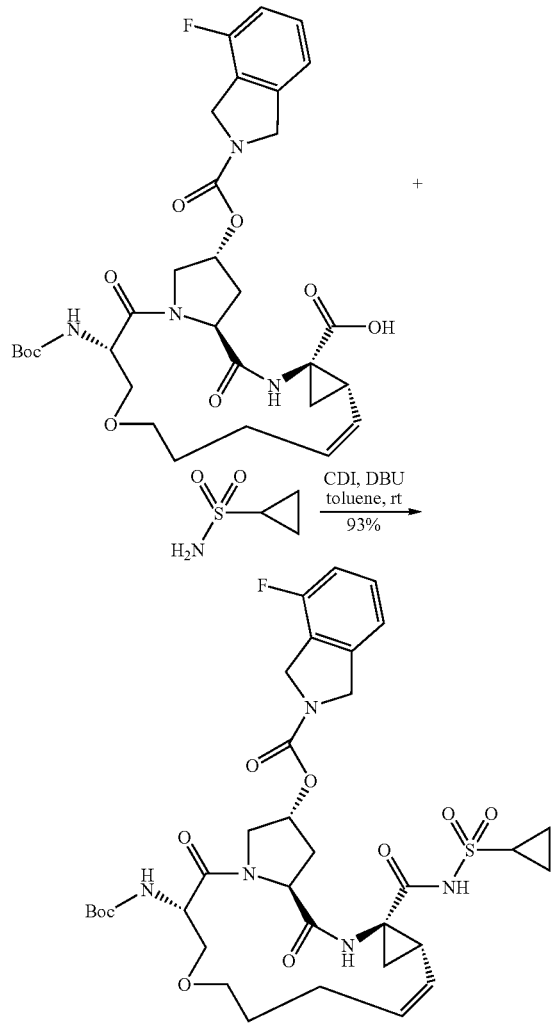

(2R,6S,13aS,14aR,16aS,Z)-6-(tert-butoxycarbonylamino)-2-(4-fluoroisoindoline-2-carbonyloxy)-5,16-dioxo-2,3,5,6,7,9,10,11,13a,14,14a,15,16,16a-tetradecahydro-1H-cyclopropa(i)pyrrolo[1,2-e][1,5,8]oxadiazacyclopentadecine-14a-carboxylic acid (0.085 g, 0.13 mmol) in toluene (3 mL) was added di(1H-imidazol-1-yl)methanone (0.028 g, 0.18 mmol) in rt. The reaction was stirred at 60° C. for 3 hrs. Cyclopropanesulfonamide (0.029 g, 0.24 mmol) was added, followed by addition of DBU (0.036 ml, 0.24 mmol). The reaction was then stirred at rt for 17 hrs. Water (5 mL) was added and acidified with saturated potassium hydrogen sulfate until pH=2~3. The mixture was extracted with ethyl acetate (20 mL), washed with brine and dried over sodium sulfate. After removal of solvent, the residue was purified by chromatography (Hexane:Ethyl acetate=1:3) to give (2R,6S,13aS,14aR,16aS,Z)-6-(tert-butoxycarbonylamino)-14a-(cyclopropylsulfonylcarbamoyl)-5,16-dioxo-2,3,5,6,7,9,10,11,13a,14,14a,15,16,16a-tetradecahydro-1H-cyclopropa(i)pyrrolo[1,2-e][1,5,8]oxadiazacyclopentadecin-2-yl 4-fluoroisoindoline-2-carboxylate as white solid (0.092 g, 93%). MS: Calcd.: 733; Found: [M+H]$^+$ 734. $^1$H NMR (400 MHz, d$^6$-DMSO) δ 11.20 (s, 1H), 8.28 (m, 1H), 7.35 (m, 1H), 7.12-7.20 (m, 2H), 7.00 (m, 1H), 5.57 (m, 1H), 5.35 (m, 1H), 5.16 (m, 1H), 4.67 (s, 4H), 4.41 (m, 2H), 4.15 (m, 1H), 3.86 (m, 1H), 3.62 (m, 1H), 3.45 (m, 1H), 3.31 (m, 1H), 2.91 (m, 1H), 2.33 (m, 4H), 1.68 (m, 2H), 1.49 (m, 3H), 1.11-1.26 (m, 14H).

Step 6: Synthesis of (2R,6S,13aR,14aR,16aS)-6-(tert-butoxycarbonylamino)-14a-(cyclopropylsulfonylcarbamoyl)-5,16-dioxohexadecahydro-1H-cyclopropa(i)pyrrolo[1,2-e][1,5,8]oxadiazacyclopentadecin-2-yl 4-fluoroisoindoline-2-carboxylate (compound 1022)

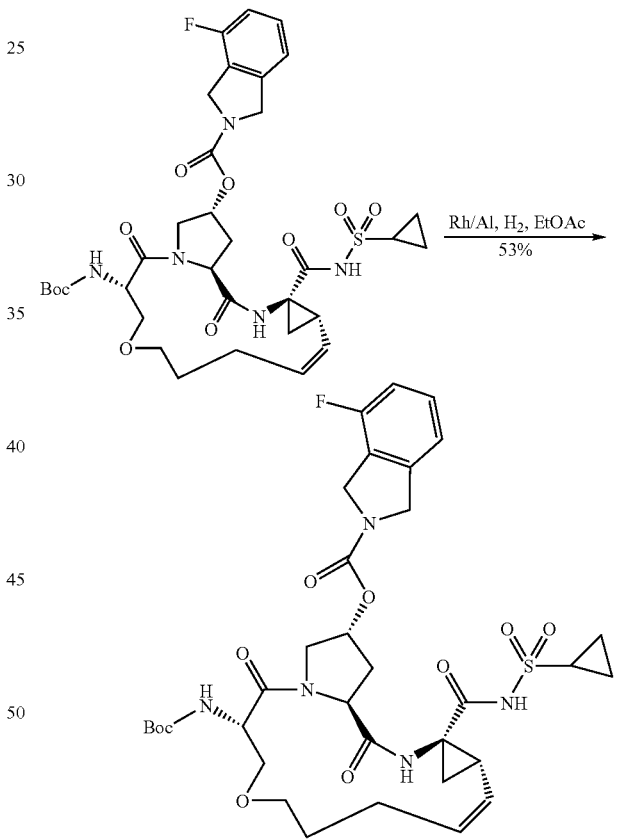

(2R,6S,13aS,14aR,16aS,Z)-6-(tert-butoxycarbonylamino)-14a-(cyclopropylsulfonylcarbamoyl)-5,16-dioxo-2,3,5,6,7,9,10,11,13a,14,14a,15,16,16a-tetradecahydro-1H-cyclopropa(i)pyrrolo[1,2-e][1,5,8]oxadiazacyclopentadecin-2-yl 4-fluoroisoindoline-2-carboxylate (0.028 g, 0.038 mmol) and Rh/Al (5%) (0.0079 g, 0.0038 mmol) in Ethyl acetate (5 mL) was charged with 1 atmosphere of hydrogen and stirred for 16 hrs. Water (3 mL) and saturated potassium hydrogen sulfate (3 mL) was added and stirred for 10 minutes. The organic phase was separated and aqueous phase extracted with ethyl acetate (10 mL), washed with brine and dried over sodium sulfate. After removal of solvent, the residue was purified by chromatography (Hexane:Ethyl acetate=1:4) to give (2R,6S,13aR,14aR,16aS)-6-(tert-butoxycarbonylamino)-14a-(cyclopropylsulfonylcarbamoyl)-5,16-dioxohexadecahydro-1H-cyclopropa(i)pyrrolo[1,2-e][1,5,8]oxadiazacyclopentadecin-2-yl 4-fluoroisoindoline-2-carboxylate as white solid (0.015 g, 53%). MS: Calcd.: 735; Found: [M+H]+ 736. $^1$H NMR (400 MHz, $CD_2Cl_2$) δ9.65 (s, 1H), 7.22-7.28 (m, 2H), 6.96-7.08 (m, 2H), 5.55 (m, 1H), 5.39 (m, 1H), 4.74 & 4.69 (s, 4H), 4.54 (m, 1H), 3.97 (m, 1H), 3.84 (m, 1H), 3.77 (m, 1H), 3.67 (m, 1H), 3.55 (m, 1H), 3.47 (m, 1H), 2.92 (m, 1H), 2.65 (m, 1H), 2.35 (m, 1H), 1.06-1.68 (m, 25H).

The following description in Scheme 9 and following experimental for the synthesis of compounds 1021 and 1023 is exemplary of compounds with the 10-oxa substitution.

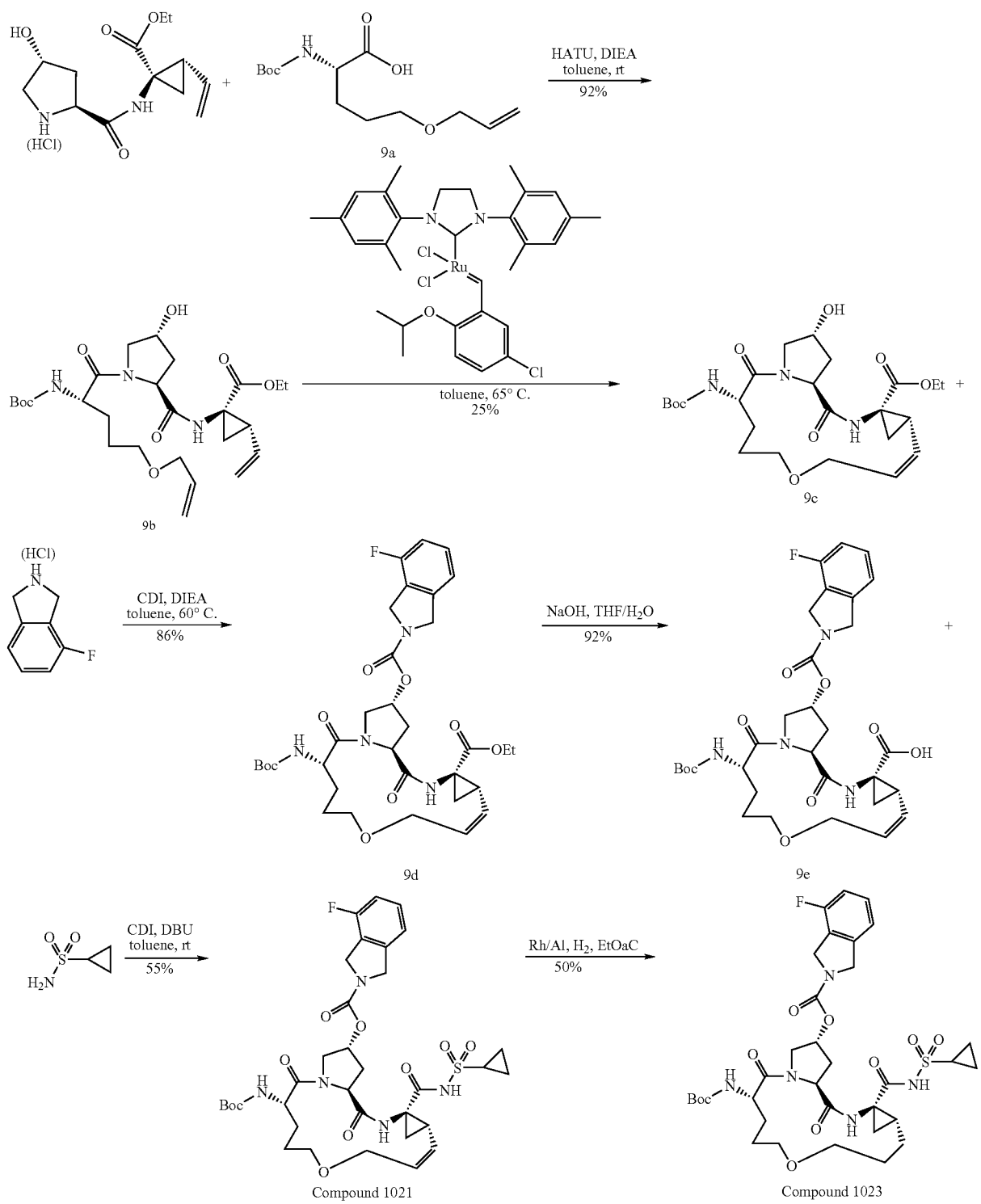

Scheme 9

Step 1: Synthesis of (1R,2S)-ethyl 1-((2S,4R)-1-((S)-5-(allyloxy)-2-(tert-butoxycarbonylamino)pentanoyl)-4-hydroxypyrrolidine-2-carboxamido)-2-vinylcyclopropanecarboxylate (9b)

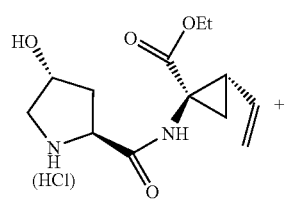

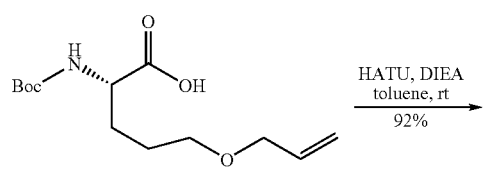

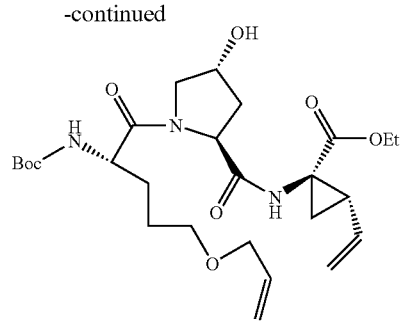

(1R,2S)-ethyl-1-((2S,4R)-4-hydroxypyrrolidine-2-carboxamido)-2-vinylcyclopropanecarboxylate hydrochloride salt (WO2005095403) (2.44 g, 7.76 mmol), (S)-5-(allyloxy)-2-(tert-butoxycarbonylamino)-pentanoic acid (WO2004094452) (2.02 g, 7.39 mmol) and HATU (3.09 g, 8.13 mmol) in toluene (36 mL) and ACN (4 mL) was added DIEA (2.58 mL, 14.78 mmol) at 0° C. The reaction warmed to rt and stirred at rt for 1 hr. Ethyl acetate (30 mL) and water (20 mL) was added. The organic layer was separated and washed with brine, dried over sodium sulfate. After removal of solvent, the residue was purified by chromatography (Ethyl acetate) to give (1R,2S)-ethyl 1-((2S,4R)-1-((S)-5-(allyloxy)-2-(tert-butoxycarbonylamino)pentanoyl)-4-hydroxypyrrolidine-2-carboxamido)-2-vinylcyclopropanecarboxylate as white wax solid (3.55 g, 92%). MS: Calcd.: 523; Found: [M+H]$^+$ 524.

Step 2: Synthesis of (2R,6S,13aS,14aR,16aS,Z)-ethyl 6-(tert-butoxycarbonylamino)-2-hydroxy-5,16-dioxo-2,3,5,6,7,8,9,11,13a,14,14a,15,16,16a-tetradecahydro-1H-cyclopropa(e)pyrrolo[2,1-i][1,7,10]oxadiazacyclopentadecine-14a-carboxylate (9c)

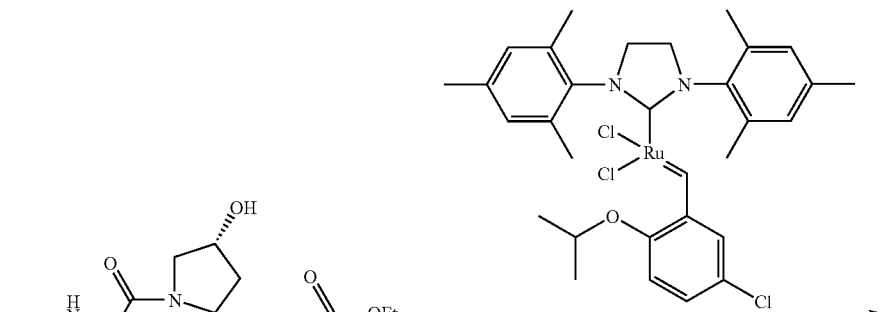

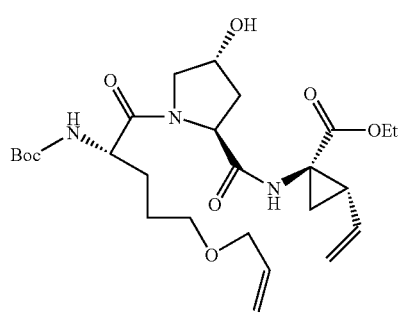

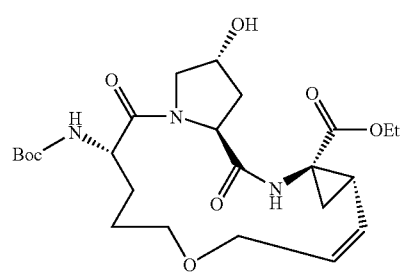

(1R,2S)-ethyl 1-((2S,4R)-1-((S)-5-(allyloxy)-2-(tert-butoxycarbonylamino)pentanoyl)-4-hydroxypyrrolidine-2-carboxamido)-2-vinylcyclopropanecarboxylate (3.55 g, 6.78 mmol) in toluene (750 mL) was degassed by bubbling a stream of nitrogen through the reaction for 1 hr at rt. (5-chloro-2-isopropoxybenzylidene)(1,3-dimesitylimidazolidin-2-yl)ruthenium(V)chloride (0.090 g, 0.14 mmol) was added to the mixture and the mixture was heated to 68° C. (oil bath) and stirred at this temperature for 4 hrs. After removal of solvent, the residue was purified by chromatography (Ethyl acetate:MeOH=40:1) to give (2R,6S,13aS,14aR,16aS,Z)-ethyl 6-(tert-butoxycarbonylamino)-2-hydroxy-5,16-dioxo-2,3,5,6,7,8,9,11,13a,14,14a,15,16,16a-tetradecahydro-1H-cyclopropa(e)pyrrolo[2,1-i][1,7,10]oxadiazacyclopentadecine-14a-carboxylate as off white solid (0.84 g, 25%). MS: Calcd.: 495; Found: [M+H]$^+$ 496. $^1$H NMR (400 MHz, d$^6$-DMSO) δ8.42 (s, 1H), 6.89 (d, J=7.6 Hz, 1H), 5.48-5.60 (m, 2H), 5.10 (d, J=3.6 Hz, 1H), 4.41 (s, 1H), 4.27 (m, 2H), 4.17 (m, 1H), 4.02 (m, 2H), 3.72 (m, 2H), 3.62 (m, 1H), 3.35 (m, 1H), 3.28 (m, 1H), 2.42 (m, 1H), 1.98 (m, 2H), 1.78 (m, 1H), 1.62 (m, 1H), 1.52 (m, 2H), 1.42 (m, 2H), 1.36 (s, 9H), 1.13 (t, J=7.2 Hz, 3H).

Step 3: Synthesis of (2R,6S,13aS,14aR,16aS,Z)-ethyl 6-(tert-butoxycarbonylamino)-2-(4-fluoroisoindoline-2-carbonyloxy)-5,16-dioxo-2,3,5,6,7,8,9,11,13a,14,14a,15,16,16a-tetradecahydro-1H-cyclopropa(e)pyrrolo[2,1-i][1,7,10]oxadiazacyclopentadecine-14a-carboxylate (9d)

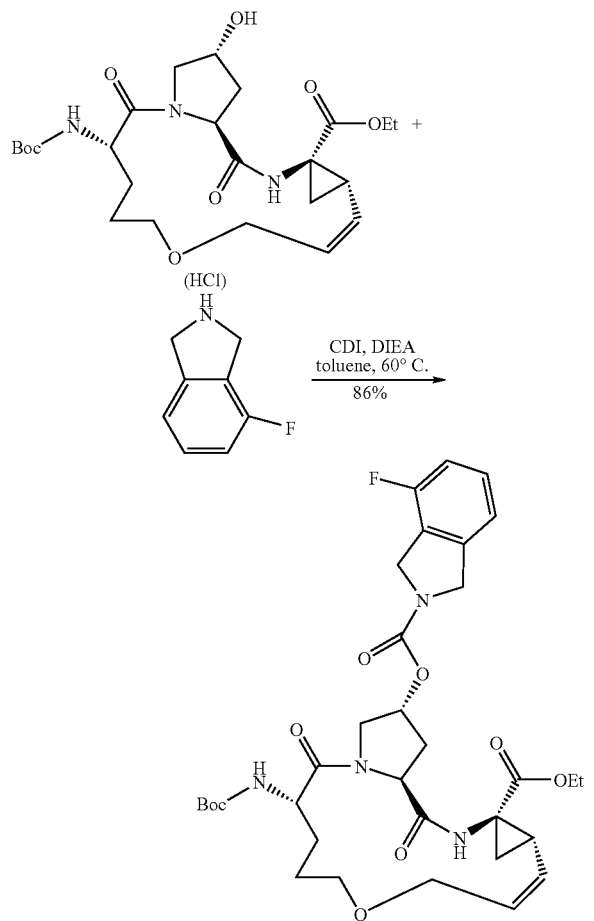

(2R,6S,13aS,14aR,16aS,Z)-ethyl 6-(tert-butoxycarbonylamino)-2-hydroxy-5,16-dioxo-2,3,5,6,7,8,9,11,13a,14,14a,15,16,16a-tetradecahydro-1H-cyclopropa(e)pyrrolo[2,1-i][1,7,10]oxadiazacyclopentadecine-14a-carboxylate (0.15 g, 0.31 mmol) in toluene (5 mL) was added di(1H-imidazol-1-yl)methanone (0.066 g, 0.40 mmol) in one portion. The reaction was stirred at rt for 3 hrs. To the reaction was then added the N-ethyl-N-isopropylpropan-2-amine (0.27 ml, 1.55 mmol), followed by 4-Fluoroisoindoline hydrochloride salts (0.17 g, 0.62 mmol). The reaction was stirred at 60° C. for 3 hrs. The solvent was removed. The residue was partitioned between ethyl acetate (20 mL) and saturated sodium bicarbonate solution. The organic layer was separated and dried over sodium sulfate. After removal of solvent, the residue was purified by chromatography (Hexane:Ethyl acetate=1:3) to give (2R,6S,13aS,14aR,16aS,Z)-ethyl 6-(tert-butoxycarbonylamino)-2-(4-fluoroisoindoline-2-carbonyloxy)-5,16-dioxo-2,3,5,6,7,8,9,11,13a,14,14a,15,16,16a-tetradecahydro-1H-cyclopropa(e)pyrrolo[2,1-i][1,7,10]oxadiazacyclopentadecine-14a-carboxylate as white solid (0.18 g, 86%). MS: Calcd.: 658; Found: [M+H]$^+$ 659.

Step 4: Synthesis of (2R,6S,13aS,14aR,16aS,Z)-6-(tert-butoxycarbonylamino)-2-(4-fluoroisoindoline-2-carbonyloxy)-5,16-dioxo-2,3,5,6,7,8,9,11,13a,14,14a,15,16,16a-tetradecahydro-1H-cyclopropa(e)pyrrolo[2,1-i][1,7,10]oxadiazacyclopentadecine-14a-carboxylic acid (9e)

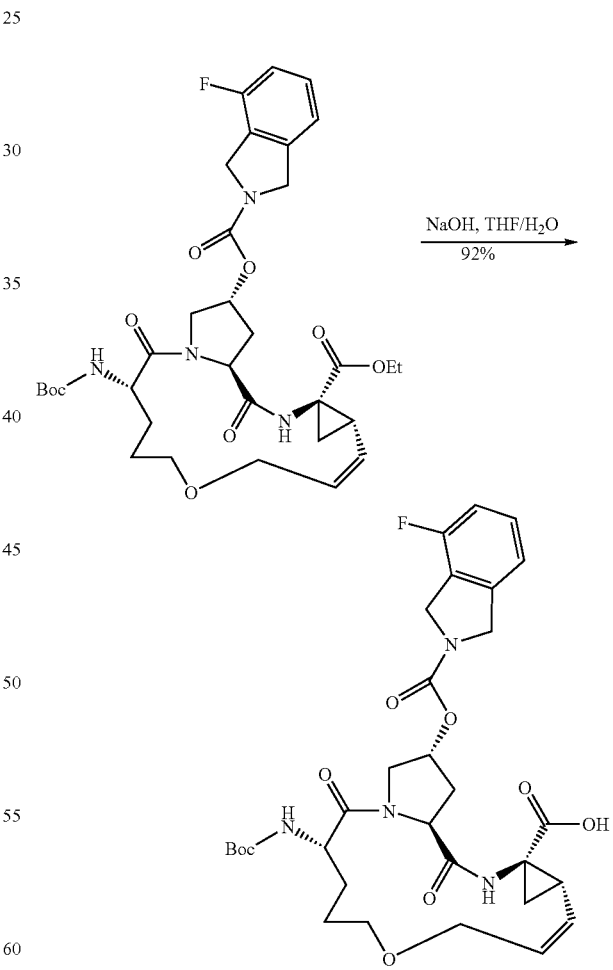

(2R,6S,13aS,14aR,16aS,Z)-ethyl 6-(tert-butoxycarbonylamino)-2-(4-fluoroisoindoline-2-carbonyloxy)-5,16-dioxo-2,3,5,6,7,8,9,11,13a,14,14a,15,16,16a-tetradecahydro-1H-cyclopropa(e)pyrrolo[2,1-i][1,7,10]oxadiazacyclopentadecine-14a-carboxylate (0.18 g, 0.27 mmol) in THF (2 mL) was added 0.1 N NaOH solution (6.64 ml, 0.62 mmol) in H₂O. The reaction was stirred at rt for 26 hr. Water (5 mL) and ether (15 mL) was added. The aqueous layer was separated and acidified by saturated potassium hydrogen sulfate solution to pH=2~3. The aqueous layer was extracted with EA (2×15 mL), washed with brine and dried over sodium sulfate. After removal of solvent, it gave (2R,6S,13aS,14aR,16aS,Z)-6-(tert-butoxycarbonylamino)-2-(4-fluoroisoindoline-2-carbonyloxy)-5,16-dioxo-2,3,5,6,7,8,9,11,13a,14,14a,15,16,16a-tetradecahydro-1H-cyclopropa(e)pyrrolo[2,1-i][1,7,10]oxadiazacyclopentadecine-14a-carboxylic acid as white solid (0.15 g, 92%). MS: Calcd.: 630; Found: [M+H]⁺ 631. ¹H NMR (400 MHz, d⁶-DMSO) δ12.29 (s, 1H), 8.59 (d, J=13.2 Hz, 1H), 7.36 (m, 1H), 7.10-7.20 (m, 3H), 5.59 (m, 1H), 5.50 (m, 1H), 5.30 (s, 1H), 4.66 (s, 4H), 4.51 (m, 1H), 4.41 (m, 1H), 4.23 (m, 1H), 3.94 (m, 1H), 3.74 (m, 1H), 3.50 (m, 1H), 3.37 (m, 2H), 2.35 (m, 1H), 1.78 (m, 2H), 1.51 (m, 2H), 1.37 (m, 2H), 1.24 (m, 2H), 1.08 & 1.09 (s, 9H).

Step 5: Synthesis of (2R,6S,13aS,14aR,16aS,Z)-6-(tert-butoxycarbonylamino)-14a-(cyclopropylsulfonylcarbamoyl)-5,16-dioxo-2,3,5,6,7,8,9,11,13a,14,14a,15,16,16a-tetradecahydro-1H-cyclopropa(e)pyrrolo[2,1-i][1,7,10]oxadiazacyclopentadecin-2-yl 4-fluoroisoindoline-2-carboxylate (Compound 1021)

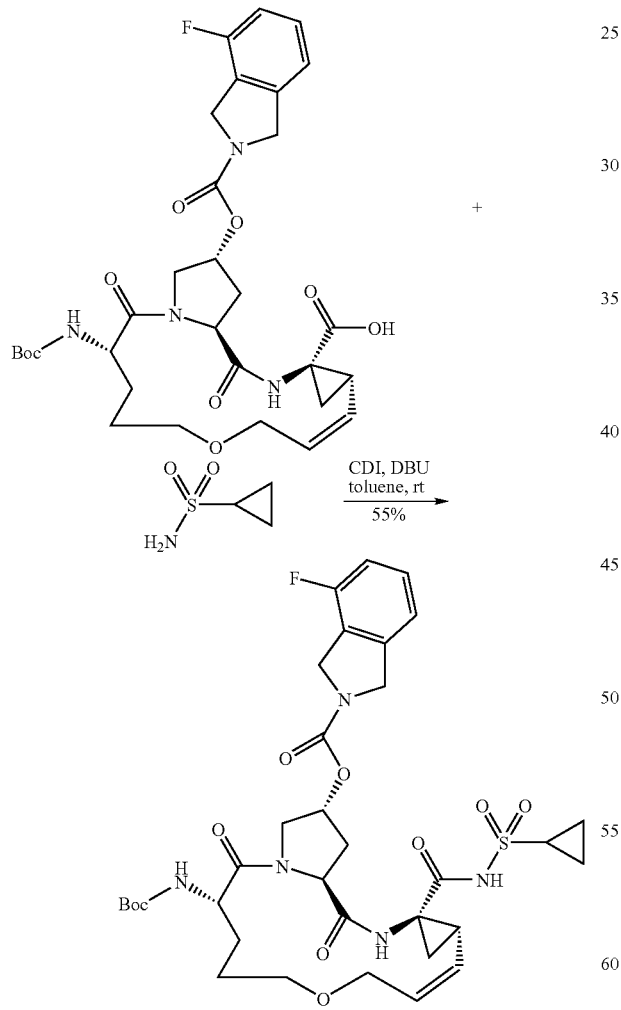

mmol) in toluene (3 mL) was added di(1H-imidazol-1-yl)methanone (0.036 g, 0.22 mmol) in rt. The reaction was stirred at 60° C. for 3 hrs. Cyclopropanesulfonamide (0.035 g, 0.29 mmol) was added, followed by addition of DBU (0.043 ml, 0.29 mmol). The reaction was then stirred at rt for 17 hrs. Water (5 mL) was added and acidified with saturated potassium hydrogen sulfate until pH=2~3. The mixture was extracted with ethyl acetate (20 mL), washed with brine and dried over sodium sulfate. After removal of solvent, the residue was purified by chromatography (Ethyl acetate) to give (2R,6S,13aS,14aR,16aS,Z)-6-(tert-butoxycarbonylamino)-14a-(cyclopropylsulfonylcarbamoyl)-5,16-dioxo-2,3,5,6,7,8,9,11,13a,14,14a,15,16,16a-tetradecahydro-1H-cyclopropa(e)pyrrolo[2,1-i][1,7,10]oxadiazacyclopentadecin-2-yl 4-fluoroisoindoline-2-carboxylate as white solid (0.064 g, 55%). MS: Calcd.: 733; Found: [M+H]⁺ 734. ¹H NMR (400 MHz, d⁶-DMSO) δ11.14 (s, 1H), 8.68 & 8.59 (s, 1H), 7.34 (m, 1H), 7.08-7.25 (m, 3H), 5.64 (m, 1H), 5.30 (m, 2H), 4.67 (s, 4H), 4.43 (m, 2H), 4.27 (m, 1H), 3.95 (m, 1H), 3.74 (m, 1H), 3.52 (m, 1H), 3.37 (m, 2H), 2.91 (m, 1H), 2.36 (m, 2H), 2.28 (m, 2H), 1.79 (m, 1H), 1.52-1.70 (m, 3H), 1.24 (m, 2H), 1.19 (m, 1H), 1.01-1.19 (m, 1H).

Step 6: Synthesis of (2R,6S,13aR,14aR,16aS)-6-(tert-butoxycarbonylamino)-14a-(cyclopropylsulfonylcarbamoyl)-5,16-dioxohexadecahydro-1H-cyclopropa(e)pyrrolo[2,1-i][1,7,10] oxadiazacyclopentadecin-2-yl 4-fluoroisoindoline-2-carboxylate (Compound 1023)

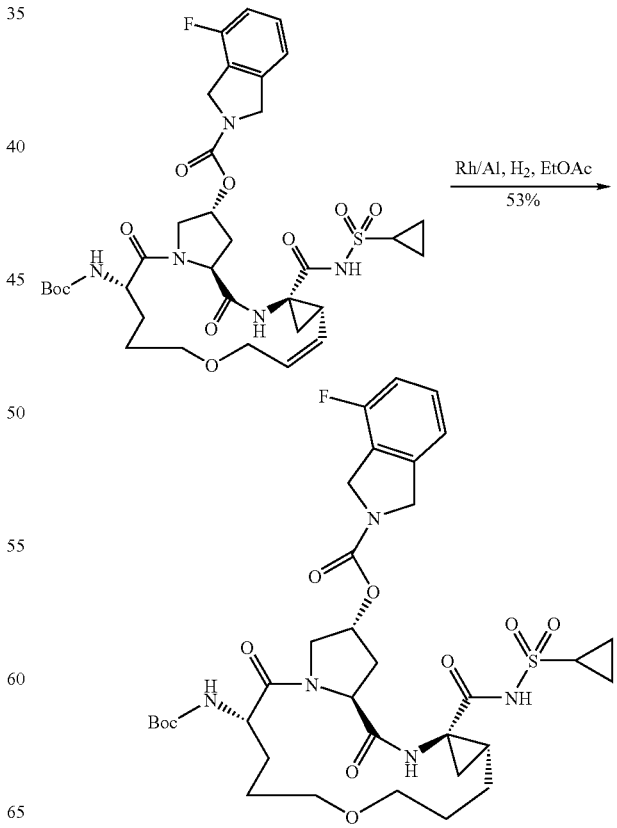

(2R,6S,13aS,14aR,16aS,Z)-6-(tert-butoxycarbonylamino)-2-(4-fluoroisoindoline-2-carbonyloxy)-5,16-dioxo-2,3,5,6,7,8,9,11,13a,14,14a,15,16,16a-tetradecahydro-1H-cyclopropa(e)pyrrolo[2,1-i][1,7,10]oxadiazacyclopentadecine-14a-carboxylic acid (0.10 g, 0.16

(2R,6S,13aS,14aR,16aS,Z)-6-(tert-butoxycarbonylamino)-14a-(cyclopropylsulfonylcarbamoyl)-5,16-dioxo-2,3,5,6,7,8,9,11,13a,14,14a,15,16,16a-tetradecahydro-1H-cyclopropa(e)pyrrolo[2,1-i][1,7,10]oxadiazacyclopentadecin-2-yl 4-fluoroisoindoline-2-carboxylate (0.022 g, 0.030 mmol) and Rh/Al (5%) (0.0062 g, 0.0030 mmol) in Ethyl acetate (5 mL) was charged with 1 atmosphere of hydrogen and stirred for 16 hrs. Water (3 mL) and saturated potassium hydrogen sulfate (3 mL) was added and stirred for 10 minutes. The organic phase was separated and aqueous phase extracted with ethyl acetate (10 mL), washed with brine and dried over sodium sulfate. After removal of solvent, the residue was purified by chromatography (Hexane:Ethyl acetate=1:2) to give (2R,6S,13aR,14aR,16aS)-6-(tert-butoxycarbonylamino)-14a-(cyclopropylsulfonylcarbamoyl)-5,16-dioxohexadecahydro-1H-cyclopropa(e)pyrrolo[2,1-i][1,7,10]oxadiazacyclopentadecin-2-yl 4-fluoroisoindoline-2-carboxylate as white solid (0.011 g, 50%). MS: Calcd.: 735; Found: [M+H]+ 736. 1H NMR (400 MHz, CD2Cl2) δ9.69 (s, 1H), 7.18 (m, 1H), 6.84-7.15 (m, 2H), 5.24 (m, 1H), 5.04 (m, 1H), 4.65 & 4.61 (s, 4H), 4.15 (m, 2H), 3.70 (m, 1H), 3.44 (m, 2H), 3.34 (m, 1H), 3.28 (m, 1H), 2.84 (m, 1H), 2.52 (m, 1H), 2.35 (m, 1H), 1.86 (m, 2H), 0.97-1.56 (m, 22H).

The following description in Scheme 10 and following experimental for the synthesis of compounds 1027 and 1028 is exemplary of compounds with the 9-oxa substitution.

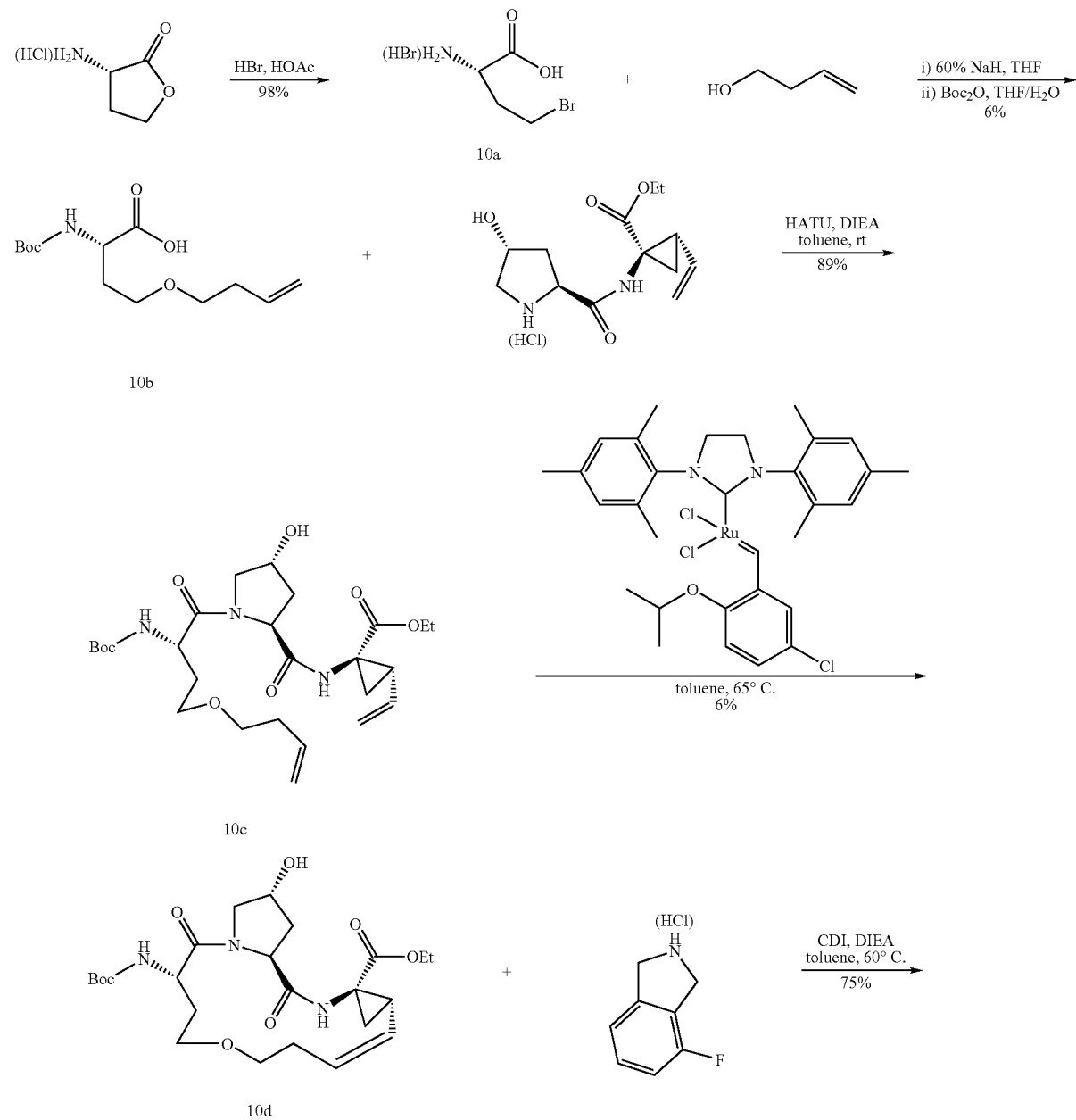

US 7,829,665 B2
357                                                           358
-continued
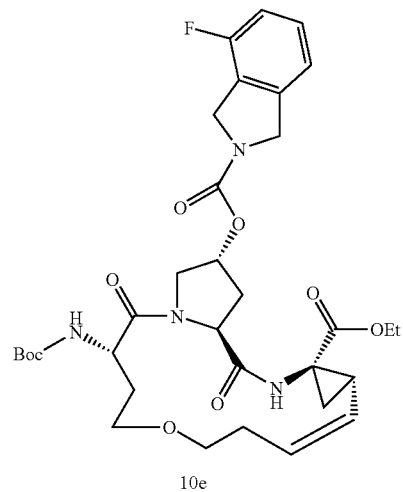
10e
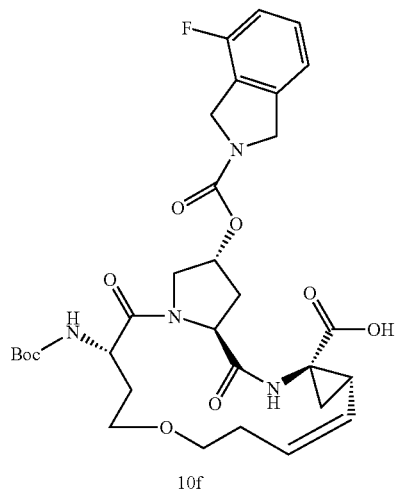
10f
NaOH, THF/H₂O
83%
+
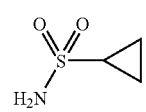
CDI, DBU
toluene, rt
68%
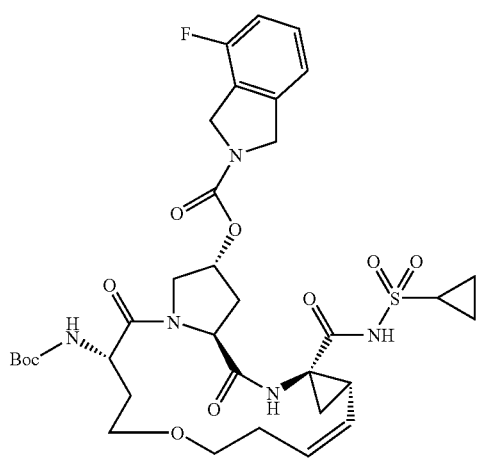
Compound 1027
Rh/Al, H₂, EtOAc
38%
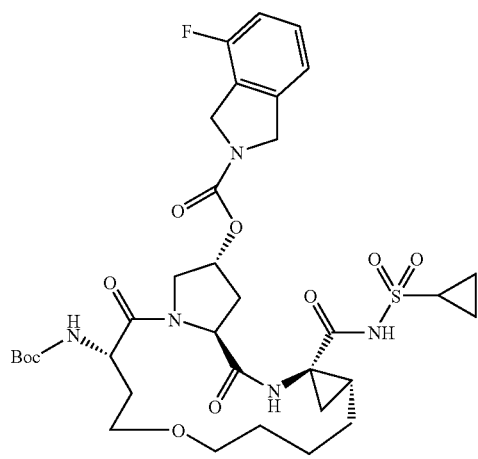
Compound 1028

Step 1: Synthesis of (S)-2-amino-4-bromobutanoic acid hydrobromide (10a)

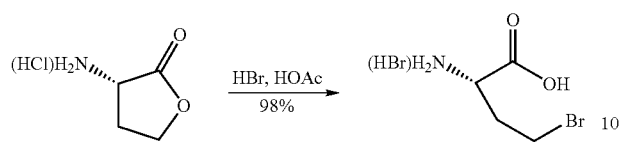

(S)-3-aminodihydrofuran-2(3H)-one hydrochloride (10.30 g, 74.87 mmol) in 58 mL of 30% w/w HBr in HOAc was stirred at 65° C. for 30 hrs. The solvent was removed under reduced pressure and the resulted solid was suspended in MTBE (200 mL) and stirred for 30 min. The solid was collected by filtration and washed with MTBE (200 mL) and dried to give (S)-2-amino-4-bromobutanoic acid hydrobromide as white solid (19.33 g, 98%). $^1$H NMR (400 MHz, d$^6$-DMSO) δ8.37 (s, 3H), 4.01 (m, 1H), 3.65 (m, 2H), 2.33 (m, 2H).

Step 2: Synthesis of (S)-4-(but-3-enyloxy)-2-(tert-butoxycarbonylamino)-butanoic acid (10b)

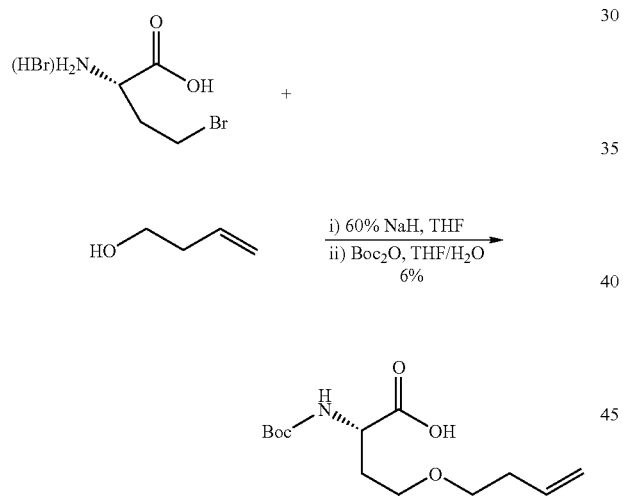

But-3-en-1-ol (98.2 ml, 1141.0 mmol) in THF (50 mL) was added NaH (27.4 g, 684.6 mmol) potion wise. When the hydrogen gas emission stopped, (S)-2-amino-4-bromobutanoic acid hydrobromide (15.0 g, 57.1 mmol) was added in one portion. The reaction was stirred at rt for 3 days. Water (100 mL) was added and all solvent was removed. Water (200 mL) was added and extracted with ether (400 mL). The aqueous layer was acidified to pH=3 and extracted with EA (2×200 mL), dried over sodium sulfate. After removal of solvent, the residue was purified by chromatography (hexane: Ethyl acetate=3:1) to give (S)-4-(but-3-enyloxy)-2-(tert-butoxycarbonylamino)-butanoic acid as pale yellow oil (1.0 g, 6%). MS: Calcd.: 273; Found: [M–H]$^+$ 272. $^1$H NMR (400 MHz, d$^6$-DMSO) δ12.44 (s, 1H), 7.01 (d, J=8.0 Hz, 1H), 5.81 (m, 1H), 5.03 (m, 2H), 3.97 (m, 1H), 3.41 (m, 4H), 2.25 (m, 2H), 1.88 (m, 1H), 1.73 (m, 1H), 1.38 (s, 9H).

Step 3: Synthesis of (1R,2S)-ethyl 1-((2S,4R)-1-((S)-4-(but-enyloxy)-2-(tert-butoxycarbonylamino)butanoyl)-4-hydroxypyrrolidine-2-carboxamido)-2-vinylcyclopropanecarboxylate (10c)

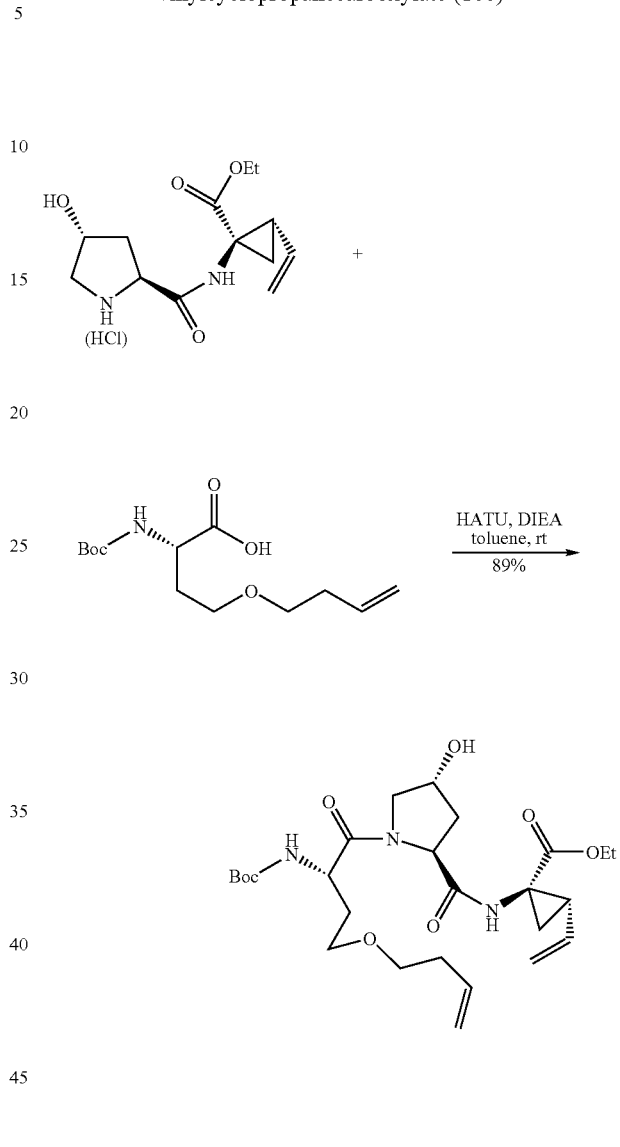

(1R,2S)-ethyl-1-((2S,4R)-4-hydroxypyrrolidine-2-carboxamido)-2-vinylcyclopropanecarboxylate hydrochloride salt (WO2005095403) (1.21 g, 3.84 mmol), (S)-4-(but-3-enyloxy)-2-(tert-butoxycarbonylamino)-butanoic acid (1.00 g, 3.66 mmol) and HATU (1.53 g, 4.03 mmol) in toluene (18 mL) and ACN (2 mL) was added DIEA (1.28 mL, 4.03 mmol) at 0° C. The reaction warmed to rt and stirred at rt for 1 hr. Ethyl acetate (30 mL) and water (20 mL) was added. The organic layer was separated and washed with brine, dried over sodium sulfate. After removal of solvent, the residue was purified by chromatography (Ethyl acetate) to give (1R,2S)-ethyl 1-((2S,4R)-1-((S)-4-(but-enyloxy)-2-(tert-butoxycarbonylamino)butanoyl)-4-hydroxypyrrolidine-2-carboxamido)-2-vinylcyclopropanecarboxylate as white wax solid (1.7 g, 89%). MS: Calcd.: 523; Found: [M+H]$^+$ 524.

Step 4: Synthesis of (2R,6S,13aS,14aR,16aS,Z)-ethyl 6-(tert-butoxycarbonylamino)-2-hydroxy-5,16-dioxo-2,3,5,6,7,8,10,11,13a,14,14a,15,16,16a-tetradecahydro-1H-cyclopropa(j)pyrrolo[1,2-f][1,6,9]oxadiazacyclopentadecine-14a-carboxylate (10d)

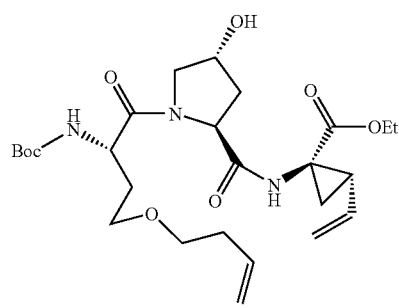
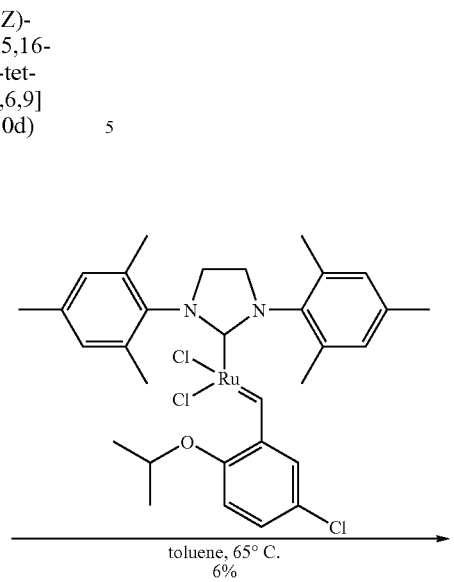

toluene, 65° C.
6%

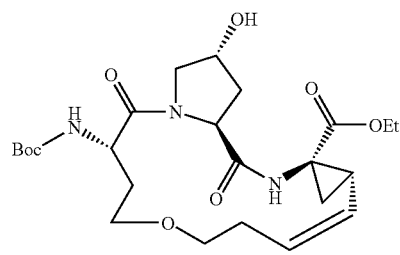

(1R,2S)-ethyl 1-((2S,4R)-1-((S)-4-(but-enyloxy)-2-(tert-butoxycarbonylamino)butanoyl)-4-hydroxypyrrolidine-2-carboxamido)-2-vinylcyclopropanecarboxylate (1.70 g, 3.25 mmol) in toluene (450 mL) was degassed by bubbling a stream of nitrogen through the reaction for 1 hr at rt. (5-chloro-2-isopropoxybenzylidene)(1,3-dimesitylimidazolidin-2-yl)ruthenium(V)chloride (0.043 g, 0.065 mmol) was added to the mixture and the mixture was heated to 68° C. (oil bath) and stirred at this temperature for 3 hrs. After removal of solvent, the residue was purified by chromatography (Ethyl acetate) to give (2R,6S,13aS,14aR,16aS,Z)-ethyl 6-(tert-butoxycarbonylamino)-2-hydroxy-5,16-dioxo-2,3,5,6,7,8,10,11,13a,14,14a,15,16,16a-tetradecahydro-1H-cyclopropa(i)pyrrolo[1,2-f][1,6,9]oxadiazacyclopentadecine-14a-carboxylate as off white solid (0.10 g, 6%). MS: Calcd.: 495; Found: [M+H]$^+$ 496. $^1$H NMR (400 MHz, d$^6$-DMSO) δ8.76 (s, 1H), 6.73 (d, J=7.2 Hz, 1H), 5.36-5.49 (m, 2H), 5.11 (d, J=3.6 Hz, 1H), 4.41 (s, 1H), 4.31 (m, 1H), 4.21 (m, 1H), 3.99 (m, 2H), 3.61 (m, 2H), 3.43 (m, 2H), 3.36 (m, 2H), 2.43 (m, 1H), 2.22 (m, 2H), 1.87-2.01 (m, 3H), 1.79 (m, 1H), 1.55 (m, 1H), 1.52 (m, 1H), 1.36 (s, 9H), 0.86 (t, J=7.6 Hz, 3H).

Step 5: Synthesis of (2R,6S,13aS,14aR,16aS,Z)-ethyl 6-(tert-butoxycarbonylamino)-2-(4-fluoroisoindoline-2-carbonyloxy)-5,16-dioxo-2,3,5,6,7,8,10,11,13a,14,14a,15,16,16a-tetradecahydro-1H-cyclopropa(j)pyrrolo[1,2-f][1,6,9]oxadiazacyclopentadecine-14a-carboxylate (10e)

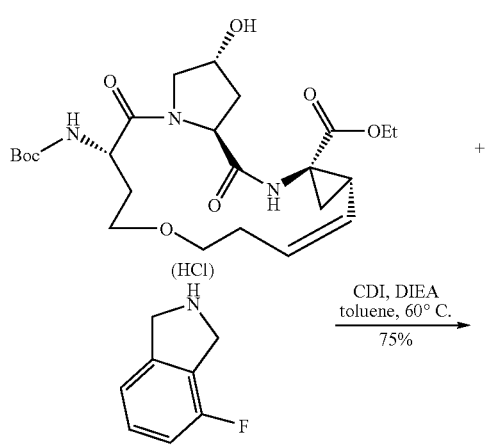

CDI, DIEA
toluene, 60° C.
75%

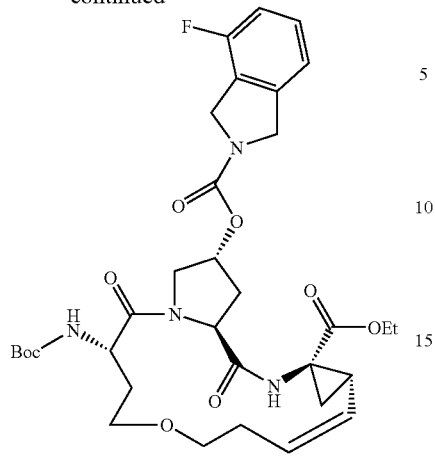

(2R,6S,13aS,14aR,16aS,Z)-ethyl 6-(tert-butoxycarbonylamino)-2-hydroxy-5,16-dioxo-2,3,5,6,7,8,10,11,13a,14,14a,15,16,16a-tetradecahydro-1H-cyclopropa(j)pyrrolo[1,2-f][1,6,9]oxadiazacyclopentadecine-14a-carboxylate (0.096 g, 0.19 mmol) in toluene (5 mL) was added di(1H-imidazol-1-yl)methanone (0.041 g, 0.25 mmol) in one portion. The reaction was stirred at rt for 3 hrs. To the reaction was then added the N-ethyl-N-isopropylpropan-2-amine (0.17 ml, 0.99 mmol), followed by 4-Fluoroisoindoline hydrochloride (0.11 g, 0.38 mmol). The reaction was stirred at 60° C. for 3 hrs. The solvent was removed. The residue was partitioned between ethyl acetate (20 mL) and saturated sodium bicarbonate solution. The organic layer was separated and dried over sodium sulfate. After removal of solvent, the residue was purified by chromatography (Hexane:Ethyl acetate=1:3) to give (2R,6S,13aS,14aR,16aS,Z)-ethyl 6-(tert-butoxycarbonylamino)-2-(4-fluoroisoindoline-2-carbonyloxy)-5,16-dioxo-2,3,5,6,7,8,10,11,13a,14,14a,15,16,16a-tetradecahydro-1H-cyclopropa(j)pyrrolo[1,2-f][1,6,9]oxadiazacyclopentadecine-14a-carboxylate as white solid (0.096 g, 75%). MS: Calcd.: 658; Found: [M+H]+ 659.

Step 6: Synthesis of (2R,6S,13aS,14aR,16aS,Z)-6-(tert-butoxycarbonylamino)-2-(4-fluoroisoindoline-2-carbonyloxy)-5,16-dioxo-2,3,5,6,7,8,10,11,13a,14,14a,15,16,16a-tetradecahydro-1H-cyclopropa(j)pyrrolo[1,2-f][1,6,9]oxadiazacyclopentadecine-14a-carboxylic acid (10f)

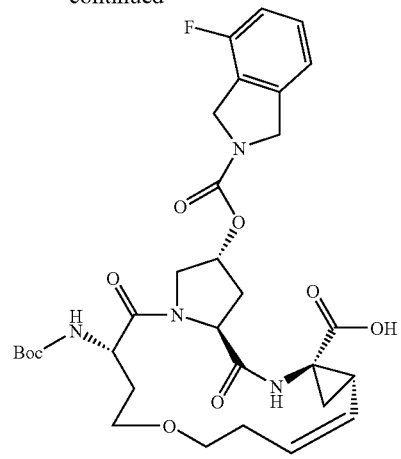

(2R,6S,13aS,14aR,16aS,Z)-ethyl 6-(tert-butoxycarbonylamino)-2-(4-fluoroisoindoline-2-carbonyloxy)-5,16-dioxo-2,3,5,6,7,8,10,11,13a,14,14a,15,16,16a-tetradecahydro-1H-cyclopropa(j)pyrrolo[1,2-f][1,6,9]oxadiazacyclopentadecine-14a-carboxylate (0.093 g, 0.14 mmol) in THF (2 mL) was added 0.1 N NaOH solution (3.53 ml, 0.35 mmol) in $H_2O$. The reaction was stirred at rt for 3 days. Water (5 mL) and ether (15 mL) was added. The aqueous layer was separated and acidified by saturated potassium hydrogen sulfate solution to pH=2~3. The aqueous layer was extracted with EA (2×15 mL), washed with brine and dried over sodium sulfate. After removal of solvent, it (2R,6S,13aS,14aR,16aS,Z)-6-(tert-butoxycarbonylamino)-2-(4-fluoroisoindoline-2-carbonyloxy)-5,16-dioxo-2,3,5,6,7,8,10,11,13a,14,14a,15,16,16a-tetradecahydro-1H-cyclopropa(j)pyrrolo[1,2-f][1,6,9]oxadiazacyclopentadecine-14a-carboxylic acid as white solid (0.074 g, 83%). MS: Calcd.: 630; Found: [M+H]+ 631. $^1$H NMR (400 MHz, d$^6$-DMSO) δ12.25 (s, 1H), 8.77 (s, 1H), 7.37 (m, 1H), 7.07-7.21 (m, 3H), 5.34-5.44 (m, 2H), 5.29 (s, 1H), 4.67 (s, 4H), 4.44 (m, 1H), 4.20 (m, 1H), 3.95 (m, 1H), 3.68 (m, 1H), 3.50 (m, 1H), 3.43 (m, 2H), 3.32 (m, 1H), 2.39 (m, 1H), 2.33 (m, 2H), 2.16 (m, 2H), 1.85 (m, 1H), 1.74 (m, 1H), 1.53 (m, 1H), 1.50 (m, 1H), 1.23 & 0.96 (s, 9H).

Step 7: Synthesis of (2R,6S,13aS,14aR,16aS,Z)-6-(tert-butoxycarbonylamino)-14a-(cyclopropylsulfonylcarbamoyl)-5,16-dioxo-2,3,5,6,7,8,10,11,13a,14,14a,15,16,16a-tetradecahydro-1H-cyclopropa(j)pyrrolo[1,2-f][1,6,9]oxadiazacyclopentadecin-2-yl 4-fluoroisoindoline-2-carboxylate (Compound 1027)

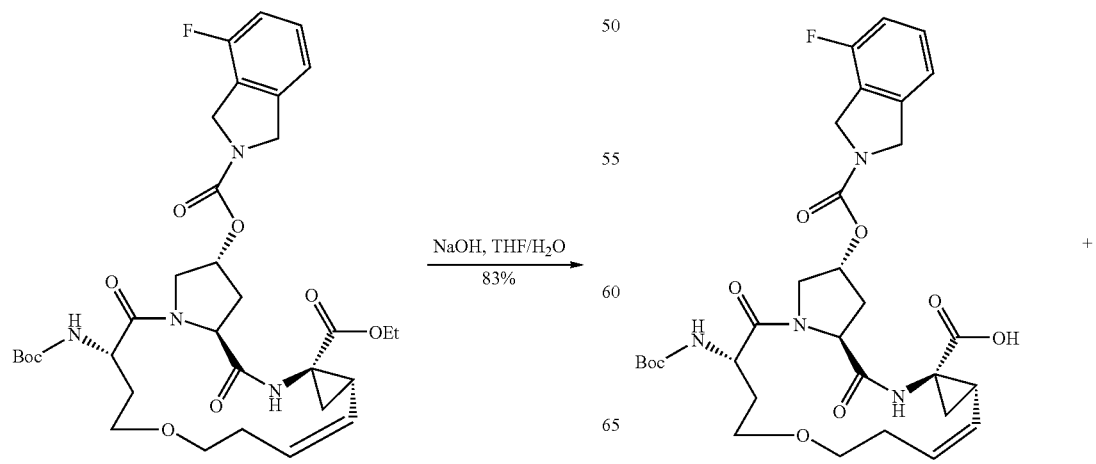

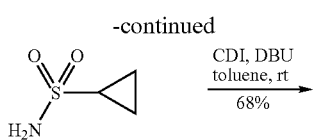

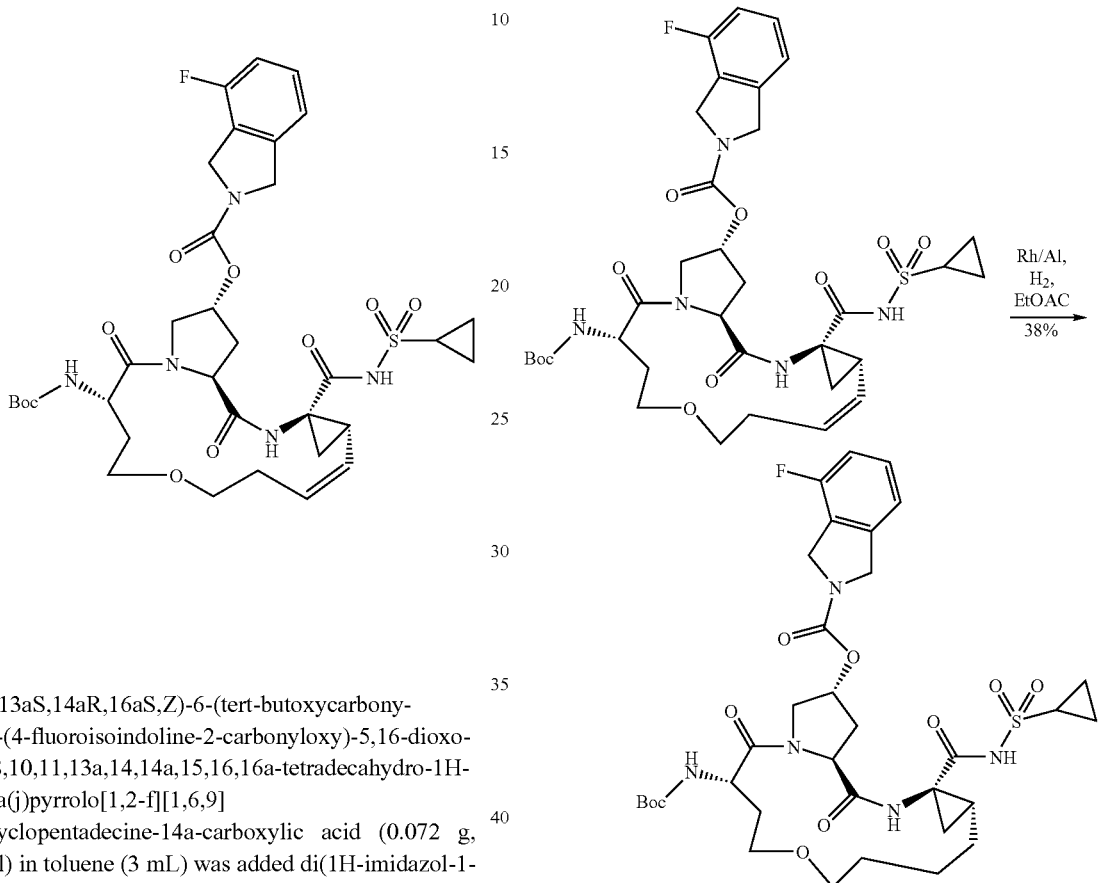

(2R,6S,13aS,14aR,16aS,Z)-6-(tert-butoxycarbonylamino)-2-(4-fluoroisoindoline-2-carbonyloxy)-5,16-dioxo-2,3,5,6,7,8,10,11,13a,14,14a,15,16,16a-tetradecahydro-1H-cyclopropa(j)pyrrolo[1,2-f][1,6,9]oxadiazacyclopentadecine-14a-carboxylic acid (0.072 g, 0.11 mmol) in toluene (3 mL) was added di(1H-imidazol-1-yl)methanone (0.024 g, 0.15 mmol) in rt. The reaction was stirred at 60° C. for 3 hrs. Cyclopropanesulfonamide (0.021 g, 0.17 mmol) was added, followed by addition of DBU (0.043 ml, 0.29 mmol). The reaction was then stirred at rt for 17 hrs. Water (5 mL) was added and acidified with saturated potassium hydrogen sulfate until pH=2~3. The mixture was extracted with ethyl acetate (20 mL), washed with brine and dried over sodium sulfate. After removal of solvent, the residue was purified by chromatography (Ethyl acetate) to (2R, 6S,13aS,14aR,16aS,Z)-6-(tert-butoxycarbonylamino)-14a-(cyclopropylsulfonylcarbamoyl)-5,16-dioxo-2,3,5,6,7,8,10, 11,13a,14,14a,15,16,16a-tetradecahydro-1H-cyclopropa(i)pyrrolo[1,2-f][1,6,9]oxadiazacyclopentadecin-2-yl 4-fluoroisoindoline-2-carboxylate as white solid (0.057 g, 68%). MS: Calcd.: 733; Found: [M+H]+ 734. $^1$H NMR (400 MHz, d$^6$-DMSO) δ11.08 (s, 1H), 9.03 (d, J=10.8 Hz, 1H), 7.34 (m, 1H), 7.11-7.33 (m, 3H), 5.46 (m, 1H), 5.30 (s, 1H), 5.23 (m, 1H), 4.67 (s, 4H), 4.42 (m, 1H), 4.28 (m, 1H), 3.95 (m, 1H), 3.69 (m, 1H), 3.56 (m, 1H), 3.41 (m, 1H), 3.32 (m, 1H), 3.26 (m, 1H), 2.91 (m, 1H), 2.18-2.40 (m, 5H), 1.92 (m, 1H), 1.75 (m, 1H), 1.61 (m, 2H), 1.00-1.28 (m, 13H).

Step 8: Synthesis of (2R,6S,13aR,14aR,16aS)-6-(tert-butoxycarbonylamino)-14a-(cyclopropylsulfonylcarbamoyl)-5,16-dioxohexadecahydro-1H-cyclopropa(j)pyrrolo[1,2-f][1,6,9]oxadiazacyclopentadecin-2-yl 4-fluoroisoindoline-2-carboxylate (Compound 1028)

(2R,6S,13aS,14aR,16aS,Z)-6-(tert-butoxycarbonylamino)-14a-(cyclopropylsulfonylcarbamoyl)-5,16-dioxo-2, 3,5,6,7,8,10,11,13a,14,14a,15,16,16a-tetradecahydro-1H-cyclopropa(j)pyrrolo[1,2-f][1,6,9]oxadiazacyclopentadecin-2-yl 4-fluoroisoindoline-2-carboxylate (0.037 g, 0.050 mmol) and Rh/Al (5%) (0.021 g, 0.010 mmol) in Ethyl acetate (5 mL) was charged with 1 atmosphere of hydrogen and stirred for 16 hrs. Water (3 mL) and saturated potassium hydrogen sulfate (3 mL) was added and stirred for 10 minutes. The organic phase was separated and aqueous phase extracted with ethyl acetate (10 mL), washed with brine and dried over sodium sulfate. After removal of solvent, the residue was purified by chromatography (Hexane:Ethyl acetate=1:2) to give (2R,6S,13aR,14aR,16aS)-6-(tert-butoxycarbonylamino)-14a-(cyclopropylsulfonylcarbamoyl)-5,16-dioxohexadecahydro-1H-cyclopropa(j)pyrrolo[1,2-f][1,6,9]oxadiazacyclopentadecin-2-yl 4-fluoroisoindoline-2-carboxylate as white solid (0.014 g, 38%). MS: Calcd.: 735; Found: [M+H]+ 736. $^1$H NMR (400 MHz, d$^6$-DMSO) δ11.08 (s, 1H), 8.79 (b, 1H), 7.34 (m, 1H), 7.10-7.20 (m, 3H), 5.28 (m, 1H), 4.66 (s, 4H), 4.41 (m, 1H), 4.20 (m, 1H), 3.94 (m, 1H), 3.74 (m, 1H), 3.42-3.47 (m, 2H), 2.97 (m, 1H), 0.79-2.38 (m, 28H).

Scheme 11
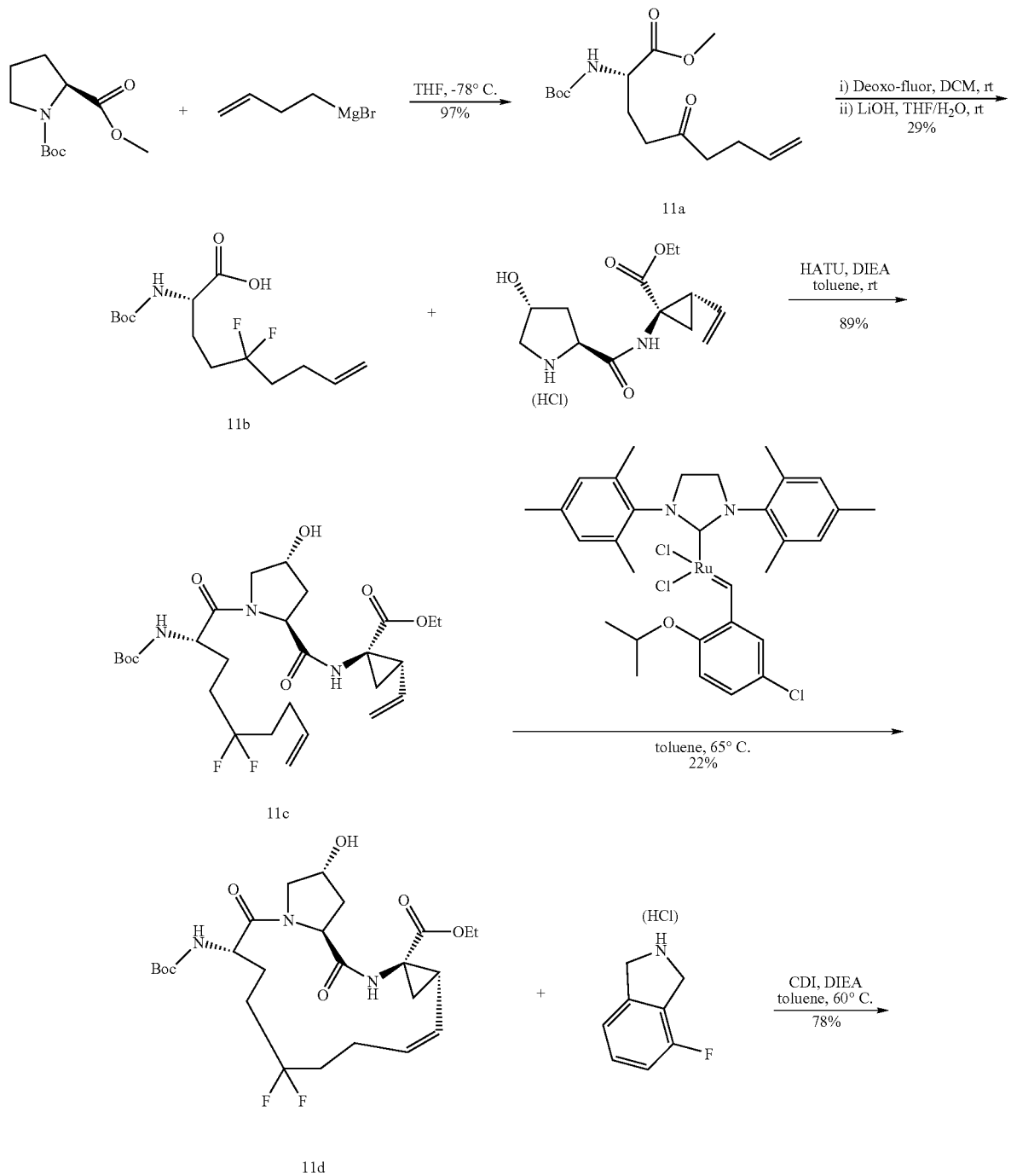

369
370
-continued
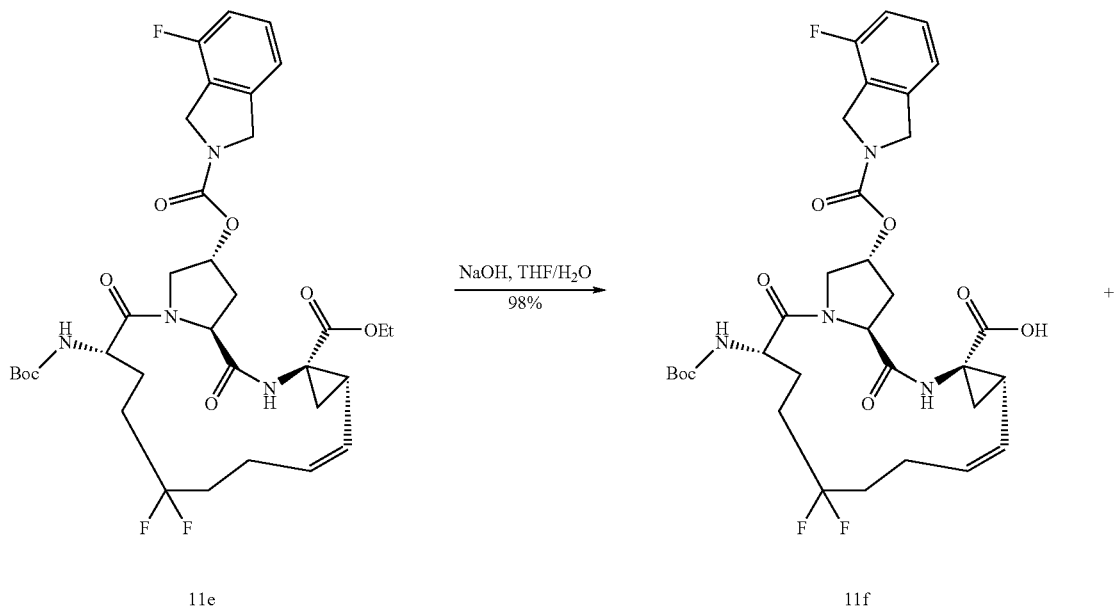
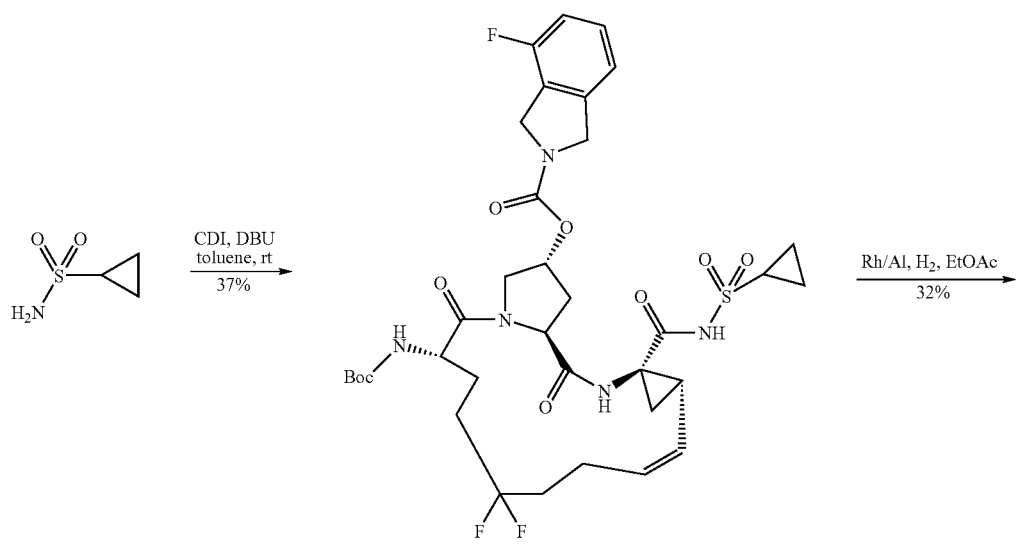
Compound 1009

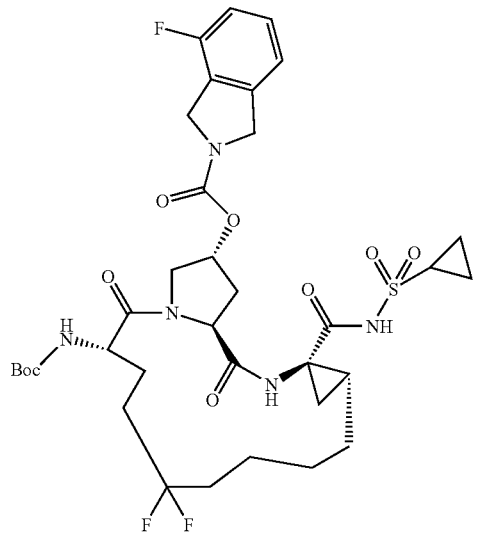

Compound 1010

Step 1: Synthesis of (S)-methyl 2-(tert-butoxycarbonylamino)-5-oxonon-8-enoate (11a)

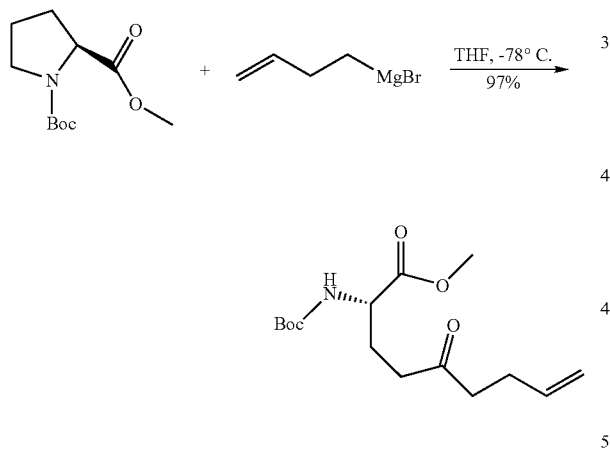

(S)-1-tert-butyl 2-methyl 5-oxopyrrolidine-1,2-dicarboxylate (1.00 g, 4.11 mmol) in THF (20 mL) was added but-3-enylmagnesium bromide (12.3 ml, 6.17 mmol) in THF at −78° C. The reaction mixture was stirred at −78° C. for 1.5 hr and 10% potassium hydrogensulfate (20 mL) was added. The reaction mixture was then poured into a mixture of brine (20 mL) and EA (40 mL). The organic layer was separated and dried over sodium sulfate. After removal of solvent, the residue was purified by chromatography (hexane:Ethyl acetate=4:1) to give the (S)-methyl 2-(tert-butoxycarbonylamino)-5-oxonon-8-enoate as colorless oil (1.12 g, 97%). $^1$H NMR (400 MHz, d$^6$-DMSO) δ7.23 (d, J=7.6 Hz, 1H), 5.79 (m, 1H), 4.93-5.03 (m, 2H), 3.92 (m, 1H), 3.61 (s, 3H), 2.48 (m, 4H), 2.20 (m, 2H), 1.88 (m, 1H), 1.69 (m, 1H), 1.38 (s, 9H).

Step 2: Synthesis of (S)-2-(tert-butoxycarbonylamino)-5,5-difluoronon-8-enoic acid (11b)

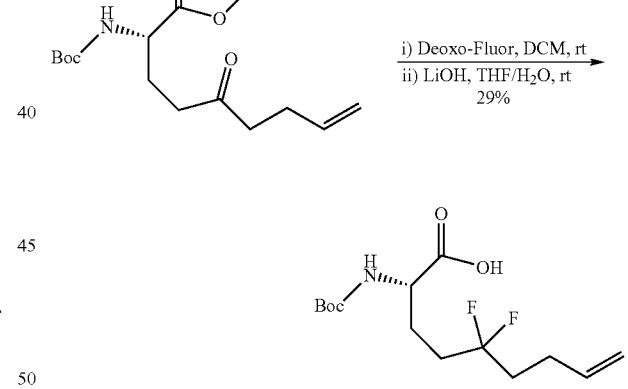

A solution of (S)-methyl 2-(tert-butoxycarbonyl)-5-oxonon-8-enoate (8.57 g, 28.63 mmol) in DCM (10 mL) was treated with Deoxo-Fluor (8.97 ml, 48.67 mmol) at 0° C. Ethanol (0.33 ml, 5.725 mmol) was added, and the mixture was stirred at rt for 20 hrs. The reaction mixture was poured into saturated sodium bicarbonate solution (20 mL) and extracted with DCM (2×20 mL). The organic layer were combined and dried over sodium sulfate. After removal of solvent, the residue was dissolved in THF (30 mL) and water (30 mL). Lithium hydroxide hydrate (1.80 g, 42.94 mmol) was added. The reaction was stirred at rt for 1 hr. Ether (200 mL) was added. The aqueous layer was separated, acidified with saturated potassium hydrogensulfate solution to pH=3, extracted with Ethyl acetate (2×100 mL) and dried over sodium sulfate. After removal of solvent, the residue was purified by chromatography (hexane:Ethyl acetate=2:1) to give the (S)-2-(tert-butoxycarbonylamino)-5,5-difluoronon-8-enoic acid as pale yellow oil (2.58 g, 29%). $^1$H NMR (400 MHz, d$^6$-DMSO) δ12.58 (s, 1H), 7.17 (d, J=7.6 Hz, 1H), 5.83 (m, 1H), 4.98-5.10 (m, 2H), 3.91 (m, 1H), 2.16 (m, 2H), 1.71-1.97 (m, 6H), 1.38 (s, 9H).

Step 3: Synthesis of (1R,2S)-ethyl 1-((2S,4R)-1-((S)-2-(tert-butoxycarbonylamino)-5,5-difluoro-8-enoyl)-4-hydroxypyrrolidine-2-carboxamido)-2-vinylcyclopropanecarboxylate (11c)

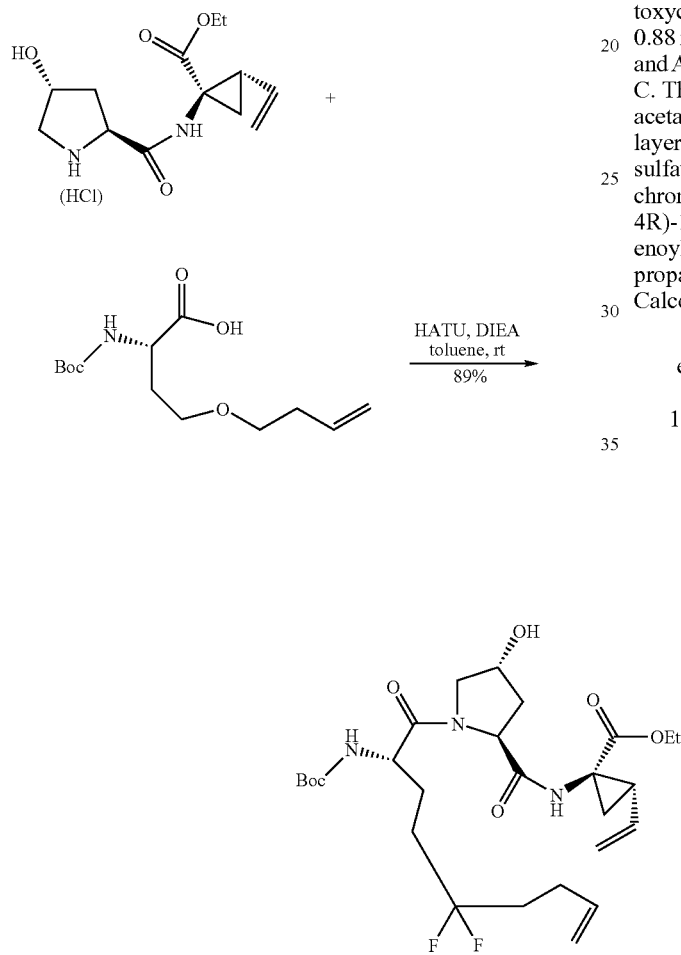

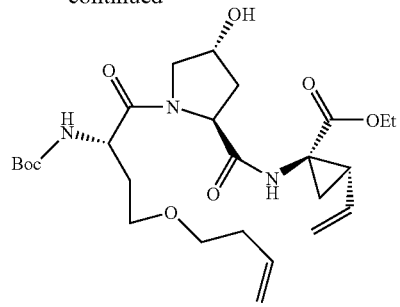

(1R,2S)-ethyl-1-((2S,4R)-4-hydroxypyrrolidine-2-carboxamido)-2-vinylcyclopropanecarboxylate hydrochloride salt (WO2005095403) (0.30 g, 0.97 mmol), (S)-2-(tert-butoxycarbonylamino)-5,5-difluoronon-8-enoic acid (0.27 g, 0.88 mmol) and HATU (0.37 g, 0.97 mmol) in toluene (9 mL) and ACN (1 mL) was added DIEA (0.31 mL, 1.76 mmol) at 0° C. The reaction warmed to rt and stirred at rt for 1 hr. Ethyl acetate (20 mL) and water (20 mL) was added. The organic layer was separated and washed with brine, dried over sodium sulfate. After removal of solvent, the residue was purified by chromatography (Ethyl acetate) to give (1R,2S)-ethyl 1-((2S,4R)-1-((S)-2-(tert-butoxycarbonylamino)-5,5-difluoro-8-enoyl)-4-hydroxypyrrolidine-2-carboxamido)-2-vinylcyclopropanecarboxylate as white wax solid (0.53 g, 89%). MS: Calcd.: 557; Found: [M+H]$^+$ 558.

Step 4: Synthesis of (2R,6S,13aS,14aR,16aS,Z)-ethyl 6-(tert-butoxycarbonylamino)-9,9-difluoro-2-hydroxy-5,16-dioxo-1,2,3,5,6,7,8,9,10,11,13a,14,14a,15,16,16a-hexadecahydrocyclopropa(e)prrolo[1,2-a][1,4]diazacyclopentadecine-14a-carboxylate (11d)

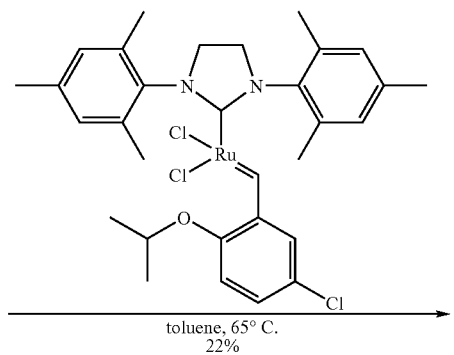

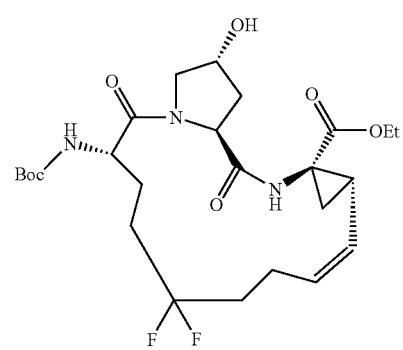

(1R,2S)-ethyl 1-((2S,4R)-1-((S)-2-(tert-butoxycarbonylamino)-5,5-difluoro-8-enoyl)-4-hydroxypyrrolidine-2-carboxamido)-2-vinylcyclopropanecarboxylate (0.53 g, 0.78 mmol) in toluene (130 mL) was degassed by bubbling a stream of nitrogen through the reaction for 1 hr at rt. (5-chloro-2-isopropoxybenzylidene)(1,3-dimesitylimidazolidin-2-yl)ruthenium(V)chloride (0.010 g, 0.016 mmol) was added to the mixture and the mixture was heated to 68° C. (oil bath) and stirred at this temperature for 3 hrs. After removal of solvent, the residue was purified by chromatography (Ethyl acetate) to give (2R,6S,13aS,14aR,16aS,Z)-ethyl 6-(tert-butoxycarbonylamino)-9,9-difluoro-2-hydroxy-5,16-dioxo-1,2,3,5,6,7,8,9,10,11,13a,14,14a,15,16,16a-hexadecahydrocyclopropa(e)prrolo[1,2-a][1,4]diazacyclopentadecine-14a-carboxylate as off white solid (0.090 g, 22%). MS: Calcd.: 529; Found: [M+H]+ 530

Step 5: Synthesis of (2R,6S,13aS,14aR,16aS,Z)-ethyl 6-(tert-butoxycarbonylamino)-9,9-difluoro-2-(4-fluoroisoindoline-2-carbonyloxy)-5,16-dioxo-1,2,3,5,6,7,8,9,10,11,13a,14,14a,15,16,16a-hexadecahydrocyclopropa(e)prrolo[1,2-a][1,4]diazacyclopentadecine-14a-carboxylate (11e)

(2R,6S,13aS,14aR,16aS,Z)-ethyl 6-(tert-butoxycarbonylamino)-9,9-difluoro-2-hydroxy-5,16-dioxo-1,2,3,5,6,7,8,9,10,11,13a,14,14a,15,16,16a-hexadecahydrocyclopropa(e)prrolo[1,2-a][1,4]diazacyclopentadecine-14a-carboxylate (0.088 g, 0.17 mmol) in toluene (5 mL) was added di(1H-imidazol-1-yl)methanone (0.035 g, 0.22 mmol) in one portion. The reaction was stirred at rt for 3 hrs. To the reaction was then added the N-ethyl-N-isopropylpropan-2-amine (0.15 ml, 0.83 mmol), followed by 4-Fluoroisoindoline hydrochloride (0.93 g, 0.33 mmol). The reaction was stirred at 60° C. for 3 hrs. The solvent was removed. The residue was partitioned between ethyl acetate (20 mL) and saturated sodium bicarbonate solution. The organic layer was separated and dried over sodium sulfate. After removal of solvent, the residue was purified by chromatography (Hexane:Ethyl acetate=1:2) to give (2R,6S,13aS,14aR,16aS,Z)-ethyl 6-(tert-butoxycarbonylamino)-9,9-difluoro-2-(4-fluoroisoindoline-2-carbonyloxy)-5,16-dioxo-1,2,3,5,6,7,8,9,10,11,13a,14,14a,15,16,16a-hexadecahydrocyclopropa(e)prrolo[t,2-a][1,4]diazacyclopentadecine-14a-carboxylate as white solid (0.090 g, 78%). MS: Calcd.: 692; Found: [M+H]+ 693.

Step 6: Synthesis of (2R,6S,13aS,14aR,16aS,Z)-6-(tert-butoxycarbonylamino)-9,9-difluoro-2-(4-fluoroisoindoline-2-carbonyloxy)-5,16-dioxo-1,2,3,5,6,7,8,9,10,11,13a,14,14a,15,16,16a-hexadecahydrocyclopropa(e)prrolo[1,2-a][1,4]diazacyclopentadecine-14a-carboxylic acid (Compound 1006)

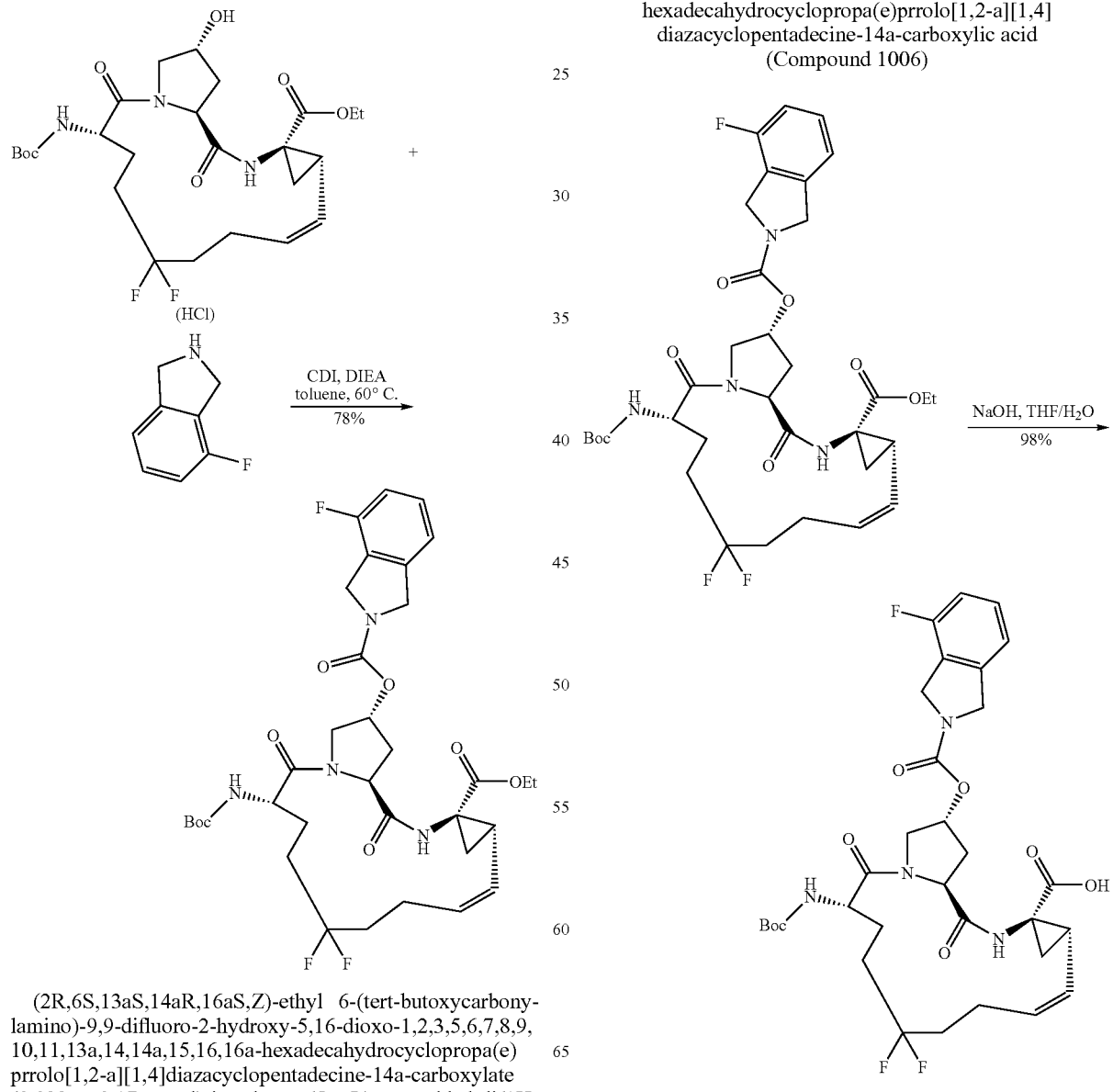

(2R,6S,13aS,14aR,16aS,Z)-ethyl 6-(tert-butoxycarbonylamino)-9,9-difluoro-2-(4-fluoroisoindoline-2-carbonyloxy)-5,16-dioxo-1,2,3,5,6,7,8,9,10,11,13a,14,14a,15,16,16a-hexadecahydrocyclopropa(e)prrolo[1,2-a][1,4]diazacyclopentadecine-14a-carboxylate (0.088 g, 0.13 mmol) in THF (2 mL) was added 0.1 N NaOH solution (3.2 ml, 0.32 mmol) in water. The reaction was stirred at rt for 3 days. Water (5 mL) and ether (15 mL) was added. The aqueous layer was separated and acidified by saturated potassium hydrogen sulfate solution to pH=2~3. The aqueous layer was extracted with EA (2×15 mL), washed with brine and dried over sodium sulfate. After removal of solvent, it gave (2R,6S,13aS,14aR,16aS,Z)-6-(tert-butoxycarbonylamino)-9,9-difluoro-2-(4-fluoroisoindoline-2-carbonyloxy)-5,16-dioxo-1,2,3,5,6,7,8,9,10,11,13a,14,14a,15,16,16a-hexadecahydrocyclopropa(e)prrolo[1,2-a][1,4]diazacyclopentadecine-14a-carboxylic acid as white solid (0.083 g, 98%). MS: Calcd.: 664; Found: [M+H]$^+$ 665. $^1$H NMR (400 MHz, d$^6$-DMSO) δ12.14 (s, 1H), 8.71 (s, 1H), 7.28 (m, 1H), 7.05-7.15 (m, 3H), 5.43 (m, 1H), 5.29 (m, 1H), 5.25 (m, 1H), 4.61 (s, 4H), 4.35 (m, 1H), 4.22 (m, 1H), 3.98 (m, 1H), 3.63 (m, 1H), 3.63 (m, 1H), 2.07-2.27 9m, 4H), 1.85-2.03 (m, 3H), 1.65 (m, 2H), 1.42-1.50 (m, 3H), 1.02-1.18 (m, 10H).

Step 7: Synthesis of (2R,6S,13aS,14aR,16aS,Z)-6-(tert-butoxycarbonylamino)-14a-(cyclopropylsulfonylcarbamoyl)-9,9-difluoro-5,16-dioxo-1,2,3,5,6,7,8,9,10,11,13a,14,14a,15,16,16a-hexadecahydrocyclopropa(e)prrolo[1,2-a][1,4]diazacyclopentadecine 2-yl 4-fluoroisoindoline-2-carboxylate (Compound 1008)

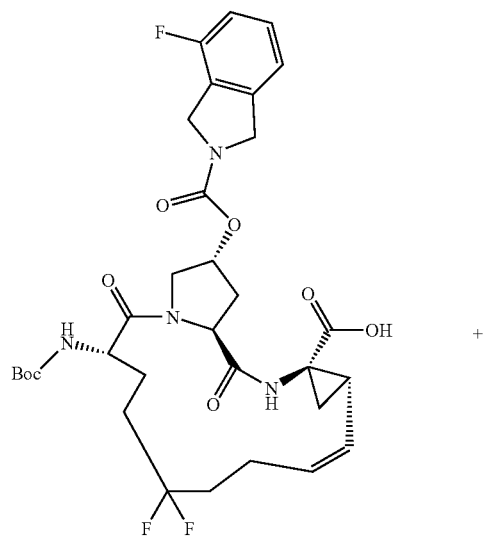

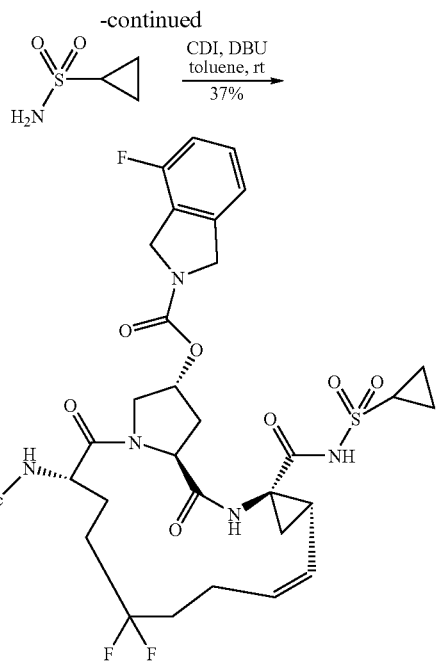

(2R,6S,13aS,14aR,16aS,Z)-6-(tert-butoxycarbonylamino)-9,9-difluoro-2-(4-fluoroisoindoline-2-carbonyloxy)-5,16-dioxo-1,2,3,5,6,7,8,9,10,11,13a,14,14a,15,16,16a-hexadecahydrocyclopropa(e)prrolo[1,2-a][1,4]diazacyclopentadecine-14a-carboxylic acid (0.079 g, 0.12 mmol) in toluene (3 mL) was added di(1H-imidazol-1-yl)methanone (0.029 g, 0.18 mmol) in rt. The reaction was stirred at 60° C. for 3 hrs. Cyclopropanesulfonamide (0.025 g, 0.24 mmol) was added, followed by addition of DBU (0.036 ml, 0.24 mmol). The reaction was then stirred at rt for 17 hrs. Water (5 mL) was added and acidified with saturated potassium hydrogen sulfate until pH=2~3. The mixture was extracted with ethyl acetate (20 mL), washed with brine and dried over sodium sulfate. After removal of solvent, the residue was purified by chromatography (Ethyl acetate) to give (2R,6S,13aS,14aR,16aS,Z)-6-(tert-butoxycarbonylamino)-14a-(cyclopropylsulfonylcarbamoyl)-9,9-difluoro-5,16-dioxo-1,2,3,5,6,7,8,9,10,11,13a,14,14a,15,16,16a-hexadecahydrocyclopropa(e)prrolo[1,2-a][1,4]diazacyclopentadecine 2-yl 4-fluoroisoindoline-2-carboxylate as white solid (0.034 g, 37%). MS: Calcd.: 767; Found: [M+H]$^+$ 768. $^1$H NMR (400 MHz, d$^6$-DMSO) δ11.09 (s, 1H), 9.07 (s, 1H), 7.35 (m, 1H), 7.11-7.25 (m, 3H), 5.58 (m, 1H), 5.30 (m, 1H), 5.18 (m, 1H), 4.67 (s, 4H), 4.44 (m, 1H), 4.34 (m, 1H), 4.03 (m, 1H), 3.73 (m, 1H), 2.90 (m, 1H), 2.40 (m, 1H), 2.22 (m, 1H), 1.99 (m, 4H), 1.61-1.71 (m, 4H), 0.98-1.24 (m, 16H).

Step 8: Synthesis of (2R,6S,13aS,14aR,16aS,Z)-6-(tert-butoxycarbonylamino)-14a-(cyclopropylsulfonylcarbamoyl)-9,9-difluoro-5,16-dioxooctadecahydrocyclopropa(e)prrolo[1,2-a][1,4]diazacyclopentadecine 2-yl 4-fluoroisoindoline-2-carboxylate (Compound 1010)

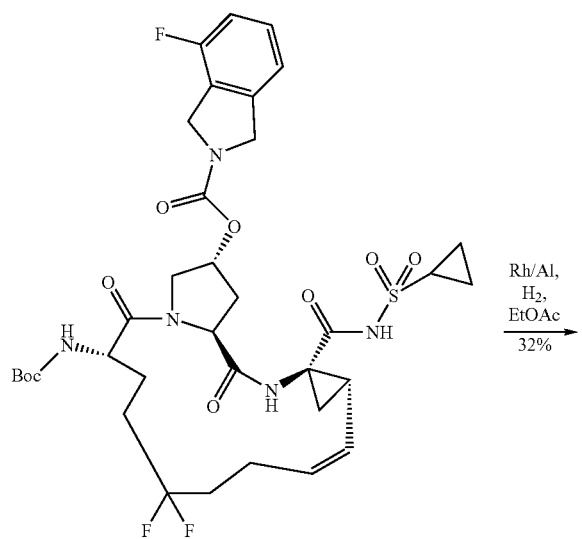

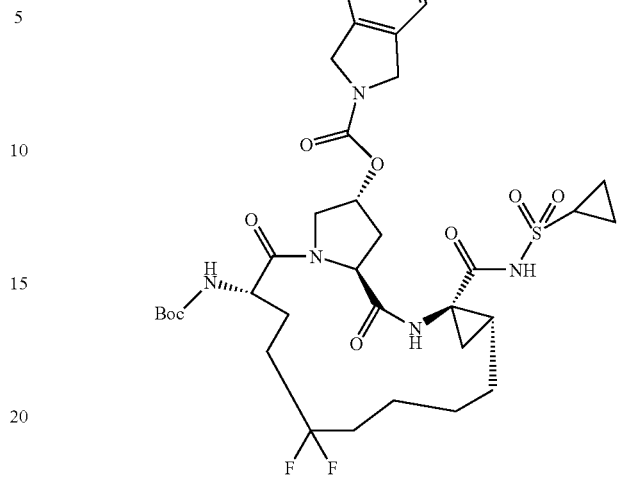

(2R,6S,13aS,14aR,16aS,Z)-6-(tert-butoxycarbonylamino)-14a-(cyclopropylsulfonylcarbamoyl)-9,9-difluoro-5,16-dioxo-1,2,3,5,6,7,8,9,10,11,13a,14,14a,15,16,16a-hexadecahydrocyclopropa(e)prrolo[1,2-a][1,4]diazacyclopentadecine 2-yl 4-fluoroisoindoline-2-carboxylate (0.075 g, 0.098 mmol) and Rh/Al (5%) (0.020 g, 0.0098 mmol) in Ethyl acetate (10 mL) was charged with 1 atmosphere of hydrogen and stirred for 16 hrs. Water (3 mL) and saturated potassium hydrogen sulfate (3 mL) was added and stirred for 10 minutes. The organic phase was separated, washed with brine and dried over sodium sulfate. After removal of solvent, the residue was purified by chromatography (Hexane:Ethyl acetate=1:2) to give (2R,6S,13aS,14aR,16aS,Z)-6-(tert-butoxycarbonylamino)-14a-(cyclopropylsulfonylcarbamoyl)-9,9-difluoro-5,16-dioxooctadecahydrocyclopropa(e)prrolo[1,2-a][1,4]diazacyclopentadecine 2-yl 4-fluoroisoindoline-2-carboxylate as white solid (0.024 g, 32%). MS: Calcd.: 769; Found: [M+H]+ 770. $^1$H NMR (400 MHz, d$^6$-DMSO) δ11.21 (s, 1H), 9.08 (s, 1H), 7.36 (m, 1H), 7.10-7.18 (m, 3H), 5.30 (m, 1H), 4.67 (s, 4H), 4.48 (m, 1H), 4.45 (m, 1H), 4.30 (m, 1H), 3.76 (m, 1H), 2.97 (m, 1H), 2.42 (m, 1H), 2.15 (m, 2H), 1.71-1.99 (m, 3H), 1.57 (m, 3H), 0.97-1.41 (m, 21H).

Scheme 12

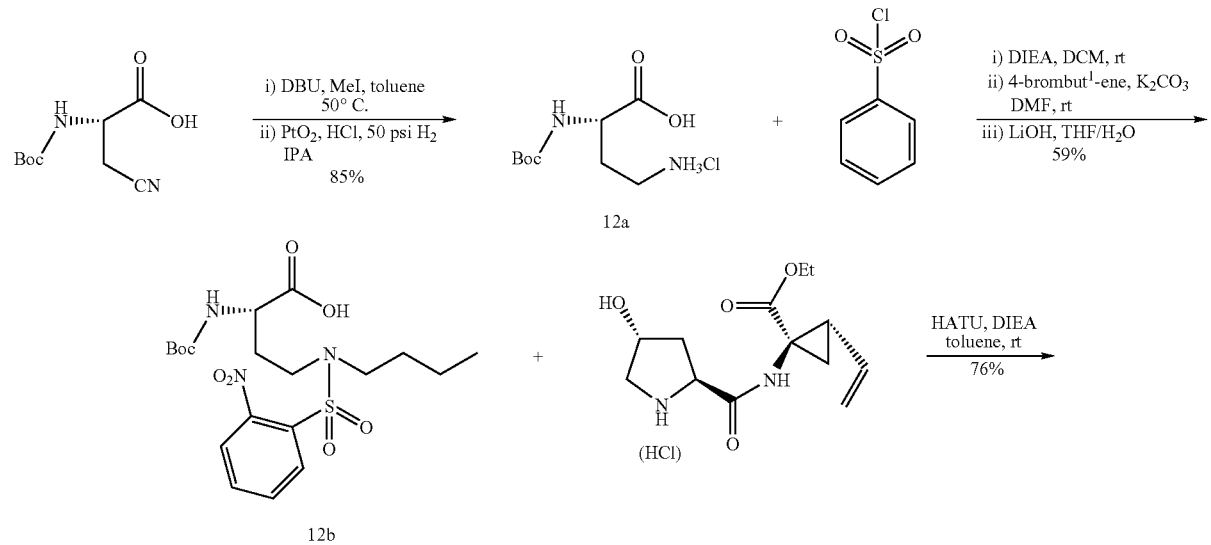

-continued
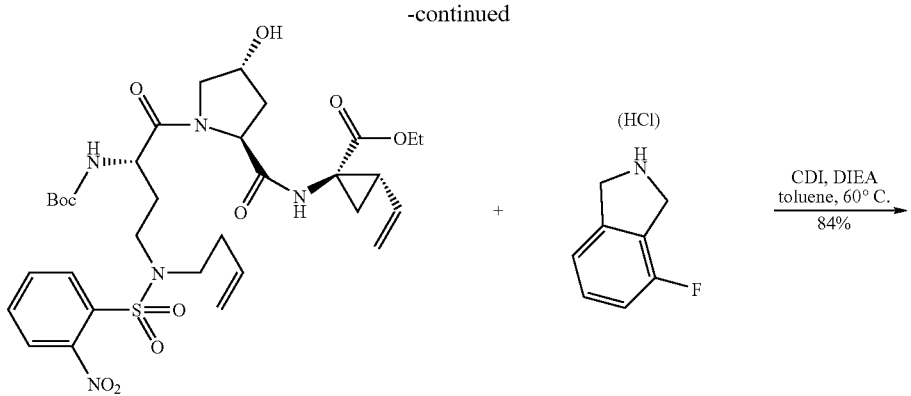
12c
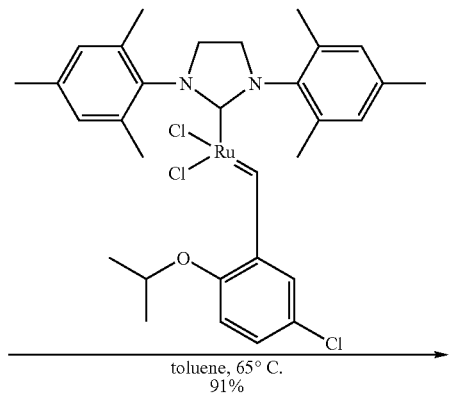
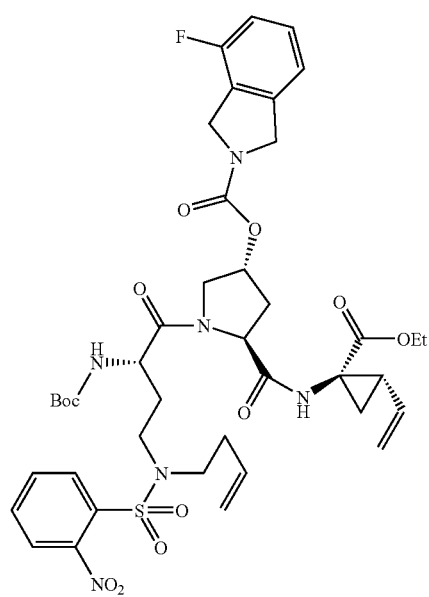
12e
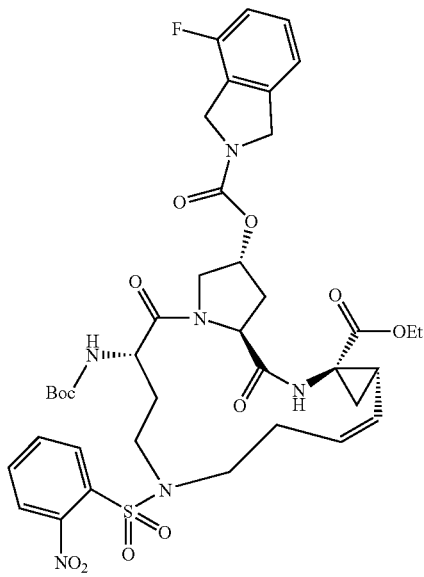
12f
NaOH, THF/H$_2$O
100%
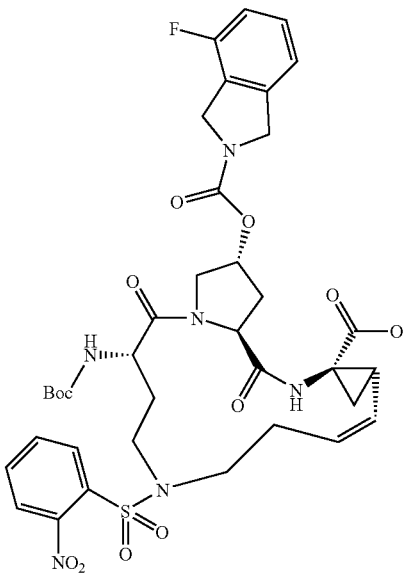
12g

-continued
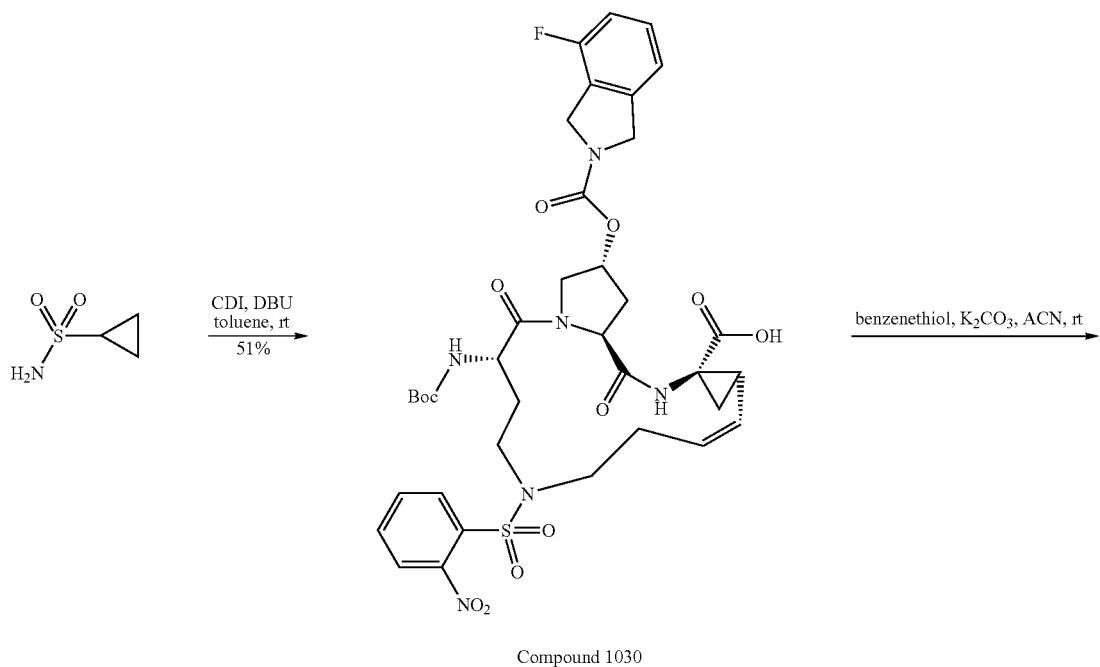
Compound 1030
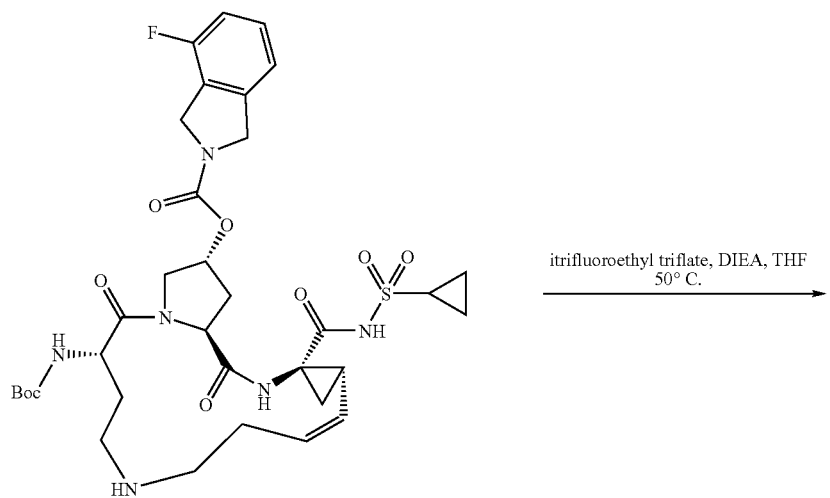
Compound 1031

-continued

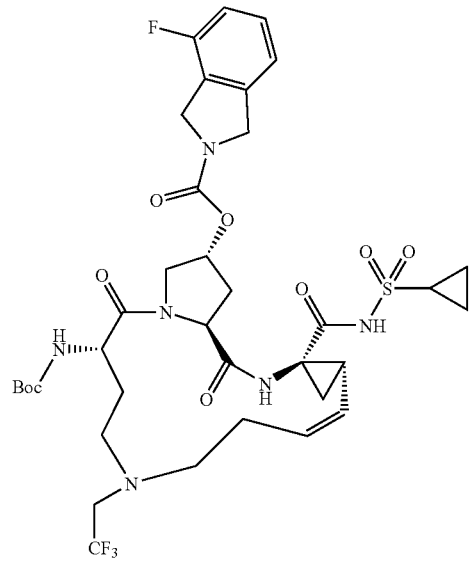

Compound 1032

Step 1: Synthesis of (S)-4-amino-2-(tert-butoxycarbonylamino)-butanoic acid hydrochloride (12a)

Step 2: Synthesis of (S)-4-(N-(but-3-enyl)-2-nitrophenylsulfonamido)-2-(tert-butoxycarbonylamino)-butanoic acid (12b)

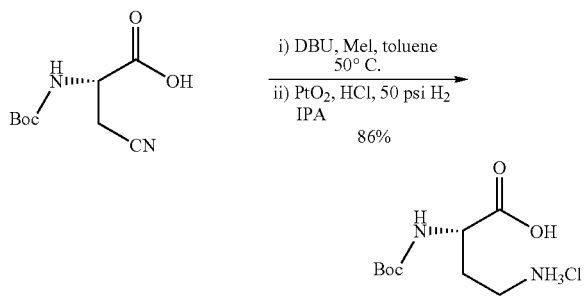

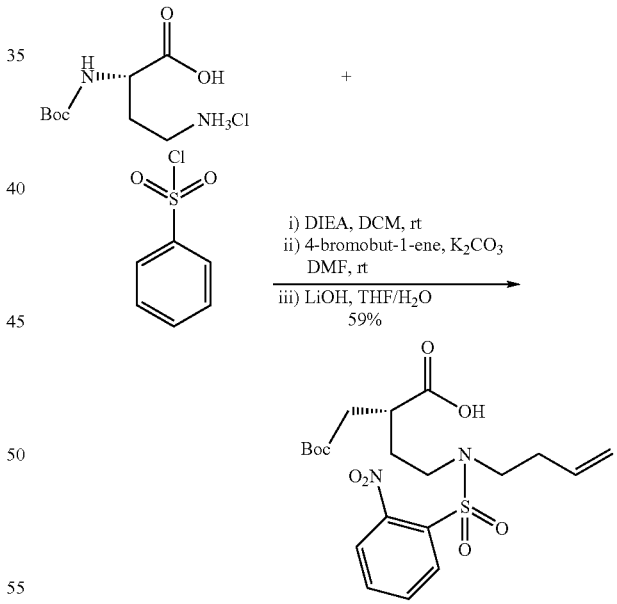

Iodomethane (2.18 ml, 35.01 mmol) was added to a mixture of (S)-2-(tert-butoxycarbonylamino)-3-cyanopropanoic acid (5.00 g, 23.34 mmol) and DBU (3.67 ml, 24.51 mmol) in toluene (20 mL) at rt. The reaction was stirred at 50 C for 2 days. Water (20 mL), saturated KHSO4 (20 mL) and ethyl acetate (50 mL) were added. The organic layer was separated, washed with brine and dried over sodium sulfate. After removal of solvent, the residue was purified by chromatography (hexane:Ethyl acetate=2:1) to give the (S)-methyl-2-(tert-butoxycarbonylamino)-3-cyanopropanoate as white solid (4.6 g, 86%). $^1$H NMR (400 MHz, d$^6$-DMSO) δ7.64 (d, J=8.8 Hz, 1H), 4.39 (m, 1H), 3.66 (s, 3H), 2.96 (dd, J=16.8 Hz & 5.1 Hz, 1H), 2.85 (dd, J=16.8 Hz & 5.2 Hz, 1H), 1.40 (s, 9H).

(S)-methyl 2-(tert-butoxycarbonyl)-3-cyanopropanoate (0.85 g, 3.72 mmol) was dissolved in cold IPA (20 mL) containing conc. HCl (0.31 ml, 3.72 mmol) and PtO$_2$ (0.085 g, 0.37 mmol) was added. The mixture was hydrogenated at 50 psi for 2 hr and filtered through the celite. The filtrate was concentrated to give the (S)-4-amino-2-(tert-butoxycarbonylamino)-butanoic acid hydrochloride as white solid (1.00 g, 100%). MS: Calcd.: 232; Found: [M+H]$^+$ 233. $^1$H NMR (400 MHz, d$^6$-DMSO) δ7.99 (s, 3H), 7.17 (d, J=7.6 Hz, 1H), 4.16 (m, 1H), 3.32 (s, 3H), 2.80 (m, 2H), 1.98 (m, 1H), 1.84 (m, 1H), 1.38 (s, 9H).

(S)-methyl 2-(tert-butoxycarbonyl)-4-(chloroamino)butanoate (0.30 g, 1.12 mmol) in DCM (10 mL) was added DIEA (0.43 ml, 2.46 mmol) and 2-nitrobenzene-1-sulfonyl chloride (0.26 g, 1.17 mmol). The mixture was stirred at rt for 2 hr. It was then concentrated, dissolved in ethyl acetate (30 mL), which was washed with water, saturated sodium bicarbonate and brine and dried over sodium sulfate. After removal of solvent, it gave the (S)-methyl 2-(tert-butoxycarbonylamino)-4-(2-nitrophenylsulfonamido)-butanoate as yellow form solid (0.42 g, 90%). MS: Calcd.: 417; Found: [M+H]$^+$ 418.

To a mixture of (S)-methyl 2-(tert-butoxycarbonyl)-4-(2-nitrophenylsulfonamido)butanoate (0.42 g, 1.01 mmol) in DMF (8 mL) was added K$_2$CO$_3$ (0.28 g, 2.01 mmol). This mixture was stirred at rt for 20 min, followed by the addition of 4-bromobut-1-ene (0.21 ml, 2.01 mmol). The reaction mixture was stirred at rt for 2 days. Water (10 mL) was added and extracted with ether (2×30 mL). The combined ether layers were washed with brine and dried over sodium sulfate. After removal of solvent, the residue was purified by chromatography (hexane:Ethyl acetate=2:1) to give the (S)-methyl 4-(N-(but-3-enyl)-2-nitrophenylsulfonamido)-2-(tert-butoxycarbonylamino)butanoate as pale yellow solid (0.32 g, 67%). MS: Calcd.: 471; Found: [M+H]$^+$ 472. $^1$H NMR (400 MHz, (d$^6$-DMSO) δ7.98 (m, 2H), 7.85 (m, 2H), 7.38 (d, J=8.0 Hz, 1H), 5.50 (m, 1H), 5.04 (m, 2H), 3.99 (m, 1H), 3.60 (s, 3H), 3.27 (m, 4H), 2.24 (m, 2H), 1.98 (m, 1H), 1.92 (m, 1H), 1.36 (s, 9H).

(S)-methyl 4-(N-(but-3-enyl)-2-nitrophenylsulfonamido)-2-(tert-butoxycarbonyl)butanoate (1.45 g, 3.08 mmol) in THF (10 mL) and H$_2$O (5 mL) was added LiOH—H$_2$O (0.32 g, 7.69 mmol). The reaction was stirred at rt for 1 hr. Water (5 ml) and ether (15 mL) was added. The aqueous layer was separated and acidified by saturated potassium hydrogensulfate solution to pH=3~4. The aqueous layer was extracted with EA (20 mL), washed with brine and dried over sodium sulfate. After removal of solvent, it gave the (S)-4-(N-(but-3-enyl)-2-nitrophenylsulfonamido)-2-(tert-butoxycarbonylamino)-butanoic acid as brown foam solid (1.38 g, 98%). MS: Calcd.: 457; Found: [M+H]$^+$ 458. $^1$H NMR (400 MHz, d$^6$-DMSO) δ12.57 (s, 1H), 7.99 (m, 2H), 7.86 (m, 2H), 7.19 (d, J=8.0 Hz, 1H), 5.68 (m, 1H), 5.02 (m, 2H), 3.89 (m, 1H), 3.22-3.40 (m, 4H), 2.25 (m, 2H), 1.90 (m, 1H), 1.80 (m, 1H), 1.38 (s, 9H).

Step 3: Synthesis of (1R,2S)-ethyl 1-((2S,4R)-1-((S)-4-(N-(but-3-enyl)-2-nitrophenylsulfonamido)-2-(tert-butoxycarbonylamino)butanoyl)-4-hydroxypyrrolidine-2-carboxamido)-2-vinylcyclopropanecarboxylate (12c)

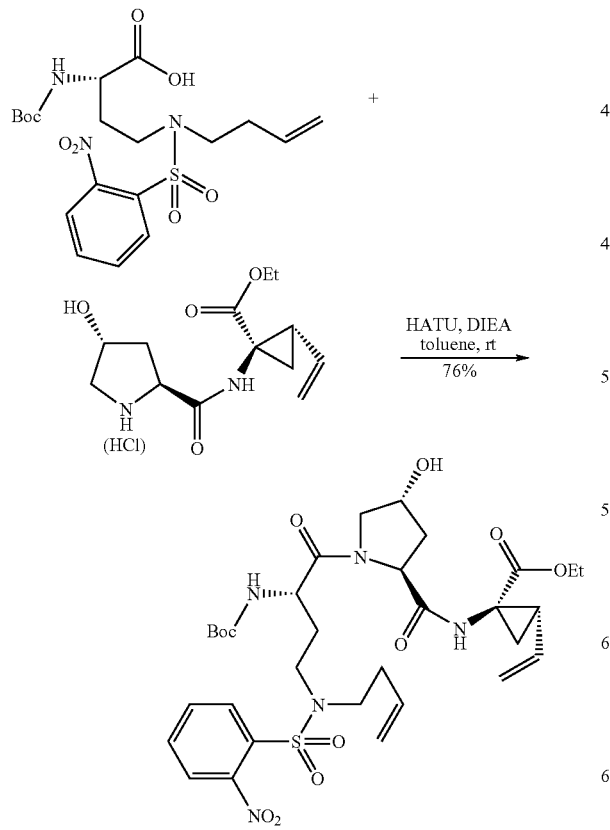

(1R,2S)-ethyl-1-((2S,4R)-4-hydroxypyrrolidine-2-carboxamido)-2-vinylcyclopropanecarboxylate hydrochloride salt (WO2005095403) (1.04 g, 3.32 mmol), (S)-4-(N-(but-3-enyl)-2-nitrophenylsulfonamido)-2-(tert-butoxycarbonylamino)-butanoic acid (1.38 g, 3.02 mmol) and HATU (1.26 g, 3.32 mmol) in toluene (36 mL) and ACN (4 mL) was added DIEA (2.05 mL, 6.03 mmol) at 0° C. The reaction warmed to rt and stirred at rt for 1 hr. Ethyl acetate (50 mL) and water (20 mL) was added. The organic layer was separated and washed with brine, dried over sodium sulfate. After removal of solvent, the residue was purified by chromatography (Ethyl acetate) to give (1R,2S)-ethyl 1-((2S,4R)-1-((S)-4-(N-(but-3-enyl)-2-nitrophenylsulfonamido)-2-(tert-butoxycarbonylamino)butanoyl)-4-hydroxypyrrolidine-2-carboxamido)-2-vinylcyclopropanecarboxylate as white foam solid (1.63 g, 76%). MS: Calcd.: 707; Found: [M+H]$^+$ 708.

Step 4: Synthesis of (3R,5S)-1-((S)-4-(N-(but-3-enyl)-2-nitrophenylsulfonamido)-2-(tert-butoxycarbonylamino)butanoyl)-5-((1R,2S)-1-(ethoxycarbonyl)-2-vinylcyclopropylcarbamoyl)pyrrolidin-3-yl 4-fluoroisoindoline-2-carboxylate (12d)

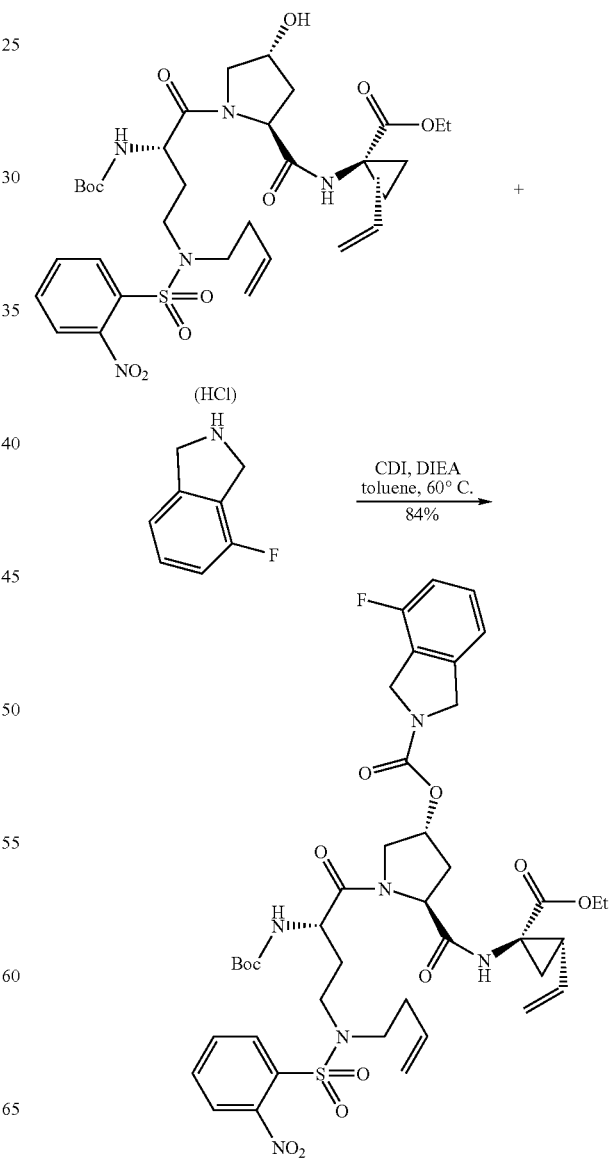

(1R,2S)-ethyl 1-((2S,4R)-1-((S)-4-(N-(but-3-enyl)-2-nitrophenylsulfonamido)-2-(tert-butoxycarbonylamino)butanoyl)-4-hydroxypyrrolidine-2-carboxamido)-2-vinylcyclopropanecarboxylate (1.60 g, 2.26 mmol) in toluene (20 mL) was added di(1H-imidazol-1-yl)methanone (0.48 g, 2.94 mmol) in one portion. The reaction was stirred at rt for 3 hrs. To the reaction was then added the N-ethyl-N-isopropylpropan-2-amine (1.97 ml, 11.30 mmol), followed by 4-Fluoroisoindoline hydrochloride (1.27 g, 4.52 mmol). The reaction was stirred at 60° C. for 3 hrs. The solvent was removed. The residue was partitioned between ethyl acetate (30 mL) and saturated sodium bicarbonate solution. The organic layer was separated and dried over sodium sulfate. After removal of solvent, the residue was purified by chromatography (Hexane:Ethyl acetate=1:2) to give (3R,5S)-1-((S)-4-(N-(but-3-enyl)-2-nitrophenylsulfonamido)-2-(tert-butoxycarbonylamino)butanoyl)-5-(((1R,2S)-1-(ethoxycarbonyl)-2-vinylcyclopropylcarbamoyl)pyrrolidin-3-yl 4-fluoroisoindoline-2-carboxylate as white solid (1.65 g, 84%). MS: Calcd.: 870; Found: [M+H]+ 871.

Step 5: Synthesis of (2R,6S,13aS,14aR,16aS,Z)-ethyl 6-(tert-butoxycarbonylamino)-2-(4-fluoroisoindoline-2-carbonyloxy)-9-(2-nitrophenylsulfonyl)-5,16-dioxo-1,2,3,5,6,7,8,9,10,11,13a,14,14a,15,16,16a-hexadecahydrocyclopropa(n)pyrrolo[2,1-c][1,4,9]triazacyclopentadecine-14a-carboxylate (12e)

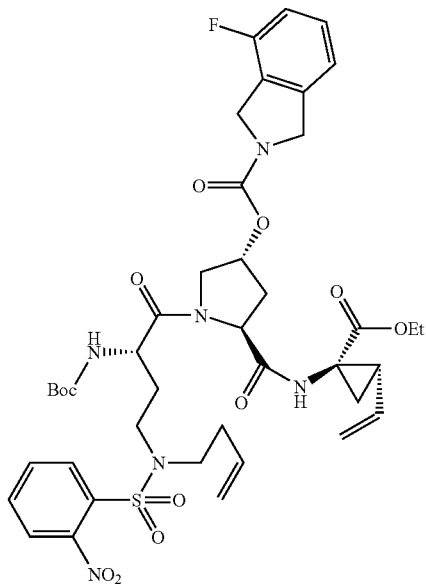
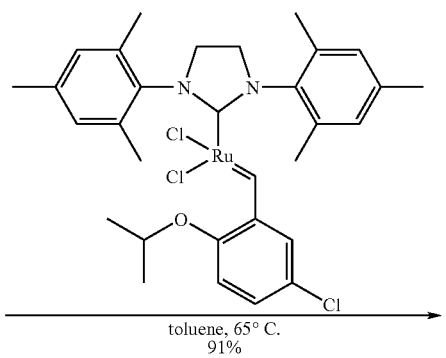

toluene, 65° C.
91%

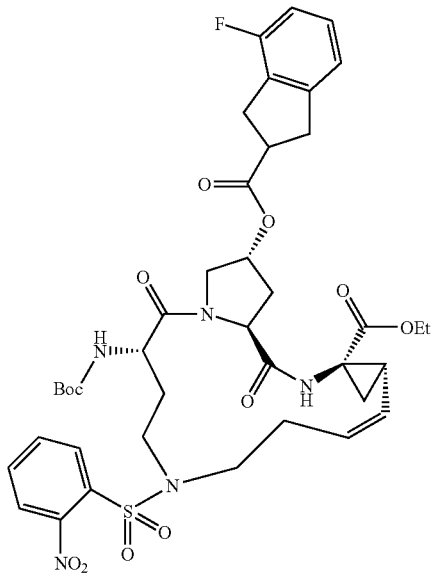

(3R,5S)-1-((S)-4-(N-(but-3-enyl)-2-nitrophenylsulfonamido)-2-(tert-butoxycarbonylamino)butanoyl)-5-((1R,2S)-1-(ethoxycarbonyl)-2-vinylcyclopropylcarbamoyl)pyrrolidin-3-yl 4-fluoroisoindoline-2-carboxylate (1.65 g, 1.89 mmol) in toluene (400 mL) was degassed by bubbling a stream of nitrogen through the reaction for 1 hr at rt. (5-chloro-2-isopropoxybenzylidene)(1,3-dimesitylimidazolidin-2-yl)ruthenium(V)chloride (0.025 g, 0.038 mmol) was added to the mixture and the mixture was heated to 68° C. (oil bath) and stirred at this temperature for 2 hrs. After removal of solvent, the residue was purified by chromatography (Hexane:Ethyl acetate=1:1) to give (2R,6S,13aS,14aR,16aS,Z)-ethyl 6-(tert-butoxycarbonylamino)-2-(4-fluoroisoindoline-2-carbonyloxy)-9-(2-nitrophenylsulfonyl)-5,16-dioxo-1,2,3,5,6,7,8,9,10,11,13a,14,14a,15,16,16a-hexadecahydrocyclopropa(n)pyrrolo[2,1-c][1,4,9]triazacyclopentadecine-14a-carboxylate as off white solid (1.45 g, 91%). MS: Calcd.: 842; Found: [M+H]+ 843

Step 6: Synthesis of (2R,6S,13aS,14aR,16aS,Z)-6-(tert-butoxycarbonylamino)-2-(4-fluoroisoindoline-2-carbonyloxy)-9-(2-nitrophenylsulfonyl)-5,16-dioxo-1,2,3,5,6,7,8,9,10,11,13a,14,14a,15,16,16a-hexadecahydrocyclopropa(n)pyrrolo[2,1-c][1,4,9]triazacyclopentadecine-14a-carboxylic acid (12f)

(2R,6S,13aS,14aR,16aS,Z)-ethyl 6-(tert-butoxycarbonylamino)-2-(4-fluoroisoindoline-2-carbonyloxy)-9-(2-nitrophenylsulfonyl)-5,16-dioxo-1,2,3,5,6,7,8,9,10,11,13a,14,14a,15,16,16a-hexadecahydrocyclopropa(n)pyrrolo[2,1-c][1,4,9]triazacyclopentadecine-14a-carboxylate (1.45 g, 1.72 mmol) in THF (22 mL) was added 0.4 N NaOH solution (10.8 ml, 4.30 mmol) in water. The reaction was stirred at rt for 6 days. Water (5 mL) and ether (15 mL) was added. The aqueous layer was separated and acidified by saturated potassium hydrogen sulfate solution to pH=2~3. The aqueous layer was extracted with EA (2×30 mL). the combined organics were washed with brine and dried over sodium sulfate. After removal of solvent, it gave (2R,6S,13aS,14aR,16aS,Z)-6-(tert-butoxycarbonylamino)-2-(4-fluoroisoindoline-2-carbonyloxy)-9-(2-nitrophenylsulfonyl)-5,16-dioxo-1,2,3,5,6,7,8,9,10,11,13a,14,14a,15,16,16a-hexadecahydrocyclopropa(n)pyrrolo[2,1-c][1,4,9]triazacyclopentadecine-14a-carboxylic acid as white solid (1.40 g, 99%). MS: Calcd.: 814; Found: [M+H]+ 815. $^1$H NMR (400 MHz, d$^6$-DMSO) δ11.24 (s, 1H), 8.84 (s, 1H), 8.01 (m, 2H), 7.86 (m, 2H), 7.36 (m, 1H), 7.10-7.26 (m, 3H), 5.49 (m, 1H), 5.39 (m, 1H), 5.27 (m, 1H), 4.67 & 4.66 (s, 4H), 4.40 (m, 1H), 4.27 (m, 1H), 3.97 (m, 1H), 3.66 (m, 1H), 3.31-3.53 (m, 2H), 3.23 (m, 1H), 2.96 (m, 1H), 2.55 (m, 1H), 2.25 (m, 2H), 1.99 (m, 2H), 1.91 (m, 2H), 0.96-1.69 (m, 11H).

Step 7: Synthesis of (2R,6S,13aS,14aR,16aS,Z)-6-(tert-butoxycarbonylamino)-14a-(cyclopropylsulfonylcarbamoyl)-9-(2-nitrophenylsulfonyl)-5,16-dioxo-1,2,3,5,6,7,8,9,10,11,13a,14,14a,15,16,16a-hexadecahydrocyclopropa(n)pyrrolo[2,1-c][1,4,9]triazacyclopentadecine-2-yl 4-fluoroisoindoline-2-carboxylate (Compound 1030)

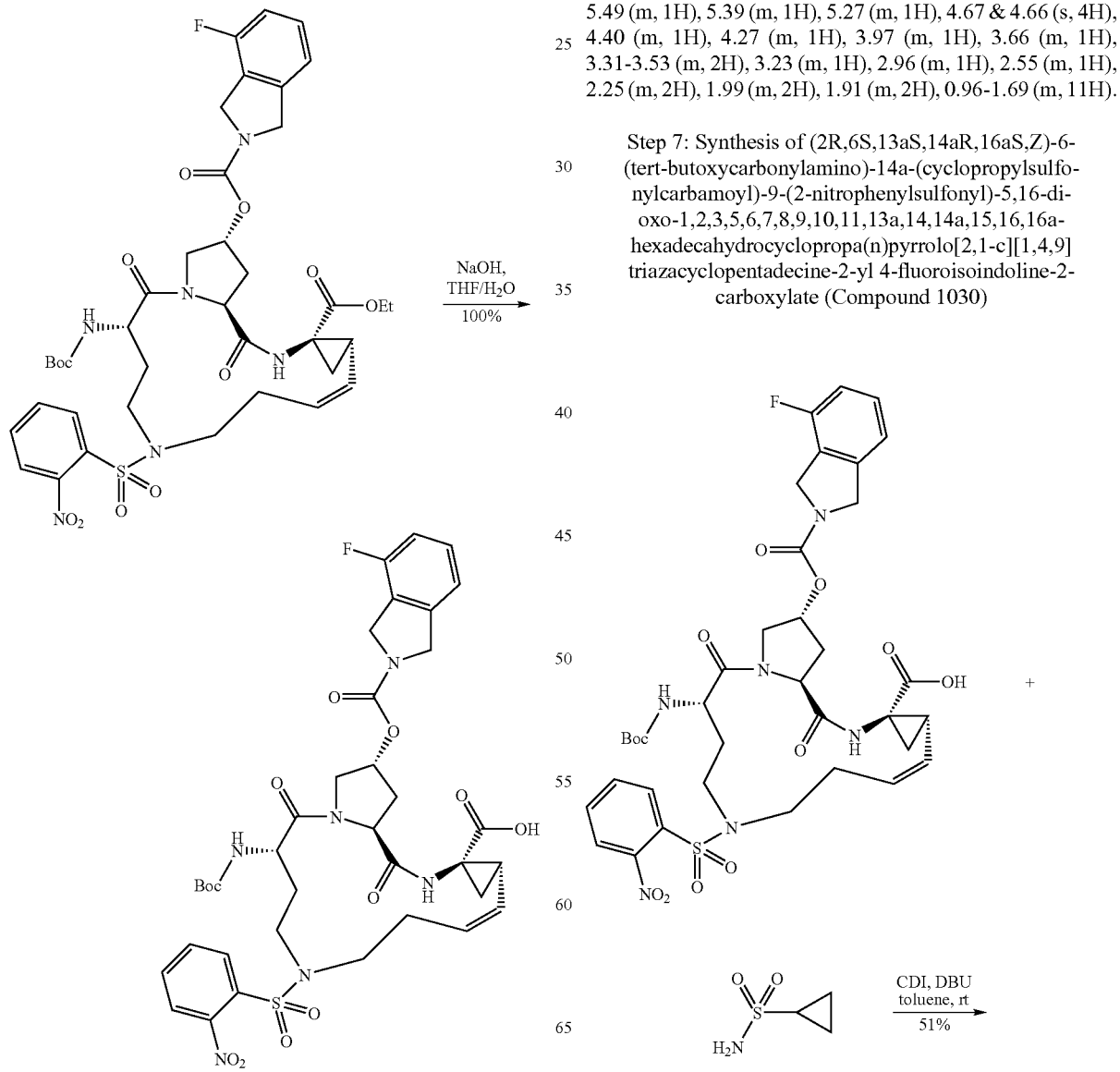

-continued

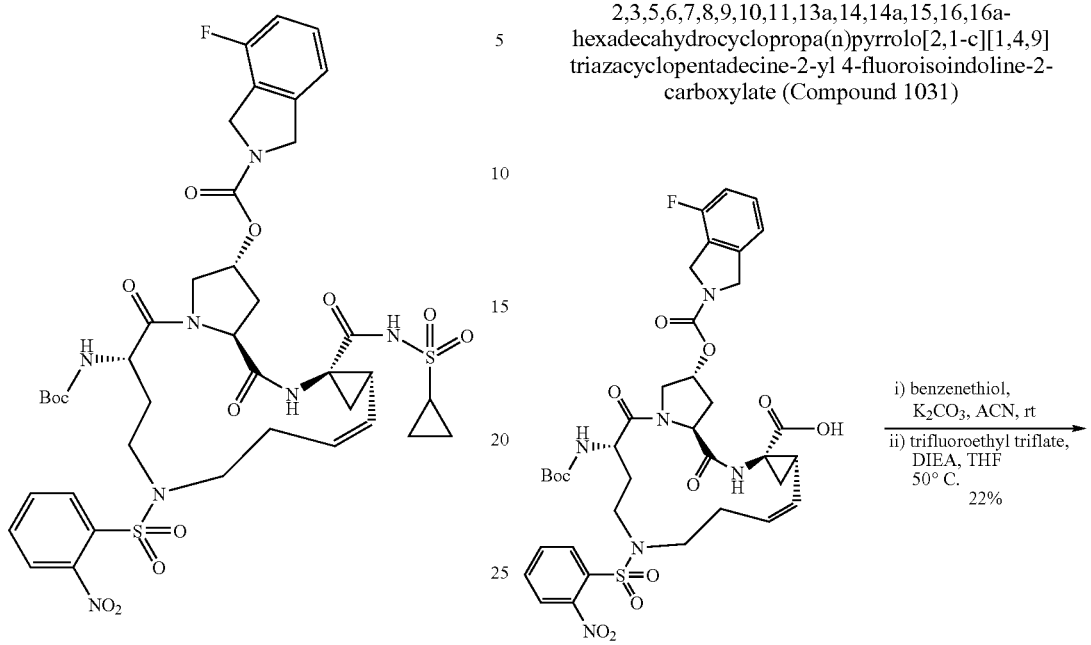

(2R,6S,13aS,14aR,16aS,Z)-6-(tert-butoxycarbonylamino)-2-(4-fluoroisoindoline-2-carbonyloxy)-9-(2-nitrophenylsulfonyl)-5,16-dioxo-1,2,3,5,6,7,8,9,10,11, 13a,14, 14a,15,16,16a-hexadecahydrocyclopropa(n)pyrrolo[2,1-c][1,4,9]triazacyclopentadecine-14a-carboxylic acid (0.71 g, 0.87 mmol) in toluene (10 mL) was added di(1H-imidazol-1-yl)methanone (0.18 g, 1.13 mmol) in rt. The reaction was stirred at 60° C. for 3 hrs. Cyclopropanesulfonamide (0.16 g, 1.31 mmol) was added, followed by addition of DBU (0.26 ml, 1.74 mmol). The reaction was then stirred at rt for 17 hrs. Water (5 mL) was added and acidified with saturated potassium hydrogen sulfate until pH=2~3. The mixture was extracted with ethyl acetate (20 mL), washed with brine and dried over sodium sulfate. After removal of solvent, the residue was purified by chromatography (Ethyl acetate) to give (2R,6S,13aS,14aR,16aS,Z)-6-(tert-butoxycarbonylamino)-14a-(cyclopropylsulfonylcarbamoyl)-9-(2-nitrophenylsulfonyl)-5,16-dioxo-1,2,3,5,6,7,8,9,10,11,13a,14,14a,15,16, 16a-hexadecahydrocyclopropa(n)pyrrolo[2,1-c][1,4,9]triazacyclopentadecine-2-yl 4-fluoroisoindoline-2-carboxylate as white solid (0.41 g, 51%). MS: Calcd.: 917; Found: [M+H]$^+$ 918. $^1$H NMR (400 MHz, d$^6$-DMSO) δ10.99 (s, 1H), 9.12 (s, 1H), 8.04 (m, 1H), 7.98 (m, 1H), 7.87 (m, 2H), 7.33 (m, 2H), 7.08-7.21 (m, 2H), 5.48 (m, 1H), 5.32 (m, 1H), 5.27 (m, 1H), 4.67 & 4.65 (s, 4H), 4.42 (m, 1H), 4.33 (m, 1H), 4.00 (m, 1H), 3.70 (m, 1H), 3.61 (m, 1H), 3.43 (m, 1H), 3.32 (m, 1H), 3.03 (m, 1H), 2.90 (m, 2H), 2.48 (m, 2H), 2.13 (m, 1H), 1.99 (m, 2H), 1.63 (m, 1H), 083-1.24 (m, 15H).

Step 8: Synthesis of (2R,6S,13aS,14aR,16aS,Z)-6-(tert-butoxycarbonylamino)-14a-(cyclopropylsulfonylcarbamoyl)-5,16-dioxo-9-(2,2,2-trifluoroethyl)-1,2,3,5,6,7,8,9,10,11,13a,14,14a,15,16,16a-hexadecahydrocyclopropa(n)pyrrolo[2,1-c][1,4,9]triazacyclopentadecine-2-yl 4-fluoroisoindoline-2-carboxylate (Compound 1031)

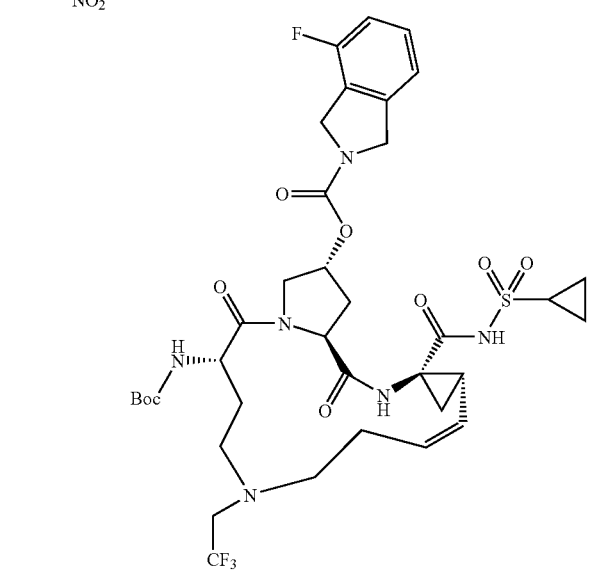

(2R,6S,13aS,14aR,16aS,Z)-6-(tert-butoxycarbonylamino)-14a-(cyclopropylsulfonylcarbamoyl)-9-(2-nitrophenylsulfonyl)-5,16-dioxo-1,2,3,5,6,7,8,9,10,11,13a,14, 14a,15,16,16a-hexadecahydrocyclopropa(n)pyrrolo[2,1-c][1,4,9]triazacyclopentadecine-2-yl 4-fluoroisoindoline-2-carboxylate (0.61 g, 0.445 mmol) in ACN (10 mL) was added K$_2$CO$_3$ (0.19 g, 1.34 mmol) and benzenethiol (0.11 g, 0.98 mmol). The reaction was stirred at rt for 2 days. The solvent was removed and the residue was dissolved in H$_2$O (10 mL). The aqueous phase was extracted with (2:1=ether:EA, 3×30 mL). The aqueous layer was acidified with saturated potassium hydrogensulfate to pH~5 and extracted with EA (30 mL), dried over sodium sulfate. After removal of solvent, it gave the (2R,6S,13aS,14aR,16aS,Z)-6-(tert-butoxycarbonylamino)-14a-(cyclopropylsulfonylcarbamoyl)-5,16-dioxo-hexadecahydrocyclopropa(n)pyrrolo[2,1-c][1,4,9]triazacyclopentadecine-2-yl 4-fluoroisoindoline-2-carboxylate as white solid (0.26 g, 70%). MS: Calcd.: 732; Found: [M+H]+ 733. ¹H NMR (400 MHz, d⁶-DMSO) δ 11.08 (s, 1H), 9.10 (s, 1H), 8.59 (b, 1H), 8.37 (b, 1H), 7.42 (m, 1H), 7.35 (m, 1H), 7.12-7.21 (m, 2H), 5.52 (m, 1H), 5.42 (m, 1H), 5.32 (m, 1H), 4.68 & 4.66 (s, 4H), 4.44 (m, 1H), 4.31 (m, 1H), 4.14 (m, 1H), 3.74 (m, 1H), 3.27 (m, 1H), 2.92 (m, 1H), 2.84 (m, 2H), 2.30-2.45 (m, 2H), 2.14 (m, 1H), 1.86-2.00 (m, 1H), 1.65 (m, 1H), 0.83-1.28 (m, 17H).

(2R,6S,13aS,14aR,16aS,Z)-6-(tert-butoxycarbonylamino)-14a-(cyclopropylsulfonylcarbamoyl)-5,16-dioxohexadecahydrocyclopropa(n)pyrrolo[2,1-c][1,4,9]triazacyclopentadecine-2-yl 4-fluoroisoindoline-2-carboxylate (0.080 g, 0.096 mmol) and DIEA (0.042 ml, 0.24 mmol) in THF (3 mL) was added 2,2,2-trifluoroethyl trifluoromethanesulfonate (0.034 g, 0.15 mmol). The reaction was stirred at 50° C. for 3 days. Water (2 mL) and saturated potassium hydrogensulfate (1 mL) was added and extracted with EA (15 mL), dried over sodium sulfate. After removal of solvent, the residue was purified by chromatography (Hexane:ethyl acetate=1:1) to give the (2R,6S,13aS,14aR,16aS,Z)-6-(tert-butoxycarbonylamino)-14a-(cyclopropylsulfonylcarbamoyl)-5,16-dioxo-9-(2,2,2-trifluoroethyl)-1,2,3, 5,6,7,8,9,10,11,13a,14,14a,15,16, 16a-hexadecahydrocyclopropa(n)pyrrolo[2,1-c][1,4,9]triazacyclopentadecine-2-yl 4-fluoroisoindoline-2-carboxylate as white solid (0.025 g, 32%). MS: Calcd.: 814; Found: [M+H]+ 815. ¹H NMR (400 MHz, d⁶-DMSO) δ11.06 (s, 1H), 9.11 (s, 1H), 7.36 (m, 1H), 7.11-7.18 (m, 3H), 5.49 (m, 1H), 5.31 (m, 1H), 5.15 (m, 1H), 4.67 & 4.65 (s, 4H), 4.47 (m, 1H), 4.34 (m, 1H), 3.89 (m, 1H), 3.70 (m, 1H), 3.20 (m, 2H), 2.91 (m, 1H), 2.70 (m, 1H), 2.40 (m, 3H), 2.18 (m, 3H), 1.80 (m, 1H), 1.61 (m, 3H), 0.96-1.24 (m, 15H).

TABLE 8

| Compound | Structure | ¹H-NMR/LCMS |
|---|---|---|
| 1001 | 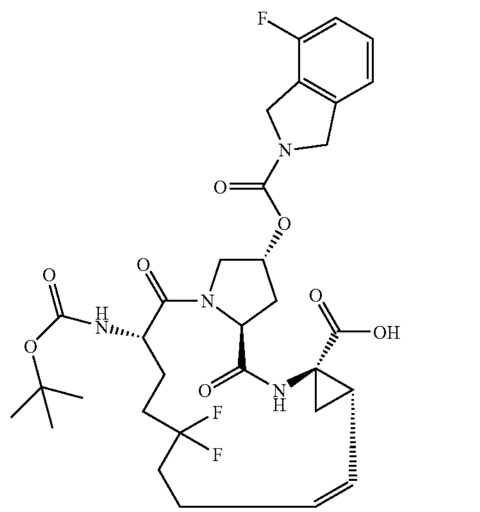 | ¹H NMR (400 MHz, d⁶-DMSO) d 12.14 (s, 1H), 8.71 (s, 1H), 7.28 (m, 1H), 7.05-7.15 (m, 3H), 5,43 (m, 1H), 5.29 (m, 1H), 5.25 (m, 1H), 4.61 (s, 4H), 4.35 (m, 1H), 4.22 (m, 1H), 3.98 (m, 1H), 3.63 (m, 1H), 3.63 (m, 1H), 2.07-2.27 9m, 4H), 1.85-2.03 (m, 3H), 1.65 (m, 2H), 1.42-1.50 (m, 3H), 1.02-1.18 (m, 10H). MS m/z 664.9 (APCI+, M + 1) |
| 1002 | 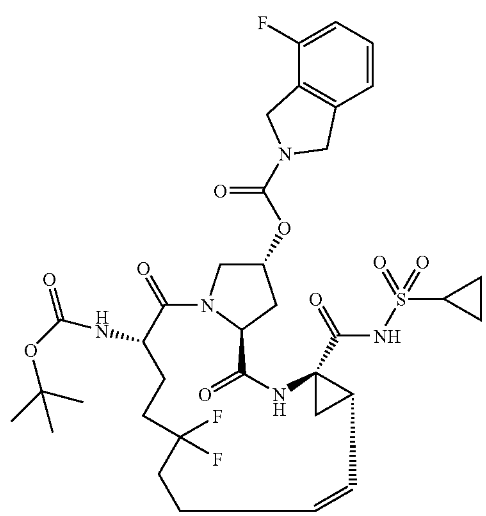 | ¹H NMR (400 MHz, d⁶-DMSO) d 11.09 (s, 1H), 9.07 (s, 1H), 7.35 (m, 1H), 7.11-7.25 (m, 3H), 5.58 (m, 1H), 5.30 (m, 1H), 5.18 (m, 1H), 4.67 (s, 4H), 4.44 (m, 1H), 4.34 (m, 1H), 4.03 (m, 1H), 3.73 (m, 1H), 2.90 (m, 1H), 2.40 (m, 1H), 2.22 (m, 1H), 1.99 (m, 4H), 1.61-1.71 (m, 4H), 0.98-1.24 (m, 16 H). MS m/z 767.8 (APCI+, M + 1) |

TABLE 8-continued
| Compound | Structure | ¹H-NMR/LCMS |
|---|---|---|
| 1003 | 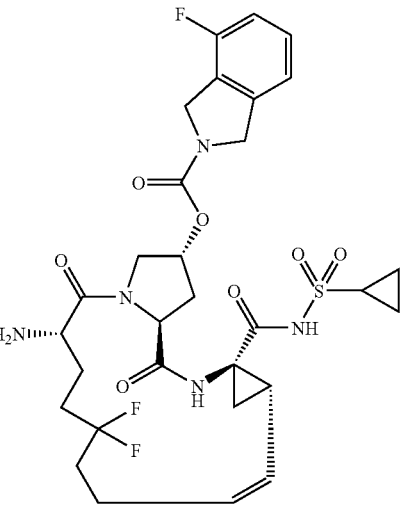 | ¹H NMR (400 MHz, d⁶-DMSO) d 11.05 (s, 1H), 9.21 (s, 1H), 8.35 (s, 3H), 7.38 (m, 1H), 7.12-7.23 (m, 2H), 5.59 (m, 1H), 5.36 (m, 1H), 5.26 (m, 1H), 4.71 (s, 4H), 4.49 (m, 1H), 4.18 (m, 1H), 4.01 (m, 1H), 3.86 (m, 1H), 2.92 (m, 1H), 2.29 (m, 3H), 2.09 (m, 3H), 1.89 (m, 2H), 1.80 (m, 2H), 1.62 (m, 2H), 1.00-1.11 (m, 5 H). MS m/z 668.1 (APCI+, M + 1) |
| 1004 | 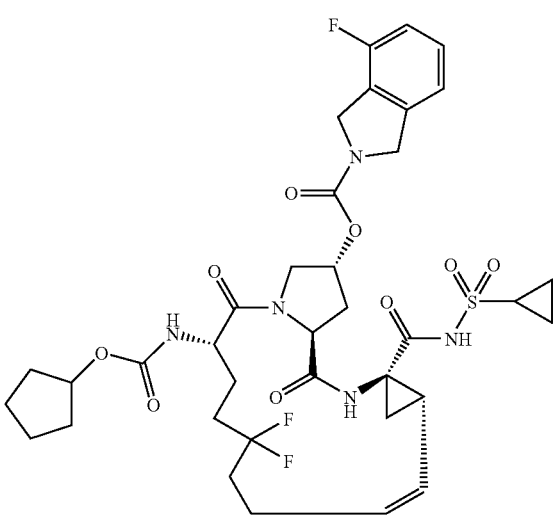 | ¹H NMR (400 MHz, d⁶-DMSO) d 11.10 (s, 1H), 9.05 (s, 1H), 7.47 (m, 1H), 7.36 (m, 1H), 7.10-7.14 (m, 2H), 5.55 (m, 1H), 5.22 (m, 1H), 5.17 (m, 1 H), 4.74 (m, 4H), 4.45 (m, 1H), 4.23-4.34 (m, 2H), 4.05 (m, 1H), 3.71 (m, 1H), 2.67 (m, 1H), 2.40 (m, 2H), 2.12 (m, 2H), 1.85-1.98 (m, 3H), 0.83-1.74 (m, 19H). MS m/z 780.1 (APCI+, M + 1) |
| 1005 | 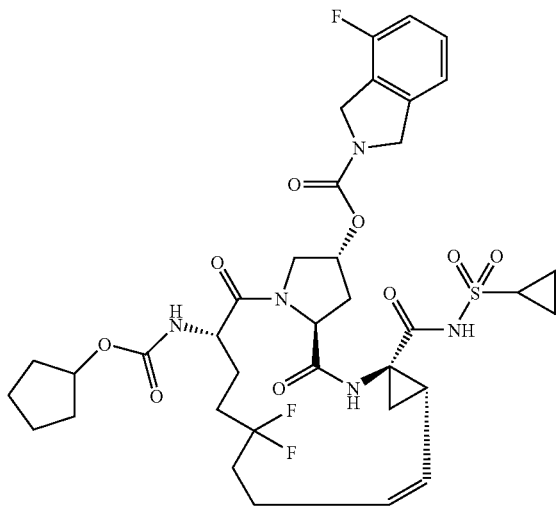 | ¹H NMR (400 MHz, d⁶-DMSO) d 11.10 (s, 1H), 9.05 (s, 1H), 7.47 (m, 1H), 7.36 (m, 1H), 7.10-7.14 (m, 2H), 5.55 (m, 1H), 5.22 (m, 1H), 5.17 (m, 1 H), 4.74 (m, 4H), 4.45 (m, 1H), 4.23-4.34 (m, 2H), 4.05 (m, 1H), 3.71 (m, 1H), 2.67 (m, 1H), 2.40 (m, 2H), 2.12 (m, 2H), 1.85-1.98 (m, 3H), 0.83-1.74 (m, 19H). MS m/z 780.1 (APCI+, M + 1) |

TABLE 8-continued
| Compound | Structure | ¹H-NMR/LCMS |
|---|---|---|
| 1006 | 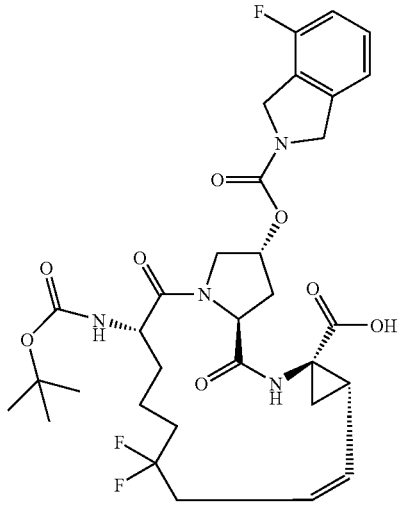 | ¹H NMR (400 MHz, d⁶-DMSO) d 12.20 (s, 1H), 8.76 (s, 1H), 7.18-7.34 (m, 5H), 5.48 (m, 1H), 5.35 (m, 1H), 5.30 (m, 1H), 4.63 & 4.62 (s, 4H), 4.40 (m, 1H), 4.28 (m, 1H), 4.04 (m, 1H), 3.70 (m, 1H), 2.24 (m, 4H), 1.96 (m, 4H), 0.94-1.75 (m, 14H). MS m/z 647.3 (APCI+, M + 1) |
| 1007 | 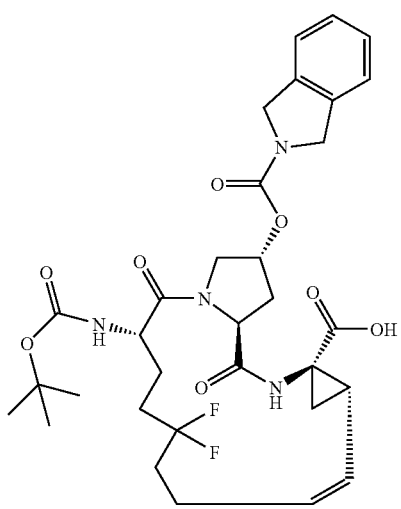 | ¹H NMR (400 MHz, d⁶-DMSO) d 12.20 (s, 1H), 8.76 (s, 1H), 7.18-7.34 (m, 5H), 5.48 (m, 1H), 5.35 (m, 1H), 5.30 (m, 1H), 4.63 & 4.62 (s, 4H), 4.40 (m, 1H), 4.28 (m, 1H), 4.04 (m, 1H), 3.70 (m, 1H), 2.24 (m, 4H), 1.96 (m, 4H), 0.94-1.75 (m, 14H). MS m/z 647.3 (APCI+, M + 1) |
| 1008 | 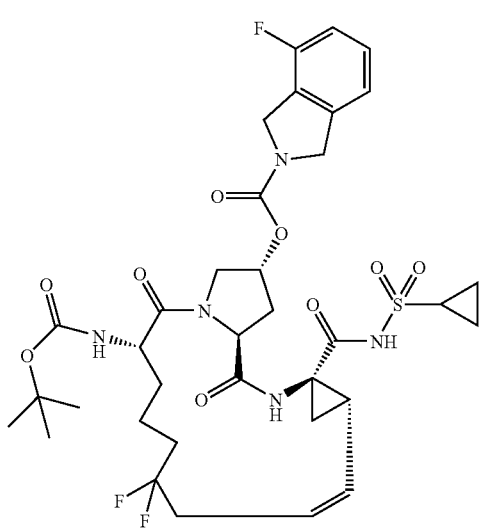 | ¹H NMR (400 MHz, d⁶-DMSO) d 11.10 (s, 1H), 9.07 (s, 1H), 7.35 (m, 1H), 7.08-7.20 (m, 3H), 5.57 (m, 1H), 5.41 (m, 1H), 5.29 (m, 1H), 4.67 (s, 4H), 4.45 (m, 1H), 4.34 (m, 1H), 3.94 (m, 1H), 3.73 (m, 1H), 3.36 (m, 2H), 2.89 (m, 1H), 2.39 (m, 1H), 2.24 (m, 2H), 2.00 (m, 1H), 0.94-1.76 (m, 20H). MS m/z 767.9 (APCI+, M + 1) |

TABLE 8-continued

| Compound | Structure | ¹H-NMR/LCMS |
|---|---|---|
| 1009 | 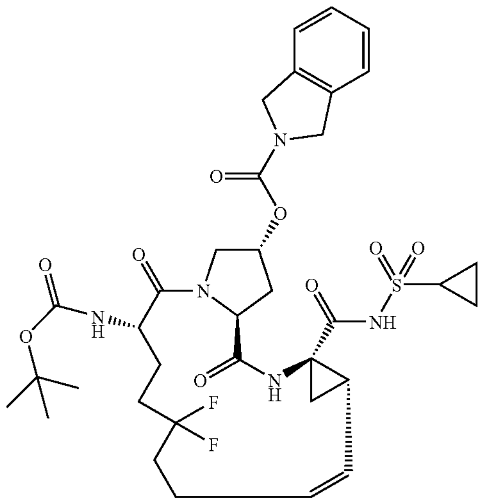 | ¹H NMR (400 MHz, d⁶-DMSO) d 11.09 (s, 1H), 9.07 (s, 1H), 7.20-7.27 (m, 5H), 5.58 (m, 1H), 5.31 (m, 1H), 5.19 (m, 1H), 4.63 (s, 4H), 4.44 (m, 1H), 4.35 (m, 1H), 4.04 (m, 1H), 3.74 (m, 1H), 2.90 (m, 1H), 2.42 (m, 1H), 2.21 (m, 2H), 1.93 (m, 4H), 1.56-1.75 (m, 5H), 1.28 (m, 3H), 0.89-1.08 (m, 12H). MS m/z 750.0 (APCI+, M + 1) |
| 1010 | 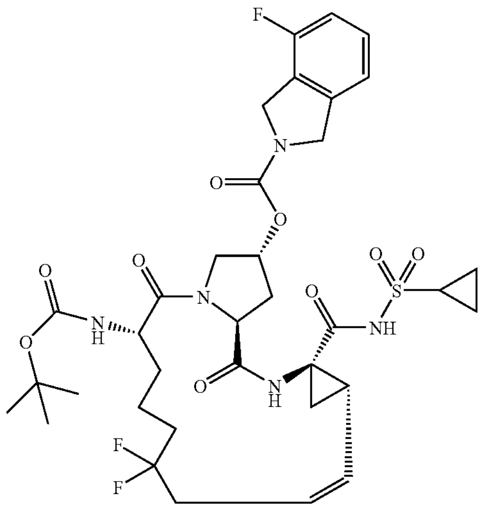 | ¹H NMR (400 MHz, d⁶-DMSO) d 11.09 (s, 1H), 9.09 (s, 1H), 7.35 (m, 1H), 7.01-7.20 (m, 3H), 5.31 (m, 1H), 4.67 & 4.66 (s, 4H), 4.46 (m, 1H), 4.30 (m, 1H), 4.01 (m, 1H), 3.75 (m, 1H), 2.97 (m, 1H), 2.16 (m, 1H), 2.14 (m, 2H), 2.00 (m, 2H), 1.02-1.81 (m, 26H). MS m/z 770.0 (APCI+, M + 1) |
| 1011 | 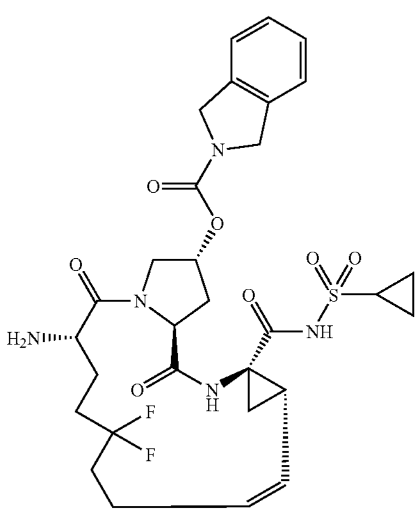 | MS m/z 650.1 (APCI+, M + 1) |

TABLE 8-continued

| Compound | Structure | ¹H-NMR/LCMS |
|---|---|---|
| 1012 | 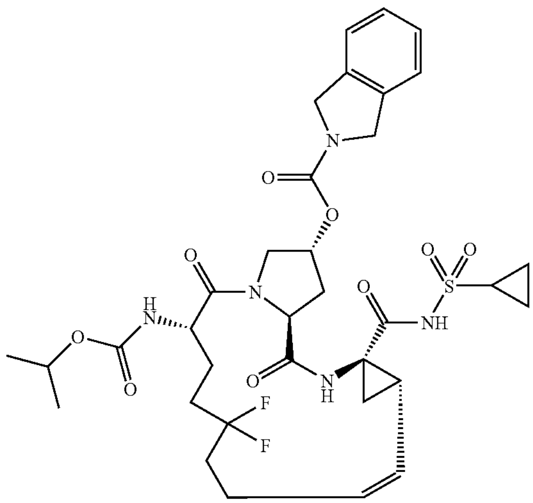 | ¹H NMR (400 MHz, d⁶-DMSO) d 11.10 (s, 1H), 9.05 (s, 1H), 7.44 (m, 1H), 7.27-7.34 (m, 4H), 5.57 (m, 1H), 5.29 (m, 1H), 5.19 (m, 1H), 4.64 (m, 4H), 4.44 (m, 1H), 4.37 (m, 1H), 4.07 (m, 1H), 3.72 (m, 1H), 2.90 (m, 1H), 2.40 (m, 2H), 2.22 (m, 1H), 1.59-1.98 (m, 8H), 0.84 (d, J=6.4 Hz, 3H), 0.76 (d, J=6.4 Hz, 3H). MS m/z 736.1 (APCI+, M + 1) |
| 1013 | 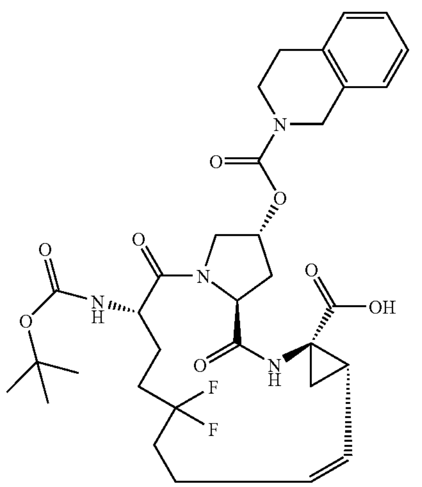 | ¹H NMR (400 MHz, d⁶-DMSO) d 12.19 (s, 1H), 8.73 (s, 1H), 7.19 (m, 5H), 5.48 (m, 1H), 5.36 (m, 1H), 5.30 (m, 1H), 4.53 (m, 2H), 4.36 (m, 1H), 4.20 (m, 1H), 4.06 (m, 1H), 3.73 (m, 1H), 3.59 (m, 2H), 2.79 (m, 2H), 1.91-2.26 (m, 5H), 1.73 (m, 1H), 1.51 (m, 3H), 1.27 (m, 13H). MS m/z 661.0 (APCI+, M + 1) |
| 1014 | 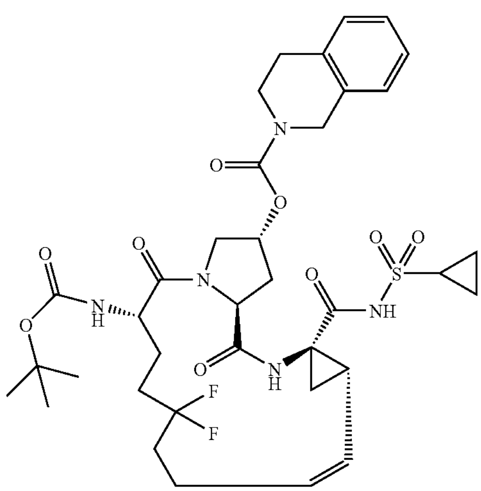 | ¹H NMR (400 MHz, d⁶-DMSO) d 11.07 (s, 1H), 9.02 (s, 1H), 7.28 (m, 1H), 7.17 (m, 4H), 5.57 (m, 1H), 5.29 (m, 1H), 5.20 (m, 1H), 4.53 (m, 2H), 4.37 (m, 1H), 4.29 (m, 1H), 4.07 (m, 1H), 3.77 (m, 1H), 3.59 (m, 2H), 2.90 (m, 1H), 2.79 (m, 2H), 2.41 (m, 2H), 2.19 (m, 1H), 1.59-2.00 (m, 10 H), 1.28 (m, 9H), 0.94-1.07 (m, 4H). 763.9 (APCI+, M + 1) |

TABLE 8-continued
| Compound | Structure | ¹H-NMR/LCMS |
|---|---|---|
| 1015 | 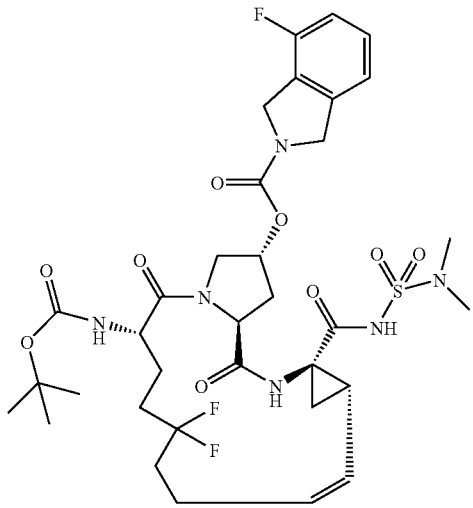 | ¹H NMR (400 MHz, d⁶-DMSO) d 10.80 (s, 1H), 9.09 (s, 1H), 7.35 (m, 1H), 7.11-7.20 (m, 3H), 5.57 (m, 1H), 5.31 (m, 1H), 5.17 (m, 1H), 4.67 (s, 4H), 4.46 (m, 1H), 4.34 (m, 1H), 4.02 (m, 1H), 3.74 (m, 1H), 2.73 (s, 6H), 2.40 (m, 1H), 2.21 (m, 2H), 1.99 (m, 3H), 1.59-1.77 (m, 5H), 1.26 (m, 2H), 1.07 & 1.10 (s, 9 H). MS m/z 770.9 (APCI+, M + 1) |
| 1016 | 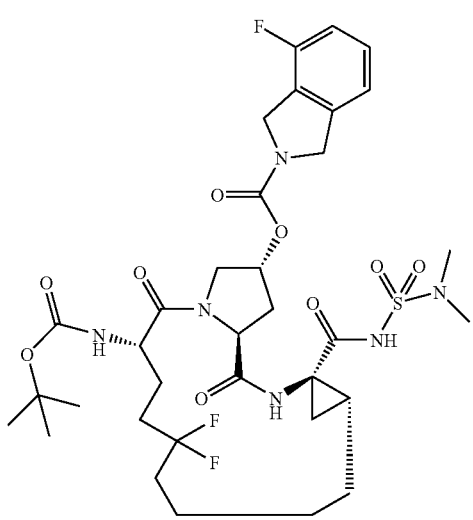 | ¹H NMR (400 MHz, d⁶-DMSO) d 11.00 (s, 1H), 9.06 (s, 1H), 7.35 (m, 1H), 7.09-7.19 (m, 3H), 5.30 (m, 1H), 4.67 & 4.66 (s, 4H), 4.48 (m, 1H), 4.36 (m, 1H), 4.05 (m, 1H), 3.77 (m, 1H), 2.78 (s, 6H), 2.40 (m, 1H), 2.12 (m, 2H), 1.87 (m, 3H), 1.72 (m, 2H), 1.24-1.54 (m, 10 H), 1.7 & 1.11 (s, 9H). MS m/z 773.0 (APCI+, M + 1) |
| 1017 | 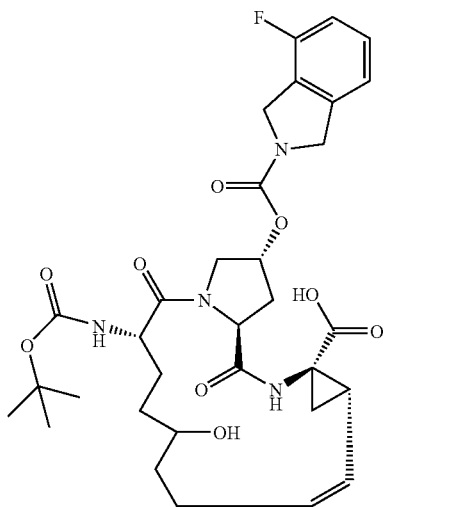 | MS m/z 645.1 (APCI+, M + 1) |

TABLE 8-continued
| Compound | Structure | ¹H-NMR/LCMS |
|---|---|---|
| 1018 | 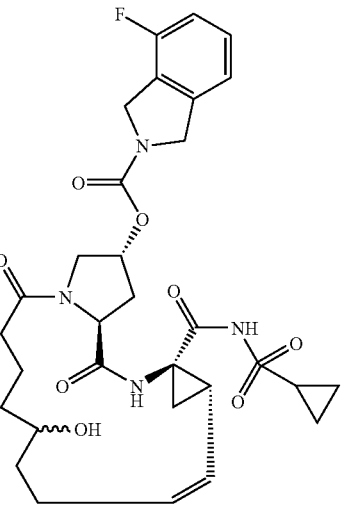 | ¹H NMR (400 MHz, d⁶-DMSO) d 11.12 & 11.11 (s, 1H), 9.00 (m, 1H), 7.34 (m, 1H), 7.08-7.32 (m, 3H), 5.59 (m, 1H), 5.31 (m, 1H), 5.06 (m, 1H), 4.67 (s, 4H), 4.28-4.45 (m, 3H), 3.90 (m, 1H), 3.71 (m, 1H), 3.58 (m, 1H), 2.89 (m, 1H), 2.26-2.36 (m, 3H), 2.00 (m, 1H), 0.96-1.60 (m, 22H). MS m/z 748.0 (APCI+, M + 1) |
| 1019 | 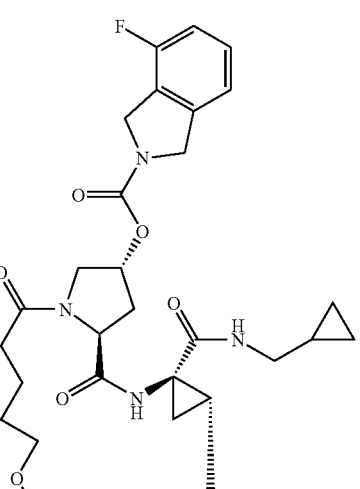 | ¹H NMR (400 MHz, d⁶-DMSO) d 8.64 & 8.59 (s 1H), 7.52 (m, 1H), 7.35 (m, 1H), 7.10-7.21 (m, 3H), 5.45-5.55 (m, 2H), 5.30 (m, 1H), 4.67 (s, 4H), 4.47 (m, 2H), 4.25 (m, 1H), 3.94 (m, 1H), 3.74 (m, 1H), 3.40 (m, 2H), 2.89-3.03 (m, 2 H), 2.30 (m, 3H), 1.80 (m, 2H), 1.49 (m, 1 H), 1.38 (m, 3H), 1.11 & 1.08 (s, 9H), 0.86 (m, 2H), 0.34 (m, 2H), 0.14 (m, 2H). MS m/z 684.1 (APCI+, M + 1) |
| 1020 | 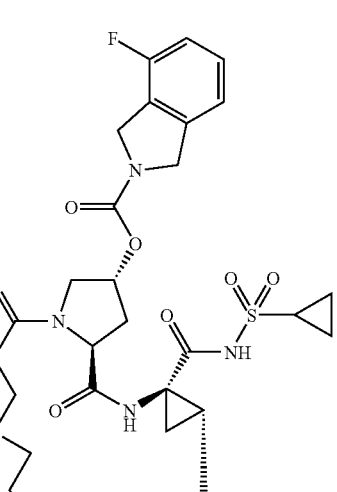 | ¹H NMR (400 MHz, d⁶-DMSO) d 11.20 (s, 1H), 8.28 (m, 1H), 7.35 (m, 1H), 7.12-7.20 (m, 2H), 7.00 (m, 1H), 5.57 (m, 1H), 5.35 (m, 1H), 5.16 (m, 1H), 4.67 (s, 4H), 4.41 (m, 2H), 4.15 (m, 1H), 3.86 (m, 1H), 3.62 (m, 1H), 3.45 (m, 1H), 3.31 (m, 1H), 2.91 (m, 1H), 2.33 (m, 4H), 1.68 (m, 2H), 1.49 (m, 3H), 1.11-1.26 (m, 14 H). MS m/z 734.0 (APCI+, M + 1) |

TABLE 8-continued
| Compound | Structure | ¹H-NMR/LCMS |
|---|---|---|
| 1021 | 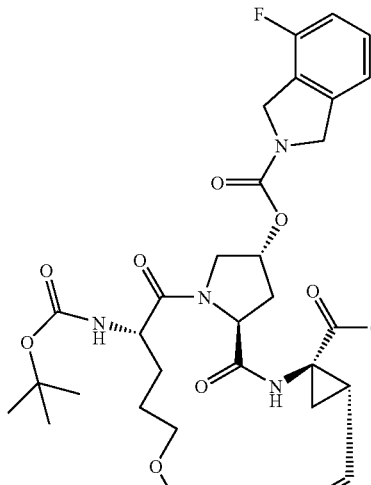 | ¹H NMR (400 MHz, d⁶-DMSO) d 12.29 (s, 1H), 8.59 (d, J=13.2 Hz, 1H), 7.36 (m, 1H), 7.10-7.20 (m, 3H), 5.59 (m, 1 H), 5.50 (m, 1H), 5.30 (s, 1H), 4.66 (s, 4H), 4.51 (m, 1H), 4.41 (m, 1H), 4.23 (m, 1H), 3.94 (m, 1 H), 3.74 (m, 1H), 3.50 (m, 1H), 3.37 (m, 2H), 2.35 (m, 1H), 1.78 (m, 2H), 1.51 (m, 2H), 1.37 (m, 2H), 1.24 (m, 2H), 1.08 & 1.09 (s, 9H). MS m/z 631.1 (APCI+, M + 1) |
| 1022 | 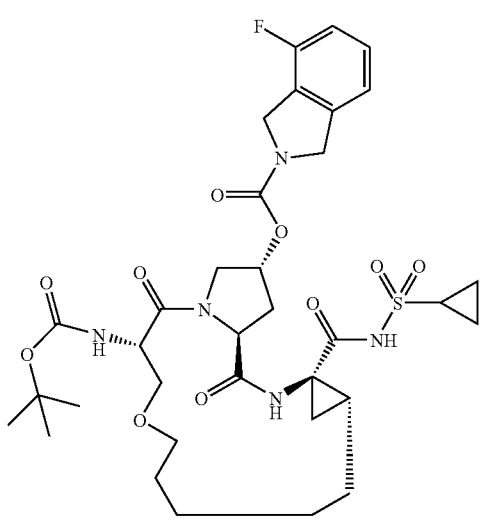 | ¹H NMR (400 MHz, d⁶-DMSO) d 9.65 (s, 1H), 7.22-7.28 (m, 2H), 6.96-7.08 (m, 2H), 5.55 (m, 1H), 5.39 (m, 1H), 4.74 & 4.69 (s, 4H), 4.54 (m, 1H), 3.97 (m, 1H), 3.84 (m, 1H), 3.77 (m, 1H), 3.67 (m, 1H), 3.55 (m, 1H), 3.47 (m, 1H), 2.92 (m, 1H), 2.65 (m, 1H), 2.35 (m, 1H), 1.06-1.68 (m, 25H). MS m/z 736.1 (APCI+, M + 1) |
| 1023 | 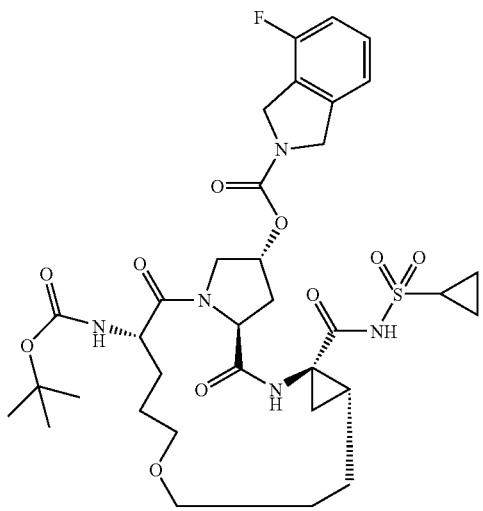 | ¹H NMR (400 MHz, d⁶-DMSO) d 9.69 (s, 1H), 7.18 (m, 1H), 6.84-7.15 (m, 2H), 5.24 (m, 1H), 5.04 (m, 1H), 4.65 & 4.61 (s, 4H), 4.15 (m, 2H), 3.70 (m, 1H), 3.44 (m, 2H), 3.34 (m, 1H), 3.28 (m, 1H), 2.84 (m, 1H), 2.52 (m, 1H), 2.35 (m, 1H), 1.86 (m, 2H), 0.97-1.56 (m, 22H).. MS m/z 736.1 (APCI+, M + 1) |

TABLE 8-continued
| Compound | Structure | $^1$H-NMR/LCMS |
|---|---|---|
| 1024 | 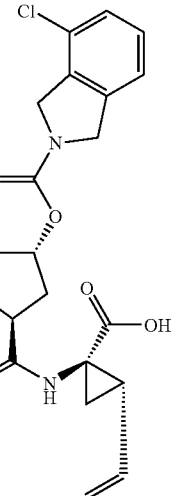 | $^1$H NMR (400 MHz, d$^6$-DMSO) d 12.37 (s, 1H), 8.10 (d, J=18.4 Hz, 1H), 7.27-7.37 (m, 3H), 6.93 (m, 1H), 5.55 (m, 1H), 5.34 (m, 1H), 5.28 (m, 1H), 4.70 (s, 2H), 4.66 (s, 2H), 4.46 (m, 1H), 4.37 (m, 1H), 4.11 (m, 1H), 3.80 (m, 1H), 3.63 (m, 1H), 3.48 (m, 2H), 2.05-2.43 (m, 4H), 1.20-1.62 (m, 15H). MS m/z 647.0 (APCI+, M + 1) |
| 1025 | 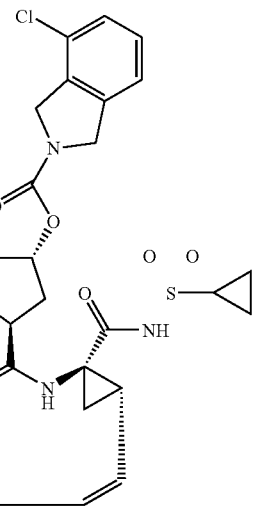 | $^1$H NMR (400 MHz, d$^6$-DMSO) d 11.20 (s, 1H), 8.36 & 8.16 (s, 1H), 7.26-7.3 8 (m, 3H), 6.99 (m, 1H), 5.59 (m, 1H), 5.34 (m, 1H), 5.16 (m, 1H), 4.68 (m, 2H), 4.58 (m, 2H), 4.42 (m, 1H), 4.37 (m, 1H), 4.17 (m, 1H), 3.86 (m, 1H), 3.61 (m, 1H), 3.45 (m, 2H), 2.92 (m, 1H), 2.27-2.45 (m, 4H), 2.01 (m, 1H), 1.68 (m, 1H), 1.50 (m, 3H), 1.11-1.26 (m, 14 H). MS m/z 750.0 (APCI+, M + 1) |
| 1026 | 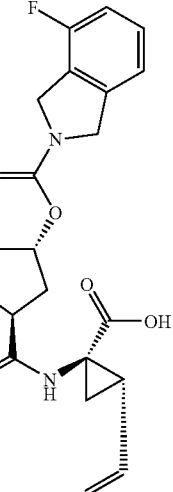 | $^1$H NMR (400 MHz, d$^6$-DMSO) d 12.25 (s, 1H), 8.77 (s, 1H), 7.37 (m, 1H), 7.07-7.21 (m, 3H), 5.34-5.44 (m, 2H), 5.29 (s, 1H), 4.67 (s, 4H), 4.44 (m, 1H), 4.20 (m, 1H), 3.95 (m, 1H), 3.68 (m, 1H), 3.50 (m, 1H), 3.43 (m, 2H), 3.32 (m, 1H), 2.39 (m, 1H), 2.33 (m, 2H), 2.16 (m, 2H), 1.85 (m, 1H), 1.74 (m, 1H), 1.53 (m, 1H), 1.50 (m, 1H), 1.23 & 0.96 (s, 9H). MS m/z 631.1 (APCI+, M + 1) |

TABLE 8-continued
| Compound | Structure | $^1$H-NMR/LCMS |
|---|---|---|
| 1027 | 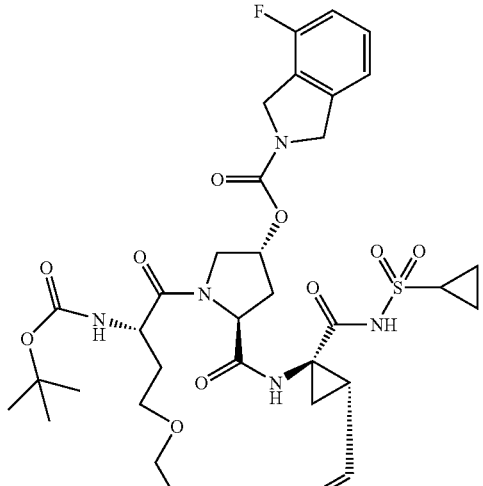 | $^1$H NMR (400 MHZ, d$^6$-DMSO) d 11.08 (s, 1H), 9.03 (d, J=10.8 Hz, 1H), 7.34 (m, 1H), 7.11-7.33 (m, 3H), 5.46 (m, 1H), 5.30 (s, 1H), 5.23 (m, 1H), 4.67 (s, 4H), 4.42 (m, 1H), 4.28 (m, 1H), 3.95 (m, 1H), 3.69 (m, 1H), 3.56 (m, 1H), 3.41 (m, 1H), 3.32 (m, 1H), 3.26 (m, 1H), 2.91 (m, 1H), 2.18-2.40 (m, 5H), 1.92 (m, 1H), 1.75 (m,1H), 1.61 (m, 2H), 1.00-1.28 (m, 13H). MS m/z 733.9 (APCI+, M + 1) |
| 1028 | 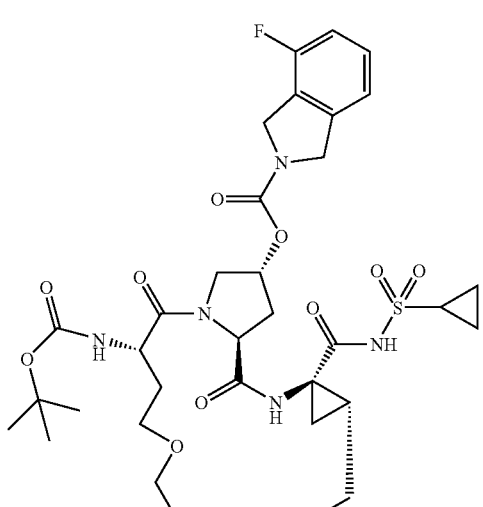 | $^1$H NMR (400 MHz, d$^6$-DMSO) d 11.08 (s, 1H), 8.79 (b, 1H), 7.34 (m, 1H), 7.10-7.20 (m, 3H), 5.28 (m, 1H), 4.66 (s, 4H), 4.41 (m, 1H), 4.20 (m, 1H), 3.94 (m, 1H), 3.74 (m, 1H), 3.42-3.47 (m, 2H), 2.97 (m, 1H), 0.79-2.38 (m, 28 H). MS m/z 736.0 (APCI+, M + 1) |
| 1029 | 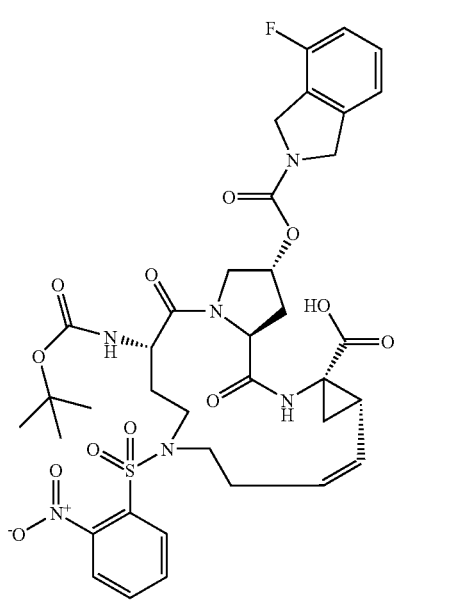 | $^1$H NMR (400 MHz, d$^6$-DMSO) d 11.24 (s, 1H), 8.84 (s, 1H), 8.01 (m, 2H), 7.86 (m, 2H), 7.36 (m, 1H), 7.10-7.26 (m, 3H), 5.49 (m, 1H), 5.39 (m, 1H), 5.27 (m, 1H), 4.67 & 4.66 (s, 4H), 4.40 (m, 1H), 4.27 (m, 1H), 3.97 (m, 1H), 3.66 (m, 1H), 3.31-3.53 (m, 2H), 3.23 (m, 1H), 2.96 (m, 1H), 2.55 (m, 1H), 2.25 (m, 2H), 1.99 (m, 2H), 1.91 (m, 2H), 0.96-1.69 (m, 11 H). MS m/z 815.2 (APCI+, M + 1) |

TABLE 8-continued
| Compound | Structure | ¹H-NMR/LCMS |
|---|---|---|
| 1030 | 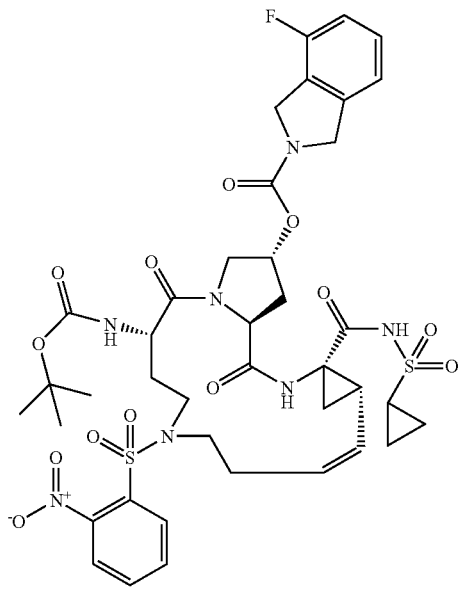 | ¹H NMR (400 MHz, d⁶-DMSO) d 10.99 (s, 1H), 9.12 (s, 1H), 8.04 (m, 1H), 7.98 (m, 1H), 7.87 (m, 2H), 7.33 (m, 2H), 7.08-7.21 (m, 2H), 5.48 (m, 1H), 5.32 (m, 1H), 5.27 (m, 1H), 4.67 & 4.65 (s, 4H), 4.42 (m, 1H), 4.33 (m, 1H), 4.00 (m, 1H), 3.70 (m, 1H), 3.61 (m, 1H), 3.43 (m, 1H), 3.32 (m, 1H), 3.03 (m, 1H), 2.90 (m, 2H), 2.48 (m, 2H), 2.13 (m, 1H), 1.99 (m, 2H), 1.63 (m, 1H), 083-1.24 (m, 15 H). MS m/z 918.1 (APCI+, M + 1) |
| 1031 | 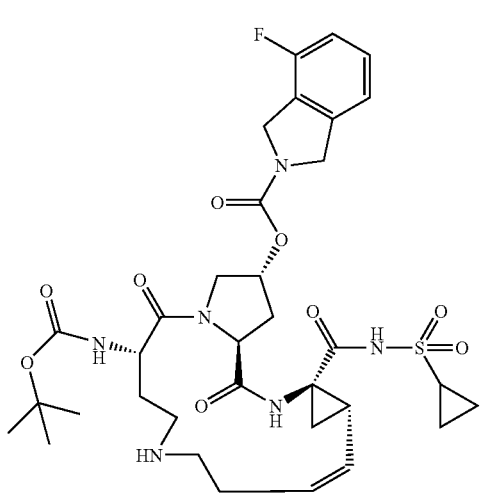 | ¹H NMR (400 MHz, d⁶-DMSO) d 11.08 (s, 1H), 9.10 (s, 1H), 8.59 (b, 1H), 8.37 (b, 1H), 7.42 (m, 1H), 7.35 (m, 1H), 7.12-7.21 (m, 2H), 5.52 (m, 1H), 5.42 (m, 1H), 5.32 (m, 1H), 4.68 & 4.66 (s, 4H), 4.44 (m, 1H), 4.31 (m, 1H), 4.14 (m, 1H), 3.74 (m, 1H), 3.27 (m, 1H), 2.92 (m, 1H), 2.84 (m, 2H), 2.30-2.45 (m, 2H), 2.14 (m, 1H), 1.86-2.00 (m, 1H), 1.65 (m, 1H), 0.83-1.28 (m, 17H). MS m/z 733.2 (APCI+, M + 1) |
| 1032 | 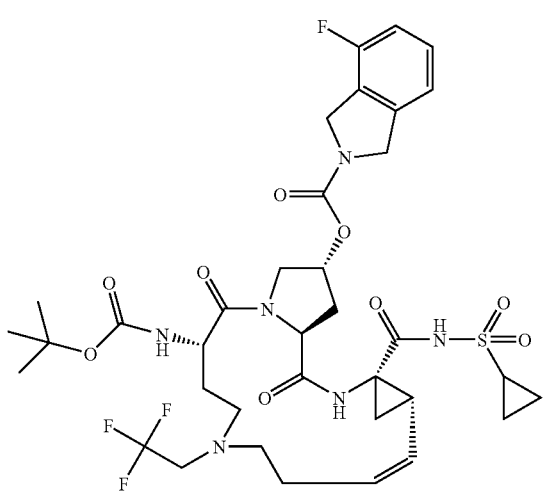 | ¹H NMR (400 MHz, d⁶-DMSO) d 11.06 (s, 1H), 9.11 (s, 1H), 7.36 (m, 1H), 7.11-7.18 (m, 3H), 5.49 (m, 1H), 5.31 (m, 1H), 5.15 (m, 1H), 4.67 & 4.65 (s, 4H), 4.47 (m, 1H), 4.34 (m, 1H), 3.89 (m, 1H), 3.70 (m, 1H), 3.20 (m, 2H), 2.91 (m, 1H), 2.70 (m, 1H), 2.40 (m, 3H), 2.18 (m, 3H), 1.80 (m, 1H), 1.61 (m, 3H), 0.96-1.24 (m 15 H). MS m/z 815.1 (APCI+, M + 1) |

Preparation of NS3 Inhibitors

Section XI

The compounds of Formula III can be synthesized according to the methods described below.

The method used in preparing compounds with general structure III utilized intermediates 1, 2, 4 and 9. Intermediates 1 and 4 were prepared according to the procedures disclosed in International Application PCT/CA00/00353 (Publication No. WO 00/59929). Intermediate 4 was also purchased from RSP Amino Acids. Intermediate 9 was prepared according to procedures disclosed in (1. Khan et al, Bioorg. & Med. Chem. Lett., 1997, 7 (23), 3017-3022. 2. International Application PCT/US02/39926, WO 03/053349).

Intermediate 2 was synthesized using the following procedure: McKenna, J. M. *Tetrahedron Letters* 2001 42, 5795-5800 and Ullman Chemistry which will be described in the following procedures.

Method:

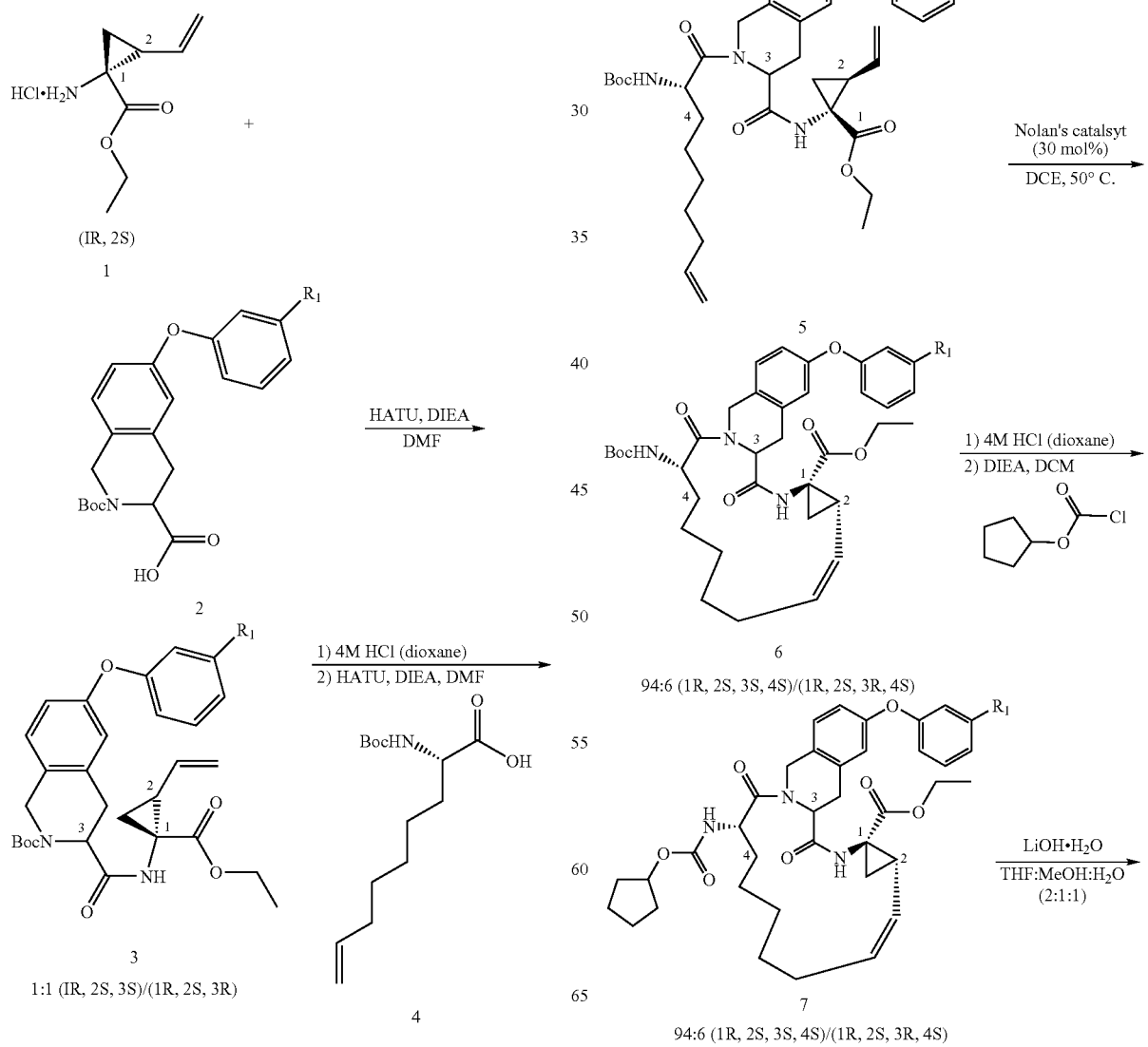

-continued
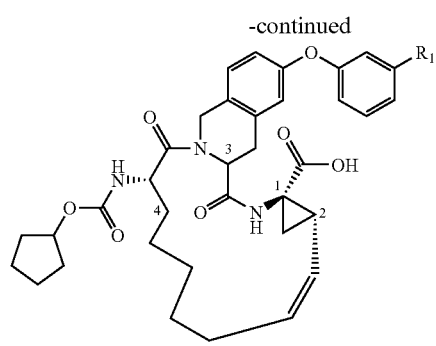
94:6 (1R, 2S, 3S, 4S)/(1R, 2S, 3R, 4S)
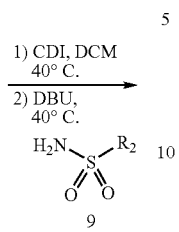
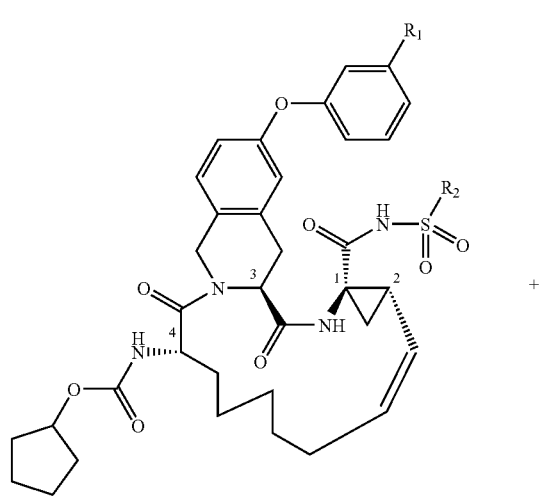
Example 13-1
Compound AR00320573
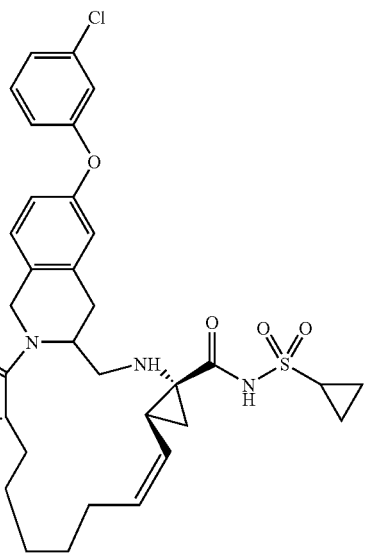
Step 1: Synthesis of tert-butyl 3-((((1R,2S)-1-(ethoxycarbonyl)-2-vinylcyclopropyl)carbamoyl)-6-(3-chlorophenoxy)-3,4-dihydroisoquinoline-2(1H)-carboxylate
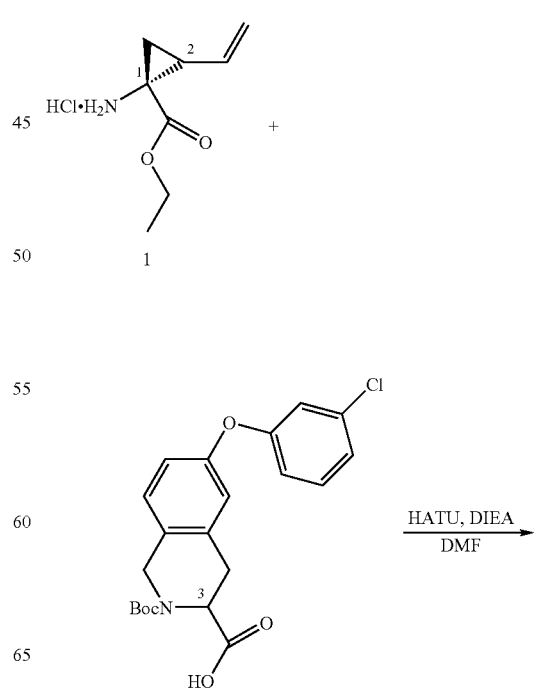

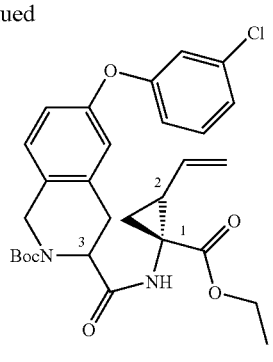

1:1 (1R, 2S, 3S)/(1R, 2S, 3R)

To a flask charged with ethyl-(1R,2S)-1-amino-2-vinylcyclopropyl carboxylate (1, 1.0 g, 5.2 mmol), 2-(tert-butoxycarbonyl)-6-(3-chlorophenoxy)-1,2,3,4-tetrahydroisoquinoline-3-carboxylic acid (2.31 g, 1.1 equiv), and HATU (2.7 g, 1.1 equiv) were added 30 mL DMF to make a solution. It was cooled to 0° C. in an ice-water bath, followed by slow addition of a solution of DIEA (4.4 mL, 4 equiv) in DMF (15 mL) while stirring. The reaction was allowed to warm up to rt and stirred overnight.

After 16 h, the reaction was complete as monitored by HPLC. It was diluted with EtOAc (100 mL), washed with water (3×40 mL), sat. NaHCO$_3$ (2×40 mL), and brine (2×40 mL), then dried over Na$_2$SO$_4$ and concentrated down to give a dark copper colored oil. The crude was purified on the Horizon Biotage instrument using a C-18 column (eluent: acetonitrile/water; gradient of 20% Acetonitrile to 80% Acetonitrile over 168-6 mL fractions), giving pure 3 as a mixture of diasteriomers (647 mg, 23%). MS m/e 442.1 (M$^+$-Boc).

Step 1a: Synthesis of 2-(tert-butoxycarbonyl)-6-(3-chlorophenoxy)-1,2,3,4-tetrahydroisoquinoline-3-carboxylic acid

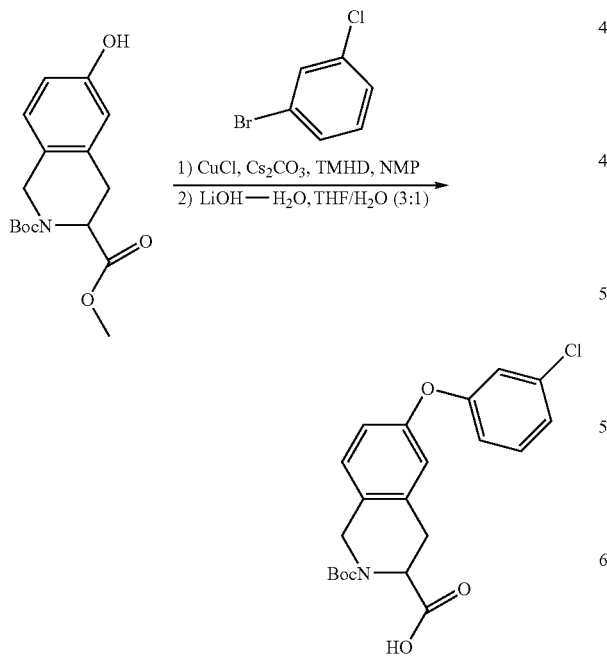

2-tert-Butyl 3-methyl 6-hydroxy-3,4-dihydroisoquinoline-2,3(1H)-dicarboxylate (200 mg, 0.65 mmol), m-chlorophenyl bromide (103 mg, 0.54 mmol), 2, 2, 6, 6-tetramethylheptane-3,5-dione (TMHD, 10 mg, 0.054 mmol), Cs$_2$CO$_3$ (326 mg, 1.00 mmol), and CuCl (27 mg, 0.27 mmol) were mixed together in NMP (1 mL) and heated to 120° C. for 6 h. The reaction was then diluted with MTBE and filtered over celite. The filtrate was washed with 1 N HCl, 1 N NaOH, and brine. The organic was dried over Na$_2$SO$_4$ and concentrated before loading on a Biotage silica column (12 m) and eluting with 10% Acetone/Hexanes to give 2-tert-butyl 3-methyl 6-(3-chlorophenoxy)-3,4-dihydroisoquinoline-2,3(1H)-dicarboxylate as a pale yellow oil (113 mg, 50%). This material was then taken up in 1 mL of a mixture of THF/H$_2$O (3:1) and LiOH (70 mg, 1.62 mmol) was added. The reaction stirred overnight at rt, before it was concentrated and quenched with 1 N HCl. The product was then extracted with EtOAc (3×). The combined extracts were dried over Na$_2$SO$_4$ and concentrated to give a pale yellow foam (100 mg, 92%). MS m/e 402.9 (M$^-$-H).

Step 2: Synthesis of (1R,2S)-ethyl 1-(2-((S)-2-(tert-butoxycarbonyl)non-8-enoyl)-6-(3-chlorophenoxy)-1,2,3,4-tetrahydroisoquinoline-3-carboxamido)-2-vinylcyclopropanecarboxylate

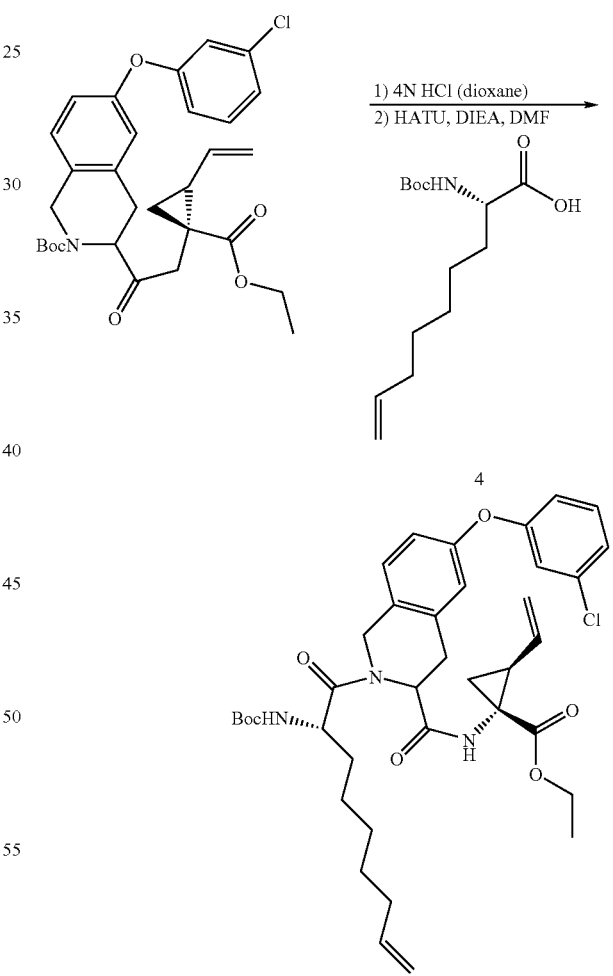

tert-Butyl 3-(((1R,2S)-1-(ethoxycarbonyl)-2-vinylcyclopropyl)carbamoyl)-6-(3-chlorophenoxy)-3,4-dihydroisoquinoline-2(1H)-carboxylate (647 mg, 1.20 mmol) was dissolved in 4 N HCl (dioxane, 8 mL) and left at rt for 90 min to remove the BOC protective group. It was then concentrated down, taken up in acetonitrile and concentrated down again twice. To this yellow oil was added 4 (357 mg, 1.1 equiv) and HATU (502 mg, 1.1 equiv), followed by 5 mL DMF. The reaction was cooled on ice-water bath for 15 min, after which DIEA (0.84 mL, 4 equiv) was added to the reaction slowly while stirring. The ice bath was left to slowly rise to rt and the reaction stirred overnight.

After 24 h, the reaction has turned dark brownish. Its aliquot TLC shows reaction complete. The reaction was diluted with EtOAc (100 mL) and washed with water (3×120 mL), sat. NaHCO$_3$ (2×120 mL), brine (120 mL), dried (Na$_2$SO$_4$), and concentrated to give (1R,2S)-ethyl 1-(2-((S)-2-(tert-butoxycarbonyl)non-8-enoyl)-6-(3-chlorophenoxy)-1,2,3,4-tetrahydroisoquinoline-3-carboxamido)-2-vinylcyclopropanecarboxylate as an orange oil (500 mg). The crude product was purified on the Horizon Biotage instrument using a C-18 column (eluent: acetonitrile/water; gradient of 20% Acetonitrile to 80% Acetonitrile over 168-6 mL fractions), giving pure (1R,2S)-ethyl 1-(2-((S)-2-(tert-butoxycarbonyl)non-8-enoyl)-6-(3-chlorophenoxy)-1,2,3,4-tetrahydroisoquinoline-3-carboxamido)-2-vinylcyclopropanecarboxylate as a beige foam (125 mg, 15%). MS m/e 594.1 (M$^+$-Boc).

Step 3: Synthesis of (1aS,9S,19aR,Z)-ethyl 9-(tert-butoxycarbonyl)-15-(3-chlorophenoxy)-10,18-dioxo-1a,4,5,6,7,8,9,10,12,17,17a,18,19,19a-tetradecahydro-1H-11,14-diaza-bicyclo[13.1.0]hexadeca-1(16),2-dieno[11,12-b]isoquinoline-19a-carboxylate

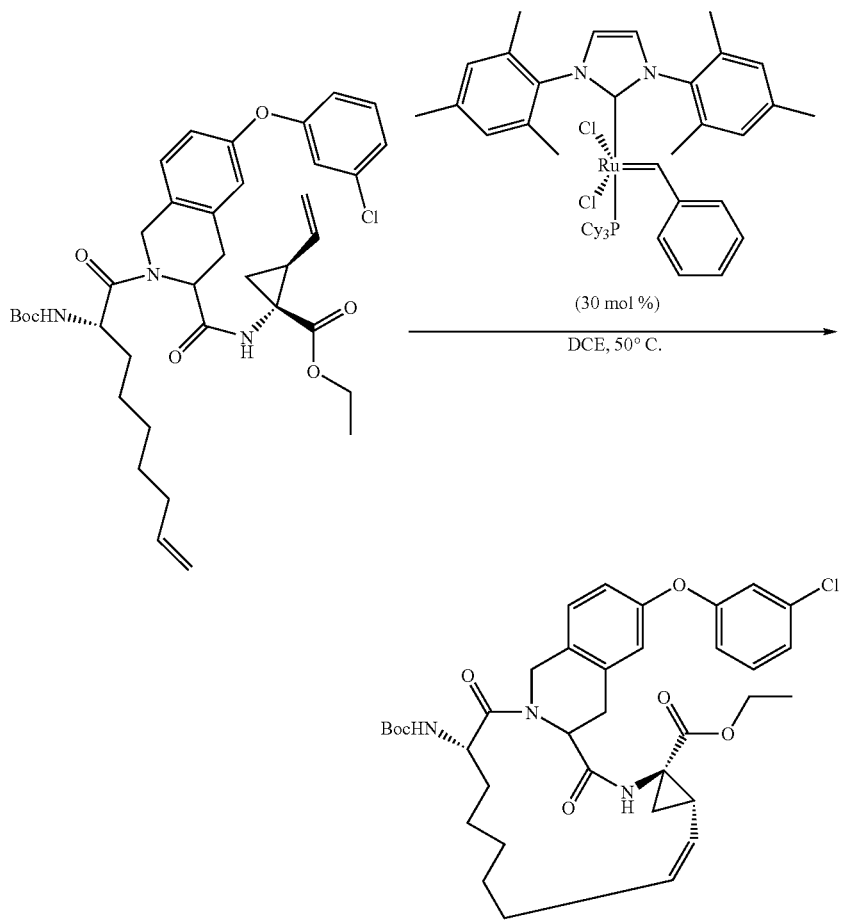

1R,2S)-ethyl 1-(2-((S)-2-(tert-butoxycarbonyl)non-8-enoyl)-6-(3-chlorophenoxy)-1,2,3,4-tetrahydroisoquinoline-3-carboxamido)-2-vinylcyclopropanecarboxylate (125 mg, 0.2 mmol) was dissolved in 20 mL DriSolve DCE to make a solution, followed by addition of the Nolan's catalyst (5 mg, 0.3 equiv) at rt under nitrogen. The solution turned purplish. The reaction was put on a pre-heated oil bath (50° C.) and stirred for overnight.

After 16 h, the reaction had turned dark brownish. TLC (Acetone/Hexanes 1:4) showed clean conversion to a new spot with slightly lower R$_f$. The reaction was concentrated down to give a purple foam (130 mg). It was directly used in the next step without further purification. MS m/e 567.2 (M$^+$-Boc).

Step 4: Synthesis of (1aS,9S,19aR,Z)-ethyl 15-(3-chlorophenoxy)-9-(cyclopentyloxycarbonyl)-10,18-dioxo-1a,4,5,6,7,8,9,10,12,17,17a,18,19,19a-tetradecahydro-1H-11,14-diaza-bicyclo[13.1.0]hexadeca-1(16), 2-dieno[11,12-b]isoquinoline-19a-carboxylate

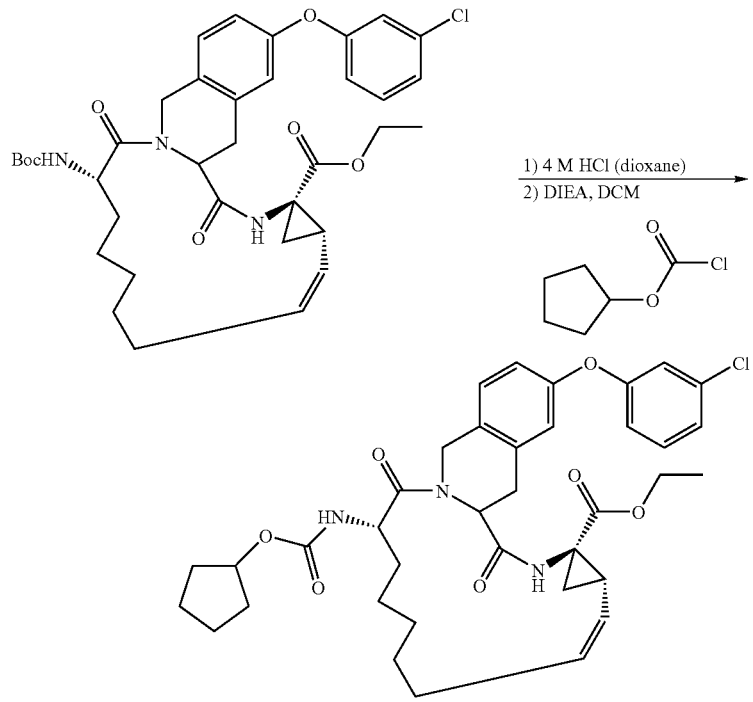

The crude (1aS,9S,19aR,Z)-ethyl 9-(tert-butoxycarbonyl)-15-(3-chlorophenoxy)-10,18-dioxo-1a,4,5,6,7,8,9,10,12,17,17a,18,19,19a-tetradecahydro-1H-11,14-diaza-bicyclo[13.1.0]hexadeca-1(16), 2-dieno[11,12-b]isoquinoline-19a-carboxylate (130 mg, 0.2 mmol) was dissolved in 1.0 mL of a solution of 4 M HCl/Dioxane. The reaction was stirred at rt for 2 h. At this time the reaction was complete by LC/MS m/e 567 (M++1). The reaction was concentrated down to dryness and taken back up in 1 mL of DCM. DIEA (70 □L, 0.4 mmol) was then added followed by cyclopentyl chloroformate (33 mg, 0.22 mmol). TLC (Acetone/Hexanes 1:4) showed reaction to be complete after 1 h. The reaction was diluted with 5 mL of DCM and washed with 1 N HCl and brine before drying the organic with $MgSO_4$. Concentration gave product (1aS,9S,19aR,Z)-ethyl 15-(3-chlorophenoxy)-9-(cyclopentyloxycarbonyl)-10,18-dioxo-1a,4,5,6,7,8,9,10,12,17,17a,18,19,19a-tetradecahydro-1H-11,14-diaza-bicyclo[13.1.0]hexadeca-1(16), 2-dieno[11,12-b]isoquinoline-19a-carboxylate as a beige foam (138 mg). It was directly used in the next step without further purification. MS m/e 678 ($M^+$+ H).

Step 5: Synthesis of (Z)-15-(3-chlorophenoxy)-9-(cyclopentyloxycarbonyl)-10,18-dioxo-1a,4,5,6,7,8,9,10,12,17,17a,18,19,19a-tetradecahydro-1H-11,14-diaza-bicyclo[13.1.0]hexadeca-1(16), 2-dieno[11,12-b]isoquinoline-19a-carboxylic acid

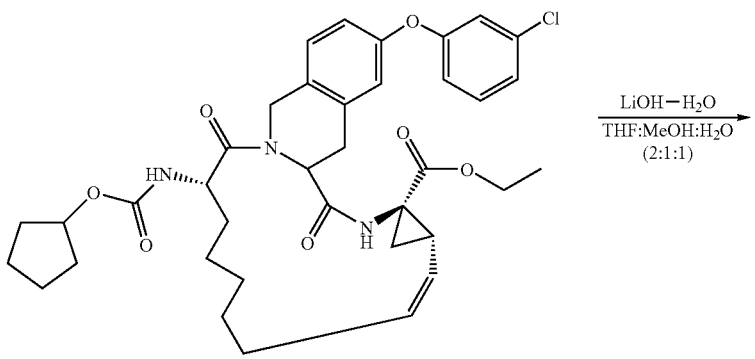

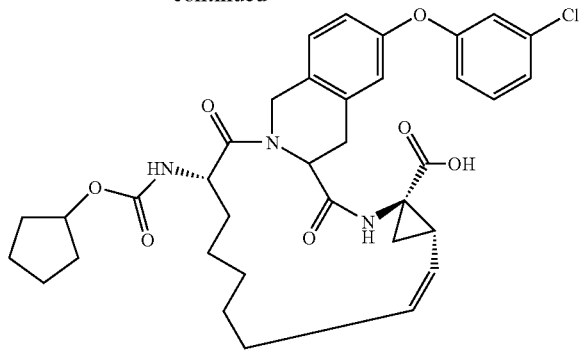

The crude (1aS,9S,19aR,Z)-ethyl 15-(3-chlorophenoxy)-9-(cyclopentyloxycarbonyl)-10,18-dioxo-1a,4,5,6,7,8,9,10,12,17,17a,18,19,19a-tetradecahydro-1H-11,14-diaza-bicyclo[13.1.0]hexadeca-1(16), 2-dieno[11,12-b]isoquinoline-19a-carboxylate (138 mg, 0.2 mmol) was dissolved in 1.0 mL of a mixture of THF:MeOH:H₂O (2:1:1). Lithium hydroxide monohydrate (50 mg, 1.2 mmol) was added and reaction stirred at rt overnight. The reaction was then concentrated under vacuum and quenched with 5 mL of 1 N HCl. The product precipitated and could be filtered off giving an off-white powder (118 mg). It was directly used in the next step without further purification. MS m/e 649 (M⁻–H).

Step 6: Synthesis of cyclopentyl (1aS,9S,19aR,Z)-15-(3-chlorophenoxy)-19a-(cyclopropylsulfonylcarbamoyl)-10,18-dioxo-1a,4,5,6,7,8,9,10,12,17,17a,18,19,19a-tetradecahydro-1H-11,14-diaza-bicyclo[13.1.0]hexadeca-1(16), 2-dieno[11,12-b]isoquinolin-9-ylcarbamate.

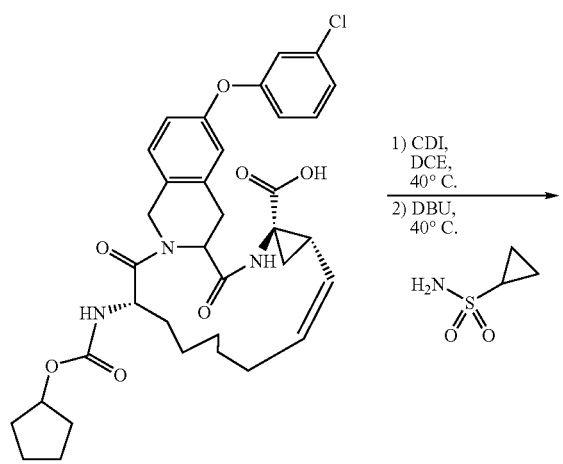

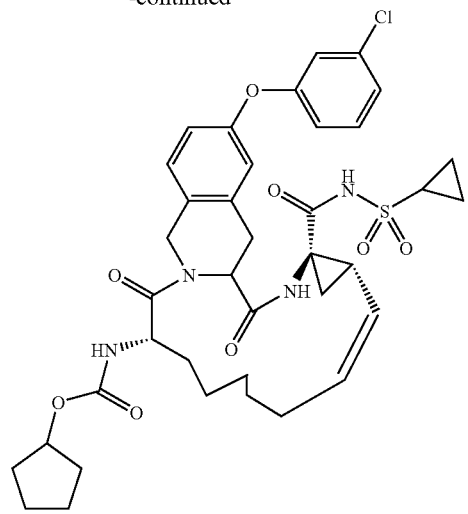

The crude (Z)-15-(3-chlorophenoxy)-9-(cyclopentyloxycarbonyl)-10,18-dioxo-1a,4,5,6,7,8,9,10,12,17,17a,18,19,19a-tetradecahydro-1H-11,14-diaza-bicyclo[13.1.0]hexadeca-1(16), 2-dieno[11,12-b]isoquinoline-19a-carboxylic acid (118 mg, 0.18 mmol) was dissolved in 1.0 mL of DCE and CDI (88 mg, 0.54 mmol) was added. The reaction was heated to 40° C. for 4 h. TLC run in 10% MeOH/CHCl₃ showed conversion to a higher R$_f$ spot. Cyclopropyl sulfonamide (65 mg, 0.54 mmol) and DBU (81 μL, 0.54 mmol) were added and the reaction heated to 50° C. and stirred overnight. The reaction was concentrated to 400 μL volume and loaded on a Biotage size 12, C-18 samplet for purification using the Horizon LC (12 m, C-18 column) eluting with a gradient from 20% acetonitrile/water to 80% acetonitrile/water with 0.1% TFA over 168-6 mL fractions. Product elutes in fractions 29-34. Upon concentration product is a white solid. AR00320573 (34 mg, 25%) ¹H NMR (CD₃OD, 500 MHz): δ 8.60 (br s, 1H), 7.68 (br s, 1H), 7.30-7.36 (m, 2H), 7.08-7.13 (m, 1H), 6.96-7.03 (m, 2H), 6.90-6.95 (m, 2H), 5.67 (q, 1H), 5.54 (q, 1H), 5.14-5.33 (m, 2H), 4.96-5.33 (m, 1H), 4.67-4.83 (m, 2H), 4.52-4.61 (m, 2H), 3.10-3.44 (m, 5H), 2.98-3.05 (m, 1H), 2.84-2.89 (m, 1H), 2.19-2.54 (m, 4H), 1.25-2.06 (m, 12H), 0.95-1.13 (m, 3H); MS m/e 752 (M⁻–H).

Example 13-2

Compound 2005

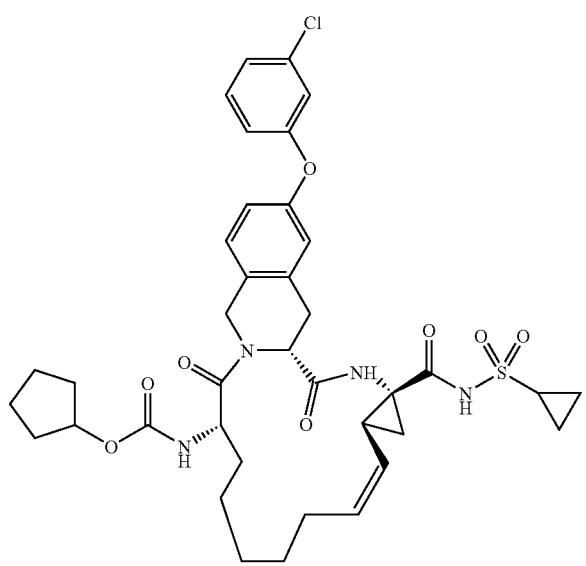

Cyclopentyl (1aS,9S,17aR,19aR,Z)-15-(3-chlorophenoxy)-19a-(cyclopropylsulfonylcarbamoyl)-10,18-dioxo-1a,4,5,6,7,8,9,10,12,17,17a,18,19,19a-tetradecahydro-1H-11,14-diaza-bicyclo[13.1.0]hexadeca-1(15), 2-dieno[11,12-b]isoquinolin-9-ylcarbamate (Compound 2005) was synthesized according to the procedure described in Example 13-1 and separated as a diasteriomer, (1 mg, 1%) MS m/e 752 (M⁻–H), using the following preparative HPLC conditions:

Column: YMC ODS-AQ, 20×250 mm, 10-micron particle size, 120-angstrom pore size
Mobile Phase Gradient: 5-95% B in 45 minutes
A: water+0.01% HFBA+1% IPA
B: MeCN+0.01% HFBA+1% IPA
Flow rate: 15 ml/min
Temperature: 25° C.
Wavelength: 220 nm

Example 13-3

Compound 2005

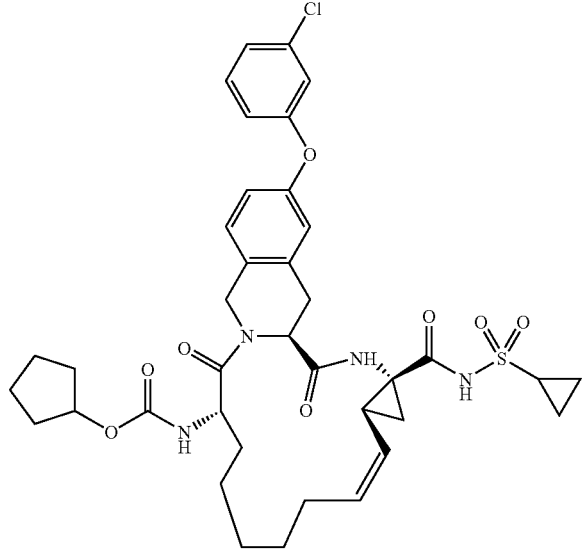

Example 13-4

Cyclopentyl (1aS,9S,17aS,19aR,Z)-15-(3-chlorophenoxy)-19a-(cyclopropylsulfonylcarbamoyl)-10,18-dioxo-1a,4,5,6,7,8,9,10,12,17,17a,18,19,19a-tetradecahydro-1H-11,14-diaza-bicyclo[13.1.0]hexadeca-1(15), 2-dieno[11,12-b]isoquinolin-9-ylcarbamate (Compound 2005) was synthesized according to the procedure described in Example 13-1 and separated as a diasteriomer, (5 mg, 4%) MS m/e 752 (M⁻–H), using the following preparative HPLC conditions:

Column: YMC ODS-AQ, 20×250 mm, 10-micron particle size, 120-angstrom pore size
Mobile Phase Gradient: 5-95% B in 45 minutes
A: Water+0.01% HFBA+1% IPA
B: MeCN+0.01% HFBA+1% IPA
Flow rate: 15 ml/min
Temperature: 25° C.
Wavelength: 220 nm

Example 13-4

Compound 2002

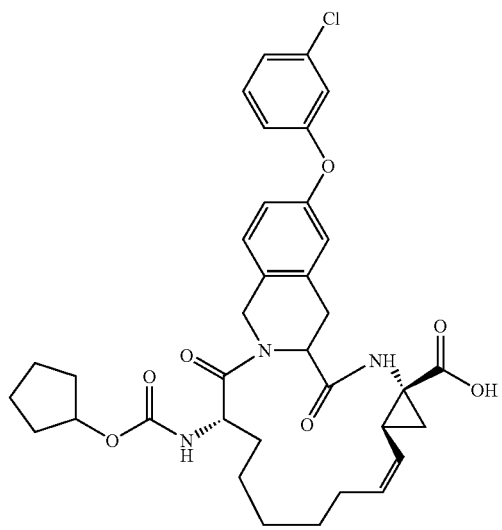

Z)-15-(3-chlorophenoxy)-9-(cyclopentyloxycarbonyl)-10,18-dioxo-1a,4,5,6,7,8,9,10,12,17,17a,18,19,19a-tetradecahydro-1H-11,14-diaza-bicyclo[13.1.0]hexadeca-1(16), 2-dieno[11,12-b]isoquinoline-19a-carboxylic acid (Compound 2002) was synthesized according to the procedure described in Example 13-1. Purification by loading crude material on a Biotage size 12, C-18 samplet for purification using the Horizon LC (12 m, C-18 column) eluting with a gradient from 20% acetonitrile/water to 80% acetonitrile/water with 0.1% TFA over 168-6 mL fractions. Product was a white solid upon concentration. MS m/e 649 (M⁻–H).

Example 13-5

Compound 2003

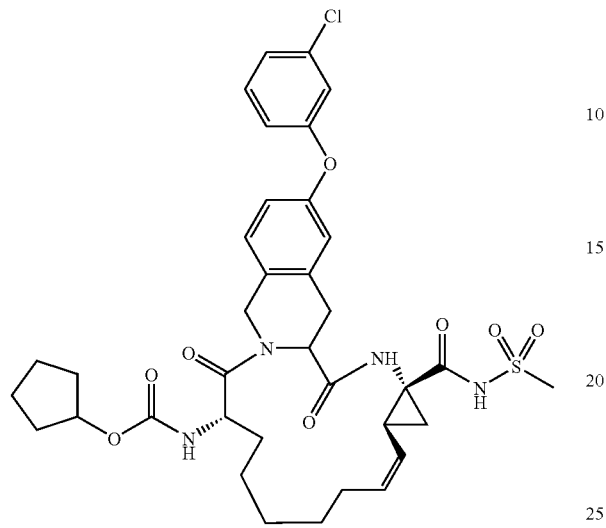

Cyclopentyl (1aS,9S,19aR,Z)-15-(3-chlorophenoxy)-19a-(methylsulfonylcarbamoyl)-10,18-dioxo-1a,4,5,6,7,8,9,10,12,17,17a,18,19,19a-tetradecahydro-1H-11,14-diaza-bicyclo[13.1.0]hexadeca-1(15), 2-dieno[11,12-b]isoquinolin-9-ylcarbamate (Compound 2003) was synthesized according to the procedure described in Example 13-1, except that methyl sulfonamide was used in step 6 instead of cyclopropyl sulfonamide. Purification by loading crude material onto a Biotage size 12 m, silica column eluting with a 5% gradient from 15% acetone/hexanes to 40% acetone/hexanes gave product eluting in fraction 64 using 13 mm test tubes and collecting for 30 seconds. Product was a white solid (8 mg, 70%) upon concentration. MS m/e 727.3 (M⁻).

Example 13-6

Compound 2004

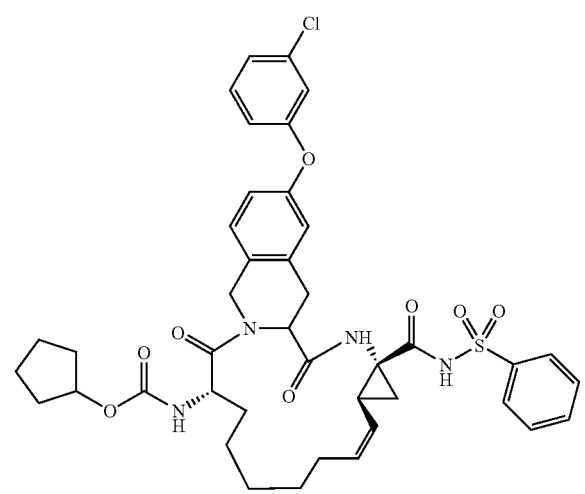

Cyclopentyl (1aS,9S,19aR,Z)-15-(3-chlorophenoxy)-10,18-dioxo-19a-(phenylsulfonylcarbamoyl)-1a,4,5,6,7,8,9,10,12,17,17a,18,19,19a-tetradecahydro-1H-11,14-diaza-bicyclo[13.1.0]hexadeca-1(15), 2-dieno[11,12-b]isoquinolin-9-ylcarbamate (Compound 2004) was synthesized according to the procedure described in Example 13-1, except that phenyl sulfonamide was used in step 6 instead of cyclopropyl sulfonamide. Purification by loading crude material on a Biotage size 12, C-18 samplet for purification using the Horizon LC (12 m, C-18 column) eluting with a gradient from 20% acetonitrile/water to 80% acetonitrile/water with 0.1% TFA over 168-6 mL fractions gave product in fractions 28-31. Product was a white solid (8 mg, 60%) upon concentration. MS m/e 789.3 (M⁻).

Example 13-7

Compound 2010

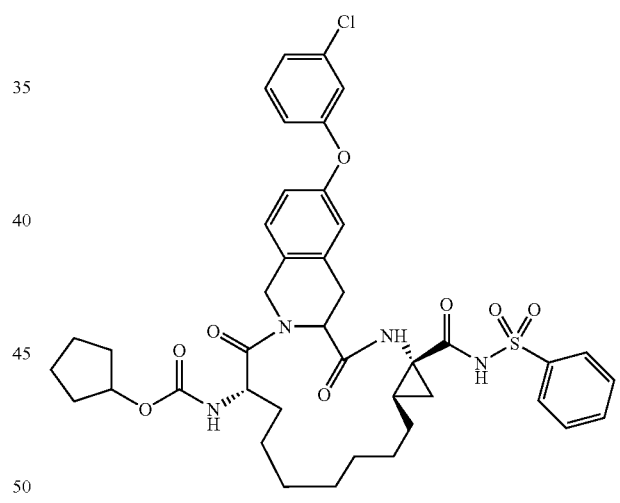

Cyclopentyl (1aR,9S,19aR)-15-(3-chlorophenoxy)-10,18-dioxo-19a-(phenylsulfonylcarbamoyl)-1a,2,3,4,5,6,7,8,9,10,12,17,17a,18,19,19a-hexadecahydro-1H-2,5-diaza-bicyclo[13.1.0]hexadec-1(15)-eno[5,4-b]isoquinolin-9-ylcarbamate (Compound 2010) was synthesized according to the procedure described in Example 13-6, except that an additional hydrogenation step was added to give the saturated macrocycle.

Step 7: Synthesis of cyclopentyl (1aR,9S,19aR)-15-(3-chlorophenoxy)-10,18-dioxo-19a-(phenylsulfonylcarbamoyl)-1a,2,3,4,5,6,7,8,9,10,12,17,17a,18,19,19a-hexadecahydro-1H-2,5-diaza-bicyclo[13.1.0]hexadec-1(15)-eno[5,4-b]isoquinolin-9-ylcarbamate

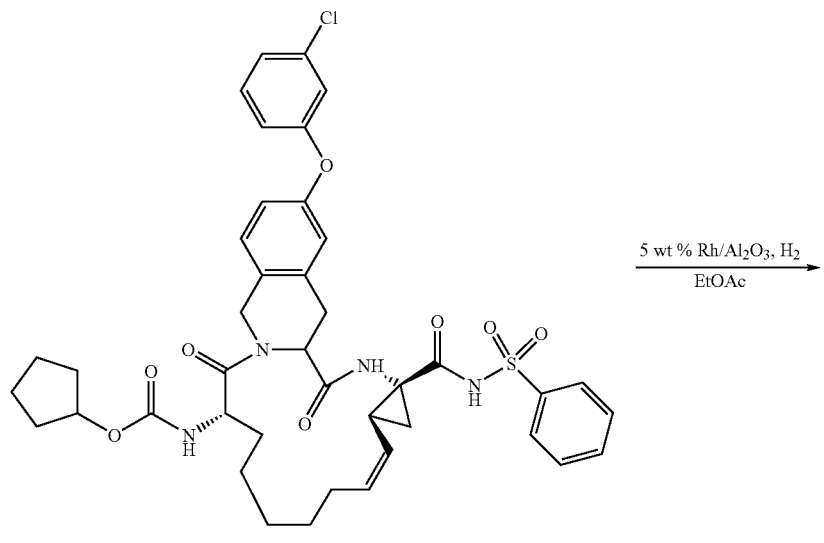

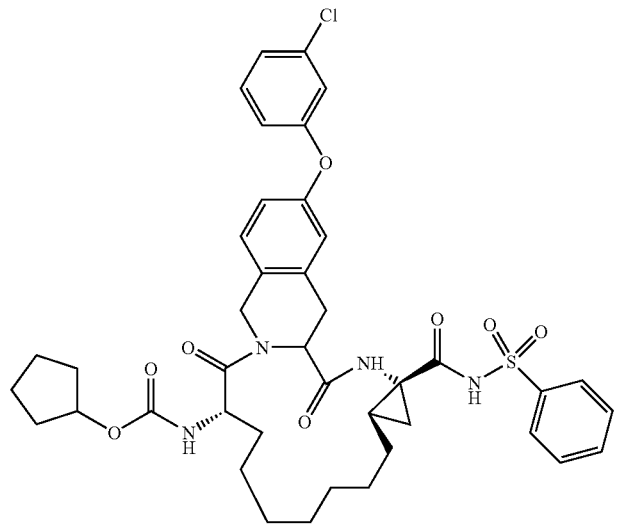

Compound 2004 (6 mg, 0.007 mmol) was taken up in EtOAc (370 μL) and 0.1 equivalent of 5 wt. % Rh/Al$_2$O$_3$ was added. The reaction was evacuated and filled with H$_2$ from a balloon 3 times, before allowing reaction to stir at rt with balloon of H$_2$ affixed over several days. Reaction was then loaded directly onto a Biotage size 12, C-18 samplet for purification using the Horizon LC (12 m, C-18 column) eluting with a gradient from 20% acetonitrile/water to 80% acetonitrile/water with 0.1% TFA over 168-6 mL fractions. Product (2 mg, 30%) was a colorless residue. MS m/e 791.3 (M$^-$).

Example 13-8 Compound 2007

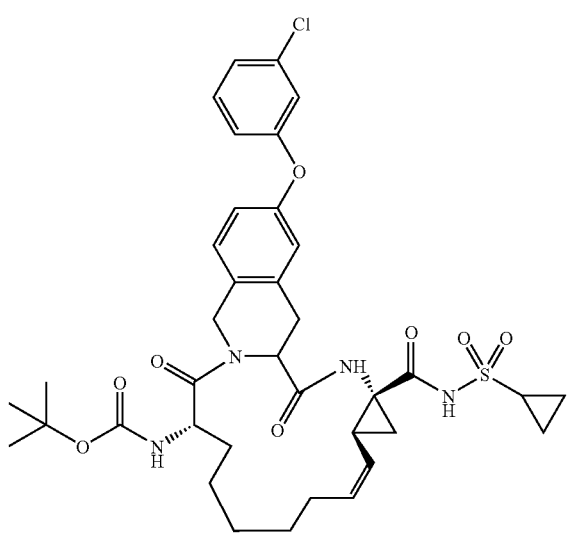

tert-Butyl (1aS,9S,19aR,Z)-15-(3-chlorophenoxy)-19a-(cyclopropylsulfonylcarbamoyl)-10,18-dioxo-1a,4,5,6,7,8,9,10,12,17,17a,18,19,19a-tetradecahydro-1H-11,14-diaza-bicyclo[13.1.0]hexadeca-1(15), 2-dieno[11,12-b]isoquinolin-9-ylcarbamate (Compound 2007) was synthesized from (1aS,9S,19aR,Z)-ethyl 9-(tert-butoxycarbonyl)-15-(3-chlorophenoxy)-10,18-dioxo-1a,4,5,6,7,8,9,10,12,17,17a,18,19,19a-tetradecahydro-1H-11,14-diaza-bicyclo[13.1.0]hexadeca-1(16), 2-dieno[11,12-b]isoquinoline-19a-carboxylate, an intermediate whose synthesis is described in Step 3 of the synthesis of Example 13-1.

Step 4: Synthesis of (1aR,9S,19aR)-9-(tert-butoxycarbonyl)-15-(3-chlorophenoxy)-10,18-dioxo-1a,2,3,4,5,6,7,8,9,10,12,17,17a,18,19,19a-hexadecahydro-1H-2,5-diaza-bicyclo[13.1.0]hexadec-1(15)-eno[5,4-b]isoquinoline-19a-carboxylic acid The crude (1aS,9S,19aR,Z)-ethyl 9-(tert-butoxycarbonyl)-15-(3-chlorophenoxy)-10,18-dioxo-1a,4,5,6,7,8,9,10,12,17,17a,18,19,19a-tetradecahydro-1H-11,14-diaza-bicyclo[13.1.0]hexadeca-1(16), 2-dieno[11,12-b]isoquinoline-19a-carboxylate (20 mg, 0.03 mmol) was dissolved in 0.4 mL of a mixture of THF:MeOH:H₂O (2:1:1). Lithium hydroxide monohydrate (8 mg, 0.18 mmol) was added and reaction stirred at rt overnight. The reaction was then concentrated under vacuum and quenched with 5 mL of 1 N HCl. The product precipitated and could be filtered off giving an off-white powder (17 mg). It was directly used in the next step without further purification. MS m/e 637 (M—H).

Step 5: Synthesis of tert-butyl (1aS,9S,19aR,Z)-15-(3-chlorophenoxy)-19a-(cyclopropylsulfonylcarbamoyl)-10,18-dioxo-1a,4,5,6,7,8,9,10,12,17,17a,18,19,19a-tetradecahydro-1H-11,14-diaza-bicyclo[13.1.0]hexadeca-1(16), 2-dieno[11,12-b]isoquinolin-9-ylcarbamate.

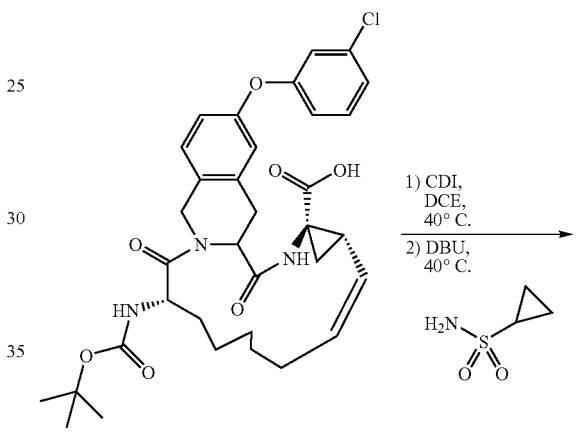

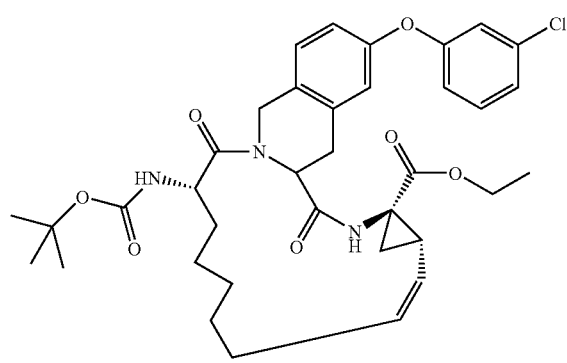

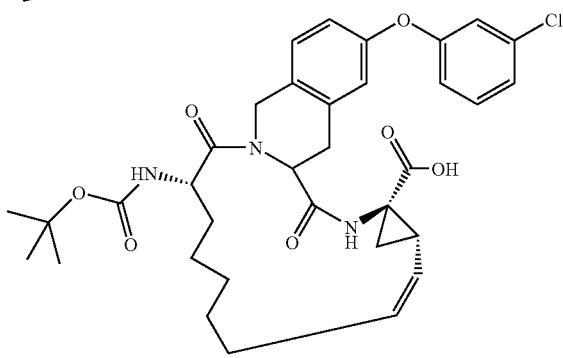

-continued

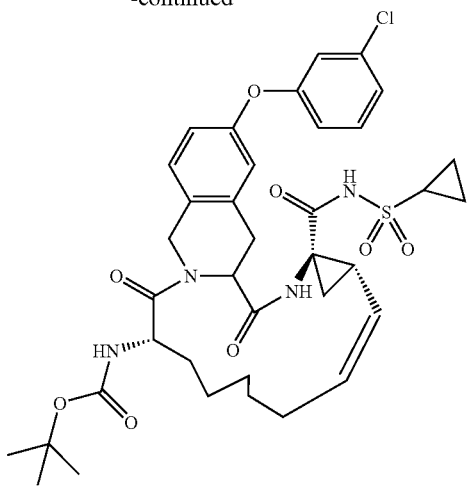

The crude (1aR,9S,19aR)-9-(tert-butoxycarbonyl)-15-(3-chlorophenoxy)-10,18-dioxo-1a,2,3,4,5,6,7,8,9,10,12,17,17a,18,19,19a-hexadecahydro-1H-2,5-diaza-bicyclo[13.1.0]hexadec-1(15)-eno[5,4-b]isoquinoline-19a-carboxylic acid (17 mg, 0.03 mmol) was dissolved in 0.1 mL of DCE and CDI (14 mg, 0.09 mmol) was added. The reaction was heated to 40° C. for 1 h. TLC run in 10% MeOH/CHCl$_3$ showed conversion to a higher R$_f$ spot. Cyclopropyl sulfonamide (11 mg, 0.09 mmol) and DBU (14 μL, 0.09 mmol) were added and the reaction heated to 50° C. and stirred overnight. The reaction was loaded onto a Biotage size 12, C-18 samplet for purification using the Horizon LC (12 m, C-18 column) eluting with a gradient from 20% acetonitrile/water to 80% acetonitrile/water with 0.1% TFA over 168-6 mL fractions. Product is a white solid (8 mg, 59%) upon concentration. MS m/e 739.5 (M$^-$–H).

Example 13-9

Compound 2008

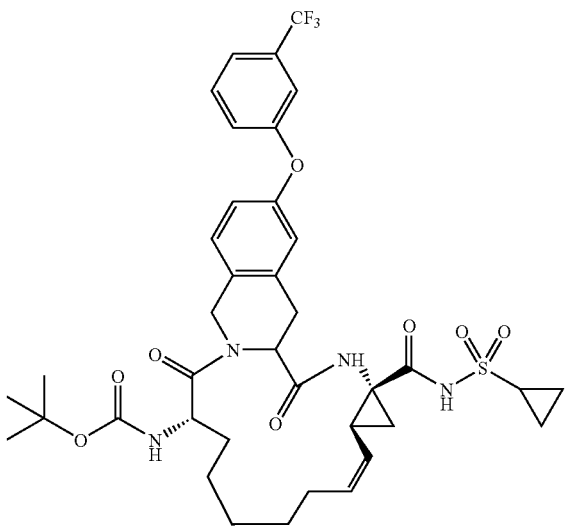

tert-Butyl (1aS,9S,19aR,Z)-19a-(cyclopropylsulfonylcarbamoyl)-10,18-dioxo-15-(3-(trifluoromethyl)phenoxy)-1a,4,5,6,7,8,9,10,12,17,17a,18,19,19a-tetradecahydro-1H-1,14-diaza-bicyclo[13.1.0]hexadeca-1(15), 2-dieno[11,12-b]isoquinolin-9-ylcarbamate (Compound 2008) was synthesized according to the procedure described in Example 13-8 except that 2-(tert-butoxycarbonyl)-6-(3-(trifluoromethyl)phenoxy)-1,2,3,4-tetrahydroisoquinoline-3-carboxylic acid was used in the first step of the synthesis instead of 2-(tert-butoxycarbonyl)-6-(3-chlorophenoxy)-1,2,3,4-tetrahydroisoquinoline-3-carboxylic acid. MS m/e 773.8 (M$^-$–H).

Step 1: Synthesis of 2-(tert-butoxycarbonyl)-6-(3-(trifluoromethyl)phenoxy)-1,2,3,4-tetrahydroisoquinoline-3-carboxylic acid

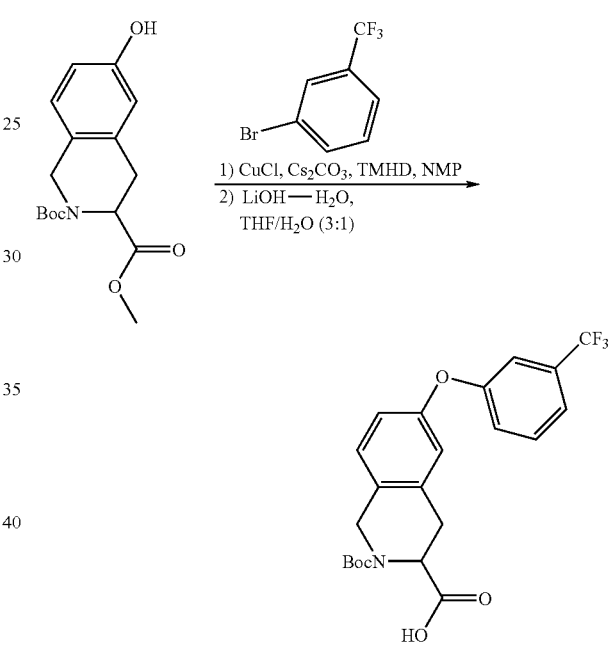

2-tert-butyl 3-methyl 6-hydroxy-3,4-dihydroisoquinoline-2,3(1H)-dicarboxylate (200 mg, 0.65 mmol), m-trifluoromethyl-phenyl bromide (122 mg, 0.54 mmol), 2,2,6,6-tetramethylheptane-3,5-dione (TMHD, 10 mg, 0.054 mmol), Cs$_2$CO$_3$ (326 mg, 1.00 mmol), and CuCl (27 mg, 0.27 mmol) were mixed together in NMP (1 mL) and heated to 120° C. for 6 h. The reaction was then diluted with MTBE and filtered over celite. The filtrate was washed with 1 N HCl, 1 N NaOH, and brine. The organic was dried over Na$_2$SO$_4$ and concentrated before loading on a Biotage silica column (12 m) and eluting with 10% Acetone/Hexanes to give 2-tert-butyl 3-methyl 6-(3-chlorophenoxy)-3,4-dihydroisoquinoline-2,3(1H)-dicarboxylate as a pale yellow oil (141 mg, 58%). This material was then taken up in 1 mL of a mixture of THF/H$_2$O (3:1) and LiOH (70 mg, 1.62 mmol) was added. The reaction stirred overnight at rt, before it was concentrated and quenched with 1 N HCl. The product was then extracted with EtOAc (3×). The combined extracts were dried over Na$_2$SO$_4$ and concentrated to give a pale yellow foam (129 mg, 94%). MS m/e 436.4 (M$^-$–H).

Example 13-10

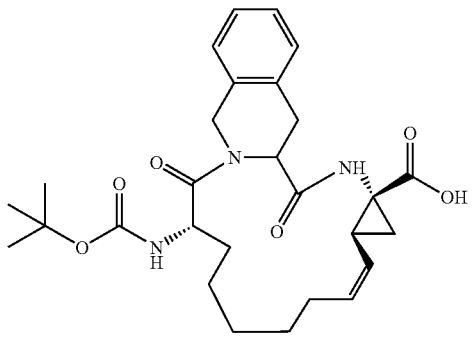

Compound 2001

(1aS,9S,19aR,Z)-9-(tert-Butoxycarbonyl)-10,18-dioxo-1a,4,5,6,7,8,9,10,12,17,17a,18,19,19a-tetradecahydro-1H-11,14-diaza-bicyclo[13.1.0]hexadeca-1(15), 2-dieno[11,12-b]isoquinoline-19a-carboxylic acid (Compound 2001) was synthesized according to the procedure described in Example 13-1 except that 2-(tert-butoxycarbonyl)-1,2,3,4-tetrahydroisoquinoline-3-carboxylic acid was used in Step 1 instead of 2-(tert-butoxycarbonyl)-6-(3-chlorophenoxy)-1,2,3,4-tetrahydroisoquinoline-3-carboxylic acid. Alternatively, in Step 4 of the procedure described in Example 13-1 the ester intermediate was hydrolyzed directly to give the corresponding carboxylic acid shown above.

Step 4: Synthesis of (1aS,9S,19aR,Z)-9-(tert-butoxycarbonyl)-10,18-dioxo-1a,4,5,6,7,8,9,10,12,17,17a,18,19,19a-tetradecahydro-1H-11,14-diaza-bicyclo[13.1.0]hexadeca-1(15), 2-dieno[11,12-b]isoquinoline-19a-carboxylic acid

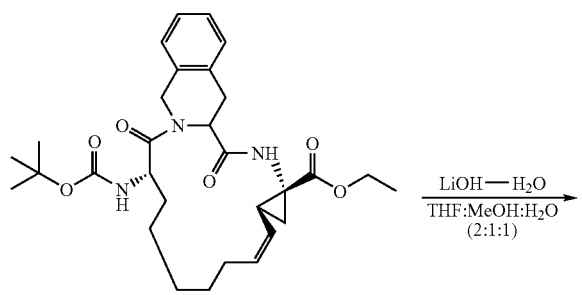

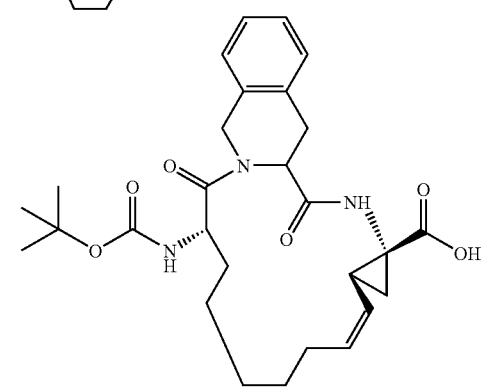

The crude (1aS,9S,19aR,Z)-ethyl 9-(tert-butoxycarbonyl)-10,18-dioxo-1a, 4,5,6,7,8,9,10,12,17,17a,18,19,19a-tetradecahydro-1H-11,14-diaza-bicyclo[13.1.0]hexadeca-1(15), 2-dieno[11,12-b]isoquinoline-19a-carboxylate (86 mg, 0.16 mmol) was dissolved in 1.0 mL of a mixture of THF:MeOH:H$_2$O (2:1:1). Lithium hydroxide monohydrate (40 mg, 0.96 mmol) was added and reaction stirred at rt overnight. The reaction was then concentrated under vacuum and quenched with 5 mL of 1 N HCl. The product was extracted into EtOAc. The organic was dried over Na$_2$SO$_4$ and concentrated before loading onto a Biotage 12s silica column and eluting with 35% EtOAc/CHCl$_3$ with 0.1% AcOH to give product in fractions 49-69 using 13 mm test tubes and collecting for 8 s. Product is a white solid (20 mg, 23%); $^1$H NMR (d-acetone, 500 MHz): δ 7.15-7.34 (m, 4H), 5.48-5.56 (m, 1H), 5.24 (t, 1H), 5.17 (d, 1H), 5.04-5.10 (m, 1H), 4.90-4.95 (m, 1H), 4.76 (d, 1H), 4.03-4.13 (m, 1H), 3.21-3.29 (m, 1H), 3.04-3.12 (m, 1H), 2.75-2.94 (m, 2H), 2.22-2.39 (m, 2H), 0.78-2.19 (m, 20H); MS m/e 510.2 (M$^-$–H).

Example 13-11

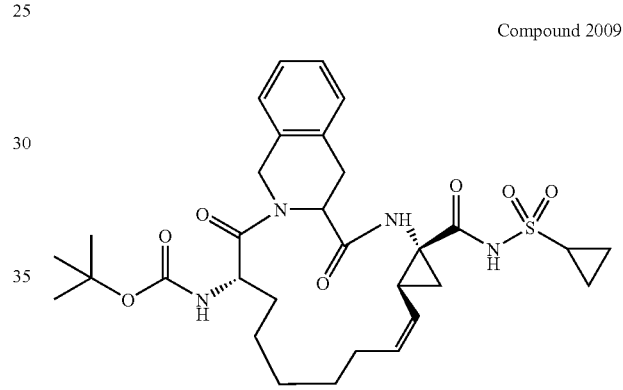

Compound 2009 tert-Butyl (1aS,9S,19aR,Z)-19a-(cyclopropylsulfonylcarbamoyl)-10,18-dioxo-1a,4,5,6,7,8,9,10,12,17,17a,18,19,19a-tetradecahydro-1H-11,14-diaza-bicyclo[13.1.0]hexadeca-1(15),2-dieno[11,12-b]isoquinolin-9-ylcarbamate (Compound 2009) was synthesized according to the procedure described in Example 13-10 with an additional coupling step.

Step 5: Synthesis of Tert-butyl (1aS,9S,19aR,Z)-19a-(cyclopropylsulfonylcarbamoyl)-10,18-dioxo-1a,4,5,6,7,8,9,10,12,17,17a,18,19,19a-tetradecahydro-1H-11,14-diaza-bicyclo[13.1.0]hexadeca-1(15),2-dieno[11,12-b]isoquinolin-9-ylcarbamate.

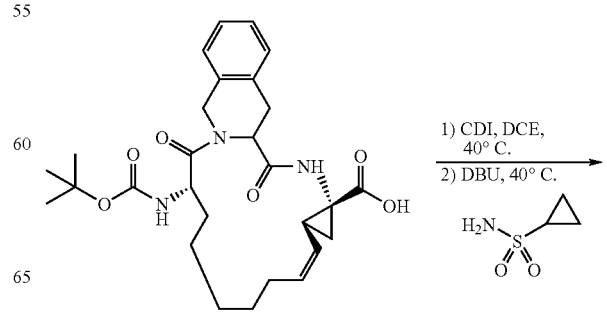

-continued

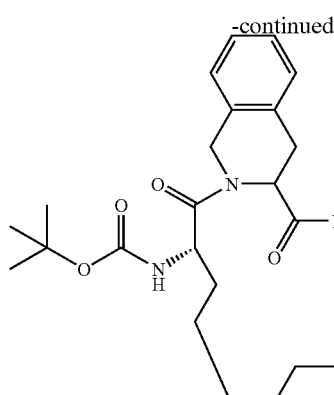

Compound 1 (4 mg, 0.008 mmol) was dissolved in 0.1 mL of DCE and CDI (4 mg, 0.02 mmol) was added. The reaction was heated to 40° C. for 4 h. TLC run in 10% MeOH/CHCl$_3$ showed conversion to a higher R$_f$ spot. Cyclopropyl sulfonamide (3 mg, 0.02 mmol) and DBU (3 μL, 0.02 mmol) were added and the reaction heated to 50° C. and stirred overnight. The reaction was loaded onto a Biotage size 12, C-18 samplet for purification using the Horizon LC (12 m, C-18 column) eluting with a gradient from 20% acetonitrile/water to 80% acetonitrile/water with 0.1% TFA over 168-6 mL fractions. Product is a white residue (1.5 mg, 30%). MS m/e 613.2 (M$^-$–H).

Example 13-12

Compound 2011

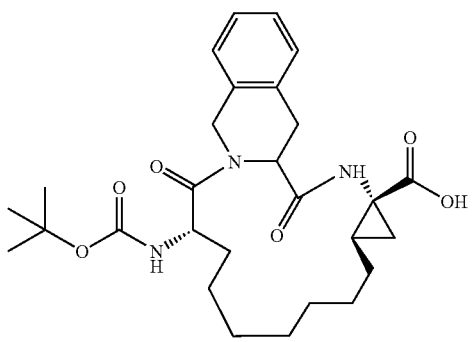

1aR,9S,19aR)-9-(tert-butoxycarbonyl)-10,18-dioxo-1a,2,3,4,5,6,7,8,9,10,12,17,17a,18,19,19a-hexadecahydro-1H-2,5-diaza-bicyclo[13.1.0]hexadec-1(15)-eno[5,4-b]isoquinoline-19a-carboxylic acid (Compound 2011) was synthesized according to the procedure described in Example 13-10 with an additional hydrogenation step.

Step 5: Synthesis of (1aR,9S,19aR)-9-(tert-butoxycarbonyl)-10,18-dioxo-1a,2,3,4,5,6,7,8,9,10,12,17,17a,18,19,19a-hexadecahydro-1H-2,5-diaza-bicyclo[13.1.0]hexadec-1(15)-eno[5,4-b]isoquinoline-19a-carboxylic acid

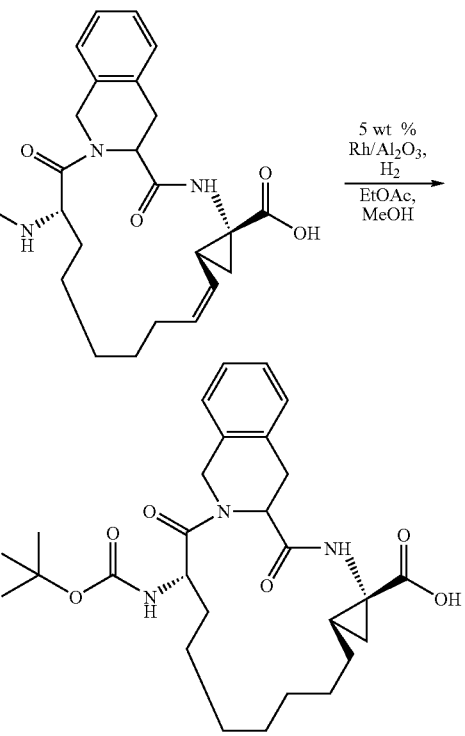

Compound 2001 (5.1 mg, 0.01 mmol) was taken up in EtOAc (400 μL) and MeOH added drop wise until starting material dissolved. 0.1 equivalent of 5 wt. % Rh/Al$_2$O$_3$ was added. The reaction was evacuated and filled with H$_2$ from a balloon 3 times, before allowing reaction to stir at rt with balloon of H$_2$ affixed over several days. Reaction was then loaded directly onto a Biotage size 12, C-18 samplet for purification using the Horizon LC (12 m, C-18 column) eluting with a gradient from 20% acetonitrile/water to 80% acetonitrile/water with 0.1% TFA over 168-6 mL fractions. Product (1.4 mg, 27%) was a colorless residue. MS m/e 512.1 (M$^-$–H).

Example 13-13

Compound 2006

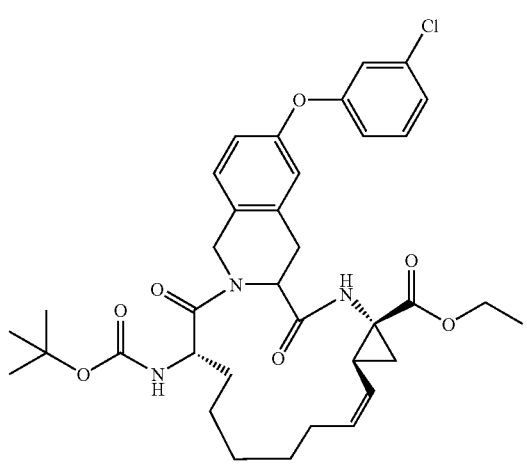

Methodology

Preparation of NS3 Inhibitors

Section XII

Certain compounds and intermediates used in the synthesis have been described elsewhere. For instance, in the scheme below, the syntheses of intermediates 1(R)-tert-butoxycarbonylamino-2(S)-vinyl-cyclopropanecarboxylic acid ethyl ester (1a) and 2(S)-tert-butoxycarbonylamino-non-8-enoic acid (1c), and the ring-closing-metathesis of tripeptide 1d were carried out in a similar fashion as described in International Application (International Publication No. WO 2005/037214) and PCT/CA00/00353 (Publication No. WO 00/59929), incorporated herein by reference.

Example 14-1

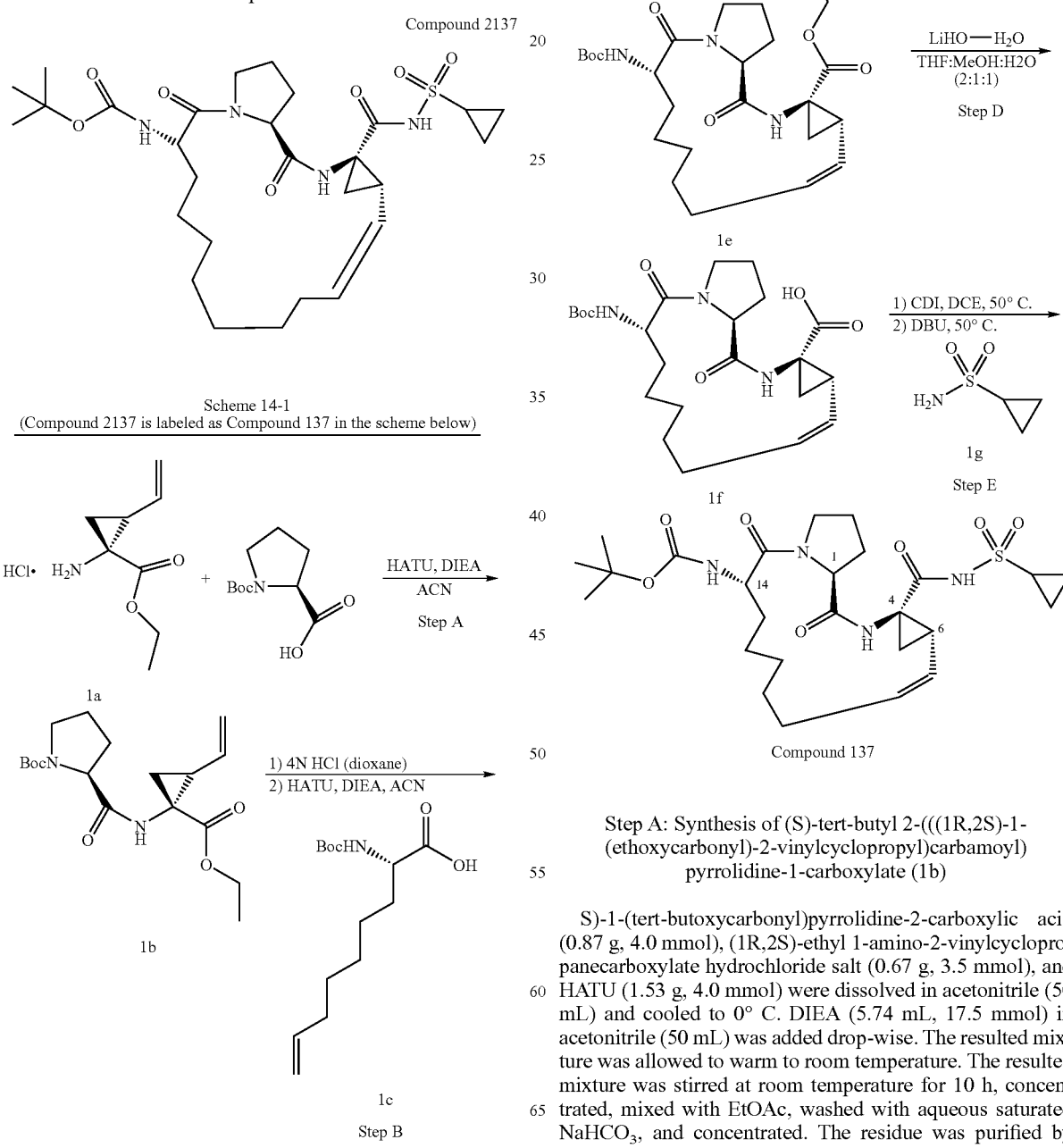

Scheme 14-1
(Compound 2137 is labeled as Compound 137 in the scheme below)

Step A: Synthesis of (S)-tert-butyl 2-(((1R,2S)-1-(ethoxycarbonyl)-2-vinylcyclopropyl)carbamoyl)pyrrolidine-1-carboxylate (1b)

S)-1-(tert-butoxycarbonyl)pyrrolidine-2-carboxylic acid (0.87 g, 4.0 mmol), (1R,2S)-ethyl 1-amino-2-vinylcyclopropanecarboxylate hydrochloride salt (0.67 g, 3.5 mmol), and HATU (1.53 g, 4.0 mmol) were dissolved in acetonitrile (50 mL) and cooled to 0° C. DIEA (5.74 mL, 17.5 mmol) in acetonitrile (50 mL) was added drop-wise. The resulted mixture was allowed to warm to room temperature. The resulted mixture was stirred at room temperature for 10 h, concentrated, mixed with EtOAc, washed with aqueous saturated NaHCO$_3$, and concentrated. The residue was purified by silica gel chromatography (10% EtOAc in hexanes, 30%

EtOAc in hexanes, and then 50% EtOAc in hexanes) to give product as pale yellow oil (1.19 g, 96%). MS (ESI+): 375 [M+23] (5) and 253 [M+1−100] (100).

Step B: Synthesis of (1R,2S)-ethyl 1-((S)-1-((S)-2-(tert-butoxycarbonyl)non-8-enoyl)pyrrolidine-5-carboxamido)-2-vinylcyclopropanecarboxylate (1d)

The dipeptide 1b from Step A (1.19 g, 3.38 mmol) was dissolved in HCl in dioxane (4.0 M, 13 mL, 51 mmol) and stirred at rt for 90 min to remove the Boc protective group. It was then concentrated down, taken up in acetonitrile and concentrated down again twice. This light brownish residue, 2(S)-tert-butoxycarbonylamino-non-8-enoic acid (0.95 g, 3.3 mmol) and HATU (1.4 g, 3.6 mmol) were dissolved in acetonitrile and cooled to 0° C. DIEA in acetonitrile was added drop-wise. The resulted mixture was allowed to warm to room temperature and stirred at room temperature for 10 h. The resulted mixture was concentrated, mixed with EtOAc, washed with aqueous saturated sodium bicarbonate, dried with $Na_2SO_4$, and concentrated. The residue was purified by silica gel chromatography (10% EtOAc and then 30% EtOAc) to give product 1d as pale yellowish oil (1.5 g, 90%). MS (ESI+): 528 [M+23] (5) and 406 [M+1−100] (100).

Step C: Synthesis of (1S,4R,6S,14S)14-tert-Butoxycarbonylamino-2,15-dioxo-3,16-diaza-tricyclo [14.3.0.0$^{4,6}$]nonadec-7-ene-4-carboxylic acid ethyl ester (1e)

The product from Step B (1d, 0.61 g, 1.2 mmol) was dissolved in 1,2-dichloroethane (120 mL), then degassed and filled with nitrogen gas (1 atm). Hoveyda 1$^{st}$ generation catalyst (0.036 g, 0.060 mmol) was added. The resulted mixture was further degassed and filled with nitrogen gas (1 atm), heated at 50° C. for 16 h, and concentrated. The residue was purified by silica gel chromatography (30% EtOAc in hexanes, 50% EtOAc in hexanes, and then 60% EtOAc in hexanes) to give product 1e as pale yellowish solid (0.44 g, 76%). MS (ESI+): 478 [M+1] (5) and 378 [M+1−100] (100).

Step D: Synthesis of (1S,4R,6S,14S)14-tert-Butoxycarbonylamino-2,15-dioxo-3,16-diaza-tricyclo [14.3.0.0$^{4,6}$]nonadec-7-ene-4-carboxylic acid (1f)

The macrocyclic ester 1e from Step C (1.0 g, 2.1 mmol) was first dissolved in THF (3.0 mL), then methanol (3.0 mL) and water (1.5 mL) were added, followed by addition of LiOH—$H_2O$ (3 equiv). The resulted mixture was stirred for 4 h and concentrated to dryness. The residue was first redissolved in water (10 mL), then acidified with aqueous HCl (3.0 N, 2.2 mL, 6.6 mmol). The aqueous was extracted with EtOAc (3×15 mL). The combined organic layers was dried with sodium sulfate and concentrated to give the acid product 1f (0.93 g, 99%). MS (ESI+): 450 [M+1] (5) and 350 [M+1−100] (100).

Step E: Synthesis of (1S,4R,6S,14S) tert-butyl 4-Cyclopropanesulfonylaminocarbonyl-2,15-dioxo-3,16-diaza-tricyclo[14.3.0.0$^{4,6}$]nonadec-7-ene-14-yl carbamate (Compound 137)

The macrocyclic acid product 1f from Step D (0.983 g, 2.19 mmol) was dissolved in DriSolve 1,2-dichloroethane (15 mL). Carbonyldiimidazole (0.479 g, 2.95 mmol) was then added. The resulted mixture was stirred at 50° C. for 2 h. The reaction was cooled down to rt, and cyclopropanesulfonamide (0.358 g, 2.95 mmol) was added, followed by addition of DBU (0.406 mL, 2.95 mmol). The reaction mixture was again heated at 50° C. and stirred for 1 h. LCMS showed reaction complete. It was cooled to room temperature, and dichloromethane (15 mL) was added. The resulted mixture was washed with aqueous hydrochloric acid (0.5 N, 5 mL) and water. The organic layer was separated, dried with sodium sulfate, and concentrated. The residue was purified by silica gel chromatography (40% EtOAc in hexanes, 60% EtOAc in hexanes, 80% EtOAc in hexanes, and then 100% EtOAc) to give the desired product as a white solid (Compound 137, 1.05 g, 87%). $^1$H NMR (d$^6$-Acetone, 400 MHz) δ0.96-1.02 (m, 2H), 1.08-1.13 (m, 1H), 1.18-1.54 (m, 18H), 1.69-1.73 (m, 1H), 1.83-2.05 (m, 3H), 2.19-2.23 (m, 2H), 2.39-2.47 (m, 2H), 2.81-2.92 (m, 2H), 3.64-3.70 (m, 1H), 4.01-4.06 (m, 1H), 4.33-4.42 (m, 2H), 4.97 (t, 1H), 5.64-5.71 (m, 1H), 5.98 (br d, 1H), 8.36 (br s, 1H), 10.70 (br s, 1H). MS (APCI+): 453.1 (MH$^+$-Boc).

The compounds in the following examples were prepared according to procedures similar to that described in Example 1 above, substituting cyclopropanesulfonamide with other appropriate sulfonamides in Step E, Scheme 14-1 instead. The sulfonamides used were either purchased from commercial sources or prepared through bubbling anhydrous ammonia gas through THF solution of the corresponding sulfonyl chlorides at −10° C., followed by filtration to remove the inorganic salt and concentration to yield the clean product, which was usually used directly without further purification.

Example 14-2

Compound 2101

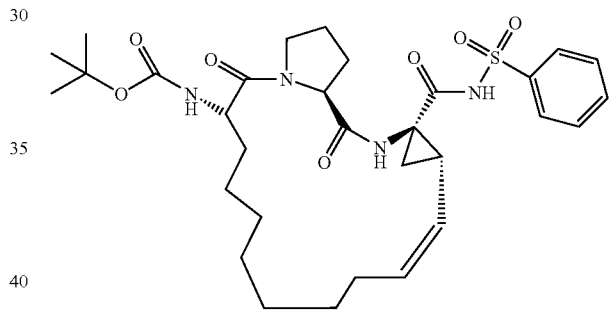

(1S,4R,6S,14S)tert-Butyl 4-benzenesulfonylaminocarbonyl-2,15-dioxo-3,16-diaza-tricyclo[14.3.0.0$^{4,6}$]nonadec-7-ene-14-yl carbamate was synthesized according to the same procedures as described in Example 1, substituting cyclopropanesulfonamide with benzenesulfonamide in Step E. $^1$H NMR (d$^6$-Acetone, 400 MHz) δ1.22-1.55 (m, 19H), 1.79-2.09 (m, 3H), 2.21-2.37 (m, 4H), 3.66-3.72 (m, 1H), 4.03 (m, 1H), 4.33-4.44 (m, 3H), 5.24 (q, 1H), 5.99 (br d, 1H), 7.58-7.62 (m, 2H), 7.69-7.73 (m, 1H), 7.94-7.97 (m, 2H), 8.36 (br s, 1H), 11.10 (br s, 1H). MS m/z 587.2 (APCI-, M−1).

Example 14-3

Compound 2102

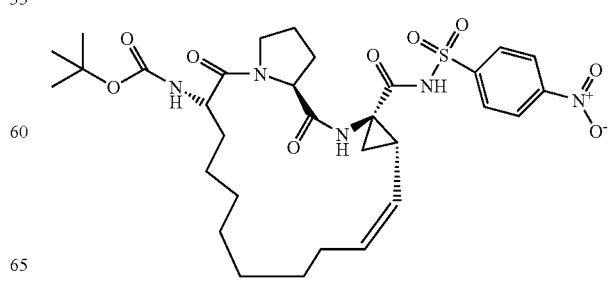

(1S,4R,6S,14S)tert-Butyl 4-(4-nitrobenzenesulfonyl)aminocarbonyl-2,15-dioxo-3,16-diaza-tricyclo[14.3.0.0⁴,⁶]nonadec-7-ene-14-yl carbamate was synthesized according to the same procedures as described in Example 1, substituting cyclopropanesulfonamide with 4-nitrobenzenesulfonamide in Step E. ¹H NMR (d⁶-Acetone, 400 MHz) δ1.23-1.59 (m, 19H), 1.81-2.09 (m, 3H), 2.23-2.44 (m, 4H), 3.66-3.72 (m, 1H), 4.05 (m, 1H), 4.32-4.46 (m, 3H), 5.24 (q, 1H), 6.01 (br d, 1H), 8.21-8.24 (m, 2H), 8.43-8.48 (m, 3H). MS m/z 632.2 (APCI–, M–1).

Example 14-4

Compound 2103

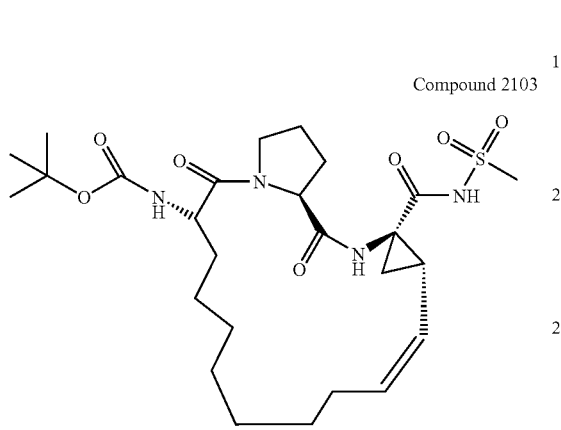

(1S,4R,6S,14S)tert-Butyl 4-methylsulfonylaminocarbonyl-2,15-dioxo-3,16-diaza-tricyclo[14.3.0.0⁴,⁶]nonadec-7-ene-14-yl carbamate was synthesized according to the same procedures as described in Example 1, substituting cyclopropanesulfonamide with methylsulfonamide in Step E. ¹H NMR (d⁶-Acetone, 400 MHz) δ1.26-1.55 (m, 18H), 1.69-1.73 (m, 1H), 1.83-2.09 (m, 3H), 2.19-2.25 (m, 2H), 2.39-2.44 (m, 1H), 2.50-2.60 (m, 1H), 3.16 (s, 3H), 3.64-3.77 (m, 1H), 3.95-4.03 (m, 1H), 4.32-4.42 (m, 2H), 4.98 (t, 1H), 5.70 (q, 1H), 6.00 (br d, 1H), 8.36 (br s, 1H), 10.74 (br s, 1H). MS m/z 525.2 (APCI–, M–1).

Example 14-5

Compound 2104

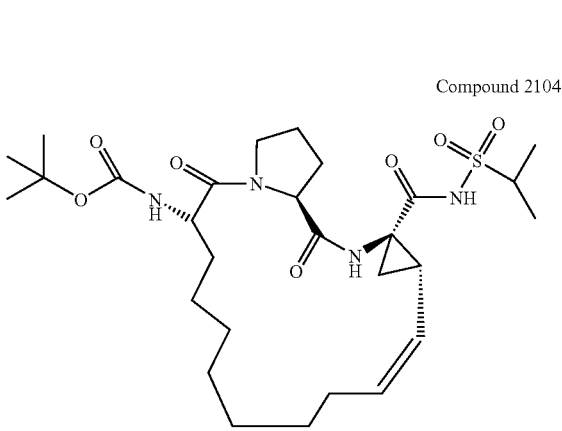

(1S,4R,6S,14S)tert-Butyl 4-isopropylsulfonylaminocarbonyl-2,15-dioxo-3,16-diaza-tricyclo[14.3.0.0⁴,⁶]nonadec-7-ene-14-yl carbamate was synthesized according to the same procedures as described in Example 1, substituting cyclopropanesulfonamide with isopropylsulfonamide in Step E. ¹H NMR (d⁶-Acetone, 400 MHz) δ1.18-1.55 (m, 24H), 1.71-1.74 (m, 1H), 1.80-2.06 (m, 3H), 2.19-2.26 (m, 2H), 2.40-2.54 (m, 2H), 3.60-3.73 (m, 2H), 4.03-4.08 (m, 1H), 4.32-4.42 (m, 2H), 4.98 (t, 1H), 5.66 (q, 1H), 6.01 (br d, 1H), 8.40 (br s, 1H), 10.36 (br s, 1H). MS m/z 553.3 (APCI–, M–1).

Example 14-6

Compound 2105

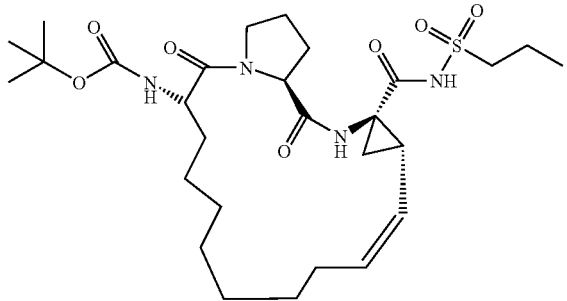

(1S,4R,6S,14S)tert-Butyl 4-propylsulfonylaminocarbonyl-2,15-dioxo-3,16-diaza-tricyclo[14.3.0.0⁴,⁶]nonadec-7-ene-14-yl carbamate was synthesized according to the same procedures as described in Example 1, substituting cyclopropanesulfonamide with propylsulfonamide in Step E. ¹H NMR (d⁶-Acetone, 400 MHz) δ1.00 (t, 3H), 1.18-1.55 (m, 18H), 1.70-2.07 (m, 6H), 2.21-2.25 (m, 2H), 2.41-2.54 (m, 2H), 3.17-3.25 (m, 1H), 3.33-3.40 (m, 1H), 3.64-3.70 (m, 1H), 4.03-4.06 (m, 1H), 4.32-4.42 (m, 2H), 4.97 (t, 1H), 5.68 (q, 1H), 6.00 (br d, 1H), 8.38 (br s, 1H), 10.46 (br s, 1H). MS m/z 553.3 (APCI–, M–1).

Example 14-7

Compound 2106

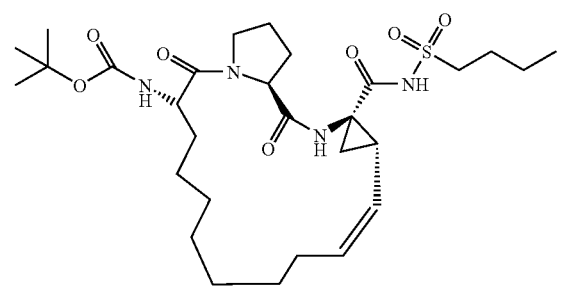

(1S,4R,6S,14S)tert-Butyl 4-(n-butylsulfonyl)aminocarbonyl-2,15-dioxo-3,16-diaza-tricyclo[14.3.0.0⁴,⁶]nonadec-7-ene-14-yl carbamate was synthesized according to the same procedures as described in Example 1, substituting cyclopropanesulfonamide with n-butylsulfonamide in Step E. ¹H NMR (d⁶-Acetone, 400 MHz) δ0.93 (t, 3H), 1.25-1.55 (m, 18H), 1.65-1.74 (m, 3H), 1.84-2.07 (m, 5H), 2.20-2.26 (m, 2H), 2.43-2.51 (m, 2H), 3.18-3.26 (m, 1H), 3.37-3.44 (m, 1H), 3.64-3.70 (m, 1H), 4.03-4.06 (m, 1H), 4.32-4.43 (m, 2H), 4.98 (t, 1H), 5.68 (q, 1H), 6.02 (br d, 1H), 8.40 (br s, 1H), 10.48 (br s, 1H). MS m/z 567.3 (APCI–, M–1).

Example 14-8

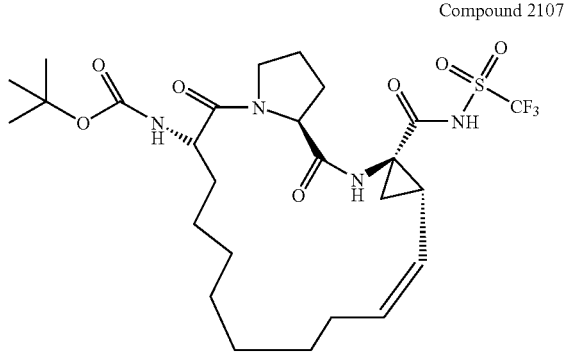

Compound 2107

(1S,4R,6S,14S)tert-Butyl 4-trifluoromethylsulfonylaminocarbonyl-2,15-dioxo-3,16-diaza-tricyclo[14.3.0.0$^{4,6}$]nonadec-7-ene-14-yl carbamate was synthesized according to the same procedures as described in Example 1, substituting cyclopropanesulfonamide with trifluoromethylsulfonamide in Step E. MS m/z 579.2 (APCI−, M−1).

Example 14-9

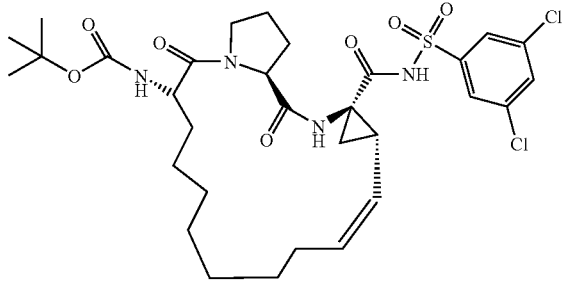

Compound 2108

(1S,4R,6S,14S)tert-Butyl 4-(3,5-dichlorobenzene)-sulfonylaminocarbonyl-2,15-dioxo-3,16-diaza-tricyclo[14.3.0.0$^{4,6}$]nonadec-7-ene-14-yl carbamate was synthesized according to the same procedures as described in Example 1, substituting cyclopropanesulfonamide with 3,5-dichlorobenzenesulfonamide in Step E. $^1$H NMR (d$^6$-Acetone, 400 MHz) δ1.18-1.63 (m, 19H), 1.82-2.11 (m, 3H), 2.20-2.37 (m, 4H), 3.67-3.73 (m, 1H), 4.03-4.06 (m, 1H), 4.32-4.50 (m, 3H), 5.31 (q, 1H), 6.00 (br d, 1H), 7.85 (s, 3H), 8.42 (br s, 1H), 11.46 (br s, 1H). MS m/z 655.2 (APCI−, M−1).

Example 14-10

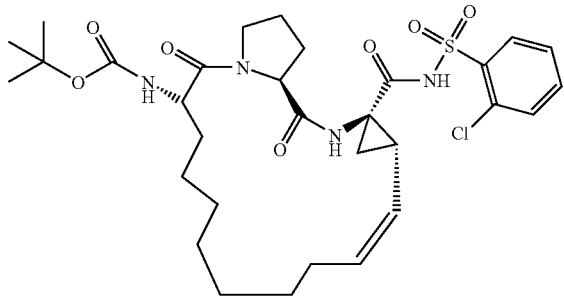

Compound 2109

(1S,4R,6S,14S)tert-Butyl 4-(2-chlorobenzene)-sulfonylaminocarbonyl-2,15-dioxo-3,16-diaza-tricyclo[14.3.0.0$^{4,6}$]nonadec-7-ene-14-yl carbamate was synthesized according to the same procedures as described in Example 1, substituting cyclopropanesulfonamide with 2-chlorobenzenesulfonamide in Step E. $^1$H NMR (d$^6$-Acetone, 400 MHz) δ1.18-1.55 (m, 19H), 1.84-2.11 (m, 3H), 2.22-2.42 (m, 4H), 3.66-3.72 (m, 1H), 4.00-4.06 (m, 1H), 4.34-4.43 (m, 2H), 4.55 (t, 1H), 5.50 (q, 1H), 5.97 (br d, 1H), 7.55-7.72 (m, 3H), 8.17 (dd, 1H), 8.39 (br s, 1H), 11.26 (br s, 1H). MS m/z 621.2 (APCI−, M−1).

Example 14-11

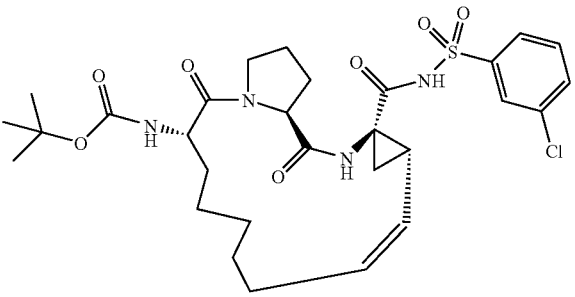

Compound 2110

(1S,4R,6S,14S)tert-Butyl 4-(3-chlorobenzene)-sulfonylaminocarbonyl-2,15-dioxo-3,16-diaza-tricyclo[14.3.0.0$^{4,6}$]nonadec-7-ene-14-yl carbamate was synthesized according to the same procedures as described in Example 1, substituting cyclopropanesulfonamide with 3-chlorobenzenesulfonamide in Step E. $^1$H NMR (d$^6$-Acetone, 400 MHz) δ1.18-1.59 (m, 19H), 1.81-2.10 (m, 3H), 2.21-2.37 (m, 4H), 3.68-3.72 (m, 1H), 4.03-4.06 (m, 1H), 4.32-4.46 (m, 3H), 5.29 (q, 1H), 6.00 (br d, 1H), 7.62-7.67 (m, 1H), 7.74-7.76 (m, 1H), 7.89-7.92 (m, 2H), 8.40 (br s, 1H), 11.28 (br s, 1H). MS m/z 621.2 (APCI−, M−1).

Example 14-12

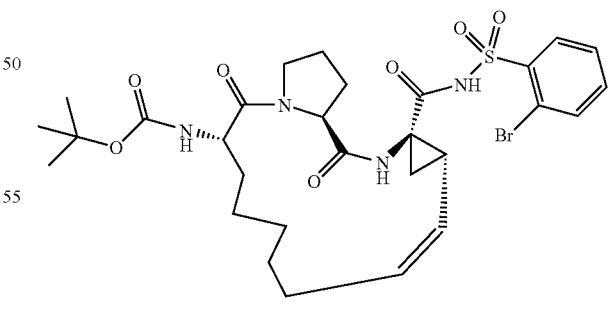

Compound 2111

(1S,4R,6S,14S)tert-Butyl 4-(2-bromobenzene)-sulfonylaminocarbonyl-2,15-dioxo-3,16-diaza-tricyclo[14.3.0.0$^{4,6}$]nonadec-7-ene-14-yl carbamate was synthesized according to the same procedures as described in Example 1, substituting cyclopropanesulfonamide with 2-bromobenzenesulfonamide in Step E. $^1$H NMR (d$^6$-Acetone, 400 MHz) δ1.18-1.57 (m, 19H), 1.84-2.12 (m, 3H), 2.21-2.41 (m, 4H), 3.66-3.72

(m, 1H), 4.03-4.06 (m, 1H), 4.34-4.43 (m, 2H), 4.61 (t, 1H), 5.53 (q, 1H), 5.98 (br d, 1H), 7.57-7.64 (m, 2H), 7.82-7.85 (m, 1H), 8.20-8.23 (m, 1H), 8.39 (br s, 1H), 11.28 (br s, 1H). MS (APCI–) m/z 667.1 (60, M+1), 586.1 (100).

Example 14-13

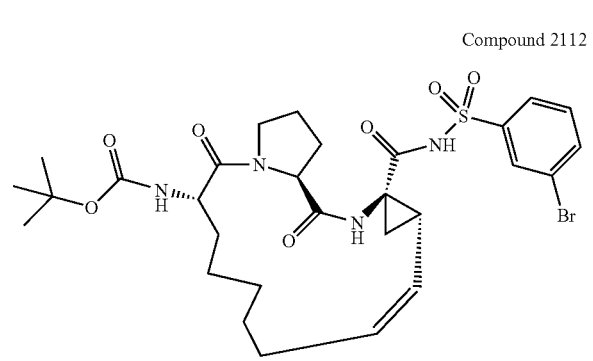

Compound 2112

(1S,4R,6S,14S)tert-Butyl 4-(3-bromobenzene)-sulfonylaminocarbonyl-2,15-dioxo-3,16-diaza-tricyclo[14.3.0.0$^{4,6}$]nonadec-7-ene-14-yl carbamate was synthesized according to the same procedures as described in Example 1, substituting cyclopropanesulfonamide with 3-bromobenzenesulfonamide in Step E. $^1$H NMR (d$^6$-Acetone, 400 MHz) δ1.18-1.59 (m, 19H), 1.81-2.10 (m, 3H), 2.20-2.40 (m, 4H), 3.66-3.72 (m, 1H), 4.03-4.06 (m, 1H), 4.32-4.46 (m, 3H), 5.31 (q, 1H), 5.99 (br d, 1H), 7.56-7.60 (m, 1H), 7.88-8.04 (m, 3H), 8.40 (br s, 1H), 11.29 (br s, 1H). MS (APCI–) m/z 667.1 (M+1).

Example 14-14

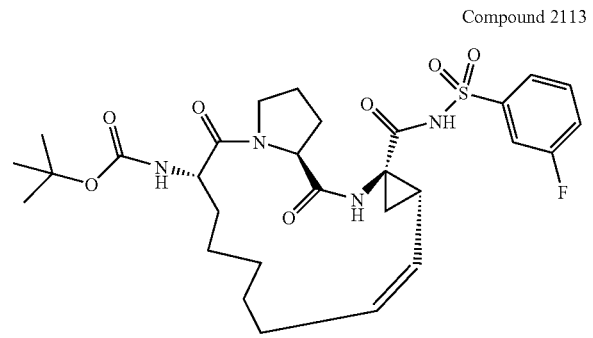

Compound 2113

(1S,4R,6S,14S)tert-Butyl 4-(3-fluorobenzene)-sulfonylaminocarbonyl-2,15-dioxo-3,16-diaza-tricyclo[14.3.0.0$^{4,6}$]nonadec-7-ene-14-yl carbamate was synthesized according to the same procedures as described in Example 1, substituting cyclopropanesulfonamide with 3-fluorobenzenesulfonamide in Step E. $^1$H NMR (d$^6$-Acetone, 400 MHz) δ1.20-1.59 (m, 19H), 1.81-2.10 (m, 3H), 2.22-2.36 (m, 4H), 3.66-3.72 (m, 1H), 4.03-4.05 (m, 1H), 4.32-4.48 (m, 3H), 5.25 (q, 1H), 5.98 (br d, 1H), 7.48-7.53 (m, 1H), 7.64-7.70 (m, 2H), 7.78-7.81 (m, 1H), 8.37 (br s, 1H), 11.22 (br s, 1H). MS (APCI–) m/z 605.2 (M–1).

Example 14-15

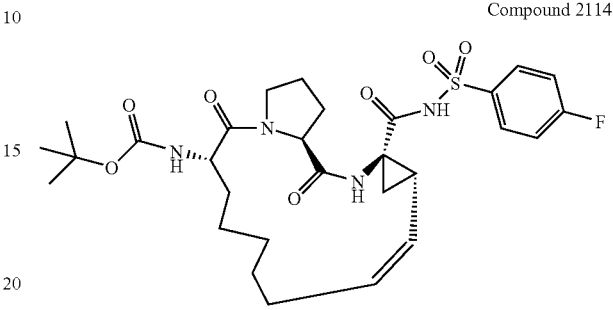

Compound 2114

(1S,4R,6S,14S)tert-Butyl 4-(4-fluorobenzene)-sulfonylaminocarbonyl-2,15-dioxo-3,16-diaza-tricyclo[14.3.0.0$^{4,6}$]nonadec-7-ene-14-yl carbamate was synthesized according to the same procedures as described in Example 1, substituting cyclopropanesulfonamide with 4-fluorobenzenesulfonamide in Step E. $^1$H NMR (d$^6$-Acetone, 400 MHz) δ1.20-1.57 (m, 19H), 1.81-2.10 (m, 3H), 2.21-2.37 (m, 4H), 3.66-3.72 (m, 1H), 4.03-4.05 (m, 1H), 4.32-4.47 (m, 3H), 5.23-5.30 (m, 1H), 6.00 (br d, 1H), 7.35-7.40 (m, 2H), 8.00-8.04 (m, 2H), 8.38 (br s, 1H). MS (APCI–) m/z 605.2 (M–1).

Example 14-16

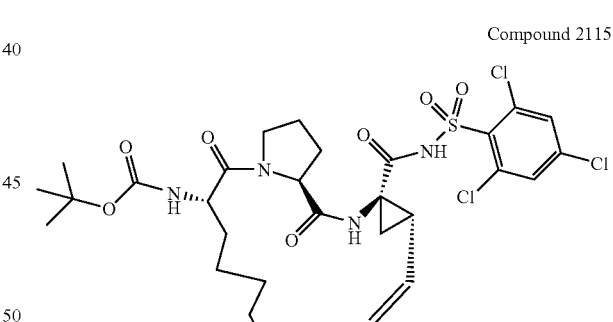

Compound 2115

(1S,4R,6S,14S)tert-Butyl 4-(2,4,6-trichlorobenzene)-sulfonylaminocarbonyl-2,15-dioxo-3,16-diaza-tricyclo[14.3.0.0$^{4,6}$]nonadec-7-ene-14-yl carbamate was synthesized according to the same procedures as described in Example 1, substituting cyclopropanesulfonamide with 2,4,6-trichlorobenzenesulfonamide in Step E. $^1$H NMR (d$^6$-Acetone, 400 MHz) δ1.18-1.62 (m, 19H), 1.84-2.10 (m, 3H), 2.22-2.42 (m, 4H), 3.66-3.72 (m, 1H), 4.03-4.06 (m, 1H), 4.34-4.38 (m, 2H), 4.57 (t, 1H), 5.53 (q, 1H), 5.99 (br d, 1H), 7.72 (s, 2H), 8.43 (br s, 1H), 11.42 (br s, 1H). MS (APCI–) m/z 691.0 (M+1).

Example 14-17

Compound 2116

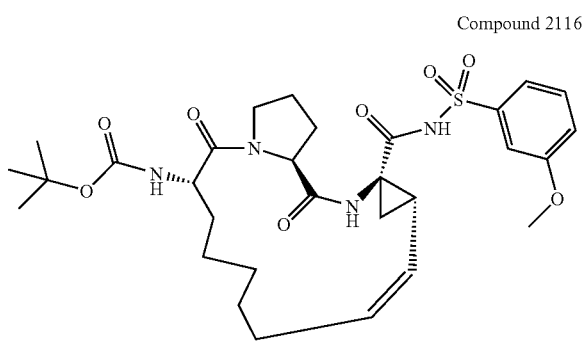

(1S,4R,6S,14S)tert-Butyl 4-(3-methoxybenzene)-sulfonylaminocarbonyl-2,15-dioxo-3,16-diaza-tricyclo[14.3.0.0$^{4,6}$]nonadec-7-ene-14-yl carbamate was synthesized according to the same procedures as described in Example 1, substituting cyclopropanesulfonamide with 3-methoxybenzenesulfonamide in Step E. $^1$H NMR (d$^6$-Acetone, 400 MHz) δ1.18-1.57 (m, 19H), 1.81-2.09 (m, 3H), 2.20-2.34 (m, 4H), 3.66-3.72 (m, 1H), 3.90 (s, 3H), 4.01-4.06 (m, 1H), 4.32-4.41 (m, 2H), 4.47 (t, 1H), 5.26 (q, 1H), 5.94 (br d, 1H), 7.23-7.26 (m, 1H), 7.46-7.53 (m, 3H), 8.38 (br s, 1H). MS (APCI−) m/z 617.3 (M+1).

Example 14-18

Compound 2117

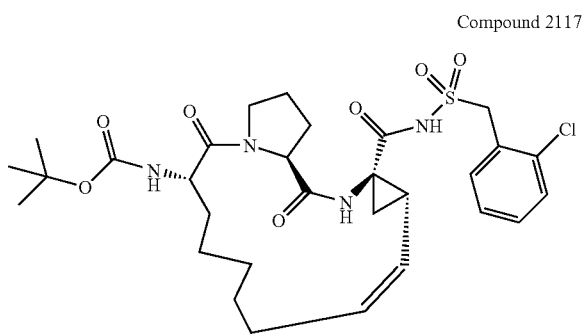

(1S,4R,6S,14S)tert-Butyl 4-((2-chlorophenyl)methane)-sulfonylaminocarbonyl-2,15-dioxo-3,16-diaza-tricyclo[14.3.0.0$^{4,6}$]nonadec-7-ene-14-yl carbamate was synthesized according to the same procedures as described in Example 1, substituting cyclopropanesulfonamide with (2-chlorophenyl)methanesulfonamide in Step E. $^1$H NMR (d$^6$-Acetone, 400 MHz) δ1.18-1.60 (m, 18H), 1.75-2.18 (m, 6H), 2.42-2.52 (m, 2H), 3.58-3.64 (m, 1H), 3.98-4.03 (m, 1H), 4.31-4.38 (m, 2H), 4.78 (d, 1H), 4.91 (d, 1H), 5.11 (t, 1H), 5.74 (q, 1H), 5.99 (br d, 1H), 7.35-7.53 (m, 4H), 8.36 (br s, 1H). MS (APCI−) m/z 635.2 (M−1).

Example 14-19

Compound 2118

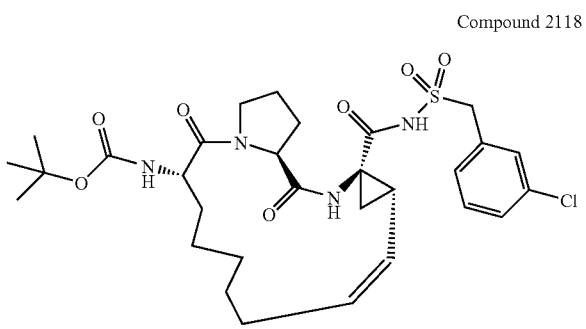

(1S,4R,6S,14S)tert-Butyl 4-((3-chlorophenyl)methane)-sulfonylaminocarbonyl-2,15-dioxo-3,16-diaza-tricyclo[14.3.0.0$^{4,6}$]nonadec-7-ene-14-yl carbamate was synthesized according to the same procedures as described in Example 1, substituting cyclopropanesulfonamide with (3-chlorophenyl)methanesulfonamide in Step E. $^1$H NMR (d$^6$-Acetone, 400 MHz) δ1.18-1.58 (m, 18H), 1.72-1.97 (m, 4H), 2.08-2.16 (m, 2H), 2.37-2.44 (m, 2H), 3.59-3.64 (m, 1H), 3.97 (m, 1H), 4.30-4.35 (m, 2H), 4.67 (s, 2H), 5.06 (t, 1H), 5.71 (q, 1H), 5.97 (br d, 1H), 7.34-7.45 (m, 4H), 8.29 (br s, 1H), 10.52 (br s, 1H). MS (APCI−) m/z 635.2 (M−1).

Example 14-20

Compound 2119

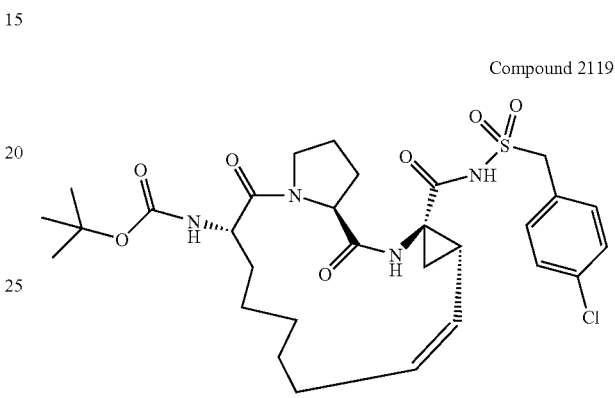

(1S,4R,6S,14S)tert-Butyl 4-((4-chlorophenyl)methane)-sulfonylaminocarbonyl-2,15-dioxo-3,16-diaza-tricyclo[14.3.0.0$^{4,6}$]nonadec-7-ene-14-yl carbamate was synthesized according to the same procedures as described in Example 1, substituting cyclopropanesulfonamide with (4-chlorophenyl)methanesulfonamide in Step E. $^1$H NMR (d$^6$-Acetone, 400 MHz) δ1.18-1.58 (m, 18H), 1.73-1.97 (m, 4H), 2.11-2.15 (m, 2H), 2.37-2.44 (m, 2H), 3.58-3.64 (m, 1H), 3.94-3.97 (m, 1H), 4.30-4.35 (m, 2H), 4.65 (s, 2H), 5.06 (t, 1H), 5.72 (q, 1H), 5.97 (br d, 1H), 7.38-7.43 (m, 4H), 8.28 (br s, 1H), 10.40 (br s, 1H). MS (APCI−) m/z 635.2 (M−1).

Example 14-21

Compound 2120

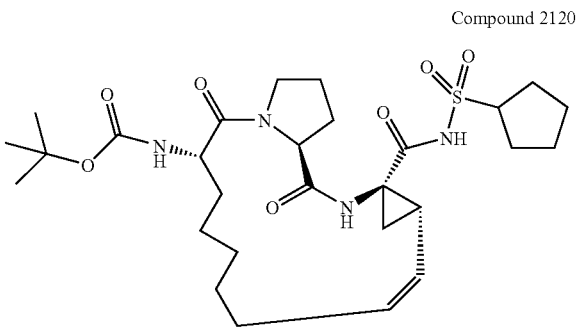

(1S,4R,6S,14S)tert-Butyl 4-cyclopentanesulfonylaminocarbonyl-2,15-dioxo-3,16-diaza-tricyclo[14.3.0.0$^{4,6}$]nonadec-7-ene-14-yl carbamate was synthesized according to the same procedures as described in Example 1, substituting cyclopropanesulfonamide with cyclopentanesulfonamide in Step E. $^1$H NMR (d$^6$-Acetone, 400 MHz) δ1.18-2.07 (m, 30H), 2.20-2.26 (m, 2H), 2.39-2.50 (m, 2H), 3.64-3.70

(m, 1H), 3.92-4.06 (m, 2H), 4.32-4.42 (m, 2H), 4.96 (t, 1H), 5.67 (q, 1H), 5.99 (br d, 1H), 8.37 (br s, 1H), 10.48 (br s, 1H). MS (APCI−) m/z 579.2 (M−1).

Example 14-22

Compound 2121

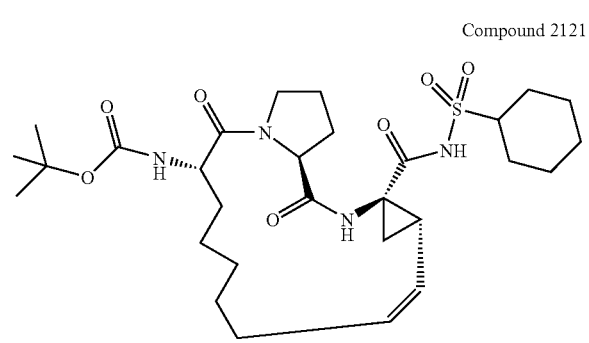

(1S,4R,6S,14S)tert-Butyl 4-cyclohexanesulfonylaminocarbonyl-2,15-dioxo-3,16-diaza-tricyclo[14.3.0.0$^{4,6}$]nonadec-7-ene-14-yl carbamate was synthesized according to the same procedures as described in Example 1, substituting cyclopropanesulfonamide with cyclohexanesulfonamide in Step E. $^1$H NMR (d$^6$-Acetone, 400 MHz) δ1.18-2.24 (m, 34H), 2.43-2.48 (m, 2H), 3.30-3.38 (m, 1H), 3.64-3.70 (m, 1H), 4.03-4.06 (m, 1H), 4.32-4.42 (m, 2H), 4.97 (t, 1H), 5.67 (q, 1H), 5.99 (br d, 1H), 8.38 (br s, 1H), 10.30 (br s, 1H). MS (APCI−) m/z 593.3 (M−1).

Example 14-23

Compound 2122

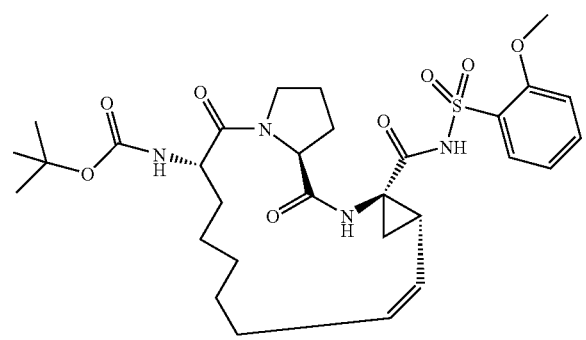

(1S,4R,6S,14S)tert-Butyl 4-(2-methoxybenzene)sulfonylaminocarbonyl-2,15-dioxo-3,16-diaza-tricyclo[14.3.0.0$^{4,6}$]nonadec-7-ene-14-yl carbamate was synthesized according to the same procedures as described in Example 1, substituting cyclopropanesulfonamide with 2-methoxybenzenesulfonamide in Step E. $^1$H NMR (d$^6$-Acetone, 400 MHz) δ1.18-1.60 (m, 19H), 1.81-2.14 (m, 3H), 2.20-2.30 (m, 4H), 3.68-3.74 (m, 1H), 3.95-3.97 (m, 1H), 3.97 (s, 3H), 4.38-4.46 (m, 2H), 4.58-4.62 (m, 1H), 5.41 (q, 1H), 5.93 (br d, 1H), 7.09 (t, 1H), 7.19 (d, 1H), 7.63 (t, 1H), 7.91 (dd, 1H), 8.30 (br s, 1H). MS (APCI−) m/z 617.2 (M−1).

Example 14-24

Compound 2123

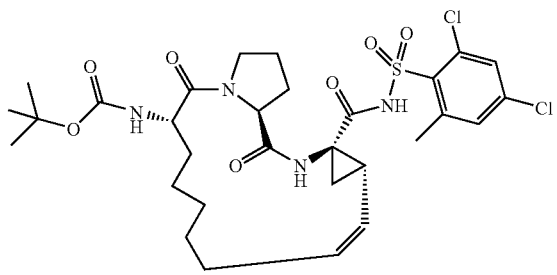

(1S,4R,6S,14S)tert-Butyl 4-(2,4-dichloro-6-methylbenzene)sulfonylaminocarbonyl-2,15-dioxo-3,16-diaza-tricyclo[14.3.0.0$^{4,6}$]nonadec-7-ene-14-yl carbamate was synthesized according to the same procedures as described in Example 1, substituting cyclopropanesulfonamide with 2,4-dichloro-6-methylbenzenesulfonamide in Step E. $^1$H NMR (d$^6$-Acetone, 400 MHz) δ1.18-1.59 (m, 19H), 1.81-2.09 (m, 3H), 2.22-2.40 (m, 4H), 2.77 (s, 3H), 3.66-3.72 (m, 1H), 4.01-4.06 (m, 1H), 4.34-4.43 (m, 2H), 4.53 (t, 1H), 5.50 (q, 1H), 5.99 (br d, 1H), 7.45 (s, 1H), 7.56 (s, 1H), 8.42 (br s, 1H), 11.33 (br s, 1H). MS (APCI−) m/z 669.1 (M−1).

Example 14-25

Compound 2124

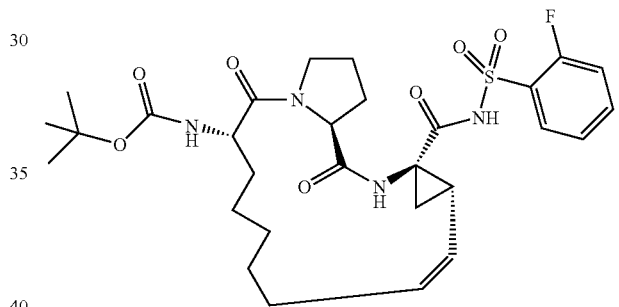

(1S,4R,6S,14S)tert-Butyl 4-(2-fluorobenzene)sulfonylaminocarbonyl-2,15-dioxo-3,16-diaza-tricyclo[14.3.0.0$^{4,6}$]nonadec-7-ene-14-yl carbamate was synthesized according to the same procedures as described in Example 1, substituting cyclopropanesulfonamide with 2-fluorobenzenesulfonamide in Step E. $^1$H NMR (d$^6$-Acetone, 400 MHz) δ1.18-1.59 (m, 19H), 1.83-2.11 (m, 3H), 2.21-2.42 (m, 4H), 3.67-3.73 (m, 1H), 4.01-4.06 (m, 1H), 4.34-4.48 (m, 3H), 5.44 (q, 1H), 5.97 (br d, 1H), 7.33-7.42 (m, 2H), 7.73-7.79 (m, 1H), 7.96-7.77 (m, 1H), 8.38 (br s, 1H), 11.30 (br s, 1H). MS (APCI−) m/z 605.2 (M−1).

Example 14-26

Compound 2125

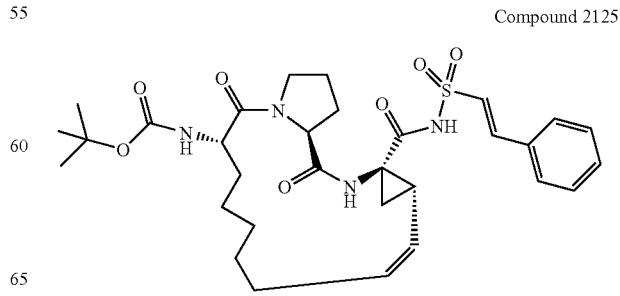

(1S,4R,6S,14S)tert-Butyl 4-((E)-2-phenylethene)sulfonylaminocarbonyl-2,15-dioxo-3,16-diaza-tricyclo[14.3.0.0$^{4,6}$]nonadec-7-ene-14-yl carbamate was synthesized according to the same procedures as described in Example 1, substituting cyclopropanesulfonamide with (E)-2-phenylethenesulfonamide in Step E. $^1$H NMR (d$^6$-Acetone, 400 MHz) δ1.18-1.54 (m, 18H), 1.65-1.68 (m, 1H), 1.81-2.09 (m, 3H), 2.18-2.26 (m, 2H), 2.34-2.46 (m, 2H), 3.65-3.71 (m, 1H), 4.01-4.06 (m, 1H), 4.32-4.42 (m, 2H), 4.85 (t, 1H), 5.44 (q, 1H), 5.98 (br d, 1H), 7.13 (d, 1H), 7.47-7.50 (m, 3H), 7.58 (d, 1H), 7.69-7.71 (m, 2H), 8.33 (br s, 1H), 10.87 (br s, 1H). MS (APCI−) m/z 613.2 (M−1).

Example 14-27

Compound 2126

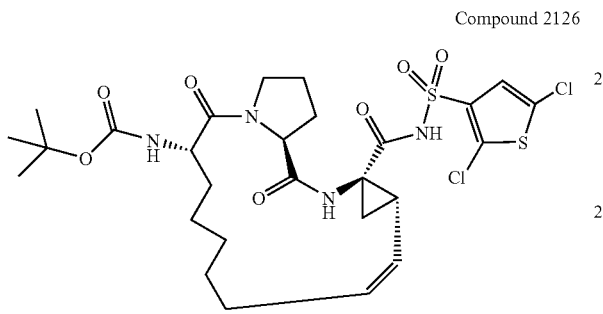

(1S,4R,6S,14S)tert-Butyl 4-(2,5-dichlorothiophene-3-sulfonyl)aminocarbonyl-2,15-dioxo-3,16-diaza-tricyclo[14.3.0.0$^{4,6}$]nonadec-7-ene-14-yl carbamate was synthesized according to the same procedures as described in Example 1, substituting cyclopropanesulfonamide with 2,5-dichlorothiophene-3-sulfonamide in Step E. $^1$H NMR (d$^6$-Acetone, 400 MHz) δ1.18-1.54 (m, 18H), 1.62-1.66 (m, 1H), 1.83-2.09 (m, 3H), 2.20-2.28 (m, 2H), 2.37-2.45 (m, 2H), 3.65-3.71 (m, 1H), 4.01-4.06 (m, 1H), 4.33-4.43 (m, 2H), 4.63 (t, 1H), 5.56 (q, 1H), 6.00 (br d, 1H), 7.28 (s, 1H), 8.44 (br s, 1H), 11.33 (br s, 1H). MS (APCI−) m/z 661.1 (M−1).

Example 14-28

Compound 2127

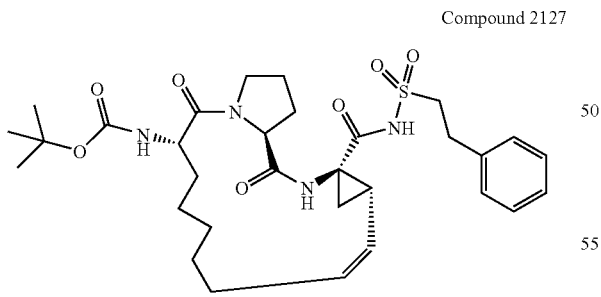

(1S,4R,6S,14S)tert-Butyl 4-(2-phenylethane)sulfonylaminocarbonyl-2,15-dioxo-3,16-diaza-tricyclo[14.3.0.0$^{4,6}$]nonadec-7-ene-14-yl carbamate was synthesized according to the same procedures as described in Example 1, substituting cyclopropanesulfonamide with 2-phenylethanesulfonamide in Step E. $^1$H NMR (d$^6$-Acetone, 400 MHz) δ1.18-1.60 (m, 18H), 1.74-1.78 (m, 1H), 1.83-2.11 (m, 3H), 2.20-2.26 (m, 2H), 2.44-2.50 (m, 2H), 2.98-3.07 (m, 2H), 3.46-3.54 (m, 1H), 3.65-3.74 (m, 2H), 4.01-4.06 (m, 1H), 4.32-4.44 (m, 2H), 5.08 (t, 1H), 5.63 (q, 1H), 6.01 (br d, 1H), 7.23-7.35 (m, 5H), 8.38 (br s, 1H), 10.60 (br s, 1H). MS (APCI−) m/z 615.2 (M−1).

Example 14-29

Compound 2128

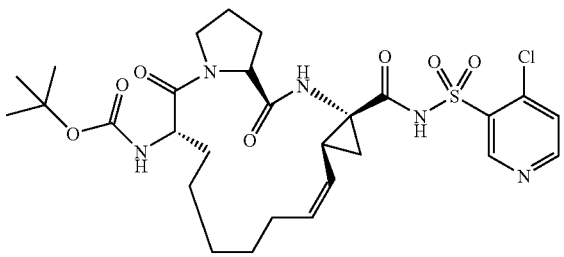

(1S,4R,6S,14S)tert-Butyl 4-(4-chloropyridine-3-sulfonyl)aminocarbonyl-2,15-dioxo-3,16-diaza-tricyclo[14.3.0.0$^{4,6}$]nonadec-7-ene-14-yl carbamate was synthesized according to the same procedures as described in Example 1, substituting cyclopropanesulfonamide with 4-chloropyridine-3-sulfonamide in Step E. MS (APCI−) m/z 623.2 (M−1).

Example 14-30

Compound 2129

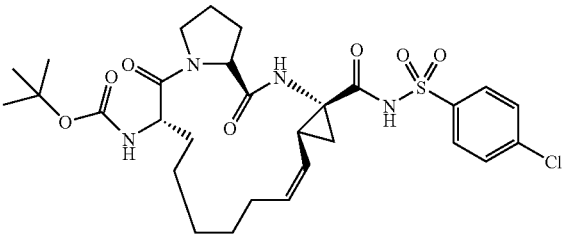

(1S,4R,6S,14S)tert-Butyl 4-(4-chlorobenzene)sulfonylaminocarbonyl-2,15-dioxo-3,16-diaza-tricyclo[14.3.0.0$^{4,6}$]nonadec-7-ene-14-yl carbamate was synthesized according to the same procedures as described in Example 1, substituting cyclopropanesulfonamide with 4-chlorobenzenesulfonamide in Step E. MS (APCI+) m/z 523.1 (MH$^+$-Boc).

Example 14-31

Compound 2130

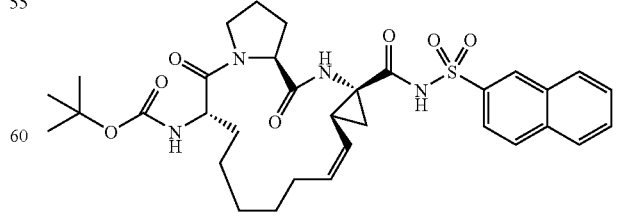

(1S,4R,6S,14S)tert-Butyl 4-(naphthalene-2-sulfonyl)aminocarbonyl-2,15-dioxo-3,16-diaza-tricyclo[14.3.0.0$^{4,6}$]nonadec-7-ene-14-yl carbamate was synthesized according to the same procedures as described in Example 1, substituting cyclopropanesulfonamide with naphthalene-2-sulfonamide in Step E. MS (APCI+) m/z 539.1 (MH⁺-Boc).

Example 14-32

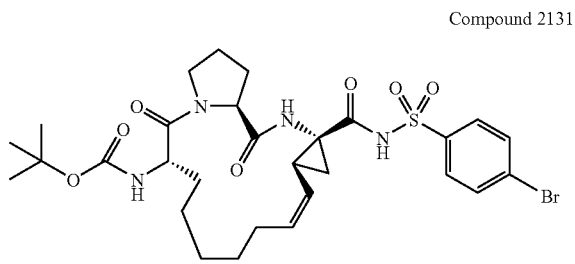

Compound 2131

(1S,4R,6S,14S)tert-Butyl 4-(4-bromobenzene)sulfonylaminocarbonyl-2,15-dioxo-3,16-diaza-tricyclo[14.3.0.0$^{4,6}$]nonadec-7-ene-14-yl carbamate was synthesized according to the same procedures as described in Example 1, substituting cyclopropanesulfonamide with 4-bromobenzenesulfonamide in Step E. MS (APCI+) m/z 567.0 (MH⁺-Boc).

Example 14-33

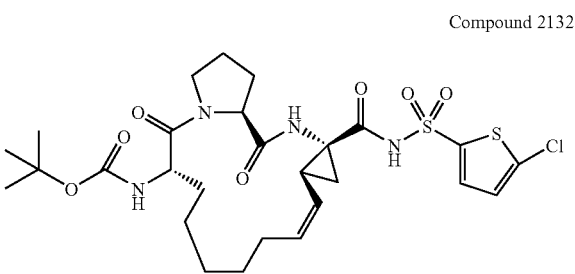

Compound 2132

(1S,4R,6S,14S)tert-Butyl 4-(5-chlorothiophene-2-sulfonyl)aminocarbonyl-2,15-dioxo-3,16-diaza-tricyclo[14.3.0.0$^{4,6}$]nonadec-7-ene-14-yl carbamate was synthesized according to the same procedures as described in Example 1, substituting cyclopropanesulfonamide with 5-chlorothiophene-2-sulfonamide in Step E. MS (APCI−) m/z 628.2 (M−1).

Example 14-34

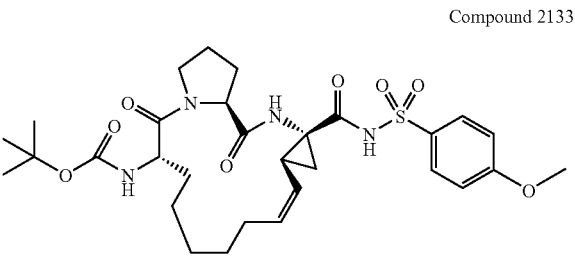

Compound 2133

(1S,4R,6S,14S)tert-Butyl 4-(4-methoxybenzene)sulfonylaminocarbonyl-2,15-dioxo-3,16-diaza-tricyclo[14.3.0.0$^{4,6}$]nonadec-7-ene-14-yl carbamate was synthesized according to the same procedures as described in Example 1, substituting cyclopropanesulfonamide with 4-methoxybenzenesulfonamide in Step E. MS (APCI−) m/z 617.2 (M−1).

Example 14-35

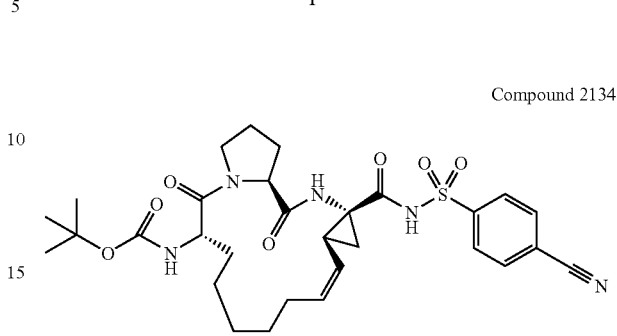

Compound 2134

(1S,4R,6S,14S)tert-Butyl 4-(4-cyanobenzene)sulfonylaminocarbonyl-2,15-dioxo-3,16-diaza-tricyclo[14.3.0.0$^{4,6}$]nonadec-7-ene-14-yl carbamate was synthesized according to the same procedures as described in Example 1, substituting cyclopropanesulfonamide with 4-cyanobenzenesulfonamide in Step E. MS (APCI−) m/z 612.2 (M−1).

Example 14-36

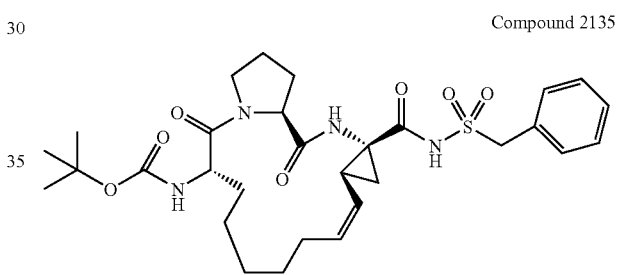

Compound 2135

(1S,4R,6S,14S)tert-Butyl 4-phenylmethanesulfonylaminocarbonyl-2,15-dioxo-3,16-diaza-tricyclo[14.3.0.0$^{4,6}$]nonadec-7-ene-14-yl carbamate was synthesized according to the same procedures as described in Example 1, substituting cyclopropanesulfonamide with phenylmethanesulfonamide in Step E. MS (APCI−) m/z 601.2 (M−1).

Example 14-37

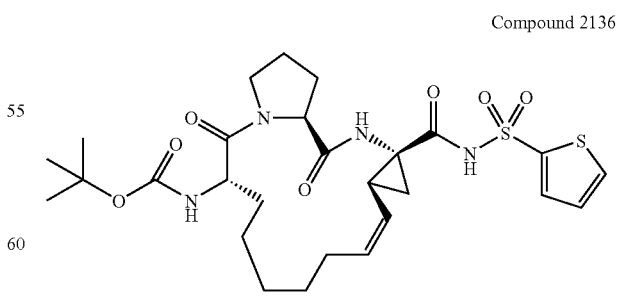

Compound 2136

(1S,4R,6S,14S)tert-Butyl 4-(thiophene-2-sulfonyl)aminocarbonyl-2,15-dioxo-3,16-diaza-tricyclo[14.3.0.0$^{4,6}$]nonadec-7-ene-14-yl carbamate was synthesized according to the same procedures as described in Example 1, substituting cyclopropanesulfonamide with thiophene-2-sulfonamide in Step E. $^1$H NMR (500 MHz, d$^6$-DMSO) δ 11.70 (br s, 1H), 8.76 (br s, 1H), 8.04 (br s, 1H), 7.73 (br s, 1H), 7.18 (br s, 1H), 7.00 (br s, 1H), 5.32 (q, 1H), 4.74 (t, 1H), 4.21 (t, 1H), 4.18-4.08 (m, 1H), 3.93-3.83 (m, 1H), 3.62-3.49 (m, 1H), 2.46-2.30 (m, 1H), 2.19-2.04 (m, 3H), 2.03-1.79 (m, 2H), 1.77-1.59 (m, 2H), 1.51-1.40 (m, 2H), 1.41-1.21 (m, 14H), 1.21-1.05 (m, 2H). MS (APCI+) m/z 495.1 (MH$^+$-Boc).

Example 14-38

Compound 2138

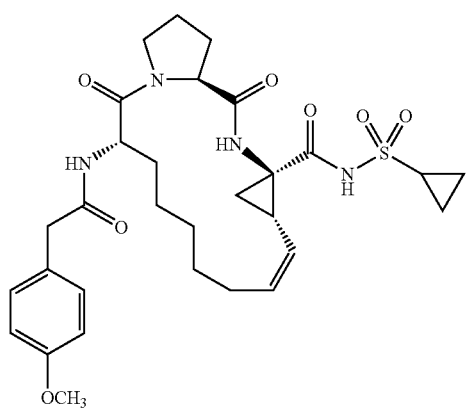

Compound 2138 (labeled in the scheme below as Compound 138) was synthesized according to Scheme 14-2 shown below:

Scheme 14-2

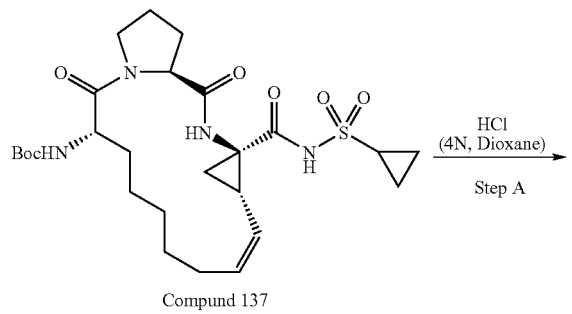

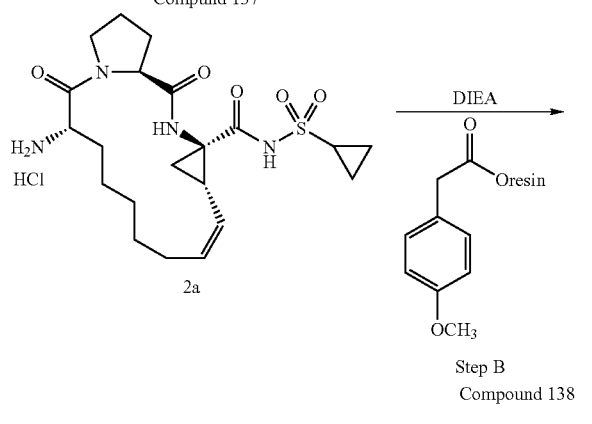

Step A: Synthesis of (1S,4R,6S,14S)Cyclopropanesulfonic acid ((Z)-14-amino-2,15-dioxo-3,16-diaza-tricyclo[14.3.0.0$^{4,6}$]nonadec-7-ene-4-carbonyl)-amide hydrochloride (2a)

Compound 137 (as labeled in the scheme depicted above) (0.25 g, 0.45 mmol) was dissolved in 4 M HCl in 1,4-dioxane (1.1 mL, 4.4 mmol). The resulted mixture was stirred for 90 min and concentrated to give 2a as light yellow solid (0.22 g, 100%).

Step B: Synthesis of (1S,4R,6S,14S)N—((Z)-4-Cyclopropanesulfonylaminocarbonyl-2,15-dioxo-3,16-diaza-tricyclo[14.3.0.0$^{4,6}$]nonadec-7-ene-14-yl)-2-(4-methoxy-phenyl)-acetamide (Compound 138)

The ammonium hydrogen chloride salt 2a (0.025 g, 0.051 mmol) was dissolved in dichloromethane and THF (1:1, 3 mL). The TFP ester resin 2b (0.077 mmol) and DIEA (0.031 mL, 0.18 mmol) were added. The resulted mixture was shaken for 16 h and filtered. The filtrate was concentrated. The residue was purified by silica gel chromatography (1% HCO$_2$H and 40% AcOEt in hexanes, 1% HCO$_2$H and 50% AcOEt in hexanes, 1% HCO$_2$H and 60% EtOAc in hexanes, 1% HCO$_2$H and 75% EtOAc in hexanes, and the 1% HCO$_2$H and 80% EtOAc in hexanes) to give the desired product as a white solid. MS (ESI+): 623 [M+23] (60), 501 [M+1] (80) and 408 (100).

Example 14-39

Compound 2139

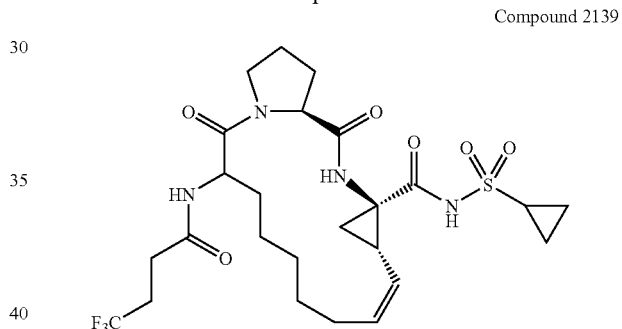

(1S,4R,6S,14S)N—((Z)-4-Cyclopropanesulfonylaminocarbonyl-2,15-dioxo-3,16-diaza-tricyclo[14.3.0.0$^{4,6}$]nonadec-7-ene-14-yl)-4,4,4-trifluoro-butyramide was synthesized according to the same procedures as described in Example 14-38, substituting 2-(4-methoxyphenyl)acetic acid TFP ester (2b, Scheme 14) with 4,4,4-trifluorobutanoic acid TFP ester in Step B instead. MS (ESI+) m/z 577 [M+1] (100).

Example 14-40

Compound 2140

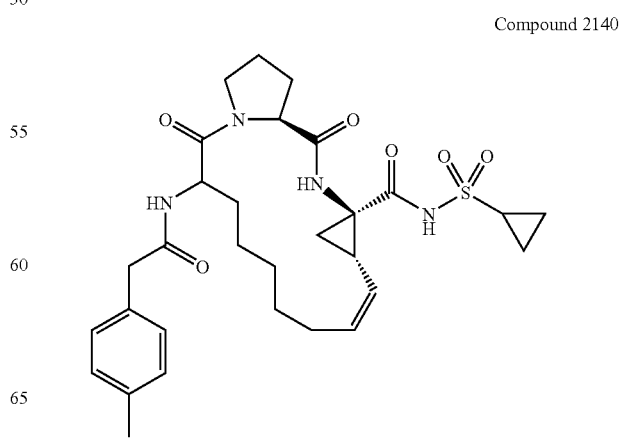

(1S,4R,6S,14S)N—((Z)-4-Cyclopropanesulfonylami-nocarbonyl-2,15-dioxo-3,16-diaza-tricyclo[14.3.0.0$^{4,6}$]nonadec-7-ene-14-yl)-2-p-tolyl-acetamide was synthesized according to the same procedures as described in Example 14-38, substituting 2-(4-methoxyphenyl)acetic acid TFP ester (2b, Scheme 14) with 2-p-tolylacetic acid TFP ester in Step B instead. MS (ESI+) m/z 585 [M+1] (100).

Example 14-41

Compound 2141

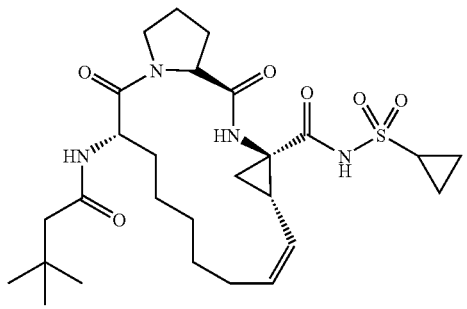

(1S,4R,6S,14S)N—((Z)-4-Cyclopropanesulfonylami-nocarbonyl-2,15-dioxo-3,16-diaza-tricyclo[14.3.0.0$^{4,6}$]nonadec-7-ene-14-yl)-3,3-dimethyl-butyramide was synthesized according to the same procedures as described in Example 14-38, substituting 2-(4-methoxyphenyl)acetic acid TFP ester (2b, Scheme 14) with 3,3-dimethylbutanoic acid TFP ester in Step B instead. MS (ESI+) m/z 573 [M+23] (100) and 551 [M+1] (40).

Example 14-42

Compound 2142

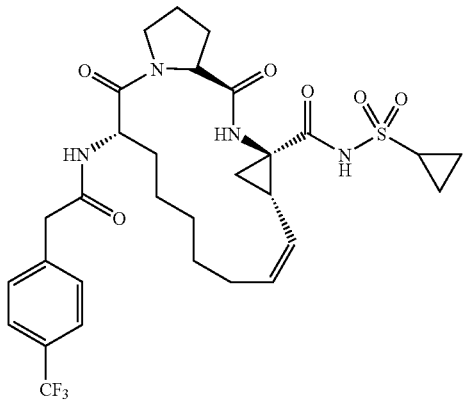

(1S,4R,6S,14S)N—((Z)-4-Cyclopropanesulfonylami-nocarbonyl-2,15-dioxo-3,16-diaza-tricyclo[14.3.0.0$^{4,6}$]nonadec-7-ene-14-yl)-2-(4-trifluoromethyl-phenyl)-aceta-mide was synthesized according to the same procedures as described in Example 14-38, substituting 2-(4-methoxyphe-nyl)acetic acid TFP ester (2b, Scheme 14) with 2-(4-(trifluo-romethyl)phenyl)acetic acid TFP ester in Step B instead. MS (ESI+) m/z 639 [M+1] (100).

Example 14-43

Compound 2143

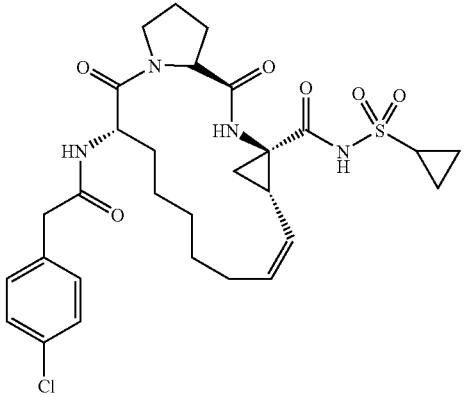

(1S,4R,6S,14S)N—((Z)-4-Cyclopropanesulfonylami-nocarbonyl-2,15-dioxo-3,16-diaza-tricyclo[14.3.0.0$^{4,6}$]nonadec-7-ene-14-yl)-2-(4-chloro-phenyl)-acetamide was synthesized according to the same procedures as described in Example 14-38, substituting 2-(4-methoxyphenyl)acetic acid TFP ester (2b, Scheme 14) with 2-(4-chlorophenyl)acetic acid TFP ester in Step B instead. MS (ESI+) m/z 605 [M] (100).

Example 14-44

Compound 2144

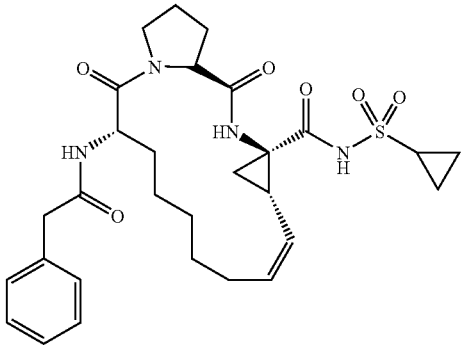

(1S,4R,6S,14S)N—((Z)-4-Cyclopropanesulfonylami-nocarbonyl-2,15-dioxo-3,16-diaza-tricyclo[14.3.0.0$^{4,6}$]nonadec-7-ene-14-yl)-2-phenyl-acetamide was synthesized according to the same procedures as described in Example 14-38, substituting 2-(4-methoxyphenyl)acetic acid TFP ester (2b, Scheme 14) with 2-phenylacetic acid TFP ester in Step B instead. MS (ESI+) m/z 593 [M+23] (40), 571 [M+1] (75) and 408 (100).

Example 14-45

Compound 2147

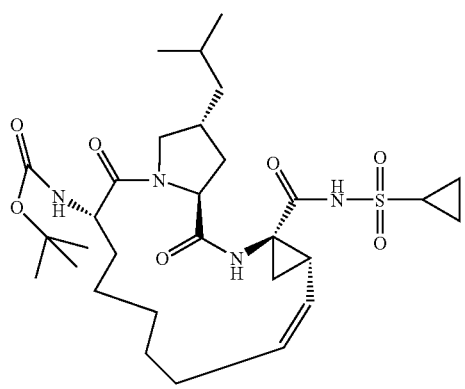

(1S,4R,6S,14S,18R)-tert-Butyl 4-cyclopropylsulfonylaminocarbonyl-2,15-dioxo-3,16-diaza-18-(2-methylpropyl)-tricyclo[14.3.0.0$^{4,6}$]nonadec-7-ene-14-yl carbamate was synthesized according to Scheme 14-3 shown below (Compound 2147 is labeled as Compound 147 in Scheme 14-3 below):

Scheme 14-3

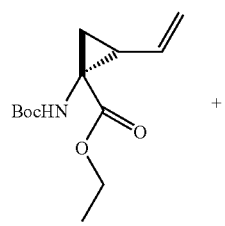

+

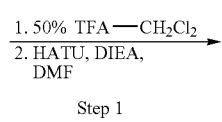

1. 50% TFA—CH$_2$Cl$_2$
2. HATU, DIEA, DMF

Step 1

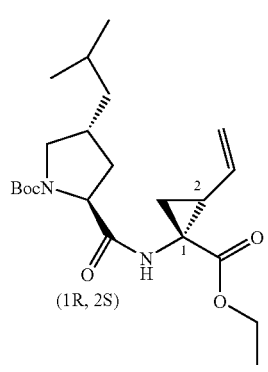

a 1. 50% TFA—CH$_2$Cl$_2$
2. HATU, DIEA, DMF

b

Step 2

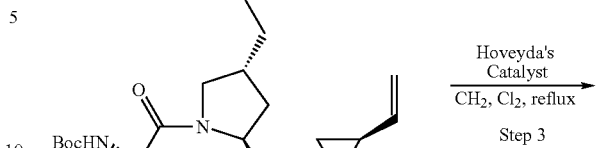

Hoveyda's Catalyst
CH$_2$Cl$_2$, reflux
Step 3 c

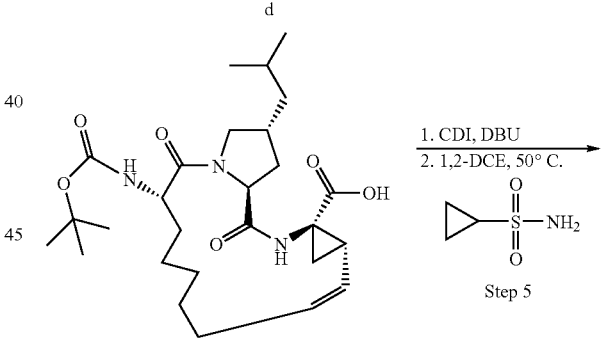

LiOH—H$_2$O
THF:MeOH:H$_2$O
(2:1:1)
Step 4 d

1. CDI, DBU
2. 1,2-DCE, 50° C.

cyclopropanesulfonamide

Step 5 e

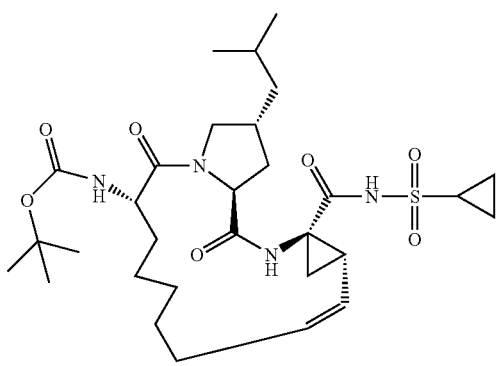

Compound 147

Step 1: The vinyl cyclopropyl Boc-amine (68 mg, 0.27 mmol) was deprotected with 50% TFA-CH$_2$Cl$_2$ at 0° C., concentrated to remove solvents and dried under vacuum. The acid a (60 mg, 0.22 mmol) in CH$_3$CN (2 ml) was cooled to 0° C., and added HATU (84 mg, 0.22 mmol), DIEA (110 mg, 0.88 mmol) followed by amine in CH$_3$CN (2 ml) and stirred for overnight at room temperature. Reaction mixture was concentrated to remove solvent, dissolved in EtOAc (5 ml), washed with water (10 ml). The separated organic layer dried (Na$_2$SO$_4$), concentrated and purified by column chromatography (20-50% EtOAc-Hexane) to give compound b as a light yellow liquid (40 mg, 45%). MS (APCI+): m/z 309.2 (M-Boc+1)

Step 2: The Boc-amine product b from Step 1 (40 mg, 0.098 mmol) was deprotected with 50% TFA-CH$_2$C$_2$ at 0° C. for 1 h. The amine concentrated and dried under vacuum. The acid (29 mg, 0.11 mmol) in CH$_3$CN (2 ml) was cooled to 0° C., and added HATU (41 mg, 0.11 mmol)), DIEA (51 mg, 0.39 mmol) followed by amine in CH$_3$CN (2 ml) and stirred for overnight at room temperature. Reaction mixture concentrated, dissolved in EtOAc (10 ml), washed with water (1×10 ml). The organic layer dried (Na$_2$SO$_4$), concentrated to give compound c as a light yellowish solid (43 mg, 78%). MS (APCI+): m/z 462.2 (M-Boc)

Step 3: To a solution of compound c (43 mg, 0.077 mmol) in CH$_2$Cl$_2$ (0.01 M) was degassed under N$_2$ for 2 h. It was added Hoveyda's 1$^{st}$ generation catalyst (3 mg) and heated to reflux for overnight. Reaction mixture concentrated, purified by column chromatography (5% MeOH—CH$_2$Cl$_2$) to give d as a brownish foam (31 mg, 76%). MS (APCI+): m/z 434.2 (M-Boc+1)

Step 4: To a solution of crude ester d (31 mg, 0.058 mmol) in THF:MeOH (2:1 ml) mixture was added LiOH.H$_2$O (in 1 ml of water) and stirred for 16 h. LC-MS showed completion of the hydrolysis. Reaction mixture concentrated to remove solvents, dissolved in EtOAc (5 ml) and neutralized with 0.1N HCl. The organic layer separated and the aq. layer was washed again with EtOAc (5 ml). The combined organic layers were dried (Na$_2$SO$_4$) and concentrated to give e as a brownish oil (30 mg, 85%).

Step 5: The crude acid e (30 mg, 0.059 mmol) in 1,2-dichloroethane (3 ml) was added CDI (29 mg, 0.18 mmol) and stirred for 2 h at 50° C. It was added cyclopropyl sulfonamide (29 mg, 0.24 mmol) followed by DBU (36 mg, 0.24 mmol) and stirring continued at the same temperature for 15 h. Reaction mixture was diluted with CH$_2$Cl$_2$ (10 ml), washed with water (20 ml). The organic layer dried (Na$_2$SO$_4$), concentrated and purified by preparative TLC (5% MeOH—CH$_2$Cl$_2$) to give 6.3 mg (17%) of the desired product Compound 2147. MS (APCI-): m/z 607.3 (M-1)

Example 14-46

Compound 2145

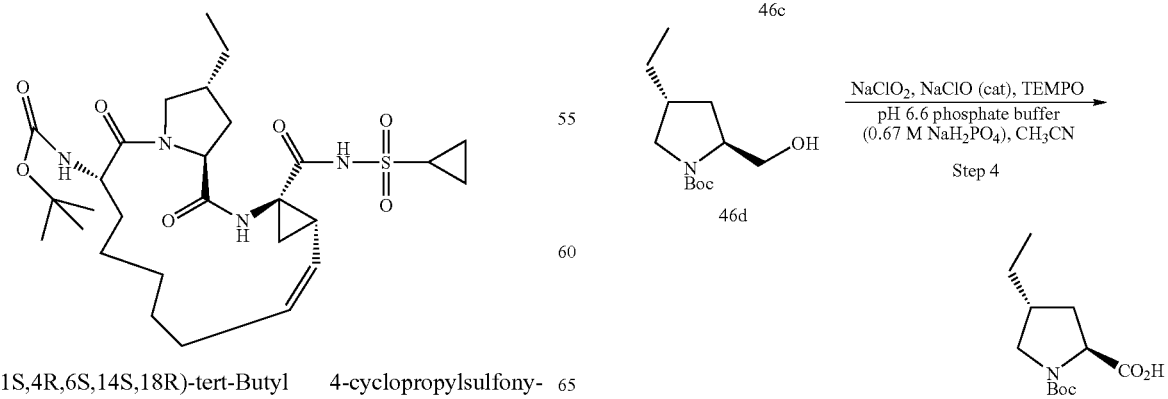

(1S,4R,6S,14S,18R)-tert-Butyl 4-cyclopropylsulfonylaminocarbonyl-2,15-dioxo-3,16-diaza-18-ethyl-tricyclo[14.3.0.0$^{4,6}$]nonadec-7-ene-14-yl carbamate was synthesized according to the same fashion as described in the synthesis of Compound 2148 above, substituting (2S,4R)-1-(tert-butoxycarbonyl)-4-isobutylpyrrolidine-2-carboxylic acid (a) with (2S,4R)-1-(tert-butoxycarbonyl)-4-ethylpyrrolidine-2-carboxylic acid in Step 1 coupling instead. MS (APCI+): m/z 481.2 (M-Boc+1)

Example 14-46a

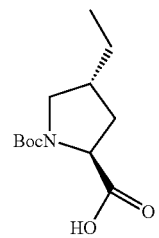

(2S,4R)-1-(tert-butoxycarbonyl)-4-ethylpyrrolidine-2-carboxylic acid was synthesized according to the following Scheme 14-4:

Scheme 14-4

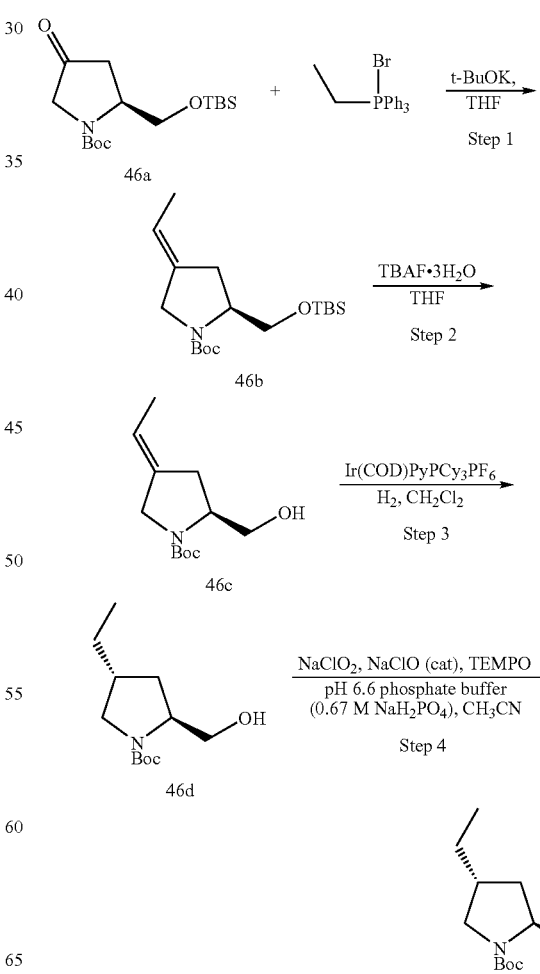

Step 1: Ethylltriphenyl phosphonium bromide (8.17 g, 22 mmol) in THF (25 ml) was added 1 M solution of potassium t-butoxide in THF (22 ml) at room temperature. After 1 h stirring, it was added a solution of the ketone 46a (2.9 g, 8.8 mmol), which was prepared according to a literature procedure from (2S,4R)-1-(tert-butoxycarbonyl)-4-hydroxypyrrolidine-2-carboxylic acid (*J. Org. Chem.* 2003, 68, 3923-3931), in THF (5 ml) and stirred for 3 h. TLC (15% EtOAc-Hexane) showed complete conversion. The reaction mixture quenched with ice-cold water (75 ml) and extracted with diethylether (2×50 ml). The combined organic layers were dried (Na$_2$SO$_4$), concentrated and purified by column chromatography (10%, 20% EtOAc/Hexane) to give 46b as a light yellowish liquid, 2.85 g (95%). MS (APCI+): m/z 130.1 (M-Boc+1).

Step 2: To a solution of the silyl ether 46b (3 g, 8.78 mmol) in THF (60 ml) was added solid TBAF.3H$_2$O (5.54 g, 17.57 mmol) and stirred for 16 h. Reaction mixture concentrated and purified by column chromatography (25, 40% EtOAc-Hexane) to give 46c, 1.98 g (98%). MS (APCI+): m/z 128.1 (M-Boc+1).

Step 3: The alcohol 46c (1.98 g, 8.71 mmol) in CH$_2$Cl$_2$ (174 ml, 0.2 M) was treated with Ir(COD)PyPCy$_3$PF$_6$ (Crabtree catalyst) (0.21 g, 0.26 mmol) for 24 h under H$_2$. Reaction mixture concentrated to remove solvent and purified by column chromatography (40% EtOAc-Hexane) to give 46d as an orange oil, 1.94 g (97%). $^1$H NMR (400 MHz, CDCl$_3$): 4.40 (br s, 1H), 4.05 (m, 1H), 3.65-3.56 (m, 2H), 3.55-3.48 (dd, 1H), 3.02-2.90 (t, 1H), 2.30-2.04 (m, 1H), 1.72-1.60 (m, 2H), 1.46 (s, 9H), 1.80-1.60 (m, 2H), 0.96 (t, 3H). MS (APCI+): m/z 130.1 (M−Boc+1).

Step 4: Two oxidant solutions were prepared prior to carrying out the reaction. The first one consisted of NaClO$_2$ (0.99 g, 8.72 mmol) in 4 ml of water (~2M). The second one comprised of 0.26 ml of bleach (NaOCl) diluted with 4 ml of water. The alcohol 46d (1 g, 4.36 mmol) was dissolved in 3:2 (30 ml: 20 ml) mixture of CH$_3$CN:NaH$_2$PO$_4$ buffer (pH 6.6, 0.67 M) and warmed to 45° C. The reaction mixture was treated with TEMPO (0.07 g, 0.44 mmol) followed by the drop wise, simultaneous addition (over 1 h) of the 2-oxidant solutions. After stirring for 15 h at 45° C., the reaction mixture was cooled to room temperature and a sat. Na$_2$SO$_3$ solution was added drop wise until the reaction mixture became colorless. Reaction mixture was concentrated to remove CH$_3$CN in vacuo and the resulting mixture basified to pH>10 with 1 M NaOH and washed twice with diethyl ether. The solution was carefully acidified with 1 M HCl at 0° C. to pH<3 and extracted with EtOAc (2×20 ml). The combined organic layers were dried (Na$_2$SO$_4$) and concentrated to give the final desired product, 1 g (99%). MS (APCI−): m/z 242.1 (M−1).

Example 14-46b

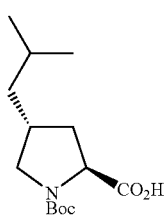

(2S,4R)-1-(tert-butoxycarbonyl)-4-isobutylpyrrolidine-2-carboxylic acid was prepared by the same fashion as described in Example 14-46a above, substituting ethylltriphenyl phosphonium bromide in Step 1 with isobutylltriphenyl phosphonium bromide instead. MS (APCI+): 172.1 (M-Boc+1)

Example 14-47

Compound 2146

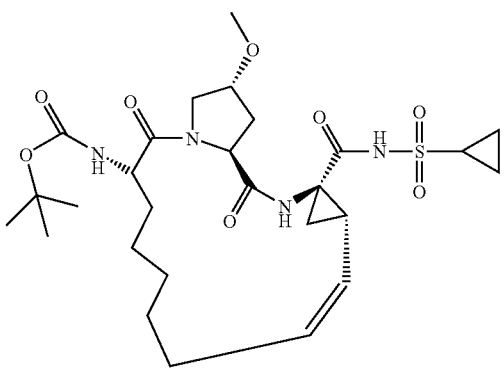

(1S,4R,6S,14S,18R)-tert-Butyl 4-cyclopropylsulfonylaminocarbonyl-2,15-dioxo-3,16-diaza-18-methoxy-tricyclo[14.3.0.0$^{4,6}$]nonadec-7-ene-14-yl carbamate (labeled as Compound 146 in scheme 14-5 below) was synthesized according to the following Scheme 14-5:

Scheme 14-5

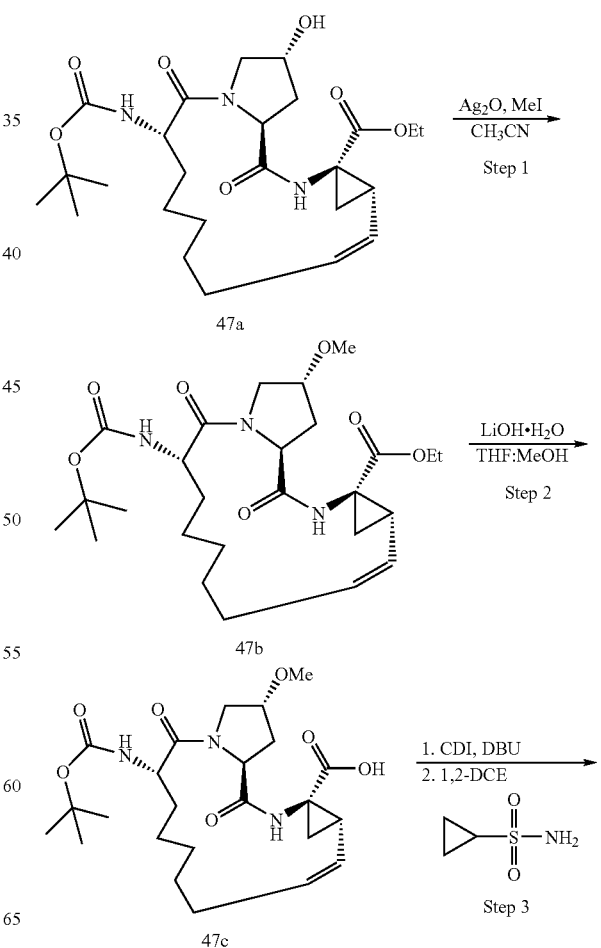

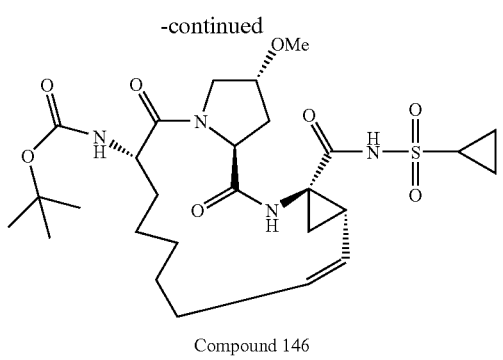

Compound 146

Step 1: To a solution of the hydroxymacrocycle 47a (200 mg, 0.405 mmol) in acetonitrile (4 ml) was added Ag$_2$O (94 mg, 0.405 mmol) followed by MeI (0.3 ml). After overnight stirring, reaction mixture concentrated and purified by column chromatography (4% MeOH—CH$_2$Cl$_2$) to give 47b as a white solid, 150 mg. MS (APCI+): m/z 408.2 (M-Boc+1)

Step 2: The crude ester 47b (150 mg, 0.295 mmol) in THF:MeOH (2:1 ml) mixture was added LiOH.H$_2$O (62 mg dissolved in 1 ml of H$_2$O) and stirred for 16 h. Reaction mixture concentrated to remove solvents, diluted with EtOAc (5 ml) and neutralized with 0.1 N HCl. The organic layer separated and the aq. layer was washed again with EtOAc (5 ml). The combined organic layers were dried (Na$_2$SO$_4$) and concentrated to give 47c (112 mg). MS (APCI+): m/z 380.1 (M-Boc)

Step 3: The crude acid 47c (112 mg, 0.234 mmol) in 1,2-dichloroethane (3 ml) was added CDI (114 mg, 0.701 mmol) and stirred at 50° C. After 3 h, it was added cyclopropyl sulfonamide (170 mg, 1.40 mmol) followed by DBU (213 mg, 1.40 mmol) and stirring continued at the same temperature for 15 h (overnight). Reaction mixture diluted with CH$_2$Cl$_2$ (10 ml), washed with water (50 ml). The organic layer dried (Na$_2$SO$_4$), concentrated and purified by column chromatography (40% EtOAc-Hexane+1% HCO$_2$H) to give the desired final product Compound 2147 (110 mg, 47% overall yield for the above 3 steps). MS (APCI+): m/z 483.2 (M-Boc+1).

Example 14-48

Compound 2148

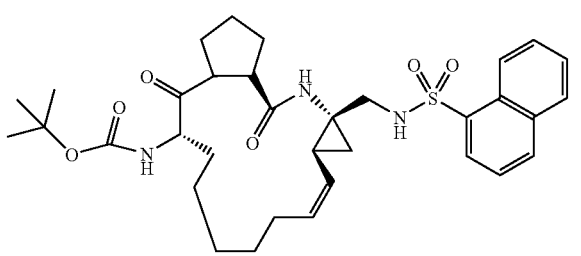

(1S,4R,6S,14S)tert-Butyl 4-(naphthalene-1-sulfonyl)aminocarbonyl-2,15-dioxo-3,16-diaza-tricyclo[14.3.0.0$^{4,6}$]nonadec-7-ene-14-yl carbamate was synthesized according to the same procedures as described in Example 1, substituting cyclopropanesulfonamide with naphthalene-1-sulfonamide in Step E. $^1$H NMR (500 MHz, d$^6$-DMSO) δ 11.88 (br s, 1H), 8.82 (br s, 1H), 8.46 (d, 1H), 8.29 (q, 2H), 8.13 (d, 1H), 7.75-7.63 (m, 3H), 6.96 (d, 1H), 5.08 (q, 1H), 4.48 (t, 1H), 4.26-4.12 (m, 2H), 3.94-3.85 (m, 1H), 3.65-3.53 (m, 1H), 2.35-1.78 (m, 7H), 1.76-1.54 (m, 2H), 1.49-1.05 (m, 17H). MS (APCI−) m/z 637.3 (M−1).

Example 14-49

Compound 2149

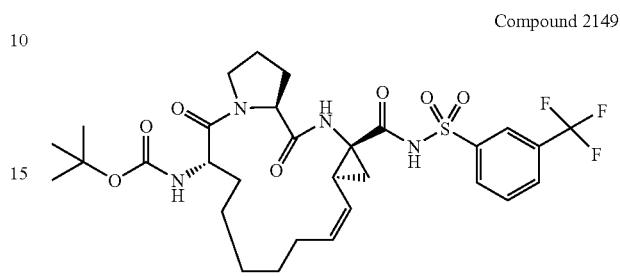

(1S,4R,6S,14S)tert-Butyl 4-(3-(trifluoromethyl)benzene)sulfonylaminocarbonyl-2,15-dioxo-3,16-diaza-tricyclo[14.3.0.0$^{4,6}$]nonadec-7-ene-14-yl carbamate was synthesized according to the same procedures as described in Example 1, substituting cyclopropanesulfonamide with 3-(trifluoromethyl)benzenesulfonamide in Step E. MS (APCI−) m/z 655.2 (M−1).

Example 14-50

Compound 2150

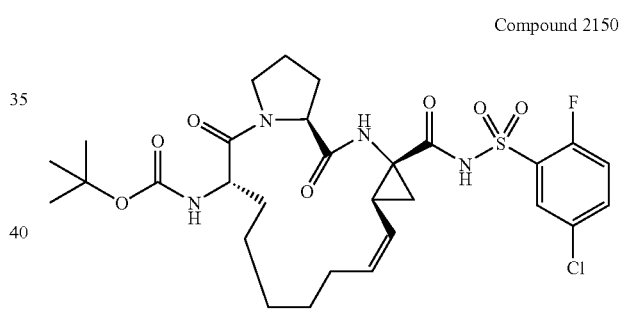

(1S,4R,6S,14S)tert-Butyl 4-(5-chloro-2-fluorobenzene)sulfonylaminocarbonyl-2,15-dioxo-3,16-diaza-tricyclo[14.3.0.0$^{4,6}$]nonadec-7-ene-14-yl carbamate was synthesized according to the same procedures as described in Example 1, substituting cyclopropanesulfonamide with 5-chloro-2-fluorobenzenesulfonamide in Step E. MS (APCI−) m/z 640.2 (M−1).

Example 14-51

Compound 2151

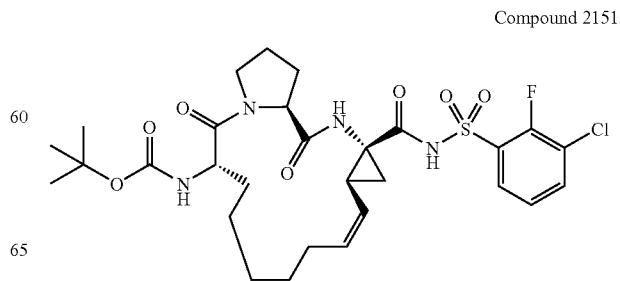

(1S,4R,6S,14S)tert-Butyl 4-(3-chloro-2-fluorobenzene)sulfonylaminocarbonyl-2,15-dioxo-3,16-diaza-tricyclo[14.3.0.0$^{4,6}$]nonadec-7-ene-14-yl carbamate was synthesized according to the same procedures as described in Example 1, substituting cyclopropanesulfonamide with 3-chloro-2-fluorobenzenesulfonamide in Step E. MS (APCI−) m/z 640.2 (M−1).

Example 14-52

Compound 2152

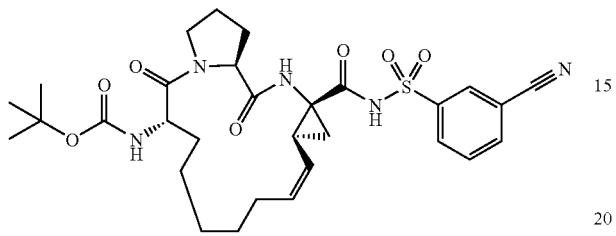

(1S,4R,6S,14S)tert-Butyl 4-(3-cyanobenzene)sulfonylaminocarbonyl-2,15-dioxo-3,16-diaza-tricyclo[14.3.0.0$^{4,6}$]nonadec-7-ene-14-yl carbamate was synthesized according to the same procedures as described in Example 1, substituting cyclopropanesulfonamide with 3-cyanobenzenesulfonamide in Step E. MS (APCI−) m/z 612.2 (M−1).

Example 14-53

Compond 2153

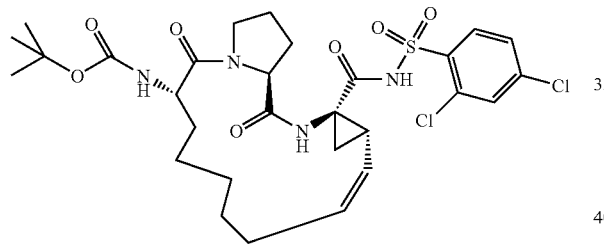

(1S,4R,6S,14S)tert-Butyl 4-(2,4-dichlorobenzene)sulfonylaminocarbonyl-2,15-dioxo-3,16-diaza-tricyclo[14.3.0.0$^{4,6}$]nonadec-7-ene-14-yl carbamate was synthesized according to the same procedures as described in Example 1, substituting cyclopropanesulfonamide with 2,4-dichlorobenzenesulfonamide in Step E. $^1$H NMR (d$^6$-Acetone, 400 MHz) δ1.18-1.57 (m, 18H), 1.80-2.11 (m, 4H), 2.21-2.29 (m, 2H), 2.35-2.46 (m, 2H), 3.66-3.72 (m, 1H), 4.01-4.06 (m, 1H), 4.34-4.43 (m, 2H), 4.54 (t, 1H), 5.52 (q, 1H), 5.98 (br d, 1H), 7.63 (dd, 1H), 7.74 (d, 1H), 8.15 (d, 1H), 8.43 (br s, 1H), 11.36 (br s, 1H). MS (APCI−) m/z 655.2 (M−1).

Example 14-54

Compound 2154

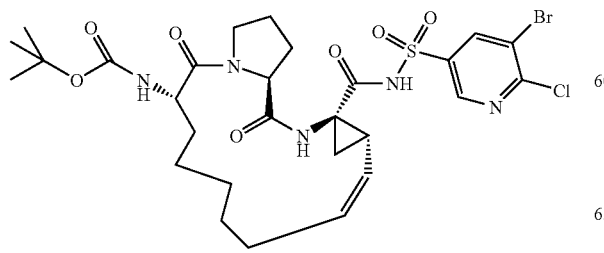

(1S,4R,6S,14S)tert-Butyl 4-(5-bromo-6-chloropyridine-3-sulfonyl)aminocarbonyl-2,15-dioxo-3,16-diaza-tricyclo[14.3.0.0$^{4,6}$]nonadec-7-ene-14-yl carbamate was synthesized according to the same procedures as described in Example 1, substituting cyclopropanesulfonamide with 5-bromo-6-chloropyridine-3-sulfonamide in Step E. $^1$H NMR (d$^6$-Acetone, 400 MHz) δ1.18-1.53 (m, 17H), 1.61-1.64 (m, 1H), 1.79-1.86 (m, 2H), 1.92-2.12 (m, 2H), 2.21-2.42 (m, 4H), 3.67-3.73 (m, 1H), 4.03-4.08 (m, 1H), 4.31-4.52 (m, 3H), 5.25 (q, 1H), 6.00 (br d, 1H), 8.39 (br s, 1H), 8.50 (d, 1H), 8.84 (d, 1H), 11.56 (br s, 1H). MS (APCI−) m/z 702.1 (M+1).

Preparation of NS3 Inhibitors

Section XIII

The compounds in this section can be synthesized with a similar fashion as described in Scheme 1, Section XII of the inhibitor synthesis, substituting the sulfonamide in the last coupling step with a sulfamide.

The sulfamides used were either purchased from commercial sources or prepared through routes A or B described in the following scheme. Similar methods to that of Route A have been described in literature (e.g. *Heteroatom Chemistry*, 2001, 12 (1), 1-5). The sulfamoylating reagent a in Route B was prepared according to a literature procedure (Winum, J-Y et al, *Organic Letters*, 2001, 3, 2241-2243).

Scheme 15-1

Route A:

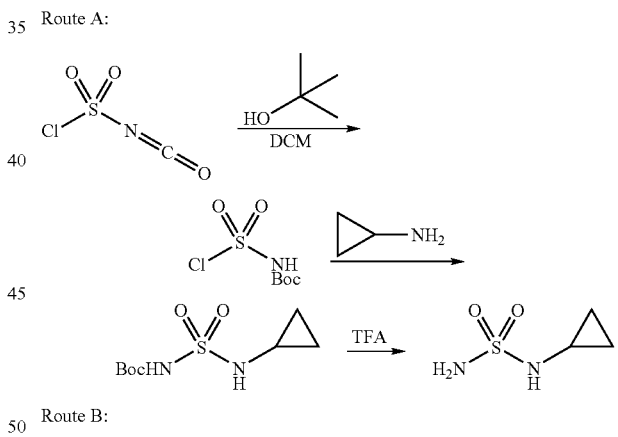

Route B:

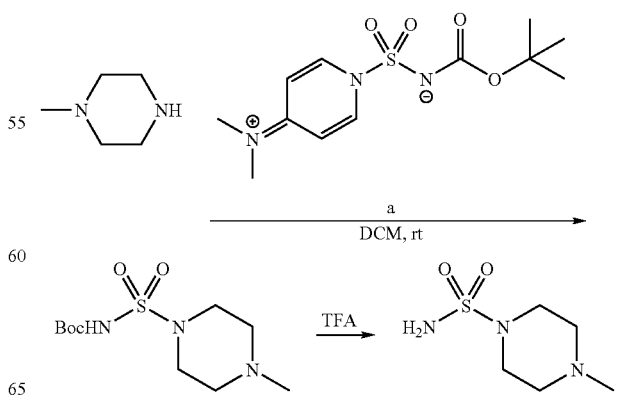

Synthesis of N-Cyclopropylsulfamide

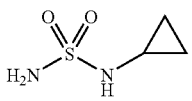

To a stirred solution of chlorosulfonyl isocyanate (1 mL, 11.5 mmol) in 20 mL DriSolve DCM was added anhydrous t-butanol (1.1 mL, 1 equiv) at 0° C. After stirring for 90 min, the resulting carbamatesulfamoyl chloride solution and 5 mL TEA in 20 mL DCM were added dropwise to a solution of cyclopropyl amine (0.66 g, 1 equiv) in 25 mL DCM and 3 mL TEA. The reaction temperature was kept under 5° C. during addition. The ice bath was removed after addition and the resulting mixture was stirred at rt for 3 h.

TLC (Hex/EA 1:1) showed one major spot with higher $R_f$. LCMS showed that product had formed. The reaction mixture was then diluted with 100 mL DCM and washed with 0.1 N HCl (2×200 mL) and brine (150 mL). The organic layer was dried over $Na_2SO_4$ and concentrated, giving the Boc-protected sulfamide as a light yellowish solid, 1.2 g. $^1$H-NMR showed it to be the desired product plus small amount of impurities. The crude product was recrystallized from EA/Hex (rt to 0° C.), giving 0.64 g offwhite crystalline pure product. $^1$H NMR (CDCl$_3$, 400 MHz) δ0.71-0.77 (m, 4H), 1.51 (s, 9H), 2.44 (m, 1H), 5.58 (br s, 1H), 7.42 (br s, 1H). MS m/z 234.7 (APCI−, M−1).

To remove the Boc protective group, the product from above was dissolved in 10 mL 1:1 (v/v) mix of DCM:TFA and let stay at rt for 1 h. It was then concentrated down on rotovap and then on high vacuum. The thick oil solidified on high vac, giving the titled product as an offwhite solid. $^1$H NMR (CDCl$_3$, 400 MHz) δ0.66-0.74 (m, 4H), 2.57-2.58 (m, 1H), 5.29 (br s, 2H), 5.42 (br s, 1H).

Synthesis of Pyrrolidinolsulfamide

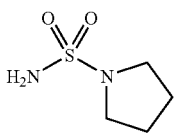

The titled compound was prepared according to the same procedures described for the synthesis of N-cyclopropylsulfamide above, substituting cyclopropyl amine with pyrrolidine. For the Boc-protected titled product: $^1$H NMR (CDCl$_3$, 400 MHz) δ1.49 (s, 9H), 1.92-1.95 (m, 4H), 3.48-3.52 (m, 4H), 7.02 (br s, 1H). MS m/z 249 (APCI−, M−1).

Synthesis of Morpholinolsulfamide

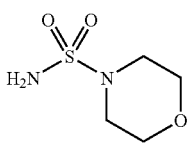

The titled compound was prepared according to the same procedures described for the synthesis of N-cyclopropylsulfamide above, substituting cyclopropyl amine with morpholine. For the Boc-protected titled product: $^1$H NMR (CDCl$_3$, 400 MHz) δ1.50 (s, 9H), 3.39 (t, 4H), 3.76 (t, 4H), 7.18 (br s, 1H). MS m/z 265 (APCI−, M−1)

Synthesis of Thiazol-2-ylaminosulfamide

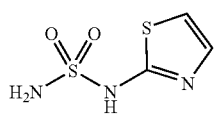

The titled compound was prepared according to the same procedures described for the synthesis of N-cyclopropylsulfamide above, substituting cyclopropyl amine with 2-amino thiazol. However, the Boc-protected intermediate was never isolated due to loss of the protection group during reaction work-up and the following recrystallization steps. The titled product was isolated after silica gel column chromatography (Biotage 40 M, eluent=5-10% MeOH in DCM). $^1$H NMR (d$^6$-DMSO, 400 MHz) δ6.52 (br s, 2H), 6.75 (d, 1H), 7.19 (d, 1H), 12.1 (br s, 1H). MS m/z 180 (ESI+, MH$^+$).

Synthesis of 4-Methyl-Piperizinosulfamide

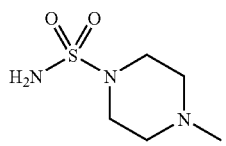

The titled compound was prepared according to Route B in Scheme 15-1. 4-Methyl-piperizine (0.15 g, 1.50 mmol) was dissolved in 3 mL DriSolve DCM in a 10 mL RBF, followed by addition of the sulfamoylating reagent a (0.45 g, 1.50 mmol). After ca. 5 min stirring the latter reagent gradually dissolved to give a clear and almost colorless solution. It was stirred at rt for overnight. After 17 h, TLC showed reaction complete (DCM:MeOH 9:1 with 1% TEA). The reaction was concentrated down and the resulting pinkish crude solid was flashed on Biotage 40 S silica gel column (eluent=DCM:MeOH 10:1 with 1% TEA), giving the Boc-protected titled product as a white powder in basically quantitative yield. $^1$H NMR (CDCl$_3$, 400 MHz) δ1.48 (s, 9H), 2.33 (s, 3H), 2.52 (t, 4H), 3.43 (t, 4H). MS m/z 278 (APCI−, M−1).

The Boc protective group was then removed by the same fashion as described in the synthesis of N-cyclopropylsulfamide, and the resulting titled product was used directly for the next coupling steps without further purification.

In addition, the following sulfamide intermediates have also been prepared according to the same procedures described for the synthesis of N-cyclopropylsulfamide above, substituting cyclopropylamine with the corresponding other amines:

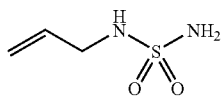

¹H NMR (500 MHz, d⁶-DMSO) δ 6.68 (t, 1H), 6.52 (br s, 2H), 5.90-5.78 (m, 1H), 5.21 (d, 1H), 5.07 (d, 1H), 3.51 t, 2H). MS (APCI−) m/z 134.9 (M−1).

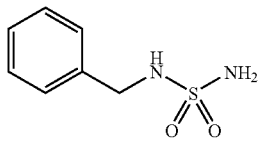

MS (APCI−) m/z 184.9 (M−1).

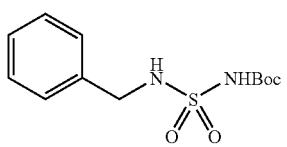

¹H NMR (500 MHz, d⁶-DMSO) δ 10.84 (s, 1H), 8.15 (t, 1H), 7.36-7.22 (m, 5H), 4.12 (d, 2H), 1.39 (s, 9H). MS (APCI−) m/z 284.9 (M−1).

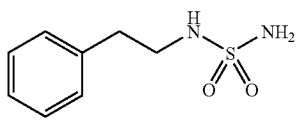

MS (APCI−) m/z 198.9 (M−1).

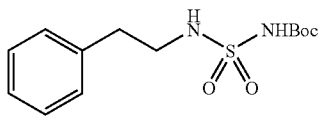

¹H NMR (500 MHz, d⁶-DMSO) δ 10.85 (s, 1H), 7.64 (br s, 1H), 7.26 (dt, 5H), 3.09 (q, 2H), 2.76 (t, 2H), 1.42 (s, 9H); MS (APCI−) m/z 298.9 (M−1).

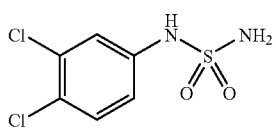

MS (APCI−) m/z 238.9 (M−1).

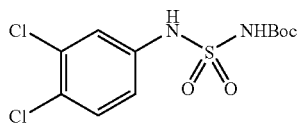

¹H NMR (500 MHz, d⁶-DMSO) δ 11.52 (s, 1H), 10.73 (br s, 1H), 7.60 (d, 1H), 7.36 (s, 1H), 7.13 (dd, 1H), 1.34 (s, 9H); MS (APCI−) m/z 338.9 (M−1).

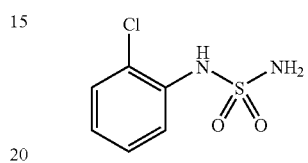

MS (APCI−) m/z 204.9 (M−1).

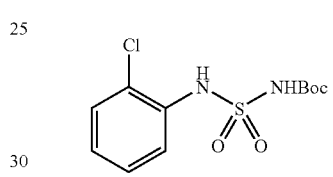

¹H NMR (500 MHz, d⁶-DMSO) δ 11.16 (s, 1H), 9.74 (br s, 1H), 7.51 (d, 1H), 7.42-7.33 (m, 2H), 7.27 (t, 1H), 1.40 (s, 9H); MS (APCI−) m/z 304.9 (M−1).

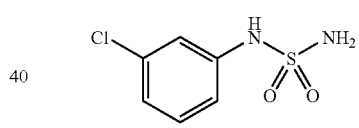

MS (APCI−) m/z 204.9 (M−1).

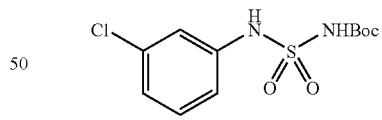

¹H NMR (500 MHz, d⁶-DMSO) δ 11.43 (s, 1H), 10.57 (br s, 1H), 7.35 (t, 1H), 7.20 (s, 1H), 7.18-7.09 (m, 2H), 1.34 (s, 9H); MS (APCI−) m/z 304.9 (M−1).

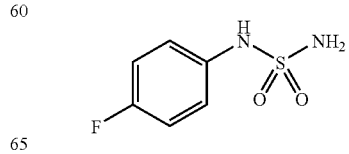

MS (APCI−) m/z 188.9 (M−1).

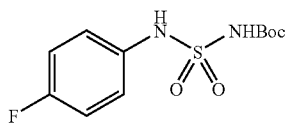

¹H NMR (500 MHz, d⁶-DMSO) δ 11.20 (s, 1H), 10.23 (br s, 1H), 7.24-7.13 (m, 1H), 7.20 (s, 1H), 7.18-7.09 (m, 4H), 1.35 (s, 9H); MS (APCI-) m/z 288.9 (M-1).

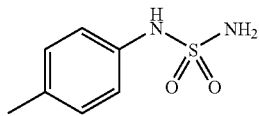

MS (APCI-) m/z 184.9 (M-1).

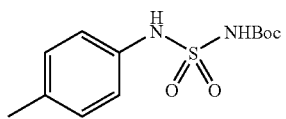

¹H NMR (500 MHz, d⁶-DMSO) δ 11.08 (s, 1H), 10.05 (br s, 1H), 7.12 (d, 2H), 7.05 (d, 2H), 2.25 (s, 3H), 1.35 (s, 9H); MS (APCI-) m/z 284.9 (M-1).

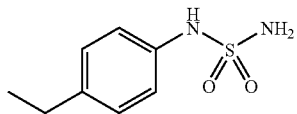

MS (APCI-) m/z 198.9 (M-1).

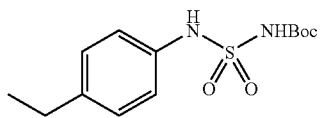

¹H NMR (500 MHz, d⁶-DMSO) δ 11.09 (s, 1H), 10.06 (br s, 1H), 7.15 (d, 2H), 7.08 (d, 2H), 2.55 (s, 2H), 1.35 (s, 9H), 1.14 (t, 3H); MS (APCI-) m/z 298.9 (M-1).

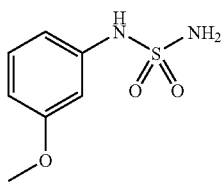

MS (APCI-) m/z 200.9 (M-1).

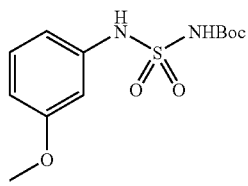

¹H NMR (500 MHz, d⁶-DMSO) δ 11.23 (s, 1H), 10.24 (s, 1H), 7.21 (t, 1H), 6.77-6.72 (m, 2H), 6.67 (d, 1H), 3.72 (s, 3H), 1.34 (s, 9H); MS (APCI-) m/z 300.9 (M-1).

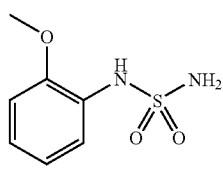

¹H NMR (500 MHz, d⁶-DMSO) δ 7.91 (s, 1H), 7.38 (d, 1H), 7.07-6.98 (m, 4H), 6.90 (t, 1H), 3.80 (s, 3H); MS (APCI-) m/z 200.9 (M-1).

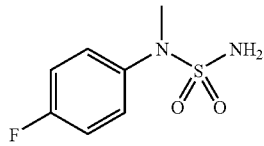

¹H NMR (500 MHz, d⁶-DMSO) δ 7.40-7.34 (m, 2H), 7.21 (t, 2H), 7.02 (s, 2H), 3.35 (s, 3H); MS (APCI-) m/z 203.2 (M-1).

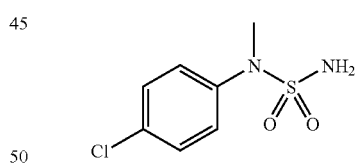

¹H NMR (500 MHz, d⁶-DMSO) δ 7.43 (d, 2H), 7.35 (d, 2H), 7.08 (s, 2H), 3.09 (s, 3H); MS (APCI-) m/z 219.2 (M-1).

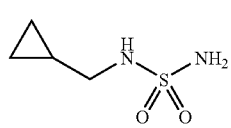

¹H NMR (500 MHz, d⁶-DMSO) δ 6.48 (br s, 2H), 3.43 (br s, 1H), 2.74 (d, 2H), 1.00-0.90 (m, 1H), 0.44-0.36 (m, 2H), 0.18-0.12 (m, 2H); MS (APCI-) m/z 149.0 (M-1).

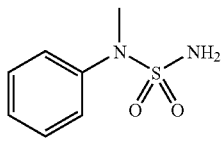

¹H NMR (500 MHz, CDCl₃) δ 7.42-7.31 (m, 4H), 7.28-7.20 (m, 1H), 7.00 (br s, 2H), 3.10 (s, 3H); MS (APCI−) m/z 185.2 (M−1).

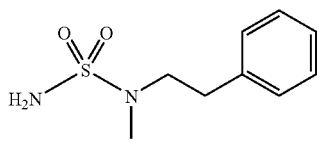

¹H NMR (500 MHz, CDCl₃) δ 7.37-7.20 (m, 5H), 3.44 (m, 2H), 2.91 (t, 2H), 2.85 (s, 3H); MS (APCI−) m/z 213.1 (M−1).

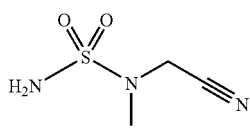

¹H NMR (500 MHz, CDCl₃) δ 3.67 (s, 2H), 2.47 (s, 3H), 2.00 (br s, 2H).

Example 15-1

Compound 2201

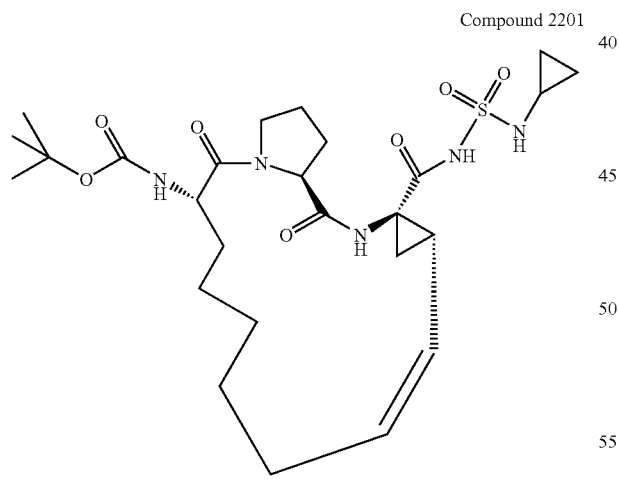

(1S,4R,6S,14S)tert-Butyl 4-(cyclopropylaminosulfonyl)aminocarbonyl-2,15-dioxo-3,16-diaza-tricyclo[14.3.0.0⁴,⁶]nonadec-7-ene-14-yl carbamate was synthesized according to the same procedures as described in Example 1 of Section XII, substituting cyclopropanesulfonamide with N-cyclopropylsulfamide in Step E instead. ¹H NMR (d⁶-Acetone, 400 MHz) δ0.56-0.73 (m, 4H), 1.23-1.56 (m, 18H), 1.68-1.72 (m, 1H), 1.83-2.09 (m, 3H), 2.19-2.25 (m, 2H), 2.37-2.45 (m, 3H), 3.65-3.71 (m, 1H), 4.02 (m, 1H), 4.33-4.43 (m, 2H), 5.02 (t, 1H), 5.62 (q, 1H), 6.00 (br d, 1H), 6.74 (br s, 1H), 8.31 (br s, 1H). MS (APCI+) m/z 468.1 (MH⁺-Boc, 20), 349.1 (100).

Example 15-2

Compound 2202

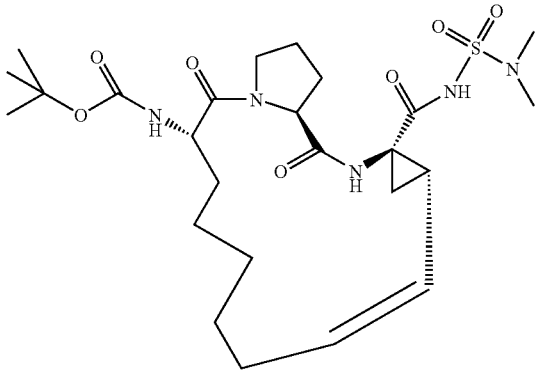

(1S,4R,6S,14S)tert-Butyl 4-(dimethylaminosulfonyl)aminocarbonyl-2,15-dioxo-3,16-diaza-tricyclo[14.3.0.0⁴,⁶]nonadec-7-ene-14-yl carbamate was synthesized according to the same procedures as described in Example 1 of Section XII, substituting cyclopropanesulfonamide with N,N-dimethylsulfamide in Step E instead. ¹H NMR (d⁶-Acetone, 400 MHz) δ1.25-1.54 (m, 18H), 1.67-1.70 (m, 1H), 1.83-2.09 (m, 3H), 2.22-2.27 (m, 2H), 2.36-2.40 (m, 1H), 2.51-2.54 (m, 1H), 2.84 (s, 6H), 3.64-3.70 (m, 1H), 4.04 (m, 1H), 4.32-4.42 (m, 2H), 4.98 (t, 1H), 5.71 (q, 1H), 6.03 (br d, 1H), 8.36 (br s, 1H), 10.45 (br s, 1H). MS (APCI+) m/z 456.2 (MH+-Boc, 40), 349.2 (100).

Example 15-3

Compound 2203

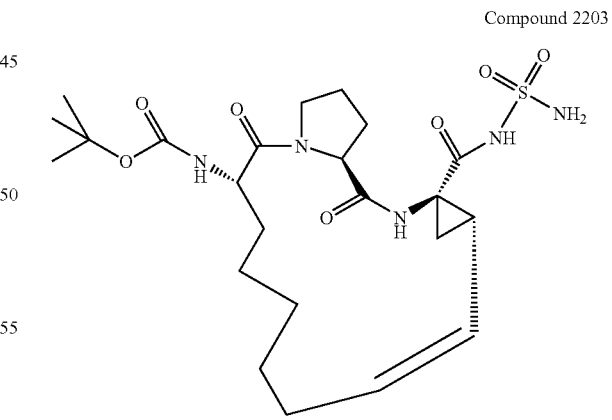

(1S,4R,6S,14S)tert-Butyl 4-aminosulfonylaminocarbonyl-2,15-dioxo-3,16-diaza-tricyclo[14.3.0.0⁴,⁶]nonadec-7-ene-14-yl carbamate was synthesized according to the same procedures as described in Example 1 of Section XII, substituting cyclopropanesulfonamide with sulfamide in Step E instead. ¹H NMR (d⁶-Acetone, 400 MHz) δ1.19-1.67 (m, 19H), 1.79-2.09 (m, 3H), 2.15-2.43 (m, 4H), 3.65-3.97 (m, 2H), 4.34-4.40 (m, 2H), 5.00-5.06 (m, 1H), 5.61 (q, 1H), 5.94 (br d, 1H), 6.56 (br s, 2H), 8.20 (br s, 1H), 10.47 (br s, 1H). MS (APCI−) m/z 526.2 (M−1).

Example 15-4

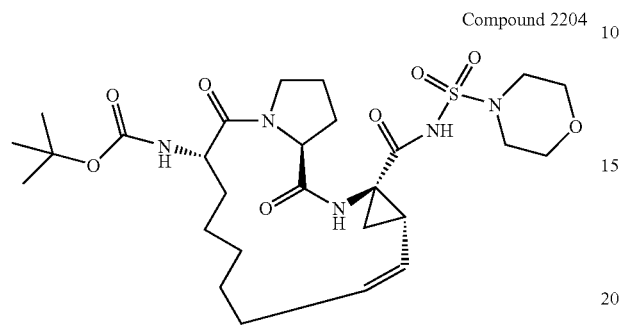

Compound 2204

(1S,4R,6S,14S)tert-Butyl 4-(morpholine-4-sulfonyl)aminocarbonyl-2,15-dioxo-3,16-diaza-tricyclo[14.3.0.0$^{4,6}$]nonadec-7-ene-14-yl carbamate was synthesized according to the same procedures as described in Example 1 of Section XII, substituting cyclopropanesulfonamide with morpholinosulfamide in Step E instead. $^1$H NMR (d$^6$-Acetone, 400 MHz) δ1.24-1.58 (m, 18H), 1.68-1.72 (m, 1H), 1.80-2.05 (m, 3H), 2.19-2.27 (m, 2H), 2.36-2.44 (m, 1H), 2.53-2.55 (m, 1H), 3.20-3.30 (m, 4H), 3.63-3.68 (m, 5H), 4.03 (m, 1H), 4.31-4.41 (m, 2H), 5.01 (t, 1H), 5.73 (q, 1H), 5.99 (br d, 1H), 8.34 (br s, 1H), 10.57 (br s, 1H). MS (APCI+) m/z 498.1 (MH+-Boc, 45), 349.2 (100).

Example 15-5

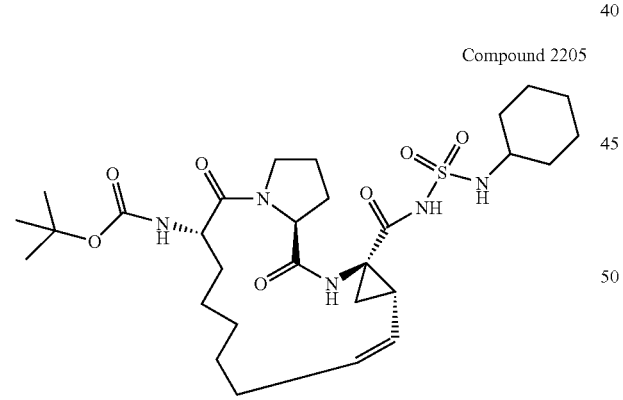

Compound 2205

(1S,4R,6S,14S)tert-Butyl 4-(cyclohexylaminosulfonyl)-aminocarbonyl-2,15-dioxo-3,16-diaza-tricyclo[14.3.0.0$^{4,6}$]nonadec-7-ene-14-yl carbamate was synthesized according to the same procedures as described in Example 1 of Section XII, substituting cyclopropanesulfonamide with N-cyclohexylsulfamide in Step E instead. $^1$H NMR (d$^6$-Acetone, 400 MHz) δ1.14-1.58 (m, 24H), 1.66-1.74 (m, 3H), 1.83-2.07 (m, 5H), 2.18-2.32 (m, 2H), 2.38-2.47 (m, 2H), 3.08-3.12 (m, 1H), 23.64-3.70 (m, 1H), 4.01 (m, 1H), 4.33-4.42 (m, 2H), 5.02 (t, 1H), 5.63 (q, 1H), 5.99 (br d, 1H), 6.18 (br s, 1H), 8.27 (br s, 1H), 10.35 (br s, 1H). MS (APCI+) m/z 510.2 (MH+-Boc, 15), 349.2 (100).

Example 15-6

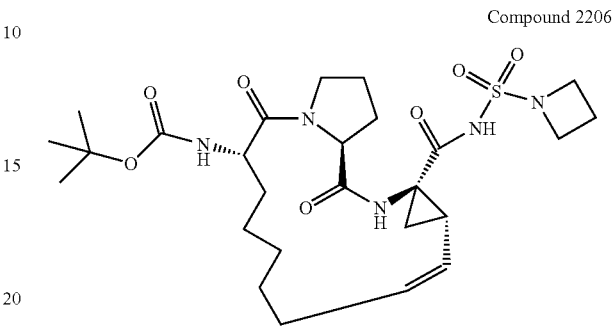

Compound 2206

(1S,4R,6S,14S)tert-Butyl 4-(azetidinosulfonyl)aminocarbonyl-2,15-dioxo-3,16-diaza-tricyclo[14.3.0.0$^{4,6}$]nonadec-7-ene-14-yl carbamate was synthesized according to the same procedures as described in Example 1 of Section XII, substituting cyclopropanesulfonamide with N-azetidinosulfamide in Step E instead. $^1$H NMR (d$^6$-Acetone, 400 MHz) δ1.25-1.56 (m, 18H), 1.74-1.78 (m, 1H), 1.84-2.04 (m, 3H), 2.13-2.26 (m, 4H), 2.42-2.48 (m, 1H), 2.52-2.64 (m, 1H), 3.64-3.70 (m, 1H), 3.90 (q, 2H), 4.04-4.06 (m, 1H), 4.16 (q, 2H), 4.33-4.43 (m, 2H), 5.09 (t, 1H), 5.77 (q, 1H), 6.04 (br d, 1H), 8.41 (br s, 1H), 10.49 (br s, 1H). MS (APCI−) m/z 566.2 (M−1).

Example 15-7

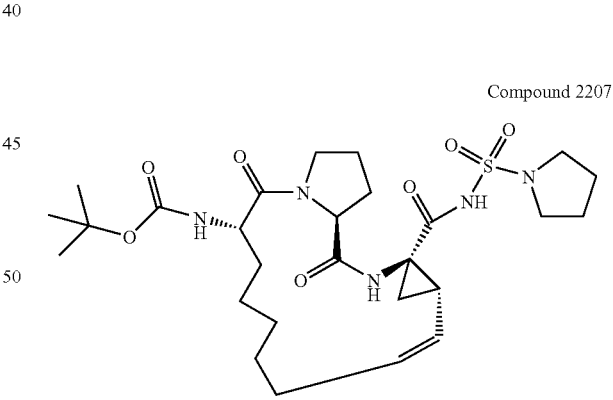

Compound 2207

(1S,4R,6S,14S)tert-Butyl 4-(pyrrolidinosulfonyl)aminocarbonyl-2,15-dioxo-3,16-diaza-tricyclo[14.3.0.0$^{4,6}$]nonadec-7-ene-14-yl carbamate was synthesized according to the same procedures as described in Example 1 of Section XII, substituting cyclopropanesulfonamide with N-pyrrolidinosulfamide in Step E instead. $^1$H NMR (d$^6$-Acetone, 400 MHz) δ1.25-1.54 (m, 18H), 1.69-1.72 (m, 1H), 1.83-2.09 (m, 7H), 2.20-2.26 (m, 2H), 2.36-2.41 (m, 1H), 2.54-2.57 (m, 1H), 3.18-3.24 (m, 2H), 3.54-3.58 (m, 2H), 3.64-3.70 (m, 1H), 4.04-4.06 (m, 1H), 4.33-4.42 (m, 2H), 4.98 (t, 1H), 5.68 (q, 1H), 6.04 (br d, 1H), 8.35 (br s, 1H), 10.37 (br s, 1H). MS (APCI−) m/z 580.3 (M−1).

Example 15-8

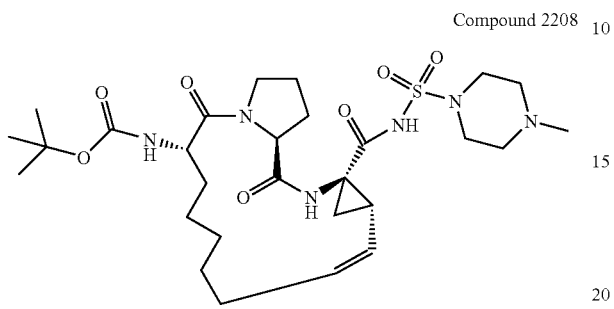

Compound 2208

(1S,4R,6S,14S)tert-Butyl 4-((1-methylpiperazino)sulfonyl)-aminocarbonyl-2,15-dioxo-3,16-diaza-tricyclo[14.3.0.0$^{4,6}$]nonadec-7-ene-14-yl carbamate was synthesized according to the same procedures as described in Example 1 of Section XII, substituting cyclopropanesulfonamide with N-(1-methylpiperazino)sulfamide in Step E instead. $^1$H NMR (d$^6$-Acetone, 400 MHz) δ1.24-1.58 (m, 18H), 1.67-1.70 (m, 1H), 1.82-2.07 (m, 3H), 2.19-2.25 (m, 2H), 2.37-2.42 (m, 1H), 2.52-2.55 (m, 1H), 2.99 (s, 3H), 3.15-4.06 (m, 10H), 4.32-4.42 (m, 2H), 5.07 (t, 1H), 5.82 (q, 1H), 6.07 (br d, 1H), 8.45 (br s, 1H), 10.89 (br s, 1H). MS (APCI−) m/z 609.3 (M−1).

Example 15-9

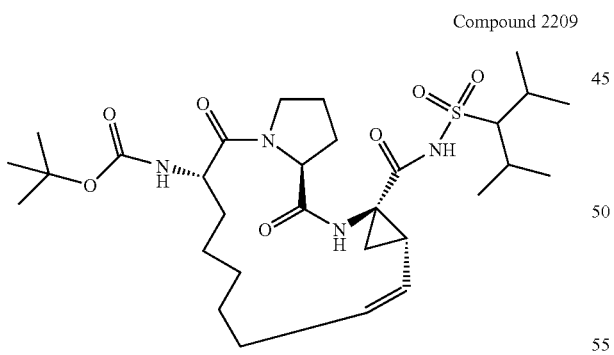

Compound 2209

(1S,4R,6S,14S)tert-Butyl 4-(N,N-diisopropylamino)sulfonyl)-aminocarbonyl-2,15-dioxo-3,16-diaza-tricyclo[14.3.0.0$^{4,6}$]nonadec-7-ene-14-yl carbamate was synthesized according to the same procedures as described in Example 1 of Section XII, substituting cyclopropanesulfonamide with N,N-diisopropylsulfamide in Step E instead. $^1$H NMR (d$^6$-Acetone, 400 MHz) δ1.25-1.54 (m, 30H), 1.64-1.68 (m, 1H), 1.79-2.09 (m, 3H), 2.19-2.26 (m, 2H), 2.32-2.50 (m, 2H), 3.64-3.70 (m, 1H), 3.94-4.01 (m, 3H), 4.33-4.41 (m, 2H), 4.98 (t, 1H), 5.61 (q, 1H), 8.31 (br s, 1H), 10.31 (br s, 1H). MS (APCI−) m/z 610.3 (M−1).

Example 15-10

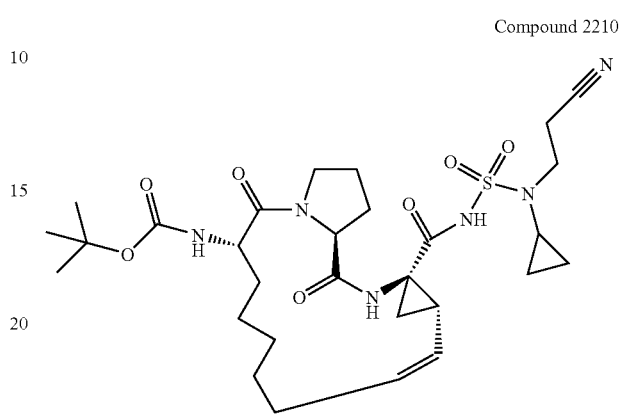

Compound 2210

(1S,4R,6S,14S)tert-Butyl 4-(N-2-cyanoethyl-N-cyclopropylsulfamoyl)-aminocarbonyl-2,15-dioxo-3,16-diaza-tricyclo[14.3.0.0$^{4,6}$]nonadec-7-ene-14-yl carbamate was synthesized according to the same procedures as described in Example 1 of Section XII, substituting cyclopropanesulfonamide with N-2-cyanoethyl-N-cyclopropylsulfamide in Step E instead. $^1$H NMR (d$^6$-Acetone, 400 MHz) δ0.73-0.78 (m, 2H), 0.97-1.01 (m, 2H), 1.24-1.55 (m, 18H), 1.70-1.74 (m, 1H), 1.83-1.97 (m, 3H), 2.20-2.26 (m, 2H), 2.42-2.50 (m, 2H), 2.54-2.58 (m, 1H), 2.80 (t, 2H), 3.49-3.57 (m, 1H), 3.64-3.70 (m, 1H), 3.96-4.03 (m, 2H), 4.32-4.41 (m, 2H), 5.00 (t, 1H), 5.67 (q, 1H), 6.00 (br d, 1H), 8.36 (br s, 1H), 10.68 (br s, 1H). MS (APCI−) m/z 619.3 (M−1).

Example 15-11

Compound 2211

(1S,4R,6S,14S)tert-Butyl 4-(cyclopropyl(1-methylpiperidin-4-yl)sulfamoyl)-aminocarbonyl-2,15-dioxo-3,16-diaza-tricyclo[14.3.0.0$^{4,6}$]nonadec-7-ene-14-yl carbamate was synthesized according to the same procedures as described in Example 1 of Section XII, substituting cyclopropanesulfonamide with cyclopropyl(1-methylpiperidin-4-yl)sulfamide in Step E instead. $^1$H NMR (d$^6$-Acetone, 400 MHz) δ0.71-0.74 (m, 2H), 0.88-1.00 (m, 2H), 1.24-1.57 (m, 18H), 1.68-1.72 (m, 1H), 1.79-2.10 (m, 5H), 2.21-2.50 (m, 6H), 2.89 (s, 3H), 3.11-3.19 (m, 2H), 3.59-3.79 (m, 4H), 4.03 (m, 1H), 4.24-4.39 (m, 3H), 5.04 (t, 1H), 5.66 (q, 1H), 8.33 (br s, 1H). MS (APCI−) m/z 663.4 (M−1).

Example 15-12

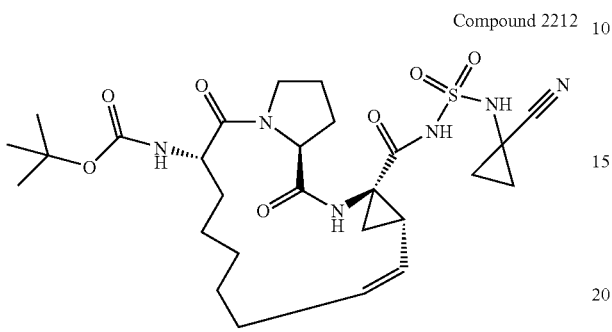

Compound 2212

(1S,4R,6S,14S)tert-Butyl 4-(1-cyanocyclopropylsulfamoyl)aminocarbonyl-2,15-dioxo-3,16-diaza-tricyclo[14.3.0.0$^{4,6}$]nonadec-7-ene-14-yl carbamate was synthesized according to the same procedures as described in Example 1 of Section XII, substituting cyclopropanesulfonamide with N-(1-cyanocyclopropyl)sulfamide in Step E instead. $^1$H NMR (d$^6$-Acetone, 400 MHz) δ1.24-1.58 (m, 21H), 1.63-1.73 (m, 2H), 1.83-2.00 (m, 3H), 2.11-2.48 (m, 4H), 3.65-3.75 (m, 1H), 3.96-4.03 (m, 1H), 4.35-4.42 (m, 2H), 5.02 (t, 1H), 5.62 (q, 1H), 6.01 (br d, 1H), 7.89 (br s, 1H), 8.25 (br s, 1H), 10.75 (br s, 1H). MS (APCI−) m/z 591.2 (M−1).

Example 15-13

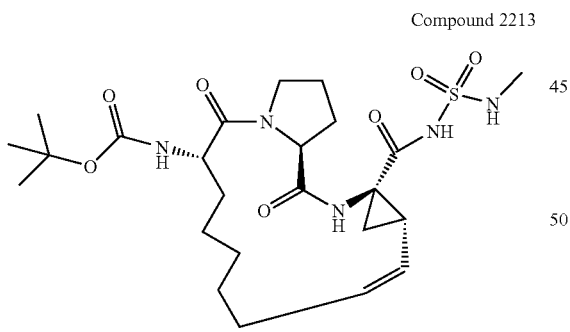

Compound 2213

(1S,4R,6S,14S)tert-Butyl 4-methylsulfamoylaminocarbonyl-2,15-dioxo-3,16-diaza-tricyclo[14.3.0.0$^{4,6}$]nonadec-7-ene-14-yl carbamate was synthesized according to the same procedures as described in Example 1 of Section XII, substituting cyclopropanesulfonamide with N-methylsulfamide in Step E instead. $^1$H NMR (d$^6$-Acetone, 400 MHz) δ1.24-1.54 (m, 18H), 1.69-1.71 (m, 1H), 1.83-1.97 (m, 3H), 2.18-2.26 (m, 2H), 2.36-2.48 (m, 2H), 2.60 (d, 3H), 3.65-3.71 (m, 1H), 4.01 (m, 1H), 4.33-4.42 (m, 2H), 4.99 (t, 1H), 5.64 (q, 1H), 6.00 (br d, 1H), 6.20 (br s, 1H), 8.30 (br s, 1H), 10.33 (br s, 1H). MS (APCI−) m/z 540.2 (M−1).

Example 15-14

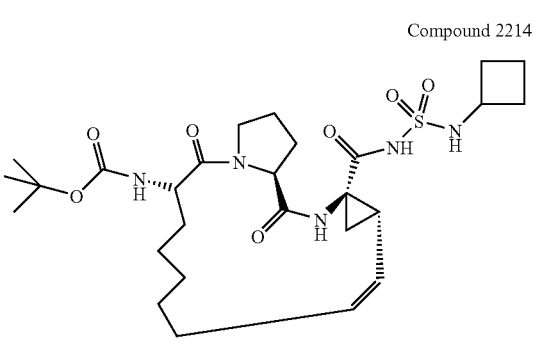

Compound 2214

(1S,4R,6S,14S)tert-Butyl 4-cyclobutylsulfamoylaminocarbonyl-2,15-dioxo-3,16-diaza-tricyclo[14.3.0.0$^{4,6}$]nonadec-7-ene-14-yl carbamate was synthesized according to the same procedures as described in Example 1 of Section XII, substituting cyclopropanesulfonamide with N-cyclobutylsulfamide in Step E instead. $^1$H NMR (d$^6$-Acetone, 400 MHz) δ1.20-1.68 (m, 21H), 1.82-2.10 (m, 5H), 2.18-2.28 (m, 4H), 2.36-2.46 (m, 2H), 3.64-3.70 (m, 1H), 3.75-3.81 (m, 1H), 3.97-4.01 (m, 1H), 4.33-4.40 (m, 2H), 5.05 (t, 1H), 5.63 (q, 1H), 5.97 (br d, 1H), 6.64 (br d, 1H), 8.20 (br s, 1H), 10.21 (br s, 1H). MS (APCI−) m/z 580.2 (M−1).

Example 15-15

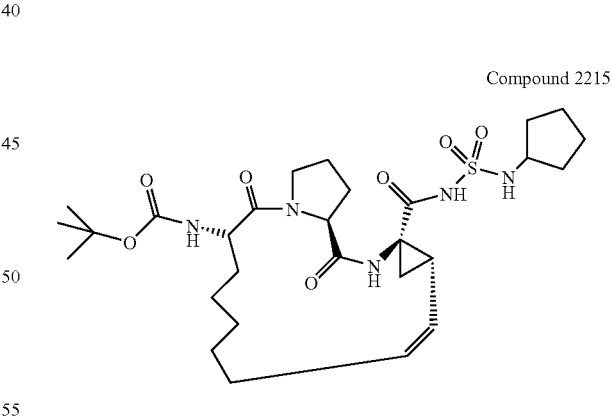

Compound 2215

(1S,4R,6S,14S)tert-Butyl 4-cyclopentylsulfamoylaminocarbonyl-2,15-dioxo-3,16-diaza-tricyclo[14.3.0.0$^{4,6}$]nonadec-7-ene-14-yl carbamate was synthesized according to the same procedures as described in Example 1 of Section XII, substituting cyclopropanesulfonamide with N-cyclopentylsulfamide in Step E instead. $^1$H NMR (d$^6$-Acetone, 400 MHz) δ1.24-1.71 (m, 24H), 1.82-2.09 (m, 6H), 2.19-2.24 (m, 2H), 2.38-2.48 (m, 2H), 3.55-3.59 (m, 1H), 3.64-3.70 (m, 1H), 3.98-4.00 (m, 1H), 4.33-4.41 (m, 2H), 5.03 (t, 1H), 5.62

(q, 1H), 5.97 (br d, 1H), 6.24 (br d, 1H), 8.25 (br s, 1H), 10.27 (br s, 1H). MS (APCI–) m/z 594.3 (M–1).

Example 15-16

Compound 2216

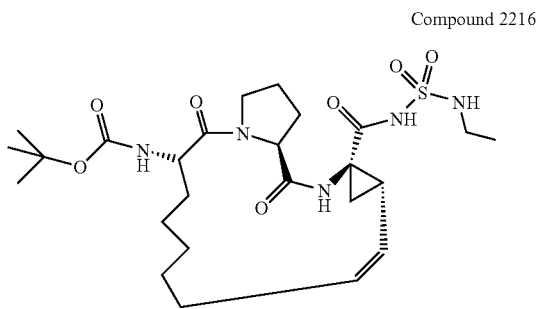

(1S,4R,6S,14S)tert-Butyl 4-ethylsulfamoylaminocarbonyl-2,15-dioxo-3,16-diaza-tricyclo[14.3.0.0$^{4,6}$]nonadec-7-ene-14-yl carbamate was synthesized according to the same procedures as described in Example 1 of Section XII, substituting cyclopropanesulfonamide with N-ethylsulfamide in Step E instead. $^1$H NMR (d$^6$-Acetone, 400 MHz) δ1.13-1.55 (m, 21H), 1.67-1.70 (m, 1H), 1.80-2.06 (m, 3H), 2.17-2.25 (m, 2H), 2.35-2.47 (m, 2H), 2.95-3.00 (m, 2H), 3.66-3.71 (m, 1H), 3.98-4.03 (m, 1H), 4.33-4.42 (m, 2H), 5.00 (t, 1H), 5.63 (q, 1H), 5.99 (br d, 1H), 6.23 (br s, 1H), 8.27 (br s, 1H). MS (APCI–) m/z 554.2 (M–1).

Example 15-17

Compound 2217

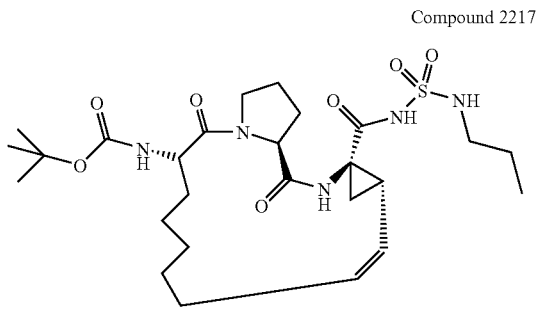

(1S,4R,6S,14S)tert-Butyl 4-propylsulfamoylaminocarbonyl-2,15-dioxo-3,16-diaza-tricyclo[14.3.0.0$^{4,6}$]nonadec-7-ene-14-yl carbamate was synthesized according to the same procedures as described in Example 1 of Section XII, substituting cyclopropanesulfonamide with N-propylsulfamide in Step E instead. $^1$H NMR (d$^6$-Acetone, 400 MHz) δ0.92 (t, 3H), 1.18-1.62 (m, 20H), 1.67-1.71 (m, 1H), 1.83-2.08 (m, 3H), 2.17-2.25 (m, 2H), 2.35-2.47 (m, 2H), 2.86-2.91 (m, 2H), 3.65-3.71 (m, 1H), 3.98-4.03 (m, 1H), 4.33-4.42 (m, 2H), 5.00 (t, 1H), 5.63 (q, 1H), 6.00 (br d, 1H), 6.23 (br s, 1H), 8.28 (br s, 1H). MS (APCI–) m/z 568.3 (M–1).

Example 15-18

Compound 2218

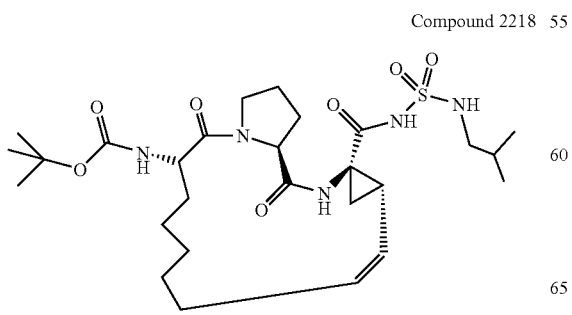

(1S,4R,6S,14S)tert-Butyl 4-isobutylsulfamoyl aminocarbonyl-2,15-dioxo-3,16-diaza-tricyclo[14.3.0.0$^{4,6}$]nonadec-7-ene-14-yl carbamate was synthesized according to the same procedures as described in Example 1 of Section XII, substituting cyclopropanesulfonamide with N-isobutylsulfamide in Step E instead. $^1$H NMR (d$^6$-Acetone, 400 MHz) δ0.91-0.94 (m, 6H), 1.20-1.59 (m, 18H), 1.68-1.71 (m, 1H), 1.80-1.88 (m, 2H), 1.94-2.05 (m, 2H), 2.18-2.26 (m, 2H), 2.36-2.48 (m, 2H), 2.72 (t, 2H), 3.65-3.71 (m, 1H), 3.98-4.03 (m, 1H), 4.33-4.42 (m, 2H), 4.99 (t, 1H), 5.64 (q, 1H), 5.99 (br d, 1H), 6.23 (br s, 1H), 8.29 (br s, 1H), 10.36 (br s, 1H). MS (APCI–) m/z 582.3 (M–1).

Example 15-19

Compound 2219

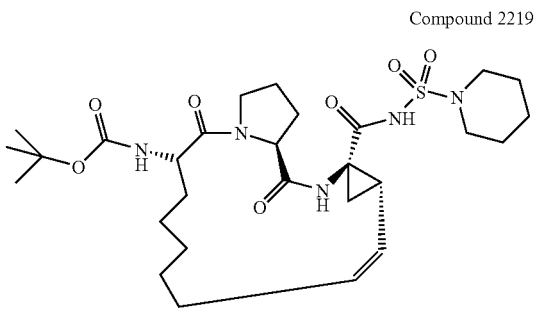

(1S,4R,6S,14S)tert-Butyl 4-(piperidine-1-sulfonyl)aminocarbonyl-2,15-dioxo-3,16-diaza-tricyclo[14.3.0.0$^{4,6}$]nonadec-7-ene-14-yl carbamate was synthesized according to the same procedures as described in Example 1 of Section XII, substituting cyclopropanesulfonamide with N-piperidinosulfamide in Step E instead. $^1$H NMR (d$^6$-Acetone, 400 MHz) δ1.18-1.59 (m, 24H), 1.66-1.70 (m, 1H), 1.80-2.07 (m, 3H), 2.20-2.26 (m, 2H), 2.34-2.40 (m, 1H), 2.49-2.52 (m, 1H), 3.22-3.25 (m, 4H), 3.66-3.70 (m, 1H), 4.03-4.06 (m, 1H), 4.32-4.41 (m, 2H), 5.00 (t, 1H), 5.70 (q, 1H), 6.00 (br d, 1H), 8.32 (br s, 1H), 10.37 (br s, 1H). MS (APCI–) m/z 594.3 (M–1).

Example 15-20

Compound 2220

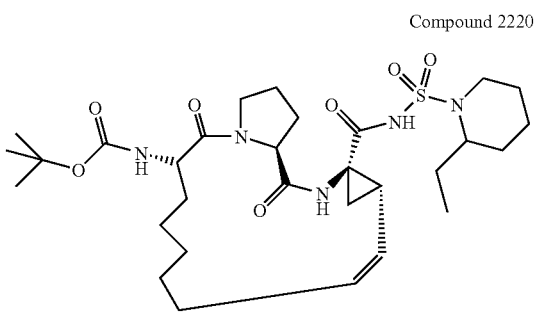

(1S,4R,6S,14S)tert-Butyl 4-(2-ethylpiperidine-1-sulfonyl)-aminocarbonyl-2,15-dioxo-3,16-diaza-tricyclo[14.3.0.0$^{4,6}$]nonadec-7-ene-14-yl carbamate was synthesized according to the same procedures as described in Example 1 of Section XII, substituting cyclopropanesulfonamide with 2-ethylpiperidinosulfamide in Step E instead. $^1$H NMR (d$^6$-Acetone, 400 MHz) δ0.86-0.89 (m, 3H), 1.18-1.61 (m, 23H), 1.65-1.85 (m, 4H), 1.94-2.09 (m, 3H), 2.18-2.24 (m, 2H), 2.34-2.39 (m, 1H), 2.45-2.50 (m, 1H), 3.00-3.07 (m, 1H), 3.62-3.81 (m, 3H), 4.03-4.06 (m, 1H), 4.28-4.40 (m, 2H), 5.01-5.10 (m, 1H), 5.49-5.65 (m, 1H), 5.95 (br d, 1H), 8.22 (br s, 1H). MS (APCI–) m/z 622.3 (M–1).

Example 15-21

Compound 2221

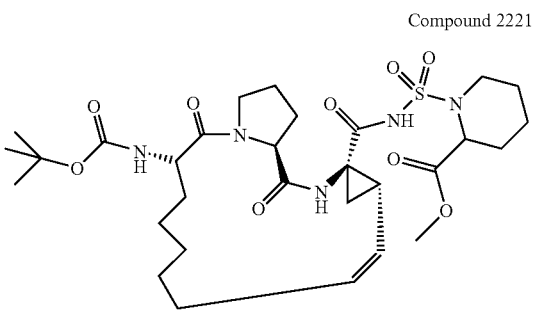

(1S,4R,6S,14S)tert-Butyl 4-(2-methylcarboxylatepiperidine-1-sulfonyl)aminocarbonyl-2,15-dioxo-3,16-diaza-tricyclo[14.3.0.0^{4,6}]nonadec-7-ene-14-yl carbamate was synthesized according to the same procedures as described in Example 1 of Section XII, substituting cyclopropanesulfonamide with 2-methylcarboxylate-piperidinosulfamide in Step E instead. $^1$H NMR (d$^6$-Acetone, 400 MHz) δ1.20-2.08 (m, 28 H), 2.18-2.50 (m, 4H), 3.25-3.39 (m, 1H), 3.57-3.83 (m, 2H), 3.73 (s, 3H), 3.98 (m, 1H), 4.35-4.38 (m, 2H), 4.54-4.79 (m, 1H), 5.06-5.13 (m, 1H), 5.59-5.66 (m, 1H), 5.92 (br d, 1H), 8.18 (br s, 1H). MS (APCI−) m/z 652.4 (M−1).

Example 15-22

Compound 2222

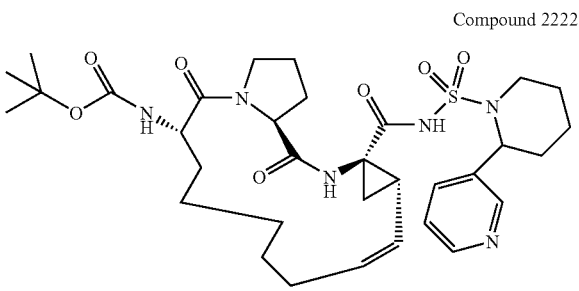

(1S,4R,6S,14S)tert-Butyl 4-(2-(pyridin-3-yl)piperidine-1-sulfonyl)aminocarbonyl-2,15-dioxo-3,16-diaza-tricyclo[14.3.0.0^{4,6}]nonadec-7-ene-14-yl carbamate was synthesized according to the same procedures as described in Example 1 of Section XII, substituting cyclopropanesulfonamide with 2-(pyridin-3-yl)piperidinosulfamide in Step E instead. MS (APCI−) m/z 671.3 (M−1).

Example 15-23

Compound 2223

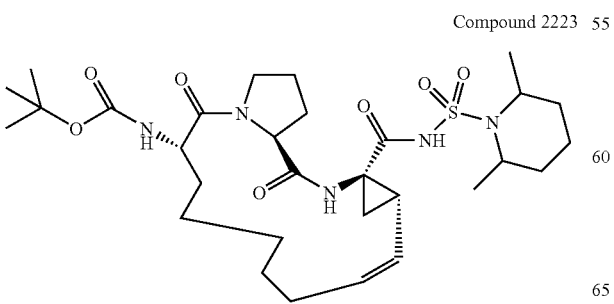

(1S,4R,6S,14S)tert-Butyl 4-(2,6-dimethylpiperidine-1-sulfonyl)aminocarbonyl-2,15-dioxo-3,16-diaza-tricyclo[14.3.0.0^{4,6}]nonadec-7-ene-14-yl carbamate was synthesized according to the same procedures as described in Example 1 of Section XII, substituting cyclopropanesulfonamide with (2,6-dimethyl)piperidinosulfamide in Step E instead. $^1$H NMR (d$^6$-Acetone, 400 MHz) δ1.18-2.07 (m, 34H), 2.15-2.43 (m, 4H), 3.66-3.78 (m, 1H), 3.94-3.97 (m, 2H), 4.28-4.39 (m, 3H), 5.08 (t, 1H), 5.60 (q, 1H), 5.91 (br d, 1H), 8.18 (br s, 1H). MS (APCI−) m/z 622.4 (M−1).

Example 15-24

Compound 2224

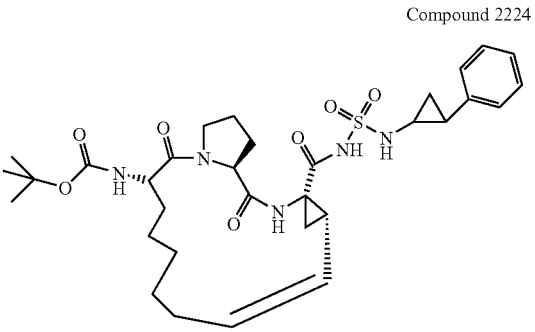

(1S,4R,6S,14S)tert-Butyl 4-(trans-2-phenylcyclopropylsulfamoyl)aminocarbonyl-2,15-dioxo-3,16-diaza-tricyclo[14.3.0.0^{4,6}]nonadec-7-ene-14-yl carbamate was synthesized according to the same procedures as described in Example 1 of Section XII, substituting cyclopropanesulfonamide with trans-(2-phenylcyclopropyl)sulfamide in Step E instead. $^1$H NMR (d$^6$-Acetone, 400 MHz) δ1.12-1.98 (m, 24H), 2.13-2.40 (m, 5H), 2.48-2.55 (m, 1H), 3.61-3.70 (m, 1H), 3.99 (m, 1H), 4.30-4.39 (m, 2H), 4.88-5.01 (m, 1H), 5.26-5.59 (m, 1H), 5.95 (br d, 1H), 6.90-7.30 (m, 6H), 8.28 (br d, 1H). MS (APCI−) m/z 643.2 (M).

Example 15-25

Compound 2225

(1S,4R,6S,14S)tert-Butyl 4-(2-methylpiperidine-1-sulfonyl)aminocarbonyl-2,15-dioxo-3,16-diaza-tricyclo[14.3.0.0^{4,6}]nonadec-7-ene-14-yl carbamate was synthesized according to the same procedures as described in Example 1 of Section XII, substituting cyclopropanesulfonamide with (2-methylpiperidino)-sulfamide in Step E instead. $^1$H NMR (d$^6$-Acetone, 400 MHz) δ1.18-2.08 (m, 31H), 2.19-2.24 (m, 2H), 2.33-2.50 (m, 2H), 3.07-3.14 (m, 1H), 3.62-3.81 (m, 2H), 4.00-4.08 (m, 2H), 4.28-4.40 (m, 2H), 5.00-5.07 (m, 1H), 5.60-5.66 (m, 1H), 5.97 (br d, 1H), 8.25 (br s, 1H). MS (APCI−) m/z 608.3 (M−1).

Example 15-26

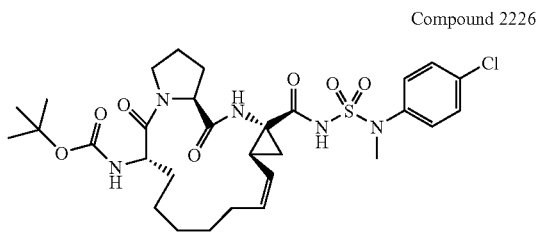

Compound 2226

(1S,4R,6S,14S)tert-Butyl 4-(4-chlorophenyl(methyl)sulfamoyl)-aminocarbonyl-2,15-dioxo-3,16-diaza-tricyclo[14.3.0.0$^{4,6}$]nonadec-7-ene-14-yl carbamate was synthesized according to the same procedures as described in Example 1 of Section XII, substituting cyclopropanesulfonamide with N,N-(4-chlorophenyl)(methyl)sulfamide in Step E instead. MS (APCI−) m/z 651.2 (M−1).

Example 15-27

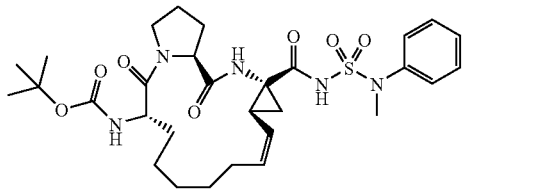

Compound 2227

(1S,4R,6S,14S)tert-Butyl 4-(methyl(phenyl)sulfamoyl)-aminocarbonyl-2,15-dioxo-3,16-diaza-tricyclo[14.3.0.0$^{4,6}$]nonadec-7-ene-14-yl carbamate was synthesized according to the same procedures as described in Example 1 of Section XII, substituting cyclopropanesulfonamide with N,N-(methyl)(phenyl)sulfamide in Step E instead. $^1$H NMR (500 MHz, d$^6$-DMSO) δ 11.03 (br s, 1H), 8.70 (br s, 1H), 7.41-7.27 (m, 5H), 6.97 (d, 1H), 5.63 (q, 1H), 5.02 (t, 1H), 4.24-4.09 (m, 2H), 3.90-3.79 (m, 1H), 3.56-3.45 (m, 1H), 3.28 (s, 3H), 2.44-2.31 (m, 1H), 2.17 (q, 1H), 2.11-1.96 (m, 2H), 1.87-1.58 (m, 5H), 1.52-1.44 (m, 1H), 1.41-1.12 (m, 16H). MS (APCI−) m/z 616.3 (M−1).

Example 15-28

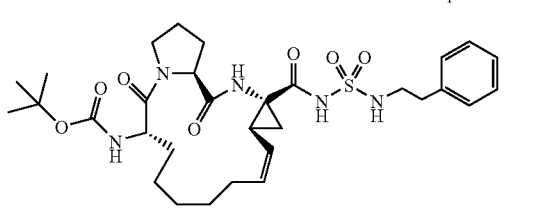

Compound 2228

(1S,4R,6S,14S)tert-Butyl 4-(phenethylsulfamoyl)-aminocarbonyl-2,15-dioxo-3,16-diaza-tricyclo[14.3.0.0$^{4,6}$]nonadec-7-ene-14-yl carbamate was synthesized according to the same procedures as described in Example 1 of Section XII, substituting cyclopropanesulfonamide with phenethylsulfamide in Step E instead. MS (APCI−) m/z 630.3 (M−1).

Example 15-29

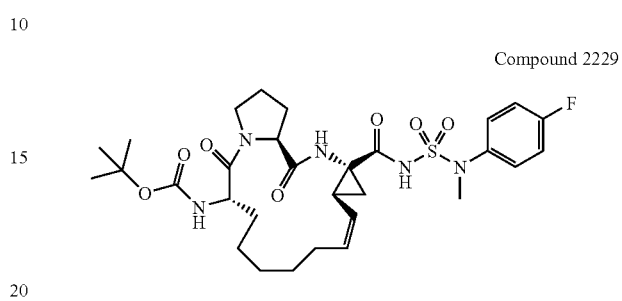

Compound 2229

(1S,4R,6S,14S)tert-Butyl 4-(4-fluorophenyl(methyl)sulfamoyl)-aminocarbonyl-2,15-dioxo-3,16-diaza-tricyclo[14.3.0.0$^{4,6}$]nonadec-7-ene-14-yl carbamate was synthesized according to the same procedures as described in Example 1 of Section XII, substituting cyclopropanesulfonamide with N,N-(4-fluorophenyl)(methyl)sulfamide in Step E instead. MS (APCI−) m/z 634.3 (M−1).

Example 15-30

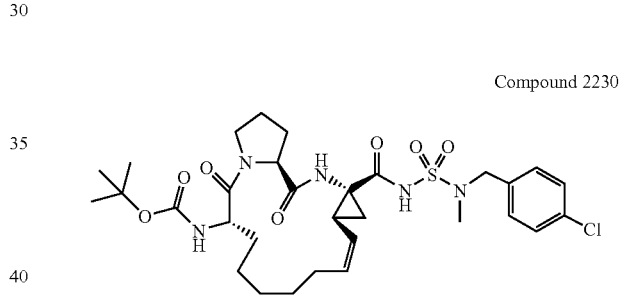

Compound 2230

(1S,4R,6S,14S)tert-Butyl 4-(4-chlorobenzyl(methyl)sulfamoyl)-aminocarbonyl-2,15-dioxo-3,16-diaza-tricyclo[14.3.0.0$^{4,6}$]nonadec-7-ene-14-yl carbamate was synthesized according to the same procedures as described in Example 1 of Section XII, substituting cyclopropanesulfonamide with N,N-(4-chlorobenzyl)(methyl)sulfamide in Step E instead. MS (APCI−) m/z 664.2 (M−1).

Example 15-31

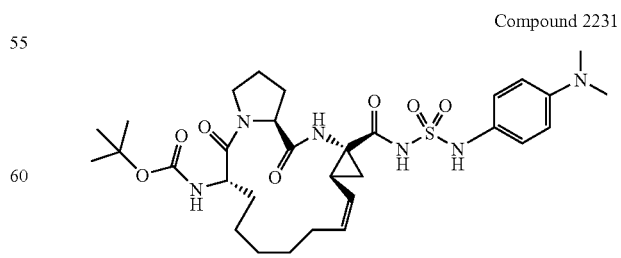

Compound 2231

(1S,4R,6S,14S)tert-Butyl 4-(4-(dimethylamino)phenylsulfamoyl)-aminocarbonyl-2,15-dioxo-3,16-diaza-tricyclo[14.3.0.0$^{4,6}$]nonadec-7-ene-14-yl carbamate was synthesized according to the same procedures as described in Example 1 of Section XII, substituting cyclopropanesulfonamide with (4-(dimethylamino)phenyl)sulfamide in Step E instead. MS (APCI−) m/z 630.2 (M−1-methyl).

Example 15-32

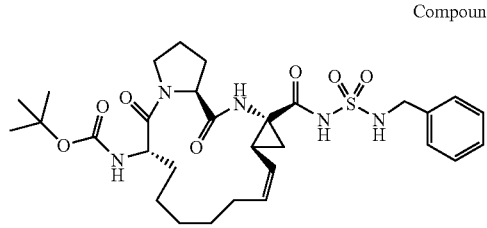

Compound 2232

(1S,4R,6S,14S)tert-Butyl 4-benzylsulfamoylaminocarbonyl-2,15-dioxo-3,16-diaza-tricyclo[14.3.0.0$^{4,6}$]nonadec-7-ene-14-yl carbamate was synthesized according to the same procedures as described in Example 1 of Section XII, substituting cyclopropanesulfonamide with benzylsulfamide in Step E instead. MS (APCI−) m/z 616.3 (M−1).

Example 15-33

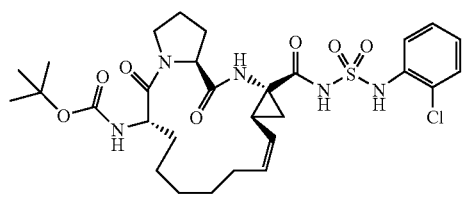

Compound 2233

(1S,4R,6S,14S)tert-Butyl 4-(2-chlorophenylsulfamoyl)-aminocarbonyl-2,15-dioxo-3,16-diaza-tricyclo[14.3.0.0$^{4,6}$]nonadec-7-ene-14-yl carbamate was synthesized according to the same procedures as described in Example 1 of Section XII, substituting cyclopropanesulfonamide with (2-chlorophenyl)sulfamide in Step E instead. MS (APCI−) m/z 637.2 (M−1).

Example 15-34

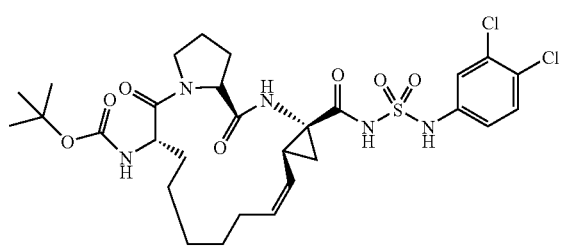

Compound 2234

(1S,4R,6S,14S)tert-Butyl 4-(3,4-dichlorophenylsulfamoyl)-aminocarbonyl-2,15-dioxo-3,16-diaza-tricyclo[14.3.0.0$^{4,6}$]nonadec-7-ene-14-yl carbamate was synthesized according to the same procedures as described in Example 1 of Section XII, substituting cyclopropanesulfonamide with (3,4-dichlorophenyl)sulfamide in Step E instead. MS (APCI−) m/z 671.2 (M−1).

Example 15-35

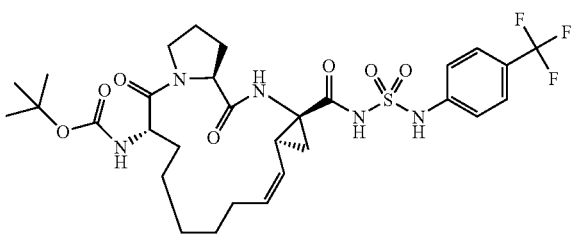

Compound 2235

(1S,4R,6S,14S)tert-Butyl 4-(4-(trifluoromethyl)phenylsulfamoyl)-aminocarbonyl-2,15-dioxo-3,16-diaza-tricyclo[14.3.0.0$^{4,6}$]nonadec-7-ene-14-yl carbamate was synthesized according to the same procedures as described in Example 1 of Section XII, substituting cyclopropanesulfonamide with (4-trifluoromethylphenyl)sulfamide in Step E instead. MS (APCI−) m/z 670.2 (M−1).

Example 15-36

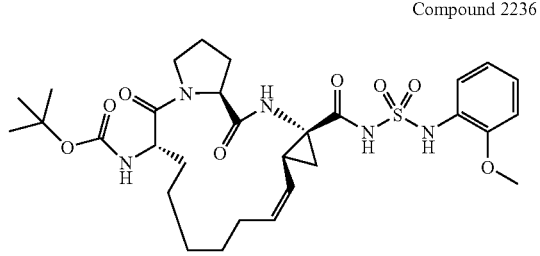

Compound 2236

(1S,4R,6S,14S)tert-Butyl 4-(2-methoxyphenylsulfamoyl)-aminocarbonyl-2,15-dioxo-3,16-diaza-tricyclo[14.3.0.0$^{4,6}$]nonadec-7-ene-14-yl carbamate was synthesized according to the same procedures as described in Example 1 of Section XII, substituting cyclopropanesulfonamide with (2-methoxyphenyl)sulfamide in Step E instead. MS (APCI−) m/z 632.3 (M−1).

Example 15-37

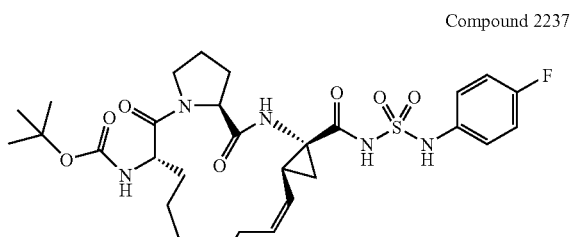

Compound 2237

(1S,4R,6S,14S)tert-Butyl 4-(4-fluorphenylsulfamoyl)-aminocarbonyl-2,15-dioxo-3,16-diaza-tricyclo[14.3.0.0$^{4,6}$]nonadec-7-ene-14-yl carbamate was synthesized according to the same procedures as described in Example 1 of Section II, substituting cyclopropanesulfonamide with (4-fluorophenyl)sulfamide in Step E instead. MS (APCI−) m/z 620.3 (M−1).

Example 15-38

Compound 2238

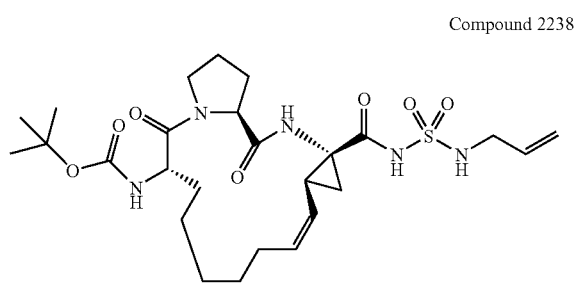

(1S,4R,6S,14S)tert-Butyl 4-(allylsulfamoylaminocarbonyl-2,15-dioxo-3,16-diaza-tricyclo[14.3.0.0$^{4,6}$]nonadec-7-ene-14-yl carbamate was synthesized according to the same procedures as described in Example 1 of Section XII, substituting cyclopropanesulfonamide with allylsulfamide in Step E instead. MS (APCI−) m/z 566.2 (M−1).

Example 15-39

Compound 2239

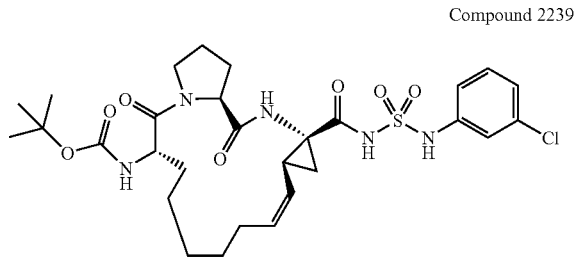

(1S,4R,6S,14S)tert-Butyl 4-((3-chlorophenyl)-sulfamoyl)-aminocarbonyl-2,15-dioxo-3,16-diaza-tricyclo[14.3.0.0$^{4,6}$]nonadec-7-ene-14-yl carbamate was synthesized according to the same procedures as described in Example 1 of Section XII, substituting cyclopropanesulfonamide with (3-chlorophenyl)sulfamide in Step E instead. MS (APCI−) m/z 637.1 (M−1).

Example 15-40

Compound 2240

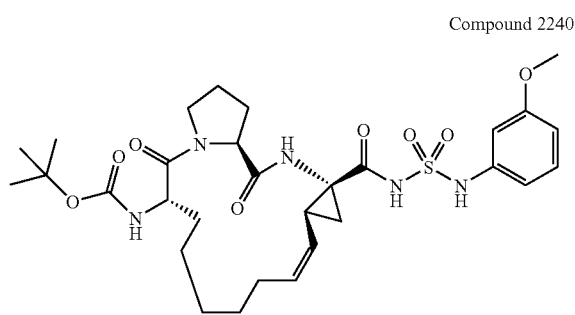

(1S,4R,6S,14S)tert-Butyl 4-((3-methoxyphenyl)-sulfamoyl)-aminocarbonyl-2,15-dioxo-3,16-diaza-tricyclo[14.3.0.0$^{4,6}$]nonadec-7-ene-14-yl carbamate was synthesized according to the same procedures as described in Example 1 of Section XII, substituting cyclopropanesulfonamide with (3-methoxyphenyl)sulfamide in Step E instead. MS (APCI−) m/z 632.2 (M−1).

Example 15-41

Compound 2241

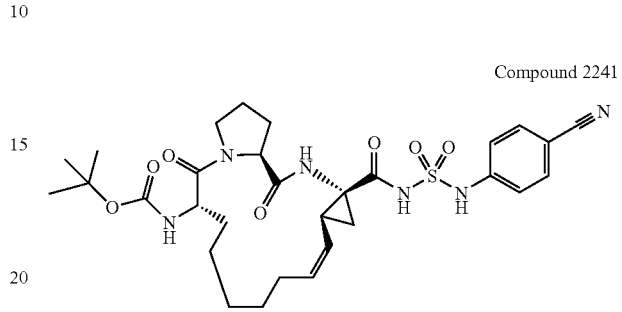

(1S,4R,6S,14S)tert-Butyl 4-((4-cyanophenyl)-sulfamoyl)-aminocarbonyl-2,15-dioxo-3,16-diaza-tricyclo[14.3.0.0$^{4,6}$]nonadec-7-ene-14-yl carbamate was synthesized according to the same procedures as described in Example 1 of Section XII, substituting cyclopropanesulfonamide with (4-cyanophenyl)sulfamide in Step E instead. MS (APCI−) m/z 627.2 (M−1).

Example 15-42

Compound 2242

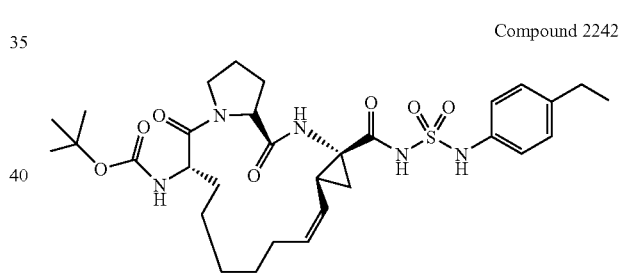

(1S,4R,6S,14S)tert-Butyl 4-((4-ethylphenyl)-sulfamoyl)-aminocarbonyl-2,15-dioxo-3,16-diaza-tricyclo[14.3.0.0$^{4,6}$]nonadec-7-ene-14-yl carbamate was synthesized according to the same procedures as described in Example 1 of Section XII, substituting cyclopropanesulfonamide with (4-ethylphenyl)sulfamide in Step E instead. MS (APCI−) m/z 630.3 (M−1).

Example 15-43

Compound 2243

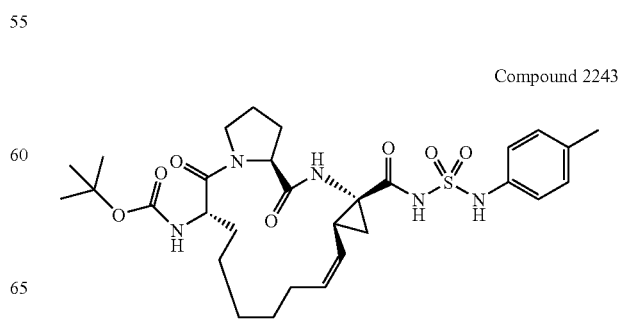

(1S,4R,6S,14S)tert-Butyl 4-((4-methylphenyl)-sulfamoyl)-aminocarbonyl-2,15-dioxo-3,16-diaza-tricyclo[14.3.0.0^{4,6}]nonadec-7-ene-14-yl carbamate was synthesized according to the same procedures as described in Example 1 of Section XII, substituting cyclopropanesulfonamide with (4-methylphenyl)sulfamide in Step E instead. MS (APCI−) m/z 616.3 (M−1).

Example 15-44

Compound 2244

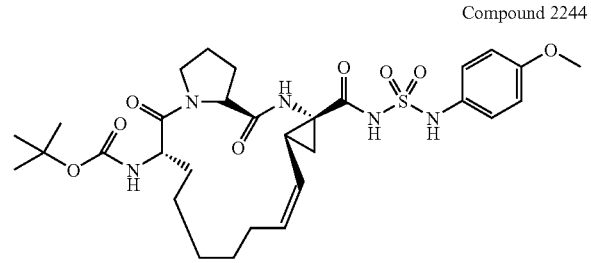

(1S,4R,6S,14S)tert-Butyl 4-((4-methoxylphenyl)-sulfamoyl)-aminocarbonyl-2,15-dioxo-3,16-diaza-tricyclo[14.3.0.0^{4,6}]nonadec-7-ene-14-yl carbamate was synthesized according to the same procedures as described in Example 1 of Section XII, substituting cyclopropanesulfonamide with (4-methoxylphenyl)sulfamide in Step E instead. MS (APCI−) m/z 632.3 (M−1).

Example 15-45

Compound 2245

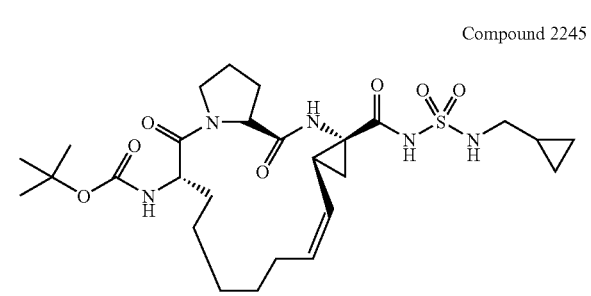

(1S,4R,6S,14S)tert-Butyl 4-(cyclopropylmethylsulfamoyl)-aminocarbonyl-2,15-dioxo-3,16-diaza-tricyclo[14.3.0.0^{4,6}]nonadec-7-ene-14-yl carbamate was synthesized according to the same procedures as described in Example 1 of Section XII, substituting cyclopropanesulfonamide with N-((cyclopropyl)methyl)sulfamide in Step E instead. $^1$H NMR (500 MHz, d$^6$-DMSO) δ 10.64 (s, 1H), 8.72 (s, 1H), 7.71 (t, 1H), 6.97 (d, 1H), 5.52 (q, 1H), 5.00 (t, 1H), 4.28-4.07 (m, 2H), 3.92-3.79 (m, 1H), 3.61-3.48 (m, 1H), 2.77-2.56 (m, 2H), 2.45-2.33 (m, 1H), 2.21-2.02 (m, 3H), 1.96-1.61 (m, 4H), 1.57 (t, 1H), 1.50-1.06 (m, 17H), 0.96-0.83 (m, 1H), 0.40 (q, 2H), 0.10 (q, 2H). MS (APCI−) m/z 580.3 (M−1).

Example 15-46

Compound 2246

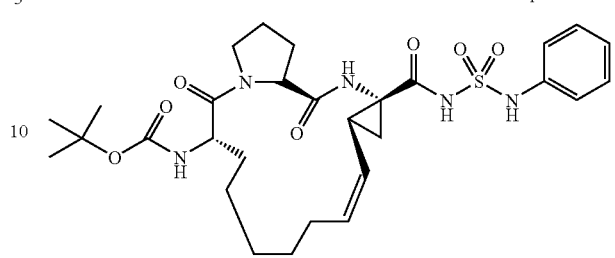

(1S,4R,6S,14S)tert-Butyl 4-phenylsulfamoylaminocarbonyl-2,15-dioxo-3,16-diaza-tricyclo[14.3.0.0^{4,6}]nonadec-7-ene-14-yl carbamate was synthesized according to the same procedures as described in Example 1 of Section II, substituting cyclopropanesulfonamide with phenylsulfamide in Step E instead. MS (APCI−) m/z 602.3 (M−1).

Example 15-47

Compound 2247

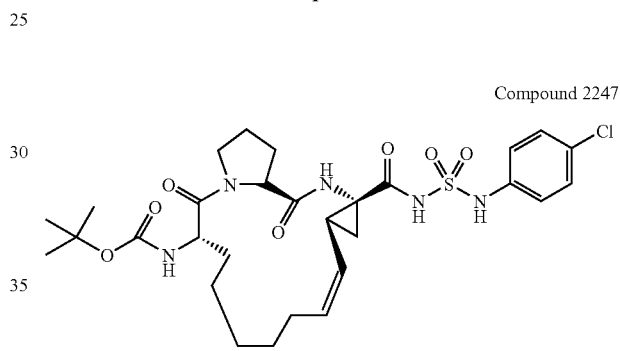

(1S,4R,6S,14S)tert-Butyl 4-((4-chlorophenyl)1sulfamoyl)-aminocarbonyl-2,15-dioxo-3,16-diaza-tricyclo[14.3.0.0^{4,6}]nonadec-7-ene-14-yl carbamate was synthesized according to the same procedures as described in Example 1 of Section XII, substituting cyclopropanesulfonamide with (4-chlorophenyl)sulfamide in Step E instead. $^1$H NMR (500 MHz, d$^6$-DMSO) δ 11.22 (br s, 1H), 10.62 (s, 1H), 8.72 (br s, 1H), 7.34 (d, 2H), 7.12 (d, 2H), 5.23 (q, 1H), 4.65 (t, 1H), 4.22-4.10 (m, 2H), 3.89-3.80 (m, 1H), 3.60-3.49 (m, 1H), 2.24-2.13 (m, 1H), 2.13-2.02 (m, 3H), 1.92-1.78 (m, 2H), 1.76-1.59 (m, 2H), 1.48 (t, 2H), 1.44-1.04 (m, 17H). MS (APCI−) m/z 637.2 (M−1).

Example 15-48

Compound 2248

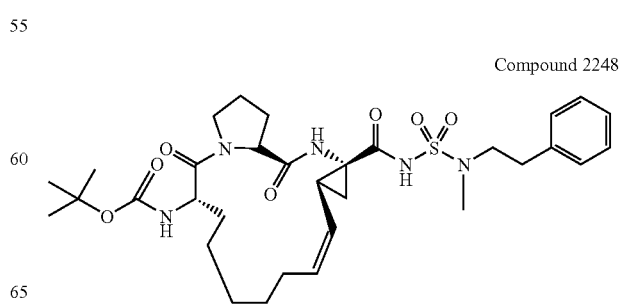

(1S,4R,6S,14S)tert-Butyl 4-methyl(phenethyl)sulfamoyl aminocarbonyl-2,15-dioxo-3,16-diaza-tricyclo[14.3.0.0$^{4,6}$] nonadec-7-ene-14-yl carbamate was synthesized according to the same procedures as described in Example 1 of Section XII, substituting cyclopropanesulfonamide with N,N-methyl (phenethyl)sulfamide in Step E instead. MS (APCI−) m/z 644.3 (M−1).

Example 15-49

Compound 2249

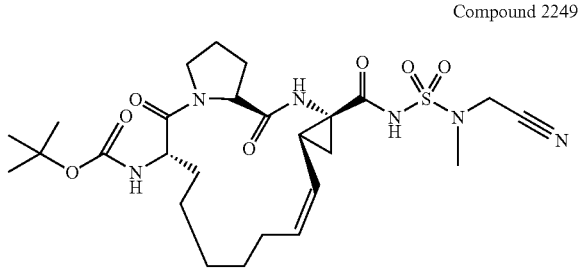

(1S,4R,6S,14S)tert-Butyl 4-methyl(cyanomethyl)sulfamoyl aminocarbonyl-2,15-dioxo-3,16-diaza-tricyclo [14.3.0.0$^{4,6}$]nonadec-7-ene-14-yl carbamate was synthesized according to the same procedures as described in Example 1 of Section XII, substituting cyclopropanesulfonamide with N,N-methyl(cyanomethyl)sulfamide in Step E instead. MS (APCI−) m/z 579.3 (M−1).

Example 15-50

Compound 2250

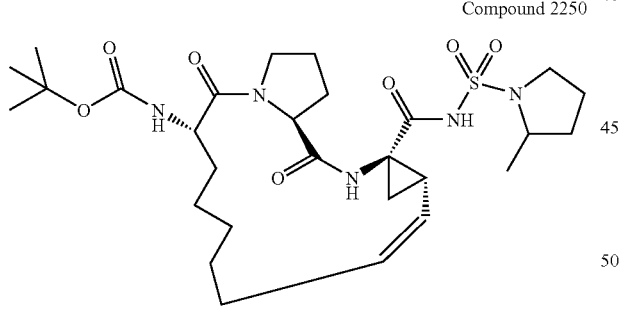

(1S,4R,6S,14S)tert-Butyl 4-(2-methylpyrrolidine-1-sulfonyl)aminocarbonyl-2,15-dioxo-3,16-diaza-tricyclo [14.3.0.0$^{4,6}$]nonadec-7-ene-14-yl carbamate was synthesized according to the same procedures as described in Example 1 of Section XII, substituting cyclopropanesulfonamide with (2-methylpyrrolidino)sulfamide in Step E instead. $^1$H NMR (d$^6$-Acetone, 400 MHz) δ1.17-2.06 (m, 29H), 2.21-2.27 (m, 2H), 2.36-2.42 (m, 1H), 2.49-2.56 (m, 1H), 3.13-3.36 (m, 1H), 3.63-4.05 (m, 3H), 4.30-4.44 (m, 3H), 4.98 (t, 1H), 5.67 (q, 1H), 5.97 (br d, 1H), 8.28 (br s, 1H), 10.36 (br s, 1H). MS (APCI−) m/z 594.3 (M−1).

Example 15-51

Compound 2251

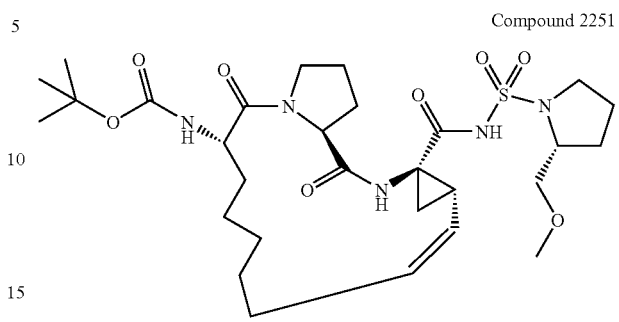

(1S,4R,6S,14S)tert-Butyl 4-(2R-(methoxymethyl)pyrrolidine-1-sulfonyl)aminocarbonyl-2,15-dioxo-3,16-diaza-tricyclo[14.3.0.0$^{4,6}$]nonadec-7-ene-14-yl carbamate was synthesized according to the same procedures as described in Example 1 of Section XII, substituting cyclopropanesulfonamide with (2-(methoxymethyl)pyrrolidino)sulfamide in Step E instead. $^1$H NMR (d$^6$-Acetone, 400 MHz) δ1.25-2.09 (m, 26H), 2.19-2.26 (m, 2H), 2.38-2.42 (m, 1H), 2.50-2.60 (m, 1H), 3.09-3.15 (m, 1H), 3.25-3.30 (m, 5H), 3.40-3.43 (m, 1H), 3.63-3.69 (m, 1H), 4.03-4.06 (m, 1H), 4.31-4.51 (m, 3H), 4.99 (t, 1H), 5.69 (q, 1H), 6.00 (br d, 1H), 8.35 (br s, 1H), 10.42 (br s, 1H). MS (APCI−) m/z 624.3 (M−1).

Example 15-52

Compound 2252

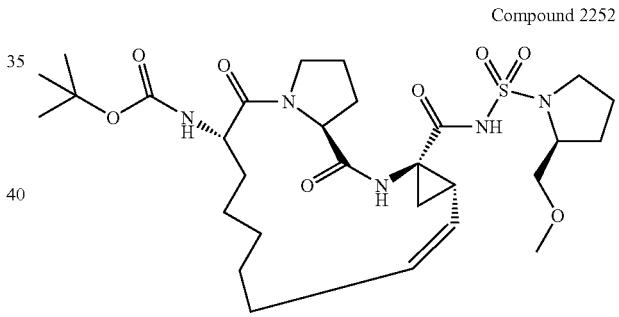

(1S,4R,6S,14S)tert-Butyl 4-(2S-(methoxymethyl)pyrrolidine-1-sulfonyl)aminocarbonyl-2,15-dioxo-3,16-diaza-tricyclo[14.3.0.0$^{4,6}$]nonadec-7-ene-14-yl carbamate was synthesized according to the same procedures as described in Example 1 of Section XII, substituting cyclopropanesulfonamide with (2S-(methoxymethyl)pyrrolidino)sulfamide in Step E instead. $^1$H NMR (d$^6$-Acetone, 400 MHz) δ1.20-1.55 (m, 18H), 1.67-1.70 (m, 1H), 1.78-2.07 (m, 7H), 2.19-2.27 (m, 2H), 2.35-2.42 (m, 1H), 2.49-2.56 (m, 1H), 3.27-3.34 (m, 5H), 3.48-3.52 (m, 1H), 3.64-3.70 (m, 1H), 3.77-3.86 (m, 2H), 4.02-4.04 (m, 1H), 4.31-4.40 (m, 2H), 4.99 (t, 1H), 5.64-5.70 (m, 1H), 5.96 (br d, 1H), 8.30 (br s, 1H), 10.53 (br s, 1H). MS (APCI−) m/z 624.3 (M−1).

Preparation of NS3 Inhibitors

Section XIV

The NS3 inhibitors in this section can be synthesized with a similar fashion as described in Scheme 1, Section XII of the inhibitor synthesis, substituting the sulfonamide in the last coupling step with an amine instead.

Example 16-1

Compound 2302

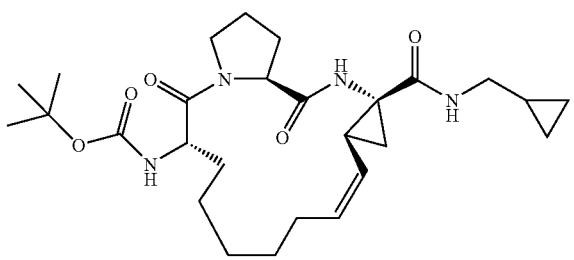

(1S,4R,6S,14S)tert-Butyl 4-(cyclopropyl(methyl))aminocarbonyl-2,15-dioxo-3,16-diaza-tricyclo[14.3.0.0$^{4,6}$]nonadec-7-ene-14-yl carbamate was synthesized according to the procedures as described below:

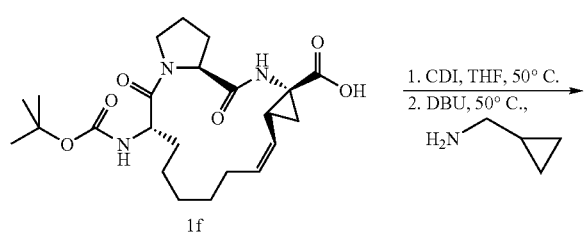

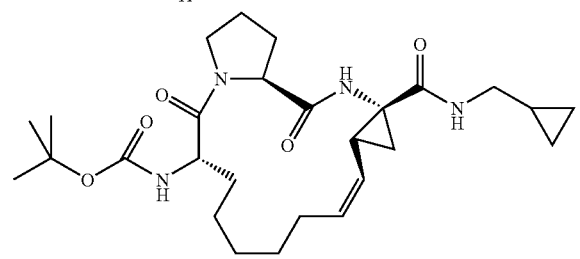

Compound 1f (30 mg, 0.07 mmol) is taken up in THF (DriSolve, 0.5 mL) and carbonyldiimidazole (CDI, 1.05 equiv.) is then added. The reaction is heated to 50° C. and stirred for an hour at this temperature. Next, the amine (2 equiv.) is added followed by DBU (2 equiv.). The reaction is then stirred at 50° C. overnight. The reaction is then concentrated and taken back up in EtOAc (2 mL) and washed with 1 N NaOH, 1 N HCl, and brine before drying the organic over Na$_2$SO$_4$. The EtOAc solution is then concentrated to give the desired amide in good purity. MS (APCI-) m/z 501.2 (M-1).

Example 16-2

Compound 2301

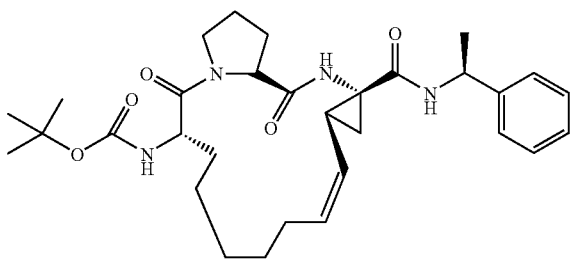

(1S,4R,6S,14S)tert-Butyl 4-(1S-phenylethanamino)carbonyl-2,15-dioxo-3,16-diaza-tricyclo[14.3.0.0$^{4,6}$]nonadec-7-ene-14-yl carbamate was synthesized according to the same procedures as described in Example 1 of Section XIV, substituting cyclopropylmethanamine with (S)-1-phenylethanamine instead. MS (APCI-) m/z 551.2 (M-1).

Example 16-3

Compound 2303

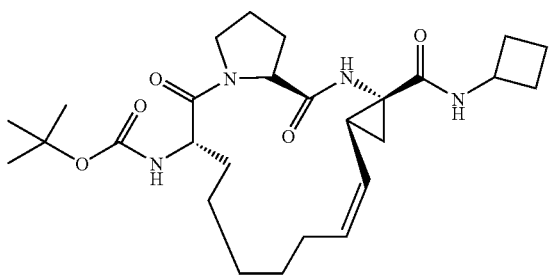

(1S,4R,6S,14S)tert-Butyl 4-(cyclobutylamino)carbonyl-2,15-dioxo-3,16-diaza-tricyclo[14.3.0.0$^{4,6}$]nonadec-7-ene-14-yl carbamate was synthesized according to the same procedures as described in Example 1 of Section XIV, substituting cyclopropylmethanamine with cyclobutylamine instead. MS (APCI-) m/z 501.1 (M-1).

Example 16-4

Compound 2304

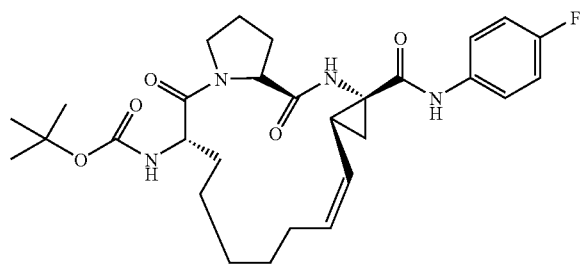

(1S,4R,6S,14S)tert-Butyl 4-((4-fluorophenyl)amino)carbonyl-2,15-dioxo-3,16-diaza-tricyclo[14.3.0.0$^{4,6}$]nonadec-7-ene-14-yl carbamate was synthesized according to the same procedures as described in Example 1 of Section XIV, substituting cyclopropylmethanamine with 4-fluoroaniline instead. MS (APCI-) m/z 541.2 (M-1).

Example 16-5

Compound 305

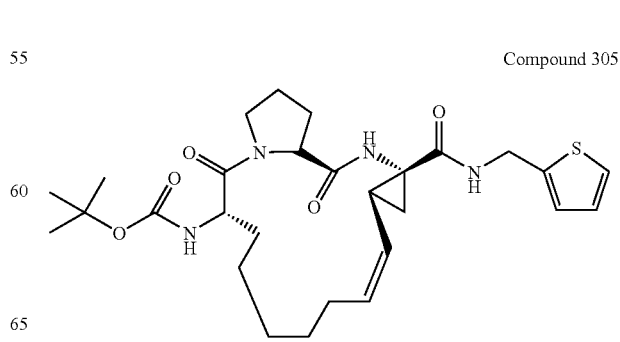

(1S,4R,6S,14S)tert-Butyl 4-((thiophen-2-yl-methanamino)carbonyl-2,15-dioxo-3,16-diaza-tricyclo[14.3.0.0⁴,⁶]nonadec-7-ene-14-yl carbamate was synthesized according to the same procedures as described in Example 1 of Section XIV, substituting cyclopropylmethanamine with thiophen-2-ylmethanamine instead. MS (APCI−) m/z 543.1 (M−1).

Example 16-6

Compound 2306

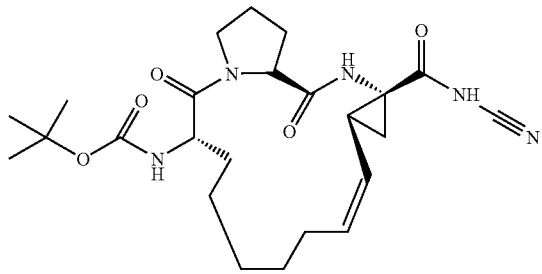

(1S,4R,6S,14S)tert-Butyl 4-cyanamidocarbonyl-2,15-dioxo-3,16-diaza-tricyclo[14.3.0.0⁴,⁶]nonadec-7-ene-14-yl carbamate was synthesized according to the same procedures as described in Example 1 of Section XIV, substituting cyclopropylmethanamine with cyanamide instead. MS (APCI−) m/z 472.1 (M−1).

Example 16-7

Compound 2307

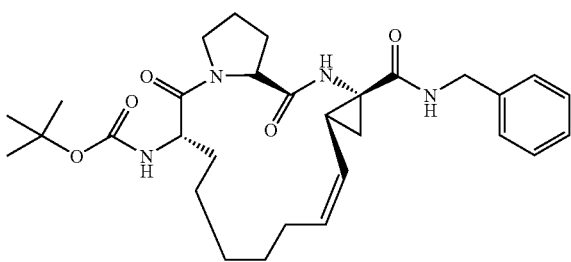

(1S,4R,6S,14S)tert-Butyl 4-benzylaminocarbonyl-2,15-dioxo-3,16-diaza-tricyclo[14.3.0.0⁴,⁶]nonadec-7-ene-14-yl carbamate was synthesized according to the same procedures as described in Example 1 of Section XIV, substituting cyclopropylmethanamine with benzylamine instead. MS (APCI+) m/z 439.2 (M-Boc+1).

Example 16-8

Compound 2308

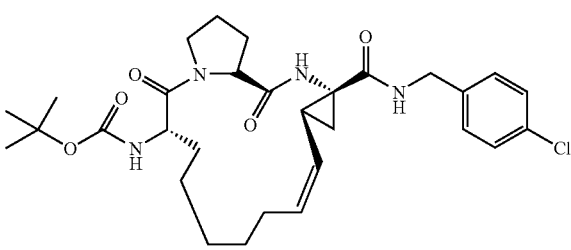

(1S,4R,6S,14S)tert-Butyl 4-((4-chlorophenyl)methanamino)-carbonyl-2,15-dioxo-3,16-diaza-tricyclo[14.3.0.0⁴,⁶]nonadec-7-ene-14-yl carbamate was synthesized according to the same procedures as described in Example 1 of Section XIV, substituting cyclopropylmethanamine with (4-chlorophenyl)methanamine instead. MS (APCI−) m/z 572.1 (M−1).

Example 16-9

Compound 2309

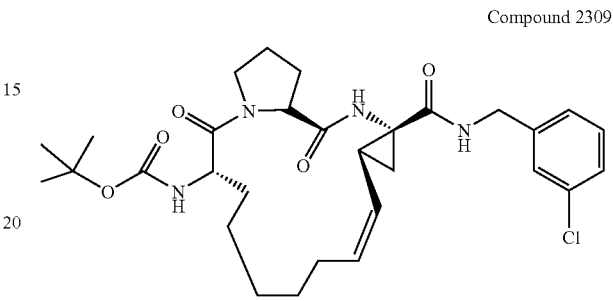

(1S,4R,6S,14S)tert-Butyl 4-((2-chlorobenzenamino)-carbonyl-2,15-dioxo-3,16-diaza-tricyclo[14.3.0.0⁴,⁶]nonadec-7-ene-14-yl carbamate was synthesized according to the same procedures as described in Example 1 of Section XIV, substituting cyclopropylmethanamine with 2-chlorobenzenamine instead. MS (APCI−) m/z 558.2 (M−1).

Example 16-10

Compound 2310

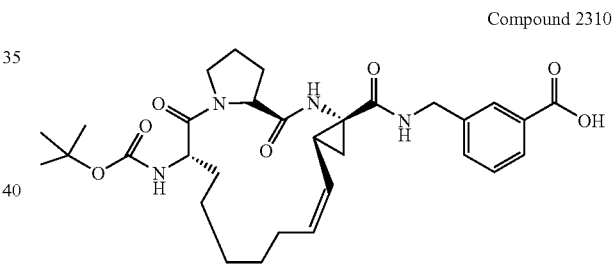

(1S,4R,6S,14S)tert-Butyl 4-((3-carboxylicacidphenyl)methanamino)-carbonyl-2,15-dioxo-3,16-diaza-tricyclo[14.3.0.0⁴,⁶]nonadec-7-ene-14-yl carbamate was synthesized according to the same procedures as described in Example 1 of Section XIV, substituting cyclopropylmethanamine with 3-(aminomethyl)benzoic acid instead. MS (APCI−) m/z 581.2 (M−1).

Example 16-11

Compound 2311

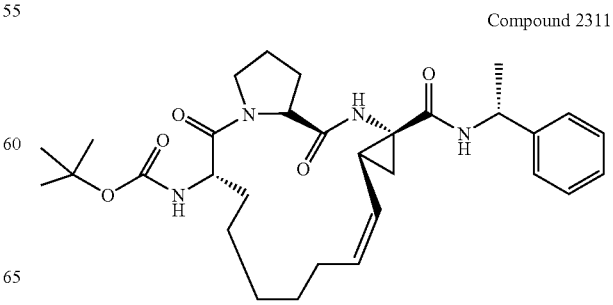

(1S,4R,6S,14S)tert-Butyl 4-(1R-phenylethanamino)-carbonyl-2,15-dioxo-3,16-diaza-tricyclo[14.3.0.0$^{4,6}$]nonadec-7-ene-14-yl carbamate was synthesized according to the same procedures as described in Example 1 of Section XIV, substituting cyclopropylmethanamine with (R)-1-phenylethanamine instead. MS (APCI−) m/z 551.2 (M−1).

Example 16-12

Compound 2312

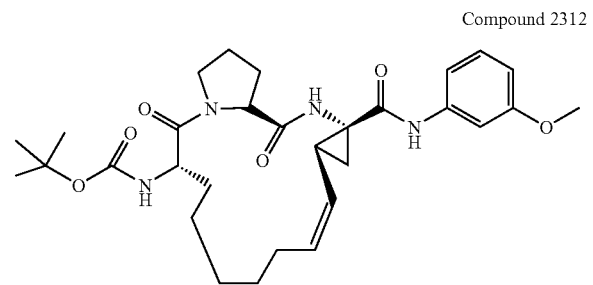

(1S,4R,6S,14S)tert-Butyl 4-(3-methoxybenzenamino)-carbonyl-2,15-dioxo-3,16-diaza-tricyclo[14.3.0.0$^{4,6}$]nonadec-7-ene-14-yl carbamate was synthesized according to the same procedures as described in Example 1 of Section XIV, substituting cyclopropylmethanamine with 3-methoxybenzenamine instead. MS (APCI−) m/z 553.2 (M−1).

Example 16-13

Compound 2313

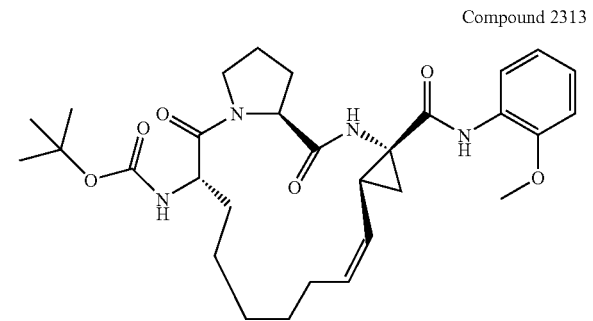

(1S,4R,6S,14S)tert-Butyl 4-(2-methoxybenzenamino)-carbonyl-2,15-dioxo-3,16-diaza-tricyclo[14.3.0.0$^{4,6}$]nonadec-7-ene-14-yl carbamate was synthesized according to the same procedures as described in Example 1 of Section XIV, substituting cyclopropylmethanamine with 2-methoxybenzenamine instead. MS (APCI−) m/z 553.2 (M−1).

Example 16-14

Compound 2314

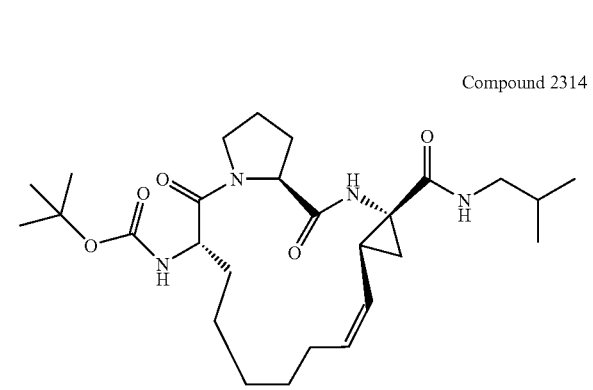

(1S,4R,6S,14S)tert-Butyl 4-(2-methylpropan-1-amino)-carbonyl-2,15-dioxo-3,16-diaza-tricyclo[14.3.0.0$^{4,6}$]nonadec-7-ene-14-yl carbamate was synthesized according to the same procedures as described in Example 1 of Section XIV, substituting cyclopropylmethanamine with 2-methylpropan-1-amine instead. MS (APCI−) m/z 503.2 (M−1).

Example 16-15

Compound 2315

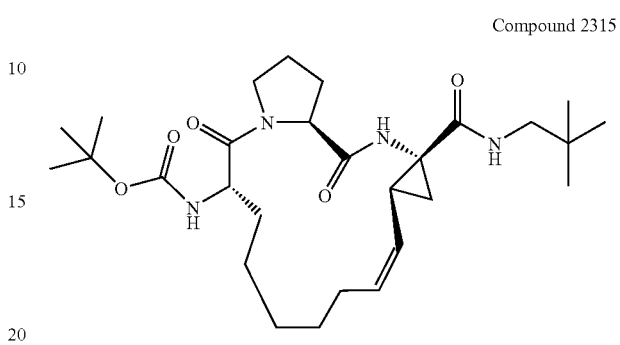

(1S,4R,6S,14S)tert-Butyl 4-(2,2-dimethylpropan-1-amino)-carbonyl-2,15-dioxo-3,16-diaza-tricyclo[14.3.0.0$^{4,6}$]nonadec-7-ene-14-yl carbamate was synthesized according to the same procedures as described in Example 1 of Section XIV, substituting cyclopropylmethanamine with 2,2-dimethylpropan-1-amine instead. MS (APCI−) m/z 517.2 (M−1).

Example 16-16

Compound 2316

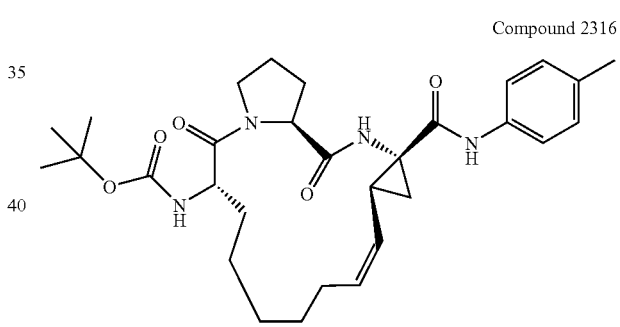

(1S,4R,6S,14S)tert-Butyl 4-(p-toluidino)carbonyl-2,15-dioxo-3,16-diaza-tricyclo[14.3.0.0$^{4,6}$]nonadec-7-ene-14-yl carbamate was synthesized according to the same procedures as described in Example 1 of Section XIV, substituting cyclopropylmethanamine with p-toluidine instead. MS (APCI−) m/z 537.2 (M−1).

Example 16-17

Compound 2317

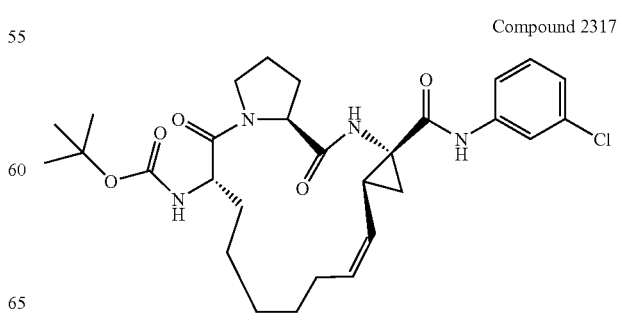

(1S,4R,6S,14S)tert-Butyl 4-(3-chlorobenzenamino)carbonyl-2,15-dioxo-3,16-diaza-tricyclo[14.3.0.0⁴,⁶]nonadec-7-ene-14-yl carbamate was synthesized according to the same procedures as described in Example 1 of Section XIV, substituting cyclopropylmethanamine with 3-chlorobenzenamine instead. MS (APCI−) m/z 558.2 (M−1).

Example 16-18

Compound 2318

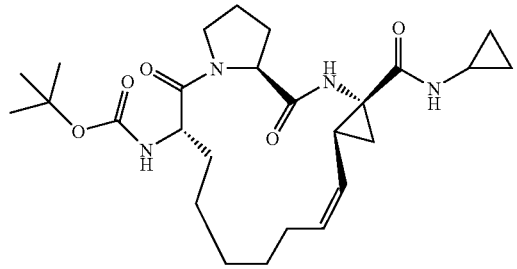

(1S,4R,6S,14S)tert-Butyl 4-cyclopropanaminocarbonyl-2,15-dioxo-3,16-diaza-tricyclo[14.3.0.0⁴,⁶]nonadec-7-ene-14-yl carbamate was synthesized according to the same procedures as described in Example 1 of Section XIV, substituting cyclopropylmethanamine with cyclopropanamine instead. MS (APCI−) m/z 487.2 (M−1).

Example 16-19

Compound 2319

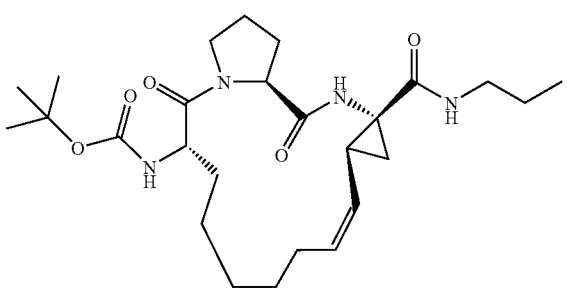

(1S,4R,6S,14S)tert-Butyl 4-(propan-1-amino)carbonyl-2,15-dioxo-3,16-diaza-tricyclo[14.3.0.0⁴,⁶]nonadec-7-ene-14-yl carbamate was synthesized according to the same procedures as described in Example 1 of Section XIV, substituting cyclopropylmethanamine with propan-1-amine instead. MS (APCI+) m/z 391.1 (M-Boc+1).

Example 16-20

Compound 2320

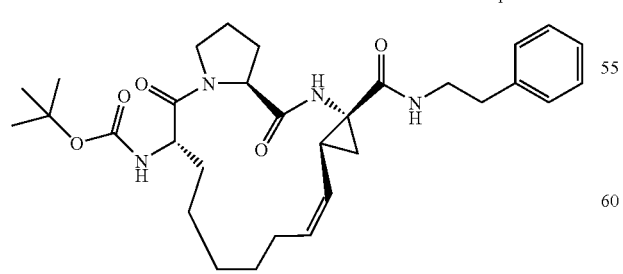

(1S,4R,6S,14S)tert-Butyl 4-(2-phenylethanamino)carbonyl-2,15-dioxo-3,16-diaza-tricyclo[14.3.0.0⁴,⁶]nonadec-7-ene-14-yl carbamate was synthesized according to the same procedures as described in Example 1 of Section XIV, substituting cyclopropylmethanamine with 2-phenylethanamine instead. MS (APCI−) m/z 551.2 (M−1).

Example 16-21

Compound 2321

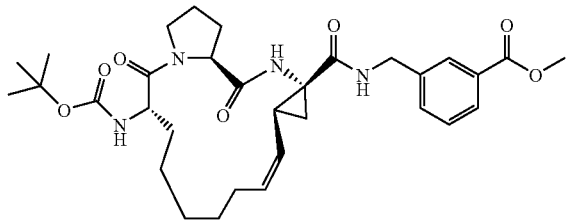

(1S,4R,6S,14S)tert-Butyl 4-((3-methylcarboxylate)phenyl)-methanamino)carbonyl-2,15-dioxo-3,16-diaza-tricyclo[14.3.0.0⁴,⁶]nonadec-7-ene-14-yl carbamate was synthesized according to the same procedures as described in Example 1 of Section XIV, substituting cyclopropylmethanamine with methyl 3-(aminomethyl)benzoate instead. MS (APCI−) m/z 595.2 (M−1).

Example 16-22

Compound 2322

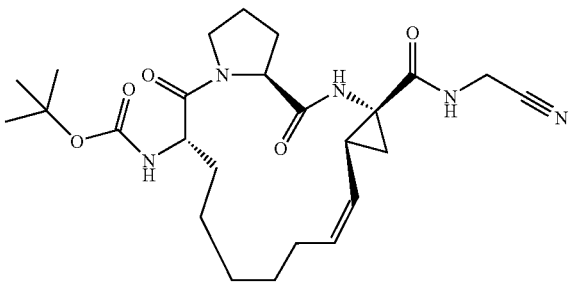

(1S,4R,6S,14S)tert-Butyl 4-cyanomethanaminocarbonyl-2,15-dioxo-3,16-diaza-tricyclo[14.3.0.0⁴,⁶]nonadec-7-ene-14-yl carbamate was synthesized according to the same procedures as described in Example 1 of Section XIV, substituting cyclopropylmethanamine with 2-aminoacetonitrile instead. MS (APCI−) m/z 486.2 (M−1).

Preparation of NS3 Inhibitors

Section XV

The NS3 inhibitors in this section can be synthesized with a similar fashion as described in Scheme 1, Section XII of the inhibitor synthesis, substituting the sulfonamide in the last coupling step with a sulfinamide instead.

Example 17-1

Compound 2401

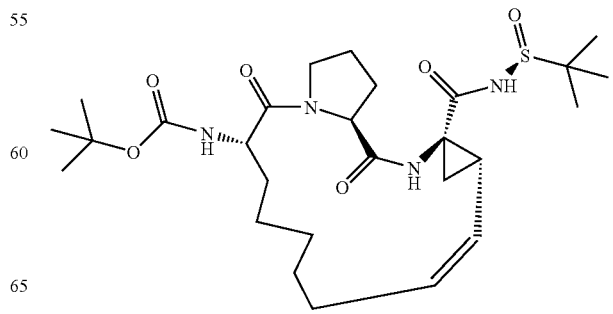

(1S,4R,6S,14S)tert-Butyl 4-((S)-2-methylpropane-2-sulfinyl)-aminocarbonyl-2,15-dioxo-3,16-diaza-tricyclo[14.3.0.0^{4,6}]nonadec-7-ene-14-yl carbamate was synthesized according to the same procedures as described in the synthesis of Compound (Example 1, Section XII), substituting cyclopropanesulfonamide with (S)-2-methylpropane-2-sulfinamide in the last coupling step instead. $^1$H NMR (d$^6$-Acetone, 400 MHz) δ1.25-1.53 (m, 9H), 1.20 (s, 9H), 1.40 (s, 9H), 1.65-1.68 (m, 1H), 1.82-2.06 (m, 3H), 2.19-2.34 (m, 3H), 2.46-2.50 (m, 1H), 3.64-3.70 (m, 1H), 3.97-3.99 (m, 1H), 4.33-4.41 (m, 2H), 4.89-4.94 (m, 1H), 5.58 (q, 1H), 5.93 (br d, 1H), 8.33 (br s, 1H), 9.57 (br s, 1H). MS (APCI−) m/z 551.2 (M−1). Scheme below labels Compound 2401 as Compound 401.

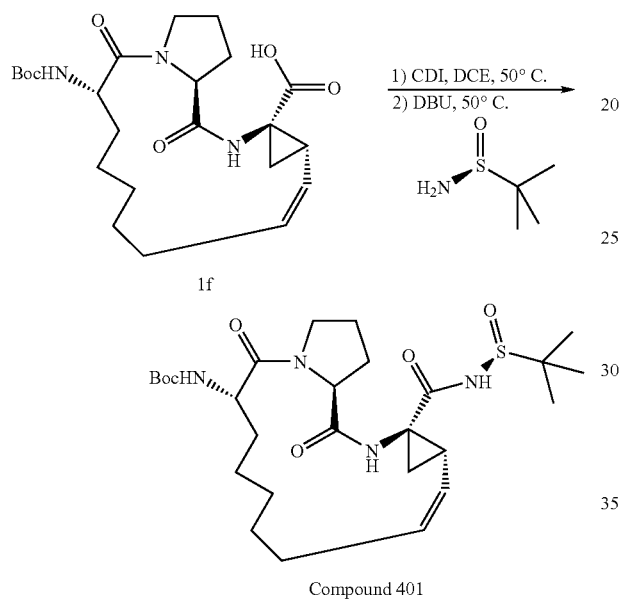

Compound 401

Example 17-2

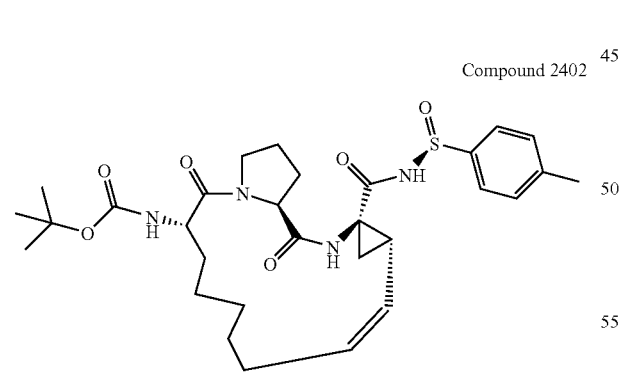

Compound 2402

(1S,4R,6S,14S)tert-Butyl 4-((S)-4-methylbenzenesulfinyl)-aminocarbonyl-2,15-dioxo-3,16-diaza-tricyclo[14.3.0.0^{4,6}]nonadec-7-ene-14-yl carbamate was synthesized according to the same procedures as described in the synthesis of Compound 2401, substituting (S)-2-methylpropane-2-sulfinamide with (S)-4-methylbenzenesulfinamide instead. $^1$H NMR (d$^6$-Acetone, 400 MHz) δ1.20-1.56 (m, 18H), 1.62-1.65 (m, 1H), 1.77-1.88 (m, 4H), 2.03-2.10 (m, 1H), 2.28-2.33 (m, 2H), 2.43 (s, 3H), 3.54-3.60 (m, 1H), 3.88-3.91 (m, 1H), 4.28-4.33 (m, 2H), 5.16 (t, 1H), 5.64 (q, 1H), 5.93 (br d, 1H), 7.41 (d, 2H), 7.56 (d, 2H), 8.16 (br s, 1H), 9.96 (br s, 1H). MS (APCI−) m/z 585.2 (M−1).

Example 17-3

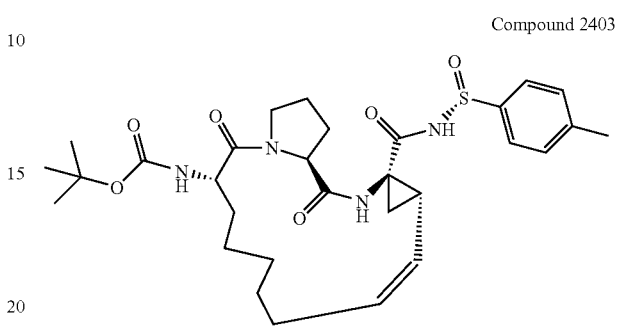

Compound 2403

(1S,4R,6S,14S)tert-Butyl 4-((R)-4-methylbenzenesulfinyl)-aminocarbonyl-2,15-dioxo-3,16-diaza-tricyclo[14.3.0.0^{4,6}]nonadec-7-ene-14-yl carbamate was synthesized according to the same procedures as described in the synthesis of Compound 2401, substituting (S)-2-methylpropane-2-sulfinamide with (R)-4-methylbenzenesulfinamide instead. $^1$H NMR (d$^6$-Acetone, 400 MHz) δ1.20-1.49 (m, 18H), 1.62-2.10 (m, 6H), 2.24-2.31 (m, 2H), 2.44 (s, 3H), 3.49-3.55 (m, 1H), 3.77-3.83 (m, 1H), 4.29-4.34 (m, 2H), 5.00 (t, 1H), 5.56-5.63 (m, 1H), 5.88 (br d, 1H), 7.43 (d, 2H), 7.60 (d, 2H), 8.24 (br s, 1H), 9.98 (br s, 1H). MS (APCI−) m/z 585.2 (M−1).

Example 17-4

Compound 2404

(1S,4R,6S,14S)tert-Butyl 4-((R)-2-methylpropane-2-sulfinyl)-aminocarbonyl-2,15-dioxo-3,16-diaza-tricyclo[14.3.0.0^{4,6}]nonadec-7-ene-14-yl carbamate was synthesized according to the same procedures as described in the synthesis of Compound 2401, substituting (S)-2-methylpropane-2-sulfinamide with (R)-2-methylpropane-2-sulfinamide instead. $^1$H NMR (d$^6$-Acetone, 400 MHz) δ1.20-1.46 (m, 27H), 1.65-1.68 (m, 1H), 1.80-2.09 (m, 3H), 2.22-2.48 (m, 4H), 3.67-3.73 (m, 1H), 3.94-3.99 (m, 1H), 4.33-4.43 (m, 2H), 4.91 (t, 1H), 5.59 (q, 1H), 5.95 (br d, 1H), 8.38 (br s, 1H), 9.69 (br s, 1H). MS (APCI) m/z 551.2 (M−1).

Preparation of NS3 Inhibitors

Section XVI

The NS3 inhibitors in this section can be synthesized with a similar fashion as described in the synthesis of Compound 2302 (Example 1, Inhibitor Synthesis Section XV), substituting the (1S,4R,6S,14S) 14-tert-Butoxycarbonylamino-2,15-dioxo-3,16-diaza-tricyclo[14.3.0.0$^{4,6}$]nonadec-7-ene-4-carboxylic acid (1f) in the coupling step with (1S,4R,6S,14S,18R)-14-tert-Butoxycarbonylamino-18-(1,3-dihydro-isoindole-2-carbonyloxyl)-2,15-dioxo-3,16-diaza-tricyclo [14.3.0.0$^{4,6}$]nonadec-7-ene-4-carboxylic acid (5a) instead.

Example 18-1

Compound 2501

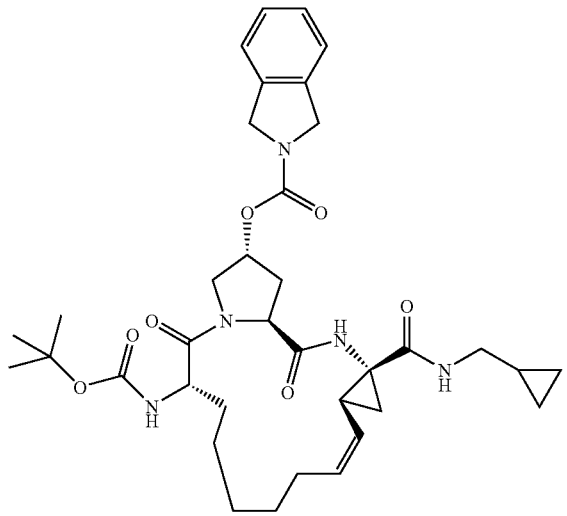

(1S,4R,6S,14S,18R)-1,3-Dihydro-isoindole-2-carbonyloxylic acid 14-tert-butoxycarbonylamino-4-cyclopropylmethanaminocarbonyl-2,15-dioxo-3,16-diaza-tricyclo [14.3.0.0$^{4,6}$]nonadec-7-ene-18-yl ester was synthesized according to the procedures as described below:

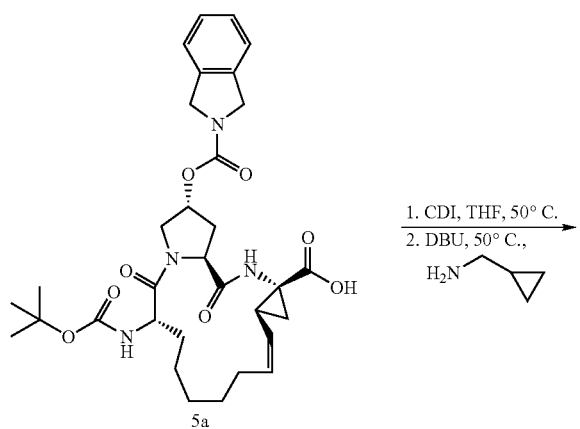

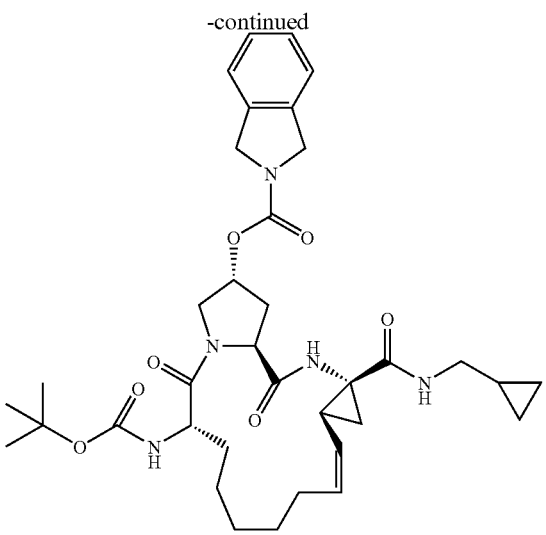

Compound 5a (30 mg, 0.05 mmol) is taken up in THF (DriSolve, 0.3 mL) and carbonyldiimidazole (CDI, 1.05 equiv.) is then added. The reaction is heated to 50° C. and stirred for an hour at this temperature. Next, the amine (2 equiv.) is added followed by DBU (2 equiv.). The reaction is then stirred at 50° C. overnight. The reaction is then concentrated and taken back up in EtOAc (2 mL) and washed with 1 N NaOH, 1 N HCl, and brine before drying the organic over Na$_2$SO$_4$. The EtOAc solution is then concentrated to give the desired amide in good purity. MS (APCI−) m/z 662.1 (M−1).

The synthesis of compound 5a has been described by us in details elsewhere (International Application No. PCT/US2004/033970, International Publication No. WO2005/037214; Compound AR00291871, Example 1-5).

Example 18-2

Compound 2502

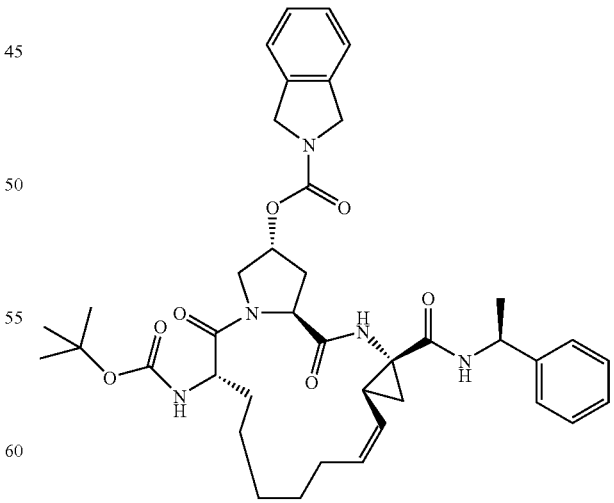

(1S,4R,6S,14S,18R)-1,3-Dihydro-isoindole-2-carbonyloxylic acid 14-tert-butoxycarbonylamino-4-((S)-1-phenylethanamino)carbonyl-2,15-dioxo-3,16-diaza-tricyclo [14.3.0.0$^{4,6}$]nonadec-7-ene-18-yl ester was synthesized according to the same procedures as described in the synthesis of Compound 2501, substituting cyclopropylmethanamine with (S)-1-phenylethanamine instead. MS (APCI−) m/z 712.2 (M−1).

Preparation of NS3 Inhibitors

Section XVII

Example 19-1

Compound 2601

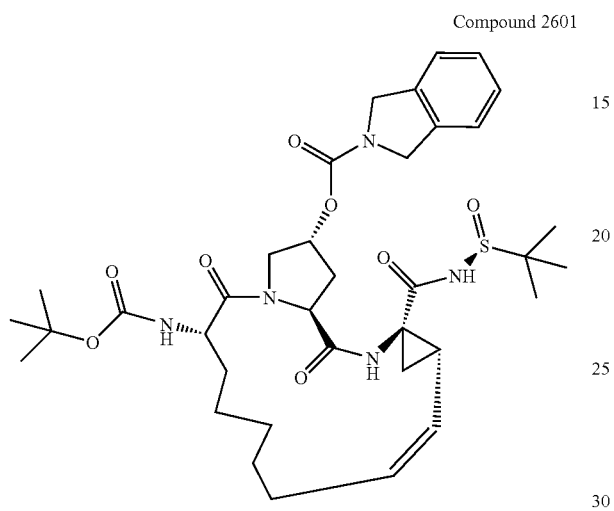

(1S,4R,6S,14S,18R)-1,3-Dihydro-isoindole-2-carbonyloxylic acid 14-tert-butoxycarbonylamino-4-((S)-2-methylpropane-2-sulfinyl)aminocarbonyl-2,15-dioxo-3,16-diaza-tricyclo[14.3.0.0$^{4,6}$]nonadec-7-ene-18-yl ester was synthesized with a similar fashion as described in the synthesis of Compound 2401 (Example 1, Inhibitor Synthesis Section XV), substituting the (1S,4R,6S,14S) 14-tert-Butoxycarbonylamino-2,15-dioxo-3,16-diaza-tricyclo[14.3.0.0$^{4,6}$]nonadec-7-ene-4-carboxylic acid (1f) in the coupling step with (1S,4R,6S,14S,18R)-14-tert-Butoxycarbonylamino-18-(1,3-dihydro-isoindole-2-carbonyloxyl)-2,15-dioxo-3,16-diaza-tricyclo[14.3.0.0$^{4,6}$]nonadec-7-ene-4-carboxylic acid (5a) instead. $^1$H NMR (d$^6$-Acetone, 400 MHz) δ1.15-1.55 (m, 26H), 1.69-1.88 (m, 3H), 2.35-2.52 (m, 3H), 2.65-2.68 (m, 1H), 3.84-3.87 (m, 1H), 4.14-4.18 (m, 1H), 4.47 (d, 1H), 4.60-4.72 (m, 5H), 4.97 (t, 1H), 5.44 (br s, 1H), 5.60 (q, 1H), 6.10 (br d, 1H), 7.24-7.36 (m, 4H), 8.30 (br s, 1H), 9.49 (br s, 1H). MS (APCI−) m/z 712.2 (M−1). Scheme below labels Compound 2601 as Compound 601.

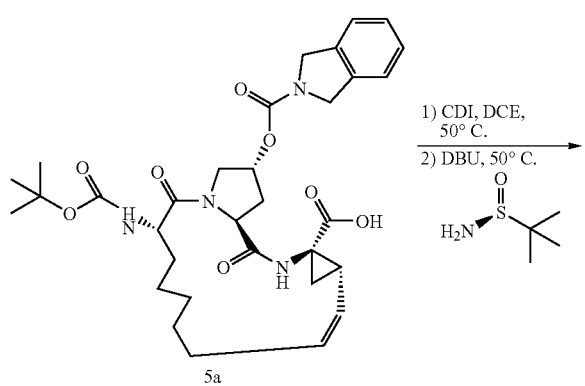

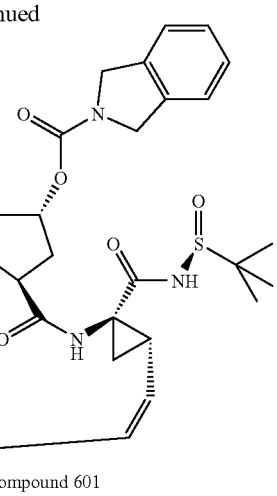

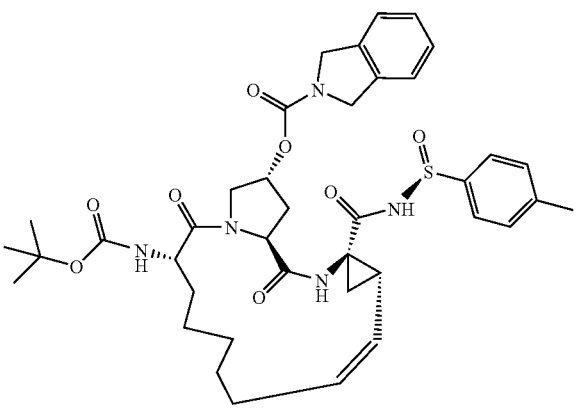

Compound 601

Example 19-2

Compound 2602

(1S,4R,6S,14S,18R)-1,3-Dihydro-isoindole-2-carbonyloxylic acid 14-tert-butoxycarbonylamino-4-((S)-4-methylbenzenesulfinyl)aminocarbonyl-2,15-dioxo-3,16-diaza-tricyclo[14.3.0.0$^{4,6}$]nonadec-7-ene-18-yl ester was synthesized with a similar fashion as described in the synthesis of Compound 2601, substituting the (S)-2-methylpropane-2-sulfinamide in the coupling with (S)-4-methylbenzenesulfinamide instead. $^1$H NMR (d$^6$-Acetone, 400 MHz) δ1.18-1.54 (m, 16H), 1.59-1.88 (m, 4H), 2.21-2.44 (m, 6H), 2.58-2.66 (m, 1H), 3.77-3.80 (m, 1H), 4.09-4.14 (m, 1H), 4.38 (br d, 1H), 4.49 (t, 1H), 4.56-4.70 (m, 4H), 5.21 (t, 1H), 5.36 (br s, 1H), 5.66 (q, 1H), 6.08 (br d, 1H), 7.21-7.35 (m, 4H), 7.42 (d, 2H), 7.55 (dd, 2H), 8.13 (br s, 1H). MS (APCI−) m/z 746.2 (M−1, 60), 608.1 (100).

Example 19-3

Compound 2603

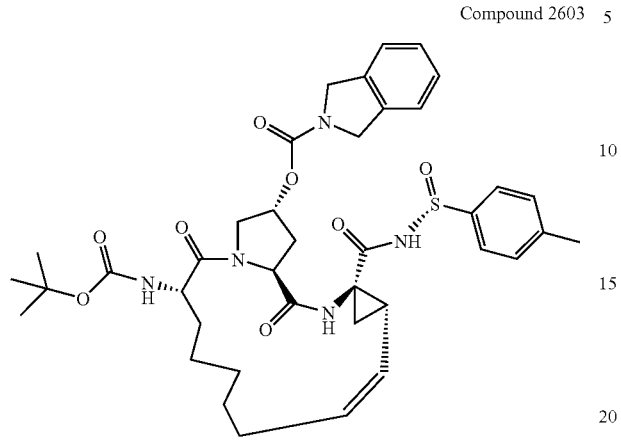

(1S,4R,6S,14S,18R)-1,3-Dihydro-isoindole-2-carbonyloxylic acid 14-tert-butoxycarbonylamino-4-((R)-4-methylbenzenesulfinyl)aminocarbonyl-2,15-dioxo-3,16-diaza-tricyclo[14.3.0.0^{4,6}]nonadec-7-ene-18-yl ester was synthesized with a similar fashion as described in the synthesis of Compound 2601, substituting the (S)-2-methylpropane-2-sulfinamide in the coupling with (R)-4-methylbenzenesulfinamide instead. $^1$H NMR (d$^6$-Acetone, 400 MHz) δ1.18-1.56 (m, 17H), 1.73-1.87 (m, 3H), 1.97-2.09 (m, 1H), 2.27-2.54 (m, 6H), 3.72-3.76 (m, 1H), 4.12-4.16 (m, 1H), 4.33 (br d, 1H), 4.52 (t, 1H), 4.59-4.68 (m, 4H), 5.03 (t, 1H), 5.28 (br s, 1H), 5.62 (q, 1H), 6.08 (br d, 1H), 7.23-7.36 (m, 4H), 7.43 (d, 2H), 7.59 (d, 2H), 8.24 (br s, 1H). MS (APCI–) m/z 746.3 (M–1, 70), 608.1 (100).

Example 19-4

Compound 2604

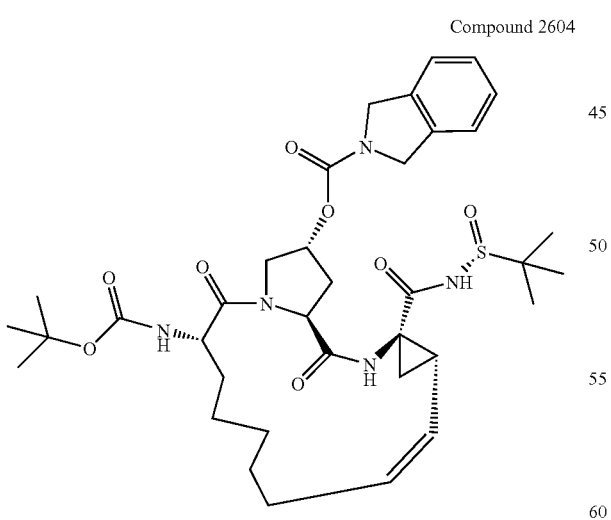

(1S,4R,6S,14S,18R)-1,3-Dihydro-isoindole-2-carbonyloxylic acid 14-tert-butoxycarbonylamino-4-((R)-2-methylpropane-2-sulfinyl)aminocarbonyl-2,15-dioxo-3,16-diaza-tricyclo[14.3.0.0^{4,6}]nonadec-7-ene-18-yl ester was synthesized with a similar fashion as described in the synthesis of Compound 2601, substituting the (S)-2-methylpropane-2-sulfinamide in the coupling with (R)-2-methylpropane-2-sulfinamide instead. $^1$H NMR (d$^6$-Acetone, 400 MHz) δ1.04-1.51 (m, 26H), 1.70-1.73 (m, 1H), 1.86-1.90 (m, 2H), 2.38-2.46 (m, 3H), 2.58-2.62 (m, 1H), 3.87-3.90 (m, 1H), 4.16-4.20 (m, 1H), 4.46 (d, 1H), 4.58-4.72 (m, 5H), 4.93 (t, 1H), 5.45 (br s, 1H), 5.63 (q, 1H), 6.10 (br d, 1H), 7.23-7.36 (m, 4H), 8.31 (br s, 1H). MS (APCI–) m/z 712.2 (M–1).

Example 20

Preparation of Azalactone

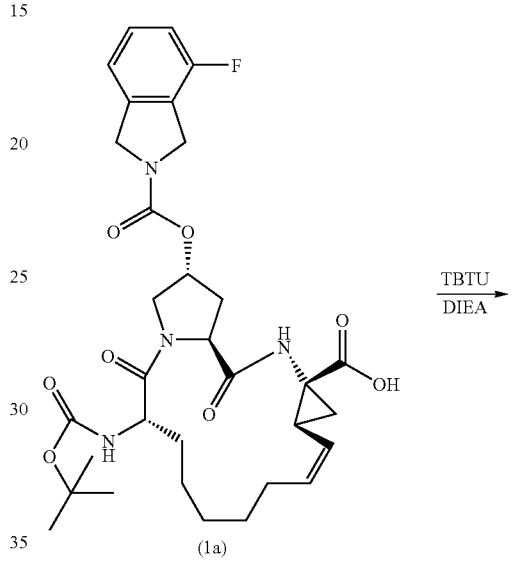

(1a)

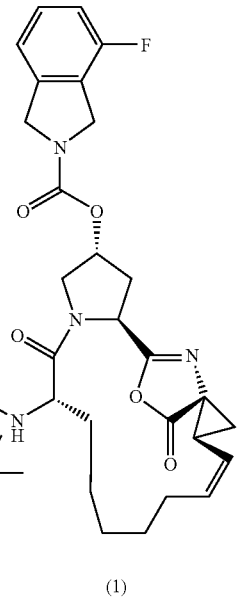

(1)

Method of making compound (1): Compound (1a) (2.000 g, 3.181 mmol) (Check KF in 20 mL of DMA after concentrating in 100 mL toluene) was added with TBTU (1.124 g, 3.499 mmol) to a 250 ml flask. DIEA (d 0.742) (1.164 ml, 6.681 mmol) was then added and the mixture stirred for 1 h. The reaction was monitored periodically by HPLC using acetate machine with L35:95 method. After 1 h reaction appeared complete. When completed, Compound (1) was precipitated with water and isolated and dried for screen reactions. After drying overnight 1.72 g was isolated (88.54% yield) (m/e 610.28 (100.0%), 611.28 (36.4%), 612.29 (6.1%), 612.28 (2.0%), 613.29 (1.2%); C, 62.94, H, 6.44, F, 3.11, N, 9.17, O 18.34). Further reference is made to Burk, M. J.; Allen, J. G. *J. Org. Chem.* 1997, 62, 7054, which is incorporated herein by reference in its entirety.

Example 21

Preparation and Crystallization of Salt Forms

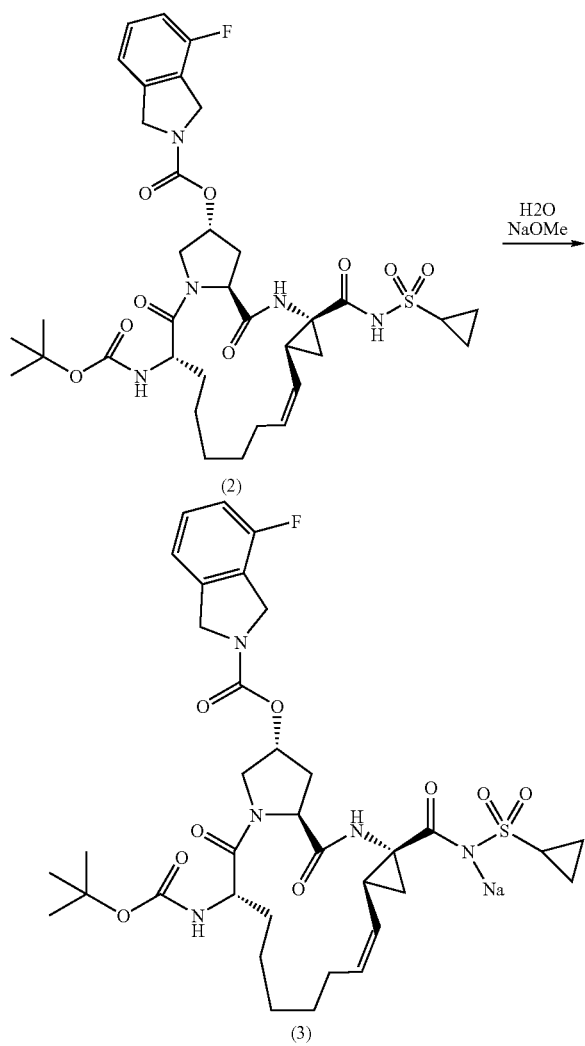

The amorphous compound (2) (49.90 g, 63.92 mmol) was taken up in 700 mL of 95:5 EtOAc:MeOH and dissolved. The resulting solution was polish filtered through GFF into a 2 L 3-neck round bottom flask equipped with a temperature probe, overhead stirring, heating mantle, and concentration side arm and then rinsed with 200 mL of 95:5 MeOH:EtOAc. All volumes were based on actual compound in the crude, ~45 g×20 volumes=900 mL total.

Sodium methanolate (15.35 ml, 67.12 mmol) was added. Potency for base equivalents was determined by adding potency of the batch with area % of acid impurity (of compound (2))=93.75. The reaction turned from yellow to orange after the last amounts of NaOMe were added. Water content was determined by Karl-Fisher (KF) analysis, KF=615 ppm. The reaction solution was concentrated by distillation. Approximately 315 mL of solvent was removed at about 30 C. internal temp under vacuum. KF after concentration was 425 ppm.

While the solution was still warm, water was added (13.82 ml, 767.1 mmol) and the mixture was allowed to cool to RT. The water was added at 43 C. The temperature dropped to 40 C. After about 15 minutes of stirring the solid precipitated, slowly at first then becoming thick and difficult to stir on the sides, but with faster stirring a flowing thin white slurry resulted and was left to stir overnight.

A centrifuge sample was taken and the filtrate showed a density of 7 mg/mL, which amounted to a 4 g loss overall. The solid was washed with EtOAc, dried and checked by HPLC. The acid level was 0.97. The solid was filtered through polyproylene filter cloth and washed with 2 volumes of EtOAc (90 mL). After air drying for about 10 minutes, the solide was transferred to a drying dish and put in the vacuum oven over the weekend at 57 C. The distillate was checked and the loss was 4.02 g. The material was 98.8% pure with 0.83% acid (purity by area %).

After 4 days, the material (41.9 g) was removed from the oven and, based on a 46.65 g theoretical yield (based on potency of the starting material), the mass yield was 90%. An additional amount ~2-3% was lost in the distillation due to bumping. NMR revealed the material had trace levels of EtOAc and residual solvent analysis by gas chromatography found EtOAc at 3742 ppm and EtOH at 1279 ppm.

Example 22

Preparation of Fluoroisoindolene

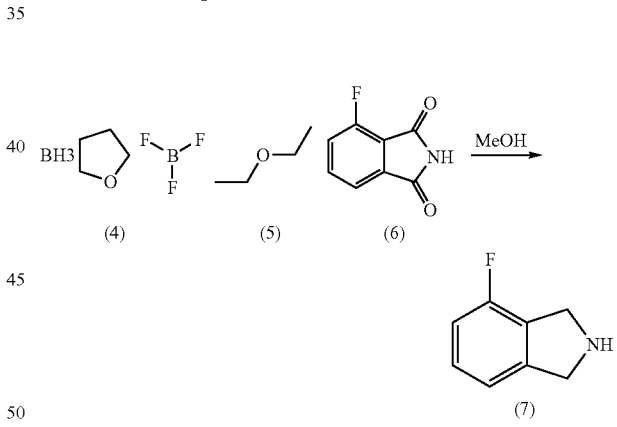

To a 4.3 C solution of imide (compound (6)) in THF (1500 mL) in a 50 L reactor with mechanical stirring, BF3OEt2 (compound (5)) was added slowly (about 15 minute addition period) by addition funnel. After the temperature had stabilized to 4.8 C (about 40 minutes), BH3 in THF (compound (4)) was added slowly in 4 portions:
1) 4800 mL (20 min addition period)
2) 4800 mL (15 min addition period)
3) 4800 mL (10 min addition period)
4) 2500 mL (20 min addition period)

The reaction outgassed but seemed stable so the ice bath was removed. After 20 minutes, the resulting solution was heated via steam bath to a 30 C target over about 10 minutes. The solution was allowed to stand for about 15 minutes to allow stabilization of solution temperature due to the exothermic reaction, and then refluxed overnight at 60 C under $N_2$. After 1 h some white solid was visible in solution, and after 2 h reflux, a sample was removed for analysis (pipet tip diluted in 1 mL MeCN+2-3 drops concentrated HCl). The desired product was the major component. The reaction was allowed to stir at 61 C overnight.

A sample was removed after an additional 2 h and indicated that the reaction was no longer progressing. The heat was removed and the reaction was allowed to cool to room temperature and then brought down to 11.5 C. Methanol was added via an addition funnel (slowly) and the temp. raised to 16.4 C with vigorous outgassing. The addition was continued so that the temp. did not rise above 18.0 C. After the first 1500 mL was added, the reaction did not continue to exotherm. Once the addition was complete the reaction contents were concentrated under vacuum (rotovap 4 hours). Once all of the material were in the tared 20 L bulb, a wt % measurement was made by HPLC. The reduction produced 414.2 g of product (91% yield, 4.9 wt % of 8421 g).

Example 23

Alternative Preparation of Fluoroisoindolene

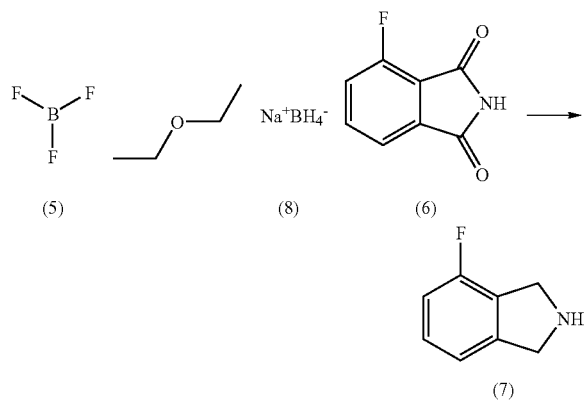

A slurry of 3-fluorophthalicimide (compound (6)) in 40 ml THF was cooled to 4 C in ice/water bath. $BF_3$ etherate (23.0 ml, 2.0 equiv.) (compound (5)) was added to the slurry over 2 mins. After the addition of $BF_3$ etherate was complete, the solution was warmed to room temperature and stirred for additional 1 hr. The slurry became very thin and can be conveniently transferred by syringe. This slurry is referred to herein as slurry A.

To a slurry of $NaBH_4$ in THF (250 ml) (compound (8)) in a 3-neck 1 L round bottom flask equipped with condenser, $N_2$ inlet, temperature probe, and mechanical stirring, $BF_3$ etherate (57.6 ml, 5.0 equiv) was carefully added by addition funnel at −20 C over 20 minutes. This slurry is referred to herein as slurry B. The bath was then removed and the slurry B was warmed to room temperature over about 45 minutes, stirred for 1 hour, and heated to 35-38 C.

Slurry A was added to the slurry B in 12 portions with a 5 ml syringe over 25 mins with care to control outgassing after addition of each portion of slurry A. After the temperature of the mixture stabilized, it was then heated to reflux at 63.4 C. The reflux lasted for 24 hrs, at which time the reaction was complete as verified by HPLC. The mixture was cooled to 0 C with ice bath and 150 ml MeOH was added slowly to quench the excess borane, after which the ice bath was removed and the mixture was warmed to rt. The mixture was filtered and the wet cake was washed with 40 ml MeOH. There was no product contained in the wet cake as verified by HPLC. The filtrate contained 10.51 g product by HPLC assay. The filtrated was concentrated to a yellow solid as crude product (84.35% yield).

Example 24

Method of Purifying Fluoroisoindolene

Step 1

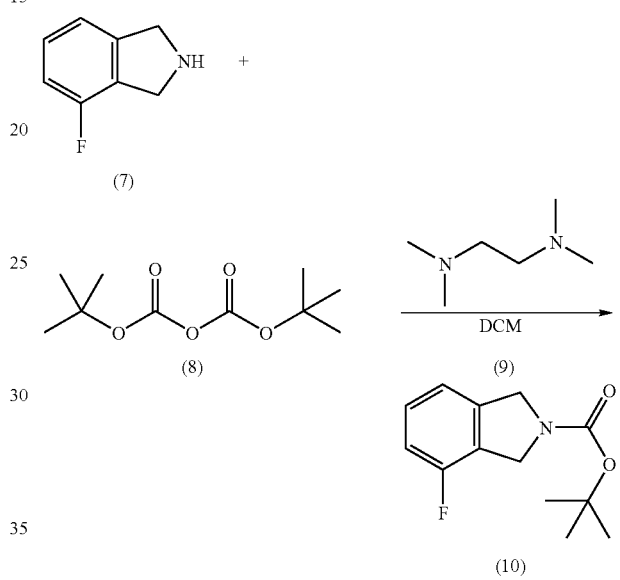

Compound (7) was slurried in 90 ml of dichloromethane (DCM) and cooled to 2.7 C (by use of an ice/water bath) in a 500 ml flask outfitted with stir bar, $N_2$ outlet and a temperature probe. A solution of Boc anhydride (compound (8)) in dichloromethane (30 ml) was added to the reaction vessel slowly over 10 minutes. After the addition was complete, the TMEDA (compound (9) as depicted above the reaction arrow) was added slowly over 15 minutes. The temperature was kept below 15 C and the mixture was left to stir overnight.

The reaction was then cooled to 3.0 C. A solution of HCl (2N, 200 ml) was added slowly to the reaction keeping the reaction temperature at or below 10 C. After stirring for 10 min the mixture was transferred to a 1 L seperatory funnel. After shaking a phase break was observed. The organic layer was removed and the acidic aqueous layer was back-extracted with DCM (50 ml). The organic layer was removed and the two organic layers were combined. The combined organic layers were washed with brine (150 ml). Complete removal of the TMEDA-HCl salt was verified by NMR analysis of the combined organic layer. The organic layer was concentrated to an oil under vacuum. To assist in removing all of the residual DCM, the crude oil was diluted in 160 ml of ethyl acetate and 120 ml of the ethyl acetate-oil mixture was removed by evaporation using the rotovap. The remaining ethyl acetate-oil mixture solution was advanced into the next step with further dilution.

Step 2

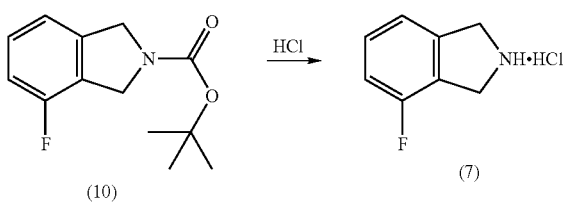

The ethyl acetate-oil mixture of Compound (10) was chilled to 2 C in a cold bath and 4M HCl in dioxane was added slowly (over about 20 min). The cold bath was removed and the mixture was allowed to warm and stir overnight. A white solid was visible after 30-40 minutes. After 15 hours, a sample was removed for analysis. An HPLC analysis of the sample showed that the reaction was complete. Methyl t-butyl ether (MTBE) (183 mL) was added to the suspension to precipitate additional product. After 1 hour, a sample was taken from the mixture and centrifuged. Analysis of this centrifugate sample by HPLC showed that the centrifugate contained 2.29 mg/ml of P2. Analysis of another sample after 3 hours of stirring showed the filtrate contained almost the same amount of P2. The reaction mixture was filtered through GF/F (Buchner funnel) and the cake was twice washed with MTBE (50 ml portion for each wash). The wet cake was analyzed by HPLC to contain two impurities (Impurity 1: 8.9% area %; Impurity 2: 0.44% area %).

The solid was slurried in 200 ml isopropyl acetate (iPAc) for 3 hours at room temperature. A sample was taken and centrifuged. Analysis of the centrifugate solid showed the decreased impurity 1 (2.1% area %) and impurity 2 was completely rejected. 100 ml iPAc was added to the mixture and the mixture was stirred for additional 2 hours. HPLC showed the solid still contained about 0.8% area % impurity 1. The mixture was filtered and the wet cake (containing 0.7% A % impurity 1) was reslurried in 150 ml iPAc at room temperature overnight.

The reaction mixture was filtered through GF/F (Buchner funnel) and the cake was twice washed with iPAc (50 ml portion for each wash). The wet cake was analyzed by HPLC (>99.5% area % of compound (10)). The wet cake was dried in vacuum oven at 40 C overnight to give an off-white solid as product (9.15 g, 58.0% yield overall).

Example 25

Method of Making 1,1,2-substituted cyclopropane

Step 1

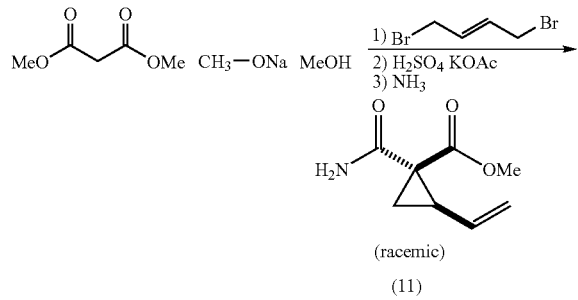

Cyclopropylmalonate formation: A 5 L, four-neck flask was charged with (E)-1,4-dibromobut-2-ene (182 g, 850.9 mmol), methanol (450 ml), and dimethyl malonate (102.4 ml, 893.4 mmol), and warmed to 22 C in a water bath until all the dibrombutene dissolved. Sodium methanolate (408.6 ml, 1787 mmol) was then slowly added to the reaction. After the addition of 50 ml of sodium methanolate, ice was placed in the water bath to control reaction temperature and the rate of addition was then adjusted to keep the temperature between 30 C and 33 C. After the addition was complete (about 20 minutes), the ice was removed, and the reaction placed in a warm water bath to maintain a temperature between 30 and 34 C. After 1 hour the reaction was judged complete by TLC by the absence of 1,4-dibromobutene (EMD Silica Gel 60 F254, 250 um layer thickness, glass plates, 9:1 hexanes/EtOAc, after staining with p-anisaldehyde, 1,4-dibromobutene was a UV-active spot which stained faint purple at rf=0.7; product appeared as a blue/green spot at rf=0.3, just above dimethyl malonate which was a blue/pink spot at rf=0.2). Sulfuric acid (12.52 g, 127.6 mmol) was then added incrementally to neutralize any excess base, and once the pH was below 7, potassium acetate (4 g, 40.76 mmol) was added to bring the pH back up to 7. The reaction was then concentrated to remove methanol to provide an oil and sodium salts. Water (800 ml) was then added followed by EtOAc (1 liter) and the reaction was transferred to a seperatory funnel. The layers were separated, and the organic layer was washed with brine (50 ml) then concentrated to an oil. This oil was taken up in methanol (300 ml) and concentrated to remove residual EtOAc.

Amination: The 3 liter flask containing the cyclopropyl malonate prepared above was charged with ammonia (1094 ml, 7658 mmol), and the reaction was stoppered with a temperature probe and the reaction was vented to permit gas evolution. The reaction was then heated to an internal temperature of 40 C. After 12 hours, the reaction was cooled in an ice bath to an internal temperature of 10 C, then the stopper removed and the reaction assayed by TLC as described above. TLC showed a mixture of cyclopropyl malonate and monoamide, slightly favoring the amide (1:1 hexanes/EtOAc, after staining with p-anisaldehyde, the cyclopropyl malonate appeared as a blue/green spot at rf=0.9, the desired monoamide appeared as a brown spot at rf=0.5, bis-amide appeared as a brown spot at rf=0.1). After 20 hours, the intensity of the cyclopropyl malonate had diminished by TLC, and some precipitate, likely the bis-amide, was observed. After 30 hours, more precipitate was observed, and the cyclopropyl malonate was faint, though clearly visible. However, TLC showed the bis-amide growing in (1:1 hexanes/EtOAc, stain with p-anisaldehyde, the bis-amide appears as a brown baseline spot, the same color as the mono-amide), so the reaction was worked up.

Work up: The reaction was cooled to 10 C (internal temperature), and the stopper removed. The reaction was filtered through GF-F filter paper to remove the solids, which were confirmed to be bis-amide, and then concentrated on the rotovap to provide a yellow solid. The solid was slurried in 10:1 EtOAc/heptane, (300 ml) and filtered to provide a first crop, which was dried under high vacuum at 40 C for 2 hours (69.9 g obtained). The liquors were concentrated to provide yellow solids which were also slurried in 10:1 EtOAc/heptane, (100 ml) and filtered to provide a second crop, which was dried under high vacuum at 40 C for 2 hours (33.5 g obtained). The filtrate was concentrated to a gummy solid, and taken up in EtOAc (~50 ml) and heated to dissolve the solids. Heptane (~5 ml) was added and the solution allowed to stir at room temperature for 8 hours. The reaction crystallized, and the yellow crystals were isolated and dried for 30 minutes under high vacuum at 40 C for 30 minutes to provide a sticky product (20.8 g). Total for all three crops=124.2 g, or 86% yield. NMR of the first two crops was similar, with the third crop having amounts of the cyclopropyl malonate present, about 25%. The three crops were combined and taken up in EtOAc (700 ml), heated to 55 C filtered, and the filtrate concentrated to ~½ volume at which point crystals had formed. The solution was heated to 55 C at which point it became homogenous, and heptane (70 ml) was added. Upon addition of heptane, the solution became cloudy and more heptane was added until the turbidity barely persisted. The solution was heated to homogeneity, then allowed to cool to room temp and stirred for 20 hours, then cooled in an ice bath for 1 hour and the crystals collected on filter paper and dried Step 2

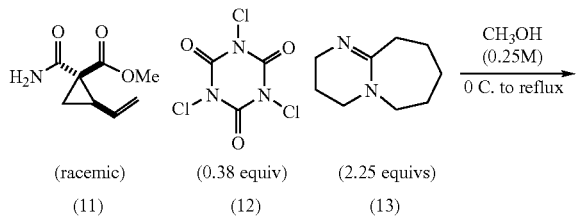

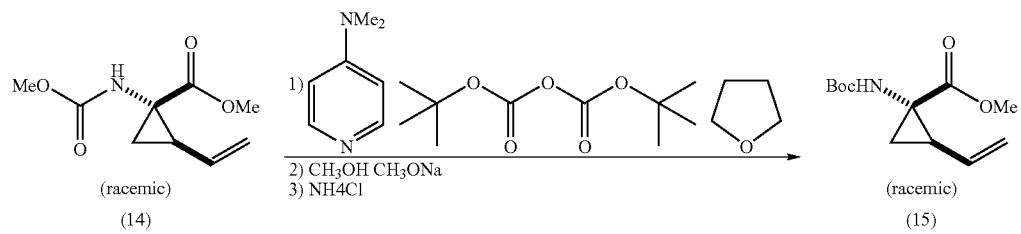

-continued

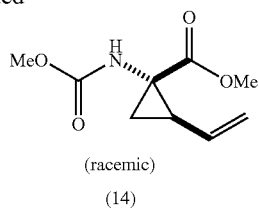

(racemic)
(14)

Reaction: A 22 liter flask open to the atmosphere was charged with (1R,2R)-methyl 1-carbamoyl-2-vinylcyclopropanecarboxylate (270 g, 1596 mmol) (compound (11)), methanol (10 volumes, 2.7 liters) and 2,3,4,6,7,8,9,10-octahydropyrimido[1,2-a]azepine (541 ml, 3591 mmol) (compound (13)), and then cooled in an ice bath to 12 C. 1,3,5-trichloro-1,3,5-triazinane-2,4,6-trione (130 g, 559 mmol) (compound (12)) was then added in approximately 5 g portions over a time of about 45 minutes to maintain temperature with about 2-3 Celsius degrees of the starting temperature. After the addition was complete, the ice bath was removed, and the reaction was allowed to warm to 26 C (1 hour). However, TLC indicated the presence of starting material (EMD Silica Gel 60 F254, 250 um layer thickness, glass plates, 1:1 hexanes EtOAc, stain with anisaldehyde, SM appears as a brown spot at rf=0.5, N-chloro intermediate appears as a pink spot at rf=0.8), so additional compound (12) (15 g) was added in four portions at 26 C. TLC showed the absence of starting material and only a spot corresponding to the chloroamide (slightly streaky). The solution was then heated to reflux and monitored by TLC. After 2 hours, TLC indicated the presence of product and a trace of the N-chloro intermediate (1:1 hexanes/EtOAc, after staining with anisaldehyde, product appeared as a dark blue spot at rf=0.8). After 2.5 hours, none of the N-chloro intermediate was observed, and the reaction was cooled to room temperature and worked up the following day.

Work up: The reaction was concentrated to a precipitate-containing oil by evaporation on a rotovap, then taken up in EtOAc (2.4 l) and washed successively with NaOH (1 N, 1.5 l), HCl (1N, 1.5 l) and brine (200 ml). The NaOH layer was back extracted with 750 ml EtOAc, and the same EtOAc solution was used to back extract the HCl and brine layers. The organic layers were combined and concentrated at reduced pressure to provide the crude product (compound (14)) as an amber oil (246 g, 77% yield).

Care was taken to avoid adding excess compound (12) because it can react with the product to form an over-oxidation byproduct.

Step 3

A five liter four neck flask equipped with a temperature probe was charged with compound (14) (242 g, 1215 mmol) in THF (1.25 liters), N,N-dimethylpyridin-4-amine (29.7 g, 243 mmol), and boc anhydride (345 g, 1579 mmol, about 1.3 equivalents) in THF (750 ml). The solution was heated to reflux for 2 hours at which point TLC (EMD Silica Gel 60 F254, 250 um layer thickness, glass plates, 3:1 hexanes/EtOAc, compound (14) appeared as a blue spot at rf=0.45, product appeared as a blue spot at rf=0.25) indicated that all compound (14) was consumed and had been cleanly converted to product. The reaction was then cooled in an ice bath to 3 C (internal temperature). Methanol (1.25 liters) and sodium methanolate (83.3 ml, 364 mmol) were added over a period of 10 minutes, and the reaction was allowed to stir for 2 hours at 3 C. TLC after ½ hour revealed the presence of three compounds: the intermediate bis carbamate, the methylcarbamate formed by hydrolysis of the Boc-carbamate, and the desired Boc-carbamate formed by hydrolysis of the methylcarbamate (3:1 hexanes/EtOAc, stained with anisaldehyde). Methylcarbamate appeared as a blue spot at Rf=0.25, bis carbamate appeared as a blue spot at Rf=0.45, Boc-carbamate appeared as a yellow spot just above the bis-carbamate at Rf=0.5).

The reaction was worked up by transferring the mixture to a 3 L round bottom flask containing ammonium chloride (19.5 g, 364 mmol) and concentrating to an oil. The oil was stored overnight. Water (500 ml) was then added to the residue followed by EtOAc (1.5 liters) and the dark oil was stirred for 15 minutes to fully dissolve all the material. The homogeneous mixture was then transferred to a 4 liter separatory funnel, and HCl (1M, 1 liter) was added. The layers were separated, and the organic layer was washed with a minimal amount of brine (100 ml). The aqueous layer was back extracted with EtOAc (600 ml) and the combined organic extracts were concentrated to dark oil (309 g). NMR revealed about 6 mol % EtOAc, or about 2 weight % EtOAc. The aqueous layer was back extracted a second time with EtOAc (600 ml), but very little product (less than 2 g) was obtained, and it was discarded. Potency of the product material was determined by HPLC against a standard and was found to be 85%, (yield of 88.6%, crude weight of 105%).

Example 26

Alternative Method of Making 1,1,2-Substituted Cyclopropane

Step 1 (Synthesis of Chiral Ni-Complex)

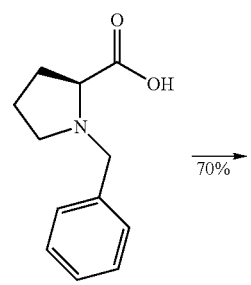

N-Benzylproline (BP)
SOL11012
(16)

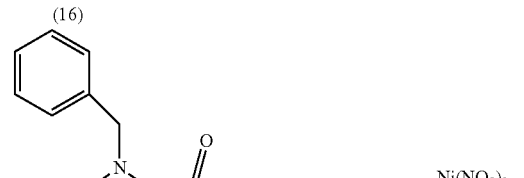

BPB
SOL11013
(17)

Gly-Ni-BPB
SOL11034
(18)

(S)-BPB (SOL11013)

(S)-Bn-Pro-OH (98.0 g, 0.48 mol) (compound (16)) and N-methylimidazole (86.2 g, 1.05 mol) were dissolved in DCM (500 ml) and cooled to 0° C. Methanesulfonyl chloride (57.4 g, 0.50 mol) was added within 10 minutes and the temperature was held in between −10° and +7° C. The mixture was stirred at 0° C. for 90 minutes. 2-Aminobenzophenone (84.7 g, 0.43 mol) was added. The mixture was stirred at ambient temperature for 90 minutes then refluxed for 5 h. After cooling to room temperature, it was washed with aqueous ammonium chloride and water. The organic layer was dried ($Na_2SO_4$), then treated with activated charcoal and filtered through a pad of cellite. It was evaporated. The oily orange residue was crystallized from ethanol to yield the product as a yellow solid (115 g, 70%).

(S)-BPB-Ni-Gly-complex (SOL11034)

To a stirred solution of SOL11013 (28.4 g, 73.7 mmol) (compound (17)) in methanol (210 ml) were added $Ni_2(NO)_3$ (42.9 g, 148 mmol) and glycine (27.7 g, 369 mmol) at rt. The mixture was heated to 37° C. A solution of KOH (29 g, 516 mmol) in methanol (100 ml) was added rapidly. The mixture was then heated to 55° C. for 90 minutes. It was cooled to 0° C. then quenched by addition of acetic acid (30 ml; exothermic reaction to 30° C.). Then the same volume of water was added slowly and the mixture was stirred over night. The red solids were isolated by filtration and dissolved in DCM. The remaining water was separated. The organic layer was dried ($Na_2SO_4$) and widely evaporated. The residue was crystallized from TBME and dried over night in HV at 60° C. Yield was 29.6 g (81%) of orange to red solid.

($\alpha_D^{20}$ +2020°, c=1.0, MeOH; Lit.[3]: +2006°)

Step 2

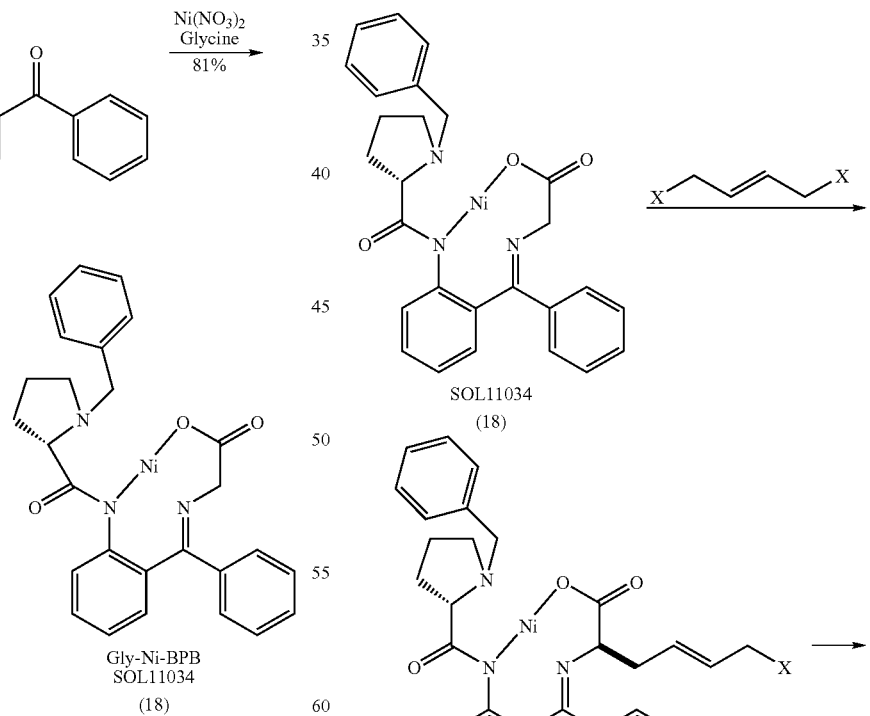

SOL11034
(18)

X = Cl: SOL11161
X = Br: not isolated
(19)

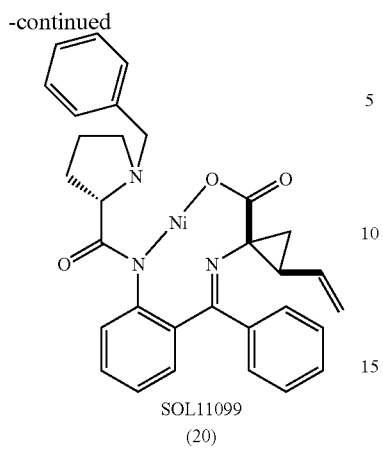

SOL11099
(20)

Each diastereomer of SOL11161 and its corresponding epimer SOL11099 showed the same retention times in HPLC and LC-MS but were distinguishable by MS.

Step 2a: SOL11034 (4.98 g, 10.0 mmol) (compound (18)) was dissolved in dry acetonitrile at 20° C. (water bath). 1,4-Dichloro-2-butene (3.13 g, 25.0 mmol) was added. After 5 minutes fine grounded sodium hydroxide (4.0 g, 100 mmol) was added in one portion. The mixture was stirred for two hours. LC-MS and HPLC analysis showed the conversion of the starting material to SOL11161 (dr ~12:1) (compound (19)) to be complete. The reaction was quenched by addition of a solution of acetic acid (5 ml) in acetonitrile (10 ml). It was filtered and the solid residue was washed with DCM. The combined organics were evaporated to dryness and further dried in HV for several hours to give a red resin (6.68 g) that still contained the excess of alkylating reagent. To get rid of remaining traces of acetic acid toluene (10 ml) was added to the residue to give a deep red solution which was evaporated to dryness (twice).

Step 2b: Dry toluene (50 ml) was added as the solvent for the intramolecular alkylation step followed by a 1 M solution of LiHMDS in THF (15 mmol). After 90 minutes LC-MS analysis showed complete conversion of SOL11161 to SOL11099. The reaction was again quenched by addition of a solution of acetic acid (5 ml) in acetonitrile (10 ml). The mixture was washed twice with 1N aqueous sodium bicarbonate (carefully), water and brine, then dried over Na$_2$SO$_4$ and evaporated to yield 6.43 g of SOL11099 (compound (20)) with a diastereomeric ratio of ~6:1 as a red resin.

Step 3

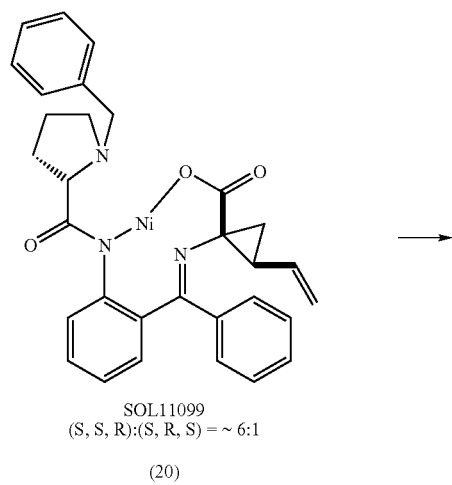

SOL11099
(S, S, R):(S, R, S) = ~ 6:1
(20)

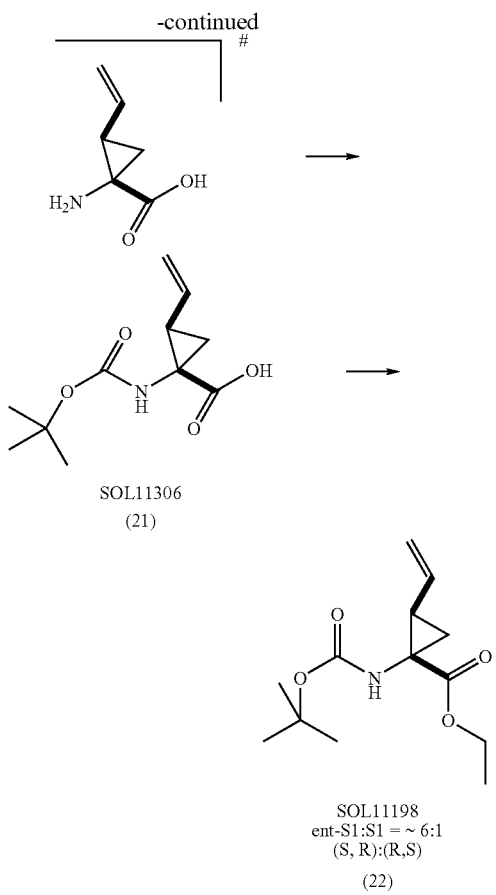

SOL11306
(21)

SOL11198
ent-S1:S1 = ~ 6:1
(S, R):(R, S)
(22)

Step 3a: For hydrolysis of the Ni-complex the residue from step 2b was dissolved in isopropanol (5 ml). A solution of hydrogen chloride in isopropanol (5-6 M, 4 ml) and water (2 ml) were added and the mixture was refluxed for 4 h. The reaction was monitored by HPLC and LC-MS. Cleavage of the Nickel-ion from the complex occurs fast, but hydrolysis of the imine to the free amino acid and the ligand BPB rather slowly under these conditions. After complete hydrolysis the mixture was evaporated to dryness and stored in HV for 24 h.

Step 3b: The residue from step 3a was dissolved in dioxane (40 ml). A 1 N solution of sodium bicarbonate was added slowly (CO$_2$ evolution), followed by a solution of Boc$_2$O (3.20 g, 15 mmol) in dioxane (20 mmol). The mixture was stirred at room temperature for 20 h. The dioxane was removed iV (evaporation to half volume of mixture). The pH was adjusted to 10 by addition of 1N sodium hydroxide. The aqueous layer was washed four times with TBME. Then dichloromethane (DCM) (same volume) was added and the aqueous layer was acidified by addition of 1N sulfuric acid to pH 1. The layers were separated and the aqueous was extracted with DCM three times. The combined organic layers were washed with 1 N sulfuric acid, water, and brine, then dried (Na$_2$SO$_4$) and evaporated to yield 1.62 g of a yellow resin. The latter still contained significant amounts of BPB, therefore the extraction, washing and back extraction was repeated as described. (beginning with adjustment to pH 10 and proceeding as described). 1.14 g of crude SOL11306 (compound (21)) was obtained, which still contained some percent of BPB.

Step 3c: 400 mg of crude material form step 3b was dissolved in DMF (10 ml) at room temperature. Solid sodium bicarbonate (840 mg, 10 mmol) was added, followed by iodoethane (1.09 g, 7 mmol). The mixture was stirred over night. Water was added and the mixture as extracted with TBME twice. The combined organic layers were washed with water and brine, dried and evaporated. Yield: 300 mg (calculated 33%) SOL11198 (ent-S1:S1=85:15=70% ee) (compound (22)).

Use of (S)-BPB-Ni-Gly leads predominantly to the enantiomer ent-S1. However, (R)-BPB-Ni-Gly is readily available and could be used in the same manner to yield S1 as the major enantiomer.

Further reference is made to "Synthesis of (1R,2S)-1-Amino-2-vinylcyclopropanecarboxylic Acid Vinyl-ACCA) Derivatives: Key Intermediates for the Preparation of Inhibitors of the Hepatitis C Virus NS3 Protease." Beaulieu, Pierre L.; Gillard, James; Bailey, Murray D.; Boucher, Colette; Duceppe, Jean-Simon; Simoneau, Bruno; Wang, Xiao-Jun; Zhang, Li; Grozinger, Karl; Houpis, Ioannis; Farina, Vittorio; Heimroth, Heidi; Krueger, Thomas; Schnaubelt, Juergen, *Journal of Organic Chemistry* (2005), 70(15), 5869-5879; "General method for the asymmetric synthesis of α-amino acids via alkylation of the chiral nickel(II) Schiff base complexes of glycine and alanine." Belokon, Yu. N.; Bakhmutov, V. I.; Chemoglazova, N. I.; Kochetkov, K. A.; Vitt, S. V.; Garbalinskaya, N. S.; Belikov, V. M., *Journal of the Chemical Society*, Perkin Transactions 1: Organic and Bio-Organic Chemistry (1972-1999) (1988), (2), 305-12; and "Improved procedures for the synthesis of (S)-2-[N—(N'-benzyl-prolyl)amino]benzophenone (BPB) and Ni(II) complexes of Schiff's bases derived from BPB and amino acids." Belokon, Yuri N.; Tararov, Vitali I.; Maleev, Viktor I.; Savel'eva, Tatiana F.; Ryzhov, Michael G., *Tetrahedron: Asymmetry* (1998), 9(23), 4249-4252; all of which are incorporated herein by reference in their entirety.

Example 27

Method of Making Substituted Heptene

Step 1 (Synthesis of Chiral Ni-Complex)

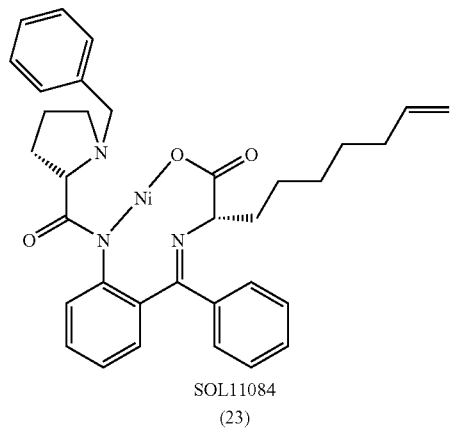

SOL11084
(23)

SOL11034 (4.98 g, 10.0 mmol) was dissolved in dry acetonitrile at 20° C. (water bath). 7-Bromo-1-heptene (1.74 g, 9.80 mmol) was added. After 5 minutes fine grounded sodium hydroxide (4.0 g, 100 mmol) was added in one portion. The mixture was stirred for 15 hours. LC-MS and HPLC analysis showed the conversion of the starting material to SOL11084 (dr ~15:1) to be complete. The reaction was quenched by addition of a solution of acetic acid (5 ml) in acetonitrile (15 ml). It was filtered and the solid residue was washed with acetonitrile. The combined organics were evaporated to dryness. The residue was dissolved in dichloromethane (DCM) and washed with water. The aqueous layer was extracted back twice, the combined organic layers were dried (Na$_2$SO$_4$) and evaporated. The residue was dried in HV for several hours to give a red resin (5.62 g).

Step 2

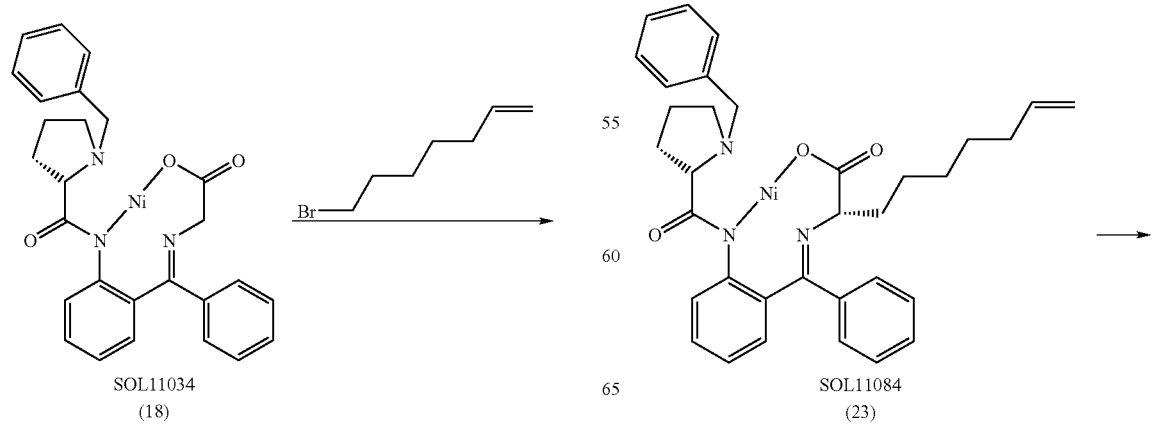

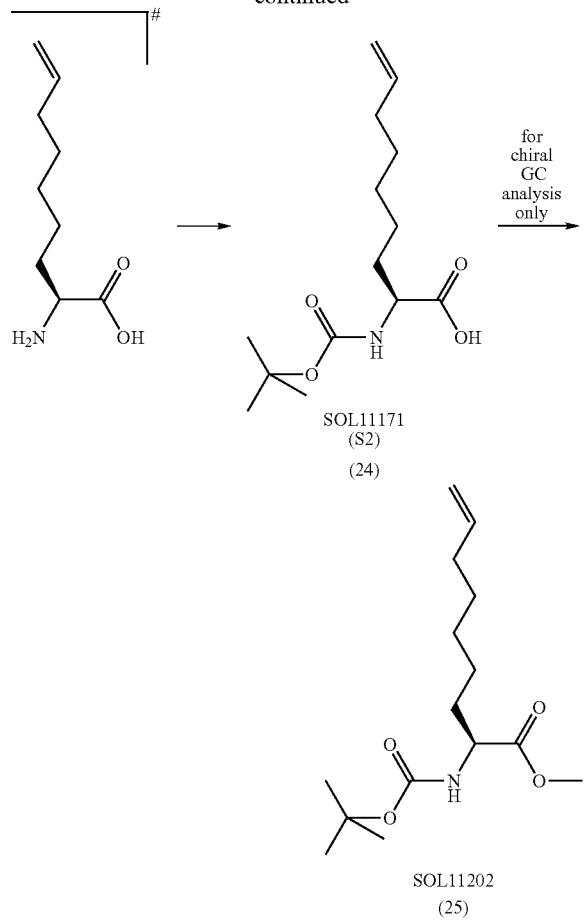

Step 2a: 2 g of the material obtained in step 1 were hydrolyzed and worked up as described above in step 3a for SOL11198, compound (22). 2.61 g of a yellow to green solid were obtained.

Step 2b: The residue from step 2a was treated with $Boc_2O$ as described above in step 3b for SOL11099, compound (20). 362 mg (calculated 37%) of SOL11171, which was contaminated with some percent of BPB, was obtained as a pale brown oil from the DCM phase. From the TBME phase was obtained 1.7 g of a brown oil, that mainly contained recovered BPB along with significant amounts of SOL11171.

For ee-determination: 2 mg of SOL11171 was dissolved in 0.5 ml of MeOH and treated with a slight excess of diazomethane (0.2 M in diethylether). A small drop of acetic acid was added carefully and then it was evaporated to dryness. The residue was dissolved in 1 ml of DCM. A ratio of S2 (S) to ent-S2 (R) of 93:7 was found, i.e. an ee of 87%.

Example A

NS3-NS4 Protease Assay

NS3 complex formation with NS4A-2.

Recombinant *E. coli* or Baculovirus full-length NS3 was diluted to 3.33 μM with assay buffer and transferred material to an eppendorf tube and place in water bath in 4° C. refrigerator. The appropriate amount of NS4A-2 to 8.3 mM in assay buffer was added to equal the volume of NS3 in step 2.1.1 (conversion factor—3.8 mg/272 μL assay buffer). The material was transferred to an eppendorf tube and place in water bath in 4° C. refrigerator.

After equilibration to 4° C., equal volumes of NS3 and NS4A-2 solutions were combined in an eppendorf tube, mix gently with a manual pipettor, and incubate mixture for 15 minutes in the 4° C. water bath. Final concentrations in the mixture are 1.67 μM NS3, 4.15 mM NS4A-2 (2485-fold molar excess NS4A-2).

After 15 minutes at 4° C., the NS3/NS4A-2 eppendorf tube was removed and place it in a room temperature water bath for 10 minutes. NS3/NS4A-2 was alliquoted at appropriate volumes and store at −80° C. (*E. coli* NS3 run at 2 nM in assay, aliquot at 25 μL. BV NS3 run at 3 nM in assay, aliquot at 30 μL).

Example B

NS3 Inhibition Assay

Sample compounds were dissolved to 10 mM in DMSO then diluted to 2.5 mM (1:4) in DMSO. Typically, compounds were added to an assay plate at 2.5 mM concentration, yielding upon dilution a starting concentration of 50 microM in the assay inhibition curve. Compounds were serial diluted in assay buffer to provide test solutions at lower concentrations.

The *E. coli*. NS3/NS4A-2 was diluted to 4 nM NS3 (1:417.5 of 1.67 μM stock–18 μL 1.67 μM stock+7497 μL assay buffer). The BV NS3/NS4A-2 was diluted to 6 nM NS3 (1:278.3 of 1.67 μM stock–24 μL 1.67 μM stock+6655 μL assay buffer). Using the manual multichannel pipettor, careful not to introduce bubbles into the plate, add 50 μL assay buffer to wells A01-H01 of a black Costar 96-well polypropylene storage plate.

Using the manual multichannel pipettor, careful not to introduce bubbles into the plate, add 50 μL of diluted NS3/NS4A-2 from step 2.2.6 to wells A02-H12 of plate in step 2.2.7. Using the manual multichannel pipettor, careful not to introduce bubbles into the plate, transfer 25 μL of the wells in drug dilution plate in step 2.2.5 to corresponding wells in assay plate in step 2.2.8. Change tips on multichannel pipettor for each row of compounds transferred. Using the manual multichannel pipettor, careful not to introduce bubbles into the plate, mix the wells from the assay plate in step 2.2.9 by aspirating and dispensing 35 μL of the 75 μL in each well five times. Change tips on multichannel pipettor for each row of wells mixed. Cover plate with a polystyrene plate lid and pre-incubate the plate from step 2.2.10 containing NS3 protease and sample compounds 10 minutes at room temperature. While plate from step 2.2.11 is pre-incubating, dilute RETS1 substrate in a 15 mL polypropylene centrifuge tube. Dilute RETS1 substrate to 8 μM (1:80.75 of 646 μM stock–65 μL 646 μM stock+5184 μL assay buffer).

After the plate in step is done pre-incubating, and using the manual multichannel, add 25 μL of substrate to all wells on the plate. Quickly mix the plate as in step 2.2.10, mixing 65 μL of the 100 μL in the wells.

Read the plate in kinetic mode on the Molecular Devices SpectraMax Gemini XS plate reader. Reader settings: Read time: 30 minutes, Interval: 36 seconds, Reads: 51, Excitation λ: 335 nm, Emission λ: 495 nm, cutoff: 475 nm, Automix: off, Calibrate: once, PMT: high, Reads/well: 6, Vmax pts: 21 or 28/51 depending on length of linearity of reaction IC$_{50}$s are determined using a four parameter curve fit equation, and converted to Ki's using the following Km's:
Full-length E. coli NS3—2.03 µM
Full-length BV NS3—1.74 µM where $Ki=IC_{50}/(1+[S]/Km))$ Quantitation by ELISA of the selectable marker protein, Neomycin phosphotransferase II (NPTII) in the HCV Sub-Genomic Replicon, GS4.3

The HCV sub-genomic replicon (1377/NS3-3', accession No. AJ242652), stably maintained in HuH-7 hepatoma cells, was created by Lohmann et al. *Science* 285: 110-113 (1999). The replicon-containing cell culture, designated GS4.3, was obtained from Dr. Christoph Seeger of the Institute for Cancer Research, Fox Chase Cancer Center, Philadelphia, Pa.

GS4.3 cells were maintained at 37° C., 5% $CO_2$, in DMEM (Gibco 11965-092) supplemented with L-glutamine 200 mM (100×) (Gibco25030-081), non-essential amino acids (NEAA) (Biowhittaker 13-114E), heat-inactivated (HI) Fetal Bovine Serum (FBS) (Hyclone SH3007.03) and 750 µg/ml geneticin (G418) (Gibco 10131-035). Cells were sub-divided 1:3 or 4 every 2-3 days.

24 h prior to the assay, GS4.3 cells were collected, counted, and plated in 96-well plates (Costar 3585) at 7500 cells/well in 100 µl standard maintenance medium (above) and incubated in the conditions above. To initiate the assay, culture medium was removed, cells were washed once with PBS (Gibco 10010-023) and 90 µl Assay Medium (DMEM, L-glutamine, NEAA, 10% HI FBS, no G418) was added. Inhibitors were made as a 10× stock in Assay Medium, (3-fold dilutions from 10 µM to 56 pM final concentration, final DMSO concentration 1%), 10 µl were added to duplicate wells, plates were rocked to mix, and incubated as above for 72 h.

An NPTII Elisa kit was obtained from AGDIA, Inc. (*Compound direct ELISA test system for Neomycin Phosphotransferase II*, PSP 73000/4800). Manufacturer's instructions were followed, with some modifications. 10×PEB-1 lysis buffer was made up to include 500 µM PMSF (Sigma P7626, 50 mM stock in isopropanol). After 72 h incubation, cells were washed once with PBS and 150 µl PEB-1 with PMSF was added per well. Plates were agitated vigorously for 15 minutes, room temperature, then frozen at −70° C. Plates were thawed, lysates were mixed thoroughly, and 100 µl were applied to an NPTII Elisa plate. A standard curve was made. Lysate from DMSO-treated control cells was pooled, serially diluted with PEB-1 with PMSF, and applied to duplicate wells of the ELISA plate, in a range of initial lysate amount of 150 ul-2.5 ul. In addition, 100 µl buffer alone was applied in duplicate as a blank. Plates were sealed and gently agitated at room temperature for 2 h. Following capture incubation, the plates were washed 5×300 µl with PBS-T (0.5% Tween-20, PBS-T was supplied in the ELISA kit). For detection, a 1× dilution of enzyme conjugate diluent MRS-2 (5×) was made in PBS-T, into which 1:100 dilutions of enzyme conjugates A and B were added, as per instructions. Plates were resealed, and incubated with agitation, covered, room temperature, for 2 h. The washing was then repeated and 100 µl of room temperature TMB substrate was added. After approximately 30 minutes incubation (room temperature, agitation, covered), the reaction was stopped with 50 µl 3M sulfuric acid. Plates were read at 450 nm on a Molecular Devices Versamax plate reader.

Inhibitor effect was expressed as a percentage of DMSO-treated control signal, and inhibition curves were calculated using a 4-parameter equation: $y=A+((B-A)/(1+((C/x)^D)))$, where C is half-maximal activity or $EC_{50}$.

Examples of Activity

TABLE 9

| Compound | NS3-NS4 IC$_{50}$ | Replicon EC$_{50}$ |
| --- | --- | --- |
| 100 | D | D |
| 101 | D | D |
| 102 | D | C |
| 103 | D | D |
| 104 | D | D |
| 105 | D | D |
| 106 | C | A |
| 107 | D | B |
| 108 | D | B |
| 109 | D | B |
| 110 | C | B |
| 111 | D | D |
| 112 | D | D |
| 113 | D | C |
| 114 | D | D |
| 115 | D | D |
| 116 | D | B |
| 117 | D | D |
| 118 | D | D |
| 119 | D | C |
| 120 | D | D |
| 121 | C | C |
| 122 | D | B |
| 123 | D | B |
| 124 | B | n/a |
| 125 | B | n/a |
| 126 | A | n/a |
| 127 | B | n/a |
| 128 | A | n/a |
| 129 | B | n/a |
| 130 | D | B |
| 131 | D | B |
| 132 | D | D |
| 133 | D | B |
| 134 | D | D |
| 135 | D | B |
| 136 | D | A |
| 137 | D | D |
| 138 | D | C |
| 139 | C | A |
| 140 | D | C |
| 141 | D | D |
| 142 | D | B |
| 143 | D | D |
| 144 | D | B |
| 145 | D | D |
| 146 | D | A |
| 147 | A | n/a |
| 148 | A | n/a |
| 149 | D | A |
| 150 | D | A |
| 151 | B | n/a |
| 152 | D | A |
| 153 | A | n/a |
| 154 | B | n/a |
| 155 | D | C |
| 156 | D | C |
| 157 | D | D |
| 158 | D | D |
| 159 | D | C |
| 160 | D | D |
| 161 | D | D |
| 162 | D | D |
| 163 | D | B |
| 164 | D | D |
| 165 | D | D |
| 166 | D | D |
| 167 | D | B |
| 168 | D | B |
| 169 | D | B |
| 170 | D | D |
| 171 | D | D |
| 172 | D | D |
| 173 | D | D |

TABLE 9-continued

| Compound | NS3-NS4 IC$_{50}$ | Replicon EC$_{50}$ |
|---|---|---|
| 174 | D | D |
| 175 | D | A |
| 176 | D | A |
| 177 | D | B |
| 178 | D | D |
| 179 | D | D |
| 180 | D | D |
| 181 | C | B |
| 182 | D | C |
| 183 | D | D |
| 184 | D | B |
| 185 | D | B |
| 186 | D | C |
| 187 | D | C |
| 188 | D | D |
| 189 | D | C |
| 190 | D | D |
| 191 | D | C |
| 192 | D | B |
| 193 | D | C |
| 194 | D | B |
| 195 | D | A |
| 196 | D | B |
| 197 | D | B |
| 198 | D | C |
| 199 | D | B |
| 237 | D | A |
| 238 | D | B |
| 239 | D | D |
| 240 | D | C |
| 241 | D | C |
| 242 | D | B |
| 243 | D | D |
| 244 | D | D |
| 245 | D | C |
| 246 | D | C |
| 247 | D | D |
| 248 | D | C |
| 249 | D | C |
| 250 | D | C |
| 251 | D | B |
| 252 | D | B |
| 253 | D | B |
| 254 | D | C |
| 255 | D | D |
| 256 | D | D |
| 257 | D | D |
| 258 | D | D |
| 259 | D | D |
| 260 | D | D |
| 261 | D | C |
| 262 | D | C |
| 263 | D | D |
| 264 | B | A |
| 265 | D | D |
| 266 | D | D |
| 267 | D | D |
| 268 | D | D |
| 269 | D | D |

TABLE 10

| Compound | NS3-NS4 IC$_{50}$ | Replicon EC$_{50}$ |
|---|---|---|
| 200 | D | D |
| 201 | D | D |
| 202 | D | B |
| 203 | C | A |
| 204 | D | D |
| 205 | D | C |
| 206 | D | D |
| 207 | D | D |

TABLE 10-continued

| Compound | NS3-NS4 IC$_{50}$ | Replicon EC$_{50}$ |
|---|---|---|
| 208 | D | B |
| 209 | D | D |
| 210 | D | D |
| 211 | D | D |
| 212 | D | C |
| 213 | D | D |
| 214 | D | D |
| 215 | D | D |
| 216 | D | D |
| 217 | D | D |
| 218 | D | D |
| 219 | D | B |
| 220 | D | C |
| 221 | D | B |
| 222 | D | B |
| 223 | D | C |
| 224 | C | B |
| 225 | D | D |
| 226 | D | D |
| 227 | D | D |
| 228 | D | D |
| 229 | D | C |
| 230 | D | C |
| 231 | D | D |
| 232 | D | D |
| 233 | D | D |
| 234 | D | D |
| 235 | D | D |
| 236 | D | D |

TABLE 11

| Compound | NS3-NS4 IC$_{50}$ | Replicon EC$_{50}$ |
|---|---|---|
| 300 | C | n/a |
| 301 | B | n/a |
| 302 | B | n/a |
| 303 | A | n/a |
| 304 | B | n/a |
| 305 | B | n/a |
| 306 | A | n/a |
| 307 | B | n/a |
| 308 | A | n/a |
| 309 | B | n/a |
| 310 | A | n/a |
| 311 | B | n/a |
| 312 | C | n/a |
| 313 | B | n/a |
| 314 | D | B |
| 315 | B | n/a |
| 316 | B | n/a |
| 317 | C | A |
| 318 | C | A |

TABLE 12

| Compound | NS3-NS4 IC$_{50}$ |
|---|---|
| 400 | B |
| 401 | B |
| 402 | A |
| 403 | B |
| 404 | B |
| 405 | B |
| 406 | A |
| 407 | A |
| 408 | B |
| 409 | B |
| 410 | A |

TABLE 12-continued

| Compound | NS3-NS4 IC$_{50}$ |
|---|---|
| 411 | A |
| 412 | B |
| 413 | A |
| 414 | A |
| 415 | A |
| 416 | B |
| 417 | B |
| 418 | A |
| 419 | B |
| 420 | A |
| 421 | A |
| 422 | A |
| 423 | B |
| 424 | A |
| 425 | A |
| 426 | A |
| 427 | A |
| 428 | B |
| 429 | B |

TABLE 13

| Compound | NS3-NS4 IC$_{50}$ |
|---|---|
| 500 | A |
| 501 | A |
| 502 | A |
| 503 | A |

TABLE 14

| Compound | NS3-NS4 IC$_{50}$ | Replicon EC$_{50}$ |
|---|---|---|
| 600 | D | C |
| 601 | D | C |
| 602 | C | C |
| 603 | C | C |
| 604 | A | A |
| 605 | C | C |
| 606 | C | C |
| 607 | A | n/a |
| 608 | A | n/a |
| 609 | D | C |
| 610 | C | A |
| 611 | C | B |
| 612 | C | C |
| 613 | C | C |
| 614 | C | C |
| 615 | C | B |
| 616 | C | C |
| 617 | D | A |
| 618 | D | B |
| 619 | D | C |
| 620 | C | B |
| 621 | A | A |
| 622 | B | B |
| 623 | B | n/a |
| 624 | B | C |
| 625 | B | B |
| 626 | C | B |
| 627 | D | D |
| 628 | C | C |
| 629 | C | B |
| 630 | C | B |
| 631 | D | C |
| 632 | C | B |
| 633 | C | C |
| 634 | C | B |
| 635 | D | C |

TABLE 14-continued

| Compound | NS3-NS4 IC$_{50}$ | Replicon EC$_{50}$ |
|---|---|---|
| 636 | C | D |
| 637 | D | A |
| 638 | C | A |
| 639 | C | A |
| 640 | D | A |
| 641 | D | B |
| 642 | C | A |
| 643 | C | A |
| 644 | D | C |
| 645 | D | n/a |
| 646 | C | A |
| 647 | D | B |
| 648 | C | A |

TABLE 15

| Compound | NS3-NS4 IC$_{50}$ | Replicon EC$_{50}$ |
|---|---|---|
| 701 | D | D |
| 702 | C | C |
| 703 | C | C |
| 704 | B | n/a |
| 705 | D | D |
| 706 | D | D |

TABLE 16

| Compound | NS3-NS4 IC$_{50}$ |
|---|---|
| 801 | B |

TABLE 17

| Compound | NS3-NS4 IC$_{50}$ | Replicon EC$_{50}$ |
|---|---|---|
| 900 | D | D |
| 901 | D | D |
| 902 | D | D |
| 903 | D | D |
| 904 | D | D |
| 905 | D | D |
| 906 | D | D |
| 907 | D | C |
| 908 | C | B |
| 909 | D | D |
| 910 | D | C |
| 911 | C | B |
| 912 | D | D |
| 913 | D | C |
| 914 | D | D |
| 915 | D | D |
| 916 | D | C |
| 917 | D | D |
| 918 | D | C |
| 919 | D | B |
| 920 | D | D |
| 921 | D | C |
| 922 | D | C |
| 923 | D | C |
| 924 | D | D |
| 925 | D | D |
| 926 | D | D |
| 927 | D | D |
| 928 | D | D |
| 929 | D | D |

TABLE 18

| Compound | NS3-NS4 IC$_{50}$ | Replicon EC$_{50}$ |
|---|---|---|
| 1001 | D | B |
| 1002 | D | D |
| 1003 | D | C |
| 1004 | D | D |
| 1005 | D | D |
| 1006 | D | B |
| 1007 | D | B |
| 1008 | D | D |
| 1009 | D | D |
| 1010 | D | D |
| 1011 | D | C |
| 1012 | D | D |
| 1013 | D | D |
| 1014 | D | D |
| 1015 | D | D |
| 1016 | D | D |
| 1017 | C | A |
| 1018 | D | C |
| 1019 | D | C |
| 1020 | D | D |
| 1021 | B | A |
| 1022 | D | D |
| 1023 | D | C |
| 1024 | D | D |
| 1025 | D | D |
| 1026 | D | B |
| 1027 | D | D |
| 1028 | D | D |
| 1029 | D | B |
| 1030 | D |   |
| 1031 | D | C |
| 1032 | D | D |

TABLE 19

| Compound | NS3-NS4A IC$_{50}$ | Replicon EC$_{50}$ |
|---|---|---|
| 2001 | A | N/A |
| 2002 | B | N/A |
| 2003 | B | N/A |
| 2004 | C | N/A |
| 2005 | D | C |
| 2006 | C | N/A |
| 2007 | C | B |
| 2008 | C | B |
| 2009 | B | N/A |
| 2010 | B | N/A |
| 2011 | A | N/A |

TABLE 20

| Compound | NS3-NS4 IC$_{50}$ |
|---|---|
| 2101 | B |
| 2102 | B |
| 2103 | C |
| 2104 | B |
| 2105 | C |
| 2106 | D |
| 2107 | C |
| 2108 | B |
| 2109 | B |
| 2110 | B |
| 2111 | B |
| 2112 | B |
| 2113 | B |
| 2114 | B |
| 2115 | D |
| 2116 | B |
| 2117 | C |
| 2118 | C |

TABLE 20-continued

| Compound | NS3-NS4 IC$_{50}$ |
|---|---|
| 2119 | C |
| 2120 | C |
| 2121 | C |
| 2122 | C |
| 2123 | C |
| 2124 | B |
| 2125 | C |
| 2126 | B |
| 2127 | B |
| 2128 | B |
| 2129 | B |
| 2130 | B |
| 2131 | B |
| 2132 | B |
| 2133 | B |
| 2134 | C |
| 2135 | C |
| 2136 | B |
| 2137 | A |
| 2138 | A |
| 2139 | A |
| 2140 | A |
| 2141 | B |
| 2142 | B |
| 2143 | A |
| 2144 | A |
| 2145 | A |
| 2146 | A |
| 2147 | A |
| 2148 | B |
| 2149 | B |
| 2150 | B |
| 2151 | C |
| 2152 | B |
| 2153 | B |
| 2154 | B |

TABLE 21

| Compound | NS3-NS4 IC$_{50}$ |
|---|---|
| 2201 | C |
| 2202 | B |
| 2203 | C |
| 2204 | C |
| 2205 | C |
| 2206 | B |
| 2207 | B |
| 2208 | C |
| 2209 | C |
| 2210 | C |
| 2211 | C |
| 2212 | C |
| 2213 | B |
| 2214 | C |
| 2215 | C |
| 2216 | B |
| 2217 | C |
| 2218 | D |
| 2219 | B |
| 2220 | C |
| 2221 | C |
| 2222 | C |
| 2223 | C |
| 2224 | B |
| 2225 | B |
| 2226 | B |
| 2227 | B |

TABLE 21-continued

| Compound | NS3-NS4 IC$_{50}$ |
|---|---|
| 2228 | B |
| 2229 | B |
| 2230 | B |
| 2231 | B |
| 2232 | B |
| 2233 | C |
| 2234 | C |
| 2235 | C |
| 2236 | C |
| 2237 | C |
| 2238 | C |
| 2239 | C |
| 2240 | C |
| 2241 | C |
| 2242 | C |
| 2243 | C |
| 2244 | D |
| 2245 | D |
| 2246 | C |
| 2247 | A |
| 2248 | B |
| 2249 | C |
| 2250 | B |
| 2251 | D |
| 2252 | C |

TABLE 22

| Compound | NS3-NS4 IC$_{50}$ |
|---|---|
| 2301 | B |
| 2302 | B |
| 2303 | C |
| 2304 | C |
| 2305 | C |
| 2306 | C |
| 2307 | C |
| 2308 | C |
| 2309 | C |
| 2310 | C |
| 2311 | C |
| 2312 | C |
| 2313 | C |
| 2314 | C |
| 2315 | C |
| 2316 | C |
| 2317 | C |
| 2318 | C |
| 2319 | D |
| 2320 | D |
| 2321 | C |
| 2322 | D |

TABLE 23

| Compound | NS3-NS4 IC$_{50}$ |
|---|---|
| 2401 | D |
| 2402 | D |
| 2403 | C |
| 2404 | C |

TABLE 24

| Compound | NS3-NS4 IC$_{50}$ |
|---|---|
| 2501 | A |
| 2502 | A |

TABLE 25

| Compound | NS3-NS4 IC$_{50}$ |
|---|---|
| 2601 | A |
| 2602 | B |
| 2603 | B |
| 2604 | A |

TABLE 26

| Compound | EC$_{50}$ |
|---|---|
| 2137 | A |
| 2138 | C |
| 2139 | C |
| 2142 | A |
| 2143 | A |
| 2144 | C | wherein

A indicates an IC50 or EC50, as indicated, of greater than 10 µM

B indicates an IC50 or EC50, as indicated, of less than 10 µM

C indicates an IC50 or EC50, as indicated, of less than 1 µM and D indicates an IC50 or EC50, as indicated, of less the 0.1 µM

CONCLUSION

Potent small molecule inhibitors of the HCV NS3 protease have been developed.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A compound having the Formula V:

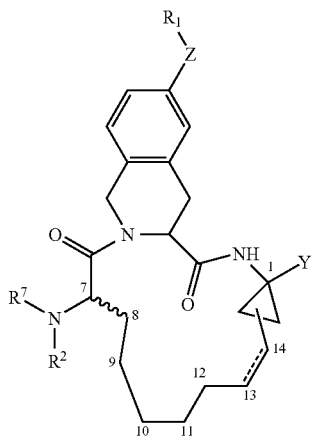

(V)

or a pharmaceutically acceptable salt, prodrug, or ester thereof wherein:

$R^1$ is H, $C_{1-7}$ alkyl, $C_{3-7}$ cycloalkyl, pyridyl, thioazolo, naphthyl, fused heterocycle, phenyl, substituted phenyl, benzyloxy, or substituted benzyloxy;

$R^2$ is H, $C_{1-6}$ alkyl, $C_{3-7}$ cycloalkyl, $C_{4-10}$ cycloalkyl-alkyl, phenyl, substituted phenyl, $C_{1-6}$ alkoxy, or substituted $C_{1-6}$ alkoxy;

$R^3$ is H, $C_{1-6}$ alkyl, $C(O)R^5$, $C(O)OR^5$, $C(O)NR^5R^6$, $C(S)NR^5R^6$, or $S(O)_2R^5$;

$R^5$ and $R^6$ are each independently selected from H, $C_{1-6}$ alkyl, $C_{3-7}$ cycloalkyl, $C_{4-10}$ cycloalkyl-alkyl, $C_{3-7}$ cycloalkyl fused to $C_6$ aryl or $C_6$ aryl heterocyclyl, benzyl, phenyl, or substituted phenyl;

Y is a sulfonimide of the formula —$C(O)NHS(O)_2R^4$ or a carboxylic acid of the formula —$C(O)OH$, wherein $R^4$ is $C_{1-6}$ alkyl, $C_{3-7}$ cycloalkyl, $C_{4-10}$ cycloalkyl-alkyl, $C_6$ aryl, or substituted $C_6$ aryl;

Z is a bond, O, or S; and the dashed line represents an optional double bond.

2. The compound of claim 1, wherein $R^1$ is phenyl substituted with halo, $C_{1-3}$ alkyl, substituted $C_{1-3}$ alkyl substituted with up to 3 fluoro, $C_{1-3}$ alkoxy, substituted $C_{1-3}$ alkoxy substituted with up to 3 fluoro, cyano, hydroxy, nitro, $NH_2$, $NHR_2$, or $NR_2R_3$.

3. The compound of claim 1, wherein $R^1$ is benzyloxy substituted with halo, $C_{1-3}$ alkyl, substituted $C_{1-3}$ alkyl with up to 3 fluoro, $C_{1-3}$ alkoxy, substituted $C_{1-3}$ alkoxy substituted with up to 3 fluoro, cyano, hydroxy, nitro, $NH_2$, $NHR_2$, or $NR_2R_3$.

4. The compound of claim 1, wherein $R^2$ is phenyl substituted with halo, cyano, nitro, hydroxy, $C_{1-6}$ alkyl, $C_{3-7}$ cycloalkyl, $C_{4-10}$ cycloalkyl-alkyl, $C_{2-6}$ alkenyl, $C_{1-6}$ alkoxy, hydroxy-$C_{1-6}$ alkyl, $C_{1-6}$ alkyl, substituted $C_{1-6}$ alkyl substituted with up to 5 fluoro, $C_{1-6}$ alkoxy, or substituted $C_{1-6}$ alkoxy substituted with up to 5 fluoro.

5. The compound of claim 1, wherein $R^5$ and $R^6$ are each individually phenyl substituted with halo, cyano, nitro, hydroxy, $C_{1-6}$ alkyl, $C_{3-7}$ cycloalkyl, $C_{4-10}$ cycloalkyl-alkyl, $C_{2-6}$ alkenyl, $C_{1-6}$ alkoxy, hydroxy-$C_{1-6}$ alkyl, $C_{1-6}$ alkyl, substituted $C_{1-6}$ alkyl substituted with up to 5 fluoro, $C_{1-6}$ alkoxy, or substituted $C_{1-6}$ alkoxy substituted with up to 5 fluoro.

6. The compound of claim 1, wherein $R^4$ is $C_6$ aryl substituted with up to three halo.

7. A compound having a formula selected from the group consisting of the compounds in Tables 1 through 7 as described in the specification and compounds numbered 100, 701-706, 801, 922, 927, 1001-1018, 2001-2011, 2101-2154, 2201-2252, 2301-2322, 2401-2404, 2501-2502, and 2601-2604.

8. A pharmaceutical composition comprising a pharmaceutically acceptable excipient and a compound of claim 1 or 7.

9. A method of inhibiting NS3/NS4 protease activity, comprising contacting a NS3/NS4 protease with a compound of claim 1 or 7.

10. The method of claim 9 in which the contacting is conducted in vivo.

11. The method of claim 9, further comprising identifying a subject suffering from a hepatitis C infection and administering the compound or composition to the subject in an amount effective to treat the infection.

12. The method of claim 9 in which the contacting is conducted ex vivo.

13. A method of treating a hepatitis C virus infection, liver fibrosis resulting from or associated with a hepatitis C virus infection, or impaired liver function resulting from or associated with a hepatitis C virus infection, the method comprising administering to an individual in need thereof an amount of a compound of claim 1 or 7 that is effective to treat a least one condition selected from the group consisting of a hepatitis C virus infection, liver fibrosis resulting from or associated with a hepatitis C virus infection, and impaired liver function resulting from or associated with a hepatitis C virus infection.

14. The method of claim 13, wherein a sustained viral response is achieved.

15. The method of claim 13, wherein the method further comprises administering to the individual a nucleoside analog.

16. The method of claim 15, wherein the nucleoside analog is selected from ribavirin, levovirin, viramidine, an L-nucleoside, and isatoribine.

17. The method of claim 13, wherein the method further comprises administering to the individual pirfenidone or a pirfenidone analog administered orally daily in an amount of from about 400 mg to about 3600 mg.

18. The method of claim 13, wherein the method further comprises administering to the individual an NS5B RNA-dependent RNA polymerase inhibitor.

19. The method of claim 13, wherein the method further comprises administering to the individual a tumor necrosis factor antagonist selected from the group consisting of etanercept, infliximab, and adalimumab.

20. The method of claim 13, wherein the method further comprises administering to the individual interferon-gamma (IFN-γ).

21. The method of claim 20, wherein the IFN-γ is administered subcutaneously in an amount of from about 10 μg to about 300 μg.

22. The method of claim 13, wherein the method further comprises administering to the individual interferon-alpha (IFN-α).

23. The method of claim 22, wherein the IFN-α is monoPEG (30 kD, linear)-ylate consensus IFN-α administered at a dosing interval of every 8 days to every 14 days.

24. The method of claim 22, wherein the IFN-α is monoPEG (30 kD, linear)-ylated consensus IFN-α administered at a dosing interval of once every 7 days.

25. The method of claim 22, wherein the IFN-α is INFERGEN consensus IFN-α.

26. The method of claim 22, wherein the IFN-α is PEGASYS® PEGylated IFN-α2a or PEG-INTRON® PEGylated IFN-α2b.

27. The method of claim 13, further comprising administering an agent selected from 3'-azidothymidine, 2',3'-dideoxyinosine, 2',3'-dideoxycytidine, 2-,3-didehydro-2',3'-dideoxythymidine, combivir, abacavir, adefovir dipoxil, cidofovir, ritonavir, and an inosine monophosphate dehydrogenase inhibitor.

28. The method of claim 13, further comprising administering interferon, another NS3 protease inhibitor, a NS5b polymerase inhibitor, or a NS3 helicase inhibitor.

29. The method of claim 28, wherein the another NS3 protease inhibitor is selected from

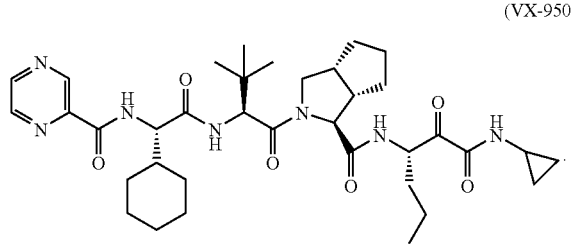
(VX-950)

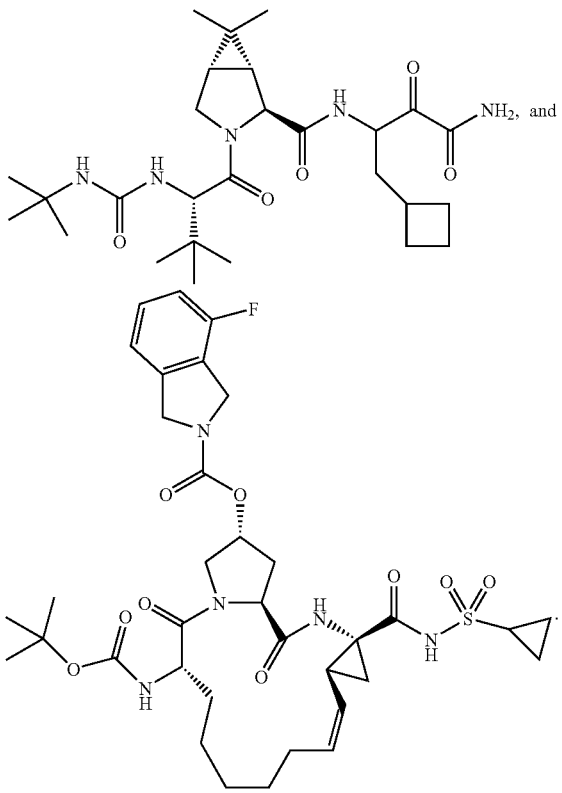
(SCH 503034)

* * * * *